US012780890B2

(12) United States Patent
Kitada et al.

(10) Patent No.: US 12,780,890 B2
(45) Date of Patent: Nov. 3, 2026

(54) EXPRESSION CONSTRUCTS AND USES THEREOF

(71) Applicant: STRAND THERAPEUTICS INC., Boston, MA (US)

(72) Inventors: Tasuku Kitada, Boston, MA (US); Jacob Becraft, Boston, MA (US); Ryan Sowell, Boston, MA (US); Jaspreet Khurana, Boston, MA (US); Anna Simon, Cambridge, MA (US); Joseph Barberio, Boston, MA (US); Weiyu Zhao, Boston, MA (US); Alexander Lemaire, Boston, MA (US); Aalok Shah, Shrewsbury, MA (US)

(73) Assignee: STRAND THERAPEUTICS INC., Boston, MA (US)

( * ) Notice: Subject to any disclaimer, the term of this patent is extended or adjusted under 35 U.S.C. 154(b) by 607 days.

(21) Appl. No.: 18/260,831

(22) PCT Filed: Jan. 10, 2022

(86) PCT No.: PCT/US2022/011841
§ 371 (c)(1),
(2) Date: Jul. 10, 2023

(87) PCT Pub. No.: WO2022/150712
PCT Pub. Date: Jul. 14, 2022

(65) Prior Publication Data

US 2024/0166707 A1 May 23, 2024

Related U.S. Application Data

(60) Provisional application No. 63/135,501, filed on Jan. 8, 2021.

(51) Int. Cl.
*C07K 14/54* (2006.01)
*A61P 35/00* (2006.01)

(52) U.S. Cl.
CPC .......... *C07K 14/5434* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,013,556 | A | 5/1991 | Woodle et al. |
| 6,310,197 | B1 | 10/2001 | Rogers |
| 6,849,405 | B2 | 2/2005 | Rogers |
| 7,141,550 | B2 | 11/2006 | Molling et al. |
| 7,183,395 | B2 | 2/2007 | Mauro et al. |
| 7,456,273 | B2 | 11/2008 | Mauro et al. |
| 7,468,275 | B2 | 12/2008 | Mauro et al. |
| 8,252,538 | B2 | 8/2012 | Croce et al. |
| 8,263,092 | B1 | 9/2012 | Smith et al. |
| 8,389,210 | B2 | 3/2013 | Croce et al. |
| 8,415,096 | B2 | 4/2013 | Mohapatra et al. |
| 8,519,110 | B2 | 8/2013 | Kowalska et al. |
| 10,238,754 | B2 | 3/2019 | Guild et al. |
| 10,646,549 | B2 | 5/2020 | Frederick et al. |
| 10,869,935 | B2 | 12/2020 | Fotin-Mleczek et al. |
| 11,066,687 | B2 | 7/2021 | Lee et al. |
| 11,524,023 | B2 | 12/2022 | Packer et al. |
| 11,583,504 | B2 | 2/2023 | Brader |
| 11,717,548 | B2 | 8/2023 | Irvine et al. |
| 12,134,777 | B2 | 11/2024 | Akahata et al. |
| 2005/0059005 | A1 | 3/2005 | Tuschl et al. |
| 2005/0261218 | A1 | 11/2005 | Esau et al. |
| 2007/0048776 | A1 | 3/2007 | Mauro et al. |
| 2009/0092974 | A1 | 4/2009 | Davison et al. |
| 2009/0131348 | A1 | 5/2009 | Labourier et al. |
| 2009/0226470 | A1 | 9/2009 | Mauro et al. |
| 2009/0263803 | A1 | 10/2009 | Beaudenon et al. |
| 2010/0286232 | A1 | 11/2010 | Schmittgen et al. |
| 2010/0323357 | A1 | 12/2010 | Nana-Sinkam et al. |
| 2011/0064751 | A1 | 3/2011 | Mossner et al. |
| 2011/0124100 | A1 | 5/2011 | Mauro et al. |
| 2011/0171646 | A1 | 7/2011 | Schmittgen et al. |
| 2011/0244026 | A1 | 10/2011 | Guild et al. |
| 2011/0281756 | A1 | 11/2011 | Wu et al. |
| 2012/0053224 | A1 | 3/2012 | Meister et al. |

(Continued)

FOREIGN PATENT DOCUMENTS

| | | | |
|---|---|---|---|
| EP | 2112235 | A1 | 10/2009 |
| EP | 2610340 | A1 | 7/2013 |

(Continued)

OTHER PUBLICATIONS

*Homo sapiens* codon usage table at www.kazusa.or.jp/codon/cgi-bin/showcodon.cgi?species=9606, captured on Jan. 18, 2019 (Year: 2019).*
GenBank Accession CAA77299.1, immunoglobulin kappa light chain subgroup V [*Homo sapiens*], published Nov. 14, 2006 (Year: 2006).*
Oberli, M., et al., "Lipid Nanoparticle Assisted mRNA Delivery for Potent Cancer Immunotherapy" Nano Lett. Mar. 8, 2017; 17(3): 1326-1335. doi:10.1021/acs.nanolett.6b03329. 20 Pages.
Anand, S. and Cheresh, D.A., "MicroRNA-Mediated Regulation of the Angiogenic Switch," Current Opinion in Hematology 18(3):171-176, Lippincott Williams and Wilkins, United States (May 2011).
Annoni, A., et al., "In Vivo Delivery of a MicroRNA-Regulated Transgene Induces Antigen-Specific Regulatory T Cells and Promotes Immunologic Tolerance," Blood 114(25):5152-5161, American Society of Hematology, United States (Dec. 2009).

(Continued)

*Primary Examiner* — Catherine Konopka
(74) *Attorney, Agent, or Firm* — Sterne, Kessler, Goldstein & Fox P.L.L.C.

(57) ABSTRACT

The present disclosure relates to an isolated polynucleotide comprising a sequence that encodes an interleukin (IL)-12 molecule, and a delivery system that can carry the polynucleotides. The disclosure also includes methods of making the polynucleotides and methods of treatment using the same.

21 Claims, 24 Drawing Sheets

Figure 1A:
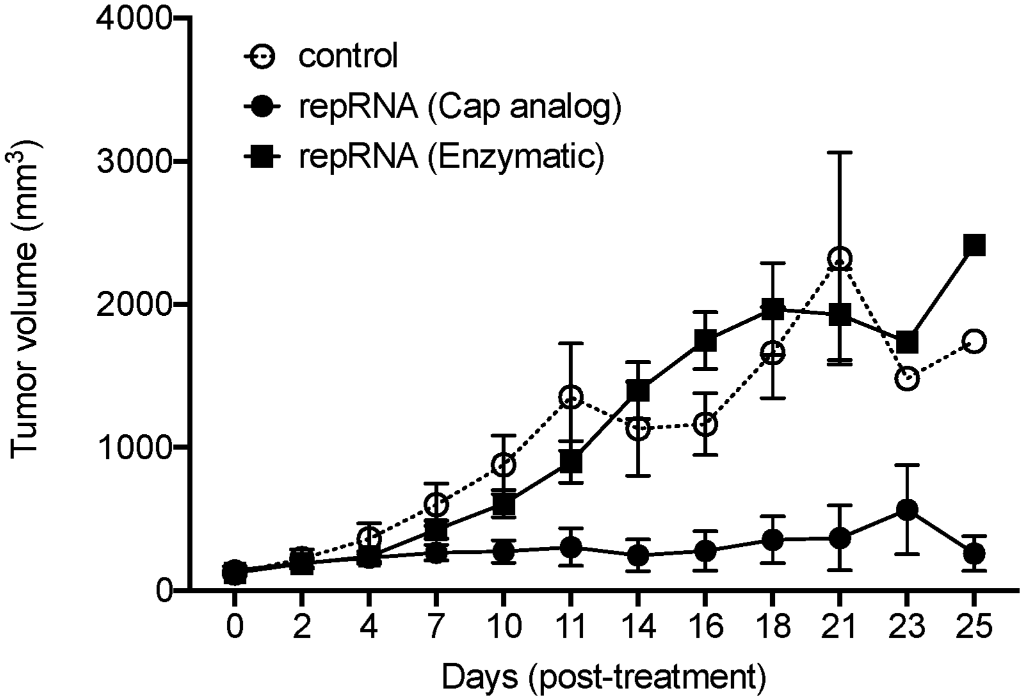

Specification includes a Sequence Listing.

(56) References Cited

U.S. PATENT DOCUMENTS

| | | | |
|---|---|---|---|
| 2012/0214699 A1 | 8/2012 | Croce et al. | |
| 2012/0264626 A1 | 10/2012 | Nana-Sinkam et al. | |
| 2012/0283310 A1 | 11/2012 | Croce et al. | |
| 2012/0309645 A1 | 12/2012 | Keller et al. | |
| 2012/0316081 A1 | 12/2012 | List et al. | |
| 2012/0329672 A1 | 12/2012 | Croce et al. | |
| 2013/0042333 A1 | 2/2013 | Judde et al. | |
| 2013/0053263 A1 | 2/2013 | Keller et al. | |
| 2013/0053264 A1 | 2/2013 | Keller et al. | |
| 2013/0059015 A1 | 3/2013 | Lancaster et al. | |
| 2013/0177581 A1 | 7/2013 | Mauro et al. | |
| 2014/0105966 A1 | 4/2014 | Bancel et al. | |
| 2014/0107189 A1 | 4/2014 | Bancel et al. | |
| 2014/0147454 A1 | 5/2014 | Chakraborty et al. | |
| 2018/0318229 A1 | 11/2018 | Frederick et al. | |
| 2018/0369374 A1 | 12/2018 | Frederick et al. | |
| 2019/0185859 A1 | 6/2019 | Fotin-Mleczek et al. | |
| 2019/0194283 A1 | 6/2019 | Hauskins et al. | |
| 2020/0171093 A1* | 6/2020 | Lu | A61K 38/20 |
| 2022/0249699 A1 | 8/2022 | Guild et al. | |
| 2023/0295257 A1 | 9/2023 | Becraft et al. | |
| 2024/0024394 A1 | 1/2024 | Irvine et al. | |

FOREIGN PATENT DOCUMENTS

| | | | |
|---|---|---|---|
| EP | 2610341 | A1 | 7/2013 |
| EP | 4013385 | B1 | 7/2024 |
| EP | 4454640 | A2 | 10/2024 |
| WO | WO-9924595 | A1 | 5/1999 |
| WO | WO-0155369 | A1 | 8/2001 |
| WO | WO-2004041203 | A2 | 5/2004 |
| WO | WO-2007025008 | A2 | 3/2007 |
| WO | WO-2007081740 | A2 | 7/2007 |
| WO | WO-2008054828 | A2 | 5/2008 |
| WO | WO-2008073915 | A2 | 6/2008 |
| WO | WO-2008154098 | A2 | 12/2008 |
| WO | WO-2009070653 | A1 | 6/2009 |
| WO | WO-2009075886 | A1 | 6/2009 |
| WO | WO-2009100430 | A2 | 8/2009 |
| WO | WO-2010018563 | A2 | 2/2010 |
| WO | WO-2011076142 | A1 | 6/2011 |
| WO | WO-2011076143 | A1 | 6/2011 |
| WO | WO-2011095623 | A2 | 8/2011 |
| WO | WO-2011157294 | A1 | 12/2011 |
| WO | WO-2012006376 | A2 | 1/2012 |
| WO | WO-2012009644 | A2 | 1/2012 |
| WO | WO-2012151212 | A1 | 11/2012 |
| WO | WO-2013011378 | A1 | 1/2013 |
| WO | WO-2013033640 | A1 | 3/2013 |
| WO | WO-2013066678 | A1 | 5/2013 |
| WO | WO-2013103659 | A1 | 7/2013 |
| WO | WO-2014011819 | A3 | 3/2014 |
| WO | WO-2015089511 | A2 | 6/2015 |
| WO | WO-2015196118 | A1 | 12/2015 |
| WO | WO-2016037053 | A1 | 3/2016 |
| WO | WO-2016170176 | A1 | 10/2016 |
| WO | WO-2017191274 | A2 | 11/2017 |
| WO | WO-2017201350 | A1 | 11/2017 |
| WO | WO-2018011406 | A1 | 1/2018 |
| WO | WO-2018033254 | A2 | 2/2018 |
| WO | WO-2018160540 | A1 | 9/2018 |
| WO | WO-2018213731 | A1 | 11/2018 |
| WO | WO-2020086965 | A1 | 4/2020 |
| WO | WO-2020123716 | A1 | 6/2020 |
| WO | WO-2021026358 | A1 | 2/2021 |
| WO | WO-2022032154 | A2 | 2/2022 |

OTHER PUBLICATIONS

Asselin-Paturel, C., et al., "Differential effect of high doses versus low doses of interleukin-12 on the adoptive transfer of human specific cytotoxic T lymphocyte in autologous lung tumors engrafted into severe combined immunodeficiency disease-nonobese diabetic mice: relation with interleukin-10 induction," Cancer 91(1): 113-122, Wiley, United States (Jan. 2001).

Bartel, D.P., "MicroRNAs: Target Recognition and Regulatory Functions," Cell 136(2):215-233, Cell Press, United States (Jan. 2009).

Bonauer, A., et al., "Vascular MicroRNAs," Current drug targets 2010 11(8):943-949, Bentham Science Publishers, United Arab Emirates (Aug. 2010).

Brown, B.D., et al., "A microRNA-regulated lentiviral vector mediates stable correction of hemophilia B mice," Blood 110(13): 4144-4152, Elsevier, United States (Dec. 2007).

Brown, B.D., et al., "Endogenous MicroRNA Regulation Suppresses Transgene Expression in Hematopoietic Lineages and Enables Stable Gene Transfer," Nature Medicine 12(5):585-591, Nature Publishing Company, United Kingdom (May 2006).

Buonaguro, L., et al., "Developments in virus-like particle-based vaccines for infectious diseases and cancer," Expert review of vaccines 10(11):1569-83, Taylor & Francis, United Kingdom (Nov. 2011).

Chen, C.Y., and Shyu, A.B. "AU-Rich Elements: Characterization and Importance in mRNA Degradation," Trends in biochemical sciences 20(11), 465-470. Elsevier, United States (Nov. 1995).

Contreras, J., et al., "MicroRNAs in Inflammation and Immune Responses," Leukemia 26(3):404-413, Nature Publishing Group, United Kingdom (Mar. 2012).

Coughlin, C. M., et al., "The effect of interleukin 12 desensitization on the antitumor efficacy of recombinant interleukin 12," Cancer research 57(12):2460-2467, American Association for Cancer Research, United States (Jun. 1997).

Epstein, D.A., et al., "Biological activity of liposome-encapsulated murine interferon gamma is mediated by a cell membrane receptor," Proceedings of the National Academy of Sciences 82(11):3688-3692, National Academy of Sciences, United States (Jun. 1985).

Fadl, T.A., et al., "Synthesis and Investigation of N4-substituted Cytarabine Derivatives as Prodrugs," Die Pharmazie 50(6):382-387, Govi-Verlag Pharmazautischer Verlag, Germany (Jun. 1995).

Gadri, Z., et al., "Synergistic effect of dendritic cell vaccination and anti-CD20 antibody treatment in the therapy of murine lymphoma," J Immunother 32(4):333-40, Lippincott Williams & Wilkins, United States (May 2009).

Gentner, B. and Naldini, L., "Exploiting MicroRNA Regulation for Genetic Engineering," Tissue Antigens 80(5):393-403, Blackwell, United Kingdom (Nov. 2012).

Grimson, A., et al., "MicroRNA Targeting Specificity in Mammals: Determinants beyond Seed Pairing," Molecular Cell 27(1):91-105, Cell Press, United States (Jul. 2007).

Guillen, G., et al., "Virus-like particles as vaccine antigens and adjuvants: application to chronic disease, cancer immunotherapy and infectious disease preventive strategies," Procedia in Vaccinology 2(2): 128-133, Elsevier, United States (Dec. 2010).

Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (Jul. 1980).

International Search Report and Written Opinion for International Application No. PCT/US2022/011841, European Patent Office, Netherlands, mailed on Jun. 20, 2022, 1 pages.

Kang, W. K., et al., "Interleukin 12 gene therapy of cancer by peritumoral injection of transduced autologous fibroblasts: outcome of a phase I study," Human gene therapy 12(6): 671-684, M.A. Liebert, United States (Apr. 2001).

Kore, A.R., et al., "Synthesis and Biological Validation of $N^7$-(4-Chlorophenoxyethyl) Substituted Dinucleotide Cap Analogs for mRNA Translation," Bioorganic & Medicinal Chemistry 21(15):4570-4574, Elsevier Science, United Kingdom (Aug. 2013).

Kulasegaran-Shylini, R., et al., "The 5'UTR-specific mutation in VEEV TC-83 genome has a strong effect on RNA replication and subgenomic RNA synthesis, but not on translation of the encoded proteins," Virology 387:(1) 211-221, Academic Press, United States (Apr. 2009).

(56) References Cited

OTHER PUBLICATIONS

Landgraf, P., et al., "A Mammalian MicroRNA Expression Atlas Based on Small RNA Library Sequencing," Cell 129(7):1401-1414, Cell Press, United States (Jun. 2007).
Lasek W., et al., "Interleukin 12: Still a Promising Candidate for Tumor Immunotherapy?," Cancer Immunology and Immunotherapy, 63(5):419-435, Springer Verlag, Berlin. (May 2014).
Lechner, M.G., et al., "Chemokines, Costimulatory Molecules and Fusion Proteins for the Immunotherapy of Solid Tumors," Immunotherapy 3(11):1317-1340, Future Medicine, United Kingdom (Nov. 2011).
Leonard, J.P, et al., "Effects of Single-dose Interleukin-12 Exposure on Interleukin-12-associated Toxicity and Interferon-gamma Production," Blood 90(7):2541-2548, Elsevier, United States (Oct. 1997).
Leppek, K., et al., "Roquin Promotes Constitutive mRNA Decay Via a Conserved Class of Stem-Loop Recognition Motifs," Cell 153(4):869-881, Cell Press, United States (May 2013).
Li, J., et al., "Methylation Protects miRNAs and siRNAs from a 3'-End Uridylation Activity in *Arabidopsis*," Current biology: CB 15(16):1501-1507, Cell Press, England (Aug. 2005).
Li, Y., et al., "In vitro evolution of enhanced RNA replicons for immunotherapy," Scientific Reports 9:6932 (2019), Nature Publishing Group, United Kingdom (May 2019).
Meijer, H.A., et al., "Translational Repression and eIF4A2 Activity are Critical For MicroRNA-Mediated Gene Regulation," Science 340(6128):82-85, American Association for the Advancement of Science, United States (Apr. 2013).
Nastala, C.L., et al., "Recombinant IL-12 administration induces tumor regression in association with IFN-gamma production," Journal of immunology 153(4): 1697-1706, American Association of Immunologists, United States (Aug. 1994).
Nomura, M., et al., "Synthesis of the Cyclic and Acyclic Acetal Derivatives of 1-(3-C-Ethynyl-Beta-D-Ribo-Pentofuranosyl) Cytosine, a Potent Antitumor Nucleoside. Design of Prodrugs to Be Selectively Activated in Tumor Tissues via the Bio-reduction-hydrolysis Mechanism," Bioorganic & Medicinal Chemistry 11(11):2453-2461, Pergamon Press, England (May 2003).
Panek, J., et al., "An Evolutionary Conserved Pattern of 18S rRNA Sequence Complementarity to mRNA 5' UTRs and its Implications for Eukaryotic Gene Translation Regulation," Nucleic Acids Research 41(16):7625-7634, Oxford University Press, England (Sep. 2013).
Parker, B.J., et al., "New Families of Human Regulatory RNA Structures Identified by Comparative Analysis of Vertebrate Genomes," Genome Research 21(11):1929-1943, Cold Spring Harbor Laboratory Press, United States (Nov. 2011).
Ray, D., et al., "A Compendium of RNA-Binding Motifs for Decoding Gene Regulation," Nature 499(7457):172-177, Nature Publishing Group, England (Jul. 2013).
Sacco, S., et al., "Protective effect of a single interleukin-12 (IL-12) predose against the toxicity of subsequent chronic IL-12 in mice: role of cytokines and glucocorticoids," Blood 90(11): 4473-4479, Elsevier, United States (Dec. 1997).
Saudemont, A., et al., "Gene transfer of CD154 and IL 12 cDNA induces an anti-leukemic immunity in a murine model of acute leukemia," Leukemia 16: 1637-1644, Nature Publishing Group, Specialist Journals, United Kingdom (Sep. 2002).
Schoenfeld, J.D., and Dranoff, G., "Anti-Angiogenesis Immunotherapy," Human vaccines (9):976-81, Landes Bioscience, United States (Sep. 2011).
Sung, Y.K. and Kim, S.W., et al., "Recent advances in the development of gene delivery systems," Biomaterials research 23(8) AAAS Science Partner Journals, United States (Mar. 2019).
Van Duin, D., et al., "Triggering TLR signaling in vaccination," Trends in Immunology 27(1):49-55, Elsevier Science Ltd, United Kingdom (Nov. 2005).
Wilusz, J.E., et al., "A Triple Helix Stabilizes the 3' Ends of Long Noncoding RNAs that Lack Poly(A) Tails," Genes and development 26(21):2392-2407, Cold Spring Harbor Laboratory Press, United States (Nov. 2012).
Yamada, A., "Peptide-based cancer vaccine therapy for prostate cancer, bladder cancer, and malignant glioma," Nihon rinsho. Japanese journal of clinical medicine 69(9):1657-61, Nippon Rinsho Co, Japan (Sep. 2011).
Yoshioka, N., et al., "Efficient generation of human iPSCs by a synthetic self-replicative RNA," Cell Stem Cell 13(2):246-54, Cell Press, United States (Aug. 2013).
Zhang, J., et al. "Targeting cancer with small molecule kinase inhibitors," Nature reviews 9(1):28-39, Nature Pub. Group, United Kingdom (Jan. 2009).
Miao, L. et al. "Delivery of mRNA vaccines with heterocyclic lipids increases anti-tumor efficacy by STING-mediated immune cell activation" Nature biotechnology 37, 1174-1185, Springer Nature, United States (Oct. 2019).
GenBank, "Synthetic construct chimeric anti-Burkholderia pseudomallei immunoglobulin light chain leader sequence gene, partial cds," Accession No. GU350793, accessed at https://www.ncbi.nlm.nih.gov/nuccore/GU350793.1, accessed on Aug. 27, 2024, 1 page.
[No Author Listed] Koch Institute Immune Engineering Symposium, 30 Pages, (Feb. 2019).
Geall, A.J., et al., "Nonviral Delivery of Self-Amplifying RNA Vaccines," Proceedings of the National Academy of Sciences USA 109(36):14604-14609, National Academy of Sciences, United States (2012).
Li, B., et al., "An Orthogonal Array Optimization of Lipid-like Nanoparticles for mRNA Delivery in Vivo," Nano Letters 15(12):8099-8107, American Chemical Society, United States (Dec. 2015).
Lundstrom, K., "Alphavirus Vectors As Tools in Neuroscience and Gene Therapy," Virus Research 216:16-25, Elsevier Science, Netherlands (May 2016).
Lundstrom, K., "Alphavirus-based Vaccines," Current Opinion in Molecular Therapeutics 4(1):28-34, Thomson Reuters (Scientific) Ltd, United Kingdom (Feb. 2002).
Lundstrom, K., "Replicon RNA Viral Vectors as Vaccines," Vaccines 4(4):39, Basel, Switzerland (Nov. 2016).
Momin, N., et al., "Anchoring of Intratumorally Administered Cytokines to Collagen Safely Potentiates Systemic Cancer Immunotherapy," Science Translational Medicine 11(498):eaaw2614, American Association for the Advancement of Science, United States (Jun. 2019).
Ren, H., et al., "Immunogene Therapy of Recurrent Glioblastoma Multiforme with a Liposomally Encapsulated Replication-incompetent Semliki Forest Virus Vector Carrying the Human Interleukin-12 gene—a Phase I/II Clinical Protocol," Journal of Neuro-oncology 64(1-2):147-154, Springer, United States (Aug. 2003).
Zhao, W., et al., "Lipid Polymer Hybrid Nanomaterials for mRNA Delivery," Cellular and Molecular Bioengineering 11(5):397-406, Springer, United States (Oct. 2018).
Genbank, "Synthetic construct single chain interleukin-12 mRNA, complete cds," Accession No. AF401989.1 accessed at https:/www.nebi.nlm.nih.gov/nuccore/AF401989.1, dated Feb. 14, 2002, 2 pages.
Li, Y., et al. "Multifunctional oncolytic nanoparticles deliver self-replicating IL-12 RNA to eliminate established tumors and prime systemic immunity," Nat Cancer. 10; 1(9):882-893, Springer Nature, United States (Aug. 2020).
Lai, I., et al., "Lipid nanoparticles that deliver IL-12 messenger RNA suppress tumorigenesis in MYC oncogene-driven hepatocellular carcinoma," Journal for immunotherapy of cancer 6(1):125, BMJ Publishing Group Ltd, United Kingdom (Nov. 2018).
GenBank, "Predicted: Suricata suricatta interleukin 12B (IL12B), transcript variant X2, mRNA," Accession No. XM_029942931.1, accessed at https://www.ncbi.nlm.nih.gov/nuccore/XM_029942931.1/, accessed on Jan. 15, 2025, 2 pages.
GenBank, " Predicted: Equus przewalskii interleukin 12A (IL12A), mRNA," Accession No. XM_008538081, accessed at https://www.nebi.nlm.nih.gov/nuccore/XM_008538081.2/, accessed on Jan. 15, 2025, 2 pages.

* cited by examiner

EXPRESSION CONSTRUCTS AND USES THEREOF

CROSS REFERENCE TO RELATED APPLICATIONS

This application claims the priority benefit of U.S. Provisional Application No. 63/135,501, filed Jan. 8, 2021, which is incorporated herein by reference in its entirety.

REFERENCE TO SEQUENCE LISTING SUBMITTED ELECTRONICALLY VIA EFS-WEB

The content of the electronically submitted sequence listing in ASCII text file (Name: 4597_005PC01_SequenceListing_ST25.txt; Size: 246,918 bytes; and Date of Creation: Jan. 9, 2022) filed with the application is herein incorporated by reference in its entirety.

BACKGROUND OF THE DISCLOSURE

Due to its ability to activate both NK cells and cytotoxic T cells, IL-12 protein has been studied as a promising anti-cancer therapeutic since 1994. See Nastala, C. L. et al., *J Immunol* 153: 1697-1706 (1994). But despite high expectations, early clinical studies did not yield satisfactory results. Lasek W. et al., *Cancer Immunol Immunother* 63: 419-435, 424 (2014). Repeated administration of IL12, in most patients, led to adaptive response and a progressive decline of IL-12-induced interferon gamma (IFN-γ) levels in blood. Id. Moreover, while it was recognized that IL-12-induced anti-cancer activity is largely mediated by the secondary secretion of IFN-γ, the concomitant induction of IFN-γ along with other cytokines (e.g., TNF-α) or chemokines (IP-10 or MIG) by IL-12 caused severe toxicity. Id.

In addition to the negative feedback and toxicity, the marginal efficacy of the IL-12 therapy in clinical settings can be caused by the strong immunosuppressive environment in humans. Id. To minimize IFN-γ toxicity and improve IL-12 efficacy, scientists tried different approaches, such as different dose and time protocols for IL-12 therapy. See Sacco, S. et al., *Blood* 90: 4473-4479 (1997); Leonard, J. P. et al., *Blood* 90: 2541-2548 (1997); Coughlin, C. M. et al., *Cancer Res.* 57: 2460-2467 (1997); Asselin-Paturel, C. et al., *Cancer* 91: 113-122 (2001); and Saudemont, A. et al., *Leukemia* 16: 1637-1644 (2002). Nonetheless, these approaches have not significantly impacted patient survival. Kang, W. K., et al., *Human Gene Therapy* 12: 671-684 (2001). Thus, there is a need in the art for an improved therapeutic approach for using IL12 to treat tumors.

BRIEF SUMMARY OF THE DISCLOSURE

Provided herein is an isolated polynucleotide comprising a nucleic acid molecule encoding a beta subunit of an IL-12 protein ("IL-12β"). In some aspects, the nucleic acid molecule comprises a nucleotide sequence that is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, or SEQ ID NO: 75.

In some aspects, the nucleic acid molecule encoding the IL-12β comprises a nucleotide sequence that is at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in 51. In some aspects, the nucleic acid molecule encoding the IL-12β comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 52. In some aspects, the nucleic acid molecule encoding the IL-12β comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 53. In some aspects, the nucleic acid molecule encoding the IL-12β comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 54. In some aspects, the nucleic acid molecule encoding the IL-12β comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 55. In some aspects, the nucleic acid molecule encoding the IL-12β comprises a nucleotide sequence that is at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 56. In some aspects, the nucleic acid molecule encoding the IL-12β comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 57. In some aspects, the nucleic acid molecule encoding the IL-12β comprises a nucleotide sequence that is at least 92%, at least 93%, at least 94%, at least 95%, at least 96%, at least 97%, at least 98%, at least 99%, or 100% identical to the sequence set forth in SEQ ID NO: 58. In some aspects, the nucleic acid molecule encoding the IL-12β comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 59. In some aspects, the nucleic acid molecule encoding the IL-12β comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 65, 69, or 74. In some aspects, the nucleic acid molecule encoding the IL-12β comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 66, 70, or 75. In some aspects, the nucleic acid molecule encoding the IL-12β comprises a nucleotide sequence that is at least 97%, at least 98%, at least 99%, or 100% identical to the sequence set forth in SEQ ID NO: 62. In some aspects, the nucleic acid molecule encoding the IL-12β comprises a nucleotide sequence that is at least 99% or 100% identical to the sequence set forth in SEQ ID NO: 63. In some aspects, the nucleic acid molecule encoding the IL-12β comprises a nucleotide sequence that is at least 98%, at least 99%, or 100% identical to the sequence set forth in SEQ ID NO: 64.

Also provided herein is an isolated polynucleotide comprising a nucleic acid molecule encoding an alpha subunit of an IL-12 protein ("IL-12α"). In some aspects, the nucleic acid molecule comprises a nucleotide sequence that is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, or SEQ ID NO: 125.

In some aspects, the nucleic acid molecule encoding the IL-12α comprises a nucleotide sequence that is at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 101. In some aspects, the nucleic acid molecule encoding the IL-12α comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 102. In some aspects, the nucleic acid molecule encoding the IL-12α comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 103. In some aspects, the nucleic acid molecule encoding the IL-12α comprises a nucleotide sequence that is at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 104. In some aspects, the nucleic acid molecule encoding the IL-12α comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 105. In some aspects, the nucleic acid molecule encoding the IL-12α comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 106. In some aspects, the nucleic acid molecule encoding the IL-12α comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 107. In some aspects, the nucleic acid molecule encoding the IL-12α comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 108. In some aspects, the nucleic acid molecule encoding the IL-12α comprises a nucleotide sequence that is at least 92%, at least 93%, at least 94%, at least 95%, at least 96%, at least 97%, at least 98%, at least 99%, or 100% identical to the sequence set forth in SEQ ID NO: 109. In some aspects, the nucleic acid molecule encoding the IL-12α comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 115, 119, or 124. In some aspects, the nucleic acid molecule encoding the IL-12α comprises a nucleotide sequence that is at least 92%, at least 93%, at least 94%, at least 95%, at least 96%, at least 97%, at least 98%, at least 99%, or 100% identical to the sequence set forth in SEQ ID NO: 116, 120, or 125. In some aspects, the nucleic acid molecule encoding the IL-12α comprises a nucleotide sequence that is at least 98%, at least 99%, or 100% identical to the sequence set forth in SEQ ID NO: 112. In some aspects, the nucleic acid molecule encoding the IL-12α comprises a nucleotide sequence that is at least 98%, at least 99%, or 100% identical to the sequence set forth in SEQ ID NO: 113. In some aspects, the nucleic acid molecule encoding the IL-12α comprises a nucleotide sequence that is at least 98%, at least 99%, or 100% identical to the sequence set forth in SEQ ID NO: 114.

The present disclosure further provides an isolated polynucleotide comprising a first nucleic acid molecule and a second nucleic acid molecule, wherein the first nucleic acid molecule encodes a beta subunit of an IL-12 protein ("IL-12β") and comprises a nucleotide sequence that is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, or SEQ ID NO: 75; and the second nucleic acid molecule encodes an alpha subunit of an IL-12 protein ("IL-12α") and comprises a nucleotide sequence that is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, or SEQ ID NO: 125.

In some aspects, the first nucleic acid molecule comprises a nucleotide sequence that is at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 51 and/or the second nucleic acid molecule comprises a nucleotide sequence that is at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 101. In some aspects, the first nucleic acid molecule comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 52 and/or the second nucleic acid molecule comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 102. In some aspects, the first nucleic acid molecule comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 53 and/or the second nucleic acid molecule comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 103. In some aspects, the first nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 54 and/or the second nucleic acid molecule comprises a nucleotide sequence that is at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 104. In some aspects, the first nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 55 and/or the second nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 105. In some aspects, the first nucleic acid molecule comprises a nucleotide sequence that is at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 56 and/or the second nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 106. In some aspects, the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 57 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 107. In some aspects, the first nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 58 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 108. In some aspects, the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 59 and/or the second nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 109. In some aspects, the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 65, 69, or 74 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 115, 119, or 124. In some aspects, the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 66, 70, or 75 and/or the second nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 116, 120, or 125. In some aspects, the first nucleic acid molecule comprises a nucleotide sequence that is at least 97%, at least 98%, at least 99%, or 100% identical to the sequence set forth in SEQ ID NO: 62 and/or the second nucleic acid molecule comprises a nucleotide sequence that is at least 98%, at least 99%, or 100% identical to the sequence set forth in SEQ ID NO: 112. In some aspects, the first nucleic acid molecule comprises a nucleotide sequence that is at least 99% or 100% identical to the sequence set forth in SEQ ID NO: 63 and/or the second nucleic acid molecule comprises a nucleotide sequence that is at least 98%, at least 99%, or 100% identical to the sequence set forth in SEQ ID NO: 113. In some aspects, the first nucleic acid molecule comprises a nucleotide sequence that is at least 98%, at least 99%, or 100% identical to the sequence set forth in SEQ ID NO: 64 and/or the second nucleic acid molecule comprises a nucleotide sequence that is at least 98%, at least 99%, or 100% identical to the sequence set forth in SEQ ID NO: 114.

In some aspects, an isolated polynucleotide disclosed herein further comprises a third nucleic acid molecule encoding a linker that joins the first nucleic acid molecule and the second nucleic acid molecule. In certain aspects, the linker comprises an amino acid linker of at least about 2, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 amino acids. In some aspects, the linker comprises a (GS) linker. In some aspects, the (GS) linker has a formula of (Gly3 Ser)n or S(Gly3 Ser)n, wherein n is a positive integer selected from the group consisting of 1, 2, 3, 4, 5, 6, 7, 8, 9, 10, 11, 12, 13, 14, 15, 16, 17, 18, 19, 20, 30, 40, 50, 60, 70, 80, or 100. In some aspects, the (Gly3Ser)n linker is (Gly3Ser)3 or (Gly3Ser)4. In certain aspects, the third nucleic acid molecule encoding the linker comprises the sequence set forth in any one of SEQ ID NOs: 168 to 170.

In some aspects, an isolated polynucleotide of the present disclosure further comprises an additional nucleic acid molecule encoding a half-life extending moiety. In certain aspects, the half-life extending moiety comprises a Fc, an albumin or a fragment thereof, an albumin binding moiety, a PAS, a HAP, a transferrin or a fragment thereof, a XTEN, or any combinations thereof.

In some aspects, an isolated polynucleotide described herein further comprises an additional nucleic acid molecule encoding a leader sequence. In certain aspects, the additional nucleic acid molecule encoding a leader sequence comprises any one of the sequence set forth in SEQ ID NO: 26 to 50.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 26; (b) the second nucleic acid molecule comprises the sequence set forth in SEQ ID NO: 51; (c) the third nucleic acid molecule comprises the sequence set forth in SEQ ID NO: 76; (d) the fourth nucleic acid molecule comprises the sequence set forth in SEQ ID NO: 101; (e) the fifth nucleic acid molecule comprises the sequence set forth in SEQ ID NO: 126; and (f) the sixth nucleic acid molecule comprise the sequence set forth in SEQ ID NO: 147.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 27; (b) the second nucleic acid molecule comprises the sequence set forth in SEQ ID NO: 52; (c) the third nucleic acid molecule comprises the sequence set forth in SEQ ID NO: 77; (d) the fourth nucleic acid molecule comprises the sequence set forth in SEQ ID NO: 102; (e) the fifth nucleic acid molecule comprises the sequence set forth in SEQ ID NO: 127; and (f) the sixth nucleic acid molecule comprise the sequence set forth in SEQ ID NO: 148.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 28; (b) the second nucleic acid molecule comprises the sequence set forth in SEQ ID NO: 53; (c) the third nucleic acid molecule comprises the sequence set forth in SEQ ID NO: 78; (d) the fourth nucleic acid molecule comprises the sequence set forth in SEQ ID NO: 103; (e) the fifth nucleic acid molecule comprises the sequence set forth in SEQ ID NO: 128; and (f) the sixth nucleic acid molecule comprise the sequence set forth in SEQ ID NO: 149.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 29; (b) the second nucleic acid molecule comprises the sequence set forth in SEQ ID NO: 54; (c) the third nucleic acid molecule comprises the sequence set forth in SEQ ID NO: 79; (d) the fourth nucleic acid molecule comprises the sequence set forth in SEQ ID NO: 104; (e) the fifth nucleic acid molecule comprises the sequence set forth in SEQ ID NO: 129; and (f) the sixth nucleic acid molecule comprise the sequence set forth in SEQ ID NO: 150.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 30; (b) the second nucleic acid molecule comprises the sequence set forth in SEQ ID NO: 55; (c) the third nucleic acid molecule comprises the sequence set forth in SEQ ID NO: 80; (d) the fourth nucleic acid molecule comprises the sequence set forth in SEQ ID NO: 105; (e) the fifth nucleic acid molecule comprises the sequence set forth in SEQ ID NO: 130; and (f) the sixth nucleic acid molecule comprise the sequence set forth in SEQ ID NO: 151.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 31; (b) the second nucleic acid molecule comprises the sequence set forth in SEQ ID NO: 56; (c) the third nucleic acid molecule comprises the sequence set forth in SEQ ID NO: 81; (d) the fourth nucleic acid molecule comprises the sequence set forth in SEQ ID NO: 106; (e) the fifth nucleic acid molecule comprises the sequence set forth in SEQ ID NO: 131; and (f) the sixth nucleic acid molecule comprise the sequence set forth in SEQ ID NO: 152.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 32; (b) the second nucleic acid molecule comprises the sequence set forth in SEQ ID NO: 57; (c) the third nucleic acid molecule comprises the sequence set forth in SEQ ID NO: 82; (d) the fourth nucleic acid molecule comprises the sequence set forth in SEQ ID NO: 107; (e) the fifth nucleic acid molecule comprises the sequence set forth in SEQ ID NO: 132; and (f) the sixth nucleic acid molecule comprise the sequence set forth in SEQ ID NO: 153.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 33; (b) the second nucleic acid molecule comprises the sequence set forth in SEQ ID NO: 58; (c) the third nucleic acid molecule comprises the sequence set forth in SEQ ID NO: 83; (d) the fourth nucleic acid molecule comprises the sequence set forth in SEQ ID NO: 108; (e) the fifth nucleic acid molecule comprises the sequence set forth in SEQ ID NO: 133; and (f) the sixth nucleic acid molecule comprise the sequence set forth in SEQ ID NO: 154.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 34; (b) the second nucleic acid molecule comprises the sequence set forth in SEQ ID NO: 59; (c) the third nucleic acid molecule comprises the sequence set forth in SEQ ID NO: 84; (d) the fourth nucleic acid molecule comprises the sequence set forth in SEQ ID NO: 109; (e) the fifth nucleic acid molecule comprises the sequence set forth in SEQ ID NO: 134; and (f) the sixth nucleic acid molecule comprise the sequence set forth in SEQ ID NO: 155.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 37; (b) the second nucleic acid molecule comprises the sequence set forth in SEQ ID NO: 62; (c) the third nucleic acid molecule comprises the sequence set forth in SEQ ID NO: 87; (d) the fourth nucleic acid molecule comprises the sequence set forth in SEQ ID NO: 112; (e) the fifth nucleic acid molecule comprises the sequence set forth in SEQ ID NO: 137; and (f) the sixth nucleic acid molecule comprise the sequence set forth in SEQ ID NO: 158.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 38; (b) the second nucleic acid molecule comprises the sequence set forth in SEQ ID NO: 63; (c) the third nucleic acid molecule comprises the sequence set forth in SEQ ID NO: 88; (d) the fourth nucleic acid molecule comprises the sequence set forth in SEQ ID NO: 113; (e) the fifth nucleic acid molecule comprises the sequence set forth in SEQ ID NO: 138; and (f) the sixth nucleic acid molecule comprise the sequence set forth in SEQ ID NO: 159.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 39; (b) the second nucleic acid molecule comprises the sequence set forth in SEQ ID NO: 64; (c) the third nucleic acid molecule comprises the sequence set forth in SEQ ID NO: 89; (d) the fourth nucleic acid molecule comprises the sequence set forth in SEQ ID NO: 114; (e) the fifth nucleic acid molecule comprises the sequence set forth in SEQ ID NO: 139; and (f) the sixth nucleic acid molecule comprise the sequence set forth in SEQ ID NO: 160.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 44; (b) the second nucleic acid molecule comprises the sequence set forth in SEQ ID NO: 69; (c) the third nucleic acid molecule comprises the sequence set forth in SEQ ID NO: 94; (d) the fourth nucleic acid molecule comprises the sequence set forth in SEQ ID NO: 119; (e) the fifth nucleic acid molecule comprises the sequence set forth in SEQ ID NO: 140; and (f) the sixth nucleic acid molecule comprise the sequence set forth in SEQ ID NO: 161.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 45; (b) the second nucleic acid molecule comprises the sequence set forth in SEQ ID NO: 70; (c) the third nucleic acid molecule comprises the sequence set forth in SEQ ID NO: 95; (d) the fourth nucleic acid molecule comprises the sequence set forth in SEQ ID NO: 120; (e) the fifth nucleic acid molecule comprises the sequence set forth in SEQ ID NO: 141; and (f) the sixth nucleic acid molecule comprise the sequence set forth in SEQ ID NO: 162.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 46; (b) the second nucleic acid molecule comprises the sequence set forth in SEQ ID NO: 71; (c) the third nucleic acid molecule comprises the sequence set forth in SEQ ID NO: 96; (d) the fourth nucleic acid molecule comprises the sequence set forth in SEQ ID NO: 121; (e) the fifth nucleic acid molecule comprises the sequence set forth in SEQ ID NO: 142; and (f) the sixth nucleic acid molecule comprise the sequence set forth in SEQ ID NO: 163.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 47; (b) the second nucleic acid molecule comprises the sequence set forth in SEQ ID NO: 72; (c) the third nucleic acid molecule comprises the sequence set forth in SEQ ID NO: 97; (d) the fourth nucleic acid molecule comprises the sequence set forth in SEQ ID NO: 122; (e) the fifth nucleic acid molecule comprises the sequence set forth in SEQ ID NO: 143; and (f) the sixth nucleic acid molecule comprise the sequence set forth in SEQ ID NO: 164.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, and (vi) a sixth nucleic acid molecule encoding a human serum albumin, wherein: (a) the first nucleic acid molecule comprises the sequence set forth in SEQ ID NO: 36; (b) the second nucleic acid molecule comprises the sequence set forth in SEQ ID NO: 61; (c) the third nucleic acid molecule comprises the sequence set forth in SEQ ID NO: 86; (d) the fourth nucleic acid molecule comprises the sequence set forth in SEQ ID NO: 111; (e) the fifth nucleic acid molecule comprises the sequence set forth in SEQ ID NO: 136; and (f) the sixth nucleic acid molecule comprise the sequence set forth in SEQ ID NO: 157.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, (vi) a sixth nucleic acid molecule encoding a human serum albumin, (vii) a seventh nucleic acid molecule encoding a third linker; and (viii) an eighth nucleic acid molecule encoding a lumican protein, wherein: (a) the first nucleic acid molecule comprises the sequence set forth in SEQ ID NO: 48; (b) the second nucleic acid molecule comprises the sequence set forth in SEQ ID NO: 73; (c) the third nucleic acid molecule comprises the sequence set forth in SEQ ID NO: 98; (d) the fourth nucleic acid molecule comprises the sequence set forth in SEQ ID NO: 123; (e) the fifth nucleic acid molecule comprises the sequence set forth in SEQ ID NO: 144; (f) the sixth nucleic acid molecule comprises the sequence set forth in SEQ ID NO: 165; (g) the seventh nucleic acid molecule comprises the sequence set forth in SEQ ID NO: 168; and (h) the eighth nucleic acid molecule comprises the sequence set forth in SEQ ID NO: 171.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, (vi) a sixth nucleic acid molecule encoding a human serum albumin, (vii) a seventh nucleic acid molecule encoding a third linker; and (viii) an eighth nucleic acid molecule encoding a lumican protein, wherein: (a) the first nucleic acid molecule comprises the sequence set forth in SEQ ID NO: 49; (b) the second nucleic acid molecule comprises the sequence set forth in SEQ ID NO: 74; (c) the third nucleic acid molecule comprises the sequence set forth in SEQ ID NO: 99; (d) the fourth nucleic acid molecule comprises the sequence set forth in SEQ ID NO: 124; (e) the fifth nucleic acid molecule comprises the sequence set forth in SEQ ID NO: 145; (f) the sixth nucleic acid molecule comprises the sequence set forth in SEQ ID NO: 166; (g) the seventh nucleic acid molecule comprises the sequence set forth in SEQ ID NO: 169; and (h) the eighth nucleic acid molecule comprises the sequence set forth in SEQ ID NO: 172.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, (iv) a fourth nucleic acid molecule encoding an alpha subunit of an IL-12 protein ("IL-12α"), (v) a fifth nucleic acid molecule encoding a second linker, (vi) a sixth nucleic acid molecule encoding a human serum albumin, (vii) a seventh nucleic acid molecule encoding a third linker; and (viii) an eighth nucleic acid molecule encoding a lumican protein, wherein: (a) the first nucleic acid molecule comprises the sequence set forth in SEQ ID NO: 50; (b) the second nucleic acid molecule comprises the sequence set forth in SEQ ID NO: 75; (c) the third nucleic acid molecule comprises the sequence set forth in SEQ ID NO: 100; (d) the fourth nucleic acid molecule comprises the sequence set forth in SEQ ID NO: 125; (e) the fifth nucleic acid molecule comprises the sequence set forth in SEQ ID NO: 146; (f) the sixth nucleic acid molecule comprises the sequence set forth in SEQ ID NO: 167; (g) the seventh nucleic acid molecule comprises the sequence set forth in SEQ ID NO: 170; and (h) the eighth nucleic acid molecule comprises the sequence set forth in SEQ ID NO: 173.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, and (iv) a fourth nucleic acid molecule encoding an alpha subunit of an IL-12 protein ("IL-12α"), wherein: (a) the first nucleic acid molecule comprises the sequence set forth in SEQ ID NO: 40; (b) the second nucleic acid molecule comprises the sequence set forth in SEQ ID NO: 65; (c) the third nucleic acid molecule comprises the sequence set forth in SEQ ID NO: 90; and (d) the fourth nucleic acid molecule comprises the sequence set forth in SEQ ID NO: 115.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, and (iv) a fourth nucleic acid molecule encoding an alpha subunit of an IL-12 protein ("IL-12α"), wherein: (a) the first nucleic acid molecule comprises the sequence set forth in SEQ ID NO: 41; (b) the second nucleic acid molecule comprises the sequence set forth in SEQ ID NO: 66; (c) the third nucleic acid molecule comprises the sequence set forth in SEQ ID NO: 91; and (d) the fourth nucleic acid molecule comprises the sequence set forth in SEQ ID NO: 116.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, and (iv) a fourth nucleic acid molecule encoding an alpha subunit of an IL-12 protein ("IL-12α"), wherein: (a) the first nucleic acid molecule comprises the sequence set forth in SEQ ID NO: 42; (b) the second nucleic acid molecule comprises the sequence set forth in SEQ ID NO: 67; (c) the third nucleic acid molecule comprises the sequence set forth in SEQ ID NO: 92; and (d) the fourth nucleic acid molecule comprises the sequence set forth in SEQ ID NO: 117.

Provided herein is an isolated polynucleotide comprising (from 5' to 3') (i) a first nucleic acid molecule encoding a leader sequence, (ii) a second nucleic acid molecule encoding a beta subunit of an IL-12 protein ("IL-12β"), (iii) a third nucleic acid molecule encoding a first linker, and (iv) a fourth nucleic acid molecule encoding an alpha subunit of an IL-12 protein ("IL-12α"), wherein: (a) the first nucleic acid molecule comprises the sequence set forth in SEQ ID NO: 43; (b) the second nucleic acid molecule comprises the sequence set forth in SEQ ID NO: 68; (c) the third nucleic acid molecule comprises the sequence set forth in SEQ ID NO: 93; and (d) the fourth nucleic acid molecule comprises the sequence set forth in SEQ ID NO: 118.

In some aspects, an isolated polynucleotide described herein further comprises a 5'-cap. In certain aspects, the 5'-cap is selected from the group consisting of $m_2^{7,2'-O}$ $Gpp_s pGRNA$, $m^7GpppG$, $m^7Gppppm^7G$, $m_2^{(7,3'-O)}GpppG$, $m_2^{(7,2'-O)}GppspG(D1)$, $m_2^{(7,2'-O)}GppspG(D2)$, $m_2^{7,3'-O}Gppp$ $(m_1^{2'-O)}ApG$, ($m^7G$-3' mppp-G; which can equivalently be designated 3' O-Me-m7G(5')ppp(5')G), N7,2'-O-dimethyl-guanosine-5'-triphosphate-5'-guanosine, $m^7Gm$-ppp-G, N7-(4-chlorophenoxyethyl)-G(5')ppp(5')G, N7-(4-chlorophenoxyethyl)-$m^{3'-O}G$(5')ppp(5')G, 7mG(5')ppp(5')N,pN2p, 7mG(5')ppp(5')NlmpNp, 7mG(5')-ppp(5')NlmpN2 mp, m(7)Gpppm(3)(6,6,2')Apm(2')Apm(2')Cpm(2)(3,2')Up, inosine, N1-methyl-guanosine, 2' fluoro-guanosine, 7-deaza-guanosine, 8-oxo-guanosine, 2-amino-guanosine, LNA-guanosine, 2-azido-guanosine, N1-methylpseudouridine, m7G(5')ppp(5')(2'OMeA)pG, and combinations thereof.

In some aspects, an isolated polynucleotide of the present disclosure further comprises a regulatory element. In certain aspects, the regulatory element is selected from the group consisting of at least one translation enhancer element (TEE), a translation initiation sequence, at least one microRNA binding site or seed thereof, a 3' tailing region of linked nucleosides, an AU rich element (ARE), a post transcription control modulator, and combinations thereof.

In some aspects, an isolated polynucleotide described herein further comprises a 3' tailing region of linked nucleosides. In certain aspects, the 3' tailing region of linked nucleosides comprises a poly-A tail, a polyA-G quartet, or a stem loop sequence.

In some aspects, an isolated polynucleotide of the present disclosure comprises at least one modified nucleoside. In certain aspects, the at least one modified nucleoside is selected from the group consisting of 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, pseudo-uridine, inosine, α-thio-guanosine, 8-oxo-guanosine, 06-methyl-guanosine, 7-deaza-guanosine, N1-methyl adenosine, 2-amino-6-chloro-purine, N6-methyl-2-amino-purine, 6-chloro-purine, N6-methyl-adenosine, α-thio-adenosine, 8-azido-adenosine, 7-deaza-adenosine, pyrrolo-cytidine, 5-methyl-cytidine, N4-acetyl-cytidine, 5-methyl-uridine, 5-iodo-cytidine, and combinations thereof.

In some aspects, an isolated polynucleotide described herein is capable of self-replicating. In certain aspects, the polynucleotide is a self-amplifying replicon RNA. In some aspects, the self-amplifying replicon RNA is derived from an alphavirus. In certain aspects, the alphavirus comprises a Venezuela Equine Encephalitis virus, Semliki Forest virus, Sindbis virus, or combinations thereof.

Present disclosure further provides a vector comprising any of the isolated polynucleotides described herein.

Present disclosure also provides a lipid nanoparticle (LNP) comprising (i) any of the isolated polynucleotides described herein, and (ii) one or more types of lipids. In certain aspects, the one or more types of lipid comprises a cationic lipid. In some aspects, the lipid is an ionizable lipid. In some aspects, the lipid is a lipidoid, e.g., N1,N3,N5-tris (3-(didodecylamino)propyl)benzene-1,3,5-tricarboxamide (TT3). In some aspects, a LNP comprises 1,2-Dioleoyl-sn-glycero-3-phosphoethanolamine (DOPE), cholesterol, C14-PEG2000, or any combination thereof.

In some aspects, a LNP described herein has a diameter of about 30-500 nm. In certain aspects, the LNP has a diameter of about 50-400 nm. In some aspects, the LNP has a diameter of about 70-300 nm. In some aspects, the LNP has a diameter of about 100-200 nm. In some aspects, the LNP has a diameter of about 100-175 nm. In some aspects, the LNP has a diameter of about 100-160 nm.

In some aspects, the lipid and the isolated polynucleotide (e.g., modified RNA) have a mass ratio of about 1:2 to about 2:1. In some aspects, the lipid and the isolated polynucleotide (e.g., modified RNA) have a mass ratio of 1:2, 1:1.5, 1:1.2, 1:1.1, 1:1, 1.1:1, 1.2:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 10.5:1, 11:1, 11.5:1, 12:1, 12.5:1, 13:1, 13.5:1, 14:1, 14.5:1, or 15:1. In some aspects, the lipid and the isolated polynucleotide (e.g., modified RNA) have a mass ratio of about 10:1.

Provided herein is a pharmaceutical composition comprising any of the isolated polynucleotides, vectors, or LNPs described herein, and a pharmaceutically acceptable carrier. In certain aspects, the pharmaceutical composition is formulated for intratumoral, intrathecal, intramuscular, intravenous, subcutaneous, inhalation, intradermal, intralymphatic, intraocular, intraperitoneal, intrapleural, intraspinal, intravascular, nasal, percutaneous, sublingual, submucosal, transdermal, or transmucosal administration.

Provided herein is a cell comprising any of the isolated polynucleotides, vectors, or LNPs described herein. In some aspects, the cell is an in vitro cell, an ex vivo cell, or an in vivo cell.

Provided herein is a method of making a polynucleotide comprising enzymatically or chemically synthesizing any of the isolated polynucleotides described herein. Provided herein is a method of producing an IL-12 protein, comprising contacting a cell with any of the isolated polynucleotides, cells, or LNPs described herein. In certain aspects, the contacting occurs in vivo or ex vivo.

Present disclosure further provides a method of treating a disease or disorder in a subject in need thereof, comprising administering to the subject any of the isolated polynucleotides, vectors, LNPs, or pharmaceutical compositions described herein. In certain aspects, the disease or disorder comprises a cancer. In some aspects, the cancer comprises a melanoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine cancer, salivary gland carcinoma, kidney cancer, prostate cancer, vulval cancer, thyroid cancer, hepatic carcinoma, gastric cancer, head and neck cancer, or combinations thereof.

In some aspects, a method of treating a disease or disorder disclosed herein further comprises administering at least one additional therapeutic agent to the subject. In certain aspects, the at least one additional therapeutic agent comprises a chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the immune checkpoint inhibitor comprises an anti-PD-1 antibody, anti-PD-L1 antibody, anti-LAG-3 antibody, anti-CTLA-4 antibody, anti-GITR antibody, anti-TIM3 antibody, or any combination thereof.

BRIEF DESCRIPTION OF THE DRAWINGS/FIGURES

Figure 1B:
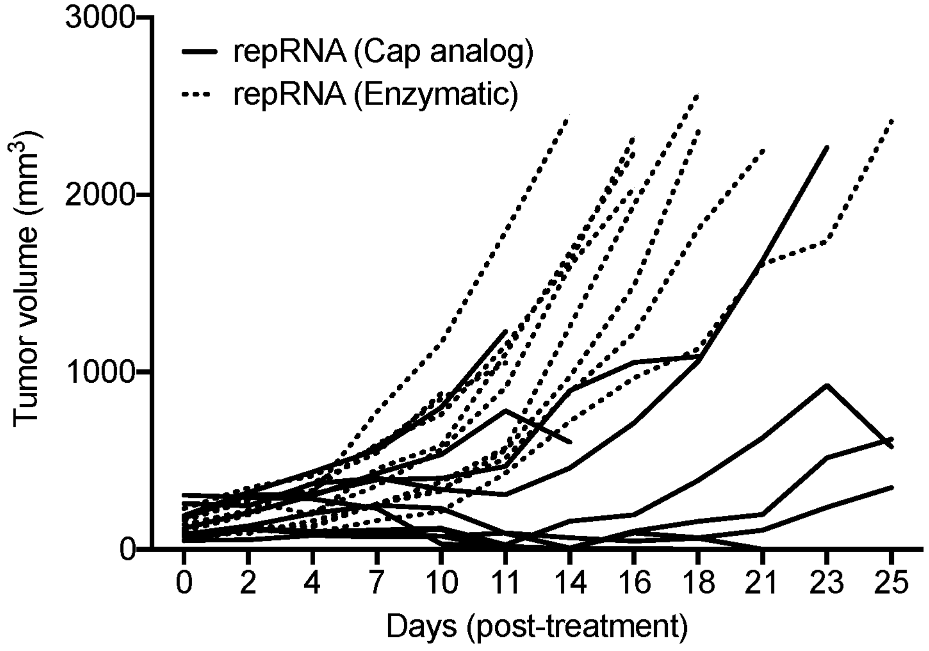

FIGS. 1A and 1B provide comparison of tumor volume in tumor-bearing mice that were treated with a single intratumoral administration of one of the following: (i) PBS (control; open circle); (ii) repRNA co-transcriptionally capped with a 5' cap analog (closed circle in FIG. 1A; solid line in FIG. 1B); and (iii) repRNA post-transcriptionally capped by enzymatic addition of 5' cap (closed square in FIG. 1A; dashed line in FIG. 1B). The tumor volumes were measured at various time points post-administration (x-axis). FIG. 1A shows the average tumor volume. FIG. 1B shows the tumor volume of the individual animals.

Figure 2:
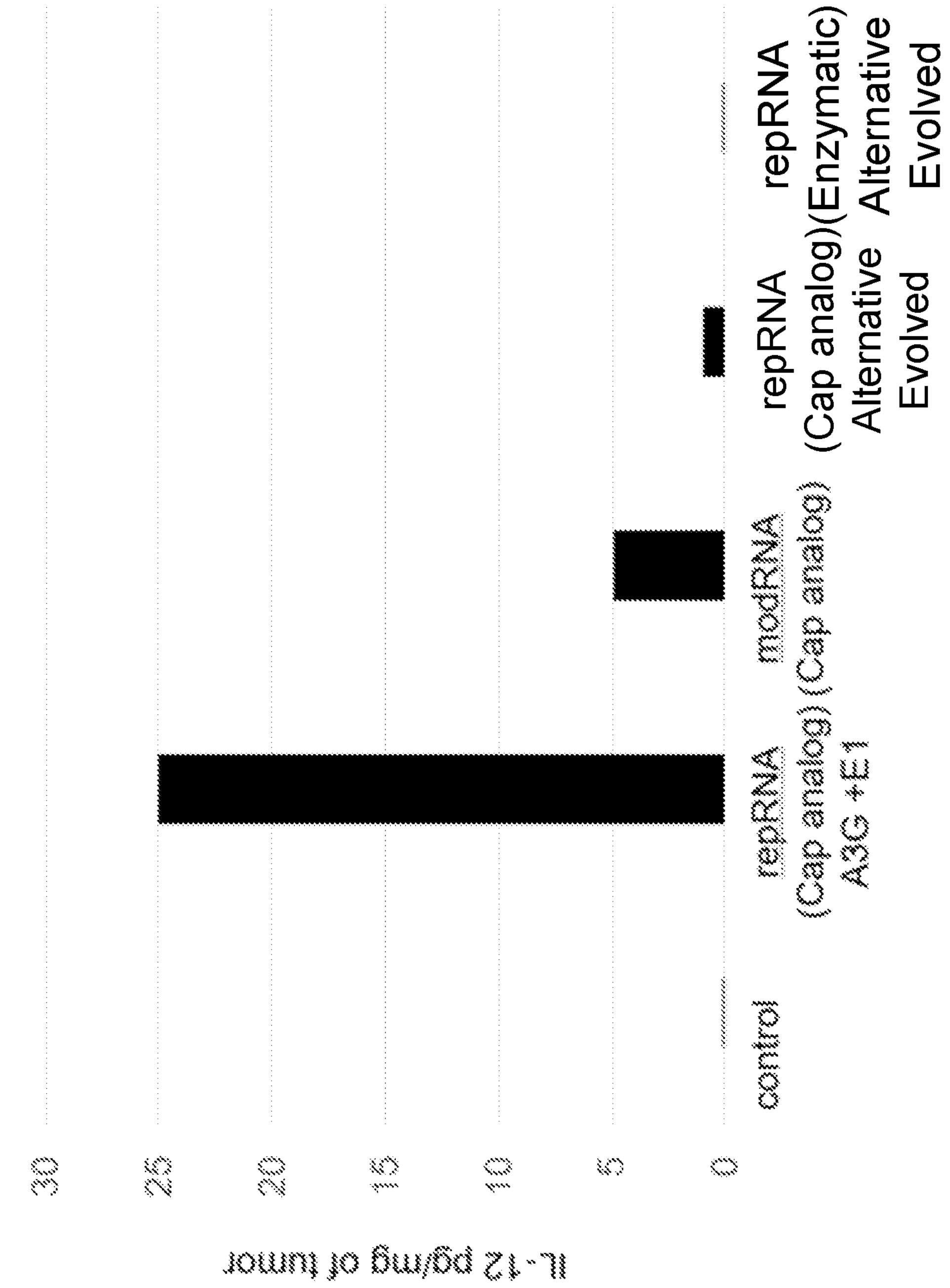

FIG. 2 provides a comparison of the IL-12 protein expression in the tumor of mice treated with one of the following: (i) PBS (control; 1st column from the left); (ii) repRNA made using the A3G+E1 vector and Cap Analog co-transcriptional capping (2nd column); (iii) modified mRNA (non-self-replicating) made using Cap Analog co-transcriptional capping (3rd column); (iv) repRNA made using the Alternative Evolved vector and Cap Analog co-transcriptional capping (4th column); and (v) repRNA made using the Alternative Evolved vector and enzymatic post-translational capping (last column).

Figure 3:
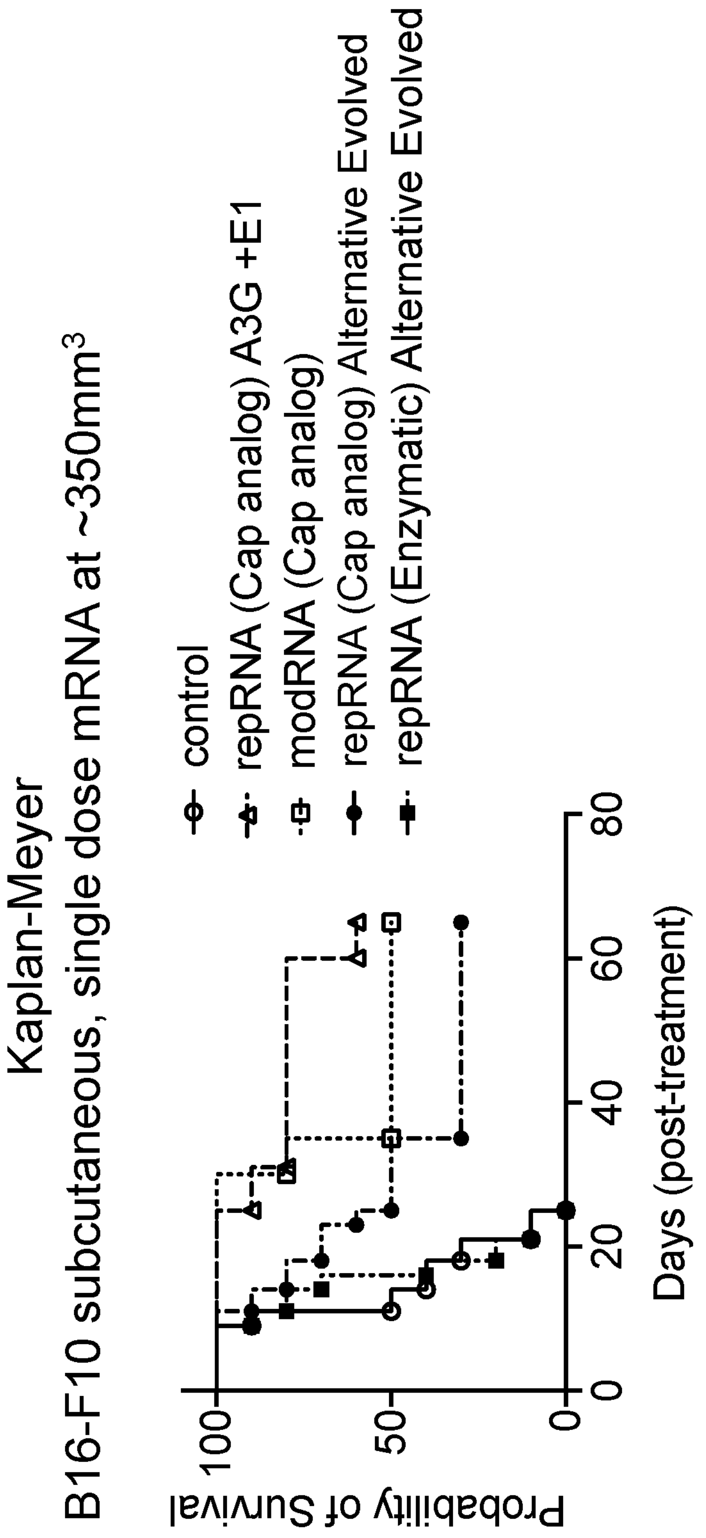

FIG. 3 provides a comparison of the Kaplan-Meyer survival analysis of tumor-bearing mice that were treated with a single intratumor administration of one of the following: (i) PBS (control; open circle); (ii) repRNA made using the A3G+E1 vector and Cap Analog co-transcriptional capping (open triangle); (iii) modified mRNA (non-self-replicating) made using Cap Analog co-transcriptional capping (open square); (iv) repRNA made using the Alternative Evolved vector and Cap Analog co-transcriptional capping (closed circle); and (v) repRNA made using the Alternative Evolved vector and enzymatic post-translational capping (closed square).

Figure 4A:
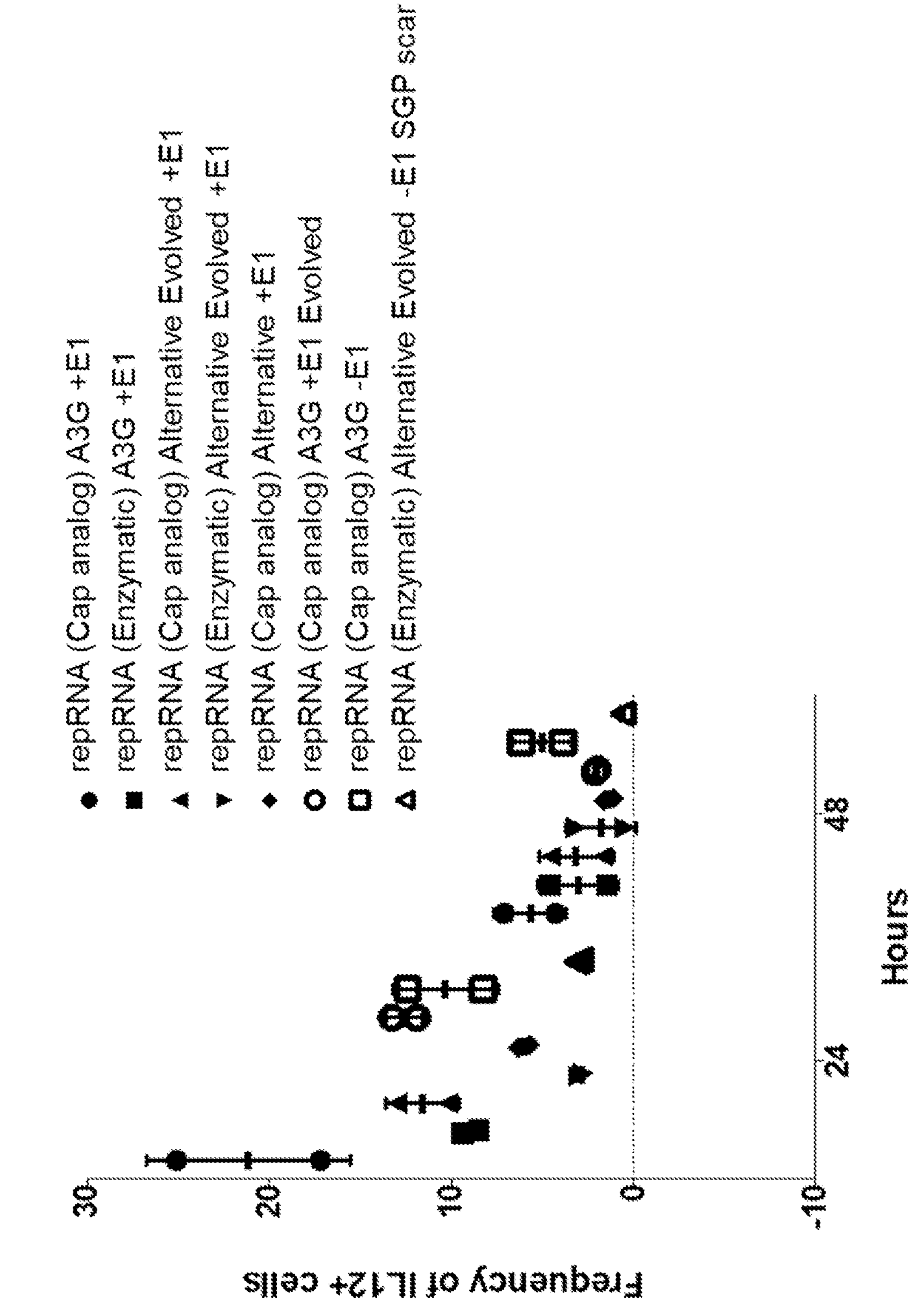
Figure 4B:
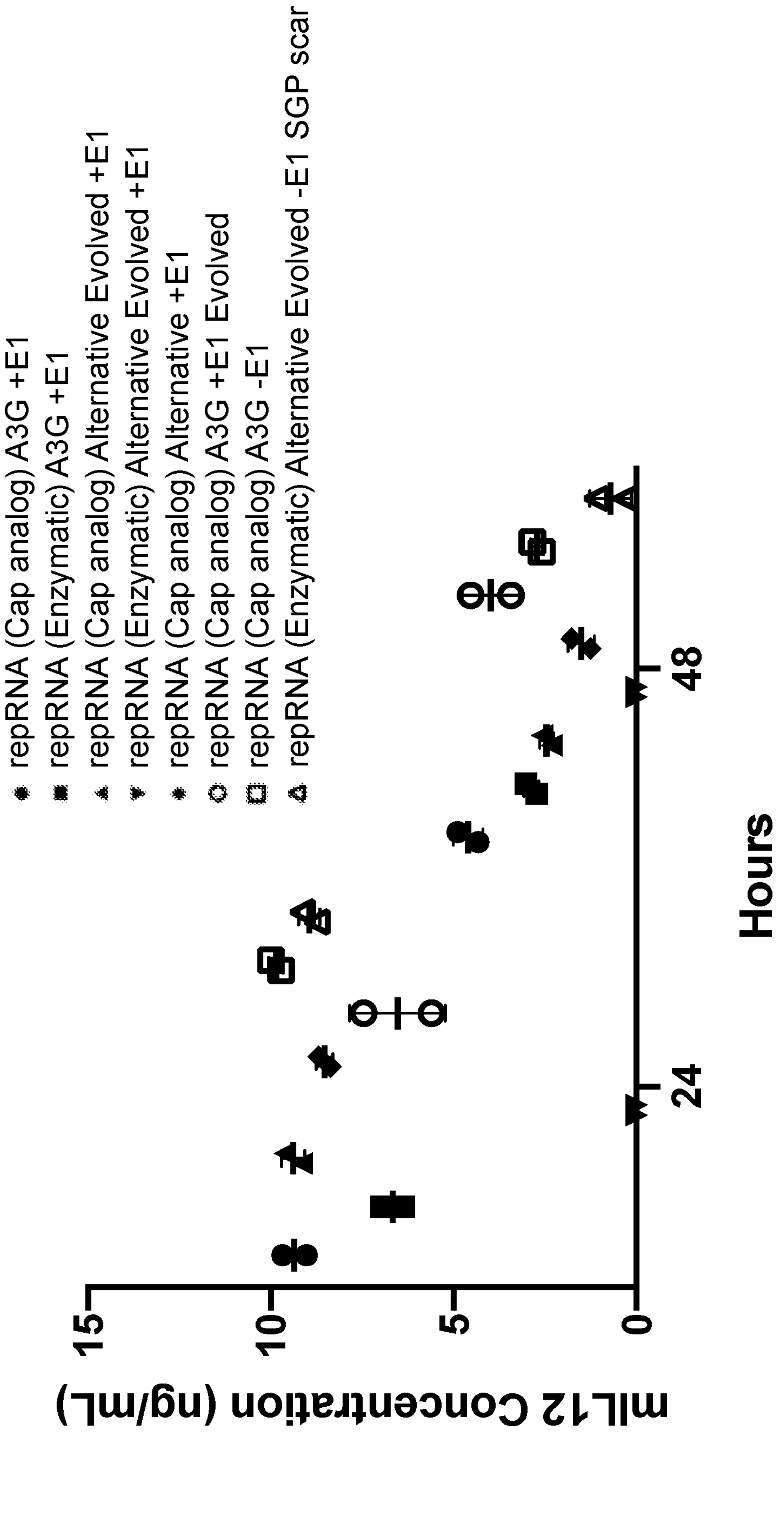

FIG. 4A provides a comparison of the in vitro transfection efficiency of the different RNA constructs described herein, as measured using FACS analysis. FIG. 4B provides a comparison of IL-12 protein concentration detected in the supernatant of cells transfected with the different RNA constructs described herein. In both FIGS. 4A and 4B, the RNA constructs tested included the following: (i) repRNA made using the A3G+E1 vector and Cap Analog co-transcriptional capping (closed circle); (ii) repRNA made using the A3G+E1 vector and enzymatic post-translational capping (closed square); (iii) repRNA made using the Alternative Evolved +E1 vector and Cap Analog co-transcriptional capping (closed triangle); (iv) repRNA made using the Alternative Evolved +E1 vector and enzymatic post-translational capping (closed inverted triangle); (v) repRNA made using the Alternative +E1 vector and Cap Analog co-transcriptional capping (diamond); (vi) repRNA made using the A3G +E1 Evolved vector and Cap Analog co-transcriptional capping (open circle); (vii) repRNA made using the A3G −E1 vector and Cap Analog co-transcriptional capping (open square); and (viii) repRNA made using the Alternative Evolved −E1 SGP scar end vector (open triangle). The transfection efficiency is shown as the frequency of IL-12+ cells observed in the different groups. The x-axis represents the hours post-transfection when the transfection efficiency was assessed.

Figure 5:
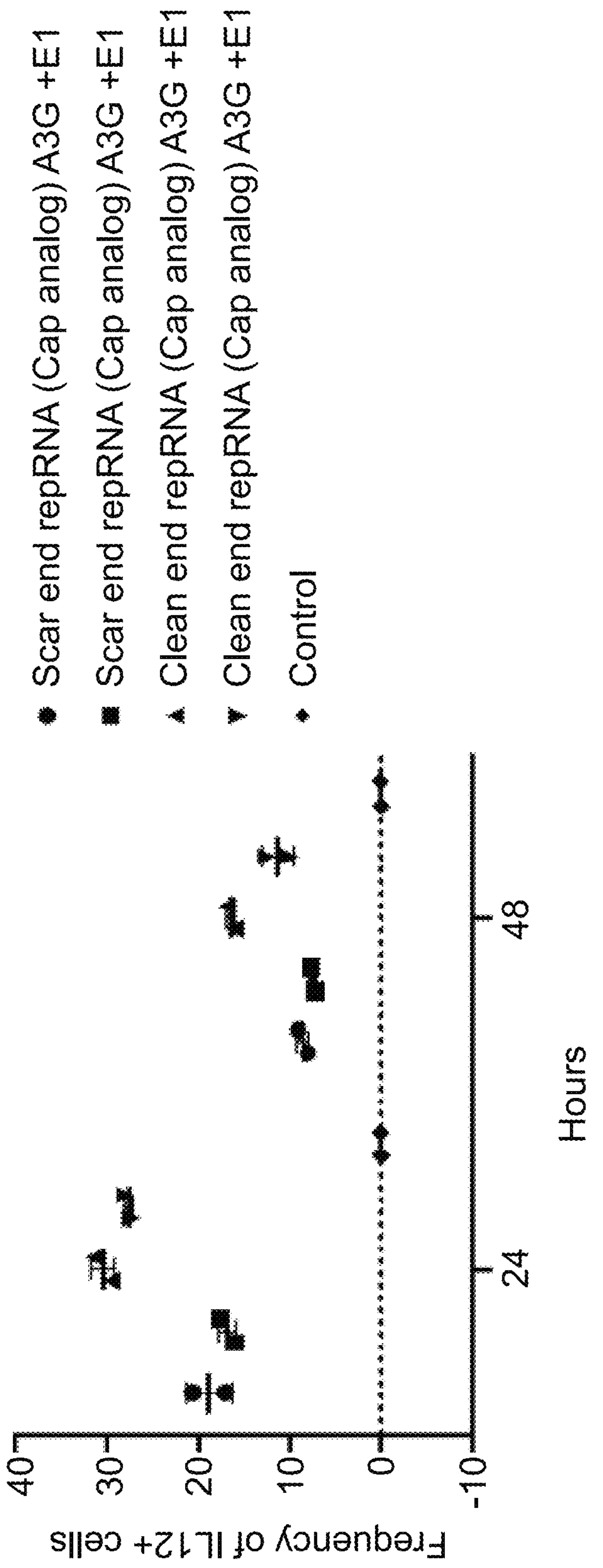

FIG. 5 provides a comparison of the in vitro transfection efficiency of the following RNA constructs, as measured using FACS analysis: (i) repRNA made using the Cap Analog co-transcriptional capping method and A3G +E1 vector with a 3'-end terminating with a restriction enzyme scar (circle); (ii) repRNA made using the Cap Analog (alternate source) method and A3G +E1 vector with a 3'-end terminating with a restriction enzyme scar (square); (iii) repRNA made using the Cap Analog co-transcriptional capping method and A3G +E1 vector with a 3'-end terminating with a clean polyA sequence (triangle); (iv) repRNA made using the Cap Analog (alternate source) method and A3G +E1 vector with a 3'-end terminating with a clean polyA sequence (inverted triangle). PBS treated cells were used as control (diamond). The transfection efficiency is shown as the frequency of IL-12+ cells observed in the different groups. The x-axis represents the hours post-transfection when the transfection efficiency was assessed.

Figure 6A:
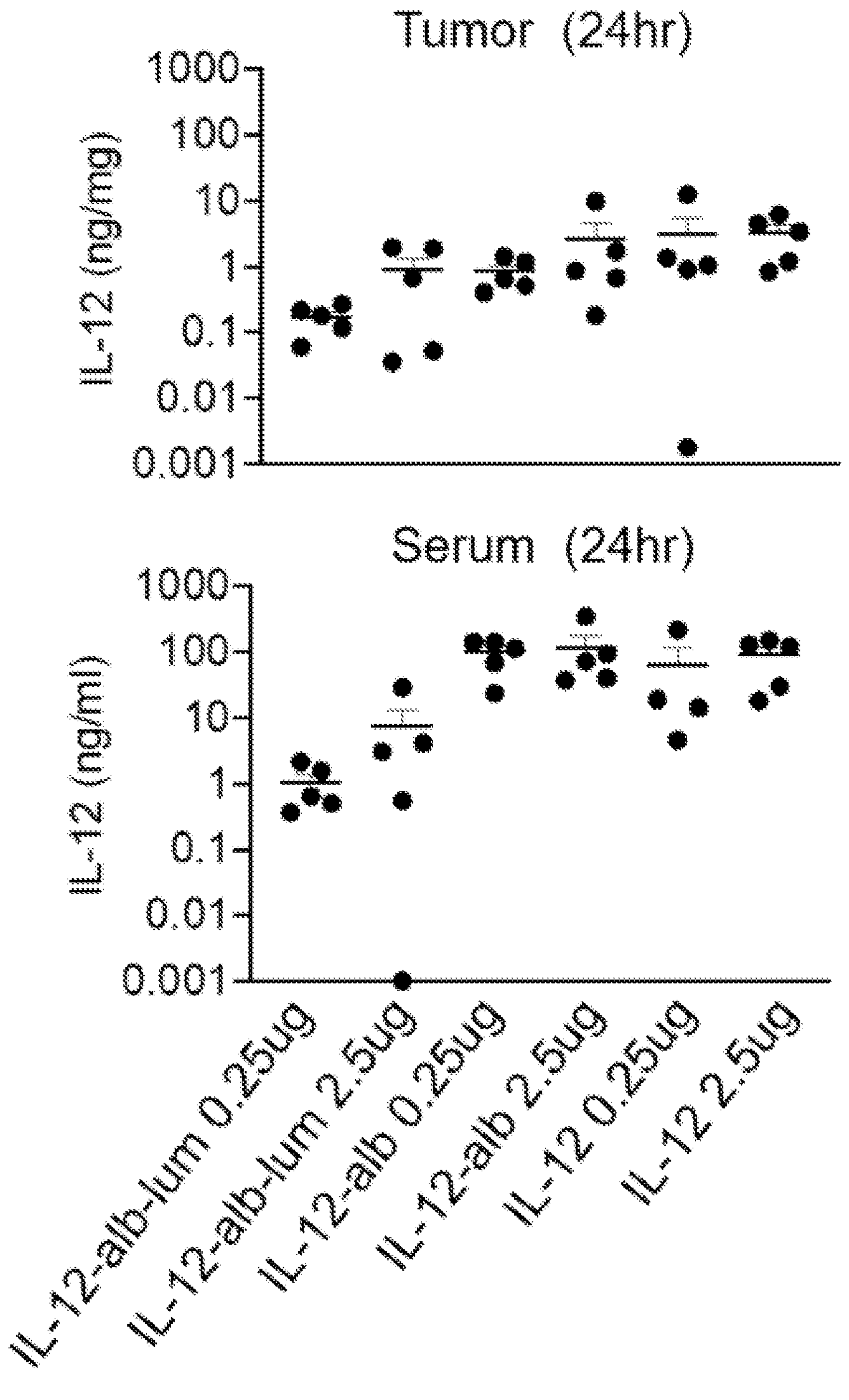
Figure 6B:
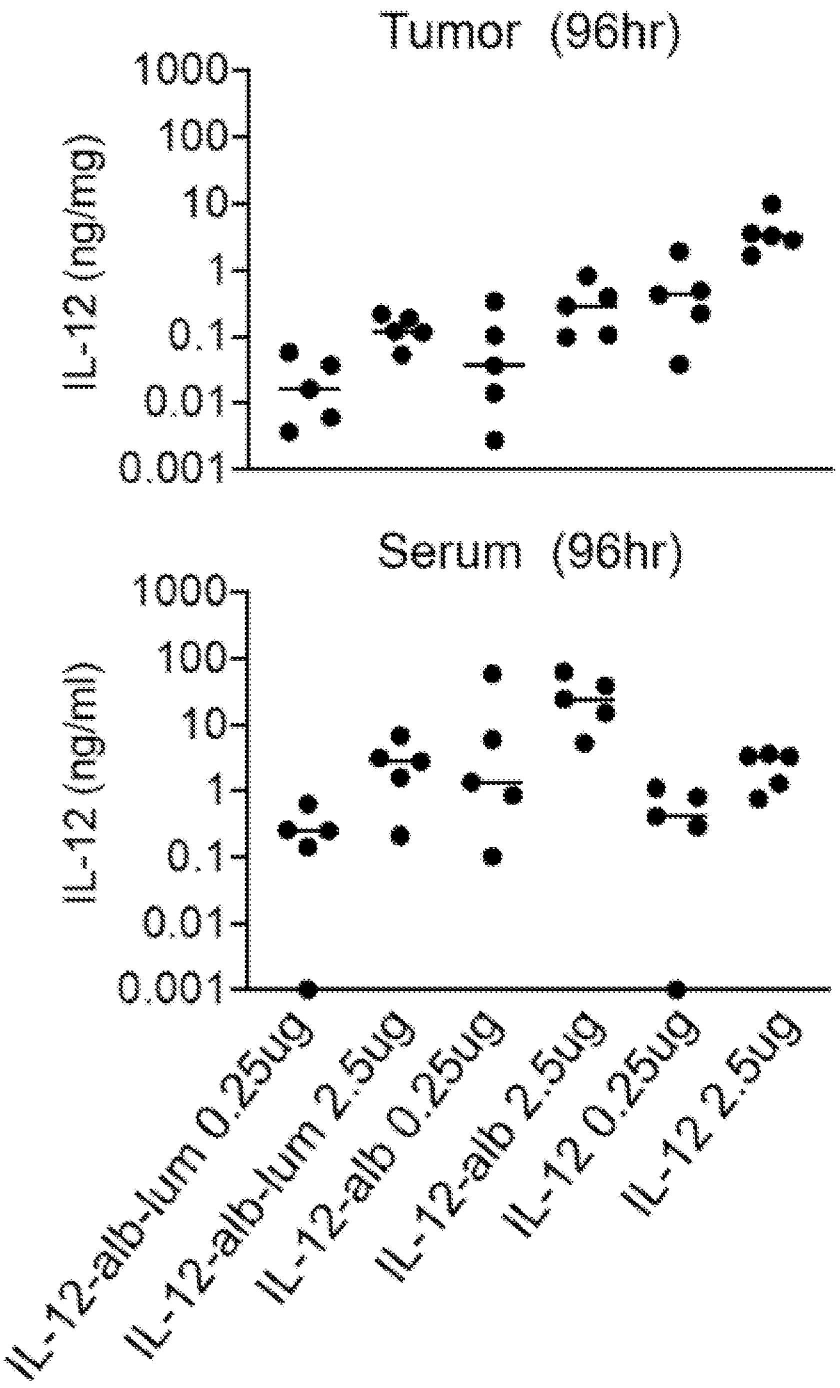

FIGS. 6A and 6B provide comparison of IL-12 protein concentration observed in tumor and serum of tumor-bearing mice treated with a single intratumoral administration of an RNA construct encoding one of the following mouse IL-12 proteins: (i) mIL-12 alone (“IL-12”); (ii) mIL-12 conjugated to albumin (“IL-12-alb”); and (iii) mIL-12 conjugated to albumin and lumican (“IL-12-alb-lum”). The different RNA constructs were administered to the animals at one of the two doses shown along the x-axis. FIG. 6A shows the IL-12 protein concentration in tumor (top graph) and serum (bottom graph) at 24 hours post-administration. FIG. 6B shows the IL-12 protein concentration in tumor (top graph) and serum (bottom graph) at 96 hours post-administration.

Figure 7A:
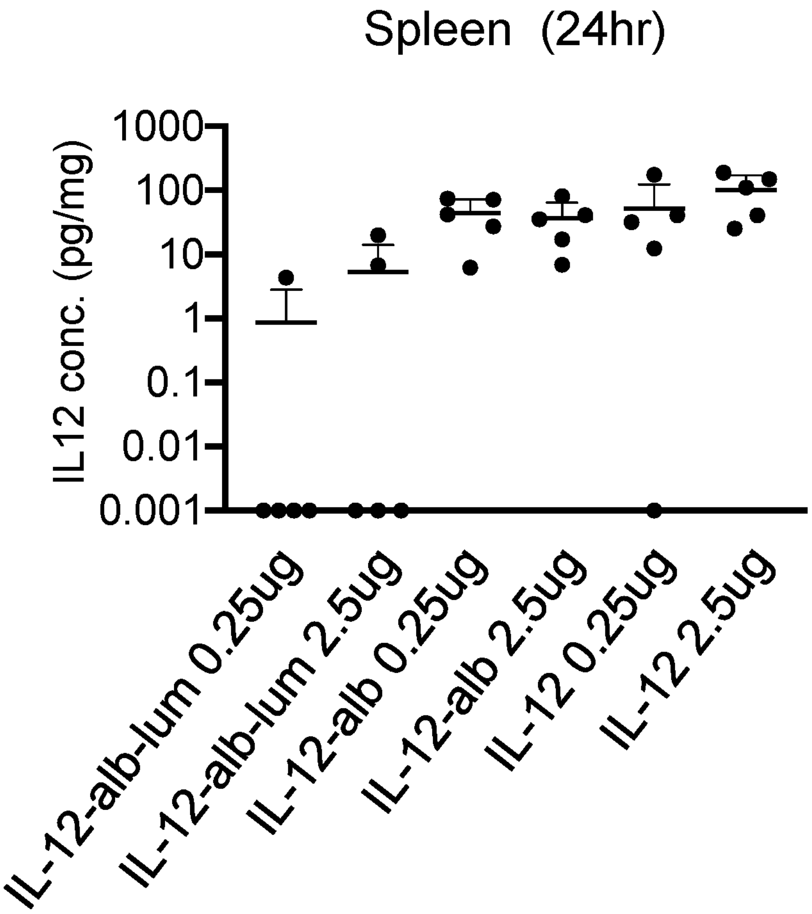
Figure 7B:
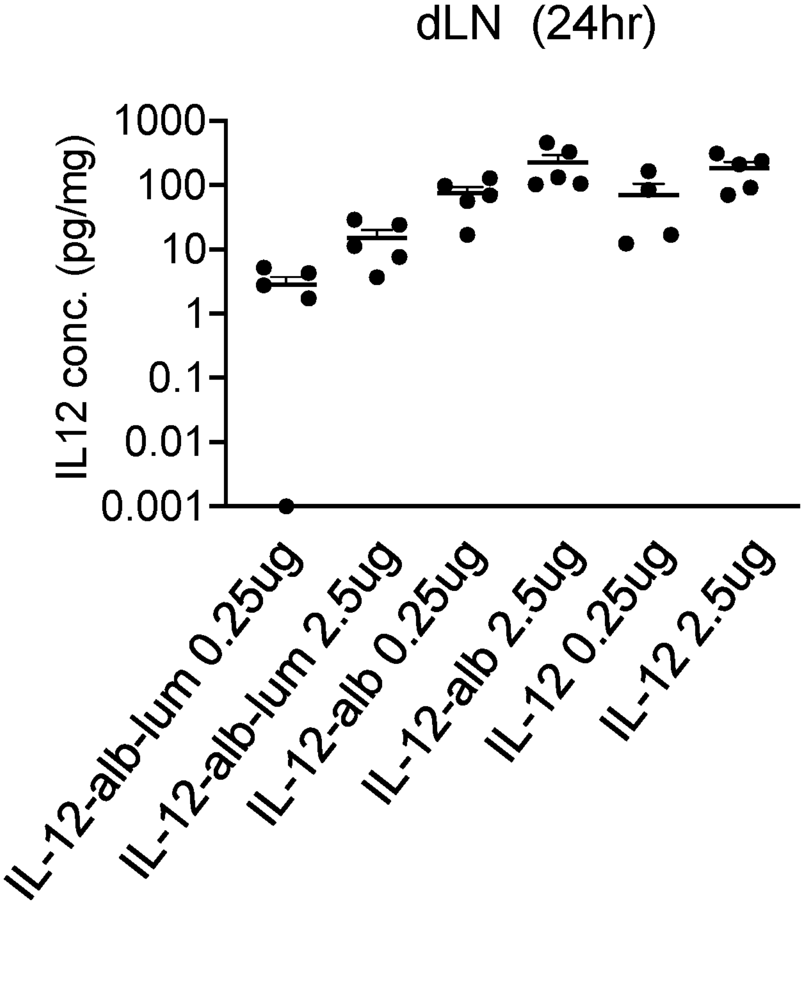
Figure 7C:
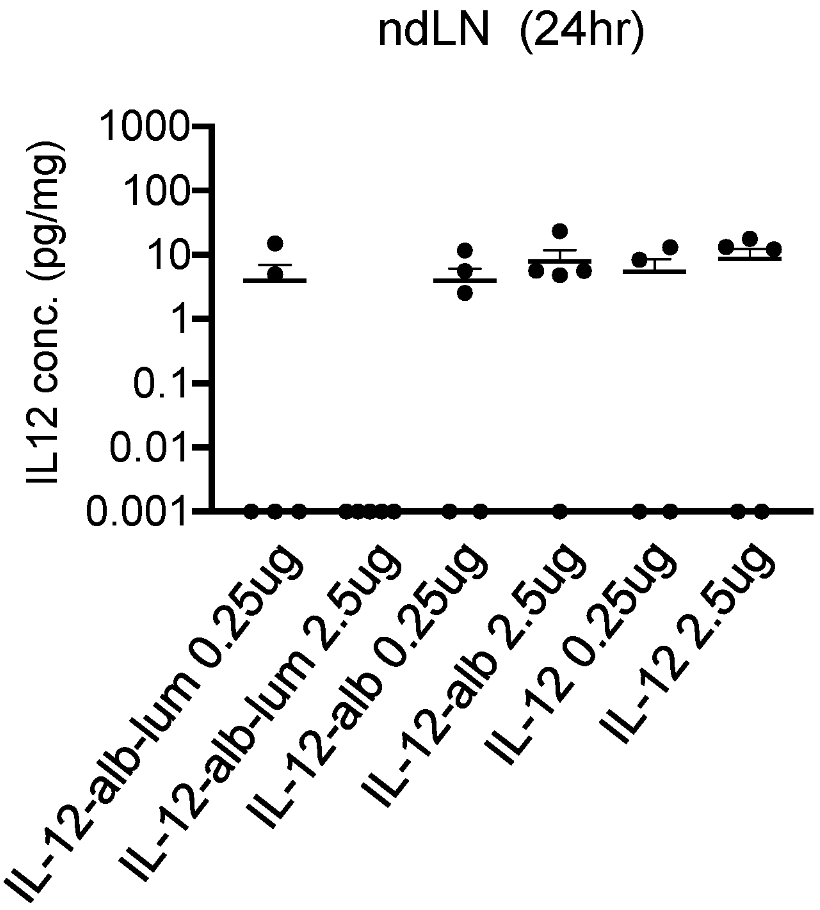

FIGS. 7A, 7B, and 7C provide comparison of IL-12 protein concentration observed in spleen, draining lymph nodes, and non-draining lymph nodes, respectively, of tumor-bearing mice at 24 hours after a single intratumoral administration of an RNA construct encoding one of the following mouse IL-12 proteins: (i) mIL-12 alone (“IL-12”); (ii) mIL-12 conjugated to albumin (“IL-12-alb”); and (iii) mIL-12 conjugated to albumin and lumican (“IL-12-alb-lum”). The different RNA constructs were administered to the animals at one of the two doses shown along the x-axis.

Figure 8A:
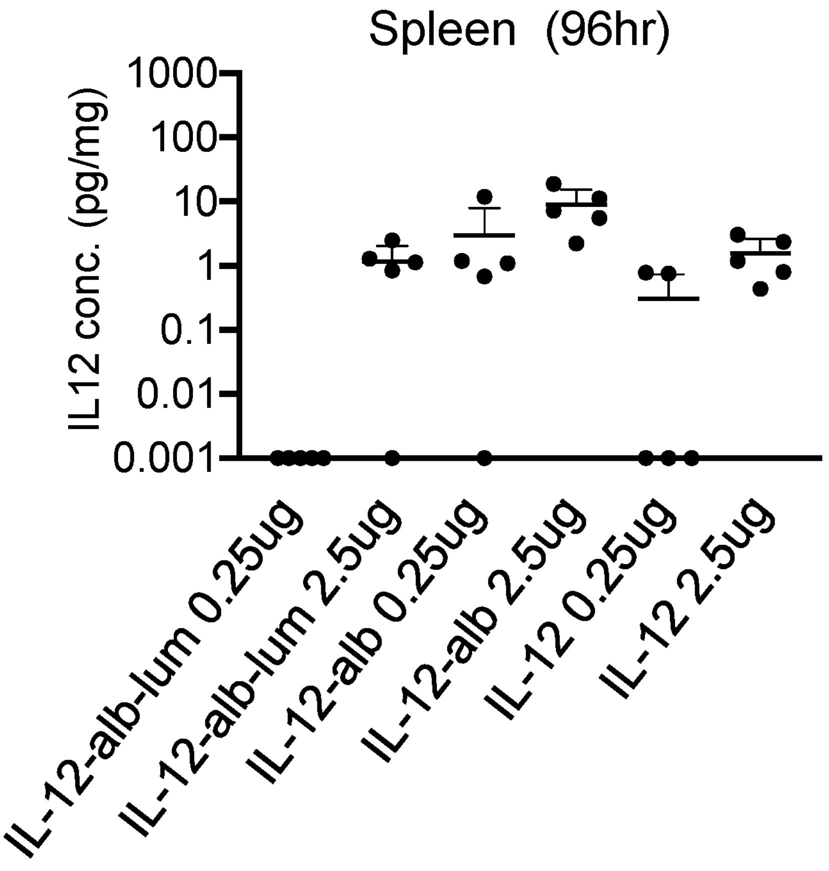
Figure 8B:
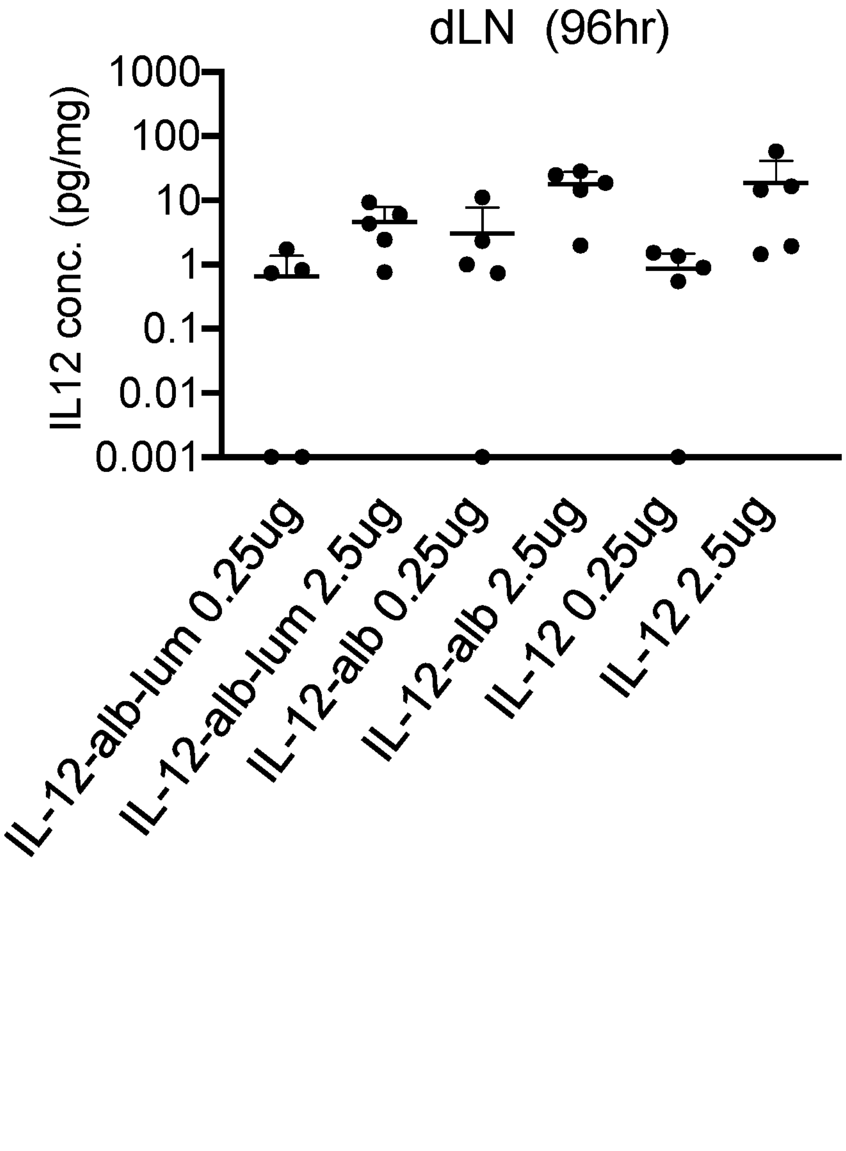
Figure 8C:
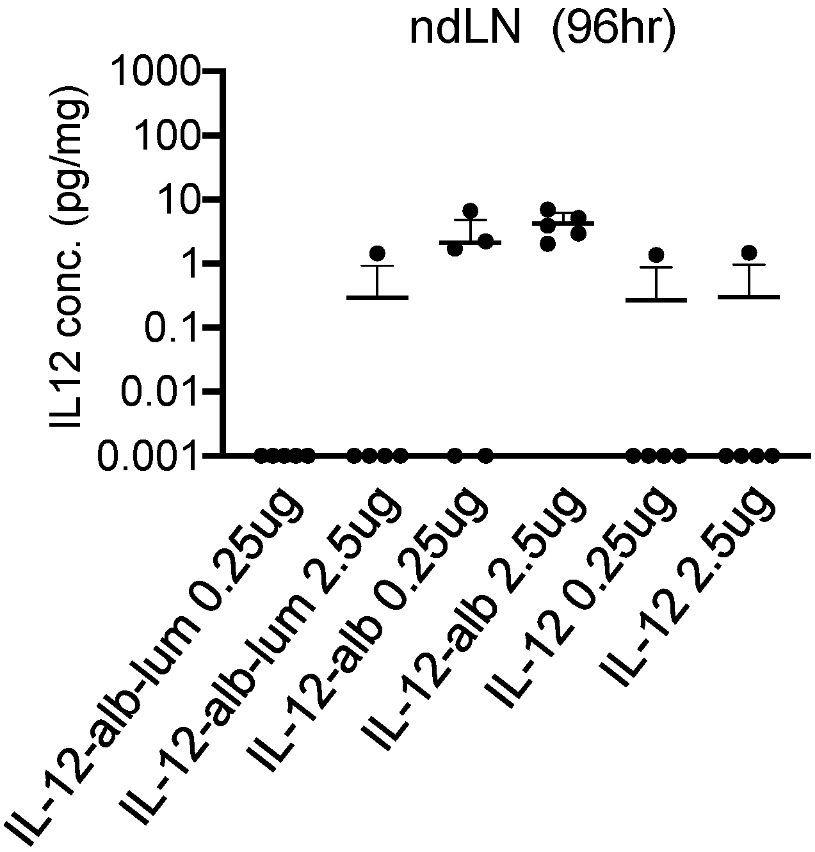

FIGS. 8A, 8B, and 8C provide comparison of IL-12 protein concentration observed in spleen, draining lymph nodes, and non-draining lymph nodes, respectively, of tumor-bearing mice at 96 hours after a single intratumoral administration of an RNA construct encoding one of the following mouse IL-12 proteins: (i) mIL-12 alone (“IL-12”); (ii) mIL-12 conjugated to albumin (“IL-12-alb”); and (iii) mIL-12 conjugated to albumin and lumican (“IL-12-alb-lum”). The different RNA constructs were administered to the animals at one of the two doses shown along the x-axis.

Figure 9A:
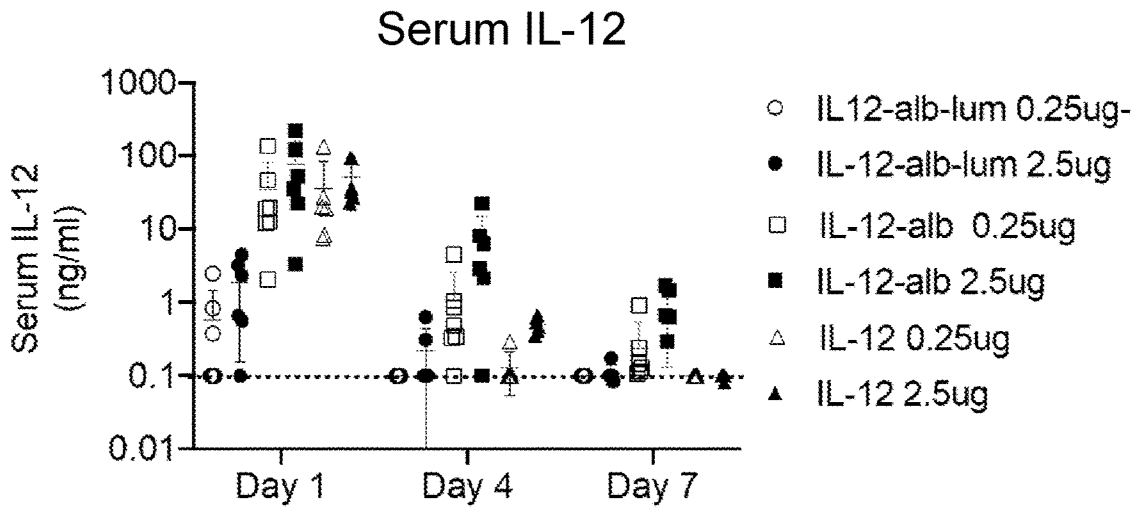
Figure 9B:
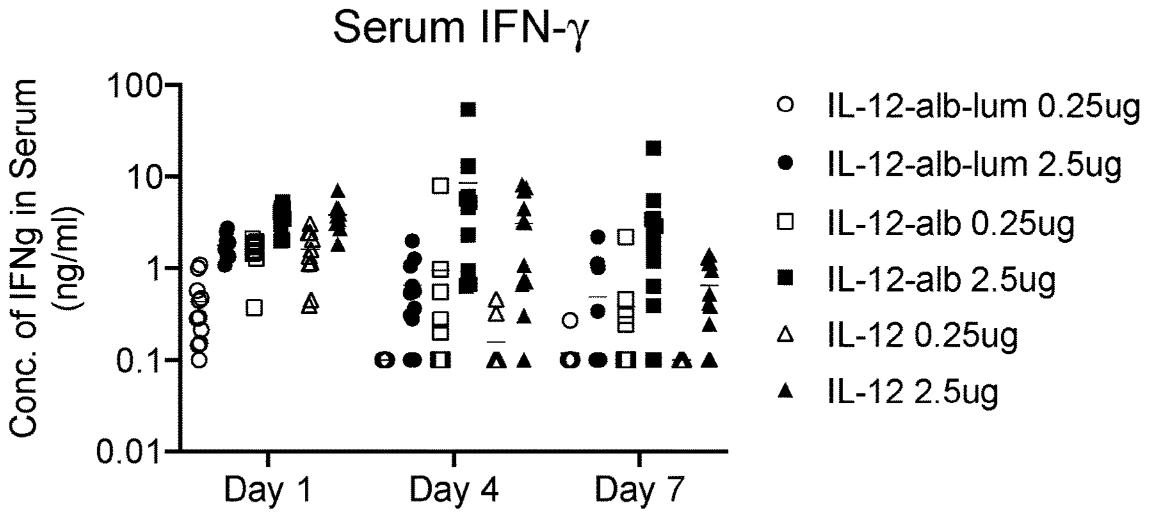

FIGS. 9A and 9B provide comparison of IL-12 protein and IFN-γ protein concentrations, respectively, measured in the serum of tumor-bearing mice treated with a single intratumoral administration of an RNA construct encoding one of the following mouse IL-12 proteins: (i) mIL-12 alone (triangle); (ii) mIL-12 conjugated to albumin (square); and (iii) mIL-12 conjugated to albumin and lumican (circle). The RNA constructs were administered the animals at the following doses: 0.25 μg (closed symbols) or 2.5 μg (open symbols). The x-axis provides the time points (post-administration) at which the IL-12 and IFN-γ concentrations were measured.

Figure 10:
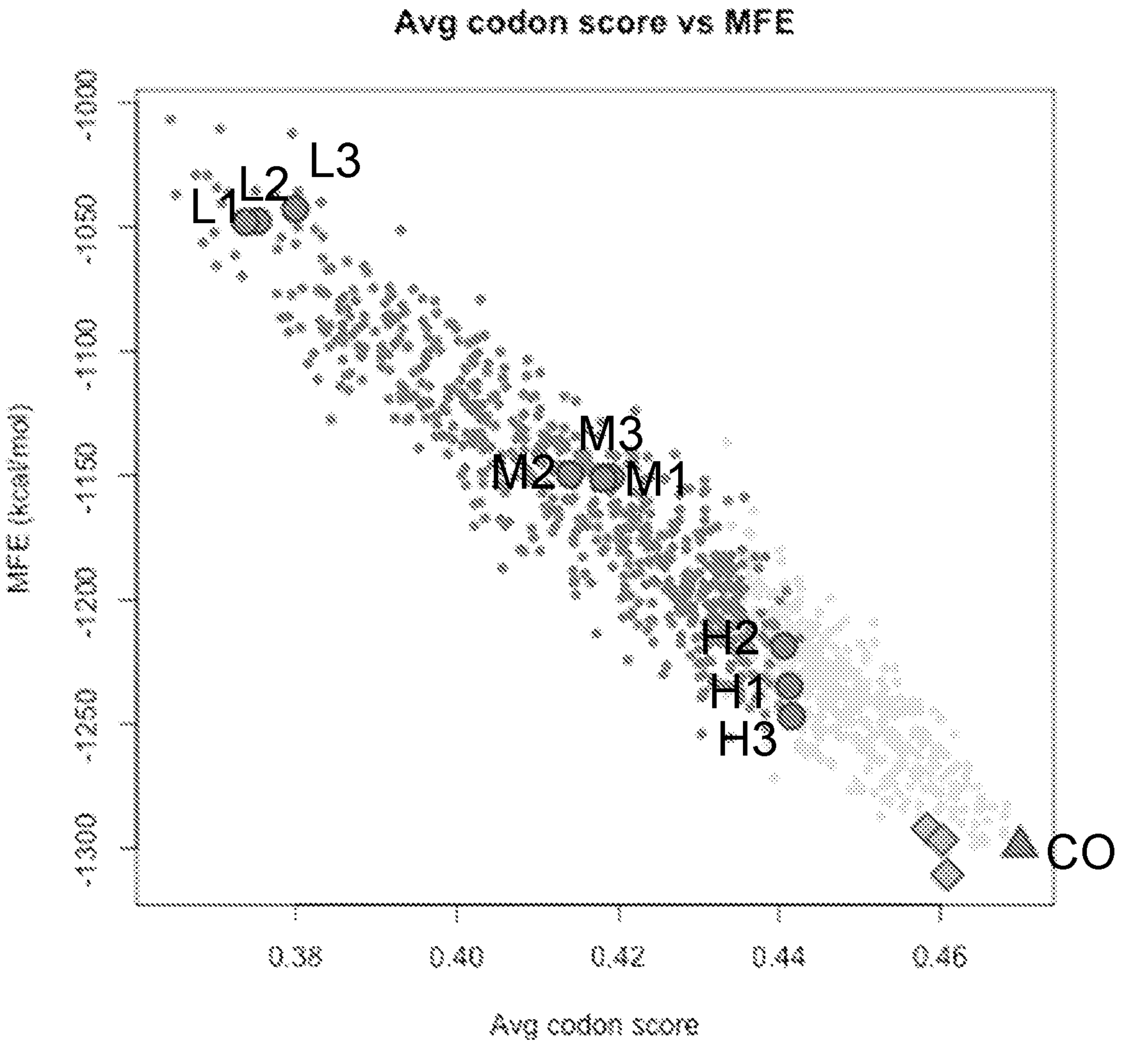

FIG. 10 presents a graphical representation of data related to optimality (avg_codon_score) vs minimum folding free energy in kcal/mol (MFE) for 1137 distinct sequences encoding the fusion protein human light chain leader—hIL12p40—GGS(GGGS)3 linker—hIL12p35—GSGGGS linker—Human serum albumin in accordance with Example 5. The L1, L2, L3, M1, M2, M3, H1, H2, and H3 codon-optimized constructs are indicated. As described in Example 5, the diamond symbol represents sequence with very high codon optimality and MFE. The triangle represents the codon optimal sequence containing the most frequently used triplet at each amino acid position.

Figure 11:
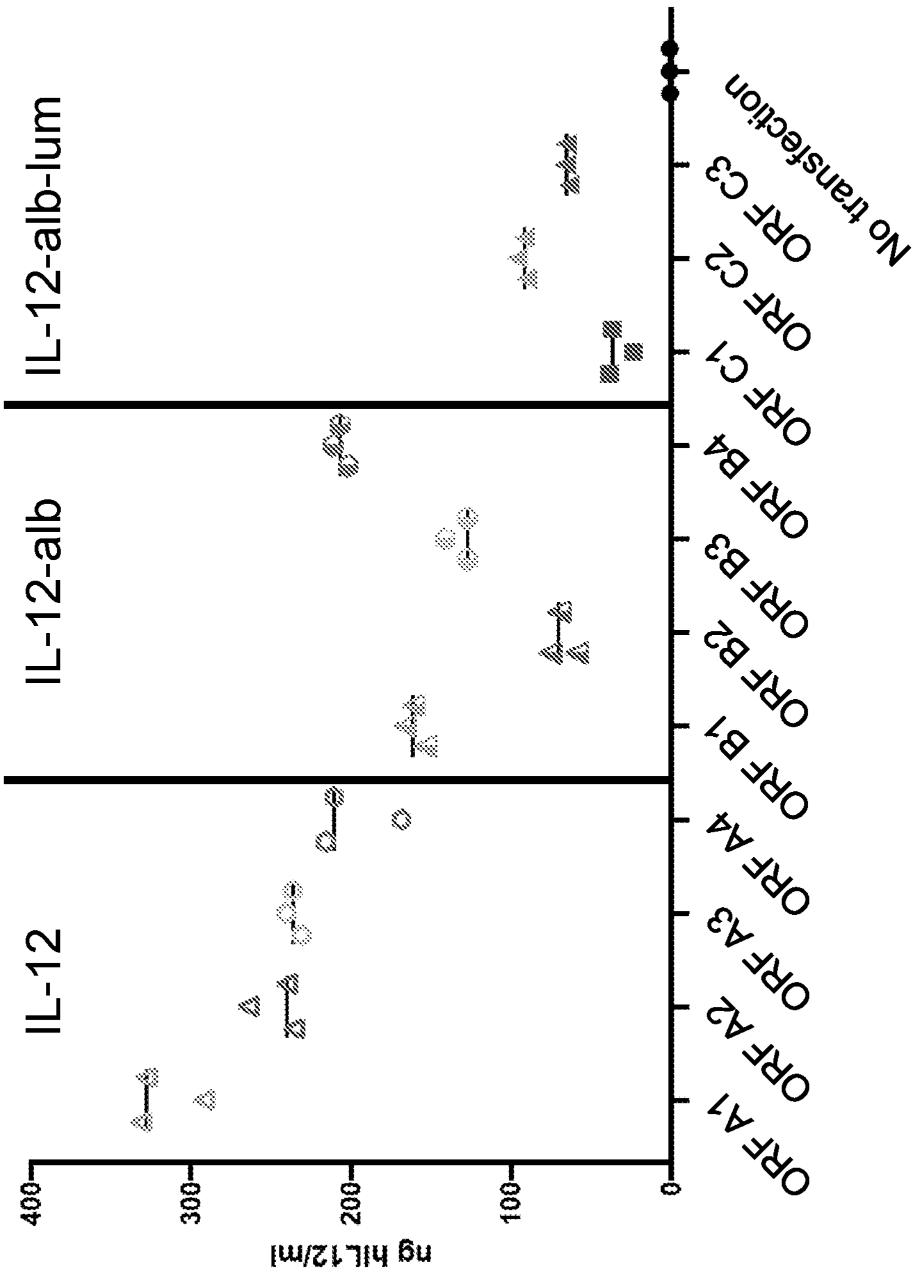

FIG. 11 provides a comparison of the IL-12 protein secretion observed in the supernatant of cells transfected with different RNA constructs comprising a codon-optimized IL-12 sequence (x-axis). As indicated, the IL-12 of constructs A1-A4 were not conjugated to any other moieties. IL-12 of constructs B1-B4 were conjugated to albumin. IL-12 of constructs C1-C3 were conjugated to albumin and lumican. Individual triplicate measurements are shown as triangular, square, octagonal, or circular points, and horizontal bars show the average of triplicate measurements. The X-axis represents the variant used and the Y-axis represents the concentration of IL-12 in ng/ml.

Figure 12A:
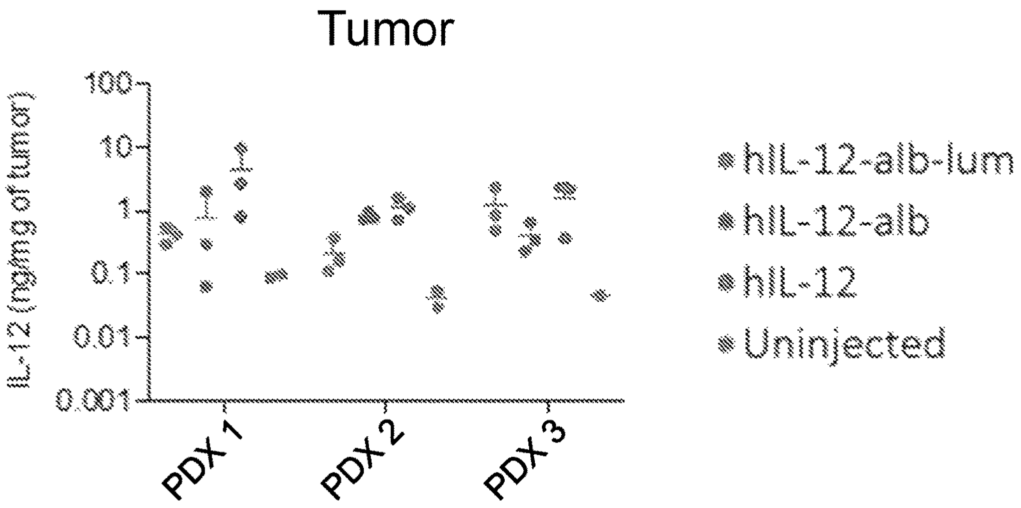
Figure 12B:
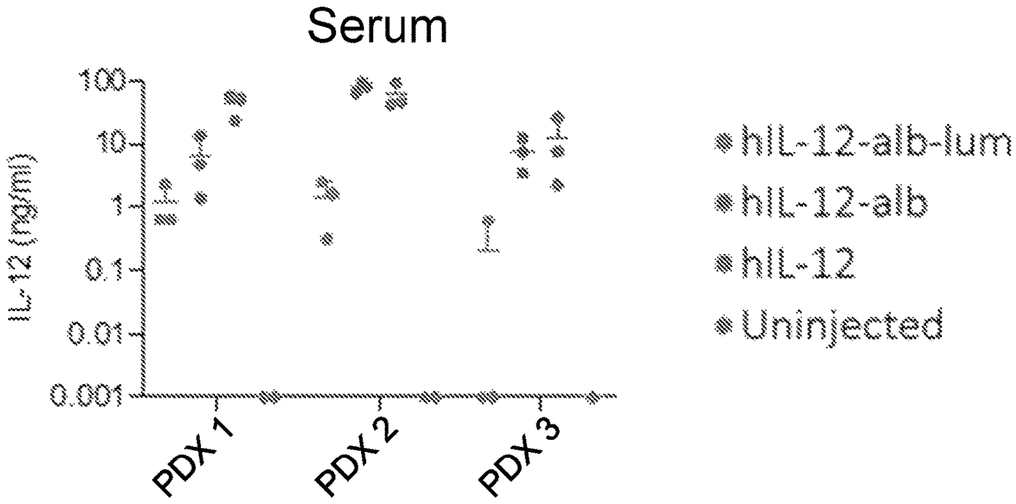
Figure 12C:
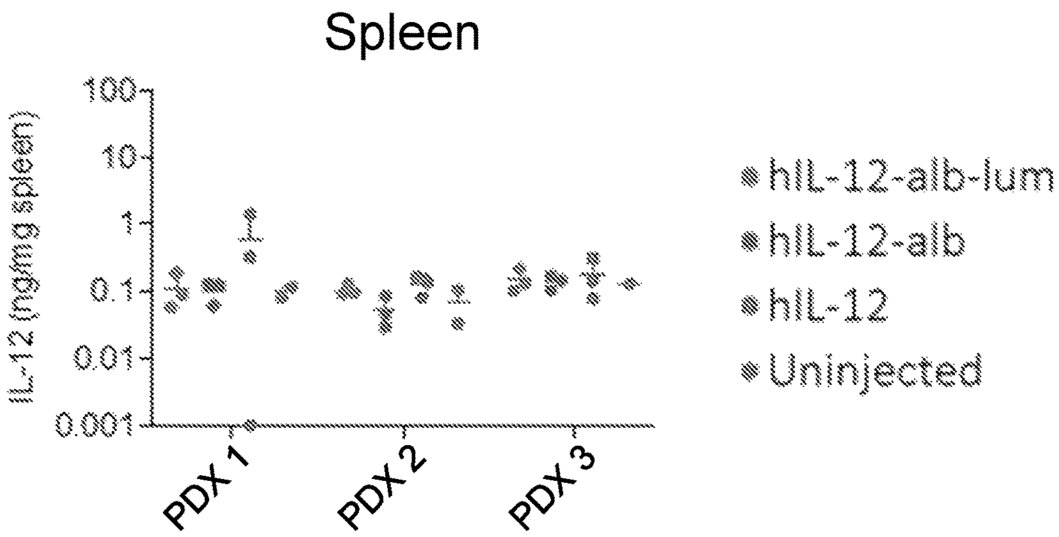

FIGS. 12A, 12B, and 12C provide comparison of IL-12 protein concentration observed in the tumor (FIG. 12A), serum (FIG. 12B), and spleen (FIG. 12C) of tumor-bearing mice that received a single intratumor administration of a RNA construct comprising (i) codon-optimized IL-12 sequence conjugated to albumin and lumican ($1^{st}$ set of circles from the left in each of PDX1, PDX2, and PDX3); (ii) codon-optimized IL-12 sequence conjugated to albumin ($2^{nd}$ set of circles in each of PDX1, PDX2, and PDX3); or (iii) codon-optimized IL-12 sequence alone ($3^{rd}$ set of circles in each of PDX1, PDX2, and PDX3). Non-treated animals were used as control (last set of circles in each of PDX1, PDX2, and PDX3). “PDX1,” “PDX2,” and “PDX3” represent xenografts derived from tumor resections from three individual patients with triple-negative breast cancer (TNBC). PDX1 and PDX3 were established from primary resected ER,PR,HER2 negative lesions, and PDX2 was established from a metastatic ER,PR,HER2-negative lesion in the lung of a TNBC patient.

Figure 13:
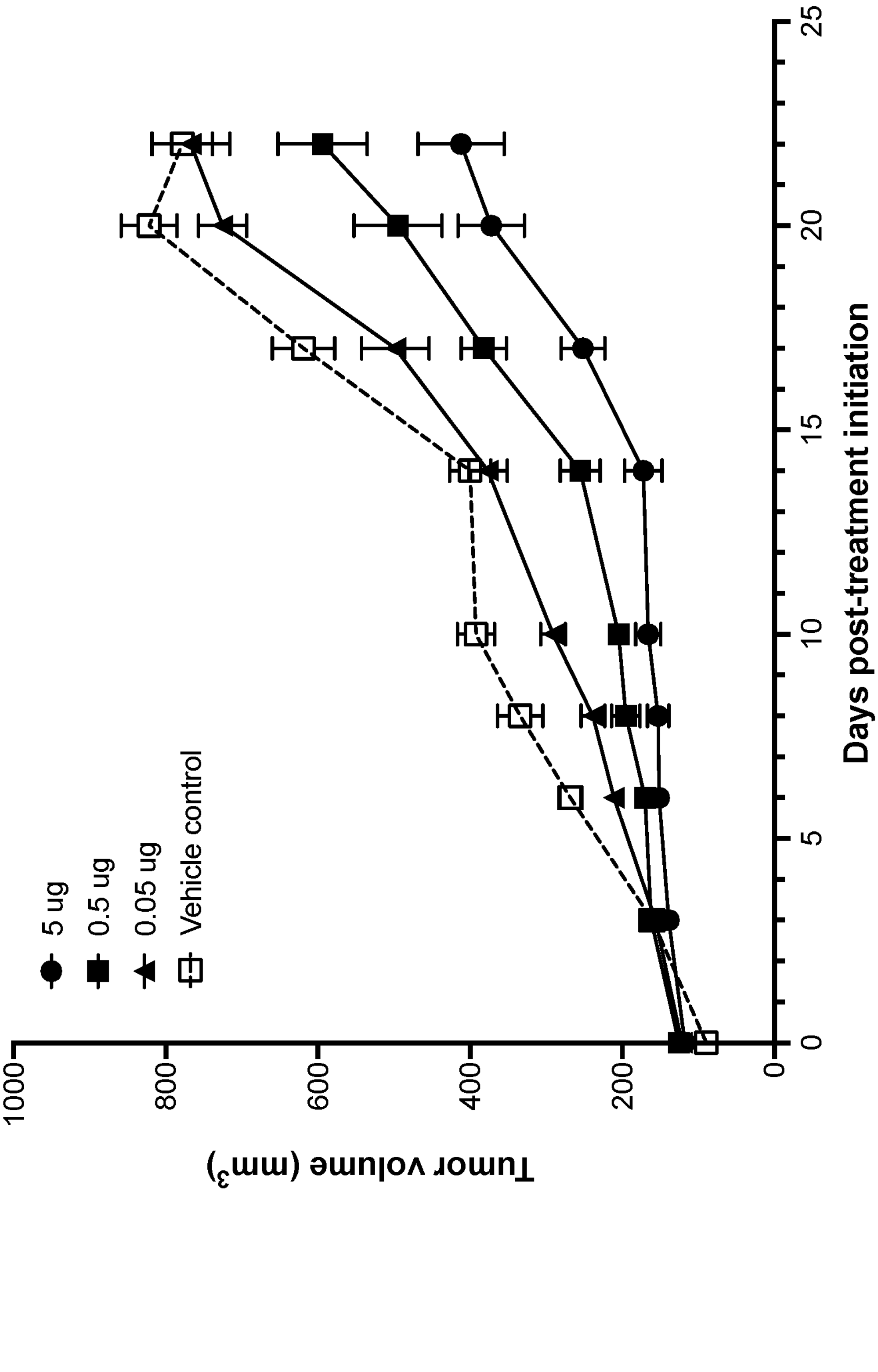

FIG. 13 provides a comparison of tumor volume in TNBC mice that were treated (weekly for a total of four doses) with the vehicle control (open square) or repRNA encoding IL-12 (repRNA). The repRNA was administered to the animals at one of the following doses: (i) 5 μg (closed circle), (ii) 0.5 μg (closed square), or (iii) 0.05 μg (closed triangle).

Figure 14:
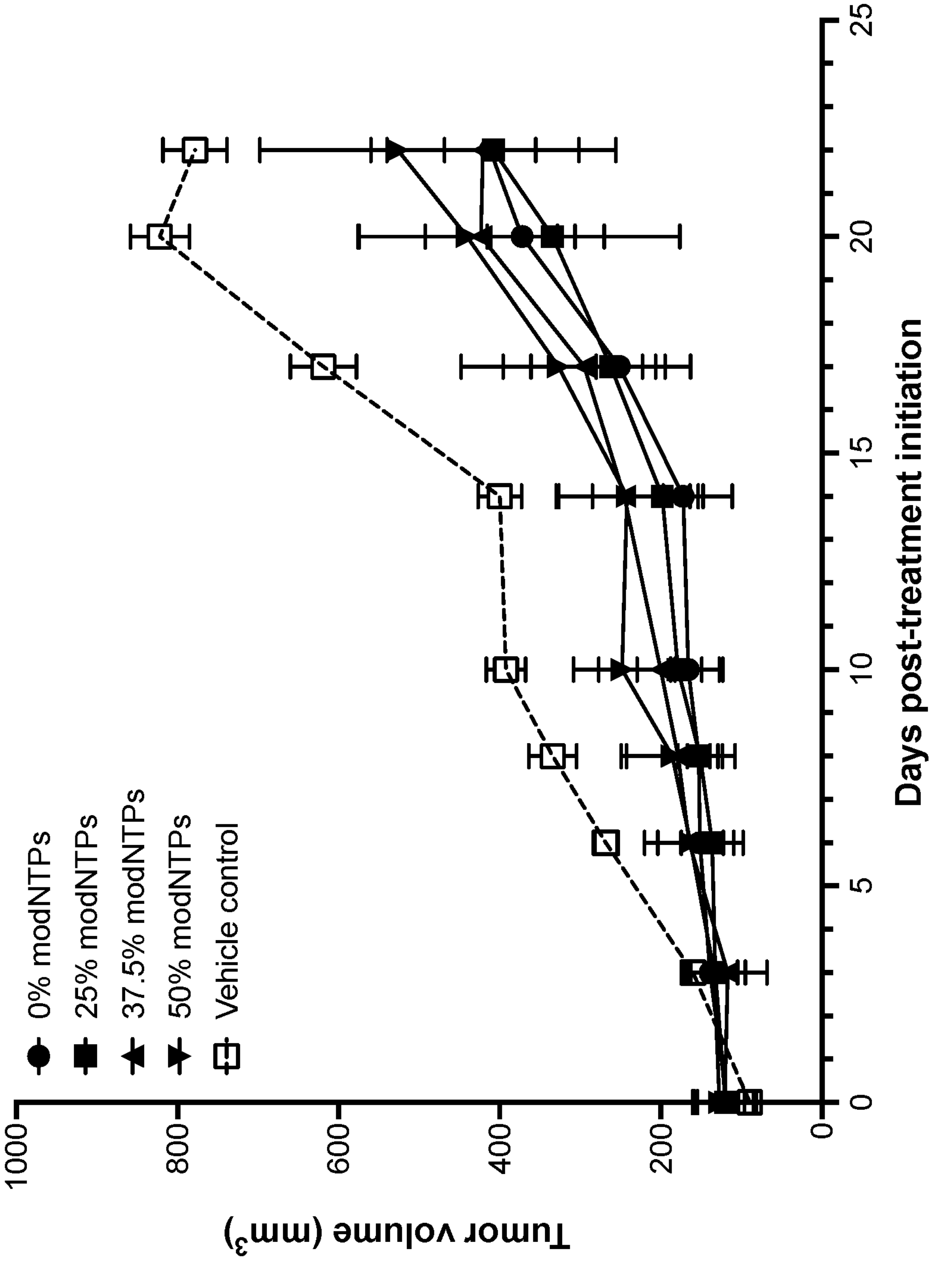

FIG. 14 provides a comparison of tumor volume in TNBC mice that were treated with rIL-12-encoding repRNA modified to comprise different amounts of modified nucleoside triphosphates (modNTPs): (i) 0% modNTP (i.e., non-modified repRNA) (closed circle); (ii) 25% modNTP (closed square); (iii) 37.5% modNTP (closed triangle); or (iv) 50% modNTP (closed inversed triangle). Animals treated with the vehicle control were used as control (open square).

Figure 15A:
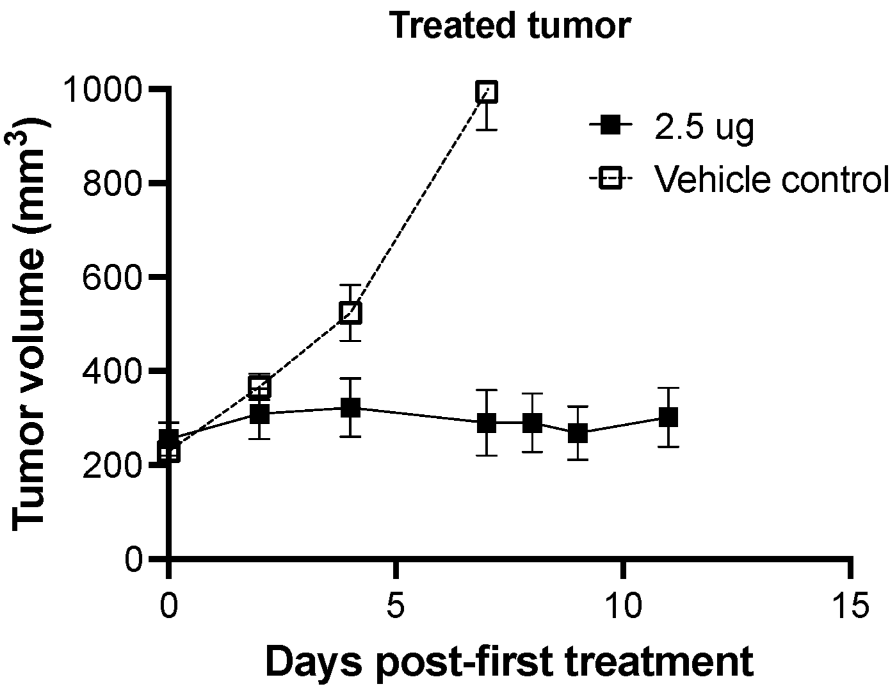
Figure 15B:
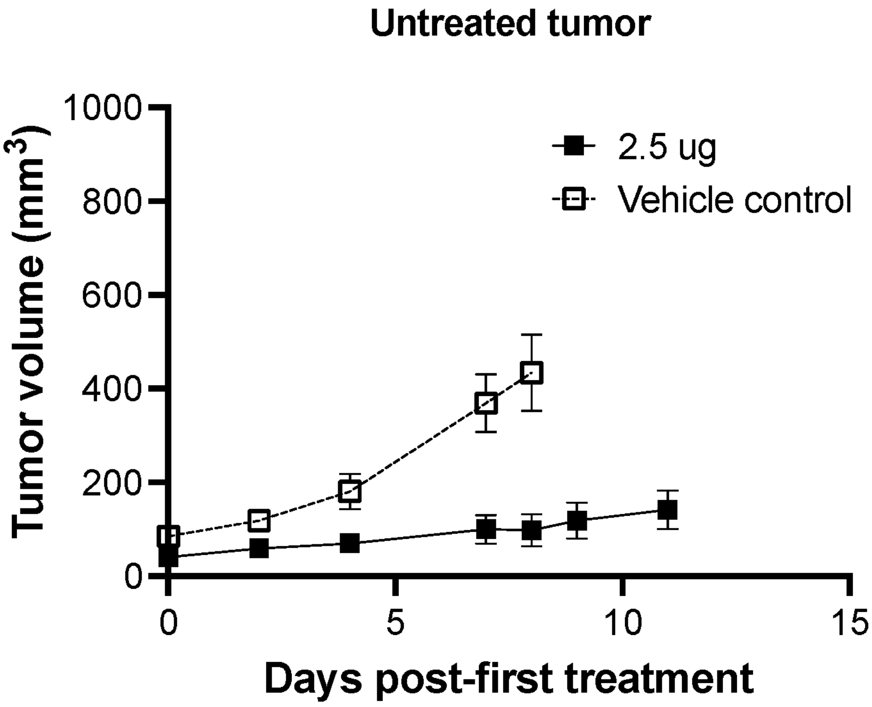

FIGS. 15A and 15B show the effects of the repRNA constructs described herein on both treated and non-treated tumors, respectively, in a B16-F10 mouse syngeneic cancer model. As further described in Example 8, the left and right flanks of the animals were subcutaneously injected with B16-F10 tumor cells. Once optimal tumor size was reached, the vehicle control or repRNA (2.5 μg) was intratumorally administered in the left flank (i.e., treated tumor). Then, tumor volume was assessed in both the left flank and the right flank (i.e., non-treated tumor).

Figure 16:
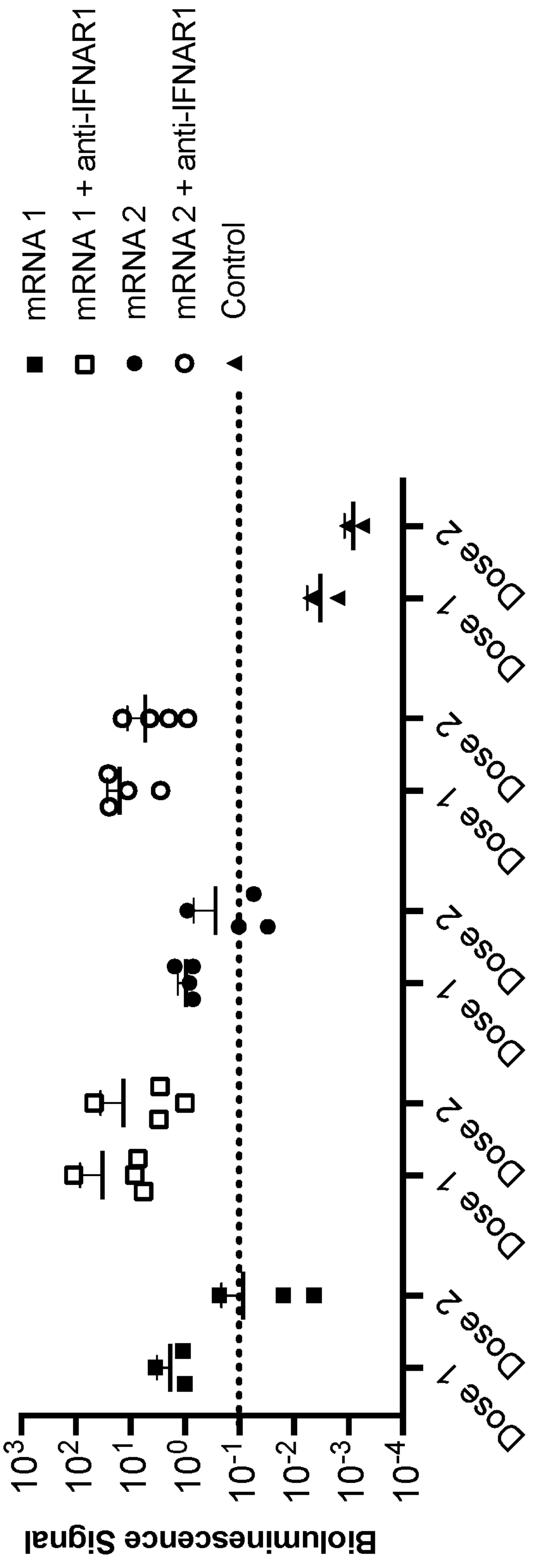

FIG. 16 provides a comparison of luciferase expression (shown as bioluminescence signal) in TNBC mouse model after re-dosing. As further described in Example 9, the mice were injected with a first dose of one of two firefly luciferase-encoding repRNA constructs (mRNA1 and mRNA2) (5 μg) ("Dose 1") and then 1 week later, injected with a second dose with the same repRNA construct (5 μg) ("Dose 2"). In some of the animals, they additionally received weekly (two total doses) administration of an anti-IFNAR1 antibody (10 mg/kg).

Figure 17:
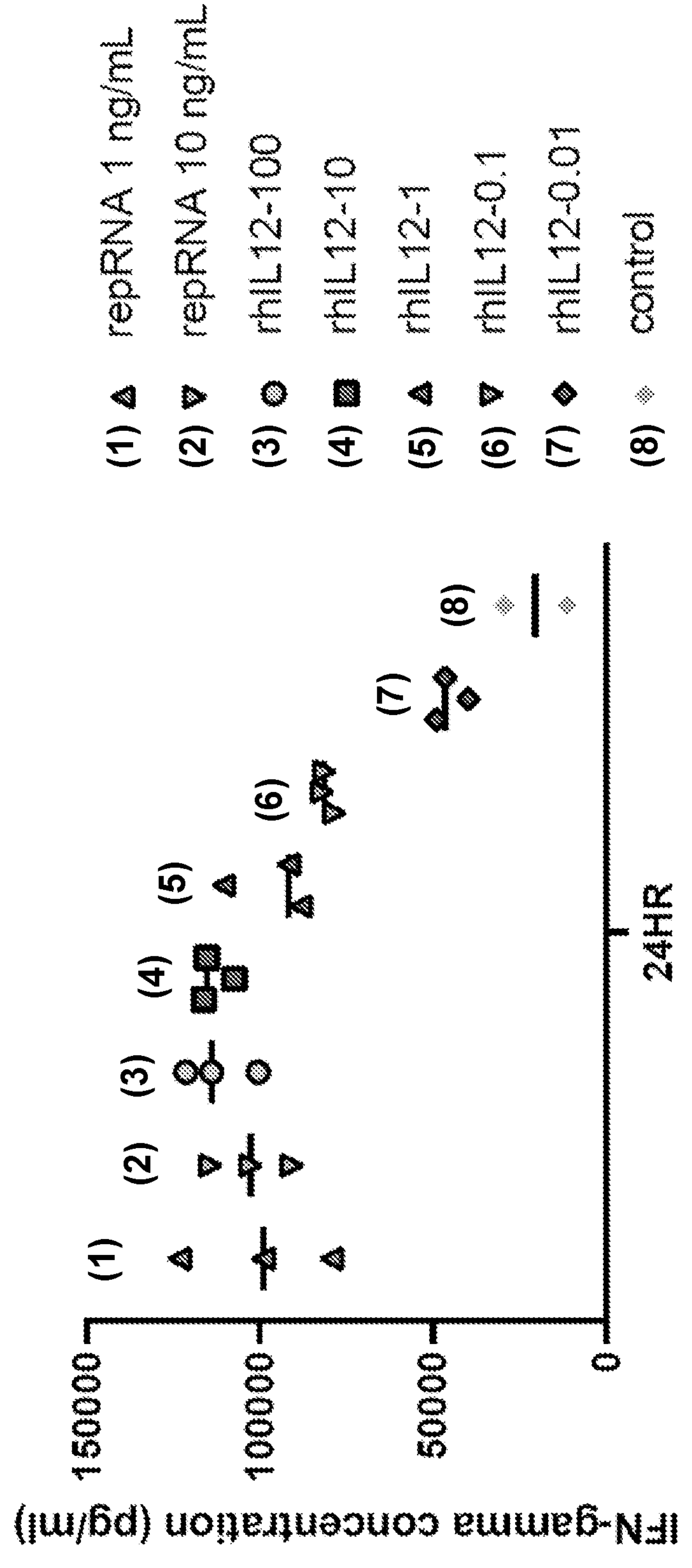

FIG. 17 provides a comparison of IFN-γ concentration in the supernatant collected from activated human PBMCs treated with recombinant human IL-12 protein (rhIL12) or conditioned media as described in Example 10 (i.e., supernatant collected from BT20 cells transfected with IL-12 encoding repRNA). The PBMCs were treated with the rhIL12 at one of the following concentrations: 100 ng/mL ("3"), 10 ng/mL ("4"), 1 ng/mL ("5"), 0.1 ng/mL ("6"), or 0.01 ng/mL ("7"). The conditioned media contained one of the following amounts of IL-12: 1 ng/mL ("1") and 10 ng/mL ("2"). Non-treated cells were used as control ("8").

DETAILED DESCRIPTION OF THE DISCLOSURE

Definitions

Unless defined otherwise, all technical and scientific terms used herein have the same meaning as commonly understood by one of ordinary skill in the art to which this disclosure belongs. In case of conflict, the present application, including the definitions, will control. Unless otherwise required by context, singular terms shall include pluralities and plural terms shall include the singular.

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower), unless indicated otherwise.

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures.

"Polynucleotide" or "nucleic acid" as used herein means a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule. Nucleotide bases are indicated herein by a single letter code: adenine (A), guanine (G), thymine (T), cytosine (C), inosine (I) and uracil (U).

As used herein, the term "polypeptide" encompasses both peptides and proteins, unless indicated otherwise.

The term "coding sequence" or sequence "encoding" is used herein to mean a DNA or RNA region (the transcribed region) which "encodes" a particular protein, e.g., such as an IL-12. A coding sequence is transcribed (DNA) and translated (RNA) into a polypeptide, in vitro or in vivo, when placed under the control of an appropriate regulatory region, such as a promoter. The boundaries of the coding sequence are determined by a start codon at the 5' (amino) terminus and a translation stop codon at the 3' (carboxy) terminus. A coding sequence can include, but is not limited to, cDNA from prokaryotes or eukaryotes, genomic DNA from prokaryotes or eukaryotes, and synthetic DNA sequences. A transcription termination sequence can be located 3' to the coding sequence.

A Kozak consensus sequence, Kozak consensus or Kozak sequence, is known as a sequence which occurs on eukaryotic mRNA and has the consensus (gcc)gccRccAUGG (SEQ ID NO: 174), where R is a purine (adenine or guanine) three bases upstream of the start codon (AUG), which is followed by another "G." In some aspects, the polynucleotide comprises a nucleic acid sequence having at least about 95% or more, e.g., at least 99% sequence identity, to the Kozak consensus sequence. In some aspects, the polynucleotide comprises a Kozak consensus sequence.

The term "RNA" is used herein to mean a molecule which comprises at least one ribonucleotide residue. "Ribonucleotide" relates to a nucleotide with a hydroxyl group at the 2'-position of a β-D-ribofuranosyl group. The term comprises double-stranded RNA, single-stranded RNA, isolated RNA such as partially or completely purified RNA, essentially pure RNA, synthetic RNA, recombinantly generated RNA such as modified RNA which differs from naturally occurring RNA by addition, deletion, substitution and/or alteration of one or more nucleotides. The term "mRNA" means "messenger-RNA" and relates to a "transcript" which is generated by using a DNA template and encodes a peptide or protein. Typically, an mRNA comprises a 5'-UTR, a protein coding region and a 3'-UTR. mRNA only possesses limited half-life in cells and in vitro. In the context of the present disclosure, mRNA can be generated by in vitro transcription from a DNA template. The in vitro transcription methodology is known to the skilled person. For example, there is a variety of in vitro transcription kits commercially available. In some aspects of the disclosure, the RNA, preferably the mRNA, is modified with a 5'-cap structure.

The term "sequence identity" is used herein to mean a relationship between two or more amino acid (polypeptide or protein) sequences or two or more nucleic acid (polynucleotide) sequences, as determined by comparing the sequences. In certain aspects, sequence identity is calculated based on the full length of two given SEQ ID NO or on part thereof. Part thereof can mean at least 10%, 20%, 30%, 40%, 50%, 60%, 70%, 80%, 90%, or 100% of both SEQ ID NO, or any other specified percentage. The term "identity" can also mean the degree of sequence relatedness between amino acid or nucleic acid sequences, as the case can be, as determined by the match between strings of such sequences.

In certain aspects, methods to determine identity are designed to give the largest match between the sequences tested. Methods to determine identity and similarity are codified in publicly available computer programs.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

As used herein, the terms "effective amount," "therapeutically effective amount," and a "sufficient amount" of, e.g., a composition comprising a polynucleotide disclosed herein, refer to a quantity sufficient to, when administered to the subject, including a human, effect beneficial or desired results, including clinical results, and, as such, an "effective amount" or synonym thereto depends on the context in which it is being applied.

The amount of a given therapeutic agent or composition will correspond to such an amount will vary depending upon various factors, such as the given agent, the pharmaceutical formulation, the route of administration, the type of disease or disorder, the identity of the subject (e.g., age, sex, and/or weight) or host being treated, and the like.

The term "half-life" relates to the period of time which is needed to eliminate half of the activity, amount, or number of molecules. In the context of the present disclosure, the half-life of an RNA is indicative for the stability of said RNA. "Development" or "progression" of a disease means initial manifestations and/or ensuing progression of the disease. Development of the disease can be detectable and assessed using standard clinical techniques as well known in the art. However, development also refers to progression that can be unpredictable. As used herein, development or progression refers to the biological course of symptoms. Development includes occurrence, recurrence, and onset. As used herein, onset or occurrence of a target disease or disorder includes initial onset and/or recurrence.

IL-12 Expressing Nucleotides

The present disclosure is directed to a polynucleotide (e.g., isolated polynucleotide) comprising a nucleic acid molecule encoding an IL-12 protein. As described herein, the polynucleotides disclosed herein comprise one or more features, such that they are distinct (e.g., structurally and/or functionally) from a reference polynucleotide that exists in nature. For instance, as further described elsewhere in the present disclosure, the nucleic acid molecules, e.g., encoding an IL-12 protein (e.g., IL-12α subunit and/or IL-12β subunit), have been codon-optimized (i.e., synthetic).

In some aspects, the nucleotide sequence encoding IL-12 comprises a translatable region and one, two, or more than two modifications. In some aspects, the nucleotide sequence encoding IL-12 exhibits reduced degradation in a cell into which the nucleic acid is introduced, relative to a corresponding unmodified nucleic acid.

In some aspects, the modification can be located on the sugar moiety of the nucleotide. In some aspects, the modification can be located on the phosphate backbone of the nucleotide.

In some aspects, it is desirable to intracellularly degrade a modified nucleic acid introduced into the cell, for example if precise timing of protein production is desired. Thus, in some aspects, the nucleotide sequence encoding IL-12 comprises a degradation domain, which is capable of being acted on in a directed manner within a cell.

In some aspects, the nucleotide sequence encoding IL-12 comprises at least one of a modified 5'-cap, a half-life extending moiety, or a regulatory element.

In some aspects, the modified 5'-cap increases the stability of the RNA, increases translation efficiency of the RNA, prolongs translation of the RNA, increases total protein expression of the RNA when compared to the same RNA without the 5'-cap structure.

In some aspects, the nucleotide sequence encoding IL-12 is cyclized, or concatemerized, to generate a translation competent molecule to assist interactions between poly-A binding proteins and 5'-end binding proteins. The mechanism of cyclization or concatemerization can occur through at least 3 different routes: 1) chemical, 2) enzymatic, and 3) ribozyme catalyzed. The newly formed 5'-/3'-linkage can be intramolecular or intermolecular.

In the first route, the 5'-end and the 3'-end of the nucleic acid contain chemically reactive groups that, when close together, form a new covalent linkage between the 5'-end and the 3'-end of the molecule. The 5'-end can contain an NETS-ester reactive group and the 3'-end can contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase can be used to enzymatically link a 5'-phosphorylated nucleic acid molecule to the 3'-hydroxyl group of a nucleic acid forming a new phosphorodiester linkage. In an example reaction, 1 μg of a nucleic acid molecule is incubated at 37° C. for 1 hour with 1-10 units of T4 RNA ligase (New England Biolabs, Ipswich, Mass.) according to the manufacturer's protocol. The ligation reaction can occur in the presence of a split oligonucleotide capable of base-pairing with both the 5'- and 3'-region in juxtaposition to assist the enzymatic ligation reaction.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme can be derived from the Group I Intron, Group I Intron, Hepatitis Delta Virus, Hairpin ribozyme or can be selected by SELEX (systematic evolution of ligands by exponential enrichment). The ribozyme ligase reaction can take 1 to 24 hours at temperatures between 0 and 37° C.

In some aspects, multiple distinct nucleic acids, nucleotide sequence encoding IL-12 or primary constructs can be linked together through the 3'-end using nucleotides which are modified at the 3'-terminus. Chemical conjugation can be used to control the stoichiometry of delivery into cells. For example, the glyoxylate cycle enzymes, isocitrate lyase and malate synthase, can be supplied into HepG2 cells at a 1:1 ratio to alter cellular fatty acid metabolism. This ratio can be controlled by chemically linking nucleic acids or modified RNA using a 3'-azido terminated nucleotide on one nucleic acids or modified RNA species and a C5-ethynyl or alkynyl-containing nucleotide on the opposite nucleic acids or nucleotide sequence species encoding IL-12. The nucleotide sequence encoding IL-12 is added post-transcriptionally using terminal transferase (New England Biolabs, Ipswich, Mass.) according to the manufacturer's protocol. After the addition of the 3'-modified nucleotide, the two nucleic acids or nucleotide sequence encoding IL-12 can be combined in an aqueous solution, in the presence or absence of copper, to form a new covalent linkage via a click chemistry mechanism as described in the literature.

In some aspects, more than two polynucleotides can be linked together using a functionalized linker molecule. For example, a functionalized saccharide molecule can be chemically modified to contain multiple chemical reactive groups (SH—, NH2-, N3, etc. . . . ) to react with the cognate moiety on a 3'-functionalized mRNA molecule (i.e., a 3'-maleimide ester, 3'-NHS-ester, alkynyl). The number of reactive groups on the modified saccharide can be controlled in a stoichiometric fashion to directly control the stoichiometric ratio of conjugated nucleic acid or mRNA.

In some aspects, to further enhance protein production, nucleotide sequence encoding IL-12, polynucleotides or primary constructs of the present disclosure can be designed to be conjugated to other polynucleotides, dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugation can result in increased stability and/or half-life and can be particularly useful in targeting the nucleotide sequence encoding IL-12 or the primary constructs to specific sites in the cell, tissue or organism.

In some aspects, the primary construct is designed to encode one or more polypeptides of interest or fragments thereof. A polypeptide of interest can include, but is not limited to, whole polypeptides, a plurality of polypeptides or fragments of polypeptides, which independently can be encoded by one or more nucleic acids, a plurality of nucleic acids, fragments of nucleic acids or variants of any of the aforementioned. As used herein, the term "polypeptides of interest" refers to any polypeptide which is selected to be encoded in the primary construct of the present disclosure. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide can be a single molecule or can be a multi-molecular complex such as a dimer, trimer or tetramer. They can also comprise single chain or multichain polypeptides such as antibodies or insulin and can be associated or linked. Most commonly disulfide linkages are found in multichain polypeptides. The term polypeptide can also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

As such, polynucleotides encoding polypeptides of interest containing substitutions, insertions and/or additions, deletions and covalent modifications with respect to reference sequences are included within the scope of this disclosure. For example, sequence tags or amino acids, such as one or more lysines, can be added to the peptide sequences of the disclosure (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein can optionally be deleted providing for truncated sequences. Certain amino acids (e.g., C-terminal or N-terminal residues) can alternatively be deleted depending on the use of the sequence, as for example, expression of the sequence as part of a larger sequence which is soluble, or linked to a solid support.

As recognized by those skilled in the art, protein fragments, functional protein domains, and homologous proteins are also considered to be within the scope of polypeptides of interest of this disclosure. For example, provided herein is any protein fragment (meaning an polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the disclosure. In certain aspects, a polypeptide to be utilized in accordance with the disclosure includes 2, 3, 4, 5, 6, 7, 8, 9, 10, or more mutations as shown in any of the sequences provided or referenced herein.

In some aspects, the nucleotide sequence encoding IL-12 comprises a modified 5'-cap, a half-life extending moiety, a regulatory element, or combinations thereof.

In some aspects, the modified 5'-cap is selected from the group consisting of $m_2^{7,2'-O}$Gpp$_s$pGRNA, $m^7$GpppG, $m^7$Gppppm$^7$G, $m_2^{(7,3'-O)}$GpppG, $m_2^{(7,2'-O)}$GppspG(D1), $m_2^{(7,2'-O)}$GppspG(D2), $m_2^{7,3'-O}$Gppp($m_1^{2'-O)}$ApG, ($m^7$G-3' mppp-G; which can equivalently be designated 3' O-Me-m7G(5')ppp(5')G), N7,2'-O-dimethyl-guanosine-5'-triphosphate-5'-guanosine, $m^7$Gm-ppp-G, N7-(4-chlorophenoxyethyl)-G(5')ppp(5')G, N7-(4-chlorophenoxyethyl)-$m^{3'-O}$G (5')ppp(5')G, 7mG(5')ppp(5')N,pN2p, 7mG(5')ppp(5') NlmpNp, 7mG(5')-ppp(5')NlmpN2 mp, m(7)Gpppm(3)(6,6, 2')Apm(2')Apm(2')Cpm(2)(3,2')Up, inosine, N1-methyl-guanosine, 2' fluoro-guanosine, 7-deaza-guanosine, 8-oxo-guanosine, 2-amino-guanosine, LNA-guanosine, 2-azido-guanosine, N1-methylpseudouridine, m7G(5')ppp(5') (2'OMeA)pG, and combinations thereof.

The disclosure also includes a polynucleotide that comprises both a 5' Cap and a nucleotide sequence encoding IL-12 of the disclosure (e.g., a polynucleotide comprising a nucleotide sequence encoding an IL12B polypeptide, an IL12A polypeptide, and/or IL12B and IL12A fusion polypeptides).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

In some aspects, the 5' terminal cap structure is a CapO, Cap1, ARC A, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

Non-limiting additional Caps include the 5' Caps disclosed in WO/2017/201350, published Nov. 23, 2017, which is incorporated herein by reference.

In some aspects, the half-life extending moiety comprises an Fc, an albumin or a fragment thereof, an albumin binding moiety, a PAS sequence, a HAP sequence, transferrin or a fragment thereof, an XTEN, or any combinations thereof.

In some aspects, the half-life extending moiety comprises an Fc. In some aspects, the half-life extending moiety comprises an albumin or a fragment thereof.

In some aspects, the regulatory element is selected from the group consisting of at least one translation enhancer element (TEE), a translation initiation sequence, at least one microRNA binding site or seed thereof, a 3' tailing region of linked nucleosides, an AU rich element (ARE), a post transcription control modulator, and combinations thereof.

In some aspects, the regulatory element further comprises a polyA region. In some aspects, the nucleotide sequence encoding IL-12 of the present disclosure (e.g., a polynucleotide comprising a nucleotide sequence encoding an IL12B polypeptide, an IL12A polypeptide, and/or IL12B and IL12A fusion polypeptides) further comprise a poly-A tail. In some aspects, terminal groups on the poly-A tail can be incorporated for stabilization. In other aspects, a poly-A tail comprises des-3' hydroxyl tails. During RNA processing, a long chain of adenine nucleotides (poly-A tail) can be added to a polynucleotide such as an mRNA molecule in order to increase stability.

Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present disclosure, terminal groups on the poly A tail can be incorporated for stabilization. Polynucleotides of the present disclosure can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety). See also WO/2017/201350, published Nov. 23, 2017, which is incorporated herein by reference, for additional poly-A tails.

In some aspects, the nucleotide sequence encoding IL-12 comprises any modification or combination of modifications described herein.

Terminal Architecture Modifications: Untranslated Regions (UTRs)

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the RNA (e.g., modified RNA) of the present disclosure to enhance the stability of the molecule. The specific features can also be incorporated to ensure controlled down-regulation of the transcript in case they are misdirected to undesired organs sites.

5' UTR and Translation Initiation

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

5'UTR secondary structures involved in elongation factor binding can interact with other RNA binding molecules in the 5'UTR or 3'UTR to regulate gene expression. For example, the elongation factor EIF4A2 binding to a secondarily structured element in the 5'UTR is necessary for microRNA mediated repression (Meijer H A et al., Science, 2013, 340, 82-85, herein incorporated by reference in its entirety). The different secondary structures in the 5'UTR can be incorporated into the flanking region to either stabilize or selectively destalized mRNAs in specific tissues or cells.

By engineering the features typically found in abundantly expressed genes of specific target organs, one can enhance the stability and protein production of the nucleic acids or mRNA of the disclosure. For example, introduction of 5' UTR of liver-expressed mRNA, such as albumin, serum amyloid A, Apolipoprotein A/B/E, transferrin, alpha feto-protein, erythropoietin, or Factor VIII, could be used to enhance expression of a nucleic acid molecule, such as a mmRNA, in hepatic cell lines or liver. Likewise, use of 5' UTR from other tissue-specific mRNA to improve expression in that tissue is possible—for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences can be incorporated into the 5' (or 3' UTR) UTRs. For example, introns or portions of introns sequences can be incorporated into the flanking regions of the nucleic acids or mRNA of the disclosure. Incorporation of intronic sequences can increase protein production as well as mRNA levels.

In some aspects of the disclosure, at least one fragment of IRES sequences from a GTX gene can be included in the 5'UTR. As a non-limiting example, the fragment can be an 18 nucleotide sequence from the IRES of the GTX gene. As another non-limiting example, an 18 nucleotide sequence fragment from the IRES sequence of a GTX gene can be tandemly repeated in the 5'UTR of a polynucleotide described herein. The 18 nucleotide sequence can be repeated in the 5'UTR at least one, at least twice, at least three times, at least four times, at least five times, at least six times, at least seven times, at least eight times, at least nine times or more than ten times.

Nucleotides can be mutated, replaced and/or removed from the 5' (or 3') UTRs. For example, one or more nucleotides upstream of the start codon can be replaced with another nucleotide. The nucleotide or nucleotides to be replaced can be 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more than 60 nucleotides upstream of the start codon. As another example, one or more nucleotides upstream of the start codon can be removed from the UTR.

3'UTR and Translation Enhancer Elements (TEEs)

In some aspects, the 5'UTR of the nucleotide sequence encoding IL-12 comprises at least one translational enhancer polynucleotide, translation enhancer element, translational enhancer elements (collectively referred to as "TEE"s). In some aspects, the TEE is located between the transcription promoter and the start codon. In some aspects, the RNA (e.g., modified RNA) with at least one TEE in the 5'UTR comprises a cap at the 5'UTR. In some aspects, the at least one TEE can be located in the 5'UTR of nucleotide sequence encoding IL-12 undergoing cap-dependent or cap-independent translation.

The term "translational enhancer element" or "translation enhancer element" (herein collectively referred to as "TEE") refers to sequences that increase the amount of polypeptide or protein produced from an mRNA.

In one aspect, TEEs are conserved elements in the UTR which can promote translational activity of a nucleic acid such as, but not limited to, cap-dependent or cap-independent translation. The conservation of these sequences has been previously shown by Panek et al (Nucleic Acids Research, 2013, 1-10; herein incorporated by reference in its entirety) across 14 species including humans.

In some aspects, the nucleotide sequence encoding IL-12 has at least one TEE that has at least about 50%, at least about 55%, at least about 60%, at least about 65%, at least about 70%, at least about 75%, at least about 80%, at least about 85%, at least about 90%, at least about 95% or at least about 99% identity with the disclosed in U.S. Application Number 2014/0147454, which is hereby incorporated by reference in its entirety. In some aspects, the RNA (e.g., modified RNA) includes at least one TEE that has at least about 50%, at least about 55%, at least about 60%, at least about 65%, at least about 70%, at least about 75%, at least about 80%, at least about 85%, at least about 90%, at least about 95% or at least about 99% identity with the TEEs described in US Patent Publication Nos. US20090226470, US20070048776, US20130177581 and US20110124100, International Patent Publication No. WO1999024595, WO2012009644, WO2009075886 and WO2007025008, European Patent Publication No. EP2610341A1 and EP2610340A1, U.S. Pat. Nos. 6,310,197, 6,849,405, 7,456,273, 7,183,395, each of which is herein incorporated by reference in its entirety.

In some aspects, the 5'UTR of the nucleotide sequence encoding IL-12 can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In some aspects, the TEE sequences in the 5'UTR of the RNA (e.g., modified RNA) are the same or different TEE sequences. In some aspects, the TEE sequences are in a pattern such as ABABAB or AABBAABBAABB or ABCABCABC or variants thereof repeated once, twice, or more than three times. In these patterns, each letter, A, B, or C represent a different TEE sequence at the nucleotide level.

In some aspects, the spacer separating two TEE sequences includes other sequences known in the art which regulate the translation of the RNA (e.g., modified RNA) such as, but not limited to, miR sequences described herein (e.g., miR binding sites and miR seeds). In some aspects, each spacer used to separate two TEE sequences includes a different miR sequence or component of a miR sequence (e.g., miR seed sequence).

In some aspects, the TEE used in the 5'UTR of the nucleotide sequence encoding IL-12 of the present disclosure is an IRES sequence such as, but not limited to, those described in U.S. Pat. No. 7,468,275 and International Patent Publication No. WO2001055369, each of which is herein incorporated by reference in its entirety.

In some aspects, the TEEs described herein are located in the 5'UTR and/or the 3'UTR of the nucleotide sequence encoding IL-12. In some aspects, the TEEs located in the 3'UTR are the same and/or different than the TEEs located in and/or described for incorporation in the 5'UTR.

In some aspects, the 3'UTR of the nucleotide sequence encoding IL-12 can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In some aspects, the TEE sequences in the 3'UTR of the nucleotide sequence encoding IL-12 of the present disclosure is the same or different TEE sequences. The TEE sequences is in a pattern such as ABABAB or AABBAABBAABB or ABCAB- CABC or variants thereof repeated once, twice, or more than three times. In these patterns, each letter, A, B, or C represent a different TEE sequence at the nucleotide level.

In some aspects, the 3'UTR includes a spacer to separate two TEE sequences. In some aspects, the spacer is a 15 nucleotide spacer and/or other spacers known in the art. In some aspects, the 3'UTR can include a TEE sequence-spacer module repeated at least once, at least twice, at least 3 times, at least 4 times, at least 5 times, at least 6 times, at least 7 times, at least 8 times and at least 9 times or more than 9 times in the 3'UTR.

In some aspects, the spacer separating two TEE sequences includes other sequences known in the art which regulate the translation of the nucleotide sequence encoding IL-12, such as, but not limited to, miR sequences described herein (e.g., miR binding sites and miR seeds). In some aspects, each spacer used to separate two TEE sequences includes a different miR sequence or component of a miR sequence (e.g., miR seed sequence).

Incorporating microRNA Binding Sites

In some aspects, the nucleotide sequence encoding IL-12 further comprises a sensor sequence. Sensor sequences include, for example, microRNA binding sites, transcription factor binding sites, structured mRNA sequences and/or motifs, artificial binding sites engineered to act as pseudo-receptors for endogenous nucleic acid binding molecules. Non-limiting examples, of polynucleotides comprising at least one sensor sequence are described U.S. Application No. 2014/0147454, which is hereby incorporated by reference in its entirety.

In some aspects, microRNA (miRNA) profiling of the target cells or tissues is conducted to determine the presence or absence of miRNA in the cells or tissues.

MicroRNAs (or miRNA) are 19-25 nucleotide long non-coding RNAs that bind to the 3'UTR of nucleic acid molecules and down-regulate gene expression either by reducing nucleic acid molecule stability or by inhibiting translation. In some aspects, the RNA (e.g., modified RNA), comprises one or more microRNA target sequences, microRNA sequences, or microRNA seeds. Such sequences can correspond to any known microRNA such as those taught in US Publication US2005/0261218 and US Publication US2005/0059005, the contents of which are incorporated herein by reference in their entirety. As a non-limiting example, known microRNAs, their sequences and seed sequences in human genome are described in U.S. Application No. 2014/0147454, which is herein incorporated by reference in its entirety.

A microRNA sequence comprises a "seed" region, i.e., a sequence in the region of positions 2-8 of the mature microRNA, which sequence has perfect Watson-Crick complementarity to the miRNA target sequence. A microRNA seed comprises positions 2-8 or 2-7 of the mature microRNA. In some aspects, a microRNA seed comprises 7 nucleotides (e.g., nucleotides 2-8 of the mature microRNA), wherein the seed-complementary site in the corresponding miRNA target is flanked by an adenine (A) opposed to microRNA position 1. In some aspects, a microRNA seed comprises 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the 3'UTR of nucleic acids or mRNA of the disclosure one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/1eu.2011.356); Bartel Cell 2009 136:215-233; Landgraf et al, Cell, 2007 129:1401-1414; Gentner and Naldini, Tissue Antigens. 2012 80:393-403 and all references therein; each of which is herein incorporated by reference in its entirety).

For example, if the mRNA is not intended to be delivered to the liver but ends up there, then miR-122, a microRNA abundant in liver, can inhibit the expression of the gene of interest if one or multiple target sites of miR-122 are engineered into the 3'UTR of the modified nucleic acids, enhanced modified RNA or ribonucleic acids. Introduction of one or multiple binding sites for different microRNA can be engineered to further decrease the longevity, stability, and protein translation of a modified nucleic acids, enhanced modified RNA or ribonucleic acids. As used herein, the term "microRNA site" refers to a microRNA target site or a microRNA recognition site, or any nucleotide sequence to which a microRNA binds or associates. It should be understood that "binding" can follow traditional Watson-Crick hybridization rules or can reflect any stable association of the microRNA with the target sequence at or adjacent to the microRNA site.

Conversely, for the purposes of the nucleotide sequence encoding IL-12 of the present disclosure, microRNA binding sites can be engineered out of (i.e. removed from) sequences in which they naturally occur in order to increase protein expression in specific tissues. For example, miR-122 binding sites can be removed to improve protein expression in the liver.

In some aspects, the nucleotide sequence encoding IL-12 includes at least one miRNA-binding site in the 3'UTR in order to direct cytotoxic or cytoprotective mRNA therapeutics to specific cells such as, but not limited to, normal and/or cancerous cells (e.g., HEP3B or SNU449).

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, microRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. It was demonstrated in the art that the immune response to exogenous nucleic acid molecules was shut-off by adding miR- 142 binding sites to the 3'UTR of the delivered gene construct, enabling more stable gene transfer in tissues and cells. miR-142 efficiently degrades the exogenous mRNA in antigen presenting cells and suppresses cytotoxic elimination of transduced cells (Annoni A et al., blood, 2009, 114, 5152-5161; Brown B D, et al., Nat med. 2006, 12(5), 585-591; Brown B D, et al., blood, 2007, 110(13): 4144-4152, each of which is herein incorporated by reference in its entirety).

Many microRNA expression studies are conducted in the art to profile the differential expression of microRNAs in various cancer cells/tissues and other diseases. Some microRNAs are abnormally over-expressed in certain cancer cells and others are under-expressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lympho nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in their entirety.)

At least one microRNA site can be engineered into the 3' UTR of the nucleotide sequence encoding IL-12. In some aspects, at least two, at least three, at least four, at least five, at least six, at least seven, at least eight, at least nine, at least ten or more microRNA sites can be engineered into the 3' UTR of the nucleotide sequence encoding IL-12. In some aspects, the microRNA sites incorporated into the nucleotide sequence encoding IL-12 are the same or different microRNA sites. In some aspects, the microRNA sites incorporated into the nucleotide sequence encoding IL-12 targets the same or different tissues in the body. As a non-limiting example, through the introduction of tissue-, cell-type-, or disease-specific microRNA binding sites in the 3' UTR of a modified nucleic acid mRNA, the degree of expression in specific cell types (e.g., hepatocytes, myeloid cells, endothelial cells, cancer cells, etc.) can be reduced.

In some aspects, a microRNA site is engineered near the 5' terminus of the 3'UTR, about halfway between the 5' terminus and 3' terminus of the 3'UTR and/or near the 3' terminus of the 3'UTR. In some aspects, a microRNA site is engineered near the 5' terminus of the 3'UTR and about halfway between the 5' terminus and 3' terminus of the 3'UTR. In some aspects, a microRNA site is engineered near the 3' terminus of the 3'UTR and about halfway between the 5' terminus and 3' terminus of the 3'UTR. In some aspects, a microRNA site is engineered near the 5' terminus of the 3'UTR and near the 3' terminus of the 3'UTR.

In some aspects, a modified messenger RNA comprises microRNA binding region sites that either have 100% identity to known seed sequences or have less than 100% identity to seed sequences. The seed sequence can be partially mutated to decrease microRNA binding affinity and as such result in reduced downmodulation of that mRNA transcript. In essence, the degree of match or mis-match between the target mRNA and the microRNA seed can act as a rheostat to more finely tune the ability of the microRNA to modulate protein expression. In addition, mutation in the non-seed region of a microRNA binding site can also impact the ability of a microRNA to modulate protein expression.

RNA Motifs for RNA Binding Proteins (RBPs)

RNA binding proteins (RBPs) can regulate numerous aspects of co- and post-transcription gene expression such as, but not limited to, RNA splicing, localization, translation, turnover, polyadenylation, capping, modification, export and localization. RNA-binding domains (RBDs), such as, but not limited to, RNA recognition motif (RR) and hnRNP K-homology (KH) domains, typically regulate the sequence association between RBPs and their RNA targets (Ray et al. Nature 2013. 499:172-177; herein incorporated by reference in its entirety). In some aspects, the canonical RBDs bind short RNA sequences. In some aspects, the canonical RBDs recognize RNA structure.

Non limiting examples of RNA binding proteins and related nucleic acid and protein sequences are described in U.S. Application No. 2014/0147454, which is herein incorporated by reference in its entirety.

In some aspects, to increase the stability of the mRNA of interest, an mRNA encoding HuR is co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

In some aspects, the nucleotide sequence encoding IL-12 comprises at least one RNA-binding motif such as, but not limited to a RNA-binding domain (RBD).

In some aspects, the first region of linked nucleosides and/or at least one flanking region comprises at least on RBD. In some aspects, the first region of linked nucleosides comprises a RBD related to splicing factors and at least one flanking region comprises a RBD for stability and/or translation factors.

Other Regulatory Elements in 3'UTR

In addition to microRNA binding sites, other regulatory sequences in the 3'-UTR of natural mRNA, which regulate mRNA stability and translation in different tissues and cells, can be removed or introduced into RNA (e.g., modified messenger RNA). Such cis-regulatory elements can include, but are not limited to, Cis-RNP (Ribonucleoprotein)/RBP (RNA binding protein) regulatory elements, AU-rich element (AUE), structured stem-loop, constitutive decay elements (CDEs), GC-richness and other structured mRNA motifs (Parker B J et al., Genome Research, 2011, 21, 1929-1943, which is herein incorporated by reference in its entirety). For example, CDEs are a class of regulatory motifs that mediate mRNA degradation through their interaction with Roquin proteins. In particular, CDEs are found in many mRNAs that encode regulators of development and inflammation to limit cytokine production in macrophage (Leppek K et al., 2013, Cell, 153, 869-881, which is herein incorporated by reference in its entirety).

In some aspects, the RNA (e.g., modified mRNA) is auxotrophic. As used herein, the term "auxotrophic" refers to mRNA that comprises at least one feature that triggers, facilitates or induces the degradation or inactivation of the mRNA in response to spatial or temporal cues such that protein expression is substantially prevented or reduced. Such spatial or temporal cues include the location of the mRNA to be translated such as a particular tissue or organ or cellular environment. Also contemplated are cues involving temperature, pH, ionic strength, moisture content and the like.

3' UTR and the AU Rich Elements

3'UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids or mRNA of the disclosure. When engineering specific nucleic acids or mRNA, one or more copies of an ARE can be introduced to make nucleic acids or mRNA of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids or mRNA of the disclosure and protein production can be assayed at various time points post-transfection. For example, cells can be transfected with different ARE-engineering molecules and by using an ELISA kit to the relevant protein and assaying protein produced at about 6 hr, about 12 hr, about 24 hr, about 48 hr, and/or about 7 days post-transfection.

3' UTR and Triple Helices

In some aspects, the nucleotide sequence encoding IL-12 comprises a triple helix on the 3' end of the modified nucleic acid, enhanced nucleotide sequence encoding IL-12 or ribonucleic acid. In some aspects, the 3' end of the nucleotide sequence encoding IL-12 include a triple helix alone or in combination with a Poly-A tail.

In some aspects, the nucleotide sequence encoding IL-12 comprises at least a first and a second U-rich region, a conserved stem loop region between the first and second region and an A-rich region. In some aspects, the first and second U-rich region and the A-rich region associate to form a triple helix on the 3' end of the nucleic acid. This triple helix can stabilize the nucleic acid, enhance the translational efficiency of the nucleic acid and/or protect the 3' end from degradation. Exemplary triple helices include, but are not limited to, the triple helix sequence of metastasis-associated lung adenocarcinoma transcript 1 (MALAT1), MEN-β and polyadenylated nuclear (PAN) RNA (See Wilusz et al., Genes & Development 2012 26:2392-2407; herein incorporated by reference in its entirety).

Stem Loop

In some aspects, the nucleotide sequence encoding IL-12 includes a stem loop such as, but not limited to, a histone stem loop. In some aspects, the stem loop is a nucleotide sequence that is about 25 or about 26 nucleotides in length such as, but not limited to, SEQ ID NOs: 7-17 as described in International Patent Publication No. WO2013103659, herein incorporated by reference in its entirety. The histone stem loop can be located 3' relative to the coding region (e.g., at the 3' terminus of the coding region). As a non-limiting example, the stem loop can be located at the 3' end of a nucleic acid described herein.

In some aspects, the nucleotide sequence encoding IL-12, which comprises the histone stem loop can be stabilized by the addition of at least one chain terminating nucleoside. Not wishing to be bound by theory, the addition of at least one chain terminating nucleoside can slow the degradation of a nucleic acid and thus can increase the half-life of the nucleic acid.

In some aspects, the chain terminating nucleoside is one described in International Patent Publication No. WO2013103659, herein incorporated by reference in its entirety. In some aspects, the chain terminating nucleosides are 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or a —O-methylnucleoside.

In some aspects, the nucleotide sequence encoding IL-12 includes a histone stem loop, a polyA tail sequence and/or a 5' cap structure. In some aspects, the histone stem loop is before and/or after the polyA tail sequence. The nucleic acids comprising the histone stem loop and a polyA tail sequence can include a chain terminating nucleoside described herein.

In some aspects, the nucleotide sequence encoding IL-12 comprises a histone stem loop and a 5' cap structure. The 5' cap structure can include, but is not limited to, those described herein and/or known in the art.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

Modifications to the RNA of the present disclosure can generate a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs can be chemically (i.e. non-enzymatically) or enzymatically synthesized and/linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m7G-3' mppp-G; which can equivalently be designated 3' O-Me-m7G(5')ppp(5')G). The 3'-O atom of the other, unmodified, guanine becomes linked to the 5'-terminal nucleotide of the capped nucleic acid molecule (e.g., an mRNA or mmRNA). The N7- and 3'-O-methylated guanine provides the terminal moiety of the capped nucleic acid molecule (e.g., mRNA or mmRNA).

Another exemplary cap is mCAP, which is similar to ARCA but has a 2'-β-methyl group on guanosine (i.e., N7,2'-O-dimethyl-guanosine-5'-triphosphate-5'-guanosine, m7Gm-ppp-G).

In some aspects, the cap is a dinucleotide cap analog. In some aspects, the dinucleotide cap analog is modified at different phosphate positions with a boranophosphate group or a phosphoroselenoate group such as the dinucleotide cap analogs described in U.S. Pat. No. 8,519,110, the contents of which are herein incorporated by reference in its entirety.

In some aspects, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m3'-OG(5')ppp(5')G cap analog (See e.g., the various cap analogs and the methods of synthesizing cap analogs described in Kore et al. Bioorganic & Medicinal Chemistry 2013 21:4570-4574; the contents of which are herein incorporated by reference in its entirety). In some aspects, a cap analog of the present disclosure is a 4-chloro/bromophenoxyethyl analog.

While cap analogs allow for the concomitant capping of a nucleic acid molecule in an in vitro transcription reaction, up to about 20% of transcripts remain uncapped. This, as well as the structural differences of a cap analog from an endogenous 5'-cap structures of nucleic acids produced by the endogenous, cellular transcription machinery, can lead to reduced translational competency and reduced cellular stability. Accordingly, in some aspects, the methods provided herein (see, e.g., Examples 1-3) are capable of increasing the capping efficiency of the produced IL-12 expressing nucleotides described herein. In some aspects, with the methods provided herein, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 100% of the polynucleotides are capped. In some aspects, with the methods provided herein, at least about 50% of the polynucleotides are capped. In some aspects, at least about 60% of the polynucleotides are capped. In some aspects, at least about 70% of the polynucleotides are capped. In some aspects, at least about 80% of the polynucleotides are capped. In some aspects, at least about 85% of the polynucleotides are capped. In some aspects, at least about 90% of the polynucleotides are capped. In some aspects, at least about 95% of the polynucleotides are capped. In some aspects, about 100% of the polynucleotides are capped. In some aspects, at least about 80% to about 100% of the polynucleotides are capped.

In some aspects, providing an RNA with a 5'-cap or 5'-cap analog is achieved by in vitro transcription of a DNA template in the presence of said 5'-cap or 5'-cap analog, wherein said 5'-cap is co-transcriptionally incorporated into the generated RNA strand, In some aspects, RNA can be generated, for example, by in vitro transcription, and the 5'-cap can be attached to the RNA post-transcriptionally using capping enzymes, for example, capping enzymes of vaccinia virus. In some aspects, the nucleotide sequence encoding IL-12 is capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5' cap structures of the present disclosure are those which, among other things, have enhanced binding of cap binding proteins, increased half-life, reduced susceptibility to 5' endonucleases and/or reduced 5' decapping, as compared to synthetic 5' cap structures known in the art (or to a wild-type, natural or physiological 5' cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. This cap results in a higher translational-competency and cellular stability and a reduced activation of cellular pro-inflammatory cytokines, as compared, e.g., to other 5' cap analog structures known in the art. Cap structures include 7mG(5')ppp(5')N,pN2p, 7mG(5')ppp(5')NlmpNp, 7mG(5')-ppp(5')NlmpN2 mp and m(7)Gpppm(3)(6,6,2')Apm(2')Apm(2')Cpm(2)(3,2')Up.

In some aspects, 5' terminal caps include endogenous caps or cap analogs. In some aspects, a 5' terminal cap comprises a guanine analog. Useful guanine analogs include inosine, N1-methyl-guanosine, 2' fluoro-guanosine, 7-deaza-guanosine, 8-oxo-guanosine, 2-amino-guanosine, LNA-guanosine, and 2-azido-guanosine.

In some aspects, the 5' cap comprises a 5' to 5' triphosphate linkage. In some aspects, the 5' cap comprises a 5' to 5' triphosphate linkage including thiophosphate modification. In some aspects, the 5' cap comprises a 2'-O or 3'-O-ribose-methylated nucleotide. In some aspects, the 5' cap comprises a modified guanosine nucleotide or modified adenosine nucleotide. In some aspects, the 5' cap comprises 7-methylguanylate. Exemplary cap structures include m7G (5')ppp(5')G, m7,2' O-mG(5')ppSp(5')G, m7G(5')ppp(5') 2'O-mG, and m7,3'O-mG(5')ppp(5')2'O-mA.

In some aspects, the nucleotide sequence encoding IL-12 comprises a modified 5' cap. A modification on the 5' cap can increase the stability of mRNA, increase the half-life of the mRNA, and could increase the mRNA translational efficiency. In some aspects, the modified 5' cap comprises one or more of the following modifications: modification at the 2' and/or 3' position of a capped guanosine triphosphate (GTP), a replacement of the sugar ring oxygen (that produced the carbocyclic ring) with a methylene moiety (CH2), a modification at the triphosphate bridge moiety of the cap structure, or a modification at the nucleobase (G) moiety.

The 5' cap structure that can be modified includes, but is not limited to, the caps described in U.S. Application No. 2014/0147454 and WO2018/160540 which is incorporated herein by reference in its entirety.

IRES Sequences

In some aspects, the nucleotide sequence encoding IL-12 comprises an internal ribosome entry site (IRES). First identified as a feature Picorna virus RNA, IRES plays an important role in initiating protein synthesis in absence of the 5' cap structure. An IRES can act as the sole ribosome binding site, or can serve as one of multiple ribosome binding sites of an mRNA. Nucleic acids or mRNA containing more than one functional ribosome binding site can encode several peptides or polypeptides that are translated independently by the ribosomes ("multicistronic nucleic acid molecules"). When nucleic acids or mRNA are provided with an IRES, further optionally provided is a second translatable region. Examples of IRES sequences that can be used according to the disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Terminal Architecture Modifications: Poly-A Tails

During RNA processing, a long chain of adenine nucleotides (poly-A tail) is normally added to a messenger RNA (mRNA) molecules to increase the stability of the molecule. Immediately after transcription, the 3' end of the transcript is cleaved to free a 3' hydroxyl. Then poly-A polymerase adds a chain of adenine nucleotides to the RNA. The process, called polyadenylation, adds a poly-A tail that is between 100 and 250 residues long.

In some aspects, the length of the 3' tail is greater than about 30 nucleotides in length. In some aspects, the poly-A tail is greater than about 35 nucleotides in length. In some aspects, the length is at least about 40 nucleotides. In some aspects, the length is at least about 45 nucleotides. In some aspects, the length is at least about 55 nucleotides. In some aspects, the length is at least about 60 nucleotides. In some aspects, the length is at least 70 nucleotides. In some aspects, the length is at least about 80 nucleotides. In some aspects, the length is at least about 90 nucleotides. In some aspects, the length is at least about 100 nucleotides. In some aspects, the length is at least about 120 nucleotides. In some aspects, the length is at least about 140 nucleotides. In some aspects, the length is at least about 160 nucleotides. In some aspects, the length is at least about 180 nucleotides. In some aspects, the length is at least about 200 nucleotides. In some aspects, the length is at least about 250 nucleotides. In some aspects, the length is at least about 300 nucleotides. In some aspects, the length is at least about 350 nucleotides. In some aspects, the length is at least about 400 nucleotides. In some aspects, the length is at least about 450 nucleotides. In some aspects, the length is at least about 500 nucleotides. In some aspects, the length is at least about 600 nucleotides. In some aspects, the length is at least about 700 nucleotides. In some aspects, the length is at least about 800 nucleotides. In some aspects, the length is at least about 900 nucleotides. In some aspects, the length is at least about 1000 nucleotides. In some aspects, the length is at least about 1100 nucleotides. In some aspects, the length is at least about 1200 nucleotides. In some aspects, the length is at least about 1300 nucleotides. In some aspects, the length is at least about 1400 nucleotides. In some aspects, the length is at least about 1500 nucleotides. In some aspects, the length is at least about 1600 nucleotides. In some aspects, the length is at least about 1700 nucleotides. In some aspects, the length is at least about 1800 nucleotides. In some aspects, the length is at least about 1900 nucleotides. In some aspects, the length is at least about 2000 nucleotides. In some aspects, the length is at least about 2500 nucleotides. In some aspects, the length is at least about 3000 nucleotides.

In some aspects, the nucleotide sequence encoding IL-12 is designed to include a polyA-G Quartet. The G-quartet is a cyclic hydrogen bonded array of four guanine nucleotides that can be formed by G-rich sequences in both DNA and RNA. In this aspect, the G-quartet is incorporated at the end of the poly-A tail. The resultant nucleic acid or mRNA can be assayed for stability, protein production and other parameters including half-life at various time points. It has been discovered that the polyA-G quartet results in protein production equivalent to at least 75% of that seen using a poly-A tail of 120 nucleotides alone.

In some aspects, the nucleotide sequence encoding IL-12 comprises a polyA tail and is stabilized by the addition of a chain terminating nucleoside. In some aspects, the nucleotide sequence encoding IL-12 with a polyA tail further comprise a 5' cap structure.

In some aspects, the nucleotide sequence encoding IL-12 comprises a polyA-G Quartet. In some aspects, the nucleotide sequence encoding IL-12 with a polyA-G Quartet further comprises a 5' cap structure.

In some aspects, the nucleotide sequence encoding IL-12, which comprise a polyA tail or a polyA-G Quartet is stabilized by the addition of an oligonucleotide that terminates in a 3'-deoxynucleoside, 2',3'-dideoxynucleoside 3'-0-methylnucleosides, 3'-0-ethylnucleosides, 3'-arabinosides, and other modified nucleosides known in the art and/or described herein.

Modified Nucleosides

In some aspects, the nucleotide sequence encoding IL-12 comprises one or more modified nucleosides. In some aspects, the one or more modified nucleosides comprises 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, pseudo-uridine, inosine, α-thio-guanosine, 8-oxo-guanosine, 06-methyl-guanosine, 7-deaza-guanosine, N1-methyl adenosine, 2-amino-6-chloro-purine, N6-methyl-2-amino-purine, 6-chloro-purine, N6-methyl-adenosine, α-thio-adenosine, 8-azido-adenosine, 7-deaza-adenosine, pyrrolo-cytidine, 5-methyl-cytidine, N4-acetyl-cytidine, 5-methyl-uridine, 5-iodo-cytidine, and combinations thereof.

In some aspects, one or more uridine in the nucleotide sequence encoding IL-12 is replaced by a modified nucleoside. In some aspects, the modified nucleoside replacing uridine is pseudouridine (ψ), N1-methyl-pseudouridine (m1ψ) or 5-methyl-uridine (m5U).

In some aspects, the nucleotide sequence encoding IL-12 comprises a nucleotide sequence encoding IL-12 as described in U.S. Application Number 2014/0147454, International Application WO2018160540, International Application WO2015/196118, or International Application WO2015/089511, which are incorporated herein by reference in their entirety.

Cytotoxic Nucleosides

In some aspects, the nucleotide sequence encoding IL-12 comprises one or more cytotoxic nucleosides. For example, cytotoxic nucleosides can be incorporated into polynucleotides such as bifunctional nucleotide sequence encoding IL-12s or mRNAs. Cytotoxic nucleoside anti-cancer agents include, but are not limited to, adenosine arabinoside, cytarabine, cytosine arabinoside, 5-fluorouracil, fludarabine, floxuridine, FTORAFUR® (a combination of tegafur and uracil), tegafur ((RS)-5-fluoro-1-(tetrahydrofuran-2-yl)pyrimidine-2,4(1H,3H)-dione), and 6-mercaptopurine.

A number of cytotoxic nucleoside analogues are in clinical use, or have been the subject of clinical trials, as anticancer agents. Examples of such analogues include, but are not limited to, cytarabine, gemcitabine, troxacitabine, decitabine, tezacitabine, 2'-deoxy-2'-methylidenecytidine (DMDC), cladribine, clofarabine, 5-azacytidine, 4'-thio-aracytidine, cyclopentenylcytosine and 1-(2-C-cyano-2-deoxy-beta-D-arabino-pentofuranosyl)-cytosine. Another example of such a compound is fludarabine phosphate. These compounds can be administered systemically and can have side effects which are typical of cytotoxic agents such as, but not limited to, little or no specificity for tumor cells over proliferating normal cells.

A number of prodrugs of cytotoxic nucleoside analogues are also reported in the art. Examples include, but are not limited to, N4-behenoyl-1-beta-D-arabinofuranosylcytosine, N4-octadecyl-1-b eta-D-arab inofuranosyl cytosine, N4-palmitoyl-1-(2-C-cyano-2-deoxy-beta-D-arabino-pentofuranosyl) cytosine, and P-4055 (cytarabine 5'-elaidic acid ester). In general, these prodrugs can be converted into the active drugs mainly in the liver and systemic circulation and display little or no selective release of active drug in the tumor tissue. For example, capecitabine, a prodrug of 5'-deoxy-5-fluorocytidine (and eventually of 5-fluorouracil), is metabolized both in the liver and in the tumor tissue. A series of capecitabine analogues containing "an easily hydrolysable radical under physiological conditions" has been claimed by Fujiu et al. (U.S. Pat. No. 4,966,891) and is herein incorporated by reference. The series described by Fujiu includes N4 alkyl and aralkyl carbamates of 5'-deoxy-5-fluorocytidine and the implication that these compounds will be activated by hydrolysis under normal physiological conditions to provide 5'-deoxy-5-fluorocytidine.

A series of cytarabine N4-carbamates has been by reported by Fadl et al (Pharmazie. 1995, 50, 382-7, herein incorporated by reference in its entirety) in which compounds were designed to convert into cytarabine in the liver and plasma. WO 2004/041203, herein incorporated by reference in its entirety, discloses prodrugs of gemcitabine, where some of the prodrugs are N4-carbamates. These compounds were designed to overcome the gastrointestinal toxicity of gemcitabine and were intended to provide gemcitabine by hydrolytic release in the liver and plasma after absorption of the intact prodrug from the gastrointestinal tract. Nomura et al (Bioorg Med. Chem. 2003, 11, 2453-61, herein incorporated by reference in its entirety) have described acetal derivatives of 1-(3-C-ethynyl-β-D-ribo-pentofuranosyl) cytosine which, on bioreduction, produced an intermediate that required further hydrolysis under acidic conditions to produce a cytotoxic nucleoside compound.

Cytotoxic nucleotides which can be chemotherapeutic also include, but are not limited to, pyrazolo[3,4-D]-pyrimidines, allopurinol, azathioprine, capecitabine, cytosine arabinoside, fluorouracil, mercaptopurine, 6-thioguanine, acyclovir, ara-adenosine, ribavirin, 7-deaza-adenosine, 7-deaza-guanosine, 6-aza-uracil, 6-aza-cytidine, thymidine ribonucleotide, 5-bromodeoxyuridine, 2-chloro-purine, and inosine, or combinations thereof.

Coding Sequences

In some aspects of the disclosure, the nucleotide sequence encoding IL-12 comprises a sequence that encodes an interleukin (IL)-12 molecule. In some aspects, the IL-12 molecule comprises is IL-12, an IL-12 subunit (e.g., IL-12 beta subunit or IL-12 alpha subunit), or a mutant IL-12 molecule that retains immunomodulatory function.

IL-12 is a heterodimeric cytokine with multiple biological effects on the immune system. It is composed of two subunits, p35 (also known as the alpha subunit) and p40 (also known as the beta subunit), which interact to produce the active heterodimer (also referred to as "p'70"). The IL-12 p35 subunit is also known in the art as IL-12α; IL-12A; Natural Killer Cell Stimulatory Factor 1; Cytotoxic Lymphocyte Maturation Factor 1, p35; CLMF P35, NKSF1; CLMF; or NF SK. The IL-12 p40 subunit is also known in the art as IL-12β; IL-12B; Natural Killer Cell Stimulatory Factor 2; Cytotoxic Lymphocyte Maturation Factor 2, P40; CLMF P40; NKSF2; CLMF2; IMD28; or IMD29. Unless indicated otherwise, the term "IL-12" (or a grammatical variant thereof) can refer to IL-12 p35 subunit, IL-12 p40 subunit, or the heterodimeric IL-12 p70.

The wild-type human IL-12 p35 protein is 219 amino acids in length. The wild-type human IL-12 p40 protein is 328 amino acids in length. The amino acid of the wild-type human IL-12 proteins are provided in Table 1 further below.

In some aspects, the IL-12 protein (e.g., encoded by a nucleic acid molecule described herein) comprises an amino acid sequence that is at least about 70%, at least about 75%, at least about 80%, at least about 85%, at least about 90%, at least about 91%, at least about 92%, at least about 93%, at least about 94% at least about 95%, at least about 96%, at least about 97%, at least about 98%, at least about 99%, or about 100% identical to SEQ ID NO: 182.

In some aspects, the IL-12 molecule comprises IL-12α and/or IL-12β subunits. In some aspects, the IL-12α subunit comprises an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identical to SEQ ID NO: 183.

In some aspects, the IL-12β subunit comprises an amino acid sequence that is at least about 70%, at least about 75%, at least about 80%, at least about 85%, at least about 90%, at least about 91%, at least about 92%, at least about 93%, at least about 94% at least about 95%, at least about 96%, at least about 97%, at least about 98%, at least about 99%, or about 100% identical to SEQ ID NO: 184.

As described herein, the nucleic acid molecules of the present disclosure have been codon optimized. Accordingly, in some aspects, the nucleotide sequence encoding an IL-12 protein (e.g., IL-12 p35 subunit, IL-12 p40 subunit, or the heterodimeric IL-12 p'70) disclosed herein differs from that of the wild-type nucleotide sequence (e.g., SEQ ID NO: 185 or SEQ ID NO: 186).

In some aspects, a nucleic acid molecule described herein encodes an IL-12β subunit and comprises a nucleotide sequence that is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in any one of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, or SEQ ID NO: 75. In certain aspects, the nucleotide sequence is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the IL-12β subunit sequence of any of the constructs provided in Table 1.

In some aspects, the nucleic acid molecule encoding the IL-12 p40 subunit comprises a nucleotide sequence that is (i) at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 51; (ii) at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 52; (iii) at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 53; (iv) at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 54; (v) at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 55; (vi) at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 56; (vii) at least 91%, at least 92%, at least 93%, at least 94%, at least 95%, at least 96%, at least 97%, at least 98%, at least 99%, or 100% identical to the sequence set forth in SEQ ID NO: 57; (viii) at least 92%, at least 93%, at least 94%, at least 95%, at least 96%, at least 97%, at least 98%, at least 99%, or 100% identical to the sequence set forth in SEQ ID NO: 58; (ix) at least 91%, at least 92%, at least 93%, at least 94%, at least 95%, at least 96%, at least 97%, at least 98%, at least 99%, or 100% identical to the sequence set forth in SEQ ID NO: 59; (x) at least 91%, at least 92%, at least 93%, at least 94%, at least 95%, at least 96%, at least 97%, at least 98%, at least 99%, or 100% identical to the sequence set forth in SEQ ID NO: 65, 69, or 74; (xi) at least 91%, at least 92%, at least 93%, at least 94%, at least 95%, at least 96%, at least 97%, at least 98%, at least 99%, or 100% identical to the sequence set forth in SEQ ID NO: 66, 70, or 75; (xii) at least 97%, at least 98%, at least 99%, or 100% identical to the sequence set forth in SEQ ID NO: 62; (xiii) at least 99% or 100% identical to the sequence set forth in SEQ ID NO: 63; or (xiv) at least 98%, at least 99%, or 100% identical to the sequence set forth in SEQ ID NO: 64.

In some aspects, the nucleic acid molecule encoding the IL-12β subunit comprises the sequence set forth in SEQ ID NO: 51. In some aspects, the nucleic acid molecule encoding the IL-12β subunit comprises the sequence set forth in SEQ ID NO: 52. In some aspects, the nucleic acid molecule encoding the IL-12β subunit comprises the sequence set forth in SEQ ID NO: 53. In some aspects, the nucleic acid molecule encoding the IL-12β subunit comprises the sequence set forth in SEQ ID NO: 54. In some aspects, the nucleic acid molecule encoding the IL-12β subunit comprises the sequence set forth in SEQ ID NO: 55. In some aspects, the nucleic acid molecule encoding the IL-12β subunit comprises the sequence set forth in SEQ ID NO: 56 In some aspects, the nucleic acid molecule encoding the IL-12β subunit comprises the sequence set forth in SEQ ID NO: 57. In some aspects, the nucleic acid molecule encoding the IL-12β subunit comprises the sequence set forth in SEQ ID NO: 58. In some aspects, the nucleic acid molecule encoding the IL-120 subunit comprises the sequence set forth in SEQ ID NO: 59. In some aspects, the nucleic acid molecule encoding the IL-12β subunit comprises the sequence set forth in SEQ ID NO: 65. In some aspects, the nucleic acid molecule encoding the IL-12β subunit comprises the sequence set forth in SEQ ID NO: 66. In some aspects, the nucleic acid molecule encoding the IL-12β subunit comprises the sequence set forth in SEQ ID NO: 67. In some aspects, the nucleic acid molecule encoding the IL-12β subunit comprises the sequence set forth in SEQ ID NO: 68. In some aspects, the nucleic acid molecule encoding the IL-12β subunit comprises the sequence set forth in SEQ ID NO: 69. In some aspects, the nucleic acid molecule encoding the IL-12β subunit comprises the sequence set forth in SEQ ID NO: 70. In some aspects, the nucleic acid molecule encoding the IL-12β subunit comprises the sequence set forth in SEQ ID NO: 71. In some aspects, the nucleic acid molecule encoding the IL-12β subunit comprises the sequence set forth in SEQ ID NO: 72. In some aspects, the nucleic acid molecule encoding the IL-12β subunit comprises the sequence set forth in SEQ ID NO: 73.

In some aspects, the nucleic acid molecule encoding the IL-12β subunit comprises the sequence set forth in SEQ ID NO: 74. In some aspects, the nucleic acid molecule encoding the IL-120 subunit comprises the sequence set forth in SEQ ID NO: 75. In some aspects, the nucleic acid molecule encoding the IL-12β subunit comprises the sequence set forth in SEQ ID NO: 62. In some aspects, the nucleic acid molecule encoding the IL-12β subunit comprises the sequence set forth in SEQ ID NO: 63. In some aspects, the nucleic acid molecule encoding the IL-12β subunit comprises the sequence set forth in or SEQ ID NO: 64. In some aspects, the nucleic acid molecule encoding the IL-12β subunit comprises the sequence set forth in SEQ ID NO: 60. In some aspects, the nucleic acid molecule encoding the IL-12β subunit comprises the sequence set forth in SEQ ID NO: 61.

In some aspects, a nucleic acid molecule described herein encodes an IL-12 p35 subunit and comprises a nucleotide sequence that is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in any one of SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, or SEQ ID NO: 125. In certain aspects, the nucleotide sequence is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the IL-12α subunit sequence of any of the constructs provided in Table 1.

In some aspects, the nucleic acid molecule encoding the IL-12 p35 subunit comprises a nucleotide sequence that is (i) at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 101; (ii) at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 102; (iii) at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 103; (iv) at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 104; (v) at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 105; (vi) at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 106; (vii) at least 91%, at least 92%, at least 93%, at least 94%, at least 95%, at least 96%, at least 97%, at least 98%, at least 99%, or 100% identical to the sequence set forth in SEQ ID NO: 107; (viii) at least 91%, at least 92%, at least 93%, at least 94%, at least 95%, at least 96%, at least 97%, at least 98%, at least 99%, or 100% identical to the sequence set forth in SEQ ID NO: 108; (ix) at least 92%, at least 93%, at least 94%, at least 95%, at least 96%, at least 97%, at least 98%, at least 99%, or 100% identical to the sequence set forth in SEQ ID NO: 109; (x) at least 91%, at least 92%, at least 93%, at least 94%, at least 95%, at least 96%, at least 97%, at least 98%, at least 99%, or 100% identical to the sequence set forth in SEQ ID NO: 115, 119, or 124; (xi) at least 92%, at least 93%, at least 94%, at least 95%, at least 96%, at least 97%, at least 98%, at least 99%, or 100% identical to the sequence set forth in SEQ ID NO: 116, 120, or 125; (xii) at least 98%, at least 99%, or 100% identical to the sequence set forth in SEQ ID NO: 112; (xiii) at least 98%, at least 99%, or 100% identical to the sequence set forth in SEQ ID NO: 113; or (xiv) at least 98%, at least 99%, or 100% identical to the sequence set forth in SEQ ID NO: 114.

In some aspects, the nucleic acid molecule encoding the IL-12α subunit comprises the sequence set forth in SEQ ID NO: 101. In some aspects, the nucleic acid molecule encoding the IL-12α subunit comprises the sequence set forth in SEQ ID NO: 102. In some aspects, the nucleic acid molecule encoding the IL-12α subunit comprises the sequence set forth in SEQ ID NO: 103. In some aspects, the nucleic acid molecule encoding the IL-12α subunit comprises the sequence set forth in SEQ ID NO: 104. In some aspects, the nucleic acid molecule encoding the IL-12α subunit comprises the sequence set forth in SEQ ID NO: 105. In some aspects, the nucleic acid molecule encoding the IL-12α subunit comprises the sequence set forth in SEQ ID NO: 106. In some aspects, the nucleic acid molecule encoding the IL-12α subunit comprises the sequence set forth in SEQ ID NO: 107. In some aspects, the nucleic acid molecule encoding the IL-12α subunit comprises the sequence set forth in SEQ ID NO: 108. In some aspects, the nucleic acid molecule encoding the IL-12α subunit comprises the sequence set forth in SEQ ID NO: 109. In some aspects, the nucleic acid molecule encoding the IL-12α subunit comprises the sequence set forth in SEQ ID NO: 115. In some aspects, the nucleic acid molecule encoding the IL-12α subunit comprises the sequence set forth in SEQ ID NO: 116. In some aspects, the nucleic acid molecule encoding the IL-12β subunit comprises the sequence set forth in SEQ ID NO: 117. In some aspects, the nucleic acid molecule encoding the IL-12β subunit comprises the sequence set forth in SEQ ID NO: 118. In some aspects, the nucleic acid molecule encoding the IL-12β subunit comprises the sequence set forth in SEQ ID NO: 119]. In some aspects, the nucleic acid molecule encoding the IL-12β subunit comprises the sequence set forth in SEQ ID NO: 120. In some aspects, the nucleic acid molecule encoding the IL-12β subunit comprises the sequence set forth in SEQ ID NO: 121. In some aspects, the nucleic acid molecule encoding the IL-12β subunit comprises the sequence set forth in SEQ ID NO: 122. In some aspects, the nucleic acid molecule encoding the IL-12β subunit comprises the sequence set forth in SEQ ID NO: 123. In some aspects, the nucleic acid molecule encoding the IL-12β subunit comprises the sequence set forth in SEQ ID NO: 124. In some aspects, the nucleic acid molecule encoding the IL-12β subunit comprises the sequence set forth in SEQ ID NO: 125. In some aspects, the nucleic acid molecule encoding the IL-12α subunit comprises the sequence set forth in SEQ ID NO: 112. In some aspects, the nucleic acid molecule encoding the IL-12α subunit comprises the sequence set forth in SEQ ID NO: 113. In some aspects, the nucleic acid molecule encoding the IL-12α subunit comprises the sequence set forth in SEQ ID NO: 114. In some aspects, the nucleic acid molecule encoding the IL-12β subunit comprises the sequence set forth in SEQ ID NO: 110. In some aspects, the nucleic acid molecule encoding the IL-12β subunit comprises the sequence set forth in SEQ ID NO: 111.

In some aspects, the nucleic acid molecule encoding the IL-12 p40 subunit and the nucleic acid molecule encoding the IL-12 p35 subunit can be conjugated to each other. For instance, in some aspects, the present disclosure provides an isolated polynucleotide comprising a first nucleic acid and a second nucleic acid, wherein the first nucleic acid encodes the IL-12 p40 subunit and the second nucleic acid encodes the IL-12 p35 subunit. In some aspects, the IL-12α subunit and the IL-12β subunit are linked by a linker. In some aspects, the linker comprises an amino acid linker of at least about 2, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 amino acids. In some aspects, the linker comprises a (GS) linker. In some aspects, the GS linker has a formula of (Gly3 Ser)n or S(Gly3 Ser)n, wherein n is a positive integer selected from the group consisting of 1, 2, 3, 4, 5, 6, 7, 8, 9, 10, 11, 12, 13, 14, 15, 16, 17, 18, 19, 20, 30, 40, 50, 60, 70, 80, or 100. In some aspects, the (Gly3Ser)n linker is (Gly3Ser)3 or (Gly3 Ser)4.

In some aspects, the first nucleic acid molecule encoding the IL-12β subunit comprises a nucleotide sequence that is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, or SEQ ID NO: 75; and the second nucleic acid molecule encoding the IL-12α subunit comprises a nucleotide sequence that is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the sequence set forth in SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, or SEQ ID NO: 125.

In some aspects, the first nucleic acid molecule encoding the IL-12β subunit comprises a nucleotide sequence that is at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the IL-12β subunit sequence of any of the constructs provided in Table 1; and the second nucleic acid molecule encoding the IL-12a subunit comprises a nucleotide sequence that is at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the IL-12α subunit sequence of any of the constructs provided in Table 1.

In some aspects, (i) the first nucleic acid molecule comprises a nucleotide sequence that is at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 51 and/or the second nucleic acid molecule comprises a nucleotide sequence that is at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 101; (ii) the first nucleic acid molecule comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 52 and/or the second nucleic acid molecule comprises a nucleotide sequence that is at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO:

102; (iii) the first nucleic acid molecule comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 53 and/or the second nucleic acid molecule comprises a nucleotide sequence that is at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 103; (iv) the first nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 54 and/or the second nucleic acid molecule comprises a nucleotide sequence that is at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 104; (v) the first nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 55 and/or the second nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 105; (vi) the first nucleic acid molecule comprises a nucleotide sequence that is at least 87%, at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 56 and/or the second nucleic acid molecule comprises a nucleotide sequence that is at least 88%, at least 89%, at least 90%, at least 91%, at least 92%, at least 93%, at least 94%, at least 95%, at least 96%, at least 97%, at least 98%, at least 99%, or 100% identical to the sequence set forth in SEQ ID NO: 106; (vii) the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 57 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 107; (viii) the first nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 58 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 108; (ix) the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 59 and/or the second nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 109; (x) the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 65, 69, or 74 and/or the second nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 115, 119, or 124; (xi) the first nucleic acid molecule comprises a nucleotide sequence that is at least 91%, at least 92%, at least 93%, at least 94%, at least 95%, at least 96%, at least 97%, at least 98%, at least 99%, or 100% identical to the sequence set forth in SEQ ID NO: 66, 70, or 75 and/or the second nucleic acid molecule comprises a nucleotide sequence that is at least 92%, at least 93%, at least 94%, at least 95%, at least 96%, at least 97%, at least 98%, at least 99%, or 100% identical to the sequence set forth in SEQ ID NO: 116, 120, or 125; (xii) the first nucleic acid molecule comprises a nucleotide sequence that is at least 97%, at least 98%, at least 99%, or 100% identical to the sequence set forth in SEQ ID NO: 62 and/or the second nucleic acid molecule comprises a nucleotide sequence that is at least 98%, at least 99%, or 100% identical to the sequence set forth in SEQ ID NO: 112; (xiii) the first nucleic acid molecule comprises a nucleotide sequence that is at least 99% or 100% identical to the sequence set forth in SEQ ID NO: 63 and/or the second nucleic acid molecule comprises a nucleotide sequence that is at least 98%, at least 99%, or 100% identical to the sequence set forth in SEQ ID NO: 113; or (xiv) the first nucleic acid molecule comprises a nucleotide sequence that is at least 98%, at least 99%, or 100% identical to the sequence set forth in SEQ ID NO: 65 and/or the second nucleic acid molecule comprises a nucleotide sequence that is at least 98%, at least 99%, or 100% identical to the sequence set forth in SEQ ID NO: 115.

In some aspects, the first nucleic acid molecule comprises the sequence set forth in SEQ ID NO: 51 and the second nucleic acid molecule comprises the sequence set forth in SEQ ID NO: 101. In some aspects, the first nucleic acid molecule comprises the sequence set forth in SEQ ID NO: 52 and the second nucleic acid molecule comprises the sequence set forth in SEQ ID NO: 102. In some aspects, In some aspects, the first nucleic acid molecule comprises the sequence set forth in SEQ ID NO: 53 and the second nucleic acid molecule comprises the sequence set forth in SEQ ID NO: 103. In some aspects, In some aspects, the first nucleic acid molecule comprises the sequence set forth in SEQ ID NO: 54 and the second nucleic acid molecule comprises the sequence set forth in SEQ ID NO: 104 In some aspects, the first nucleic acid molecule comprises the sequence set forth in SEQ ID NO: 55 and the second nucleic acid molecule comprises the sequence set forth in SEQ ID NO: 105. In some aspects, the first nucleic acid molecule comprises the sequence set forth in SEQ ID NO: 56 and the second nucleic acid molecule comprises the sequence set forth in SEQ ID NO: 106. In some aspects, the first nucleic acid molecule comprises the sequence set forth in SEQ ID NO: 57 and the second nucleic acid molecule comprises the sequence set forth in SEQ ID NO: 107. In some aspects, the first nucleic acid molecule comprises the sequence set forth in SEQ ID NO: 58 and the second nucleic acid molecule comprises the sequence set forth in SEQ ID NO: 118. In some aspects, the first nucleic acid molecule comprises the sequence set forth in SEQ ID NO: 59 and the second nucleic acid molecule comprises the sequence set forth in SEQ ID NO: 119. In some aspects, the first nucleic acid molecule comprises the sequence set forth in SEQ ID NO: 65 and the second nucleic acid molecule comprises the sequence set forth in SEQ ID NO: 115. In some aspects, the first nucleic acid molecule comprises the sequence set forth in SEQ ID NO: 66 and the second nucleic acid molecule comprises the sequence set forth in SEQ ID NO: 116. In some aspects, the first nucleic acid molecule comprises the sequence set forth in SEQ ID NO: 67 and the second nucleic acid molecule comprises the sequence set forth in SEQ ID NO: 117. In some aspects, the first nucleic acid molecule comprises the sequence set forth in SEQ ID NO: 68 and the second nucleic acid molecule comprises the sequence set forth in SEQ ID NO: 118. In some aspects, the first nucleic acid molecule comprises the sequence set forth in SEQ ID NO: 69 and the second nucleic acid molecule comprises the sequence set forth in SEQ ID NO: 119. In some aspects, the first nucleic acid molecule comprises the sequence set forth in SEQ ID NO: 70 and the second nucleic acid molecule comprises the sequence set forth in SEQ ID NO: 120. In some aspects, the first nucleic acid molecule comprises the sequence set forth in SEQ ID NO: 71 and the second nucleic acid molecule comprises the sequence set forth in SEQ ID NO: 121. In some aspects, the first nucleic acid molecule comprises the sequence set forth in SEQ ID NO: 72 and the second nucleic acid molecule comprises the sequence set forth in SEQ ID NO: 122. In some aspects, the first nucleic acid molecule comprises the sequence set forth in SEQ ID NO: 73 and the second nucleic acid molecule comprises the sequence set forth in SEQ ID NO: 123. In some aspects, the first nucleic acid molecule comprises the sequence set forth in SEQ ID NO: 74 and the second nucleic acid molecule comprises the sequence set forth in SEQ ID NO: 124. In some aspects, the first nucleic acid molecule comprises the sequence set forth in SEQ ID NO: 75 and the second nucleic acid molecule comprises the sequence set forth in SEQ ID NO: 125. In some aspects, the first nucleic acid molecule comprises the sequence set forth in SEQ ID NO: 62 and the second nucleic acid molecule comprises the sequence set forth in SEQ ID NO: 112. In some aspects, the first nucleic acid molecule comprises the sequence set forth in SEQ ID NO: 63 and the second nucleic acid molecule comprises the sequence set forth in SEQ ID NO: 113. In some aspects, the first nucleic acid molecule comprises the sequence set forth in SEQ ID NO: 64 and the second nucleic acid molecule comprises the sequence set forth in SEQ ID NO: 114. In some aspects, the first nucleic acid molecule comprises the sequence set forth in SEQ ID NO: 60 and the second nucleic acid molecule comprises the sequence set forth in SEQ ID NO: 110. In some aspects, the first nucleic acid molecule comprises the sequence set forth in SEQ ID NO: 61 and the second nucleic acid molecule comprises the sequence set forth in SEQ ID NO: 111. In some aspects, the first nucleic acid molecule comprises the IL-120 subunit sequence of any of the constructs provided in Table 1, and the second nucleic acid molecule comprises the IL-12α subunit sequence of any of the constructs provided in Table 1.

TABLE 1

| Description | Sequence |
|---|---|
| Wild-type human IL-12 (i.e., combination of the IL-12α and IL-12β subunits) (amino acid sequence) (SEQ ID NO: 182) (signal peptides for the subunits are in lower case) | mcparslllvatlvlldhlslaRNLPVATPDPGMFPCLHHSQNLLRAVSNMLQKARQTLEF<br>YPCTSEEIDHEDITKDKTSTVEACLPLELTKNESCLNSRETSFITNGSCLASRKTSFMMAL<br>CLSSIYEDLKMYQVEFKTMNAKLLMDPKRQIFLDQNMLAVIDELMQALNFNSETVPQKSSL<br>EEPDFYKTKIKLCILLHAFRIRAVTIDRVMSYLNASmchqqlviswfslvflasplvaIWE<br>LKKDVYVVELDWYPDAPGEMVVLTCDTPEEDGITWTLDQSSEVLGSGKTLTIQVKEFGDAG<br>QYTCHKGGEVLSHSLLLLHKKEDGIWSTDILKDQKEPKNKTFLRCEAKNYSGRFTCWWLTT<br>ISTDLTFSVKSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPDTWSTPHSYF<br>SLTFCVQVQGKSKREKKDRVFTDKTSATVICRKNASISVRAQDRYYSSSWSEWASVPCS |
| Wild-type human IL-12α subunit (signal peptide is in lower case) (SEQ ID NO: 183) | mcparslllvatlvlldhlslaRNLPVATPDPGMFPCLHHSQNLLRAVSNMLQKARQTLEF<br>YPCTSEEIDHEDITKDKTSTVEACLPLELTKNESCLNSRETSFITNGSCLASRKTSFMMAL<br>CLSSIYEDLKMYQVEFKTMNAKLLMDPKRQIFLDQNMLAVIDELMQALNFNSETVPQKSSL<br>EEPDFYKTKIKLCILLHAFRIRAVTIDRVMSYLNAS |
| Wild-type human IL-12β subunit (signal peptide is in lower case) (SEQ ID NO: 184) | mchqqlviswfslvflasplvaIWELKKDVYVVELDWYPDAPGEMVVLTCDTPEEDGITWT<br>LDQSSEVLGSGKTLTIQVKEFGDAGQYTCHKGGEVLSHSLLLLHKKEDGIWSTDILKDQKE<br>PKNKTFLRCEAKNYSGRFTCWWLTTISTDLTFSVKSSRGSSDPQGVTCGAATLSAERVRGD<br>NKEYEYSVECQEDSACPAAEESLPIEVMVDAVHKLKYENYTSSFFIRDIIKPDPPKNLQLK<br>PLKNSRQVEVSWEYPDTWSTPHSYFSLTFCVQVQGKSKREKKDRVFTDKTSATVICRKNAS<br>ISVRAQDRYYSSSWSEWASVPCS |
| L1 construct (SEQ ID NO: 1)-includes (1) leader sequence (lower case; SEQ ID NO: 26); (2) IL-12β (bolded and underlined; SEQ ID NO: 51); (3) first GS linker (italicized; SEQ ID NO: 76); (4) IL-12α (bolded; SEQ ID NO: 101); (5) second GS linker | atgcgagttcctgctcagctgcttggtctgttactgctgtggttgccgggcgcacgatgtg<br>ct**ATCTGGGAATTAAAGAAAGATGTGTACGTGGTGGAATTGGATTGGTACCCAGATGCTCC**<br>**GGGCGAAATGGTTGTACTCACATGCGATACTCCGGAGGAAGACGGTATCACTTGGACATTG**<br>**GATCAGTCGAGTGAGGTTCTCGGTAGTGGTAAAACACTAACGATCCAAGTCAAAGAATTCG**<br>**GTGATGCGGGGCAATATACCTGTCATAAAGGCGGCGAAGTACTATCTCATAGCCTCCTGCT**<br>**GTTACACAAGAAGGAAGATGGCATATGGTCCACCGACATCCTTAAGGATCAGAAAGAACCC**<br>**AAGAACAAAACTTTCTTGCGTTGCGAAGCTAAGAACTACTCCGGCCGCTTCACATGCTGGT**<br>**GGTTGACAACGATCAGTACGGATCTAACCTTCTCTGTTAAGTCCAGTCGGGGGAGTTCGGA**<br>**CCCCCAAGGCGTCACGTGTGGAGCTGCCACACTTTCCGCTGAGCGCGTACGTGGAGATAAT**<br>**AAAGAGTATGAATACTCCGTTGAGTGCCAGGAGGACTCCGCGTGCCCCGCTGCCGAGGAGA**<br>**GTCTCCCCATAGAGGTGATGGTCGACGCTGTTCACAAACTGAAATATGAGAACTATACCTC**<br>**ATCCTTCTTTATACGTGACATAATTAAGCCAGATCCCCCGAAGAACTTACAATTGAAACCA**<br>**TTGAAGAATTCACGTCAAGTCGAGGTATCCTGGGAGTATCCCGACACCTGGTCCACGCCAC**<br>**ACTCATATTTCTCTCTGACCTTCTGTGTGCAGGTACAAGGCAAGAGCAAACGAGAAAAAAA** |

TABLE 1-continued

| Description | Sequence |
|---|---|
| (italicized and underlined; SEQ ID NO: 126); and (6) albumin (lower case and underlined; SEQ ID NO: 147) | GGACAGAGTTTTCACGGATAAGACTAGCGCCACAGTGATATGTAGGAAAAACGCATCGATC<br>TCAGTCCGCGCGCAAGATCGGTATTACTCAAGCAGTTGGTCAGAGTGGGCATCGGTGCCCT<br>GCTCGGGGGGTTCTGGTGGGGCAGTGGAGGAGGATCAGGTGGCGGCAGTCGCAATCTACC<br>CGTGGCAACACCAGACCCGGGAATGTTCCCATGTCTGCACCACAGTCAAAACCTCTTAAGG<br>GCCGTGTCAAATATGCTACAGAAGGCGAGACAGACTTTAGAATTCTACCCTTGTACAAGCG<br>AGGAGATTGACCACGAGGACATCACCAAAGATAAGACGAGCACCGTCGAGGCTTGCCTGCC<br>TCTAGAACTAACAAAAAATGAATCATGCTTGAACTCGAGGGAGACCAGTTTCATTACTAAC<br>GGTTCATGTCTTGCATCGAGGAAGACCTCATTCATGATGGCCCTGTGCCTCTCGTCCATTT<br>ATGAAGACCTAAAGATGTACCAGGTAGAGTTTAAGACCATGAACGCCAAGCTCCTCATGGA<br>TCCAAAACGGCAAATATTCTTAGATCAGAATATGCTCGCTGTTATCGACGAACTCATGCAG<br>GCGCTTAACTTCAACTCAGAAACCGTTCCCCAAAAGTCGAGTCTAGAAGAACCGGACTTTT<br>ATAAGACCAAAATTAAACTGTGTATACTACTTCACGCCTTCAGGATAAGAGCAGTGACGAT<br>TGACAGGGTGATGTCCTACTTGAATGCATCAGGATCAGGGGGAGGCTCGgacgcccataag<br>agcgaagtcgcccaccgcttcaaggatttgggtgaggaaaacttcaaagccctggtcctga<br>tagcgtttgcccaatatttgcagcagtgtccattcgaagatcacgtgaaattggtgaacga<br>ggtaacagaatttgctaagacttgtgtggctgacgagtcggccgaaaactgtgataagagt<br>cttcatacactgtttggcgataagctatgtactgtcgctacacttagggagacttacggtg<br>agatggccgactgctgcgccaagcaagagccagaacgaaacgagtgttttctgcaacataa<br>ggacgacaatcccaacctgcccagattggttcgccctgaagttgatgttatgtgcaccgca<br>tttcacgacaacgaagaaacctttcttaaaaagtatctgtacgagatagctcgacgtcacc<br>cttacttctacgcgcccgaacttctgtttttcgccaagcgatacaaagccgctttcacaga<br>gtgttgccaagctgccgacaaagccgcttgccttctaccaaagcttgacgagctcagagat<br>gaagggaaagctagttcggcaaagcaacgattaaagtgtgcatcactgcaaaaattcggcg<br>aacgagcctttaaagcatgggcagttgccaggttatcccaaaggttcccgaaagctgaatt<br>cgctgaggtgagcaagttagtcacggaccttacgaaggtacataccgaatgctgccacggg<br>gacctcttggagtgcgctgacgacagggcggacttagctaaatacatttgcgagaatcagg<br>actcaatcagttctaaacttaaagaatgctgcgagaaaccgctcctggaaaaatcacattg<br>catcgccgaggtggaaaacgatgagatgccagcagatttaccatctctagccgccgacttc<br>gtggaaagtaaggatgtgtgtaaaaactatgcggaagcaaaagacgtgttcctcggaatgt<br>ttctatacgaatacgctagaaggcatcctgactattctgtcgttttactgcttagactagc<br>gaagacatatgaaacgacgttagagaaatgctgcgcggccgctgaccccccacgaatgttac<br>gcgaaggtctttgatgagttcaagcccctggttgaggagccgcaaaaccttattaaacaga<br>attgtgagctatttgagcagttaggcgaatataaattccagaatgcacttctagtacgata<br>caccaaaaaggtccctcaagtgagcaccccccactcttgtggaggtatccagaaatctagga<br>aaggtaggctctaaatgctgcaagcatcccgaagccaagagaatgccatgcgctgaagact<br>accttagcgttgttctgaatcagttgtgtgtccttcacgaaaagacgccggtgagtgatcg<br>tgtcacgaagtgctgtacagagagcctcgtcaaccgtaggccatgtttctccgctctcgag<br>gtggatgaaacatatgtacctaaggaatttaatgcggaaactttcacctttcacgcggaca<br>tctgtaccctgagcgagaaggagaggcagataaaaaagcagacggctcttgtagagttggt<br>caaacataagcctaaggccactaaagagcagctaaaggcagtaatggacgactttgcggct<br>ttcgttgagaagtgctgcaaggccgacgataaagagacctgtttcgcggaagaaggtaaaa<br>agttagtggccgcctcccaggcggccctgggcctgtag |
| L2 Construct (SEQ ID NO: 2)-includes (1) leader sequence (lower case; SEQ ID NO: 27); (2) IL-12β (bolded and underlined; SEQ ID NO: 52); (3) first GS linker (italicized; SEQ ID NO: 77); (4) IL-12α (bolded; SEQ ID NO: 102); (5) second GS linker (italicized and underlined; SEQ ID NO: 127); and (6) albumin (lower case and underlined; SEQ ID NO: 148) | atgcgcgtgcccgcacaattgctcggactgctgctactgtggctgcccggggctcgctgcg<br>caATTTGGGAACTTAAGAAGGACGTATACGTTGTGGAACTTGACTGGTACCCTGATGCTCC<br>AGGGGAGATGGTGGTTTTGACGTGTGACACCCCGGAAGAAGATGGAATTACATGGACCTTA<br>GACCAATCCTCCGAGGTTCTTGGCTCGGGCAAAACCTTGACCATTCAGGTCAAGGAATTTG<br>GCGATGCTGGCCAATACACCTGCCATAAAGGTGGTGAAGTTTTATCTCACTCCCTACTGTT<br>GCTCCATAAGAAAGAAGACGGCATTTGGTCGACAGACATATTGAAGGATCAGAAGGAACCT<br>AAGAATAAGACCTTCTTACGATGTGAGGCCAAGAATTATTCCGGACGTTTTACGTGTTGGT<br>GGTTGACCACGATCTCCACTGACTTAACCTTCTCAGTGAAATCCTCACGAGGTAGTTCCGA<br>TCCCCAGGGTGTGACGTGCGGTGCGGCCACGTTAAGTGCTGAGAGAGTACGGGGCGACAAT<br>AAGGAATACGAGTACTCAGTTGAATGCCAAGAGGACTCGGCCTGTCCCGCGGCAGAGGAGA<br>GTCTCCCTATCGGAGTGATGGTGGATGCGGTGCACAAGCTCAAGTATGAAAATTACACATC<br>ATCTTTTTTCATCAGAGACATTATAAAGCCCGACCCACCAAAGAACCTCCAGTTAAAGCCC<br>TTAAAGAACAGTAGACAGGTTGAAGTATCATGGGAATACCCAGACACCTGGTCCACACCCC<br>ATTCGTATTTTTCCTTGACGTTTTGCGTACAAGTTCAGGGAAAGTCCAAACGGAAAAGAA<br>AGACCGCGTTTTTACAGACAAAACTTCTGCCACTGTCATCTGTAGAAAGAACGCATCAATT<br>AGCGTGCGAGCGCAAGACAGATACTATTCAAGTAGCTGGAGCGAGTGGGCCAGTGTTCCAT<br>GTTCTGGCGGTTCGGGCGGAGGGTCCGGCGGTGGTAGCGGAGGCGGGAGCAGGAACTTGCC<br>CGTGGCTACTCCAGACCCTGGCATGTTCCCCTGTTTACACCACTCCCAGAACTTATTACGT<br>GCTGTTAGCAACATGTTGCAAAAGGCCCGTCAAACCCTCGAGTTTTACCCCTGTACTAGTG<br>AAGAAATCGACCACGAAGACATAACAAAAGACAAGACAAGCACAGTTGAGGCATGCTTACC<br>CCTGGAGTTAACAAAGAACGAGAGCTGTCTGAACTCTCGAGAGACGAGCTTCATCACCAAT<br>GGGAGTTGCCTTGCTTCTCGAAAAACGTCGTTCATGATGGCCCTGTGCCTGTCGTCTATCT<br>ATGAGGATCTGAAAATGTATCAGGTTGAATTCAAGACAATGAATGCCAAACTACTCATGGA<br>TCCAAAACGGCAGATATTCCTCGATCAGAATATGCTCGCAGTTATTGACGAACTAATGCAG<br>GCTCTGAATTTTAACAGCGAGACCGTTCCTCAGAAGTCAAGTTTGGAAGAACCTGACTTCT<br>ACAAAACTAAAATAAAATTATGCATCTTACTGCATGCTTTCAGAATTAGAGCTGTCACTAT<br>TGATCGAGTGATGTCATACTTGAATGCTTCCGGATCAGGAGGTGGGAGCgacgcgcacaaa<br>agcgaggtagcgcatcgctttaaagacttaggagaggaaaactttaaggcgctggtgctca<br>tcgcatttgcccaatacttacagcagtgtccttttgaggaccacgtaaagcttgtaaacga<br>agtcactgaattcgccaagacatgtgttgctgacgaaagcgcagagaactgtgacaaaagc<br>cttcataccctctttggtgacaaactctgcaccgtggcaactctaagagaaacctacgggg<br>aaatggcagactgctgcgcaaagcaggaacccgaacgcaatgagtgtttcctgcagcacaa<br>ggatgataatcccaatctgccacgacttgtacggccggaggtagatgttatgtgcactgct<br>tttcatgacaacgaggaaactttccttaagaaatatctgtatgagatcgcaaggcggcacc<br>cttacttctacgcacccgaactgttgtttttcgcaaagaggtataaggccgcatttaccga |

TABLE 1-continued

| Description | Sequence |
|---|---|
| | gtgttgtcaggccgctgataaagccgcctgtcttttgccaaaattagatgaactaagggac<br>gaaggcaaagcgagtagcgccaaacaaagattaaaatgtgcaagcctccaaaaattcggtg<br>aaagagcatttaaggcgtgggctgtcgcccgactttcacaacgcttccccaaagctgaatt<br>cgctgaggtttcgaagctggttaccgacctaactaaagtgcatacagagtgctgtcatggg<br>gatctcttagagtgcgcggatgaccgggcagacctggctaagtacatatgtgagaaccagg<br>acagtatatcatcaaagctgaaagagtgttgtgagaagccactactcgagaagagtcactg<br>tattgccgaggtggaaaatgatgagatgccagccgatcttccttctttggccgctgacttt<br>gtagagagcaaggatgtctgtaagaactacgctgaggccaaggatgtctttttggggatgt<br>tcctctatgagtacgcccgacgacaccctgactatagtgtagtacttttgcttagactggc<br>taaaacatatgagacgactctcgaaaagtgctgtgccgctgccgatccacacgagtgctac<br>gctaaggtgtttgatgagtttaagccgctggtggaggaaccccagaacctgatcaagcaga<br>actgtgaactattcgagcaactaggggagtacaaattccagaacgcacttttagtgcggta<br>caccaaaaaagtgccacaggtcagtacaccaacattagtggaagtatccaggaacctgggc<br>aaagtgggcagcaaatgctgcaaacatccggaggctaagcggatgccctgtgcagaggact<br>acctgtccgtggtgcttaaccagctgtgtgtgcttcacgagaaaacgcctgtgtccgaccg<br>ggtgaccaagtgctgtacggagtcactggtaaatcgacgaccgtgtttttcagcactagaa<br>gttgatgaaacttatgtaccgaaagagtttaacgcagagacctttacattccacgccgaca<br>tctgcacgctgtccgagaaggaaagacagattaaaaagcagactgccctagtcgagcttgt<br>caaacacaaaccgaaggcaaccaaggaacagttaaaagcagtgatggatgattttgctgcg<br>ttcgtcgaaaaatgttgcaaagcggacgacaaggagacttgcttcgcagaggaagggaaga<br>aattggttgcggcgtcccaagcggccttagggctatag |
| L3 Construct (SEQ ID NO: 3)-includes (1) leader sequence (lower case; SEQ ID NO: 28); (2) IL-12β (bolded and underlined; SEQ ID NO: 53); (3) first GS linker (italicized; SEQ ID NO: 78); (4) IL-12α (bolded; SEQ ID NO: 103); (5) second GS linker (italicized and underlined; SEQ ID NO: 128); and (6) albumin (lower case and underlined; SEQ ID NO: 149) | atgagagttcctgctcaactactagggctgctgttgttgtggttgcccggcgcgcgatgcg<br>caATATGGGAGCTCAAGAAGGACGTTTATGTCGTTGAGCTGGATTGGTACCCTGATGCCCC<br>GGGCGAAATGGTTGTGCTTACGTGCGATACCCCCGAGGAGGATGGCATAACATGGACGTTA<br>GATCAGTCTTCCGAGGTCCTTGGTTCCGGTAAGACTCTTACTATCCAGGTGAAGGAGTTCG<br>GCGATGCCGGCCAGTACACTTGCCATAAAGGCGGTGAAGTTCTAAGCCACTCTCTACTGCT<br>TTTGCACAAGAAGGAAGATGGAATATGGTCCACCGACATCTTGAAGGACCAGAAAGAACCA<br>AAAAATAAGACATTTTTGAGGTGTGAGGCAAAAAATTATTCGGGACGCTTCACCTGCTGGT<br>GGTTGACGACGATTTCAACCGACCTCACCTTCTCAGTAAAGAGTTCGAGAGGTAGTTCCGA<br>TCCCCAAGGTGTGACATGTGGCGCTGCGACTCTAAGCGCTGAACGCGTAAGAGGTGATAAC<br>AAAGAGTACGAATACAGTGTGGAATGCCAAGAAGATAGCGCGTGTCCAGCCGCAGAAGAAT<br>CTTTACCAATAGAGGTTATGGTTGATGCCGTTCACAAATTGAAATATGAGAATTACACCTC<br>AAGCTTTTTCATTCGAGACATAATAAAGCCCGACCCTCCTAAGAATCTTCAGTTAAAACCG<br>CTGAAGAACAGTAGACAAGTTGAGGTTAGCTGGGAATATCCTGATACCTGGTCAACGCCGC<br>ACTCGTATTTCTCCCTGACTTTCTGTGTTCAGGTTCAAGGAAAATCTAAAAGGGAGAAGAA<br>AGACCGTGTTTTCACCGACAAGACATCTGCCACAGTCATATGTAGGAAGAACGCTTCAATC<br>AGCGTGCGAGCGCAGGACCGATACTACAGCTCTAGTTGGTCCGAATGGGCCAGCGTACCAT<br>GCTCTGGCGGTTCCGGCGGGGGCTCGGGGGGCGGGAGCGGTGGAGGCAGCAGGAATCTTCC<br>TGTCGCGACCCCTGATCCCGGCATGTTTCCTTGCCTGCACCACAGTCAGAACTTATTACGC<br>GCCGTTTCCAATATGTTACAGAAGGCCAGACAGACATTAGAGTTTTATCCTTGCACATCGG<br>AGGAGATCGACCATGAAGATATCACAAAAGATAAAACATCCACCGTTGAGGCCTGCCTGCC<br>ACTTGAACTTACTAAAAACGAGAGCTGCCTGAATAGCCGGGAAACTTCTTTCATCACTAAT<br>GGATCGTGTCTAGCAAGCCGAAAAACCAGCTTCATGATGGCTTTGTGCCTCTCGTCCATCT<br>ATGAAGACCTGAAAATGTATCAAGTAGAATTTAAAACGATGAATGCCAAACTGCTTATGGA<br>TCCCAAACGCCAGATATTTCTAGACCAGAATATGCTGGCCGTCATTGATGAGCTAATGCAG<br>GCTCTCAATTTTAATAGCGAAACAGTGCCCCAAAAAAGCTCTTTGGAAGAGCCGGATTTTT<br>ACAAAACCAAGATTAAGCTATGTATCCTGCTGCATGCTTTCAGAATTCGAGCTGTTACAAT<br>TGATCGGGTTATGAGCTACTTAAACGCCTCGGGTAGTGGCGGGGGGAGCgacgcccacaag<br>tctgaagtggcacaccggttcaaggacctcggggaggagaattttaaagccctcgtgctga<br>tcgctttcgcgcagtacttgcagcagtgcccctttgaggaccatgtcaaattagtaaacga<br>agtgacggaattcgcaaagacttgcgtagcggatgagtcagcagagaattgcgacaagtcg<br>ctacacactctgttcggggataagttgtgcacagttgctaccttacgagagacctatggag<br>agatggctgactgctgcgccaaacaagagcctgaaagaaacgagtgcttcttacaacacaa<br>agacgataacccgaatttgccaaggcttgtaagacccgaagtagatgttatgtgcacagct<br>tttcacgacaacgaggagacgttccttaagaaatatctgtatgaaatagcccgtcggcacc<br>cctatttttatgctcccgaactattgttcttcgccaaacgatacaaggctgcgttcactga<br>gtgctgtcaggctgcagacaaagcagcctgcttgcttcccaaattggacgaactacgggac<br>gaaggtaaggcgagctccgcaaaacagcggttgaaatgcgcgtcactacagaagtttgggg<br>aaagagcgttcaaagcttgggctgtggcacgattgagccaacgcttccccaaagcagagtt<br>tgcggaagtttcgaaactcgtgacagacttaacaaaggttcacaccgagtgctgtcacggc<br>gatctgctcgaatgcgctgatgaccgcgctgacttggctaaatacatttgtgagaaccagg<br>actctatatcgagcaaactcaaggaatgctgcgaaaagcccctgcttgagaagtcccactg<br>catcgctgaggtagagaatgatgagatgcctgcggatcttccgagtttagcagctgatttc<br>gtcgagagcaaagatgtgtgcaaaaattatgccgaagcaaaagacgtatttcttgggatgt<br>tcttatacgagtatgcacggcgccacccagattactccgtagtgctactgttaagattggc<br>gaagacctatgaaaccacattggaaaagtgctgcgccgccgccgaccccccacgagtgttac<br>gcgaaggtgttcgatgaatttaaaccgcttgttgaggagccgcaaaacctaataaagcaaa<br>actgtgagctctttgagcaactaggtgaatacaagtttcagaatgcactcctagttcggta<br>caccaaaaaagtacctcaggtatctacgccaacgttagtcgaggtctcgcggaatttgggt<br>aaagtaggttccaagtgttgcaaacacccggaagctaaacgtatgccgtgtgctgaggact<br>atctcagcgttgtgttaaaccaactttgcgtactccacgagaaaacacctgtctcagatcg<br>ggtaaccaaatgctgcacggagtcgctagtaaatcgtcgcccatgcttttctgcgttagag<br>gtggacgaaacttatgtaccgaaagaatttaacgcggaaacctttacattccatgcagata<br>tctgtacactgtccgagaaagagagacagattaagaaacagacggcgctggtggagcttgt<br>gaagcacaagcctaaagctacgaaggagcaactgaaggcagtcatggatgactttgcggcg<br>tttgtggagaagtgctgtaaagcggacgataaggaaacatgcttcgcagaagaaggaaaga<br>agctggtcgccgctagccaagcggctctgggcctgtag |

TABLE 1-continued

| Description | Sequence |
|---|---|
| M1 Construct (SEQ ID NO: 4)-includes (1) leader sequence (lower case; SEQ ID NO: 29); (2) IL-12β (bolded and underlined; SEQ ID NO: 54); (3) first GS linker (italicized; SEQ ID NO: 79); (4) IL-1α (bolded; SEQ ID NO: 104); (5) second GS linker (italicized and underlined; SEQ ID NO: 129); and (6) albumin (lower case and underlined; SEQ ID NO: 150) | atgagagtccccgcccagctgctggggcttcttttgctttggcttcctggcgcaagatgcg<br>ca**ATATGGGAGCTCAAGAAGGACGTTTATGTCGTTGAGCTGGATTGGTACCCTGATGCCCC**<br>**GGGCGAAATGGTTGTGCTTACGTGCGATACCCCCGAGGAGGATGGCATAACATGGACGTTA**<br>**GATCAGTCTTCCGAGGTCCTTGGTTCCGGTAAGACTCTTACTATCCAGGTGAAGGAGTTCG**<br>**GCGATGCCGGCCAGTACACTTGCCATAAAGGCGGTGAAGTTCTAAGCCACTCTCTACTGCT**<br>**TTTGCACAAGAAGGAAGATGGAATATGGTCCACCGACATCTTGAAGGACCAGAAAGAACCA**<br>**AAAAATAAGACATTTTTGAGGTGTGAGGCAAAAAATTATTCGGGACGCTTCACCTGCTGGT**<br>**GGTTGACGACGATTTCAACCGACCTCACCTTCTCAGTAAAGAGTTCGAGAGGTAGTTCCGA**<br>**TCCCCAAGGTGTGACATGTGGCGCTGCGACTCTAAGCGCTGAACGCGTAAGAGGTGATAAC**<br>**AAAGAGTACGAATACAGTGTGGAATGCCAAGAAGATAGCGCGTGTCCAGCCGCAGAAGAAT**<br>**CTTTACCAATAGAGGTTATGGTTGATGCCGTTCACAAATTGAAATATGAGAATTACACCTC**<br>**AAGCTTTTTCATTCGAGACATAATAAAGCCCGACCCTCCTAAGAATCTTCAGTTAAAACCG**<br>**CTGAAGAACAGTAGACAAGTTGAGGTTAGCTGGGAATATCCTGATACCTGGTCAACGCCGC**<br>**ACTCGTATTTCTCCCTGACTTTCTGTGTTCAGGTTCAAGGAAAATCTAAAAGGGAGAAGAA**<br>**AGACCGTGTTTTCACCGACAAGACATCTGCCACAGTCATATGTAGGAAGAACGCTTCAATC**<br>**AGCGTGCGAGCGCAGGACCGATACTACAGCTCTAGTTGGTCCGAATGGGCCAGCGTACCAT**<br>**GCTCT***GGCGGCAGCGGCGGCGGGAGCGGCGGAGGCTCCGGGGGAGGTAGC***CGGAATCTGCC**<br>**TGTCGCCACTCCAGACCCCGGCATGTTCCCATGTCTGCATCATTCTCAGAACCTGCTGAGG**<br>**GCCGTATCCAATATGCTGCAGAAAGCCAGACAGACCTTAGAGTTCTATCCCTGTACAAGCG**<br>**AGGAGATAGATCACGAGGATATTACGAAGGACAAAACTTCTACTGTTGAGGCGTGTCTTCC**<br>**ATTAGAGCTGACCAAGAACGAAAGCTGTCTGAATAGCAGAGAGACTTCATTTATCACCAAT**<br>**GGGAGTTGCTTGGCTAGCAGAAAGACCAGCTTCATGATGGCCCTTTGCTTGTCTTCGATAT**<br>**ACGAAGATCTTAAGATGTATCAAGTGGAATTTAAGACGATGAACGCCAAGCTGCTTATGGA**<br>**TCCCAAGCGCCAAATCTTCCTGGATCAGAACATGTTGGCCGTGATTGACGAGCTGATGCAA**<br>**GCCCTGAATTTCAACTCCGAGACCGTGCCTCAGAAGAGCAGCCTCGAGGAGCCCGACTTCT**<br>**ACAAAACAAAGATCAAACTCTGCATCCTTCTGCACGCCTTCAGAATTAGAGCCGTGACCAT**<br>**CGACAGAGTTATGAGCTACCTGAATGCCAGC***GGCAGCGGCGGCGGATCC*gatgcccataaa<br>tctgaggtggcccatagattcaaggatctgggcgaagaaaacttcaaagccttggtcttga<br>tcgcctttgcccagtacctgcagcagtgcccctttgaggaccacgtgaagctggtgaatga<br>agtgaccgagtttgccaagacgtgcgtggctgatgagagcgccgaaaactgcgacaaaagc<br>ctgcacaccctgtttggcgacaagctgtgcaccgtagccaccctgagagaaacttacggcg<br>agatggctgactgctgcgccaagcaggagcccgagagaaacgagtgctttctgcagcacaa<br>ggacgacaatcccaacctgcccagactggtgagacccgaagtggatgttatgtgcaccgct<br>ttccacgacaatgaagagacatttctcaagaagtacttgtacgagattgcaagaagacacc<br>cttacttttacgcccccgaattactgttcttcgctaagaggtataaggcagccttcactga<br>atgctgccaggctgccgacaaagcagcttgcctgctgccaaagctggatgaactgcgagac<br>gaaggaaaggcgtcctccgccaagcagcgtttgaagtgcgccagccttcagaagtttggcg<br>agcgggccttcaaggcatgggccgtggctcgacttagccagcgttttcccaaggctgaatt<br>tgcagaggtgagtaaactggttaccgatctgacaaaggtgcacaccgagtgctgtcacggt<br>gacctcttagagtgcgccgacgacagagccgacctcgccaagtacatttgtgaaaaccaag<br>actcaatctcttcaaagttaaaggagtgctgcgaaaagcccctgcttgaaaagagccactg<br>cattgccgaagtcgagaatgatgagatgcctgcagacttgcccagcttggcagccgacttc<br>gttgagtctaaggacgtgtgcaagaattacgccgaggcaaaagacgtgttcctgggcatgt<br>tcctttatgagtacgctagaagacatcccgactacagcgtggtccttctccttaggctcgc<br>taagacttacgagacgacgttggagaagtgttgtgccgctgcggacccccacgagtgctat<br>gccaaagtgttcgatgagtttaaacccctggtggaggaacctcagaaccttatcaagcaga<br>attgtgagttgttcgaacagctaggcgagtacaagttccagaatgccctgctggtgagata<br>cacaaaaaaggtgccccaggtgtcaaccccgaccttagtggaagtgtccagaaacctgggc<br>aaggtgggcagcaagtgctgcaagcaccccgaagctaagagaatgccgtgcgcggaggatt<br>acctgagcgtggtgctcaaccagctgtgtgtgcttcacgagaaaacacccgtgagcgacag<br>ggtgacaaaatgttgcacagaaagccttgtgaaccggagaccttgtttcagcgccctggag<br>gttgacgagacctatgttcctaaggagttcaacgctgagactttcacatttcacgctgata<br>tatgtaccctgagcgagaaagaaagacagatcaagaagcagaccgccctggtcgagctggt<br>gaaacacaagcctaaggccacgaaggagcagctgaaggccgtcatggacgacttcgcagcc<br>ttcgtcgagaaatgctgcaaagccgacgacaaggaaacctgcttcgccgaagagggaaaga<br>agctggtggccgcctcccaggccgcccttgggctctag |
| M2 Construct (SEQ ID NO: 5)-includes (1) leader sequence (lower case; SEQ ID NO: 30); (2) IL-12β (bolded and underlined; SEQ ID NO: 55); (3) first GS linker (italicized; SEQ ID NO: 80); (4) IL-12α (bolded; SEQ ID NO: 105); (5) second GS linker (italicized and underlined; SEQ ID NO: 130); and (6) albumin (lower case and underlined; SEQ ID NO: 151) | atgagagtccccgcccagctgctagggctgctgctgctgtggttacccggcgcccggtgtg<br>ca**ATTTGGGAGTTGAAGAAGGACGTGTACGTGGTGGAGCTGGACTGGTACCCGGATGCTCC**<br>**CGGCGAGATGGTGGTACTCACCTGCGACACACCTGAGGAAGACGGCATCACCTGGACCCTC**<br>**GATCAGAGCAGCGAGGTTCTGGGAAGCGGCAAAACCCTGACCATCCAAGTGAAAGAGTTTG**<br>**GCGACGCCGGTCAGTACACCTGCCACAAGGGAGGCGAGGTCCTGTCTCACTCTCTGCTGCT**<br>**GCTCCATAAGAAGGAGGACGGTATTTGGAGCACTGACATCTTGAAGGATCAAAAAGAGCCA**<br>**AAGAATAAAACGTTCCTGAGGTGCGAAGCTAAGAATTACTCCGGGCGTTTTACGTGCTGGT**<br>**GGCTGACCACGATCAGCACCGATCTGACCTTCAGCGTGAAGAGCAGCCGGGGCAGCAGCGA**<br>**CCCCCAAGGCGTGACTTGCGGCGCTGCGACCCTGAGCGCTGAGCGTGTGCGCGGCGACAAC**<br>**AAGGAGTATGAGTATTCAGTGGAGTGTCAGGAGGACTCCGCCTGTCCCGCGGCCGAAGAGA**<br>**GTCTGCCTATTGAGGTGATGGTGGACGCCGTGCACAAGCTGAAGTACGAGAACTACACATC**<br>**GTCATTCTTTATCCGCGACATCATAAAGCCCGACCCCCCCAAGAACCTGCAGCTGAAGCCT**<br>**CTCAAGAATTCCCGGCAAGTGGAGGTGAGCTGGGAGTACCCTGATACCTGGTCTACCCCTC**<br>**ACAGCTACTTTAGCCTGACCTTCTGCGTCCAGGTGCAAGGAAAGTCGAAGCGCGAGAAGAA**<br>**AGATAGAGTCTTCACCGATAAAACCAGTGCCACCGTGATTTGCCGCAAAAACGCCTCCATC**<br>**AGCGTGCGGGCTCAGGATAGATACTACTCTAGCAGCTGGAGCGAATGGGCCTCAGTTCCTT**<br>**GCAGC***GGCGGCAGCGGTGGAGGAAGCGGCGGTGGCAGTGGGGGGGGGAGC***AGAAATCTGCC**<br>**CGTCGCCACTCCAGATCCTGGCATGTTCCCGTGCCTGCATCACAGCCAAAACCTGCTGCGG**<br>**GCGGTGTCTAACATGCTGCAGAAGGCTAGGCAGACCTTGGAATTCTATCCCTGCACAAGCG**<br>**AGGAAATAGACCATGAGGACATCACCAAGGATAAGACCAGCACGGTCGAAGCTTGCCTGCC** |

TABLE 1-continued

| Description | Sequence |
|---|---|
| | **ACTGGAACTGACAAAAAACGAGAGTTGCCTGAACTCCCGCGAGACATCCTTCATCACAAAC**<br>**GGCAGCTGCCTGGCTAGCAGGAAGACCAGCTTCATGATGGCCCTGTGCCTGTCTTCCATCT**<br>**ACGAGGACCTGAAAATGTACCAAGTGGAGTTCAAGACTATGAACGCCAAGCTGCTAATGGA**<br>**TCCCAAGCGACAGATCTTTCTAGACCAGAACATGCTGGCCGTCATTGACGAGCTGATGCAG**<br>**GCACTCAATTTTAACTCAGAGACCGTGCCACAGAAGTCCAGCCTGGAGGAGCCTGACTTCT**<br>**ATAAGACCAAGATTAAGCTGTGCATCCTGCTGCATGCCTTCCGAATAAGAGCCGTGACCAT**<br>**TGACCGAGTGATGTCATACTTGAACGCAAGC***GGCTCAGGCGGAGGGAGT*gacgcccacaag<br>tctgaagtggctcaccggtttaaggaccttggcgaggagaactttaaagccctggtgctga<br>ttgcctttgcccagtatttacaacaatgccctttcgaagaccacgtgaagctcgtcaatga<br>ggtcaccgagttcgctaagacctgcgtagccgacgaaagtgccgagaactgcgacaagagc<br>ctgcacaccctgttcggggacaaactctgtaccgtggccaccctacgggagacatatgggg<br>agatggccgactgctgcgcaaaacaggagcccgagagaaatgagtgcttcctgcagcacaa<br>ggatgacaaccccaatctgcccagactggtgcgccccgaggtagacgttatgtgcaccgcc<br>ttccatgacaatgaggagacgttcctgaagaaatacctgtacgagatcgcaagacgtcacc<br>cctatttctatgcacctgagctgcttttcttcgccaagagatataaggccgccttcaccga<br>atgctgccaggcagccgataaggcagcttgcctcctgccaaagctggacgagctgagagat<br>gagggcaaggcctccagcgcgaagcagagactcaaatgcgcaagccttcagaagttcggag<br>aacgcgcctttaaagcctgggccgtcgccagactgagccagcgcttccctaaagccgaatt<br>cgcagaagtgagcaagctggtaacggacctgacaaaggtgcatactgagtgctgccatggc<br>gatctgctggagtgcgctgatgacagagcagatttggcgaaatatatttgcgaaaatcagg<br>atagcatcagctctaagctcaaggagtgttgtgagaagcccctgctggaaaaaagccactg<br>cattgcagaggttgagaacgatgaaatgccagccgaccttccatcattggccgccgatttc<br>gtggagtcgaaggatgtgtgtaagaactacgccgaggccaaggacgtgttcctgggcatgt<br>tcctgtacgagtatgctagaagacatcccgattacagtgtggtgctgctattgagactggc<br>caagacctacgaaaccaccctggagaaatgttgcgccgcggcagatcctcacgaatgttac<br>gccaaagtgtttgacgaattcaagccactggtagaggagccccagaacttaataaagcaga<br>attgcgagctattcgagcagttgggcgagtacaaattccagaacgcccttctggtgaggta<br>taccaaaaaggtgccccaggtgtctacccctaccctggtggaggtcagccgaaatctggga<br>aaggtcggatccaagtgctgcaagcacccggaggccaagaggatgccttgcgctgaggact<br>atctcagtgtcgtcctgaatcagctatgcgtgttgcacgagaaaaccccagtgagtgaccg<br>cgtgactaaatgctgcaccgaaagcttggtgaatcggaggccctgtttctctgcactggaa<br>gttgacgagacttacgtcccgaaggaattcaacgccgagacattcaccttccatgctgaca<br>tatgtactctgtcagaaaaggagcgtcagatcaagaagcagacagccctggtggaactggt<br>taagcataagcctaaagcgaccaaagagcagctgaaagccgtgatggacgattttgccgcc<br>ttcgtggagaaatgttgtaaggcagacgacaaagagacatgtttcgccgaagaggggaaga<br>aactggtggccgcaagccaggccgctctgggtctgtag |
| M3 Construct (SEQ ID NO: 6)-includes (1) leader sequence (lower case; SEQ ID NO: 31); (2) IL-12β (bolded and underlined; SEQ ID NO: 56); (3) first GS linker (italicized; SEQ ID NO: 81); (4) IL-12α (bolded; SEQ ID NO: 106); (5) second GS linker (italicized and underlined; SEQ ID NO: 131); and (6) albumin (lower case and underlined; SEQ ID NO: 152) | atgagagtcccagctcagctgctgggcctactgctgctatggctccccggcgcgcggtgcg<br>CC**ATTTGGGAGCTCAAGAAGGACGTGTACGTGGTGGAACTTGACTGGTACCCGGACGCGCC**<br>**CGGGGAAATGGTGGTGCTAACCTGTGACACCCCCGAAGAGGACGGCATCACCTGGACCCTG**<br>**GACCAGAGCAGTGAGGTGCTAGGTAGTGGCAAAACGTTAACCATCCAGGTCAAGGAGTTCG**<br>**GCGACGCCGGGCAATACACCTGTCACAAGGGGGGGGAGGTACTATCCCACTCCCTGCTGCT**<br>**CCTGCACAAGAAAGAGGACGGGATCTGGAGCACCGACATTCTGAAAGACCAAAAGGAGCCC**<br>**AAAAACAAAACCTTCCTTAGATGTGAAGCCAAGAACTACAGCGGCCGTTTCACCTGCTGGT**<br>**GGCTGACCACCATATCTACGGACCTTACCTTTTCGGTGAAGAGCAGCAGGGGGAGTTCCGA**<br>**CCCGCAAGGCGTAACTTGCGGAGCCGCAACCCTGAGCGCCGAGAGAGTGCGCGGCGACAAC**<br>**AAGGAGTACGAGTATAGCGTGGAGTGCCAAGAGGACAGCGCATGCCCAGCCGCCGAAGAGA**<br>**GCCTGCCAATAGAGGTCATGGTAGACGCCGTGCACAAGCTAAAATATGAAAACTACACCAG**<br>**CAGCTTTTTCATCAGGGATATCATCAAACCCGACCCACCAAAAAACTTACAGCTTAAGCCT**<br>**CTGAAAAACAGCAGACAAGTTGAGGTCAGCTGGGAGTACCCCGACACTTGGAGCACACCCC**<br>**ACTCCTATTTCAGTTTGACATTCTGCGTGCAGGTGCAGGGTAAAAGCAAGAGAGAAAAGAA**<br>**GGACAGAGTGTTCACAGATAAGACCTCAGCCACAGTGATCTGCCGTAAGAATGCCAGCATC**<br>**AGCGTCCGGGCTCAGGACAGGTACTACTCTTCCTCATGGAGCGAGTGGGCCTCTGTCCCCT**<br>**GCAGC***GGCGGCAGCGGCGGTGGCAGCGGCGGCGGTTCTGGCGGCGGTTCA***AGAAACCTCCC**<br>**AGTCGCTACCCCCGATCCCGGAATGTTCCCCTGCCTGCACCACTCCCAGAATCTGCTCCGA**<br>**GCCGTTAGCAACATGCTGCAAAAGGCCCGGCAGACCCTGGAGTTCTACCCATGCACCTCGG**<br>**AAGAAATCGATCACGAGGACATCACCAAGGACAAGACTAGCACCGTCGAGGCCTGCCTGCC**<br>**GCTGGAACTAACCAAGAATGAAAGCTGCCTCAACTCGCGGGAGACCTCTTTCATAACCAAC**<br>**GGCTCATGCCTGGCCAGCCGGAAAACTAGCTTTATGATGGCTCTGTGCTTAAGCAGCATCT**<br>**ACGAGGATCTGAAGATGTACCAGGTAGAGTTCAAGACCATGAATGCCAAGCTGCTGATGGA**<br>**CCCCAAGAGACAAATCTTCCTGGACCAGAACATGCTGGCCGTAATTGATGAACTGATGCAG**<br>**GCCCTGAATTTCAACAGCGAGACCGTACCCCAGAAAAGCTCACTGGAGGAGCCCGACTTTT**<br>**ATAAGACGAAAATAAAGTTGTGCATCCTTCTTCACGCTTTCCGGATTAGAGCCGTGACCAT**<br>**CGATAGAGTGATGTCATACCTGAACGCATCG***GGGAGTGGCGGTGGCAGC*gatgcccacaaa<br>agcgaagtcgcacacagattcaaggacttgggtgaggagaactttaaagccctggtgctga<br>tcgccttcgcgcagtatctccagcagtgccccttcgaagatcatgtgaaactggtgaacga<br>ggtaaccgagttcgcgaagacatgcgttgctgatgagagcgccgaaaattgcgacaaaagc<br>ctgcatactctgttcggggacaagctgtgcacggtcgcaaccctgagagaaacctacggcg<br>agatggcagactgctgcgccaagcaggagcctgagaggaacgagtgttttctgcagcacaa<br>ggacgataatcctaaccttcctcgtctagtgagacccgaagtggacgttatgtgtaccgcc<br>tttcacgacaatgaggaaacattcctgaaaaagtacctgtacgagatcgccagacggcacc<br>catatttctacgcccccgagctgctcttcttcgcaaagaggtacaaggctgccttcaccga<br>gtgctgccaggcggccgacaaggcggcgtgtttgctgcctaagctggacgaactacgtgac<br>gaaggaaaagctagcagcgccaagcagagacttaagtgcgcgtccttacagaagtttggcg<br>aaagagcgtttaaggcctgggccgtggcaaggctgtctcaaagattccccaaggcggagtt<br>cgccgaggtgtcaaaactggtgaccgacttaaccaaggtgcacaccgaatgctgccacggc<br>gatctgctcgagtgcgccgacgacagagccgatctggcaaaatacatctgcgaaaaccagg<br>atagcatcagctccaaactgaaggagtgctgtgaaaaaccactgcttgaaaaatcgcattg |

TABLE 1-continued

| Description | Sequence |
|---|---|
| | tatagcggaggtggagaatgacgagatgcccgccgacctgccaagcctggccgccgatttc<br>gttgaatccaaggacgtttgcaagaactatgcagaagcgaaggacgtgttcttaggaatgt<br>tcctatacgagtacgcgagaagacatcccgactacagcgtggttctgctgttgagattagc<br>caagacgtatgagacaaccctcgaaaagtgctgcgccgccgccgacccccacgagtgttac<br>gcaaaggtgttcgatgagtttaaaccgctggttgaggaaccgcaaaacctgatcaagcaga<br>actgcgagctgttcgagcagctgggtgaatacaagtttcagaatgcactgttggtgcgata<br>taccaagaaggtgcctcaggtgagcacccctacccttgttgaggtgtcccgcaatctgggt<br>aaggttgggagcaagtgttgcaaacaccccgaggccaagagaatgccctgcgcggaagatt<br>atctcagtgtcgtgcttaatcagttatgtgtcctgcatgagaagacccccgtgagcgacag<br>agtgaccaagtgctgtaccgaatctctcgtgaacagacgcccgtgcttcagcgccttggag<br>gtagacgagacctacgtgcccaaggagttcaacgcagagaccttcacctttcacgccgata<br>tctgcaccctgtccgagaaggagagacaaatcaagaaacaaacggccctcgtggagctggt<br>caagcacaaacccaaggccacaaaagagcagctgaaggccgtgatggacgacttcgcagcc<br>tttgtggagaaatgctgcaaggctgacgacaaggagacatgcttcgccgaggaaggcaaga<br>agttggtggccgccagccaggcggccctgggcctgtag |
| H1 Construct (SEQ ID NO: 7)- includes (1) leader sequence (lower case; SEQ ID NO: 32); (2) IL-12β (bolded and underlined; SEQ ID NO: 57); (3) first GS linker (italicized; SEQ ID NO: 82); (4) IL-12α (bolded; SEQ ID NO: 107); (5) second GS linker (italicized and underlined; SEQ ID NO: 132); and (6) albumin (lower case and underlined; SEQ ID NO: 153) | atgagagtgcccgcccagttgcttggcctgctgctcctatggcttcccggcgccagatgcg<br>ccATCTGGGAGCTGAAGAAAGACGTGTACGTGGTGGAGCTGGACTGGTACCCCGACGCCCC<br>**CGGTGAAATGGTGGTTCTGACCTGCGACACACCAGAGGAGGACGGCATCACCTGGACCCTG**<br>**GACCAGTCCAGCGAGGTCCTGGGCTCTGGCAAGACCCTGACCATCCAGGTTAAGGAATTTG**<br>**GCGACGCCGGCCAGTACACCTGCCACAAAGGCGGCGAGGTCCTTTCGCACAGTCTGCTGCT**<br>**GCTGCATAAAAAGGAGGACGGCATTTGGAGCACCGACATTCTGAAGGATCAGAAAGAGCCC**<br>**AAGAACAAGACCTTTCTGAGATGTGAGGCCAAAAACTACTCTGGACGCTTCACCTGTTGGT**<br>**GGCTGACCACCATCAGCACAGACCTGACCTTCTCGGTGAAGTCTAGTAGGGGCAGCAGTGA**<br>**CCCCCAGGGCGTAACATGCGGCGCCGCTACCCTGAGCGCCGAGAGAGTGAGAGGCGATAAC**<br>**AAGGAGTACGAGTACTCCGTGGAGTGCCAAGAGGACTCAGCCTGCCCCGCCGCCGAGGAGT**<br>**CGCTGCCCATCGAGGTGATGGTGGATGCAGTGCACAAGCTGAAGTACGAGAACTACACCAG**<br>**TAGCTTTTTCATCAGAGATATCATTAAACCCGACCCTCCCAAGAACCTGCAGCTGAAGCCC**<br>**TTAAAGAACAGCCGGCAGGTGGAAGTGTCATGGGAGTACCCAGACACCTGGAGCACTCCGC**<br>**ACAGCTACTTCAGCCTGACCTTCTGCGTTCAGGTGCAGGGAAAAAGCAAGAGAGAGAAGAA**<br>**AGACAGAGTGTTCACCGACAAGACCAGCGCAACCGTGATCTGTAGAAAGAACGCCTCGATC**<br>**AGCGTGAGAGCCCAGGACAGATACTACAGCAGCAGCTGGAGCGAGTGGGCCAGTGTACCTT**<br>GCAGCGGTGGCAGCGGCGGCGGCTCCGGCGGCGGGAGTGGCGGCGGCAGCAGAAATCTGCC<br>**CGTAGCCACCCCCGACCCCGGCATGTTTCCCTGTCTGCACCATTCTCAAAACCTGTTACGG**<br>**GCCGTGAGCAACATGCTGCAGAAGGCCAGACAGACACTGGAGTTTTACCCCTGTACCTCAG**<br>**AGGAGATCGATCATGAGGACATTACTAAGGACAAGACCAGCACCGTGGAAGCCTGCCTGCC**<br>**CCTAGAGCTAACCAAGAACGAGAGCTGCCTGAACTCTAGAGAGACAAGCTTCATCACGAAC**<br>**GGCTCATGCCTGGCCAGTAGGAAAACCAGCTTCATGATGGCTCTGTGCCTGAGCTCCATAT**<br>**ATGAGGACCTTAAGATGTACCAGGTGGAGTTCAAAACCATGAACGCCAAGCTGCTGATGGA**<br>**CCCAAAGAGACAGATCTTCCTTGACCAGAACATGCTGGCCGTTATCGATGAGCTGATGCAG**<br>**GCCCTGAACTTCAACAGCGAGACCGTGCCCCAGAAGAGCAGCCTGGAGGAACCCGACTTCT**<br>**ACAAAACCAAGATCAAGCTGTGCATTCTGCTGCATGCCTTCCGCATTAGAGCCGTGACCAT**<br>CGATAGGGTGATGAGCTACCTGAACGCCAGCGGCTCTGGCGGCGGCAGTgacgcccacaag<br>tccgaggtcgcccacagattcaaggatttgggcgaggagaacttcaaggccctggtgctga<br>tcgccttcgcccagtacttgcagcagtgtcccttcgaggaccatgtgaagctggtgaacga<br>ggtgaccgagttcgccaagacctgtgtggccgacgagagcgccgagaactgcgataagtct<br>ctgcacaccctttttggcgacaaactgtgcaccgtggccaccctgagagagacctacggcg<br>agatggccgactgctgtgcgaagcaggagcccgagcgcaatgagtgtttcctgcagcataa<br>ggacgacaaccccaacctgcccagactggtgagacccgaggtggacgtgatgtgcaccgcc<br>ttccacgacaacgaggagacctttctgaaaaaatacctgtacgagatcgcaagacgccacc<br>cctacttctacgcccccgagctgctgttcttcgccaagcgctacaaggctgccttcaccga<br>gtgctgccaggccgccgataaggccgcgtgcttactgccaaagctggacgagctgagagac<br>gaggggaaagcctctagcgccaaacagagattgaagtgtgccagcctgcagaaattcggtg<br>agagagccttcaaggcctgggccgtggccagattatcacagcggttccccaaggctgaatt<br>cgccgaggtgagcaaacttgtcaccgatctgacaaaagtgcacaccgagtgctgccatggc<br>gacctgctggagtgcgccgacgaccgggccgacctggccaagtacatctgcgagaaccagg<br>acagcatctccagcaagctgaaggagtgctgcgagaagcccctgctggagaagagccactg<br>catcgccgaggtggagaatgacgaaatgcccgccgacctgcccagcctggccgccgacttc<br>gtggaaagcaaggacgtgtgcaaaaattacgccgaagccaaggatgtgttcttgggcatgt<br>tcttgtacgagtacgccagacgccaccccgactacagcgtggtgctgctgctgcggctggc<br>caagacctacgagaccaccctggagaagtgctgtgctgccgccgacccccacgagtgctac<br>gccaaggtatttgacgagttcaagcccctggtggaggagcctcagaacctgattaagcaga<br>actgtgagctgttcgagcagctgggcgagtacaagttccagaacgccctcctggtgagata<br>caccaaaaaggtgcctcaggtaagcactcccaccctggtggaggtgagcaggaacctcggc<br>aaggtgggcagcaaatgctgcaagcacccagaggccaaaagaatgccctgcgcagaagact<br>acctcagcgtggtcctgaaccagctgtgcgtgctgcacgaaaagacccctgtgagcgatag<br>agtgacaaagtgctgcaccgagagcctggtgaacagaagaccctgttttagcgccctggag<br>gtggacgagacctacgtgcccaaggagttcaacgccgagacgttcactttccacgcggaca<br>tctgcaccctgagcgagaaggagagacaaatcaagaagcagaccgccctagtcgagctggt<br>aaaacacaagcccaaggccaccaaggagcagctgaaggccgtgatggacgactttgcagcc<br>ttcgtggagaagtgctgcaaggctgacgacaaggagacctgcttcgccgaggagggcaaga<br>agctcgtagccgccagcaggccgctctcggcctttag |
| H2 Construct (SEQ ID NO: 8)- includes (1) leader sequence (lower case; SEQ ID NO: | atgagagtgcccgcccagctgctgggcctgctgctcttatggctgcccggcgcccgctgtg<br>ctATTTGGGAGCTGAAGAAGGACGTGTACGTGGTGGAGCTGGATTGGTATCCAGACGCCCC<br>**CGGCGAGATGGTCGTGTTGACCTGCGATACTCCCGAGGAGGACGGAATCACCTGGACACTT**<br>**GACCAGAGCAGCGAGGTGCTGGGCAGCGGGAAGACCCTGACTATCCAGGTGAAGGAGTTTG**<br>**GCGATGCCGGACAGTACACCTGCCACAAGGGCGGCGAGGTGTTATCTCATAGCCTGCTGCT** |

TABLE 1-continued

| Description | Sequence |
|---|---|
| 33); (2) IL-12β (bolded and underlined; SEQ ID NO: 58); (3) first GS linker (italicized; SEQ ID NO: 83); (4) IL-12α (bolded; SEQ ID NO: 108); (5) second GS linker (italicized and underlined; SEQ ID NO: 133); and (6) albumin (lower case and underlined; SEQ ID NO: 154) | **GCTGCACAAAAAGGAGGACGGGATCTGGAGCACTGACATCCTGAAGGACCAGAAGGAGCCC**<br>**AAAAACAAGACCTTCCTGCGTTGCGAGGCCAAGAACTACAGCGGGAGATTCACCTGTTGGT**<br>**GGCTGACCACTATCAGCACTGACCTAACCTTCAGCGTGAAGAGCAGCCGGGGAAGCTCTGA**<br>**CCCCCAGGGGGTGACATGCGGCGCCGCCACACTGAGCGCCGAGAGGGTGAGAGGGGACAAT**<br>**AAGGAATACGAGTATAGCGTGGAGTGTCAGGAAGATTCCGCCTGCCCCGCCGCCGAGGAGA**<br>**GCCTGCCTATCGAGGTCATGGTGGACGCCGTCCATAAACTGAAGTACGAAAACTATACTTC**<br>**AAGCTTCTTCATCAGAGACATCATAAAGCCCGACCCCCCCAAGAACCTGCAGCTAAAGCCC**<br>**CTGAAGAACAGCAGACAGGTCGAAGTGAGCTGGGAGTACCCCGATACCTGGAGCACCCCGC**<br>**ACAGCTACTTCAGCCTGACCTTTTGCGTCCAGGTGCAGGGCAAGAGCAAGAGAGAGAAGAA**<br>**GGACAGGGTGTTCACTGACAAGACAAGCGCCACTGTTATCTGCAGAAAGAACGCCAGTATC**<br>**AGCGTGCGCGCCCAAGACAGGTATTACTCCAGCAGCTGGTCTGAATGGGCCAGCGTGCCTT**<br>**GCAGC***GGGGGGAGCGGCGGTGGCAGCGGGGGGGGCAGCGGCGGGGGCAGC***AGAAACCTGCC**<br>**CGTGGCCACACCCGATCCCGGCATGTTCCCCTGTCTGCACCACAGCCAAAACCTGCTGCGT**<br>**GCCGTGAGCAACATGCTGCAGAAGGCGCGGCAGACCCTGGAGTTCTATCCCTGCACCAGTG**<br>**AGGAGATTGACCACGAGGATATCACCAAAGACAAGACCAGCACCGTGGAGGCCTGCCTCCC**<br>**CCTGGAGCTGACCAAGAACGAGTCCTGCTTGAATTCAAGAGAGACCAGCTTCATCACCAAC**<br>**GGCTCCTGCTTAGCCAGCAGAAAGACTAGCTTCATGATGGCCTTGTGCTTGTCTAGCATCT**<br>**ATGAGGATCTGAAGATGTACCAGGTCGAGTTCAAGACTATGAACGCCAAGCTGCTGATGGA**<br>**CCCCAAAAGACAGATCTTCCTGGACCAGAACATGCTGGCCGTCATCGACGAGCTGATGCAG**<br>**GCCCTTAATTTCAATAGCGAGACAGTGCCCCAGAAATCTTCTCTGGAGGAGCCCGATTTTT**<br>**ACAAAACCAAGATCAAACTATGCATCCTGTTGCACGCCTTCCGGATCCGCGCCGTGACCAT**<br>**CGACAGAGTAATGTCCTACCTGAACGCCAGC***GGCAGCGGCGGCGGTAGC*gacgcccacaag<br>agcgaagtggcccatagattcaaggacctgggcgaggagaacttcaaggccctcgtgctga<br>tcgccttcgcccagtacctgcagcagtgccctttcgaggaccacgttaaactggtgaatga<br>agtgaccgagttcgccaaaacctgcgtggccgacgagtctgccgaaaattgcgacaaaagc<br>ttacacaccctgttcggcgacaagctgtgcaccgtggccaccttaagagaaacctacggcg<br>agatggccgactgctgcgctaagcaggagcccgagagaaacgaatgcttcctgcagcacaa<br>ggacgataacccaaatctgcctagactggtgagacccgaggtggacgtgatgtgcacagcc<br>ttccacgataacgaagagacattcctgaaaaagtacctgtacgagatcgccagaagacatc<br>cttacttctatgcccccgagcttctgttcttcgccaagagatataaggccgccttcaccga<br>gtgctgccaagccgccgacaaggcagcctgcctgctgccaaagcttgacgagctgagagac<br>gagggcaaagccagcagcgccaagcagagactgaagtgcgcctccctgcagaagttcggcg<br>agagagcctttaaggcctgggccgtggccagattgagtcagagattccccaaggccgagtt<br>cgccgaggtgagcaaactggtgaccgacctcactaaagtgcacacagaatgttgccatggc<br>gatctcctggaatgcgccgatgacagggccgacctggccaagtacatctgtgagaaccagg<br>acagcatttcgagcaagctgaaggagtgctgcgagaaacccctgctggagaagtcccactg<br>catcgccgaggtggagaacgacgagatgcccgccgacctgcccagcctggccgcagatttc<br>gtggagagcaaggacgtatgcaagaactacgcagaggccaaggatgtgttcctgggcatgt<br>tcctgtacgaatacgccagaaggcaccccgactacagcgtcgtgctgttactgagactggc<br>caagacctacgagacaaccttagagaagtgctgcgcggccgcagacccgcacgagtgctac<br>gccaaggtgttcgacgagttcaagcccctggtggaggaacctcagaatctgattaagcaga<br>attgtgagctgttcgagcagctgggagagtacaagttccagaacgcgctgctggtgagata<br>taccaagaaggtgccccaggtgagcacccccaccctggtggaggtgagtcgcaacctgggc<br>aaggtggggagcaagtgttgcaagcatcccgaggccaaaagaatgccctgcgcagaggact<br>atctgagcgttgtgcttaaccagctgtgcgtgctgcacgagaagacccccgtgagcgacag<br>agtgaccaagtgttgcaccgagagcctggtaaacagaagaccctgcttcagcgccctggag<br>gtggacgagacctacgtgcccaaggagttcaacgccgagacctttaccttccacgcagaca<br>tttgcaccctgagcgagaaagagaggcagatcaagaaacagaccgctctggtcgagcttgt<br>gaagcacaagcccaaagctaccaaggagcagctgaaggccgtgatggatgatttcgccgcc<br>ttcgtagagaaatgctgcaaggccgacgataaagagacctgctttgccgaggagggcaaga<br>aactggtggccgccagccaggcggccctgggcctgtag |
| H3 Construct (SEQ ID NO: 9)-includes (1) leader sequence (lower case; SEQ ID NO: 34); (2) IL-12β (bolded and underlined; SEQ ID NO: 59); (3) first GS linker (italicized; SEQ ID NO: 84); (4) IL-12α (bolded; SEQ ID NO: 109); (5) second GS linker (italicized and underlined; SEQ ID NO: 134); and (6) albumin (lower case and underlined; SEQ ID NO: 155) | atgagagtgcccgcccagctgctgggcctgctgttgctgtggctgcccggcgccagatgcg<br>cc**ATCTGGGAACTGAAGAAGGACGTCTACGTGGTGGAGCTGGATTGGTACCCCGACGCCCC**<br>**CGGCGAGATGGTCGTGCTGACCTGTGACACCCCTGAGGAGGACGGAATCACATGGACCCTG**<br>**GACCAGAGCAGCGAAGTGTTGGGCAGCGGCAAGACCCTGACCATCCAAGTGAAGGAATTCG**<br>**GCGACGCGGGCCAGTATACTTGCCACCAGGGCGGGGAGGTTCTGAGCCACAGCCTGCTGCT**<br>**GCTCCACAAGAAAGAGGATGGCATCTGGTCTACCGACATCCTGAAGGACCAAAAGGAGCCA**<br>**AAGAACAAGACCTTCCTAAGATGCGAGGCCAAGAACTACTCAGGTCGTTTCACCTGCTGGT**<br>**GGCTGACCACAATCTCCACCGACCTGACCTTCAGCGTGAAGAGCAGCCGCGGCAGTAGCGA**<br>**CCCACAGGGCGTGACCTGCGGGGCCGCCACTCTGAGCGCCGAGAGAGTGCGCGGCGATAAT**<br>**AAGGAATACGAGTACAGCGTGGAGTGCCAGGAAGACTCAGCCTGCCCCGCCGCAGAAGAAA**<br>**GTCTGCCAATAGAGGTGATGGTTGACGCCGTGCACAAGCTAAAGTACGAGAACTACACCAG**<br>**CAGCTTCTTTATCCGGGACATCATCAAGCCAGATCCCCCCAAGAACCTGCAGCTTAAGCCC**<br>**CTGAAGAACAGCAGACAGGTGGAGGTGTCATGGGAATACCCCGACACCTGGAGCACCCCCC**<br>**ATAGCTACTTCTCACTGACCTTCTGCGTGCAGGTGCAGGGCAAGAGCAAGAGAGAGAAGAA**<br>**GGATAGGGTATTCACGGACAAGACCTCAGCCACCGTGATCTGCCGAAAGAACGCCAGCATC**<br>**AGCGTGAGAGCCCAGGACAGATACTATAGCTCCTCGTGGAGCGAGTGGGCCAGCGTACCTT**<br>**GCAGC***GGCGGGAGCGGCGGCGGCAGCGGCGGTGGCAGTGGCGGGGGCAGC***AGAAACCTGCC**<br>**CGTGGCCACCCCCGACCCCGGGATGTTTCCTTGCCTGCACCACTCCCAGAACCTCCTGAGA**<br>**GCCGTGTCCAACATGCTGCAGAAAGCCAGACAGACCCTCGAGTTCTATCCCTGCACAAGCG**<br>**AGGAGATCGACCACGAGGACATCACTAAGGACAAGACCAGCACAGTGGAAGCCTGCCTCCC**<br>**GCTGGAGCTGACTAAGAACGAGAGCTGTCTGAACAGCAGGGAGACCAGCTTCATCACCAAC**<br>**GGCAGCTGCCTGGCGAGCAGAAAAACCTCCTTTATGATGGCGCTCTGCCTGAGCTCAATCT**<br>**ATGAGGACCTGAAGATGTACCAGGTGGAGTTTAAAACCATGAATGCCAAGCTGCTTATGGA**<br>**CCCTAAGAGACAGATTTTCCTGGATCAGAACATGCTGGCCGTGATTGATGAATTAATGCAG**<br>**GCGCTGAACTTTAACAGCGAGACCGTGCCCCAGAAGAGCAGCCTGGAGGAGCCCGACTTTT**<br>**ACAAGACCAAGATCAAGTTGTGCATCCTCCTGCACGCCTTCAGAATCAGAGCGGTGACGAT** |

TABLE 1-continued

| Description | Sequence |
|---|---|
| | **CGACAGAGTCATGAGCTACCTCAACGCTAGC***GGCAGCGGTGGCGGCAGC*gacgcccacaag<br>agcgaggtggcccacagattcaaggatctcggggaggagaacttcaaggccctggtgctga<br>tcgccttcgcacagtacctgcagcagtgccccttcgaggaccacgtaaaactggtgaacga<br>ggtgacggagttcgccaagacctgtgttgccgacgagtcggccgagaattgcgacaagagc<br>ctgcataccctgttcggcgacaagctgtgcaccgtggccaccctgagagagacctacggcg<br>agatggccgactgctgcgccaagcaagagcccgagagaaacgagtgcttcctgcagcacaa<br>ggacgacaaccccaacctgccccggctggtgagacccgaggtggacgtgatgtgcaccgcc<br>ttccacgacaacgaggagaccttcctgaagaagtatctgtacgagatcgccagaagacacc<br>cttatttttacgcccccgagctgctcttcttcgctaagagatataaggcagccttcaccga<br>gtgttgtcaggccgccgataaggccgcttgcctgctgcccaagttggacgagctcagagac<br>gagggcaaggcgagcagcgccaagcagagactgaagtgcgccagcctgcagaagttcggcg<br>agagggccttcaaggcctgggcggtggccagactgtcccagagatttcccaaggccgagtt<br>cgccgaggtaagcaagctggtcaccgacctgaccaaggtgcacaccgagtgttgccacggc<br>gacctgctggaatgcgccgatgaccgtgccgacctggccaagtacatctgcgagaatcagg<br>actccatcagcagcaaactgaaggagtgttgcgagaagcccctgctggagaagagccattg<br>catcgctgaggtggaaaacgacgagatgcccgcagacctgcccagcctggccgcagacttt<br>gtggaaagtaaggacgtgtgcaagaactacgcggaggccaaagacgtgtttctgggcatgt<br>tcctatacgagtatgccagaagacaccccgactacagcgttgtgttattgctgagactggc<br>caagacctacgagactaccttggagaagtgctgcgccgccgccgacccccacgagtgctat<br>gccaaggtgttcgacgagttcaagcccctggtggaggagccccagaatctgattaagcaga<br>attgcgagcttttttgagcagctgggcgagtataagttccagaacgccctgctggtgagata<br>caccaaaaaggtacctcaggtgagcacccccaccctggtggaggtgagcagaaatctgggc<br>aaggtgggcagcaagtgctgcaagcacccggaggccaagagaatgccctgtgccgaggatt<br>acctgtcagtggtgctgaaccagctgtgcgttctgcacgaaaagacgcccgtgtcggacag<br>agtgaccaagtgctgcacggagagcctggtgaacagaagaccgtgcttcagcgccctagag<br>gtggacgagacctacgtgcccaaggagttcaacgccgagaccttcaccttccacgccgaca<br>tctgtaccctgtcagagaaggagagacagatcaagaagcagaccgccttagtggagctggt<br>gaagcacaagcccaaggccaccaaggagcagctgaaagccgtgatggacgatttcgcagcc<br>ttcgtcgagaagtgctgcaaggccgacgacaaggaaacttgcttcgccgaggagggcaaga<br>agctggtggctgcctcgcaggccgccctcggcctgtag |
| CO Construct (SEQ ID NO: 10)-includes (1) leader sequence (lower case; SEQ ID NO: 35); (2) IL-12β (bolded and underlined; SEQ ID NO: 60); (3) first GS linker (italicized; SEQ ID NO: 85); (4) IL-12α (bolded; SEQ ID NO: 110); (5) second GS linker (italicized and underlined; SEQ ID NO: 135); and (6) albumin (lower case and underlined; SEQ ID NO: 156) | atgagagtgcccgcccagctgctgggcctgctgctgctgtggctgcccggcgccagatgcg<br>ccA**TCTGGGAGCTGAAGAAGGACGTGTACGTGGTGGAGCTGGACTGGTACCCCGACGCCCC**<br>**CGGCGAGATGGTGGTGCTGACCTGCGACACCCCCGAGGAGGACGGCATCACCTGGACCCTG**<br>**GACCAGAGCAGCGAGGTGCTGGGCAGCGGCAAGACCCTGACCATCCAGGTGAAGGAGTTCG**<br>**GCGACGCCGGCCAGTACACCTGCCACAAGGGCGGCGAGGTGCTGAGCCACAGCCTGCTGCT**<br>**GCTGCACAAGAAGGAGGACGGCATCTGGAGCACCGACATCCTGAAGGACCAGAAGGAGCCC**<br>**AAGAACAAGACCTTCCTGAGATGCGAGGCCAAGAACTACAGCGGCAGATTCACCTGCTGGT**<br>**GGCTGACCACCATCAGCACCGACCTGACCTTCAGCGTGAAGAGCAGCAGAGGCAGCAGCGA**<br>**CCCCCAGGGCGTGACCTGCGGCGCCGCCACCCTGAGCGCCGAGAGAGTGAGAGGCGACAAC**<br>**AAGGAGTACGAGTACAGCGTGGAGTGCCAGGAGGACAGCGCCTGCCCCGCCGCCGAGGAGA**<br>**GCCTGCCCATCGAGGTGATGGTGGACGCCGTGCACAAGCTGAAGTACGAGAACTACACCAG**<br>**CAGCTTCTTCATCAGAGACATCATCAAGCCCGACCCCCCCAAGAACCTGCAGCTGAAGCCC**<br>**CTGAAGAACAGCAGACAGGTGGAGGTGAGCTGGGAGTACCCCGACACCTGGAGCACCCCCC**<br>**ACAGCTACTTCAGCCTGACCTTCTGCGTGCAGGTGCAGGGCAAGAGCAAGAGAGAGAAGAA**<br>**GGACAGAGTGTTCACCGACAAGACCAGCGCCACCGTGATCTGCAGAAAGAACGCCAGCATC**<br>**AGCGTGAGAGCCCAGGACAGATACTACAGCAGCAGCTGGAGCGAGTGGGCCAGCGTGCCCT**<br>**GCAGC***GGCGGCAGCGGCGGCGGCAGCGGCGGCGGCAGCGGCGGCGGCAGC***AGAAACCTGCC**<br>**CGTGGCCACCCCCGACCCCGGCATGTTCCCCTGCCTGCACCACAGCCAGAACCTGCTGAGA**<br>**GCCGTGAGCAACATGCTGCAGAAGGCCAGACAGACCCTGGAGTTCTACCCCTGCACCAGCG**<br>**AGGAGATCGACCACGAGGACATCACCAAGGACAAGACCAGCACCGTGGAGGCCTGCCTGCC**<br>**CCTGGAGCTGACCAAGAACGAGAGCTGCCTGAACAGCAGAGAGACCAGCTTCATCACCAAC**<br>**GGCAGCTGCCTGGCCAGCAGAAAGACCAGCTTCATGATGGCCCTGTGCCTGAGCAGCATCT**<br>**ACGAGGACCTGAAGATGTACCAGGTGGAGTTCAAGACCATGAACGCCAAGCTGCTGATGGA**<br>**CCCCAAGAGACAGATCTTCCTGGACCAGAACATGCTGGCCGTGATCGACGAGCTGATGCAG**<br>**GCCCTGAACTTCAACAGCGAGACCGTGCCCCAGAAGAGCAGCCTGGAGGAGCCCGACTTCT**<br>**ACAAGACCAAGATCAAGCTGTGCATCCTGCTGCACGCCTTCAGAATCAGAGCCGTGACCAT**<br>**CGACAGAGTGATGAGCTACCTGAACGCCAGC***GGCAGCGGCGGCGGCAGC*gacgcccacaag<br>agcgaggtggcccacagattcaaggacctgggcgaggagaacttcaaggccctggtgctga<br>tcgccttcgcccagtacctgcagcagtgccccttcgaggaccacgtgaagctggtgaacga<br>ggtgaccgagttcgccaagacctgcgtggccgacgagagcgccgagaactgcgacaagagc<br>ctgcacaccctgttcggcgacaagctgtgcaccgtggccaccctgagagagacctacggcg<br>agatggccgactgctgcgccaagcaggagcccgagagaaacgagtgcttcctgcagcacaa<br>ggacgacaaccccaacctgcccagactggtgagacccgaggtggacgtgatgtgcaccgcc<br>ttccacgacaacgaggagaccttcctgaagaagtacctgtacgagatcgccagaagacacc<br>cctacttctacgcccccgagctgctgttcttcgccaagagatacaaggccgccttcaccga<br>gtgctgccaggccgccgacaaggccgcctgcctgctgcccaagctggacgagctgagagac<br>gagggcaaggccagcagcgccaagcagagactgaagtgcgccagcctgcagaagttcggcg<br>agagagccttcaaggcctgggccgtggccagactgagccagagattccccaaggccgagtt<br>cgccgaggtgagcaagctggtgaccgacctgaccaaggtgcacaccgagtgctgccacggc<br>gacctgctggagtgcgccga gacagagccgacctggccaagtacatctgcgagaaccagg<br>acagcatcagcagcaagctgaaggagtgctgcgagaagcccctgctggagaagagccactg<br>catcgccgaggtggagaacgacgagatgcccgccgacctgcccagcctggccgccgacttc<br>gtggagagcaaggacgtgtgcaagaactacgccgaggccaaggacgtgttcctgggcatgt<br>tcctgtacgagtacgccagaagacaccccgactacagcgtggtgctgctgctgagactggc<br>caagacctacgagaccaccctggagaagtgctgcgccgccgccgacccccacgagtgctac<br>gccaaggtgttcgacgagttcaagcccctggtggaggagccccagaacctgatcaagcaga<br>actgcgagctgttcgagcagctgggcgagtacaagttccagaacgccctgctggtgagata |

TABLE 1-continued

| Description | Sequence |
|---|---|
| | caccaagaaggtgccccaggtgagcacccccaccctggtggaggtgagcagaaacctgggc<br>aaggtgggcagcaagtgctgcaagcaccccgaggccaagagaatgccctgcgccgaggact<br>acctgagcgtggtgctgaaccagctgtgcgtgctgcacgagaagacccccgtgagcgacag<br>agtgaccaagtgctgcaccgagagcctggtgaacagaagaccctgcttcagcgccctggag<br>gtggacgagacctacgtgcccaaggagttcaacgccgagaccttcaccttccacgccgaca<br>tctgcaccctgagcgagaaggagagacagatcaagaagcagaccgccctggtggagctggt<br>gaagcacaagcccaaggccaccaaggagcagctgaaggccgtgatggacgacttcgccgcc<br>ttcgtggagaagtgctgcaaggccgacgacaaggagacctgcttcgccgaggagggcaaga<br>agctggtggccgccagccaggccgccctgggcctgtag |
| CP Construct (SEQ ID NO: 11)-includes (1) leader sequence (lower case; SEQ ID NO: 36); (2) IL-12β (bolded and underlined; SEQ ID NO: 61); (3) first GS linker (italicized; SEQ ID NO: 86); (4) IL-12α (bolded; SEQ ID NO: 111); (5) second GS linker (italicized and underlined; SEQ ID NO: 136); and (6) albumin (lower case and underlined; SEQ ID NO: 157) | atgagggtccccgctcagctcctggggctcctgctgctctggctcccaggtgcacgatgtg<br>ccATCTGGGAGCTGAAGAAGGATGTGTATGTGGTGGAGCTGGACTGGTACCCAGATGCCCC<br>TGGAGAGATGGTGGTGCTGACCTGTGACACCCCAGAGGAGGATGGCATCACCTGGACCCTG<br>GACCAGAGCAGCGAGGTGCTGGGCAGCGGCAAGACCCTGACCATCCAGGTGAAGGAGTTTG<br>GCGACGCCGGCCAGTACACCTGCCACAAGGGCGGCGAGGTGCTGAGCCACAGCCTGCTGCT<br>GCTGCACAAGAAGGAGGATGGCATCTGGAGCACAGACATCCTGAAGGACCAGAAGGAGCCC<br>AAGAACAAGACCTTCCTGAGATGCGAGGCCAAGAACTACAGCGGCAGATTCACCTGCTGGT<br>GGCTGACCACCATCAGCACCGACCTGACCTTCAGCGTGAAGAGCAGCAGAGGCAGCAGCGA<br>CCCCCAGGGCGTGACCTGCGGCGCCGCCACCCTGAGCGCCGAGAGAGTGAGAGGCGACAAC<br>AAGGAGTACGAGTACAGCGTGGAGTGCCAGGAGGACAGCGCCTGCCCCGCCGCCGAGGAGA<br>GCCTGCCCATCGAGGTGATGGTGGACGCCGTGCACAAGCTGAAGTACGAGAACTACACCAG<br>CAGCTTCTTCATCAGAGACATCATCAAGCCCGACCCCCCCAAGAACCTGCAGCTGAAGCCC<br>CTGAAGAACAGCAGACAGGTGGAGGTGAGCTGGGAGTACCCCGACACCTGGAGCACCCCCC<br>ACAGCTACTTCAGCCTGACCTTCTGCGTGCAGGTGCAGGGCAAGAGCAAGAGAGAGAAGAA<br>GGACAGAGTGTTCACCGACAAGACCAGCGCCACCGTGATCTGCAGAAAGAACGCCAGCATC<br>AGCGTGAGAGCCCAGGACAGATACTACAGCAGCAGCTGGAGCGAGTGGGCCAGCGTGCCCT<br>GCAGCGGCGGCAGCGGCGGCGGCAGCGGCGGCGGCAGCGGCGGCGGCAGCAGAAACCTGCC<br>CGTGGCCACCCCCGACCCCGGCATGTTCCCCTGCCTGCACCACAGCCAGAACCTGCTGCGG<br>GCTGTGAGCAACATGCTGCAGAAGGCCCGGCAGACCCTGGAGTTCTACCCCTGCACCAGCG<br>AGGAGATTGACCACGAGGACATCACCAAGGACAAGACCAGCACAGTGGAGGCCTGCCTGCC<br>CCTGGAGCTGACCAAGAATGAAAGCTGCCTGAACAGCCGGGAGACCAGCTTCATCACCAAC<br>GGCAGCTGCCTGGCCAGCAGGAAGACCAGCTTCATGATGGCCCTGTGCCTGAGCAGCATCT<br>ATGAGGACCTGAAGATGTACCAGGTGGAGTTCAAGACCATGAATGCCAAGCTGCTGATGGA<br>CCCCAAGAGGCAGATCTTCCTGGACCAGAACATGCTGGCCGTGATTGATGAGCTGATGCAG<br>GCCCTGAACTTCAACAGCGAGACCGTGCCCCAGAAAAGCAGCCTGGAGGAGCCAGACTTCT<br>ACAAGACCAAGATCAAGCTGTGCATCCTGCTGCACGCCTTCCGCATCCGGGCTGTGACCAT<br>CGACAGAGTGATGAGCTACCTGAATGCCAGCGGCAGCGGCGGCGGCAGTgatgcccacaag<br>tctgaggtggcccaccgcttcaaggacctgggggaggagaacttcaaggccctggtgctga<br>ttgcctttgcccagtacctgcagcagtgcccctttgaggaccacgtgaagctggtgaatga<br>ggtgacagaatttgccaagacctgtgtggctgatgaatctgctgagaactgtgacaagagc<br>ctgcacaccctgtttggagacaagctgtgcaccgtggccaccctgcgggagacctatggag<br>agatggctgactgctgtgccaagcaggagcctgagagaaatgaatgcttcctgcagcacaa<br>ggatgacaaccccaacctgccccggctggtgcggcctgaggtggatgtgatgtgcacagcc<br>ttccatgacaatgaggagaccttcctgaagaagtacctgtatgaaattgcccggcggcacc<br>cctacttctacgcccctgagctgctgttctttgccaagcgctacaaggccgccttcacaga<br>gtgctgccaggccgctgacaaggccgcctgcctgctgcccaagctggatgagctgagagat<br>gagggcaaggccagcagcgccaagcagaggctgaagtgtgccagcctgcagaagtttggag<br>agcgggccttcaaggcctgggccgtggcccggctgagccagcgcttccccaaggccgagtt<br>tgctgaggtgtccaagctggtgacagacctgaccaaggtgcacacagagtgctgccacggg<br>gacctgctggagtgtgctgatgacagagctgacctggccaagtacatctgtgagaaccagg<br>acagcatcagcagcaagctgaaggagtgctgtgagaagcccctgctggaaaagagccactg<br>catcgccgaggtggagaatgatgagatgcctgctgacctgcccagcctggccgctgacttt<br>gtggagagcaaggatgtgtgcaagaactacgccagggccaaggatgtgttcctgggcatgt<br>tcctgtacgagtacgccagaagacaccccgactacagcgtggtgctgctgctgagactggc<br>caagacctatgagaccaccctggagaagtgctgtgccgctgctgacccccatgaatgttat<br>gccaaggtgtttgatgagttcaagcccctggtggaggagccccagaacctgatcaagcaga<br>actgtgagctgtttgagcagctgggggagtacaagttccagaatgccctgctggtgcgcta<br>caccaagaaggtgccccaggtgtccacccccaccctggtggaggtgtccaggaacctgggc<br>aaggtgggcagcaagtgctgcaagcaccctgaggccaagaggatgccctgtgccgaggact<br>acctgtctgtggtgctgaaccagctgtgtgtgctgcacgagaagacccctgtgtctgacag<br>agtgaccaagtgctgcacagagagcctggtgaacagaagaccctgcttcagcgccctggag<br>gtggatgagacctacgtgcccaaggagttcaatgctgagaccttcaccttccacgccgaca<br>tctgcaccctgtctgagaaggagcggcagatcaagaagcagacagccctggtggagctggt<br>gaagcacaagcccaaggccaccaaggagcagctgaaggctgtgatggatgactttgctgcc<br>tttgtggagaagtgctgcaaggcagatgacaaggagacctgctttgctgaggagggcaaga<br>agctggtggccgccagccaggccgccctgggcctg |
| vH1 Construct (SEQ ID NO: 12)-includes (1) leader case; SEQ ID NO: 37); (2) IL-12β (bolded and underlined; SEQ ID NO: 62); (3) first GS linker (italicized; SEQ ID NO: 87); (4) IL-12α (bolded; | atgagagtgcccgcccagctgctgggcctgctgctgctgtggctgcccggcgccagatgcg<br>ccATCTGGGAGCTGAAGAAGGACGTGTACGTGGTGGAGCTGGACTGGTACCCCGACGCCCC<br>CGGCGAGATGGTGGTGCTGACCTGCGACACCCCCGAGGAGGACGGGATCACCTGGACCCTG<br>GATCAGAGCAGCGAGGTGCTGGGCAGCGGCAAGACCCTGACCATCCAGGTGAAGGAGTTTG<br>GTGACGCCGGCCAGTACACCTGCCACAAGGGCGGCGAGGTGCTGAGCCACTCACTGCTGCT<br>GCTGCACAAGAAGGAGGACGGCATCTGGAGCACCGACATTCTGAAGGATCAGAAGGAGCCC<br>AAGAACAAGACCTTCCTGAGATGCGAGGCCAAGAACTACAGCGGCAGATTCACCTGTTGGT<br>GGCTGACTACTATCAGCACTGATCTGACCTTCAGCGTGAAGAGCTCAAGAGGCAGCAGCGA<br>TCCCCAGGGCGTGACCTGCGGCGCCGCCACCCTGAGCGCCGAGAGAGTGAGAGGCGACAAC<br>AAGGAGTACGAGTACAGCGTGGAGTGCCAGGAAGACAGCGCCTGCCCCGCTGCAGAGGAGT<br>CTCTGCCCATCGAGGTGATGGTGGACGCCGTGCACAAGCTTAAGTACGAGAACTACACCAG |

TABLE 1-continued

| Description | Sequence |
|---|---|
| SEQ ID NO: 112); (5) second GS linker (italicized and underlined; SEQ ID NO: 137); and (6) albumin (lower case and underlined; SEQ ID NO: 158) | **CTCCTTCTTCATTAGAGACATCATCAAGCCCGACCCGCCCAAAAACCTGCAGCTGAAGCCC**<br>**CTGAAGAACAGCAGACAGGTGGAGGTCAGCTGGGAGTACCCCGACACCTGGAGCACCCCCC**<br>**ACAGCTACTTCAGCCTGACCTTCTGCGTGCAGGTGCAGGGCAAGAGCAAGAGAGAGAAGAA**<br>**GGACAGAGTGTTCACCGACAAAACCAGCGCCACCGTGATCTGCAGAAAAAACGCCAGCATT**<br>**AGCGTGAGAGCTCAGGATAGATACTACAGCAGCAGCTGGAGTGAGTGGGCCAGCGTGCCCT**<br>**GCAGC***GGCGGCTCAGGCGGCGGCTCAGGCGGCGGCAGCGGCGGCGGCAGC***AGAAACCTGCC**<br>**CGTGGCCACGCCCGACCCCGGCATGTTTCCCTGCCTGCACCATAGCCAGAATCTGCTGAGA**<br>**GCCGTGAGCAACATGCTGCAGAAGGCCAGACAGACGCTCGAGTTCTACCCCTGCACCAGCG**<br>**AGGAGATTGACCACGAGGACATCACCAAGGACAAGACCAGCACCGTGGAGGCCTGCCTGCC**<br>**CCTCGAGCTGACCAAGAACGAGAGCTGCCTGAACAGCAGAGAGACCAGCTTCATCACCAAC**<br>**GGCAGCTGCCTGGCCAGCAGAAAGACCAGCTTCATGATGGCCCTGTGCCTGAGCAGCATCT**<br>**ACGAGGACCTGAAGATGTACCAGGTGGAGTTCAAGACAATGAACGCCAAGCTGCTGATGGA**<br>**CCCCAAGAGGCAGATTTTTCTGGACCAGAACATGCTGGCCGTTATCGACGAGCTGATGCAG**<br>**GCCCTGAATTTCAATAGCGAAACCGTGCCCCAGAAGAGCAGCCTGGAGGAGCCTGACTTCT**<br>**ACAAAACCAAGATCAAGCTTTGCATCCTGCTGCACGCCTTCAGAATCAGAGCCGTGACCAT**<br>**CGACAGAGTGATGAGCTACCTGAACGCCAGC***GGCAGCGGCGGCGGCAGC*gacgcccacaag<br>agcgaggtggcccataggttcaaggacctgggcgaggagaacttcaaggccctggtactca<br>tcgccttcgcccaatacctgcaacagtgccccttcgaggaccatgttaagctggtgaacga<br>ggtgaccgagttcgccaagacctgcgtggccgacgagagcgccgagaactgcgacaagagc<br>ctgcacaccctgttcggcgacaagctgtgcaccgtggccaccctgagagagacctacggcg<br>agatggccgactgctgcgccaagcaggagcccgaacgtaacgagtgcttcctgcagcacaa<br>ggacgacaaccccaacctgccccgactggtcagacccgaggtggacgtgatgtgcacagcc<br>ttccacgacaacgaggagaccttcctgaagaagtacctctacgagatcgccagaagacatc<br>catacttctacgcccccgagctgctgttcttcgccaagaggtacaaggccgccttcacaga<br>gtgctgccaggccgccgacaaggccgcttgcctgctgcctaagttggacgagctgagagac<br>gagggcaaggccagcagcgccaagcagagactgaagtgcgcaagcctgcagaaattcggcg<br>agagagcctttaaggcctgggccgtggccagactgagccagcgcttccccaaggccgagtt<br>cgccgaggtgagcaagctggtgaccgacctgaccaaagtgcacaccgagtgctgccacggc<br>gacctgctggagtgcgccgacgacagagccgacctggccaagtacatctgcgagaaccagg<br>acagcatcagcagcaagttgaaggagtgctgcgagaagcccctgctggagaagagccactg<br>catcgccgaggtggagaacgacgagatgcccgccgacctgcccagcctggccgccgacttc<br>gtggagagcaaggacgtgtgcaagaactacgccgaggccaaggacgtgttcctgggcatgt<br>tcctgtacgagtacgcccggagacaccccgactacagcgtggtgctgctgctgagactggc<br>caagacctacgagaccaccctggagaagtgctgtgccgccgccgacccccacgagtgctac<br>gccaaggtgttcgacgagttcaagcccctggtggaggagccccagaacctgatcaagcaga<br>actgcgagctgttcgagcagctgggcgagtataagttccagaacgccctgctggtgagata<br>caccaagaaggtgccccaggtcagcacccccaccctggtggaggtgagcagaaatctgggc<br>aaggtgggcagcaaatgctgcaagcaccccgaggccaagagaatgccctgcgccgaggact<br>acctgtcagtggtgctgaaccagctgtgtgtgctgcacgagaagacccccgtgagcgacag<br>agtgaccaagtgctgcaccgagagtctcgtgaacagacggccctgcttcagcgccctggag<br>gtggacgaaacatacgtgcccaaggagttcaacgcagagaccttcaccttccacgcagaca<br>tctgcaccctgagcgagaaggagagacagatcaagaagcagaccgccctggttgagcttgt<br>gaagcacaagcccaaggccaccaaggagcagctgaaggccgtgatggacgacttcgccgcc<br>ttcgtggagaagtgctgcaaggccgacgacaaggagacctgcttcgccgaggagggcaaga<br>agctggtggccgccagccaggccgccctgggcctgtag |
| vH2 Construct (SEQ ID NO: 13)-includes (1) leader sequence (lower case; SEQ ID NO: 38); (2) IL-12β (bolded and underlined; SEQ ID NO: 63); (3) first GS linker (italicized; SEQ ID NO: 88); (4) IL-12α (bolded; SEQ ID NO: 113); (5) second GS linker (italicized and underlined; SEQ ID NO: 138); and (6) albumin (lower case and underlined; SEQ ID NO: 159) | atgagagtgcccgcccagctgctgggcctgctgctgctgtggctgcccggcgccagatgtg<br>cc**ATCTGGGAGCTGAAGAAGGACGTGTACGTGGTGGAGCTGGACTGGTACCCCGACGCCCC**<br>**CGGAGAGATGGTGGTGCTGACCTGCGAGACCCCCGAAGAGGACGGCATCACCTGGACCCTG**<br>**GACCAGAGCAGCGAGGTGCTGGGCAGCGGGAAGACCCTGACCATCCAGGTGAAGGAGTTCT**<br>**GCGACGCCGGCCAGTACACCTGTCACAAGGGCGGCGAGGTGCTGAGCCACAGCCTGCTGCT**<br>**GCTGCACAAGAAGGAGGACGGCATATGGAGCACCGACATCCTGAAGGACCAGAAGGAGCCC**<br>**AAGAACAAGACCTTTCTGAGATGCGAGGCTAAGAATTACAGCGGCAGATTCACCTGCTGGT**<br>**GGCTGACCACCATCAGCACCGACCTGACCTTCAGCGTGAAGAGCAGCAGAGGCAGCAGCGA**<br>**CCCCCAGGGCGTGACATGCGGCGCCGCCACCCTGAGCGCCGAGAGAGTGAGAGGCGACAAC**<br>**AAGGAGTACGAGTACAGCGTGGAGTGCCAGGAGGACTCCGCTTGCCCCGCCGCCGAGGAGA**<br>**GCTTGCCCATCGAGGTGATGGTGGACGCCGTGCACAAGCTCAAGTACGAAAACTACACCAG**<br>**CAGCTTCTTCATCAGAGACATCATCAAGCCCGACCCCCCCAAGAACCTGCAGCTGAAGCCC**<br>**CTGAAAAACAGCAGACAGGTGGAGGTGAGCTGGGAGTACCCCGACACCTGGAGCACCCCCC**<br>**ACAGCTACTTCAGCCTGACCTTCTGCGTGCAGGTGCAGGGAAAAAGCAAGAGAGAGAAGAA**<br>**GGACAGAGTGTTCACCGACAAGACCAGCGCCACCGTGATCTGCAGAAAGAACGCCAGCATC**<br>**TCCGTGAGAGCCCAGGACAGATACTACAGCAGCAGCTGGAGCGAGTGGGCCAGCGTGCCCT**<br>**GTAGC***GGCGGCAGCGGCGGCGGCAGCGGCGGCGGCAGCGGCGGCGGCAGC***AGAAACCTGCC**<br>**CGTGGCCACCCCCGACCCCGGCATGTTCCCCTGCCTGCACCACAGCCAGAACCTGCTGAGA**<br>**GCCGTGAGCAACATGCTGCAGAAGGCCAGACAGACCCTGGAGTTCTACCCCTGCACCAGCG**<br>**AGGAGATCGACCATGAGGACATCACCAAGGACAAGACCAGCACCGTGGAGGCCTGCCTGCC**<br>**CCTGGAGCTGACCAAGAACGAAAGCTGCCTGAACAGCAGAGAGACCAGCTTCATCACCAAC**<br>**GGCAGCTGTCTGGCCTCAAGAAAGACCAGCTTTATGATGGCCCTGTGCCTGTCTAGCATCT**<br>**ACGAGGATCTGAAGATGTACCAGGTGGAGTTCAAGACCATGAACGCCAAGCTGCTGATGGA**<br>**CCCCAAGAGACAGATCTTCCTGGACCAGAACATGTTAGCCGTGATTGACGAGCTGATGCAG**<br>**GCCCTGAACTTCAATAGCGAGACCGTGCCCCAGAAAAGCAGCCTGGAGGAGCCCGACTTCT**<br>**ACAAGACCAAGATCAAGCTGTGCATCCTGCTGCACGCCTTCAGAATCAGAGCCGTAACCAT**<br>**CGACAGAGTGATGAGCTACCTGAACGCCAGT***GGCAGCGGCGGTGGCAGC*gacgctcacaag<br>agcgaggtggcccacagattcaaggacctgggcgaggagaacttcaaggccctggtcctga<br>tcgccttcgcccagtacctgcagcagtgccccttcgaggaccacgtgaagctggtgaacga<br>ggtgaccgagttcgccaagacctgcgtggccgacgagtcggccgagaactgcgacaagagc<br>ctgcacaccctgttcggcgacaagctgtgcaccgtggccaccctgagagaaacctacgggg<br>agatggccgactgctgcgcaaagcaggagcccgagcgaaacgagtgcttcctgcagcacaa |

TABLE 1-continued

| Description | Sequence |
|---|---|
| | ggacgacaaccccaacttgcccagactggtaagacccgaggtggacgtcatgtgcaccgct<br>ttccacgacaacgaggagaccttcctgaagaagtacctgtacgagatcgccagaagacacc<br>cctatttctatgcccctgagctgctgttcttcgccaagcgctacaaggccgccttcaccga<br>gtgctgccaggccgccgacaaggccgcctgcctgctccccaagctggacgagctgagagac<br>gaaggcaaggccagcagcgccaagcagagactgaagtgcgccagcctgcagaagttcggcg<br>agagagccttcaaggcctgggccgtggccagactgtcgcagagattccccaaggccgagtt<br>cgccgaggtgagcaagctggttaccgacctgactaaggtgcacaccgagtgctgccacggc<br>gacctgctggagtgcgccgacgacagagccgacctggccaagtacatctgcgagaaccagg<br>atagcatcagcagcaagctgaaggagtgctgcgagaagccccttctggagaagtcccactg<br>catcgccgaggtggagaacgacgagatgcccgccgacctgcctagcctggccgccgacttc<br>gtggagagcaaggacgtgtgcaagaactacgccgaggccaaggacgtgttcctgggcatgt<br>tcctgtacgagtacgccagaagacaccccgactacagcgtggtgctgctgctgagactggc<br>caagacctacgagactacccttgagaagtgctgcgccgccgccgacccacatgagtgctac<br>gccaaggtgttcgacgagttcaagcccctggtggaagagccccagaacctgatcaagcaga<br>actgcgagctgttcgagcagctgggcgagtacaagttccagaacgcccttctggtgagata<br>caccaagaaggtgcctcaggtgagcaccccccacccttgtggaggtgagcagaaacctcggc<br>aaggtgggcagcaagtgctgcaagcatccagaggccaagagaatgccctgcgccgaggact<br>acctgagcgtggtgctgaaccagctgtgcgtgctgcacgagaaaactcccgtgagcgacag<br>agtgaccaagtgctgcaccgagagtctggtgaacagaagaccctgcttcagcgccctggag<br>gtggacgagacctacgtgcccaaggagttcaacgccgagaccttcaccttccacgccgaca<br>tctgcaccctgagcgagaaggagcggcagatcaagaagcagaccgccctggtggagctggt<br>gaagcacaagcccaaggccaccaaggagcagctcaaggccgtgatggacgacttcgccgcg<br>ttcgtggagaagtgctgcaaggccgacgacaaagagacctgcttcgccgaggagggcaaga<br>agcttgtggccgccagccaggccgccctgggcctgtag |
| vH3 Construct (SEQ ID NO: 14)-includes (1) leader sequence (lower case; SEQ ID NO: 39); (2) IL-12β (bolded and underlined; SEQ ID NO: 64); (3) first GS linker (italicized; SEQ ID NO: 89); (4) IL-12α (bolded; SEQ ID NO: 114); (5) second GS linker (italicized and underlined; SEQ ID NO: 139); and (6) albumin (lower case and underlined; SEQ ID NO: 160) | atgagagtgcccgcccagcttctgggcctgctgctgctgtggctgcccggcgccagatgcg<br>cc**ATCTGGGAGCTGAAGAAGGACGTGTACGTGGTGGAGCTGGACTGGTACCCGGACGCCCC**<br>**GGGCGAGATGGTCGTGCTGACCTGCGACACCCCCGAGGAGGACGGCATCACCTGGACCCTG**<br>**GACCAGTCTAGCGAGGTGCTGGGCAGCGGCAAGACCCTGACCATCCAGGTGAAGGAGTTCG**<br>**GCGACGCCGGCCAGTACACCTGCCACAAGGGCGGCGAGGTGCTGAGCCACAGCCTGCTGCT**<br>**GCTGCACAAGAAGGAGGACGGCATCTGGAGCACCGACATCCTGAAGGACCAGAAGGAGCCT**<br>**AAGAACAAGACCTTCCTGAGATGTGAGGCCAAGAACTACAGCGGCAGATTCACCTGCTGGT**<br>**GGCTGACCACCATCAGCACCGATCTGACCTTCAGCGTGAAGAGCAGCAGAGGCAGCTCAGA**<br>**CCCCCAGGGCGTGACCTGCGGCGCCGCGACCCTGAGCGCCGAGAGAGTGAGAGGCGACAAC**<br>**AAGGAGTACGAGTACAGCGTGGAGTGCCAGGAGGACAGCGCCTGCCCCGCGGCCGAGGAGA**<br>**GCCTGCCCATCGAGGTGATGGTGGACGCCGTGCATAAGCTGAAGTACGAGAACTACACCAG**<br>**CAGCTTCTTCATCAGAGACATCATCAAGCCCGATCCCCCCAAGAACCTGCAGCTGAAGCCA**<br>**CTGAAGAACAGCAGACAGGTGGAGGTGAGCTGGGAGTACCCCGACACCTGGAGCACCCCCC**<br>**ACAGCTACTTCAGCCTGACCTTCTGCGTGCAGGTGCAGGGCAAGAGCAAGAGAGAGAAGAA**<br>**GGACCGGGTGTTCACCGACAAGACCAGCGCCACTGTGATCTGCAGAAAGAACGCCAGCATC**<br>**AGCGTGAGAGCCCAGGACAGATACTACAGCTCCAGCTGGTCAGAGTGGGCCAGCGTGCCCT**<br>**GCAGC***GGCGGCAGCGGTGGCGGGAGCGGCGGCGGGAGCGGCGGCGGAAGC***AGAAACCTGCC**<br>**CGTGGCCACCCCTGACCCCGGCATGTTCCCCTGCCTGCACCACAGCCAGAACCTGCTGAGA**<br>**GCCGTAAGCAACATGCTGCAGAAGGCCAGACAGACTCTGGAGTTCTACCCCTGCACCAGCG**<br>**AGGAGATCGATCACGAGGACATCACCAAGGACAAGACCAGTACCGTGGAGGCCTGCCTGCC**<br>**CCTGGAGCTGACCAAGAACGAGAGCTGCCTGAACAGCAGAGAGACCAGCTTTATAACCAAC**<br>**GGCAGCTGTCTGGCTAGCAGAAAGACCAGCTTCATGATGGCCCTGTGCCTGAGCAGCATCT**<br>**ACGAGGACTTGAAGATGTACCAGGTGGAGTTCAAGACCATGAACGCCAAGCTTCTGATGGA**<br>**CCCCAAGAGACAGATCTTTCTGGACCAGAACATGCTGGCCGTGATCGATGAACTGATGCAG**<br>**GCCCTGAACTTCAACAGCGAGACCGTGCCCCAGAAGAGCAGTCTGGAGGAGCCCGACTTCT**<br>**ACAAGACTAAGATCAAGCTGTGCATCCTGCTGCACGCCTTCAGAATCAGAGCCGTGACCAT**<br>**CGACAGAGTGATGAGCTACCTGAACGCCTCA***GGCAGCGGCGGCGGGAGC*gacgcccacaag<br>agcgaggtggcccacagattcaaggacctcggcgaggagaacttcaaggccctggtgctga<br>tcgctttcgcccagtacctgcagcagtgccccttcgaggaccacgtgaaactggtgaacga<br>ggtgaccgagttcgccaagacctgcgtggccgacgagagcgccgagaactgcgacaagagc<br>ctgcacacgttgttcggcgacaagctgtgcaccgtggccaccctgagagagacctacggcg<br>agatggccgactgctgcgccaagcaggagcccgagagaaacgaatgcttcctgcagcacaa<br>ggacgacaaccccaacctgccccgcctggtgagacccgaggtggacgtgatgtgcaccgcc<br>ttccacgacaacgaggagaccttcctgaagaagtacttgtacgagatcgcaagaagacacc<br>cgtacttctacgcccccgagctgctgttcttcgccaagagatacaaggccgccttcaccga<br>gtgctgccaggccgccgacaaggccgcctgcctgctgcccaagctggacgagctcagagac<br>gagggcaaggccagcagcgccaagcagagactgaagtgcgccagcctgcagaagttcggcg<br>agagagcctttaaggcctgggccgtggccagactgagccagagattccccaaggccgagtt<br>cgccgaagtgagcaagctggtgaccgacctgacgaaggtgcacaccgagtgctgccacggc<br>gacctgctggagtgcgccgacgacagagcagacctggccaagtacatctgcgagaaccagg<br>acagcatcagcagcaagctgaaggagtgctgcgagaagcccctgctggagaagagccactg<br>catcgccgaggtggagaacgacgagatgcccgccgacctgcccagtctggccgcagacttc<br>gtggagagcaaggatgtgtgcaagaactacgccgaggccaaggacgtgttcctgggcatgt<br>tcctgtacgagtacgcaagaagacaccccgactacagcgtggtgctgctgctgagactggc<br>caagacctacgagaccaccctggagaagtgctgcgccgccgccgacccccacgagtgctac<br>gccaaggtgttcgacgagttcaagcccctggtggaggagccccagaacctgatcaagcaga<br>actgcgaactgttcgagcagcttggcgagtacaagtttcagaacgccctgctggtcagata<br>caccaagaaggtgccccaggtgagcacccccaccctggtggaggtgtccagaaacctgggc<br>aaggtgggcagcaagtgctgcaagcacccccgaggcaaagagaatgccctgcgccgaggact<br>atctgagcgtggtgctgaaccagctgtgcgtgctgcacgagaagaccccccgtgagcgacag<br>agtgaccaagtgctgcaccgagagcctggtgaatagaagaccctgcttcagcgcactggag<br>gtggacgagacctacgtgcccaaggagttcaacgccgagacattcaccttccacgccgata<br>tctgcaccctgagcgagaaggagagacagatcaagaagcagaccgccctggtggagctggt |

TABLE 1-continued

| Description | Sequence |
|---|---|
| | gaagcacaagcccaaggccaccaaggagcagttgaaggccgtgatggacgacttcgccgcc<br>ttcgtggagaaatgctgcaaggccgacgacaaggagacctgcttcgccgaggagggcaaga<br>agctggtggccgccagccaggccgccctgggcctgtag |
| A1 Construct (SEQ ID NO: 15)-includes (1) leader sequence (lower case; SEQ ID NO: 40); (2) IL-12β (bolded and underlined; SEQ ID NO: 65); (3) GS linker (italicized; SEQ ID NO: 90); and (4) IL-12α (bolded; SEQ ID NO: 115) | atgagggtccccgctcagctcctggggctcctgctgctctggctcccaggtgcacgatgtg<br>cc**ATCTGGGAGCTGAAGAAAGACGTGTACGTGGTGGAGCTTGACTGGTACCCCGACGCCCC**<br>**CGGTGAAATGGTGGTTCTGACCTGCGACACACCAGAGGAGGACGGCATCACCTGGACCCTG**<br>**GACCAGTCCAGCGAGGTCCTGGGATCTGGCAAGACCCTGACCATCCAGGTTAAGGAATTTG**<br>**GCGACGCCGGCCAGTACACCTGCCACAAAGGCGGCGAGGTCCTTTCGCACAGTCTGCTGCT**<br>**GCTGCATAAAAAGGAGGACGGCATTTGGAGCACCGACATTCTGAAGGATCAGAAAGAGCCC**<br>**AAGAACAAGACCTTTCTGAGATGTGAGGCCAAAAACTACTCTGGACGCTTCACCTGTTGGT**<br>**GGCTGACCACCATCAGCACAGACCTGACCTTCTCGGTGAAGTCTAGTAGGGGCAGCAGTGA**<br>**CCCCCAGGGCGTAACATGCGGCGCCGCTACCCTGAGCGCCGAGAGAGTGAGAGGCGATAAC**<br>**AAGGAGTACGAGTACTCCGTGGAGTGCCAAGAGGACTCAGCCTGCCCCGCCGCCGAGGAGT**<br>**CGCTGCCCATCGAGGTGATGGTGGATGCAGTGCACAAGCTGAAGTACGAGAACTACACCAG**<br>**TAGCTTTTTCATCAGAGATATCATTAAACCCGACCCTCCCAAGAACCTGCAGCTGAAGCCC**<br>**TTAAAGAACAGCCGGCAGGTGGAAGTGTCATGGGAGTACCCAGACACCTGGAGCACTCCGC**<br>**ACAGCTACTTCAGCCTGACCTTCTGCGTTCAGGTGCAGGGAAAAAGCAAGAGAGAGAAGAA**<br>**AGACAGAGTGTTCACCGACAAGACCAGCGCAACCGTGATCTGTAGAAAGAACGCCTCGATC**<br>**AGCGTGAGAGCCCAGGACAGATACTACAGCAGCAGCTGGAGCGAGTGGGCCAGTGTACCTT**<br>**GCAGC***GGTGGAAGCGGCGGAGGCTCTGGCGGAGGGAGTGGCGGAGGCAGC***AGAAATCTTCC**<br>**AGTAGCTACCCCCGACCCCGGCATGTTTCCCTGTCTGCACCATTCTCAAAACCTGTTACGG**<br>**GCCGTGAGCAACATGCTGCAGAAGGCCAGACAGACACTGGAGTTTTACCCCTGTACCTCAG**<br>**AGGAGATCGATCATGAGGACATTACTAAGGACAAGACCAGCACCGTGGAAGCCTGCCTGCC**<br>**CCTAGAGCTAACCAAGAACGAGAGCTGCCTGAACTCTAGAGAGACAAGCTTCATCACGAAC**<br>**GGCTCATGCCTGGCCAGTAGGAAAACCAGCTTCATGATGGCTCTGTGCCTGAGCTCCATAT**<br>**ATGAGGACCTTAAGATGTACCAGGTGGAGTTCAAAACCATGAACGCCAAGCTGCTGATGGA**<br>**CCCAAAGAGACAGATCTTCCTTGACCAGAACATGCTGGCCGTTATCGATGAGCTGATGCAG**<br>**GCCCTGAACTTCAACAGCGAGACCGTGCCCCAGAAAAGCAGCCTGGAGGAACCCGACTTCT**<br>**ACAAAACCAAGATCAAGCTGTGCATTCTGCTGCATGCCTTCCGCATTAGAGCCGTGACCAT**<br>**CGATAGGGTGATGAGCTACCTGAACGCCAGC** |
| A2 Construct (SEQ ID NO: 16)-includes (1) leader sequence (lower case; SEQ ID NO: 41); (2) IL-12β (bolded and underlined; SEQ ID NO: 66); (3) GS linker (italicized; SEQ ID NO: 91); and (4) IL-12α (bolded; SEQ ID NO: 116) | atgagggtccccgctcagctcctggggctcctgctgctctggctcccaggtgcacgatgtg<br>cc**ATCTGGGAACTGAAGAAGGACGTCTACGTGGTGGAGCTGGATTGGTACCCCGACGCCCC**<br>**CGGCGAGATGGTCGTGCTGACCTGTGACACCCCTGAGGAGGACGGAATCACATGGACCCTG**<br>**GACCAGAGCAGCGAAGTGTTGGGCAGCGGCAAGACCCTGACCATCCAAGTGAAGGAATTCG**<br>**GCGACGCGGGCCAGTATACTTGCCACAAGGGCGGGGAGGTTCTGAGCCACAGCCTGCTGCT**<br>**GCTCCACAAGAAAGAGGATGGCATCTGGTCTACCGACATCCTGAAGGACCAAAAGGAGCCA**<br>**AAGAACAAGACCTTCCTAAGATGCGAGGCCAAGAACTACTCAGGTCGTTTCACCTGCTGGT**<br>**GGCTGACCACAATCTCCACCGACCTGACCTTCAGCGTGAAAAGCAGCCGCGGCAGTAGCGA**<br>**CCCACAGGGCGTGACCTGCGGGGCCGCCACTCTGAGCGCCGAGAGAGTGCGCGGCGATAAT**<br>**AAGGAATACGAGTACAGCGTGGAGTGCCAGGAAGACTCAGCCTGCCCCGCCGCAGAAGAAA**<br>**GTCTGCCAATAGAGGTGATGGTTGACGCCGTGCACAAGCTAAAGTACGAGAACTACACCAG**<br>**CAGCTTCTTTATCCGGGACATCATCAAGCCAGATCCCCCCAAGAACCTGCAGCTTAAGCCC**<br>**CTGAAGAACAGCAGACAGGTGGAGGTGTCATGGGAATACCCCGACACCTGGAGCACCCCCC**<br>**ATAGCTACTTCTCACTGACCTTCTGCGTGCAGGTGCAGGGCAAGAGCAAGAGAGAGAAGAA**<br>**GGATAGGGTATTCACGGACAAGACCTCAGCCACCGTGATCTGCCGAAAGAACGCCAGCATC**<br>**AGCGTGAGAGCCCAGGACAGATACTATAGCTCCTCGTGGAGCGAGTGGGCCAGCGTACCTT**<br>**GCAGC***GGCGGGAGCGGCGGCGGCAGCGGAGGTGGCAGTGGCGGAGGCAGC***AGAAACCTCCC**<br>**CGTGGCAACCCCTGACCCCGGGATGTTTCCTTGCCTGCACCACTCCCAGAACCTCCTGAGA**<br>**GCCGTGTCCAACATGCTGCAGAAAGCCAGACAGACCCTCGAGTTCTATCCCTGCACAAGCG**<br>**AGGAGATCGACCACGAGGACATCACTAAGGACAAGACCAGCACAGTGGAAGCCTGCCTCCC**<br>**GCTGGAGCTGACTAAGAACGAGAGCTGTCTGAACAGCAGGGAGACCAGCTTCATCACCAAC**<br>**GGCAGCTGCCTGGCGAGCAGAAAAACCTCCTTTATGATGGCGCTCTGCCTGAGCTCAATCT**<br>**ATGAGGACCTGAAGATGTACCAGGTGGAGTTTAAAACCATGAATGCCAAGCTGCTTATGGA**<br>**CCCTAAGAGACAGATTTTCCTGGATCAGAACATGCTGGCCGTGATTGATGAATTAATGCAG**<br>**GCGCTGAACTTTAACAGCGAGACCGTGCCCCAGAAAAGCAGCCTGGAGGAGCCCGACTTTT**<br>**ACAAGACCAAGATCAAGTTGTGCATCCTCCTGCACGCCTTCAGAATCAGAGCGGTGACGAT**<br>**CGACAGAGTCATGAGCTACCTCAACGCT** |
| A3 Construct (SEQ ID NO: 17)-includes (1) leader sequence (lower case; SEQ ID NO: 42); (2) IL-12β (bolded and underlined; SEQ ID NO: 67); (3) GS linker (italicized; SEQ ID NO: 92); and (4) IL-12α (bolded; SEQ ID NO: 117) | atgagggtccccgctcagctcctggggctcctgctgctctggctcccaggtgcacgatgtg<br>cc**ATCTGGGAGCTGAAGAAGGACGTGTACGTGGTGGAGCTGGACTGGTACCCCGACGCCCC**<br>**CGGCGAGATGGTGGTGCTGACCTGCGACACCCCCGAGGAGGACGGCATCACCTGGACCCTG**<br>**GACCAGAGCAGCGAGGTGCTGGGCAGCGGCAAGACCCTGACCATCCAGGTGAAGGAGTTCG**<br>**GCGACGCCGGCCAGTACACCTGCCACAAGGGCGGCGAGGTGCTGAGCCACAGCCTGCTGCT**<br>**GCTGCACAAGAAGGAGGACGGCATCTGGAGCACCGACATCCTGAAGGACCAGAAGGAGCCC**<br>**AAGAACAAGACCTTCCTGAGATGCGAGGCCAAGAACTACAGCGGCAGATTCACCTGCTGGT**<br>**GGCTGACCACCATCAGCACCGACCTGACCTTCAGCGTGAAAAGCAGCAGAGGCAGCAGCGA**<br>**CCCCCAGGGCGTGACCTGCGGCGCCGCCACCCTGAGCGCCGAGAGAGTGAGAGGCGACAAC**<br>**AAGGAGTACGAGTACAGCGTGGAGTGCCAGGAGGACAGCGCCTGCCCCGCCGCCGAGGAGA**<br>**GCCTGCCCATCGAGGTGATGGTGGACGCCGTGCACAAGCTGAAGTACGAGAACTACACCAG**<br>**CAGCTTCTTCATCAGAGACATCATCAAGCCCGACCCCCCCAAGAACCTGCAGCTGAAGCCC**<br>**CTGAAGAACAGCAGACAGGTGGAGGTGAGCTGGGAGTACCCCGACACCTGGAGCACCCCCC**<br>**ACAGCTACTTCAGCCTGACCTTCTGCGTGCAGGTGCAGGGCAAGAGCAAGAGAGAGAAGAA**<br>**GGACAGAGTGTTCACCGACAAGACCAGCGCCACCGTGATCTGCAGAAAGAACGCCAGCATC**<br>**AGCGTGAGAGCCCAGGACAGATACTACAGCAGCAGCTGGAGCGAGTGGGCCAGCGTGCCCT**<br>**GCAGC***GGCGGCAGCGGCGGCGGCAGCGGCGGCGGCAGCGGCGGCGGCAGC***AGAAACCTGCC**<br>**CGTGGCCACCCCCGACCCCGGCATGTTCCCCTGCCTGCACCACAGCCAGAACCTGCTGAGA** |

TABLE 1-continued

| Description | Sequence |
|---|---|
| | GCCGTGAGCAACATGCTGCAGAAGGCCAGACAGACCCTGGAGTTCTACCCCTGCACCAGCG<br>AGGAGATCGACCACGAGGACATCACCAAGGACAAGACCAGCACCGTGGAGGCCTGCCTGCC<br>CCTGGAGCTGACCAAGAACGAGAGCTGCCTGAACAGCAGAGAGACCAGCTTCATCACCAAC<br>GGCAGCTGCCTGGCCAGCAGAAAGACCAGCTTCATGATGGCCCTGTGCCTGAGCAGCATCT<br>ACGAGGACCTGAAGATGTACCAGGTGGAGTTCAAGACCATGAACGCCAAGCTGCTGATGGA<br>CCCCAAGAGACAGATCTTCCTGGACCAGAACATGCTGGCCGTGATCGACGAGCTGATGCAG<br>GCCCTGAACTTCAACAGCGAGACCGTGCCCCAGAAAAGCAGCCTGGAGGAGCCCGACTTCT<br>ACAAGACCAAGATCAAGCTGTGCATCCTGCTGCACGCCTTCAGAATCAGAGCCGTGACCAT<br>CGACAGAGTGATGAGCTACCTGAACGCCAGC |
| A4 Construct (SEQ ID NO: 18)- includes (1) leader sequence (lower case; SEQ ID NO: 43); (2) IL-12β (bolded and underlined; SEQ ID NO: 68); (3) GS linker (italicized; SEQ ID NO: 93); and (4) IL-12α (bolded; SEQ ID NO: 118) | atgagggtccccgctcagctcctggggctcctgctgctctggctcccaggtgcacgatgtg<br>ccATCTGGGAGCTGAAGAAGGATGTGTATGTGGTGGAGCTGGACTGGTACCCAGATGCCCC<br>TGGAGAGATGGTGGTGCTGACCTGTGACACCCCAGAGGAGGATGGCATCACCTGGACCCTG<br>GACCAGAGCAGCGAGGTGCTGGGCAGCGGCAAGACCCTGACCATCCAGGTGAAGGAGTTTG<br>GAGATGCTGGCCAGTACACCTGCCACAAGGGCGGGGAGGTGCTGAGCCACAGCCTGCTGCT<br>GCTGCACAAGAAGGAGGATGGCATCTGGAGCACAGACATCCTGAAGGACCAGAAGGAGCCC<br>AAGAACAAGACCTTCCTGCGCTGTGAGGCCAAGAACTACAGCGGCCGCTTCACCTGCTGGT<br>GGCTGACCACCATCAGCACAGACCTGACCTTCTCTGTGAAAAGCAGCCGGGGCAGCAGTGA<br>CCCCCAGGGCGTGACCTGTGGGGCCGCCACCCTGTCTGCTGAGCGGGTGCGGGGGGACAAC<br>AAGGAGTATGAGTACAGCGTGGAGTGCCAGGAGGACAGCGCCTGCCCAGCTGCTGAGGAGA<br>GCCTGCCCATCGAGGTGATGGTGGATGCTGTGCACAAGCTGAAGTATGAGAACTACACCAG<br>CAGCTTCTTCATCCGGGACATCATCAAGCCAGACCCCCCCAAGAACCTGCAGCTGAAGCCC<br>CTGAAGAACAGCCGGCAGGTGGAGGTGTCCTGGGAGTACCCAGACACCTGGAGCACCCCCC<br>ACAGCTACTTCAGCCTGACCTTCTGTGTGCAGGTGCAGGGCAAGAGCAAGCGGGAGAAGAA<br>GGACAGAGTCTTCACAGACAAGACCAGCGCCACCGTCATCTGCAGGAAGAATGCCAGCATC<br>TCTGTGCGGGCCCAGGACCGCTACTACAGCAGCTCCTGGAGCGAGTGGGCCTCTGTGCCCT<br>GCAGCGGCGGCAGCGGCGGCGGCAGCGGCGGCGGCAGCGGCGGCGGCAGCAGGAACCTGCC<br>TGTGGCCACCCCAGACCCCGGCATGTTCCCCTGCCTGCACCACAGCCAGAACCTGCTGCGG<br>GCTGTGAGCAACATGCTGCAGAAGGCCCGGCAGACCCTGGAGTTCTACCCCTGCACCAGCG<br>AGGAGATTGACCACGAGGACATCACCAAGGACAAGACCAGCACAGTGGAGGCCTGCCTGCC<br>CCTGGAGCTGACCAAGAATGAAAGCTGCCTGAACAGCCGGGAGACCAGCTTCATCACCAAC<br>GGCAGCTGCCTGGCCAGCAGGAAGACCAGCTTCATGATGGCCCTGTGCCTGAGCAGCATCT<br>ATGAGGACCTGAAGATGTACCAGGTGGAGTTCAAGACCATGAATGCCAAGCTGCTGATGGA<br>CCCCAAGAGGCAGATCTTCCTGGACCAGAACATGCTGGCCGTGATTGATGAGCTGATGCAG<br>GCCCTGAACTTCAACAGCGAGACCGTGCCCCAGAAAAGCAGCCTGGAGGAGCCAGACTTCT<br>ACAAGACCAAGATCAAGCTGTGCATCCTGCTGCACGCCTTCCGCATCCGGGCTGTGACCAT<br>CGACAGAGTGATGAGCTACCTGAATGCCAGC |
| B1 Construct (SEQ ID NO: 19)- includes (1) leader sequence (lower case; SEQ ID NO: 44); (2) IL-12β (bolded and underlined; SEQ ID NO: 69); (3) first GS linker (italicized; SEQ ID NO: 94); (4) IL-12α (bolded; SEQ ID NO: 119); (5) second GS linker (italicized and underlined; SEQ ID NO: 140); and (6) albumin (lower case and underlined; SEQ ID NO: 161) | atgagggtccccgctcagctcctggggctcctgctgctctggctcccaggtgcacgatgtg<br>ccATCTGGGAGCTGAAGAAAGACGTGTACGTGGTGGAGCTTGACTGGTACCCCGACGCCCC<br>CGGTGAAATGGTGGTTCTGACCTGCGACACACCAGAGGAGGACGGCATCACCTGGACCCTG<br>GACCAGTCCAGCGAGGTCCTGGGATCTGGCAAGACCCTGACCATCCAGGTTAAGGAATTTG<br>GCGACGCCGGCCAGTACACCTGCCACAAAGGCGGCGAGGTCCTTTCGCACAGTCTGCTGCT<br>GCTGCATAAAAAGGAGGACGGCATTTGGAGCACCGACATTCTGAAGGATCAGAAAGAGCCC<br>AAGAACAAGACCTTTCTGAGATGTGAGGCCAAAAACTACTCTGGACGCTTCACCTGTTGGT<br>GGCTGACCACCATCAGCACAGACCTGACCTTCTCGGTGAAGTCTAGTAGGGGCAGCAGTGA<br>CCCCCAGGGCGTAACATGCGGCGCCGCTACCCTGAGCGCCGAGAGAGTGAGAGGCGATAAC<br>AAGGAGTACGAGTACTCCGTGGAGTGCCAAGAGGACTCAGCCTGGCCCGCCGCCGAGGAGT<br>CGCTGCCCATCGAGGTGATGGTGGATGCAGTGCACAAGCTGAAGTACGAGAACTACACCAG<br>TAGCTTTTTCATCAGAGATATCATTAAACCCGACCCTCCCAAGAACCTGCAGCTGAAGCCC<br>TTAAAGAACAGCCGGCAGGTGGAAGTGTCATGGGAGTACCCAGACACCTGGAGCACTCCGC<br>ACAGCTACTTCAGCCTGACCTTCTGCGTTCAGGTGCAGGGAAAAAGCAAGAGAGAGAAGAA<br>AGACAGAGTGTTCACCGACAAGACCAGCGCAACCGTGATCTGTAGAAAGAACGCCTCGATC<br>AGCGTGAGAGCCCAGGACAGATACTACAGCAGCAGCTGGAGCGAGTGGGCCAGTGTACCTT<br>GCAGCGGTGGAAGCGGCGGAGGCTCTGGCGGAGGGAGTGGCGGAGGCAGCAGAAATCTTCC<br>AGTAGCTACCCCCGACCCCGGCATGTTTCCCTGTCTGCACCATTCTCAAAACCTGTTACGG<br>GCCGTGAGCAACATGCTGCAGAAGGCCAGACAGACACTGGAGTTTTACCCCTGTACCTCAG<br>AGGAGATCGATCATGAGGACATTACTAAGGACAAGACCAGCACCGTGGAAGCCTGCCTGCC<br>CCTAGAGCTAACCAAGAACGAGAGCTGCCTGAACTCTAGAGAGACAAGCTTCATCACGAAC<br>GGCTCATGCCTGGCCAGTAGGAAAACCAGCTTCATGATGGCTCTGTGCCTGAGCTCCATAT<br>ATGAGGACCTTAAGATGTACCAGGTGGAGTTCAAAACCATGAACGCCAAGCTGCTGATGGA<br>CCCAAAGAGACAGATCTTCCTTGACCAGAACATGCTGGCCGTTATCGATGAGCTGATGCAG<br>GCCCTGAACTTCAACAGCGAGACCGTGCCCCAGAAAAGCAGCCTGGAGGAACCCGACTTCT<br>ACAAAACCAAGATCAAGCTGTGCATTCTGCTGCATGCCTTCCGCATTAGAGCCGTGACCAT<br>CGATAGGGTGATGAGCTACCTGAACGCCAGCGGCTCTGGCGGCGGCAGTgacgcccacaag<br>tccgaggtcgcccacagattcaaggatttgggcgaggagaacttcaaggccctggtgctga<br>tcgccttcgcccagtacttgcagcagtgtcccttcgaggaccatgtgaagctggtgaacga<br>ggtgaccgagttcgccaagacctgtgtggccgacgagagcgccgagaactgcgataagtct<br>ctgcacacccttttggcgacaaactgtgcaccgtggccaccctgagagagacctacggcg<br>agatggccgactgctgtgcgaagcaggagcccgagcgcaatgagtgtttcctgcagcataa<br>ggacgacaaccccaacctgcccagactggtgagacccgaggtggacgtgatgtgcaccgcc<br>ttccacgacaacgaggagacctttctgaaaaaatacctgtacgagatcgcaagacgccacc<br>cctacttctacgcccccgagctgctgttcttcgccaagcgctacaaggctgccttcaccga<br>atgctgccaggccgccgataaggccgcgtgcttactgccaaagctggacgagctgagagac<br>gaggggaaagcctctagcgccaaacagagattgaagtgtgccagcctgcagaaattcggtg<br>agagagccttcaaggcctgggccgtggccagattatcacagcggttccccaaggctgaatt<br>cgccgaggtgagcaaacttgtcaccgatctgacaaaagtgcacaccgagtgctgccatggc<br>gacctgctggagtgcgccgacgaccgggccgacctggccaagtacatctgcgagaaccagg |

TABLE 1-continued

| Description | Sequence |
|---|---|
| | acagcatctccagcaagctgaaggagtgctgcgagaagcccctgctggagaaaagccactg<br>catcgccgaggtggagaatgacgaaatgcccgccgacctgcccagcctggccgccgacttc<br>gtggaaagcaaggacgtgtgcaaaaattacgccgaagccaaggatgtgttcttgggcatgt<br>tcttgtacgagtacgccagacgccaccccgactacagcgtggtgctgctgctgcggctggc<br>caagacctacgagaccaccctggagaagtgctgtgctgccgccgacccccacgagtgctac<br>gccaaggtatttgacgagttcaagcccctggtggaggagcctcagaacctgattaagcaga<br>actgtgagctgttcgagcagctgggcgagtacaagttccagaacgccctcctggtgagata<br>caccaaaaaggtgcctcaggtaagcactcccaccctggtggaggtgagcaggaacctcggc<br>aaggtgggcagcaaatgctgcaagcacccagaggccaaaagaatgccctgcgcagaagact<br>acctcagcgtggtcctgaaccagctgtgcgtgctgcacgaaaagacccctgtgagcgatag<br>agtgacaaagtgctgcaccgagagcctggtgaacagaagaccctgttttagcgccctggag<br>gtggacgagacctacgtgcccaaggagttcaacgccgagacgttcactttccacgcggaca<br>tctgcaccctgagcgagaaggagagacaaatcaagaagcagaccgccctagtcgagctggt<br>aaaacacaagcccaaggccaccaaggagcagctgaaggccgtgatggacgactttgcagcc<br>ttcgtggagaagtgctgcaaggctgacgacaaggagacctgcttcgccgaggagggcaaga<br>agctcgtagccgccagccaggccgctctcggcctt |
| B2 Construct (SEQ ID NO: 20)-includes (1) leader sequence (lower case; SEQ ID NO: 45); (2) IL-12β (bolded and underlined; SEQ ID NO: 70); (3) first GS linker (italicized; SEQ ID NO: 95); (4) IL-12α (bolded; SEQ ID NO: 120); (5) second GS linker (italicized and underlined; SEQ ID NO: 141); and (6) albumin (lower case and underlined; SEQ ID NO: 162) | atgagggtccccgctcagctcctggggctcctgctgctctggctcccaggtgcacgatgtg<br>ccATCTGGGAACTGAAGAAGGACGTCTACGTGGTGGAGCTGGATTGGTACCCCGACGCCCC<br>CGGCGAGATGGTCGTGCTGACCTGTGACACCCCTGAGGAGGACGGAATCACATGGACCCTG<br>GACCAGAGCAGCGAAGTGTTGGGCAGCGGCAAGACCCTGACCATCCAAGTGAAGGAATTCG<br>GCGACGCGGGCCAGTATACTTGCCACAAGGGCGGGGAGGTTCTGAGCCACAGCCTGCTGCT<br>GCTCCACAAGAAAGAGGATGGCATCTGGTCTACCGACATCCTGAAGGACCAAAAGGAGCCA<br>AAGAACAAGACCTTCCTAAGATGCGAGGCCAAGAACTACTCAGGTCGTTTCACCTGCTGGT<br>GGCTGACCACAATCTCCACCGACCTGACCTTCAGCGTGAAAAGCAGCCGCGGCAGTAGCGA<br>CCCACAGGGCGTGACCTGCGGGGCCGCCACTCTGAGCGCCGAGAGAGTGCGCGGCGATAAT<br>AAGGAATACGAGTACAGCGTGGAGTGCCAGGAAGACTCAGCCTGCCCCGCCGCAGAAGAAA<br>GTCTGCCAATAGAGGTGATGGTTGACGCCGTGCACAAGCTAAAGTACGAGAACTACACCAG<br>CAGCTTCTTTATCCGGGACATCATCAAGCCAGATCCCCCCAAGAACCTGCAGCTTAAGCCC<br>CTGAAGAACAGCAGACAGGTGGAGGTGTCATGGGAATACCCCGACACCTGGAGCACCCCCC<br>ATAGCTACTTCTCACTGACCTTCTGCGTGCAGGTGCAGGGCAAGAGCAAGAGAGAGAAGAA<br>GGATAGGGTATTCACGGACAAGACCTCAGCCACCGTGATCTGCCGAAAGAACGCCAGCATC<br>AGCGTGAGAGCCCAGGACAGATACTATAGCTCCTCGTGGAGCGAGTGGGCCAGCGTACCTT<br>GCAGCGGCGGGAGCGGCGGCGGCAGCGGAGGTGGCAGTGGCGGAGGCAGCAGAAACCTCCC<br>CGTGGCAACCCCTGACCCCGGGATGTTTCCTTGCCTGCACCACTCCCAGAACCTCCTGAGA<br>GCCGTGTCCAACATGCTGCAGAAAGCCAGACAGACCCTCGAGTTCTATCCCTGCACAAGCG<br>AGGAGATCGACCACGAGGACATCACTAAGGACAAGACCAGCACAGTGGAAGCCTGCCTCCC<br>GCTGGAGCTGACTAAGAACGAGAGCTGTCTGAACAGCAGGGAGACCAGCTTCATCACCAAC<br>GGCAGCTGCCTGGCGAGCAGAAAAACCTCCTTTATGATGGCGCTCTGCCTGAGCTCAATCT<br>ATGAGGACCTGAAGATGTACCAGGTGGAGTTTAAAACCATGAATGCCAAGCTGCTTATGGA<br>CCCTAAGAGACAGATTTTCCTGGATCAGAACATGCTGGCCGTGATTGATGAATTAATGCAG<br>GCGCTGAACTTTAACAGCGAGACCGTGCCCCAGAAAAGCAGCCTGGAGGAGCCCGACTTTT<br>ACAAGACCAAGATCAAGTTGTGCATCCTCCTGCACGCCTTCAGAATCAGAGCGGTGACGAT<br>CGACAGAGTCATGAGCTACCTCAACGCTAGCGGCAGCGGTGGCGGCAGCgacgcccacaag<br>agcgaggtggcccacagattcaaggatctcggggaggagaacttcaaggccctggtgctga<br>tcgccttcgcacagtacctgcagcagtgccccttcgaggaccacgtaaaactggtgaacga<br>ggtgacggagttcgccaagacctgtgttgccgacgagtcggccgagaattgcgacaagagc<br>ctgcataccctgttcggcgacaagctgtgcaccgtggccaccctgagagagacctacggcg<br>agatggccgactgctgcgccaagcaagagcccgagagaaacgagtgcttcctgcagcacaa<br>ggacgacaaccccaacctgccccggctggtgagacccgaggtggacgtgatgtgcaccgcc<br>ttccacgacaacgaggagaccttcctgaagaagtatctgtacgagatcgccagaagacacc<br>cttatttttacgcccccgagctgctgttcttcgctaagagatataaggcagccttcaccga<br>gtgttgtcaggccgccgataaggccgcttgcctgctgcccaagttggacgagctcagagac<br>gagggcaaggcgagcagcgccaagcagagactgaagtgcgccagcctgcagaagttcggcg<br>agagggccttcaaggcctgggcggtggccagactgtcccagagatttcccaaggccgagtt<br>cgccgaggtaagcaagctggtcaccgacctgaccaaggtgcacaccgagtgttgccacggc<br>gacctgctggaatgcgccgatgaccgtgccgacctggccaagtacatctgcgagaatcagg<br>actccatcagcagcaaactgaaggagtgttgcgagaagcccctgctggaaaagagccattg<br>catcgctgaggtggaaaacgacgagatgcccgcagacctgcccagcctggccgcagacttt<br>gtggaaagtaaggacgtgtgcaagaactacgcggaggccaaagacgtgtttctgggcatgt<br>tcctatacgagtatgccagaagacaccccgactacagcgttgtgttattgctgagactggc<br>caagacctacgagactaccttggagaagtgctgcgccgccgccgacccccacgagtgctat<br>gccaaggtgttcgacgagttcaagcccctggtggaggagccccagaatctgattaagcaga<br>attgcgagctttttgagcagctgggcgagtataagttccagaacgccctgctggtgagata<br>caccaaaaaggtacctcaggtgagcacccccaccctggtggaggtgagcagaaatctgggc<br>aaggtgggcagcaagtgctgcaagcacccggaggccaagagaatgccctgtgccgaggatt<br>acctgtcagtggtgctgaaccagctgtgcgttctgcacgaaaagacgcccgtgtcggacag<br>agtgaccaagtgctgcacggagagcctggtgaacagaagaccgtgcttcagcgccctagag<br>gtggacgagacctacgtgcccaaggagttcaacgccgagaccttcaccttccacgccgaca<br>tctgtaccctgtcagagaaggagagacagatcaagaagcagaccgccttagtggagctggt<br>gaagcacaagcccaaggccaccaaggagcagctgaaagccgtgatggacgatttcgcagcc<br>ttcgtcgagaagtgctgcaaggccgacgacaaggaaacttgcttcgccgaggagggcaaga<br>agctggtggctgcctcgcaggccgccctcggcctg |
| B3 Construct (SEQ ID NO: 21)-includes (1) leader sequence (lower | atgagggtccccgctcagctcctggggctcctgctgctctggctcccaggtgcacgatgtg<br>ccATCTGGGAGCTGAAGAAGGACGTGTACGTGGTGGAGCTGGACTGGTACCCCGACGCCCC<br>CGGCGAGATGGTGGTGCTGACCTGCGACACCCCCGAGGAGGACGGCATCACCTGGACCCTG<br>GACCAGAGCAGCGAGGTGCTGGGCAGCGGCAAGACCCTGACCATCCAGGTGAAGGAGTTCG |

TABLE 1-continued

| Description | Sequence |
| --- | --- |
| case; SEQ ID NO: 46); (2) IL-12β (bolded and underlined; SEQ ID NO: 71); (3) first GS linker (italicized; SEQ ID NO: 96); (4) IL-12α (bolded; SEQ ID NO: 121); (5) second GS linker (italicized and underlined; SEQ ID NO: 142); and (6) albumin (lower case and underlined; SEQ ID NO: 163) | GCGACGCCGGCCAGTACACCTGCCACAAGGGCGGCGAGGTGCTGAGCCACAGCCTGCTGCT<br>GCTGCACAAGAAGGAGGACGGCATCTGGAGCACCGACATCCTGAAGGACCAGAAGGAGCCC<br>AAGAACAAGACCTTCCTGAGATGCGAGGCCAAGAACTACAGCGGCAGATTCACCTGCTGGT<br>GGCTGACCACCATCAGCACCGACCTGACCTTCAGCGTGAAAAGCAGCAGAGGCAGCAGCGA<br>CCCCCAGGGCGTGACCTGCGGCGCCGCCACCCTGAGCGCCGAGAGAGTGAGAGGCGACAAC<br>AAGGAGTACGAGTACAGCGTGGAGTGCCAGGAGGACAGCGCCTGCCCCGCCGCCGAGGAGA<br>GCCTGCCCATCGAGGTGATGGTGGACGCCGTGCACAAGCTGAAGTACGAGAACTACACCAG<br>CAGCTTCTTCATCAGAGACATCAATCAAGCCGACCCCCCCAAGAACCTGCAGCTGAAGCCC<br>CTGAAGAACAGCAGACAGGTGGAGGTGAGCTGGGAGTACCCCGACACCTGGAGCACCCCCC<br>ACAGCTACTTCAGCCTGACCTTCTGCGTGCAGGTGCAGGGCAAGAGCAAGAGAGAGAAGAA<br>GGACAGAGTGTTCACCGACAAGACCAGCGCCACCGTGATCTGCAGAAAGAACGCCAGCATC<br>AGCGTGAGAGCCCAGGACAGATACTACAGCAGCAGCTGGAGCGAGTGGGCCAGCGTGCCCT<br>GCAGC*GGCGGCAGCGGCGGCGGCAGCGGCGGCGGCAGCGGCGGCGGCAGC*AGAAACCTGCC<br>CGTGGCCACCCCCGACCCCGGCATGTTCCCCTGCCTGCACCACAGCCAGAACCTGCTGAGA<br>GCCGTGAGCAACATGCTGCAGAAGGCCAGACAGACCCTGGAGTTCTACCCCTGCACCAGCG<br>AGGAGATCGACCACGAGGACATCACCAAGGACAAGACCAGCACCGTGGAGGCCTGCCTGCC<br>CCTGGAGCTGACCAAGAACGAGAGCTGCCTGAACAGCAGAGAGACCAGCTTCATCACCAAC<br>GGCAGCTGCCTGGCCAGCAGAAAGACCAGCTTCATGATGGCCCTGTGCCTGAGCAGCATCT<br>ACGAGGACCTGAAGATGTACCAGGTGGAGTTCAAGACCATGAACGCCAAGCTGCTGATGGA<br>CCCCAAGAGACAGATCTTCCTGGACCAGAACATGCTGGCCGTGATCGACGAGCTGATGCAG<br>GCCCTGAACTTCAACAGCGAGACCGTGCCCCAGAAAAGCAGCCTGGAGGAGCCCGACTTCT<br>ACAAGACCAAGATCAAGCTGTGCATCCTGCTGCACGCCTTCAGAATCAGAGCCGTGACCAT<br>CGACAGAGTGATGAGCTACCTGAACGCCAGC*GGCAGCGGCGGCGGCAGC*gacgcccacaag<br>agcgaggtggcccacagattcaaggacctgggcgaggagaacttcaaggccctggtgctga<br>tcgccttcgcccagtacctgcagcagtgccccttcgaggaccacgtgaagctggtgaacga<br>ggtgaccgagttcgccaagacctgcgtggccgacgagagcgccgagaactgcgacaagagc<br>ctgcacaccctgttcggcgacaagctgtgcaccgtggccaccctgagagagacctacggcg<br>agatggccgactgctgcgccaagcaggagcccgagagaaacgagtgcttcctgcagcacaa<br>ggacgacaaccccaacctgcccagactggtgagacccgaggtggacgtgatgtgcaccgcc<br>ttccacgacaacgaggagaccttcctgaagaagtacctgtacgagatcgccagaagacacc<br>cctacttctacgcccccgagctgctgttcttcgccaagagatacaaggccgccttcaccga<br>gtgctgccaggccgccgacaaggccgcctgcctgctgcccaagctggacgagctgagagac<br>gagggcaaggccagcagcgccaagcagagactgaagtgcgccagcctgcagaagttcggcg<br>agagagccttcaaggcctgggccgtggccagactgagccagagattccccaaggccgagtt<br>cgccgaggtgagcaagctggtgaccgacctgaccaaggtgcacaccgagtgctgccacggc<br>gacctgctggagtgcgccgacgacagagccgacctggccaagtacatctgcgagaaccagg<br>acagcatcagcagcaagctgaaggagtgctgcgagaagcccctgctggagaaaagccactg<br>catcgccgaggtggagaacgacgagatgcccgccgacctgcccagcctggccgccgacttc<br>gtggagagcaaggacgtgtgcaagaactacgccgaggccaaggacgtgttcctgggcatgt<br>tcctgtacgagtacgccagaagacaccccgactacagcgtggtgctgctgctgagactggc<br>caagacctacgagaccaccctggagaagtgctgcgccgccgccgacccccacgagtgctac<br>gccaaggtgttcgacgagttcaagcccctggtggaggagccccagaacctgatcaagcaga<br>actgcgagctgttcgagcagctgggcgagtacaagttccagaacgccctgctggtgagata<br>caccaagaaggtgccccaggtgagcacccccaccctggtggaggtgagcagaaacctgggc<br>aaggtgggcagcaagtgctgcaagcaccccgaggccaagagaatgccctgcgccgaggact<br>acctgagcgtggtgctgaaccagctgtgcgtgctgcacgagaagacccccgtgagcgacag<br>agtgaccaagtgctgcaccgagagcctggtgaacagaagaccctgcttcagcgccctggag<br>gtggacgagacctacgtgcccaaggagttcaacgccgagaccttcaccttccacgccgaca<br>tctgcaccctgagcgagaaggagagacagatcaagaagcagaccgccctggtggagctggt<br>gaagcacaagcccaaggccaccaaggagcagctgaaggccgtgatggacgacttcgccgcc<br>ttcgtggagaagtgctgcaaggccgacgacaaggagacctgcttcgccgaggagggcaaga<br>agctggtggccgccagccaggccgccctgggcctg |
| B4 Construct (SEQ ID NO: 22)-includes (1) leader sequence (lower case; SEQ ID NO: 47); (2) IL-12β (bolded and underlined; SEQ ID NO: 72); (3) first GS linker (italicized; SEQ ID NO: 97); (4) IL-12α (bolded; SEQ ID NO: 122); (5) second GS linker (italicized and underlined; SEQ ID NO: 143); and (6) albumin (lower case and underlined; SEQ ID NO: 164) | atgagggtccccgctcagctcctggggctcctgctgctctggctcccaggtgcacgatgtg<br>ccATCTGGGAGCTGAAGAAGGATGTGTATGTGGTGGAGCTGGACTGGTACCCAGATGCCCC<br>TGGAGAGATGGTGGTGCTGACCTGTGACACCCCAGAGGAGGATGGCATCACCTGGACCCTG<br>GACCAGAGCAGCGAGGTGCTGGGCAGCGGCAAGACCCTGACCATCCAGGTGAAGGAGTTTG<br>GAGATGCTGGCCAGTACACCTGCCACAAGGGCGGGGAGGTGCTGAGCCACAGCCTGCTGCT<br>GCTGCACAAGAAGGAGGATGGCATCTGGAGCACAGACATCCTGAAGGACCAGAAGGAGCCC<br>AAGAACAAGACCTTCCTGCGCTGTGAGGCCAAGAACTACAGCGGCCGCTTCACCTGCTGGT<br>GGCTGACCACCATCAGCACAGACCTGACCTTCTCTGTGAAAAGCAGCCGGGGCAGCAGTGA<br>CCCCCAGGGCGTGACCTGTGGGGCCGCCACCCTGTCTGCTGAGCGGGTGCGGGGGGACAAC<br>AAGGAGTATGAGTACAGCGTGGAGTGCCAGGAGGACAGCGCCTGCCCAGCTGCTGAGGAGA<br>CAGCTTCTTCATCCGGGACATCATCAAGCCAGACCCCCCCAAGAACCTGCAGCTGAAGCCC<br>CTGAAGAACAGCCGGCAGGTGGAGGTGTCCTGGGAGTACCCAGACACCTGGAGCACCCCCC<br>ACAGCTACTTCAGCCTGACCTTCTGTGTGCAGGTGCAGGGCAAGAGCAAGCGGGAGAAGAA<br>GGACAGAGTCTTCACAGACAAGACCAGCGCCACCGTCATCTGCAGGAAGAATGCCAGCATC<br>TCTGTGCGGGCCCAGGACCGCTACTACAGCAGCTCCTGGAGCGAGTGGGCCTCTGTGCCCT<br>GCAGC*GGCGGCAGCGGCGGCGGCAGCGGCGGCGGCAGCGGCGGCGGCAGC*AGGAACCTGCC<br>GCAGCGGCGGCAGCGGCGGCGGCAGCGGCGGCGGCAGCGGCGGCGGCAGCAGGAACCTGCC<br>TGTGGCCACCCCAGACCCCGGCATGTTCCCCTGCCTGCACCACAGCCAGAACCTGCTGCGG<br>GCTGTGAGCAACATGCTGCAGAAGGCCCGGCAGACCCTGGAGTTCTACCCCTGCACCAGCG<br>AGGAGATTGACCACGAGGACATCACCAAGGACAAGACCAGCACAGTGGAGGCCTGCCTGCC<br>CCTGGAGCTGACCAAGAATGAAAGCTGCCTGAACAGCCGGGAGACCAGCTTCATCACCAAC<br>GGCAGCTGCCTGGCCAGCAGGAAGACCAGCTTCATGATGGCCCTGTGCCTGAGCAGCATCT<br>ATGAGGACCTGAAGATGTACCAGGTGGAGTTCAAGACCATGAATGCCAAGCTGCTGATGGA<br>CCCCAAGAGGCAGATCTTCCTGGACCAGAACATGCTGGCCGTGATTGATGAGCTGATGCAG<br>GCCCTGAACTTCAACAGCGAGACCGTGCCCCAGAAAAGCAGCCTGGAGGAGCCAGACTTCT |

TABLE 1-continued

| Description | Sequence |
| --- | --- |
| | **ACAAGACCAAGATCAAGCTGTGCATCCTGCTGCACGCCTTCCGCATCCGGGCTGTGACCAT**<br>**CGACAGAGTGATGAGCTACCTGAATGCCAGC***GGCAGCGGCGGCGGCAGT*gatgcccacaag<br>tctgaggtggcccaccgcttcaaggacctgggggaggagaacttcaaggccctggtgctga<br>ttgcctttgcccagtacctgcagcagtgcccctttgaggaccacgtgaagctggtgaatga<br>ggtgacagaatttgccaagacctgtgtggctgatgaatctgctgagaactgtgacaagagc<br>ctgcacaccctgtttggagacaagctgtgcaccgtggccaccctgcgggagacctatggag<br>agatggctgactgctgtgccaagcaggagcctgagagaaatgaatgcttcctgcagcacaa<br>ggatgacaaccccaacctgccccggctggtgcggcctgaggtggatgtgatgtgcacagcc<br>ttccatgacaatgaggagaccttcctgaagaagtacctgtatgaaattgcccggcggcacc<br>cctacttctacgcccctgagctgctgttctttgccaagcgctacaaggccgccttcacaga<br>gtgctgccaggccgctgacaaggccgcctgcctgctgcccaagctggatgagctgagagat<br>gagggcaaggccagcagcgccaagcagaggctgaagtgtgccagcctgcagaagtttggag<br>agcgggccttcaaggcctgggccgtggcccggctgagccagcgcttccccaaggccgagtt<br>tgctgaggtgtccaagctggtgacagacctgaccaaggtgcacacagagtgctgccacggg<br>gacctgctggagtgtgctgatgacagagctgacctggccaagtacatctgtgagaaccagg<br>acagcatcagcagcaagctgaaggagtgctgtgagaagcccctgctggaaaagagccactg<br>catcgccgaggtggagaatgatgagatgcctgctgacctgcccagcctggccgctgacttt<br>gtggagagcaaggatgtgtgcaagaactatgcagaggccaaggatgtgttcctgggcatgt<br>tcctgtatgaatatgcccggcggcacccagactacagcgtggtgctgctgctgcggctggc<br>caagacctatgagaccaccctggagaagtgctgtgccgctgctgacccccatgaatgttat<br>gccaaggtgtttgatgagttcaagcccctggtggaggagccccagaacctgatcaagcaga<br>actgtgagctgtttgagcagctgggggagtacaagttccagaatgccctgctggtgcgcta<br>caccaagaaggtgccccaggtgtccacccccaccctggtggaggtgtccaggaacctgggc<br>aaggtgggcagcaagtgctgcaagcaccctgaggccaagaggatgccctgtgccgaggact<br>acctgtctgtggtgctgaaccagctgtgtgtgctgcacgagaagacccctgtgtctgacag<br>agtgaccaagtgctgcacagagagcctggtgaacagaagaccctgcttcagcgccctggag<br>gtggatgagacctacgtgcccaaggagttcaatgctgagaccttcaccttccacgccgaca<br>tctgcaccctgtctgagaaggagcggcagatcaagaagcagacagccctggtggagctggt<br>gaagcacaagcccaaggccaccaaggagcagctgaaggctgtgatggatgactttgctgcc<br>tttgtggagaagtgctgcaaggcagatgacaaggagacctgctttgctgaggagggcaaga<br>agctggtggccgccagccaggccgccctgggcctg |
| C1 Construct (SEQ ID NO: 23)-includes (1) leader sequence (lower case; SEQ ID NO: 48); (2) IL-12β (bolded and underlined; SEQ ID NO: 73); (3) first GS linker (italicized; SEQ ID NO: 98); (4) IL-12α (bolded; SEQ ID NO: 123); (5) second GS linker (italicized and underlined; SEQ ID NO: 144); (6) albumin (lower case and underlined; SEQ ID NO: 165); (7) third GS linker (lower case and italicized; SEQ ID NO: 168); and (8) lumican (lower case, italicized, and underlined; SEQ ID NO: 171) | atgagggtccccgctcagctcctggggctcctgctgctctggctcccaggtgcacgatgtg<br>cc**ATCTGGGAGCTGAAAAAGGACGTGTACGTGGTGGAACTTGACTGGTACCCCGACGCCCC**<br>**CGGCGAGATGGTGGTACTGACCTGCGACACTCCCGAGGAAGACGGCATTACCTGGACCTTG**<br>**GACCAGAGCAGCGAGGTTCTGGGCTCCGGAAAAACCTTGACAATCCAAGTGAAAGAATTCG**<br>**GCGACGCTGGCCAGTACACCTGCCACAAGGGCGGCGAGGTGCTGTCCCACAGCCTGCTGCT**<br>**GCTGCATAAGAAAGAAGACGGGATTTGGAGCACCGATATACTGAAGGATCAGAAGGAGCCC**<br>**AAGAACAAGACCTTCCTGAGGTGCGAGGCCAAAAATTACAGCGGCAGATTCACCTGCTGGT**<br>**GGCTGACCACCATTAGCACAGACCTGACTTTCAGCGTAAAGTCTTCAAGGGGCAGCTCAGA**<br>**CCCCCAGGGAGTAACTTGCGGAGCGGCAACGTTGTCTGCCGAGCGGGTCAGAGGCGACAAT**<br>**AAGGAGTACGAGTATTCAGTAGAGTGTCAGGAAGATAGCGCCTGTCCCGCCGCGGAGGAGA**<br>**GCCTCCCCATCGAGGTGATGGTGGACGCCGTGCACAAGTTAAAGTACGAGAATTACACCAG**<br>**CTCATTTTTTATCAGAGACATTATCAAGCCGGACCCCCCGAAGAACTTACAGCTTAAACCC**<br>**CTAAAGAACAGCAGGCAGGTTGAGGTCAGCTGGGAATATCCTGACACCTGGTCAACCCCCC**<br>**ACAGCTACTTCTCCCTTACTTTCTGTGTGCAAGTGCAGGGCAAGAGCAAGAGAGAAAAGAA**<br>**GGACCGGGTGTTTACCGACAAGACTAGCGCCACCGTGATTTGCAGAAAGAACGCCAGCATT**<br>**AGTGTGAGAGCCCAGGACAGGTATTACTCCAGCTCATGGTCTGAGTGGGCTAGTGTGCCTT**<br>**GCTCT***GGAGGCAGCGGTGGCGGGAGCGGCGGAGGCTCCGGGGGAGGTAGC***CGGAATCTGCC**<br>**TGTCGCCACTCCAGACCCCGGCATGTTCCCATGTCTGCATCATTCTCAGAACCTGCTGAGG**<br>**GCCGTATCCAATATGCTGCAGAAAGCCAGACAGACCTTAGAGTTCTATCCCTGTACAAGCG**<br>**AGGAGATAGATCACGAGGATATTACGAAGGACAAAACTTCTACTGTTGAGGCGTGTCTTCC**<br>**ATTAGAGCTGACCAAGAACGAAAGCTGTCTGAATAGCAGAGAGACTTCATTTATCACCAAT**<br>**GGGAGTTGCTTGGCTAGCAGAAAGACCAGCTTCATGATGGCCCTTTGCTTGTCTTCGATAT**<br>**ACGAAGATCTTAAGATGTATCAAGTGGAATTTAAGACGATGAACGCCAAGCTGCTTATGGA**<br>**TCCCAAGCGCCAAATCTTCCTGGATCAGAACATGTTGGCCGTGATTGACGAGCTGATGCAA**<br>**GCCCTGAATTTCAACTCCGAGACCGTGCCTCAGAAAAGCAGCCTCGAGGAGCCCGACTTCT**<br>**ACAAAACAAAGATCAAACTCTGCATCCTTCTGCACGCCTTCAGAATTAGAGCCGTGACCAT**<br>**CGACAGAGTTATGAGCTACCTGAATGCCAGC***GGCAGCGGCGGCGGATCC*gatgcccataaa<br>tctgaggtggcccatagattcaaggatctgggcgaagaaaacttcaaagccttggtcttga<br>tcgcctttgcccagtacctgcagcagtgcccctttgaggaccacgtgaagctggtgaatga<br>agtgaccgagtttgccaagacgtgcgtggctgatgagagcgccgaaaactgcgacaaaagc<br>ctgcacaccctgtttggcgacaagctgtgcaccgtagccaccctgagagaaacttacggcg<br>agatggctgactgctgcgccaagcaggagcccgagagaaacgagtgctttctgcagcacaa<br>ggacgacaatcccaacctgcccagactggtgagacccgaagtggatgttatgtgcaccgct<br>ttccacgacaatgaagagacatttctcaagaagtacttgtacgagattgcaagaagacacc<br>cttacttttacgcccccgaattactgttcttcgctaagaggtataaggcagccttcactga<br>atgctgccaggctgccgacaaagcagcttgcctgctgccaaagctggatgaactgcgagac<br>gaaggaaaggcgtcctccgccaagcagcgtttgaagtgcgccagccttcagaagtttggcg<br>agcgggccttcaaggcatgggccgtggctcgacttagccagcgttttcccaaggctgaatt<br>tgcagaggtgagtaaactggttaccgatctgacaaaggtgcacaccgagtgctgtcacggt<br>gacctcttagagtgcgccgacgacagagccgacctcgccaagtacatttgtgaaaaccaag<br>actcaatctcttcaaagttaaaggagtgctgcgaaaagcccctgcttgaaaagagccactg<br>cattgccgaagtcgagaatgatgagatgcctgcagacttgcccagcttggcagccgacttc<br>gttgagtctaaggacgtgtgcaagaattacgccgaggcaaaagacgtgttcctgggcatgt<br>tcctttatgagtacgctagaagacatcccgactacagcgtggtccttctccttaggctcgc<br>taagacttacgagacgacgttggagaagtgttgtgccgctgcggacccccacgagtgctat<br>gccaaagtgttcgatgagtttaaacccctggtggaggaacctcagaaccttatcaagcaga |

TABLE 1-continued

| Description | Sequence |
|---|---|
| | attgtgagttgttcgaacagctaggcgagtacaagttccagaatgccctgctggtgagata<br>cacaaaaaaggtgccccaggtgtcaaccccgaccttagtggaagtgtccagaaacctgggc<br>aaggtgggcagcaagtgctgcaagcaccccgaagctaagagaatgccgtgcgcggaggatt<br>acctgagcgtggtgctcaaccagctgtgtgtgcttcacgagaaaacacccgtgagcgacag<br>ggtgacaaaatgttgcacagaaagccttgtgaaccggagaccttgtttcagcgccctggag<br>gttgacgagacctatgttcctaaggagttcaacgctgagactttcacatttcacgctgata<br>tatgtaccctgagcgagaaagaaagacagatcaagaagcagaccgccctggtcgagctggt<br>gaaacacaagcctaaggccacgaaggagcagctgaaggccgtcatggacgacttcgcagcc<br>ttcgtcgagaaatgctgcaaagccgacgacaaggaaacctgcttcgccgaagagggaaaga<br>agctggtggccgcctcccaggccgcccttgggctcggt*ggcgggtctggtggcggttctca*<br>*gtactacgattacgacttccccctgagtatctacggtcagtcctcacctaactgcgcccca*<br>*gagtgtaactgccccgaaagctacccgagcgccatgtactgcgacgagctgaagttgaagt*<br>*ccgtgcccatggtgcccccaggcatcaagtacttatacttgaggaacaaccaaatcgatca*<br>*tatcgacgagaaggccttcgaaaacgtaaccgacctgcagtggctgatactggatcacaat*<br>*ctgctagagaattccaagatcaagggcagagtgttctcgaagctgaaacaactgaagaagc*<br>*tgcacatcaaccataacaatctcaccgagagcgtgggtcccctgcccaagtcgctggagga*<br>*cctgcagctgacccacaacaaaataaccaaactaggcagcttcgaggggttggtgaatctg*<br>*accttcatccatttgcagcataacagactaaaggaggatgccgtgagcgccgccttcaaag*<br>*gcctcaagagccttgagtacctggacctgagcttcaaccagatcgcccggctgcccagtgg*<br>*gctgcccgtgagcctgctgacgctgtatctggacaataacaaaatcagcaacatccccgac*<br>*gaatacttcaaaagattcaacgccttacagtacctgcgactcagccacaatgagctcgctg*<br>*acagcggcatccctggcaacagcttcaacgtgtcatccctggtggagctggacctgagtta*<br>*caataagctgaagaacatcccaactgtcaatgagaatttggaaaactactacctggaggtg*<br>*aaccagctggagaagttcgacattaagagcttttgcaaaatcctgggcccactgtcatata*<br>*gcaagatcaagcacctgcgactggacggcaaccgaatcagtgaaacttccctacccctga*<br>*catgtacgagtgcctgagagtagcaaatgaggtgaccctgaac* |
| C2 Construct (SEQ ID NO: 24)-includes (1) leader sequence (lower case; SEQ ID NO: 49); (2) IL-12β (bolded and underlined; SEQ ID NO: 74); (3) first GS linker (italicized; SEQ ID NO: 99); (4) IL-12α (bolded; SEQ ID NO: 124); (5) second GS linker (italicized and underlined; SEQ ID NO: 145); (6) albumin (lower case and underlined; SEQ ID NO: 166); (7) third GS linker (lower case and italicized; SEQ ID NO: 169); and (8) lumican (lower case, italicized, and underlined; SEQ ID NO: 172) | atgagggtccccgctcagctcctggggctcctgctgctctggctcccaggtgcacgatgtg<br>cc**ATCTGGGAGCTGAAGAAAGACGTGTACGTGGTGGAGCTTGACTGGTACCCCGACGCCCC**<br>**CGGTGAAATGGTGGTTCTGACCTGCGACACACCAGAGGAGGACGGCATCACCTGGACCCTG**<br>**GACCAGTCCAGCGAGGTCCTGGGATCTGGCAAGACCCTGACCATCCAGGTTAAGGAATTTG**<br>**GCGACGCCGGCCAGTACACCTGCCACAAAGGCGGCGAGGTCCTTTCGCACAGTCTGCTGCT**<br>**GCTGCATAAAAAGGAGGACGGCATTTGGAGCACCGACATTCTGAAGGATCAGAAAGAGCCC**<br>**AAGAACAAGACCTTTCTGAGATGTGAGGCCAAAAACTACTCTGGACGCTTCACCTGTTGGT**<br>**GGCTGACCACCATCAGCACAGACCTGACCTTCTCGGTGAAGTCTAGTAGGGGCAGCAGTGA**<br>**CCCCCAGGGCGTAACATGCGGCGCCGCTACCCTGAGCGCCGAGAGAGTGAGAGGCGATAAC**<br>**AAGGAGTACGAGTACTCCGTGGAGTGCCAAGAGGACTCAGCCTGCCCCGCCGCCGAGGAGT**<br>**CGCTGCCCATCGAGGTGATGGTGGATGCAGTGCACAAGCTGAAGTACGAGAACTACACCAG**<br>**TAGCTTTTTCATCAGAGATATCATTAAACCCGACCCTCCCAAGAACCTGCAGCTGAAGCCC**<br>**TTAAAGAACAGCCGGCAGGTGGAAGTGTCATGGGAGTACCCAGACACCTGGAGCACTCCGC**<br>**ACAGCTACTTCAGCCTGACCTTCTGCGTTCAGGTGCAGGGAAAAAGCAAGAGAGAGAAGAA**<br>**AGACAGAGTGTTCACCGACAAGACCAGCGCAACCGTGATCTGTAGAAAGAACGCCTCGATC**<br>**AGCGTGAGAGCCCAGGACAGATACTACAGCAGCAGCTGGAGCGAGTGGGCCAGTGTACCTT**<br>**GCAGC***GGTGGAAGCGGCGGAGGCTCTGGCGGAGGGAGTGGCGGAGGCAGC***AGAAATCTTCC**<br>**AGTAGCTACCCCCGACCCCGGCATGTTTCCCTGTCTGCACCATTCTCAAAACCTGTTACGG**<br>**GCCGTGAGCAACATGCTGCAGAAGGCCAGACAGACACTGGAGTTTTACCCCTGTACCTCAG**<br>**AGGAGATCGATCATGAGGACATTACTAAGGACAAGACCAGCACCGTGGAAGCCTGCCTGCC**<br>**CCTAGAGCTAACCAAGAACGAGAGCTGCCTGAACTCTAGAGAGACAAGCTTCATCACGAAC**<br>**GGCTCATGCCTGGCCAGTAGGAAAACCAGCTTCATGATGGCTCTGTGCCTGAGCTCCATAT**<br>**ATGAGGACCTTAAGATGTACCAGGTGGAGTTCAAAACCATGAACGCCAAGCTGCTGATGGA**<br>**CCCAAAGAGACAGATCTTCCTTGACCAGAACATGCTGGCCGTTATCGATGAGCTGATGCAG**<br>**GCCCTGAACTTCAACAGCGAGACCGTGCCCCAGAAAAGCAGCCTGGAGGAACCCGACTTCT**<br>**ACAAAACCAAGATCAAGCTGTGCATTCTGCTGCATGCCTTCCGCATTAGAGCCGTGACCAT**<br>**CGATAGGGTGATGAGCTACCTGAACGCCAGC***GGCTCTGGCGGCGGCAGT*gacgcccacaag<br>tccgaggtcgcccacagattcaaggatttgggcgaggagaacttcaaggccctggtgctga<br>tcgccttcgcccagtacttgcagcagtgtcccttcgaggaccatgtgaagctggtgaacga<br>ggtgaccgagttcgccaagacctgtgtggccgacgagagcgccgagaactgcgataagtct<br>ctgcacaccctttttggcgacaaactgtgcaccgtggccaccctgagagagacctacggcg<br>agatggccgactgctgtgcgaagcaggagcccgagcgcaatgagtgtttcctgcagcataa<br>ggacgacaaccccaacctgcccagactggtgagacccgaggtggacgtgatgtgcaccgcc<br>ttccacgacaacgaggagacctttctgaaaaaatacctgtacgagatcgcaagacgccacc<br>cctacttctacgcccccgagctgctgttcttcgccaagcgctacaaggctgccttcaccga<br>atgctgccaggccgccgataaggccgcgtgcttactgccaaagctggacgagctgagagac<br>gaggggaaagcctctagcgccaaacagagattgaagtgtgccagcctgcagaaattcggtg<br>agagagccttcaaggcctgggccgtggccagattatcacagcggttccccaaggctgaatt<br>cgccgaggtgagcaaacttgtcaccgatctgacaaaagtgcacaccgagtgctgccatggc<br>gacctgctggagtgcgccgacgaccgggccgacctggccaagtacatctgcgagaaccagg<br>acagcatctccagcaagctgaaggagtgctgcgagaagcccctgctggagaaaagccactg<br>catcgccgaggtggagaatgacgaaatgcccgccgacctgcccagcctggccgccgacttc<br>gtggaaagcaaggacgtgtgcaaaaattacgccgaagccaaggatgtgttcttgggcatgt<br>tcttgtacgagtacgccagacgccaccccgactacagcgtggtgctgctgctgcggctggc<br>caagacctacgagaccaccctggagaagtgctgtgctgccgccgacccccacgagtgctac<br>gccaaggtatttgacgagttcaagcccctggtggaggagcctcagaacctgattaagcaga<br>actgtgagctgttcgagcagctgggcgagtacaagttccagaacgccctcctggtgagata<br>caccaaaaaggtgcctcaggtaagcactcccaccctggtggaggtgagcaggaacctcggc<br>aaggtgggcagcaaatgctgcaagcacccagaggccaaaagaatgccctgcgcagaagact<br>acctcagcgtggtcctgaaccagctgtgcgtgctgcacgaaaagacccctgtgagcgatag<br>agtgacaaagtgctgcaccgagagcctggtgaacagaagaccctgttttagcgccctggag |

TABLE 1-continued

| Description | Sequence |
| --- | --- |
| | gtggacgagacctacgtgcccaaggagttcaacgccgagacgttcactttccacgcggaca<br>tctgcaccctgagcgagaaggagagacaaatcaagaagcagaccgccctagtcgagctggt<br>aaaacacaagcccaaggccaccaaggagcagctgaaggccgtgatggacgactttgcagcc<br>ttcgtggagaagtgctgcaaggctgacgacaaggagacctgcttcgccgaggagggcaaga<br>agctcgtagccgccagccaggccgctctcggccttggtggcg*ggtctggtggcggttctca*<br>*gtattacgactacgatttccccctgagcatctatggccagagcagccctaactgcgccccg*<br>*gagtgcaactgccccgaaagctacccaagcgccatgtactgcgatgagctgaagctgaagt*<br>*ctgtgcctatggtgcctcccggcatcaagtacctgtacctgagaaacaaccagatagacca*<br>*catcgatgagaaagccttcgagaacgtcaccgacctgcagtggctgattctggaccacaat*<br>*ttactggagaactccaagatcaagggcagagtgttctccaagttaaagcagctgaagaaac*<br>*tgcacatcaatcacaacaacctgaccgagagcgtgggcccactgcccaagagcctagagga*<br>*tctgcagctcacccacaacaagatcactaagttgggcagcttcgagggcctcgtaaacttg*<br>*acattcatacatctgcagcacaacagacttaaggaagacgccgtgagtgcggcctttaagg*<br>*gtctgaaaagcctggagtacttagacctgagcttcaaccagatcgcaaggctgcccagcgg*<br>*ccttccggtcagtctgctgaccctgtatctggacaacaacaagatcagcaacatccccgac*<br>*gagtacttcaagcggtttaacgccctccagtacctgagactgagccacaacgagttagctg*<br>*actcgggcatacccggtaacagcttcaatgttagcagcctagttgagcttgacttgagcta*<br>*caacaagcttaagaacatcccaaccgtgaacgagaacctcgagaattactacctggaagtc*<br>*aaccagctggagaagttcgacattaagagcttctgcaaaatcctgggcccactgtcctata*<br>*gcaagatcaagcacctgcgccttgacggaaacagaattagcgagaccagccttccaccaga*<br>*catgtacgagtgcctgagggtggccaacgaggtgaccctgaac* |
| C3 Construct (SEQ ID NO: 25)-includes (1) leader sequence (lower case; SEQ ID NO: 50); (2) IL-12β (bolded and underlined; SEQ ID NO: 75); (3) first GS linker (italicized; SEQ ID NO: 100); (4) IL-12α (bolded; SEQ ID NO: 125); (5) second GS linker (italicized and underlined; SEQ ID NO: 146); (6) albumin (lower case and underlined; SEQ ID NO: 167); (7) third GS linker (lower case and italicized; SEQ ID NO: 170); and (8) lumican (lower case, italicized, and underlined; SEQ ID NO: 173) | atgagggtccccgctcagctcctggggctcctgctgctctggctcccaggtgcacgatgtg<br>cc**ATCTGGGAACTGAAGAAGGACGTCTACGTGGTGGAGCTGGATTGGTACCCCGACGCCCC**<br>**CGGCGAGATGGTCGTGCTGACCTGTGACACCCCTGAGGAGGACGGAATCACATGGACCCTG**<br>**GACCAGAGCAGCGAAGTGTTGGGCAGCGGCAAGACCCTGACCATCCAAGTGAAGGAATTCG**<br>**GCGACGCGGGCCAGTATACTTGCCACAAGGGGGGGGAGGTTCTGAGCCACAGCCTGCTGCT**<br>**GCTCCACAAGAAAGAGGATGGCATCTGGTCTACCGACATCCTGAAGGACCAAAAGGAGCCA**<br>**AAGAACAAGACCTTCCTAAGATGCGAGGCCAAGAACTACTCAGGTCGTTTCACCTGCTGGT**<br>**GGCTGACCACAATCTCCACCGACCTGACCTTCAGCGTGAAAAGCAGCCGCGGCAGTAGCGA**<br>**CCCACAGGGCGTGACCTGCGGGGCCGCCACTCTGAGCGCCGAGAGAGTGCGCGGCGATAAT**<br>**AAGGAATACGAGTACAGCGTGGAGTGCCAGGAAGACTCAGCCTGCCCCGCCGCAGAAGAAA**<br>**GTCTGCCAATAGAGGTGATGGTTGACGCCGTGCACAAGCTAAAGTACGAGAACTACACCAG**<br>**CAGCTTCTTTATCCGGGACATCATCAAGCCAGATCCCCCCAAGAACCTGCAGCTTAAGCCC**<br>**CTGAAGAACAGCAGACAGGTGGAGGTGTCATGGGAATACCCCGACACCTGGAGCACCCCCC**<br>**ATAGCTACTTCTCACTGACCTTCTGCGTGCAGGTGCAGGGCAAGAGCAAGAGAGAGAAGAA**<br>**GGATAGGGTATTCACGGACAAGACCTCAGCCACCGTGATCTGCCGAAAGAACGCCAGCATC**<br>**AGCGTGAGAGCCCAGGACAGATACTATAGCTCCTCGTGGAGCGAGTGGGCCAGCGTACCTT**<br>**GCAGC***GGCGGGAGCGGCGGCGGCAGCGGAGGTGGCAGTGGCGGAGGCAGC***AGAAACCTCCC**<br>**CGTGGCAACCCCTGACCCCGGGATGTTTCCTTGCCTGCACCACTCCCAGAACCTCCTGAGA**<br>**GCCGTGTCCAACATGCTGCAGAAAGCCAGACAGACCCTCGAGTTCTATCCCTGCACAAGCG**<br>**AGGAGATCGACCACGAGGACATCACTAAGGACAAGACCAGCACAGTGGAAGCCTGCCTCCC**<br>**GCTGGAGCTGACTAAGAACGAGAGCTGTCTGAACAGCAGGGAGACCAGCTTCATCACCAAC**<br>**GGCAGCTGCCTGGCGAGCAGAAAAACCTCCTTTATGATGGCGCTCTGCCTGAGCTCAATCT**<br>**ATGAGGACCTGAAGATGTACCAGGTGGAGTTTAAAACCATGAATGCCAAGCTGCTTATGGA**<br>**CCCTAAGAGACAGATTTTCCTGGATCAGAACATGCTGGCCGTGATTGATGAATTAATGCAG**<br>**GCGCTGAACTTTAACAGCGAGACCGTGCCCCAGAAAAGCAGCCTGGAGGAGCCCGACTTTT**<br>**ACAAGACCAAGATCAAGTTGTGCATCCTCCTGCACGCCTTCAGAATCAGAGCGGTGACGAT**<br>**CGACAGAGTCATGAGCTACCTCAACGCTAGC***GGCAGCGGTGGCGGCAGC*gacgcccacaag<br>agcgaggtggcccacagattcaaggatctcggggaggagaacttcaaggccctggtgctga<br>tcgccttcgcacagtacctgcagcagtgccccttcgaggaccacgtaaaactggtgaacga<br>ggtgacggagttcgccaagacctgtgttgccgacgagtcggccgagaattgcgacaagagc<br>ctgcataccctgttcggcgacaagctgtgcaccgtggccaccctgagagagacctacggcg<br>agatggccgactgctgcgccaagcaagagcccgagagaaacgagtgcttcctgcagcacaa<br>ggacgacaaccccaacctgccccggctggtgagacccgaggtggacgtgatgtgcaccgcc<br>ttccacgacaacgaggagaccttcctgaagaagtatctgtacgagatcgccagaagacacc<br>cttatttttacgcccccgagctgctgttcttcgctaagagatataaggcagccttcaccga<br>gtgttgtcaggccgccgataaggccgcttgcctgctgcccaagttggacgagctcagagac<br>gagggcaaggcgagcagcgccaagcagagactgaagtgcgccagcctgcagaagttcggcg<br>agagggccttcaaggcctgggcggtggccagactgtcccagagatttcccaaggccgagtt<br>cgccgaggtaagcaagctggtcaccgacctgaccaaggtgcacaccgagtgttgccacggc<br>gacctgctggaatgcgccgatgaccgtgccgacctggccaagtacatctgcgagaatcagg<br>actccatcagcagcaaactgaaggagtgttgcgagaagcccctgctggaaaagagccattg<br>catcgctgaggtggaaaacgacgagatgcccgcagacctgcccagcctggccgcagacttt<br>gtggaaagtaaggacgtgtgcaagaactacgcggaggccaaagacgtgtttctgggcatgt<br>tcctatacgagtatgccagaagacaccccgactacagcgttgtgttattgctgagactggc<br>caagacctacgagactaccttggagaagtgctgcgccgccgccgacccccacgagtgctat<br>gccaaggtgttcgacgagttcaagcccctggtggaggagccccagaatctgattaagcaga<br>attgcgagctttttgagcagctgggcgagtataagttccagaacgccctgctggtgagata<br>caccaaaaaggtacctcaggtgagcacccccaccctggtggaggtgagcagaaatctgggc<br>aaggtgggcagcaagtgctgcaagcacccggaggccaagagaatgccctgtgccgaggatt<br>acctgtcagtggtgctgaaccagctgtgcgttctgcacgaaaagacgcccgtgtcggacag<br>agtgaccaagtgctgcacggagagcctggtgaacagaagaccgtgcttcagcgccctagag<br>gtggacgagacctacgtgcccaaggagttcaacgccgagaccttcaccttccacgccgaca<br>tctgtaccctgtcagagaaggagagacagatcaagaagcagaccgccttagtggagctggt<br>gaagcacaagcccaaggccaccaaggagcagctgaaagccgtgatggacgatttcgcagcc<br>ttcgtcgagaagtgctgcaaggccgacgacaaggaaacttgcttcgccgaggagggcaaga<br>agctggtggctgcctcgcaggccgccctcggcctgggtggcg*ggtctggtggcggttctca* |

TABLE 1-continued

| Description | Sequence |
|---|---|
| | gtactacgactacgatttccccctatccatctacgggcagagctcgcctaactgcgccccc gagtgtaactgccccgagtcgtaccccagcgccatgtactgtgacgagctgaagctgaaaa gcgtgcccatggtgcccccggcatcaagtacctgtacttgagaaacaaccagatcgacca cattgacgaaaaggccttcgagaacgtaaccgacctgcagtggctgatcctggaccacaac ctgcttgagaacagcaagatcaagggccgcgtgttcagcaagctgaagcagctgaagaagc tgcacatcaaccacaacaacttgactgagtctgttggccccctaccaaagagcctggagga cctgcagctgacccacaataagataaccaagctgggctcattcgagggcctggtgaacttg acctttattcacctgcagcataacagactgaaggaggacgccgtgagcgccgcctttaagg ggctgaaaagcctggagtacctggacctgagttttaaccagatcgccagactgccctcagg cctgcccgtgagtttgctgactctgtacctggacaacaataagatcagcaacattcctgac gagtatttcaaaagattcaatgctctgcagtacctgagactaagccacaacgagctggccg acagcggaatccccggcaacagcttcaacgtgagcagcttggtggagttggacctgagcta caacaaactgaagaacatccccaccgtcaatgagaacttggagaattactacctcgaggtt aaccagcttgagaagttcgacatcaagagcttctgcaagatcctgggcccccctcagctaca gcaagatcaagcacttgagactggacgggaacagaatcagcgaaaccagccttcctcccga catgtacgagtgccttagagtggcaaatgaggtgaccctgaac |

In some aspects, an isolated polynucleotide described herein, i.e., comprising a nucleic acid molecule encoding IL-12 (e.g., IL-12α subunit and/or IL-12β subunit), comprises one or more heterologous moieties (e.g., gene(s) of experimental and/or therapeutic interest). As used herein, the term "heterologous moiety" refers to any molecule (chemical or biological) that is different from an IL-12 protein (e.g., IL-12α subunit and/or IL-12β subunit) encoded by a nucleic acid molecule disclosed herein. Such heterologous moieties can be genetically fused, conjugated, and/or otherwise associated to an IL-12 protein. For instance, in some aspects, a heterologous moiety can be fused to the 3'-end of an IL-12α subunit. In some aspects, a heterologous moiety can be conjugated to the 3'-end of an IL-12α subunit via a linker (e.g., GS linker). In some aspects, a heterologous moiety can be fused to the 3'-end of an IL-12β subunit. In some aspects, a heterologous moiety can be conjugated to the 3'-end of an IL-12β subunit via a linker (e.g., GS linker).

In some aspects, a heterologous moiety comprises a half-life extending moiety. The term "half-life extending moiety" refers to a pharmaceutically acceptable moiety, domain, or molecule covalently linked ("conjugated" or "fused") to an IL-12 protein (e.g., IL-12α subunit and/or IL-12β subunit) encoded by a nucleic acid molecule the present disclosure, optionally via a non-naturally encoded amino acid, directly or via a linker, that prevents or mitigates in vivo proteolytic degradation or other activity-diminishing chemical modification of the IL-12 protein, increases half-life, and/or improves or alters other pharmacokinetic or biophysical properties including but not limited to increasing the rate of absorption, reducing toxicity, improving solubility, reducing protein aggregation, increasing biological activity and/or target selectivity of the IL-12 protein, increasing manufacturability, and/or reducing immunogenicity of the IL-12 protein, compared to a reference compound such as a non-conjugated or non-fused form of the IL-12 protein.

In the context of the present disclosure, the terms "fused" or "fusion" indicate that at least two polypeptide chains (e.g., encoded by the nucleic acid molecules described herein) have been operably linked and recombinantly expressed. In some aspects, two polypeptide chains can be "fused" as a result of chemical synthesis. In the context of the present disclosure, the terms "conjugate" or "conjugation" denote that two molecular entities (e.g., two polypeptides, or a polypeptide and a polymer such as PEG) have been chemically linked.

In some aspects, the half-life extending moiety comprises an Fc region, albumin, albumin binding polypeptide, a fatty acid, Pro/Ala/Ser (PAS), a glycine-rich homo-amino-acid polymer (HAP), the β subunit of the C-terminal peptide (CTP) of human chorionic gonadotropin, polyethylene glycol (PEG), hydroxyethyl starch (HES), long unstructured hydrophilic sequences of amino acids (XTEN), albumin-binding small molecules, or a combination thereof. See, e.g., WO 2013/041730 A1, which is incorporated herein by reference in its entirety. In certain aspects, the half-life extending moiety is albumin (e.g., human serum albumin).

In some aspects, a heterologous moiety comprises a lumican. Lumican binds to collagen, which is abundantly and ubiquitously expressed in tumors. In certain aspects, conjugating a lumican to an IL-12 protein (e.g., IL-12α subunit and/or IL-12β subunit) can improve the targeting of the IL-12 protein to the tumors (e.g., by preventing and/or reducing the IL-12 protein from entering systemic circulation), and thereby reduce toxicity of the IL-12 protein. Additional disclosure relating to lumican (e.g., sequences) that can be used are provided elsewhere in the present disclosure.

In some aspects, the heterologous moieties encode cytokines, chemokines, or growth factors other than IL-12. Cytokines are known in the art, and the term itself refers to a generalized grouping of small proteins that are secreted by certain cells within the immune system and have an effect on other cells. Cytokines are known to enhance the cellular immune response and, as used herein, can include, but are not limited to, TNFα, IFN-γ, IFN-α, TGFβ, IL-1, IL-2, Il-4, IL-10, IL-13, IL-17, IL-18, and chemokines. Chemokines are useful for studies investigating response to infection, immune responses, inflammation, trauma, sepsis, cancer, and reproduction, among other applications. Chemokines are known in the art, and are a type of cytokine that induce chemotaxis in nearby responsive cells, typically of white blood cells, to sites of infection. Non-limiting examples of chemokines include, CCL14, CCL19, CCL20, CCL21, CCL25, CCL27, CXCL12, CXCL13, CXCL-8, CCL2, CCL3, CCL4, CCL5, CCL11, and CXCL10. Growth factors are known in the art and the term itself is sometimes interchangeable with the term cytokines. As used herein, the term "growth factors" refers to a naturally occurring substance capable of signaling between cells and stimulating cellular growth. While cytokines can be growth factors, certain types of cytokines can also have an inhibitory effect on cell growth, thus differentiating the two terms. Non-limiting examples of growth factors include Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EFG), Ephrin A1, Ephrin A2, Ephrin A3, Ephrin A4, Ephrin A5, Ephrin B1, Ephrin B2, Ephrin B3, Erythropoietin (EPO), Fibroblast growth factor-1 (FGF1), Fibroblast growth factor 2 (FGF2), Fibroblast growth factor 3 (FGF3), Fibroblast growth factor 4 (FGF4), Fibroblast growth factor 5 (FGF5), Fibroblast growth factor 6 (FGF6), Fibroblast growth factor 7 (FGF7), Fibroblast growth factor 8 (FGF8), Fibroblast growth factor 9 (FGF9), Fibroblast growth factor 10 (FGF10), Fibroblast growth factor 11 (FGF11), Fibroblast growth factor 12 (FGF12), Fibroblast growth factor 13 (FGF13), Fibroblast growth factor 14 (FGF14), Fibroblast growth factor 15 (FGF15), Fibroblast growth factor 16 (FGF16), Fibroblast growth factor 17 (FGF17), Fibroblast growth factor 18 (FGF18), Fibroblast growth factor 19 (FGF19), Fibroblast growth factor 20 (FGF20), Fibroblast growth factor 21 (FGF21), Fibroblast growth factor 22 (FGF22), Fibroblast growth factor 23 (FGF23), Fetal Bovine Somatotrophin (FBS), Glial cell line-derived neurotrophic factor (GDNF), Neurturin, Peresphin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Interleukin-1 (IL-1), IL-2, IL-3, IL-4, IL-5, IL-6, IL-7, Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG 4), Brain-derived neurotrophic factor (BDNF), Nerve growth factor (NGF), Neurotrophin-3 (NT-3), Neurotrophin-4 (NT-4), Placental growth factor (TCGF), Thrombopoietin (TPO), Transforming growth factor alpha (TGF-α), Transforming growth factor beta (TGF-β), Tumor necrosis factor-alpha (TNF-α), and Vascular endothelial growth factor (VEGF).

In some aspects, a polynucleotide (e.g., isolated polynucleotide) of the present disclosure further comprises a nucleic acid molecule encoding a leader sequence. As used herein, the term "leader sequence" refers to a sequence located at the amino terminal end of the precursor form of a protein. Leader sequences are cleaved off during maturation. In certain aspects, a leader sequence comprises a signal peptide. The term "signal peptide" refers to a leader sequence ensuring entry of the protein into the secretory pathway. Additional description of leader sequences are provided in, e.g., US 2007/0141666 A1, which is incorporated herein by reference in its entirety. In some aspects, a leader sequence that can be used with the present disclosure comprises the amino acid sequence MRVPAQLLGLLLLWLPGARCA (SEQ ID NO: 180). In some aspects, a nucleic acid molecule encoding such a leader sequence comprises the sequence set forth in any one of SEQ ID NOs: 26 to 50. In some aspects, a nucleic acid molecule encoding the leader sequence comprises a sequence encoding the leader sequence of any of the constructs provided in Table 1.

As will be apparent from the above disclosure, in some aspects, a polynucleotide (e.g., isolated polynucleotide) of the present disclosure comprises multiple nucleic acid molecules. For instance, in certain aspects, a polynucleotide (e.g., isolated polynucleotide) comprises (from 5' to 3'): (i) a first nucleic acid molecule encoding a leader sequence; (ii) a second nucleic acid molecule encoding an IL-12β subunit; (iii) a third nucleic acid molecule encoding a linker (e.g., GS linker); and (iv) a fourth nucleic acid molecule encoding an IL-12α subunit. As described herein, in some aspects, such a polynucleotide further comprises one or more additional features described herein. For example, in some aspects, a polynucleotide described herein comprises (from 5' to 3'): (1) a 5'-cap, (2) a first nucleotide sequence encoding a leader sequence, (3) a second nucleotide sequence encoding an IL-12β subunit, (4) a third nucleotide sequence encoding a linker (e.g., GS linker), (5) a fourth nucleotide sequence encoding an IL-12α subunit, and (6) a poly(A) tail. In some aspects, a polynucleotide described herein comprises (from 5' to 3'): (1) a 5'-cap, (2) a 5'-UTR, (3) a promoter, (4) a first nucleotide sequence encoding a leader sequence, (5) a second nucleotide sequence encoding an IL-12β subunit, (6) a third nucleotide sequence encoding a linker (e.g., GS linker), (7) a fourth nucleotide sequence encoding an IL-12α subunit, (8) a 3'-UTR, and (9) a poly(A) tail. Additional description of exemplary constructs are provided below.

In some aspects, (i) the first nucleic acid molecule (i.e., encoding the leader sequence) comprises the sequence set forth in SEQ ID NO: 40; (ii) the second nucleic acid molecule (i.e., encoding the IL-12β subunit) comprises the sequence set forth in SEQ ID NO: 65; (iii) the third nucleic acid molecule (i.e., encoding the linker) comprises the sequence set forth in SEQ ID NO: 90; and (iv) the fourth nucleic acid molecule (i.e., encoding the IL-12α subunit) comprises the sequence set forth in SEQ ID NO: 115. Accordingly, in certain aspects, a polynucleotide (e.g., isolated polynucleotide) described herein comprises the sequence set forth in SEQ ID NO: 15. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 40 (i.e., leader sequence), (3) a second nucleotide sequence comprising the sequence set forth in SEQ ID NO: 65 (i.e., IL-12β subunit), (4) a third nucleotide sequence comprising the sequence set forth in SEQ ID NO: 90 (i.e., GS linker), (5) a fourth nucleotide sequence comprising the sequence set forth in SEQ ID NO: 115 (i.e., IL-12α subunit), and (6) a poly(A) tail. An example of such a polynucleotide is described herein as the "A1 Construct."

In some aspects, (i) the first nucleic acid molecule comprises the sequence set forth in SEQ ID NO: 41; (ii) the second nucleic acid molecule comprises the sequence set forth in SEQ ID NO: 66; (iii) the third nucleic acid molecule comprises the sequence set forth in SEQ ID NO: 91; and (iv) the fourth nucleic acid molecule comprises the sequence set forth in SEQ ID NO: 116. Accordingly, in certain aspects, a polynucleotide (e.g., isolated polynucleotide) described herein comprises the sequence set forth in SEQ ID NO: 16. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 41 (i.e., leader sequence), (3) a second nucleotide sequence comprising the sequence set forth in SEQ ID NO: 66 (i.e., IL-12β subunit), (4) a third nucleotide sequence comprising the sequence set forth in SEQ ID NO: 91 (i.e., GS linker), (5) a fourth nucleotide sequence comprising the sequence set forth in SEQ ID NO: 116 (i.e., IL-12α subunit), and (6) a poly(A) tail. An example of such a polynucleotide is described herein as the "A2 Construct."

In some aspects, (i) the first nucleic acid molecule comprises the sequence set forth in SEQ ID NO: 42; (ii) the second nucleic acid molecule comprises the sequence set forth in SEQ ID NO: 67; (iii) the third nucleic acid molecule comprises the sequence set forth in SEQ ID NO: 92; and (iv) the fourth nucleic acid molecule comprises the sequence set forth in SEQ ID NO: 117. Accordingly, in certain aspects, a polynucleotide (e.g., isolated polynucleotide) described herein comprises the sequence set forth in SEQ ID NO: 17. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 42 (i.e., leader sequence), (3) a second nucleotide sequence comprising the sequence set forth in SEQ ID NO: 67 (i.e., IL-12β subunit), (4) a third nucleotide sequence comprising the sequence set forth in SEQ ID NO: 92 (i.e., GS linker), (5) a fourth nucleotide sequence comprising the sequence set forth in SEQ ID NO: 117 (i.e., IL-12α subunit), and (6) a poly(A) tail. An example of such a polynucleotide is described herein as the "A3 Construct."

In some aspects, (i) the first nucleic acid molecule comprises the sequence set forth in SEQ ID NO: 43; (ii) the second nucleic acid molecule comprises the sequence set forth in SEQ ID NO: 68; (iii) the third nucleic acid molecule comprises the sequence set forth in SEQ ID NO: 93; and (iv) the fourth nucleic acid molecule comprises the sequence set forth in SEQ ID NO: 118. Accordingly, in certain aspects, a polynucleotide (e.g., isolated polynucleotide) described herein comprises the sequence set forth in SEQ ID NO: 18. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 43 (i.e., leader sequence), (3) a second nucleotide sequence comprising the sequence set forth in SEQ ID NO: 68 (i.e., IL-12β subunit), (4) a third nucleotide sequence comprising the sequence set forth in SEQ ID NO: 93 (i.e., GS linker), (5) a fourth nucleotide sequence comprising the sequence set forth in SEQ ID NO: 118 (i.e., IL-12α subunit), and (6) a poly(A) tail. An example of such a polynucleotide is described herein as the "A4 Construct."

In some aspects, a polynucleotide (e.g., isolated polynucleotide) described herein comprises (from 5' to 3'): (i) a first nucleic acid molecule encoding a leader sequence; (ii) a second nucleic acid molecule encoding an IL-12β subunit; (iii) a third nucleic acid molecule encoding a first linker (e.g., first GS linker); (iv) a fourth nucleic acid molecule encoding an IL-12α subunit; (v) a fifth nucleic acid molecule encoding a second linker (e.g., second GS linker); and (vi) a sixth nucleic acid molecule encoding a half-life extending moiety (e.g., human serum albumin). As described herein, in some aspects, such a polynucleotide further comprises one or more additional features described herein. For example, in some aspects, a polynucleotide described herein comprises (from 5' to 3'): (1) a 5'-cap, (2) a first nucleotide sequence encoding a leader sequence, (3) a second nucleotide sequence encoding an IL-12β subunit, (4) a third nucleotide sequence encoding a first linker (e.g., GS linker), (5) a fourth nucleotide sequence encoding an IL-12α subunit, (6) a fifth nucleotide sequence encoding a second linker (e.g., GS linker), (7) a sixth nucleotide sequence encoding a half-life extending moiety (e.g., human serum albumin), and (8) a poly(A) tail. In some aspects, a polynucleotide described herein comprises (from 5' to 3'): (1) a 5'-cap, (2) a 5'-UTR, (3) a promoter, (4) a first nucleotide sequence encoding a leader sequence, (5) a second nucleotide sequence encoding an IL-12β subunit, (6) a third nucleotide sequence encoding a first linker (e.g., GS linker), (7) a fourth nucleotide sequence encoding an IL-12α subunit, (8) a fifth nucleotide sequence encoding a second linker (e.g., GS linker), (9) a sixth nucleotide sequence encoding a heterologous moiety (e.g., albumin), (10) a 3'-UTR, and (11) a poly(A) tail. Additional description of such exemplary constructs are provided below.

In some aspects, (i) the first nucleic acid molecule (i.e., encoding the leader sequence) comprises the sequence set forth in SEQ ID NO: 26; (ii) the second nucleic acid molecule (i.e., encoding the IL-12β subunit) comprises the sequence set forth in SEQ ID NO: 51; (iii) the third nucleic acid molecule (i.e., encoding the first linker) comprises the sequence set forth in SEQ ID NO: 76; (iv) the fourth nucleic acid molecule (i.e., encoding the IL-12α subunit) comprises the sequence set forth in SEQ ID NO: 101; (v) the fifth nucleic acid molecule (i.e., encoding the second linker) comprises the sequence set forth in SEQ ID NO: 126; and (vi) the sixth nucleic acid molecule (i.e., encoding the half-life extending moiety) comprises the sequence set forth in SEQ ID NO: 147. Accordingly, in certain aspects, a polynucleotide (e.g., isolated polynucleotide) described herein comprises the sequence set forth in SEQ ID NO: 1. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 26 (i.e., leader sequence), (3) a second nucleotide sequence comprising the sequence set forth in SEQ ID NO: 51 (i.e., IL-12β subunit), (4) a third nucleotide sequence comprising the sequence set forth in SEQ ID NO: 76 (i.e., first GS linker), (5) a fourth nucleotide sequence comprising the sequence set forth in SEQ ID NO: 101 (i.e., IL-12α subunit), (6) a fifth nucleotide sequence comprising the sequence set forth in SEQ ID NO: 126 (i.e., second GS linker), (7) a sixth nucleotide sequence comprising the sequence set forth in SEQ ID NO: 147 (i.e., human serum albumin), and (8) a poly(A) tail. An example of such a polynucleotide is described herein as the "L1 Construct."

In some aspects, (i) the first nucleic acid molecule comprises the sequence set forth in SEQ ID NO: 27; (ii) the second nucleic acid molecule comprises the sequence set forth in SEQ ID NO: 52; (iii) the third nucleic acid molecule comprises the sequence set forth in SEQ ID NO: 77 (iv) the fourth nucleic acid molecule comprises the sequence set forth in SEQ ID NO: 102; (v) the fifth nucleic acid molecule comprises the sequence set forth in SEQ ID NO: 127; and (vi) the sixth nucleic acid molecule comprises the sequence set forth in SEQ ID NO: 148. Accordingly, in certain aspects, a polynucleotide (e.g., isolated polynucleotide) described herein comprises the sequence set forth in SEQ ID NO: 2. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 27 (i.e., leader sequence), (3) a second nucleotide sequence comprising the sequence set forth in SEQ ID NO: 52 (i.e., IL-12β subunit), (4) a third nucleotide sequence comprising the sequence set forth in SEQ ID NO: 77 (i.e., GS linker), (5) a fourth nucleotide sequence comprising the sequence set forth in SEQ ID NO: 102 (i.e., IL-12α subunit), (6) a fifth nucleotide sequence comprising the sequence st forth in SEQ ID NO: 127 (i.e., second GS linker), (7) a sixth nucleotide sequence comprising the sequence set forth in SEQ ID NO: 148 (i.e., human serum albumin), and (8) a poly(A) tail. An example of such a polynucleotide is described herein as the "L2 Construct."

In some aspects, (i) the first nucleic acid molecule comprises the sequence set forth in SEQ ID NO: 28; (ii) the second nucleic acid molecule comprises the sequence set forth in SEQ ID NO: 53; (iii) the third nucleic acid molecule comprises the sequence set forth in SEQ ID NO: 78; (iv) the fourth nucleic acid molecule comprises the sequence set forth in SEQ ID NO: 103; (v) the fifth nucleic acid molecule comprises the sequence set forth in SEQ ID NO: 128; and (vi) the sixth nucleic acid molecule comprises the sequence set forth in SEQ ID NO: 149. Accordingly, in certain aspects, a polynucleotide (e.g., isolated polynucleotide) described herein comprises the sequence set forth in SEQ ID NO: 3. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 28 (i.e., leader sequence), (3) a second nucleotide sequence comprising the sequence set forth in SEQ ID NO: 53 (i.e., IL-12β subunit), (4) a third nucleotide sequence comprising the sequence set forth in SEQ ID NO: 78 (i.e., GS linker), (5) a fourth nucleotide sequence comprising the sequence set forth in SEQ ID NO: 103 (i.e., IL-12α subunit), (6) a fifth nucleotide sequence comprising the sequence st forth in SEQ ID NO: 128 (i.e., second GS linker), (7) a sixth nucleotide sequence comprising the sequence set forth in SEQ ID NO: 149 (i.e., human serum albumin), and (8) a poly(A) tail. An example of such a polynucleotide is described herein as the "L3 Construct."

In some aspects, (i) the first nucleic acid molecule comprises the sequence set forth in SEQ ID NO: 29; (ii) the second nucleic acid molecule comprises the sequence set forth in SEQ ID NO: 54; (iii) the third nucleic acid molecule comprises the sequence set forth in SEQ ID NO: 79; (iv) the fourth nucleic acid molecule comprises the sequence set forth in SEQ ID NO: 104; (v) the fifth nucleic acid molecule comprises the sequence set forth in SEQ ID NO: 129; and (vi) the sixth nucleic acid molecule comprises the sequence set forth in SEQ ID NO: 150. Accordingly, in certain aspects, a polynucleotide (e.g., isolated polynucleotide) described herein comprises the sequence set forth in SEQ ID NO: 4. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 29 (i.e., leader sequence), (3) a second nucleotide sequence comprising the sequence set forth in SEQ ID NO: 54 (i.e., IL-12β subunit), (4) a third nucleotide sequence comprising the sequence set forth in SEQ ID NO: 79 (i.e., GS linker), (5) a fourth nucleotide sequence comprising the sequence set forth in SEQ ID NO: 104 (i.e., IL-12α subunit), (6) a fifth nucleotide sequence comprising the sequence st forth in SEQ ID NO: 129 (i.e., second GS linker), (7) a sixth nucleotide sequence comprising the sequence set forth in SEQ ID NO: 150 (i.e., human serum albumin), and (8) a poly(A) tail. An example of such a polynucleotide is described herein as the "M1 Construct."

In some aspects, (i) the first nucleic acid molecule comprises the sequence set forth in SEQ ID NO: 30; (ii) the second nucleic acid molecule comprises the sequence set forth in SEQ ID NO: 55; (iii) the third nucleic acid molecule comprises the sequence set forth in SEQ ID NO: 80; (iv) the fourth nucleic acid molecule comprises the sequence set forth in SEQ ID NO: 105; (v) the fifth nucleic acid molecule comprises the sequence set forth in SEQ ID NO: 130; and (vi) the sixth nucleic acid molecule comprises the sequence set forth in SEQ ID NO: 151. Accordingly, in certain aspects, a polynucleotide (e.g., isolated polynucleotide) described herein comprises the sequence set forth in SEQ ID NO: 5. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 30 (i.e., leader sequence), (3) a second nucleotide sequence comprising the sequence set forth in SEQ ID NO: 55 (i.e., IL-12β subunit), (4) a third nucleotide sequence comprising the sequence set forth in SEQ ID NO: 80 (i.e., GS linker), (5) a fourth nucleotide sequence comprising the sequence set forth in SEQ ID NO: 105 (i.e., IL-12α subunit), (6) a fifth nucleotide sequence comprising the sequence st forth in SEQ ID NO: 130 (i.e., second GS linker), (7) a sixth nucleotide sequence comprising the sequence set forth in SEQ ID NO: 151 (i.e., human serum albumin), and (8) a poly(A) tail. An example of such a polynucleotide is described herein as the "M2 Construct."

In some aspects, (i) the first nucleic acid molecule comprises the sequence set forth in SEQ ID NO: 31; (ii) the second nucleic acid molecule comprises the sequence set forth in SEQ ID NO: 56; (iii) the third nucleic acid molecule comprises the sequence set forth in SEQ ID NO: 81; (iv) the fourth nucleic acid molecule comprises the sequence set forth in SEQ ID NO: 106; (v) the fifth nucleic acid molecule comprises the sequence set forth in SEQ ID NO: 131; and (vi) the sixth nucleic acid molecule comprises the sequence set forth in SEQ ID NO: 152. Accordingly, in certain aspects, a polynucleotide (e.g., isolated polynucleotide) described herein comprises the sequence set forth in SEQ ID NO: 6. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 31 (i.e., leader sequence), (3) a second nucleotide sequence comprising the sequence set forth in SEQ ID NO: 56 (i.e., IL-12β subunit), (4) a third nucleotide sequence comprising the sequence set forth in SEQ ID NO: 81 (i.e., GS linker), (5) a fourth nucleotide sequence comprising the sequence set forth in SEQ ID NO: 106 (i.e., IL-12α subunit), (6) a fifth nucleotide sequence comprising the sequence st forth in SEQ ID NO: 131 (i.e., second GS linker), (7) a sixth nucleotide sequence comprising the sequence set forth in SEQ ID NO: 152 (i.e., human serum albumin), and (8) a poly(A) tail. An example of such a polynucleotide is described herein as the "M3 Construct."

In some aspects, (i) the first nucleic acid molecule comprises the sequence set forth in SEQ ID NO: 32; (ii) the second nucleic acid molecule comprises the sequence set forth in SEQ ID NO: 57; (iii) the third nucleic acid molecule comprises the sequence set forth in SEQ ID NO: 82; (iv) the fourth nucleic acid molecule comprises the sequence set forth in SEQ ID NO: 107; (v) the fifth nucleic acid molecule comprises the sequence set forth in SEQ ID NO: 132; and (vi) the sixth nucleic acid molecule comprises the sequence set forth in SEQ ID NO: 153. Accordingly, in certain aspects, a polynucleotide (e.g., isolated polynucleotide) described herein comprises the sequence set forth in SEQ ID NO: 7. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 32 (i.e., leader sequence), (3) a second nucleotide sequence comprising the sequence set forth in SEQ ID NO: 57 (i.e., IL-12β subunit), (4) a third nucleotide sequence comprising the sequence set forth in SEQ ID NO: 82 (i.e., GS linker), (5) a fourth nucleotide sequence comprising the sequence set forth in SEQ ID NO: 107 (i.e., IL-12α subunit), (6) a fifth nucleotide sequence comprising the sequence st forth in SEQ ID NO: 132 (i.e., second GS linker), (7) a sixth nucleotide sequence comprising the sequence set forth in SEQ ID NO: 153 (i.e., human serum albumin), and (8) a poly(A) tail. An example of such a polynucleotide is described herein as the "H1 Construct."

In some aspects, (i) the first nucleic acid molecule comprises the sequence set forth in SEQ ID NO: 33; (ii) the second nucleic acid molecule comprises the sequence set forth in SEQ ID NO: 58; (iii) the third nucleic acid molecule comprises the sequence set forth in SEQ ID NO: 83; (iv) the fourth nucleic acid molecule comprises the sequence set forth in SEQ ID NO: 108; (v) the fifth nucleic acid molecule comprises the sequence set forth in SEQ ID NO: 133; and (vi) the sixth nucleic acid molecule comprises the sequence set forth in SEQ ID NO: 154. Accordingly, in certain aspects, a polynucleotide (e.g., isolated polynucleotide) described herein comprises the sequence set forth in SEQ ID NO: 8. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 33 (i.e., leader sequence), (3) a second nucleotide sequence comprising the sequence set forth in SEQ ID NO: 58 (i.e., IL-12β subunit), (4) a third nucleotide sequence comprising the sequence set forth in SEQ ID NO: 83 (i.e., GS linker), (5) a fourth nucleotide sequence comprising the sequence set forth in SEQ ID NO: 108 (i.e., IL-12α subunit), (6) a fifth nucleotide sequence comprising the sequence st forth in SEQ ID NO: 133 (i.e., second GS linker), (7) a sixth nucleotide sequence comprising the sequence set forth in SEQ ID NO: 154 (i.e., human serum albumin), and (8) a poly(A) tail. An example of such a polynucleotide is described herein as the "H2 Construct."

In some aspects, (i) the first nucleic acid molecule comprises the sequence set forth in SEQ ID NO: 34; (ii) the second nucleic acid molecule comprises the sequence set forth in SEQ ID NO: 59; (iii) the third nucleic acid molecule comprises the sequence set forth in SEQ ID NO: 84; (iv) the fourth nucleic acid molecule comprises the sequence set forth in SEQ ID NO: 109; (v) the fifth nucleic acid molecule comprises the sequence set forth in SEQ ID NO: 134; and (vi) the sixth nucleic acid molecule comprises the sequence set forth in SEQ ID NO: 155. Accordingly, in certain aspects, a polynucleotide (e.g., isolated polynucleotide) described herein comprises the sequence set forth in SEQ ID NO: 9. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 34 (i.e., leader sequence), (3) a second nucleotide sequence comprising the sequence set forth in SEQ ID NO: 59 (i.e., IL-12β subunit), (4) a third nucleotide sequence comprising the sequence set forth in SEQ ID NO: 84 (i.e., GS linker), (5) a fourth nucleotide sequence comprising the sequence set forth in SEQ ID NO: 109 (i.e., IL-12α subunit), (6) a fifth nucleotide sequence comprising the sequence st forth in SEQ ID NO: 134 (i.e., second GS linker), (7) a sixth nucleotide sequence comprising the sequence set forth in SEQ ID NO: 155 (i.e., human serum albumin), and (8) a poly(A) tail. An example of such a polynucleotide is described herein as the "H3 Construct."

In some aspects, (i) the first nucleic acid molecule comprises the sequence set forth in SEQ ID NO: 37; (ii) the second nucleic acid molecule comprises the sequence set forth in SEQ ID NO: 62; (iii) the third nucleic acid molecule comprises the sequence set forth in SEQ ID NO: 87; (iv) the fourth nucleic acid molecule comprises the sequence set forth in SEQ ID NO: 112; (v) the fifth nucleic acid molecule comprises the sequence set forth in SEQ ID NO: 137; and (vi) the sixth nucleic acid molecule comprises the sequence set forth in SEQ ID NO: 158. Accordingly, in certain aspects, a polynucleotide (e.g., isolated polynucleotide) described herein comprises the sequence set forth in SEQ ID NO: 12. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 37 (i.e., leader sequence), (3) a second nucleotide sequence comprising the sequence set forth in SEQ ID NO: 62 (i.e., IL-12β subunit), (4) a third nucleotide sequence comprising the sequence set forth in SEQ ID NO: 87 (i.e., GS linker), (5) a fourth nucleotide sequence comprising the sequence set forth in SEQ ID NO: 112 (i.e., IL-12α subunit), (6) a fifth nucleotide sequence comprising the sequence st forth in SEQ ID NO: 137 (i.e., second GS linker), (7) a sixth nucleotide sequence comprising the sequence set forth in SEQ ID NO: 158 (i.e., human serum albumin), and (8) a poly(A) tail. An example of such a polynucleotide is described herein as the "vH1 Construct."

In some aspects, (i) the first nucleic acid molecule comprises the sequence set forth in SEQ ID NO: 38; (ii) the second nucleic acid molecule comprises the sequence set forth in SEQ ID NO: 63; (iii) the third nucleic acid molecule comprises the sequence set forth in SEQ ID NO: 88; (iv) the fourth nucleic acid molecule comprises the sequence set forth in SEQ ID NO: 113; (v) the fifth nucleic acid molecule comprises the sequence set forth in SEQ ID NO: 138; and (vi) the sixth nucleic acid molecule comprises the sequence set forth in SEQ ID NO: 159. Accordingly, in certain aspects, a polynucleotide (e.g., isolated polynucleotide) described herein comprises the sequence set forth in SEQ ID NO: 13. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 38 (i.e., leader sequence), (3) a second nucleotide sequence comprising the sequence set forth in SEQ ID NO: 63 (i.e., IL-12β subunit), (4) a third nucleotide sequence comprising the sequence set forth in SEQ ID NO: 88 (i.e., GS linker), (5) a fourth nucleotide sequence comprising the sequence set forth in SEQ ID NO: 113 (i.e., IL-12α subunit), (6) a fifth nucleotide sequence comprising the sequence st forth in SEQ ID NO: 138 (i.e., second GS linker), (7) a sixth nucleotide sequence comprising the sequence set forth in SEQ ID NO: 159 (i.e., human serum albumin), and (8) a poly(A) tail. An example of such a polynucleotide is described herein as the "vH2 Construct."

In some aspects, (i) the first nucleic acid molecule comprises the sequence set forth in SEQ ID NO: 39; (ii) the second nucleic acid molecule comprises the sequence set forth in SEQ ID NO: 64; (iii) the third nucleic acid molecule comprises the sequence set forth in SEQ ID NO: 89; (iv) the fourth nucleic acid molecule comprises the sequence set forth in SEQ ID NO: 114; (v) the fifth nucleic acid molecule comprises the sequence set forth in SEQ ID NO: 139; and (vi) the sixth nucleic acid molecule comprises the sequence set forth in SEQ ID NO: 160. Accordingly, in certain aspects, a polynucleotide (e.g., isolated polynucleotide) described herein comprises the sequence set forth in SEQ ID NO: 14. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 39 (i.e., leader sequence), (3) a second nucleotide sequence comprising the sequence set forth in SEQ ID NO: 64 (i.e., IL-12β subunit), (4) a third nucleotide sequence comprising the sequence set forth in SEQ ID NO: 89 (i.e., GS linker), (5) a fourth nucleotide sequence comprising the sequence set forth in SEQ ID NO: 114 (i.e., IL-12α subunit), (6) a fifth nucleotide sequence comprising the sequence st forth in SEQ ID NO: 139 (i.e., second GS linker), (7) a sixth nucleotide sequence comprising the sequence set forth in SEQ ID NO: 160 (i.e., human serum albumin), and (8) a poly(A) tail. An example of such a polynucleotide is described herein as the "vH3 Construct."

In some aspects, (i) the first nucleic acid molecule comprises the sequence set forth in SEQ ID NO: 44; (ii) the second nucleic acid molecule comprises the sequence set forth in SEQ ID NO: 69; (iii) the third nucleic acid molecule comprises the sequence set forth in SEQ ID NO: 94; (iv) the fourth nucleic acid molecule comprises the sequence set forth in SEQ ID NO: 119; (v) the fifth nucleic acid molecule comprises the sequence set forth in SEQ ID NO: 140; and (vi) the sixth nucleic acid molecule comprises the sequence set forth in SEQ ID NO: 161. Accordingly, in certain aspects, a polynucleotide (e.g., isolated polynucleotide) described herein comprises the sequence set forth in SEQ ID NO: 19. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 44 (i.e., leader sequence), (3) a second nucleotide sequence comprising the sequence set forth in SEQ ID NO: 69 (i.e., IL-12β subunit), (4) a third nucleotide sequence comprising the sequence set forth in SEQ ID NO: 94 (i.e., GS linker), (5) a fourth nucleotide sequence comprising the sequence set forth in SEQ ID NO: 119 (i.e., IL-12α subunit), (6) a fifth nucleotide sequence comprising the sequence st forth in SEQ ID NO: 140 (i.e., second GS linker), (7) a sixth nucleotide sequence comprising the sequence set forth in SEQ ID NO: 161 (i.e., human serum albumin), and (8) a poly(A) tail. An example of such a polynucleotide is described herein as the "B1 Construct."

In some aspects, (i) the first nucleic acid molecule comprises the sequence set forth in SEQ ID NO: 45; (ii) the second nucleic acid molecule comprises the sequence set forth in SEQ ID NO: 70; (iii) the third nucleic acid molecule comprises the sequence set forth in SEQ ID NO: 95; (iv) the fourth nucleic acid molecule comprises the sequence set forth in SEQ ID NO: 120; (v) the fifth nucleic acid molecule comprises the sequence set forth in SEQ ID NO: 141; and (vi) the sixth nucleic acid molecule comprises the sequence set forth in SEQ ID NO: 162. Accordingly, in certain aspects, a polynucleotide (e.g., isolated polynucleotide) described herein comprises the sequence set forth in SEQ ID NO: 20. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 45 (i.e., leader sequence), (3) a second nucleotide sequence comprising the sequence set forth in SEQ ID NO: 70 (i.e., IL-12β subunit), (4) a third nucleotide sequence comprising the sequence set forth in SEQ ID NO: 95 (i.e., GS linker), (5) a fourth nucleotide sequence comprising the sequence set forth in SEQ ID NO: 120 (i.e., IL-12α subunit), (6) a fifth nucleotide sequence comprising the sequence st forth in SEQ ID NO: 141 (i.e., second GS linker), (7) a sixth nucleotide sequence comprising the sequence set forth in SEQ ID NO: 162 (i.e., human serum albumin), and (8) a poly(A) tail. An example of such a polynucleotide is described herein as the "B2 Construct."

In some aspects, (i) the first nucleic acid molecule comprises the sequence set forth in SEQ ID NO: 46; (ii) the second nucleic acid molecule comprises the sequence set forth in SEQ ID NO: 71; (iii) the third nucleic acid molecule comprises the sequence set forth in SEQ ID NO: 96; (iv) the fourth nucleic acid molecule comprises the sequence set forth in SEQ ID NO: 121; (v) the fifth nucleic acid molecule comprises the sequence set forth in SEQ ID NO: 142; and (vi) the sixth nucleic acid molecule comprises the sequence set forth in SEQ ID NO: 163. Accordingly, in certain aspects, a polynucleotide (e.g., isolated polynucleotide) described herein comprises the sequence set forth in SEQ ID NO: 21. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 46 (i.e., leader sequence), (3) a second nucleotide sequence comprising the sequence set forth in SEQ ID NO: 71 (i.e., IL-12β subunit), (4) a third nucleotide sequence comprising the sequence set forth in SEQ ID NO: 96 (i.e., GS linker), (5) a fourth nucleotide sequence comprising the sequence set forth in SEQ ID NO: 121 (i.e., IL-12α subunit), (6) a fifth nucleotide sequence comprising the sequence st forth in SEQ ID NO: 142 (i.e., second GS linker), (7) a sixth nucleotide sequence comprising the sequence set forth in SEQ ID NO: 163 (i.e., human serum albumin), and (8) a poly(A) tail. An example of such a polynucleotide is described herein as the "B3 Construct."

In some aspects, (i) the first nucleic acid molecule comprises the sequence set forth in SEQ ID NO: 47; (ii) the second nucleic acid molecule comprises the sequence set forth in SEQ ID NO: 72; (iii) the third nucleic acid molecule comprises the sequence set forth in SEQ ID NO: 97; (iv) the fourth nucleic acid molecule comprises the sequence set forth in SEQ ID NO: 122; (v) the fifth nucleic acid molecule comprises the sequence set forth in SEQ ID NO: 143; and (vi) the sixth nucleic acid molecule comprises the sequence set forth in SEQ ID NO: 164. Accordingly, in certain aspects, a polynucleotide (e.g., isolated polynucleotide) described herein comprises the sequence set forth in SEQ ID NO: 22. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 47 (i.e., leader sequence), (3) a second nucleotide sequence comprising the sequence set forth in SEQ ID NO: 72 (i.e., IL-12β subunit), (4) a third nucleotide sequence comprising the sequence set forth in SEQ ID NO: 97 (i.e., GS linker), (5) a fourth nucleotide sequence comprising the sequence set forth in SEQ ID NO: 122 (i.e., IL-12α subunit), (6) a fifth nucleotide sequence comprising the sequence st forth in SEQ ID NO: 143 (i.e., second GS linker), (7) a sixth nucleotide sequence comprising the sequence set forth in SEQ ID NO: 164 (i.e., human serum albumin), and (8) a poly(A) tail. An example of such a polynucleotide is described herein as the "B4 Construct."

In some aspects, (i) the first nucleic acid molecule comprises the sequence set forth in SEQ ID NO: 35; (ii) the second nucleic acid molecule comprises the sequence set forth in SEQ ID NO: 60; (iii) the third nucleic acid molecule comprises the sequence set forth in SEQ ID NO: 85; (iv) the fourth nucleic acid molecule comprises the sequence set forth in SEQ ID NO: 110; (v) the fifth nucleic acid molecule comprises the sequence set forth in SEQ ID NO: 135; and (vi) the sixth nucleic acid molecule comprises the sequence set forth in SEQ ID NO: 156. Accordingly, in certain aspects, a polynucleotide (e.g., isolated polynucleotide) described herein comprises the sequence set forth in SEQ ID NO: 10. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 35 (i.e., leader sequence), (3) a second nucleotide sequence comprising the sequence set forth in SEQ ID NO: 60 (i.e., IL-12β subunit), (4) a third nucleotide sequence comprising the sequence set forth in SEQ ID NO: 85 (i.e., GS linker), (5) a fourth nucleotide sequence comprising the sequence set forth in SEQ ID NO: 110 (i.e., IL-12α subunit), (6) a fifth nucleotide sequence comprising the sequence st forth in SEQ ID NO: 135 (i.e., second GS linker), (7) a sixth nucleotide sequence comprising the sequence set forth in SEQ ID NO: 156 (i.e., human serum albumin), and (8) a poly(A) tail. An example of such a polynucleotide is described herein as the "CO Construct."

In some aspects, (i) the first nucleic acid molecule comprises the sequence set forth in SEQ ID NO: 36; (ii) the second nucleic acid molecule comprises the sequence set forth in SEQ ID NO: 61; (iii) the third nucleic acid molecule comprises the sequence set forth in SEQ ID NO: 86; (iv) the fourth nucleic acid molecule comprises the sequence set forth in SEQ ID NO: 111; (v) the fifth nucleic acid molecule comprises the sequence set forth in SEQ ID NO: 136; and (vi) the sixth nucleic acid molecule comprises the sequence set forth in SEQ ID NO: 157. Accordingly, in certain aspects, a polynucleotide (e.g., isolated polynucleotide) described herein comprises the sequence set forth in SEQ ID NO: 11. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 36 (i.e., leader sequence), (3) a second nucleotide sequence comprising the sequence set forth in SEQ ID NO: 61 (i.e., IL-12β subunit), (4) a third nucleotide sequence comprising the sequence set forth in SEQ ID NO: 86 (i.e., GS linker), (5) a fourth nucleotide sequence comprising the sequence set forth in SEQ ID NO: 111 (i.e., IL-12α subunit), (6) a fifth nucleotide sequence comprising the sequence st forth in SEQ ID NO: 136 (i.e., second GS linker), (7) a sixth nucleotide sequence comprising the sequence set forth in SEQ ID NO: 157 (i.e., human serum albumin), and (8) a poly(A) tail. An example of such a polynucleotide is described herein as the "CP Construct."

In some aspects, a polynucleotide (e.g., isolated polynucleotide) described herein comprises (from 5' to 3'): (i) a first nucleic acid molecule encoding a leader sequence; (ii) a second nucleic acid molecule encoding an IL-12β subunit; (iii) a third nucleic acid molecule encoding a first linker (e.g., first GS linker); (iv) a fourth nucleic acid molecule encoding an IL-12α subunit; (v) a fifth nucleic acid molecule encoding a second linker (e.g., second GS linker); (vi) a sixth nucleic acid molecule encoding a half-life extending moiety (e.g., human serum albumin); (vii) a seventh nucleic acid molecule encoding a third linker (e.g., third GS linker); and (viii) an eighth nucleic acid molecule encoding a lumican. As described herein, in some aspects, such a polynucleotide further comprises one or more additional features described herein. In some aspects, a polynucleotide described herein comprises (from 5' to 3'): (1) a 5'-cap, (2) a first nucleotide sequence encoding a leader sequence, (3) a second nucleotide sequence encoding an IL-12β subunit, (4) a third nucleotide sequence encoding a first linker (e.g., GS linker), (5) a fourth nucleotide sequence encoding an IL-12α subunit, (6) a fifth nucleotide sequence encoding a second linker (e.g., GS linker), (7) a sixth nucleotide sequence encoding a heterologous moiety (e.g., albumin), (8) a seventh nucleotide sequence encoding a third linker (e.g., GS linker), (9) an eighth nucleotide sequence encoding an additional moiety (e.g., lumican), and (12) a poly(A) tail. In some aspects, a polynucleotide described herein comprises (from 5' to 3'): (1) a 5'-cap, (2) a 5'-UTR, (3) a promoter, (4) a first nucleotide sequence encoding a leader sequence, (5) a second nucleotide sequence encoding an IL-12β subunit, (6) a third nucleotide sequence encoding a first linker (e.g., GS linker), (7) a fourth nucleotide sequence encoding an IL-12α subunit, (8) a fifth nucleotide sequence encoding a second linker (e.g., GS linker), (9) a sixth nucleotide sequence encoding a heterologous moiety (e.g., albumin), (10) a seventh nucleotide sequence encoding a third linker (e.g., GS linker), (11) an eighth nucleotide sequence encoding an additional moiety (e.g., lumican), (12) a 3'-UTR, and (13) a poly(A) tail. Additional description of such exemplary constructs are provided below.

In some aspects, (i) the first nucleic acid molecule (i.e., encoding the leader sequence) comprises the sequence set forth in SEQ ID NO: 48; (ii) the second nucleic acid molecule (i.e., encoding the IL-12β subunit) comprises the sequence set forth in SEQ ID NO: 73; (iii) the third nucleic acid molecule (i.e., encoding the first linker) comprises the sequence set forth in SEQ ID NO: 98; (iv) the fourth nucleic acid molecule (i.e., encoding the IL-12α subunit) comprises the sequence set forth in SEQ ID NO: 123; (v) the fifth nucleic acid molecule (i.e., encoding the second linker) comprises the sequence set forth in SEQ ID NO: 144; (vi) the sixth nucleic acid molecule (i.e., encoding the half-life extending moiety) comprises the nucleic acid sequence set forth in SEQ ID NO: 165; (vii) the seventh nucleic acid molecule (i.e., encoding the third linker) comprises the sequence set forth in SEQ ID NO: 168; and (viii) the eighth nucleic acid molecule (i.e., encoding the lumican) comprises the sequence set forth in SEQ ID NO: 171. Accordingly, in certain aspects, a polynucleotide (e.g., isolated polynucleotide) described herein comprises the sequence set forth in SEQ ID NO: 23. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 48 (i.e., leader sequence), (3) a second nucleotide sequence comprising the sequence set forth in SEQ ID NO: 73 (i.e., IL-12β subunit), (4) a third nucleotide sequence comprising the sequence set forth in SEQ ID NO: 98 (i.e., first GS linker), (5) a fourth nucleotide sequence comprising the sequence set forth in SEQ ID NO: 123 (i.e., IL-12α subunit), (6) a fifth nucleotide sequence comprising the sequence set forth in SEQ ID NO: 144 (i.e., second GS linker), (7) a sixth nucleotide sequence comprising the sequence set forth in SEQ ID NO: 165 (i.e., human serum albumin), (8) a seventh nucleotide sequence comprising the sequence set forth in SEQ ID NO: 168 (i.e., third GS linker), (9) an eighth nucleotide sequence comprising the sequence set forth in SEQ ID NO: 171 (i.e., lumican), and (10) a poly(A) tail. An example of such a polynucleotide is described herein as the "C1 Construct."

In some aspects, (i) the first nucleic acid molecule comprises the sequence set forth in SEQ ID NO: 49; (ii) the second nucleic acid molecule comprises the sequence set forth in SEQ ID NO: 74; (iii) the third nucleic acid molecule comprises the sequence set forth in SEQ ID NO: 99; (iv) the fourth nucleic acid molecule comprises the sequence set forth in SEQ ID NO: 124; (v) the fifth nucleic acid molecule comprises the sequence set forth in SEQ ID NO: 145; (vi) the sixth nucleic acid molecule comprises the sequence set forth in SEQ ID NO: 166; (vii) the seventh nucleic acid molecule comprises the sequence set forth in SEQ ID NO: 169; and (viii) the eighth nucleic acid molecule comprises the sequence set forth in SEQ ID NO: 172. Accordingly, in certain aspects, a polynucleotide (e.g., isolated polynucleotide) described herein comprises the sequence set forth in SEQ ID NO: 24. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 49 (i.e., leader sequence), (3) a second nucleotide sequence comprising the sequence set forth in SEQ ID NO: 74 (i.e., IL-12β subunit), (4) a third nucleotide sequence comprising the sequence set forth in SEQ ID NO: 99 (i.e., first GS linker), (5) a fourth nucleotide sequence comprising the sequence set forth in SEQ ID NO: 124 (i.e., IL-12α subunit), (6) a fifth nucleotide sequence comprising the sequence set forth in SEQ ID NO: 145 (i.e., second GS linker), (7) a sixth nucleotide sequence comprising the sequence set forth in SEQ ID NO: 166 (i.e., human serum albumin), (8) a seventh nucleotide sequence comprising the sequence set forth in SEQ ID NO: 169 (i.e., third GS linker), (9) an eighth nucleotide sequence comprising the sequence set forth in SEQ ID NO: 172 (i.e., lumican), and (10) a poly(A) tail. An example of such a polynucleotide is described herein as the "C2 Construct."

In some aspects, (i) the first nucleic acid molecule comprises the sequence set forth in SEQ ID NO: 50; (ii) the second nucleic acid molecule comprises the sequence set forth in SEQ ID NO: 75; (iii) the third nucleic acid molecule comprises the sequence set forth in SEQ ID NO: 100; (iv) the fourth nucleic acid molecule comprises the sequence set forth in SEQ ID NO: 125; (v) the fifth nucleic acid molecule comprises the sequence set forth in SEQ ID NO: 146; (vi) the sixth nucleic acid molecule comprises the sequence set forth in SEQ ID NO: 167; (vii) the seventh nucleic acid molecule comprises the sequence set forth in SEQ ID NO: 170; and (viii) the eighth nucleic acid molecule comprises the sequence set forth in SEQ ID NO: 173. Accordingly, in certain aspects, a polynucleotide (e.g., isolated polynucleotide) described herein comprises the sequence set forth in SEQ ID NO: 25. In some aspects, the polynucleotide comprises one or more additional features described herein. For example, in some aspects, a polynucleotide provided herein comprises (from 5' to 3'): (1) a 5'-cap (or cap analog), (2) a first nucleotide sequence comprising the sequence set forth in SEQ ID NO: 50 (i.e., leader sequence), (3) a second nucleotide sequence comprising the sequence set forth in SEQ ID NO: 75 (i.e., IL-12β subunit), (4) a third nucleotide sequence comprising the sequence set forth in SEQ ID NO: 100 (i.e., first GS linker), (5) a fourth nucleotide sequence comprising the sequence set forth in SEQ ID NO: 125 (i.e., IL-12α subunit), (6) a fifth nucleotide sequence comprising the sequence set forth in SEQ ID NO: 146 (i.e., second GS linker), (7) a sixth nucleotide sequence comprising the sequence set forth in SEQ ID NO: 167 (i.e., human serum albumin), (8) a seventh nucleotide sequence comprising the sequence set forth in SEQ ID NO: 170 (i.e., third GS linker), (9) an eighth nucleotide sequence comprising the sequence set forth in SEQ ID NO: 173 (i.e., lumican), and (10) a poly(A) tail. An example of such a polynucleotide is described herein as the "C3 Construct."

Lipid Nanoparticle and Delivery System

In some aspects, the present disclosure relates to the delivery of biologically active molecules (e.g., an IL-12 protein) to cells. In certain aspects, the delivery can occur in vivo (e.g., by administering a polynucleotide described herein to a subject) or ex vivo (e.g., by culturing a polynucleotide described herein with the cells in vitro). In some aspects, delivery of a polynucleotide (e.g., isolated polynucleotide) described herein can be performed using any suitable delivery system known in the art. In certain aspects, the delivery system is a vector. Accordingly, in some aspects, the present disclosure provides a vector comprising a polynucleotide of the present disclosure. Suitable vectors that can be used are known in the art. See, e.g., Sung et al., *Biomater Res* 23(8) (2019).

In some aspects, a polynucleotide described herein (e.g., an isolated polynucleotide comprising a nucleic acid molecule encoding an IL-12 protein) is delivered using lipid nanoparticles. Accordingly, in some aspects, the present disclosure relates to an IL-12-expressing polynucleotide (e.g., RNA) encapsulated by lipid nanoparticles, the composition thereof, and use of the composition thereof to treat a subject having cancer or suspected of having cancer.

A "lipid nanoparticle" (LNP), as used herein, refers to a vesicle, such as a spherical vesicle, having a contiguous lipid bilayer. Lipid nanoparticles can be used in methods by which pharmaceutical therapies are delivered to targeted locations. Non-limiting examples of LNPs include liposomes, bolaamphihiles, solid lipid nanoparticles (SLN), nanostructured lipid carriers (NLC), and monolayer membrane structures (e.g., archaeosomes and micelles).

In some aspects, the lipid nanoparticle comprises one or more types of lipids. A lipid, as used herein, refers to a group of organic compounds that include, but are not limited to, esters of fatty acids and in some aspects are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids. Non-limiting examples of lipids include triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate). In some aspects, the one or more types of lipids in the LNP comprises a cationic lipid. In some aspects, the one or more types of lipids in the LNP comprises a lipidoid, e.g., TT3. Accordingly, in some aspects, any of the polynucleotides described herein (e.g., comprising the sequence set forth in any one of SEQ ID Nos: 1-25, a 5'-cap (or a cap analog), and a poly(A) tail) can be encapsulated in a lipidoid nanoparticle (e.g., TT3). In some aspects, a polynucleotide comprises the sequence set forth in SEQ ID NO: 1, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 2, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 3, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 4, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 5, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 6, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 7, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 8, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 9, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 10, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 11, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 12, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 13, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 14, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 15, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 16, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 17, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 18, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 19, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 20, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 21, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 22, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 23, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 24, 5'-cap (or a cap analog), and a poly(A) tail, wherein the polynucleotide is encapsulated in a lipidoid nanoparticle (e.g., TT3). In some aspects, a polynucleotide comprises the sequence set forth in SEQ ID NO: 25, 5'-cap (or a cap analog), and a poly(A) tail, wherein the polynucleotide is encapsulated in a lipidoid nanoparticle (e.g., TT3).

Such lipids useful for the present disclosure include, but are not limited to N1,N3,N5-tris(3-(didodecylamino)propyl) benzene-1,3,5-tricarboxamide (TT3), N-(2,3-dioleoyloxy) propyl)-N,N,N-trimethylammonium chloride (DOTAP); lipofectamine; 1,2-DiLinoleyloxy-N,N-dimethylaminopropane (DLinDMA), 1,2-Dilinolenyloxy-N,N-dimethylaminopropane (DLenDMA); dioctadecyldimethylammonium (DODMA), Distearyldimethylammonium (DSDMA), N,N-dioleyl-N,N,-dimethylammonium chloride (DODAC); N-(2,3-dioleyloxy)propyl)-N,N,N-trimethylammonium chloride (DOTMA); N—N-distearyl-N,N-dimethylammonium bromide (DDAB); 3-(N—(N',N'-dimethylaminoethane)-carbamoyl)cholesterol (DC-Chol) and N-(1,2-dimyristyloxprop-3-yl)-N,N-dimethyl-N-hydroxyethyl ammonium bromide (DMRIE).

In some aspects of the disclosure, the lipids, e.g., lipidoid, is TT3. TT3, as used herein, is capable of forming lipid nanoparticles for delivery of various biologic active agents into the cells. In addition, the present disclosure also demonstrates that an unloaded TT3-LNP can induce immunogenic cell death (ICD) in cancer cells in vivo and in vitro. Immunogenic cell death, as described herein, refers to a form of cell death that can induce an effective immune response through activation of dendritic cells (DCs) and consequent activation of specific T cell response. In some aspects of the disclosure, the cells that undergo immunogenic cell death are tumor cells. Immunogenic tumor cell death can trigger an effective anti-tumor immune response. In some aspects of the disclosure, the lipid nanoparticle comprises TT3-LNP encapsulating a nucleotide sequence encoding IL-12 (modRNA) encoding only a reporter gene (TT3-LNP-modRNA). The nucleotide sequence encoding IL-12 can work synergistically with the TT3-LNP to induce higher level of ICD in tumor cells compared to TT3-LNP alone. In some aspects of the disclosure, the lipid nanoparticle comprises a TT3-LNP encapsulating a modRNA encoding an IL-12 molecule. IL-12, which is an immunoregulatory cytokine, elicits a potent immune response against the local tumor. The combination of TT3-LNP, modRNA, and IL-12 expression, not only is effective in synergistic inhibition of tumor cells on site, but also elicits a systemic anti-tumor immune response to kill distal tumor cells and prevent the recurrence of tumors.

In some aspects of the disclosure, the cationic lipid is DOTAP. DOTAP, as used herein, is also capable of forming lipid nanoparticles. DOTAP can be used for the highly efficient transfection of DNA including yeast artificial chromosomes (YACs) into eukaryotic cells for transient or stable gene expression, and is also suitable for the efficient transfer of other negatively charged molecules, such as RNA, oligonucleotides, nucleotides, ribonucleoprotein (RNP) complexes, and proteins into research samples of mammalian cells.

In some aspects of the disclosure, the cationic lipid is lipofectamine. Lipfectamine, as used herein, is a common transfection reagent, produced and sold by Invitrogen, used in molecular and cellular biology. It is used to increase the transfection efficiency of RNA (including mRNA and siRNA) or plasmid DNA into in vitro cell cultures by lipofection. Lipofectamine contains lipid subunits that can form liposomes or lipid nanoparticles in an aqueous environment, which entrap the transfection payload, e.g., modRNA. The RNA-containing liposomes (positively charged on their surface) can fuse with the negatively charged plasma membrane of living cells, due to the neutral co-lipid mediating fusion of the liposome with the cell membrane, allowing nucleic acid cargo molecules to cross into the cytoplasm for replication or expression.

In some aspects of the disclosure, LNPs are composed primarily of cationic lipids along with other lipid ingredients. These typically include other lipid molecules belonging but not limited to the phophatidylcholine (PC) class (e.g., 1,s-Distearoyl-sn-glycero-3-phophocholine (DSPC), and 1,2-Dioleoyl-sn-glycero-3-phophoethanolamine (DOPE), sterols (e.g., cholesterol) and Polyethylene glycol (PEG)-lipid conjugates (e.g., 1,2-distearoyl-sn-glycero-3-phosphoethanolamine-N-[folate(polyethylene glycol)-2000 (DSPE-PEG2000), and C14-PEG2000. Table 2 shows the formulation of exemplary LNPs, TT3-LNP and DOTAP-LNP.

TABLE 2

| | | | | |
|---|---|---|---|---|
| DOTAP-LNP | DOTAP | DSPC | Cholesterol | DSPE-PEG2000 |
| Molar ratio | 40 | 10 | 48 | 2 |
| TT3-LNP | TT3 | DOPE | Cholesterol | C14-PEG2000 |
| Molar Ratio | 20 | 30 | 40 | 0.75 |

In some aspects, the LNP comprises C14-PEG2000. In certain aspects, C14-PEG2000 comprises 1,2-dimyristoyl-rac-glycero-3-methoxypolyethylene glycol-2000 (DMG-PEG2000), 1,2-dimyristoyl-sn-glycero-3-phosphoethanolamine-N-[methoxy(polyethylene glycol)-2000] (DMPE-PEG2000), or both. As described herein (see, e.g., Example 3), in some aspects, the C14-PEG2000 (or other lipid ingredients disclosed herein) can be embedded in the LNP prior to the encapsulation of the polynucleotide. In some aspects, the C14-PEG2000 (or other lipid ingredients disclosed herein) can be added to the LNP after the encapsulation of the polynucleotide. For example, in certain aspects, a polynucleotide (e.g., isolated polynucleotide) comprising a nucleic acid molecule encoding an IL-12 protein (e.g., IL-12α and/or IL-12β subunit) is encapsulated in the LNP, and then the C14-PEG2000 (other lipid ingredients disclosed herein) is attached to the LNP using, e.g., micelles.

Particle size of lipid nanoparticles can affect drug release rate, bio-distribution, mucoadhesion, cellular uptake of water and buffer exchange to the interior of the nanoparticles, and protein diffusion. In some aspects of the disclosure, the diameter of the LNPs ranges from about 30 to about 500 nm. In some aspects of the disclosure, the diameter of the LNPs ranges from about 30 to about 500 nm, about 50 to about 400 nm, about 70 to about 300 nm, about 100 to about 200 nm, about 100 to about 175 nm, or about 100 to about 160 nm. In some aspects of the disclosure, the diameter of the LNPs ranges from 100-160 nm. In some aspects of the disclosure, the diameter of the LNPs can be about 30 nm, about 40 nm, about 50 nm, about 60 nm, about 70 nm, about 80 nm, about 90 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 130 nm, about 140 nm, about 150 nm, or about 160 nm. In certain aspects, the lipid nanoparticle has a diameter of about 140 nm.

Zeta potential is a measure of the effective electric charge on the lipid nanoparticle surface. The magnitude of the zeta potential provides information about particle stability. In some aspects of the disclosure, the zeta potential of the LNPs ranges from about 3 to about 6 my. In some aspects of the disclosure, the zeta potential of the LNPs can be about 3 my, about 3.1 my, about 3.2 my, about 3.3 my, about 3.4 my, about 3.5 my, about 3.6 my, about 3.7 my, about 3.8 my, about 3.9 my, about 4 my, about 4.1 my, about 4.2 my, about 4.3 my, about 4.4 my, about 4.5 my, about 4.6 my, about 4.7 my, about 4.8 my, about 4.9 my, about 5 my, about 5.1 my, about 5.2 my, about 5.3 my, about 5.4 my, about 5.5 my, about 5.6 my, about 5.7 my, about 5.8 my, about 5.9 my, or about 6 my.

In some aspects, the disclosure is related to encapsulated polynucleotide (e.g., mRNA) with lipid nanoparticles (LNPs). In some aspects of the disclosure, the mass ratio between the lipid of LNPs and the polynucleotide (e.g., mRNA) ranges from about 1:2 to about 15:1. In some aspects, the mass ratio between the lipid and the polynucleotide (e.g., mRNA) can be about 1:2, about 1:1.9, about 1:1.8, about 1:1.7, about 1:1.6, about 1:1.5, about 1:1.4, about 1:1.3, about 1:1.2, about 1:1.1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, or about 15:1. In some aspects of the disclosure, the mass ratio between the lipid and the polynucleotide (e.g., mRNA) is about 10:1.

Pharmaceutical Compositions

In some aspects, the disclosure relates to a pharmaceutical composition comprising the polynucleotide, vector, and/or lipid nanoparticle described herein. In some aspects of the disclosure, the pharmaceutical composition further comprises a pharmaceutically acceptable carrier (excipient). "Acceptable", as used herein, means that the carrier must be compatible with the active ingredient of the composition and not deleterious to the subject to be treated. In some aspects, the carrier is capable of stabilizing the active ingredient. Pharmaceutically acceptable excipients (carriers) include buffers, which are well known in the art. See, e.g., Remington: The Science and Practice of Pharmacy 20th Ed. (2000) Lippincott Williams and Wilkoins, Ed. K. E. Hoover.

The pharmaceutical compositions to be used for in vivo administration must be sterile. This is readily accomplished by, for example, filtration through sterile filtration membranes. The lipid nanoparticles can be placed into a container having a sterile access port, for example, an intravenous solution bag or vial having a stopper pierceable by a hypodermic injection needle.

In some aspects of the disclosure, the pharmaceutical composition can be formulated for intratumoral, intrathecal, intramuscular, intravenous, subcutaneous, inhalation, intradermal, intralymphatic, intraocular, intraperitoneal, intrapleural, intraspinal, intravascular, nasal, percutaneous, sublingual, submucosal, transdermal, or transmucosal administration. In some aspects of the disclosure, the pharmaceutical composition can be formulated for intratumoral injection. Intratumoral injection, as used herein, refers to direct injections into the tumor. A high concentration of composition can be achieved in situ, while using small amounts of drugs. Local delivery of immunotherapies allows multiple combination therapies, while preventing significant system exposure and off-target toxicities.

In some aspects of the disclosure, the pharmaceutical composition can be formulated for intramuscular injection, intravenous injection, or subcutaneous injection.

In some aspects of the disclosure, the pharmaceutical composition comprises pharmaceutically acceptable carriers, buffer agents, excipients, salts, or stabilizers in the form of lyophilized formulations or aqueous solutions. See, e.g., Remington: The Science and Practice of Pharmacy $20^{th}$ Ed. (2000) Lippincott Williams and Wilkins, Ed. K. E. Hoover. Acceptable carriers and excipients, or stabilizers are nontoxic to recipients at the dosages and concentrations used, and comprises buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

In some aspects, the pharmaceutical composition described herein comprises lipid nanoparticles which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545, which are hereby incorporated by reference in their entirety. Liposomes with enhanced circulation time are disclosed in U.S. Pat. No. 5,013,556, which is hereby incorporated by reference in its entirety. In some aspects, liposomes can be generated by the reverse phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

In some aspects of the disclosure, the pharmaceutical composition is formulated in sustained-release format. Suitable examples of sustained-release preparations include semipermeable matrices of solid hydrophobic polymers containing the lipid nanoparticles which matrices are in the form of shaped articles, e.g., films or microcapsules. Examples of sustained-release matrices include, but are not limited to, polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPROM DEPOT™ (injectable microspheres composed of lactic acid-glycolic acid copolymer and leuprolide acetate), sucrose acetate isobutyrate, and poly-D-(−)-3-hydroxybutyric acid.

In some aspects, suitable surface-active agents include, but are not limited to, non-ionic agents, such as polyoxyethylenesorbitans (e.g., TWEEN™ 20, 40, 60, 80 or 85) and other sorbitans (e.g., SPAN™ 20, 30, 60, 80, or 85). In some aspects, compositions with a surface-active agent comprise between 0.05 and 5% surface-active agent. In some aspects the composition comprises 0.1 and 2.5%. It will be appreciated that other ingredients can be added, for example mannitol or other pharmaceutically acceptable vehicles, if necessary.

In some aspects, the pharmaceutical composition is in unit dosage forms such as tablets, pills, capsules, powders, granules, solutions or suspensions, or suppositories, for oral, parenteral, or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g, water, to form a solid preformulation composition containing a homogenous mixture of a compound of the present disclosure, or a non-toxic pharmaceutically acceptable salt thereof. When referring to these preformulation compositions as homogeneous, it is meant that the active ingredient is dispersed evenly throughout the composition so that the composition can be readily subdivided into equally effective unit dosage forms such as tablets, pills, and capsules. This solid preformulation composition is then subdivided into unit dosage forms of the type described above containing from about 0.1 to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials include a number of polymeric acids and mixtures of polymeric acids with such materials as shellac, cetyl alcohol, and cellulose acetate.

Suitable emulsions can be prepared using commercially available fat emulsions, such as INTRALIPID™, LIPOSYN™, INFONUTROL™, LIPOFUNDIN™, and LIPIPHYSAN™. The active ingredient can be either dissolved in a pre-mixed emulsion composition or alternatively it can be dissolved in an oil (e.g., soybean oil, safflower oil, cottonseed oil, sesame oil, corn oil, or almond oil) and an emulsion formed upon mixing with a phospholipid (e.g., egg phospholipids, soybean phospholipids, or soybean lecithin) and water. It will be appreciated that other ingredients can be added, for example glycerol or glucose, to adjust tonicity of the emulsion. Suitable emulsions will typically contain up to about 20% oil, for example, between about 5 and about 20%. The fat emulsion can comprise fat droplets having a suitable size and can have a pH in the range of about 5.5 to about 8.0.

Pharmaceutical compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as set out above. In some aspects, the composition is administered by the oral or nasal respiratory route for local or systemic effect.

Compositions in pharmaceutically acceptable solvents can be nebulized by use of gases. Nebulized solutions can be breathed directly from the nebulizing device or the nebulizing device can be attached to a face mask, tent or intermittent positive pressure breathing machine. Solution, suspension, or powder compositions can be administered from devices which deliver the formulation in an appropriate manner.

Therapeutic Applications

In some aspects of the disclosure, the polynucleotides, vectors, lipid nanoparticles, and/or pharmaceutical compositions described herein (also collectively referred to herein as "compositions") are used to treat a disease or disorder. In certain aspects, the disease or disorder comprises a cancer. Non-limiting examples of cancers that can be treated are provided elsewhere in the present disclosure.

In some aspects, an effective amount of any of the compositions described herein is administered to a subject in need thereof via a suitable route, such as intratumoral administration, intravenous administration (e.g, as a bolus or by continuous infusion over a period of time), by intramuscular, intraperitoneal, intracerebrospinal, subcutaneous, intra-articular, intrasynovial, intrathecal, oral, inhalation, or topical routes. Commercially available nebulizers for liquid formulations, including jet nebulizers and ultrasonic nebulizers are useful for administration. Liquid formulations can be nebulized and lyophilized powder can be nebulized after reconstitution. In some aspects, the pharmaceutical composition described herein is aerolized using a fluorocarbon formulation and a metered dose inhaler, or inhaled as a lyophilized and milled powder. In some aspects, the pharmaceutical composition described herein is formulated for intratumoral injection. In some aspects, the pharmaceutical composition described herein is administered to a subject via a local route, for example, injected to a local site such as a tumor site or an infectious site. In some aspects, the subject is a human.

As will be apparent from the present disclosure, in some aspects, the compositions described herein are administered to a subject in an effective amount to confer a therapeutic effect, either alone or in combination with one or more other active agents. In some aspects, the compositions are administered to a subject suffering from a cancer, and the therapeutic effect comprises reduced tumor burden, reduction of cancer cells, increased immune activity, or combinations thereof. Whether the administered composition (e.g., a lipid nanoparticle) achieved the therapeutic effect can be determined using any suitable methods known in the art (e.g., measuring tumor volume and/or T cell activity). Effective amounts vary, as recognized by those skilled in the art, depending on the particular condition being treated, the severity of the condition, the individual patient parameters including age, physical condition, size, gender and weight, the duration of the treatment, the nature of the concurrent therapy (if any), the specific route of administration and like factors within the knowledge of expertise of the health practitioner.

Empirical considerations, such as the half-life, generally will contribute to the determination of the dosage. Frequency of administration can be determined and adjusted over the course of therapy, and is generally, but not necessarily, based on treatment and/or suppression and/or amelioration and/or delay of a target disease/disorder. Alternatively, sustained continuous release formulations of a composition described herein (e.g., lipid nanoparticle) can be appropriate. Various formulations and devices for achieving sustained release are known in the art.

In some aspects of the disclosure, the treatment is a single injection of the composition disclosed herein. In some aspects, the single injection is administered intratumorally to the subject in need thereof.

In some aspects of the disclosure, dosages for a composition described herein can be determined empirically in individuals who have been given one or more administration(s) of the composition (e.g., lipid nanoparticle described herein). In some aspects, the individuals are given incremental dosages of the composition described herein. To assess efficacy of the composition herein, an indicator of disease/disorder can be followed. For repeated administrations over several days or longer, depending on the condition, in some aspects, the treatment is sustained until a desired suppression of symptoms occurs or until sufficient therapeutic levels are achieved to alleviate a target disease or disorder, or symptom thereof.

In some aspects of the disclosure, dosing frequency is about once every week, about once every 2 weeks, about once every 3 weeks, about once every 4 weeks, about once every 5 weeks, about once every 6 weeks, about once every 7 weeks, about once every 8 weeks, about once every 9 weeks, or about once every 10 weeks; or about once a month, about every 2 months, or about every 3 months, or longer. The dosing regimen (e.g., dosage and/or dosing frequency) of the composition described herein (e.g., lipid nanoparticle) used can vary over time.

In some aspects of the disclosure, the method comprises administering to a subject in need thereof one or multiple doses of a composition described herein.

The appropriate dosage of the composition (e.g., lipid nanoparticle described herein) will depend on the specific composition (e.g., lipid nanoparticle), the type and severity of the disease/disorder (e.g., cancer), whether the composition (e.g., lipid nanoparticle) is administered for preventive or therapeutic purposes, previous therapy, the subject's clinical history and response to the composition (e.g., lipid nanoparticle), and the discretion of the attending physician. In some aspects, a clinician can administer a composition disclosed herein until a dosage is reached that achieves the desired result. In some aspects, the desired result is a decrease in tumor burden, a decrease in cancer cells, or increased immune activity. Administration of one or more compositions described herein can be continuous or intermittent, depending, for example, upon the recipient's physiological condition, whether the purpose of the administration is therapeutic or prophylactic, and other factors known to skilled practitioners. The administration of the composition described herein can be essentially continuous over a preselected period of time or can be in a series of spaced doses, e.g., either before, during, or after developing a target disease or disorder.

As used herein, alleviating a target disease/disorder includes delaying the development or progression of the disease, or reducing disease severity. Alleviating the disease does not necessarily require curative results. As used herein, "delaying" the development of a target disease or disorder means to defer, hinder, slow, retard, stabilize, and/or postpone progression of the disease. This delay can be for varying lengths of time, depending on the history of the disease and/or subject being treated. A method that delays or alleviates the development of a disease, or delays the onset of the disease, is a method that reduces probability of developing one or more symptoms of the disease in a given time frame and/or reduces the extent of the symptoms in a given time frame, when compared to not using the method. Such comparisons are typically based on clinical studies, using a number of subjects sufficient to give a statistically significant result.

In some aspects, a composition described herein is administered to a subject in need thereof at an amount sufficient to reduce tumor burden or cancer cell growth in vivo by at least about 5%, at least about 10%, at least about 20%, at least about 30%, at least about 40%, at least about 50%, at least about 60%, at least about 70%, at least about 80%, at least about 90%, or greater. In some aspects, the composition described herein is administered in an amount effective in increasing immune activity by at least about 5%, at least about 10%, at least about 20%, at least about 30%, at least about 40%, at least about 50%, at least about 60%, at least about 70%, at least about 80%, at least about 90%, or greater.

In some aspects, administering the composition (e.g., the polynucleotide, vector, lipid nanoparticle, or pharmaceutical composition described herein) to a subject enhances immune activity, such as T cell activity, in the subject. In certain aspects, the immune activity is enhanced or increased by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold or more, compared to the immune activity of a reference subject (e.g., the subject prior to the administration of the composition or a corresponding subject that did not reactive an administration of the composition).

In some aspects, the subject is a human having, suspected of having, or at risk for a cancer. In some aspects the cancer is selected from the group consisting of melanoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine cancer, salivary gland carcinoma, kidney cancer, prostate cancer, vulval cancer, thyroid cancer, hepatic carcinoma, gastric cancer, and various types of head and neck cancer, including squamous cell head and neck cancer. In some aspects, the cancer can be melanoma, lung cancer, colorectal cancer, renal-cell cancer, urothelial carcinoma, or Hodgkin's lymphoma.

A subject having a target disease or disorder can be identified by routine medical examination, e.g., laboratory tests, organ functional tests, CT scans, or ultrasounds. A subject suspected of having a target disease or disorder might show one or more symptoms of the disease or disorder. A subject at risk for the disease or disorder can be a subject having one or more of the risk factors associated with that disease or disorder. A subject at risk for a disease or disorder can also be identified by routine medical practices.

In some aspects, the composition described herein is co-administered with at least one additional suitable therapeutic agent. In some aspects, the at least one additional suitable therapeutic agent comprises an anti-cancer agent, an anti-viral agent, an anti-bacterial agent, or other agents that serve to enhance and/or complement the immunostimulatory effect of the composition (e.g., lipid nanoparticle) described herein. Further examples of additional therapeutic agents that can be used in combination with the compositions described herein include: a chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the composition described herein and the at least one additional therapeutic agent are administered to the subject in a sequential manner, i.e, each therapeutic agent is administered at a different time. In some aspects, the composition described herein and the at least one additional therapeutic agent are administered to the subject in a substantially simultaneous manner.

It will be appreciated by one of skill in the art that any combination of the composition described herein and another anti-cancer agent (e.g., a chemotherapeutic agent) can be used in any sequence for treating a cancer. The combinations described herein can be selected on the basis of a number of factors, which include, but are not limited to, the effectiveness or reducing tumor formation or tumor growth, reducing cancer cells, increasing immune activity, and/or alleviating at least one symptom associated with the cancer, or the effectiveness for mitigating the side effects of another agent of the combination. For example, a combined therapy described herein can reduce any of the side effects associated with each individual members of the combination, for example, a side effect associated with the anti-cancer agent.

In some aspects, the other anti-cancer therapeutic agent is a chemotherapy, a radiation therapy, a surgical therapy, an immunotherapy, or combinations thereof. In some aspects, the chemotherapeutic agent is carboplatin, cisplatin, docetaxel, gemcitabine, nab-paclitaxel, pemetrexed, vinorelbine, or combinations thereof. In some aspects, the radiation therapy is ionizing radiation, gamma-radiation, neutron beam radiotherapy, electron beam radiotherapy, proton therapy, brachytherapy, systemic radioactive isotopes, radiosensitizers, or combinations thereof. In some aspects, the surgical therapy is a curative surgery (e.g., tumor removal surgery), a preventative surgery, a laparoscopic surgery, a laser surgery, or combinations thereof. In some aspects, the immunotherapy is adoptive cell transfer, therapeutic cancer vaccines, or combinations thereof.

In some aspects, the chemotherapeutic agent is platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HCl, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capecitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemelamine, and relatives); Antibiotics, such as Hydroxyurea, Anthracyclines (e.g., doxorubicin agent, daunorubicin, epirubicin and other derivatives); Anthracenediones (e.g., Mitoxantrone and relatives); *Streptomyces* family (e.g., Bleomycin, Mitomycin C, Actinomycin, Plicamycin); Ultraviolet light; and combinations thereof.

In some aspects, the other anti-cancer therapeutic agent is an antibody. Antibodies (preferably monoclonal antibodies) achieve their therapeutic effect against cancer cells through various mechanisms. They can have direct effects in producing apoptosis or programmed cell death. They can block components of signal transduction pathways such as e.g., growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g., demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present disclosure: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin av(33), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (IL-1β), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1BB), Volociximab (integrin α5β1), Votumumab (tumor antigen CTAA16.88), Zalutumumab (EGFR), Zanolimumab (CD4).

In some aspects, the other anti-cancer therapeutic agent is a cytokine, chemokine, costimulatory molecule, fusion protein, or combinations thereof. Examples of chemokines include, but are not limited to, CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g., B7 ligands (B7.1 and B7.2) are useful. Also useful are other cytokines such as e.g., interleukins especially (e.g., IL-1 to IL17), interferons (e.g., IFNalpha1 to IFNalpha8, IFNalpha10, IFNalpha13, IFNalpha14, IFNalpha16, IFNalpha17, IFNalpha21, IFNbeta1, IFNW, IFNE1 and IFNK), hematopoietic factors, TGFs (e.g., TGF-α, TGF-β, and other members of the TGF family), finally members of the tumor necrosis factor family of receptors and their ligands as well as other stimulatory molecules, comprising but not limited to 41BB, 41BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

In some aspects, the other anti-cancer therapeutic is a bacterial treatment. Researchers have been using anaerobic bacteria, such as *Clostridium novyi*, to consume the interior of oxygen-poor tumors. These should then die when they come in contact with the tumor's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumor, the enzyme is expressed solely in the tumor. Thus, a systemically applied prodrug is metabolized to the toxic drug only in the tumor. This has been demonstrated to be effective with the non-pathogenic anaerobe *Clostridium sporogenes*.

In some aspects, the other anti-cancer therapeutic agent is a kinase inhibitor. The growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g., BCR-ABL, B-Raf, EGFR, HER-2/ErbB2, IGF-IR, PDGFR-α, PDGFR-β, c-Kit, Flt-4, Flt3, FGFR1, FGFR3, FGFR4, CSF1R, c-Met, RON, c-Ret, ALK, cytoplasmic tyrosine kinases e.g., c-SRC, c-YES, Abl, JAK-2, serine/threonine kinases e.g., ATM, Aurora A & B, CDKs, mTOR, PKCi, PLKs, b-Raf, S6K, STK11/LKB1 and lipid kinases e.g., PI3K, SK1. Small molecule kinase inhibitors are e.g., PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g., Zhang et al. 2009: Targeting cancer with small molecule kinase inhibitors. Nature Reviews Cancer 9, 28-39.

In some aspects, the other anti-cancer therapeutic agent is a toll-like receptor. The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR8 have been examined for cancer therapy in passive immunotherapy approaches. The closely related TLR7 and TLR8 contribute to antitumor responses by affecting immune cells, tumor cells, and the tumor microenvironment and can be activated by nucleoside analogue structures. All TLR's have been used as stand-alone immunotherapeutics or cancer vaccine adjuvants and can be synergistically combined with the formulations and methods of the present disclosure. For more information see van Duin et al. 2005: Triggering TLR signaling in vaccination. Trends in Immunology, 27(1):49-55.

In some aspects, the other anti-cancer therapeutic agent is an angiogenesis inhibitor. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which can be combined with the present disclosure are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g., bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactina Vβ3 inhibitors, linomide, tasquinimod, For review see Schoenfeld and Dranoff 2011: Anti-angiogenesis immunotherapy. Hum Vaccin. (9):976-81.

In some aspects, the other anti-cancer therapeutic agent is a virus-based vaccine. There are a number of virus-based cancer vaccines available or under development which can be used in a combined therapeutic approach together with the formulations of the present disclosure. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting anti-tumor specific responses. Recombinant viruses such as vaccinia viruses, herpes simplex viruses, adenoviruses, adeno-associated viruses, retroviruses and avipox viruses have been used in animal tumor models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g., the hepatitis B virus or other virus families including Parvoviridae (e.g., adeno-associated virus), Retroviridae (e.g., HIV), and Flaviviridae (e.g., Hepatitis C virus). For a general review see Sorensen and Thompsen 2007: "Virus-based immunotherapy of cancer: what do we know and where are we going?" APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillen et al. 2010: Virus-like particles as vaccine antigens and adjuvants: application to chronic disease, cancer immunotherapy and infectious disease preventive strategies. Procedia in Vaccinology 2 (2), 128-133.

In some aspects, the other anti-cancer therapeutic agent is a peptide-based target therapy. Peptides can bind to cell surface receptors or affected extracellular matrix surrounding the tumor. Radionuclides which are attached to these peptides (e.g., RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

In some aspects, a therapeutic application of a polynucleotide (e.g., isolated polynucleotide) described herein comprises producing the encoded IL-12 protein. Accordingly, in some aspects, the present disclosure relates to a method of producing an IL-12 protein. In certain aspects, the method comprises contacting a cell with any of the compositions described herein (e.g., polynucleotides, vectors, and/or lipid nanoparticles) under conditions suitable for producing the encoded IL-12 protein. In some aspects, the method further comprises purifying the produced IL-12 protein. In some aspects, the contacting occurs in vivo (e.g., by administering the polynucleotide, vector, and/or lipid nanoparticle to a subject). In some aspects, the contacting occurs ex vivo (e.g., by culturing cells with the polynucleotide, vector, and/or lipid nanoparticles in vitro). Cells (e.g., host cells) comprising the polynucleotide, vector, and/or lipid nanoparticle are encompassed herein. Non-limiting examples of cells that can be used include immortal hybridoma cell, NS/0 myeloma cell, 293 cell, Chinese hamster ovary (CHO) cell, HeLa cell, human amniotic fluid-derived cell (CapT cell), COS cell, or combinations thereof.

Kits for Use in Therapy

The present disclosure also provides kits for use in immunotherapy against a disease or disorder, such as a cancer (e.g., melanoma, lung cancer, colorectal cancer, or renal-cell cancer), and/or treating or reducing the risk for the disease or disorder (e.g., cancer). In some aspects, the kit includes one or more containers comprising a composition described herein.

In some aspects, the kit comprises instructions for use in accordance with any of the methods described herein. For example, the included instructions can comprise a description of administration of the pharmaceutical composition described herein to treat, delay the onset, or alleviate a target disease. In some aspects, the instructions comprise a description of administering the composition described herein to a subject at risk of the target disease/disorder (e.g., cancer).

In some aspects, the instructions comprise dosage information, dosing schedule, and route of administration. In some aspects, the containers are unit doses, bulk packages (e.g., multi-dose packages) or sub-unit doses. In some aspects, the instructions are written instructions on a label or package insert (e.g., a paper sheet included in the kit). In some aspects, the instructions are machine-readable instructions (e.g., instructions carried on a magnetic or optical storage disk).

In some aspects, the label or package insert indicates that the composition disclosed herein is used for treating, delaying the onset, and/or alleviating a disease or disorder associated with cancer, such as those described herein. Instructions can be provided for practicing any of the methods described herein.

In some aspects, the kits described herein are in suitable packaging. In some aspects, suitable packing comprises vials, bottles, jars, flexible packaging (e.g., seal Mylar or plastic bags), or combinations thereof. In some aspects, the packaging comprises packages for use in combination with a specific device such as an inhaler, nasal administration device (e.g., an atomizer), or an infusion device such as a minipump. In some aspects, the kit comprises a sterile access port (for example the container can be an intravenous solution bag or a vial having a stopper pierceable by a hypodermic injection needle). In some aspects, the container can also have a sterile access port (for example the container can be an intravenous solution bag or a vial having a stopper pierceable by a hypodermic injection needle). In some aspects, at least one active agent is a composition as described herein.

In some aspects, the kits further comprise additional components such as buffers and interpretive information. In some aspects, the kit comprises a container and a label or package insert(s) on or associated with the container. In some aspects, the disclosure provides articles of manufacture comprising the contents of the kits described herein.

General Techniques

The practice of the present disclosure will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Giffiths, and D. G. Newell, eds., 1993-8) J. Wiley and Sons; Method of Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987): PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane, Cold Spring Harbor Laboratory Press, 1999); The Antibodies (M. Zanette and J. D. Capra, eds., Harwood Academic Publishers, 1995). Without further elaboration, it is believed that one skilled in the art can, based on the above description, utilize the present disclosure to its fullest extent. All publications cited herein (including those listed above and elsewhere in the present disclosure) are incorporated by reference in their entirety.

EXAMPLES

Example 1: Construction of Nucleotide Sequence Encoding IL-12S

To construct the polynucleotides disclosed herein (i.e., comprising a nucleic acid molecule encoding an IL-12 protein), the following materials and methods were used:

Template Preparation

For replicon RNA, a VEE replicon vector containing the payload was prepared. VEE replicon vector backbones used included one or more of the following modifications: (i) "A3G": represents a change in the 5' UTR of the TC-83 VEE backbone that enhances expression (see, e.g., Kulasegaran-Shylini, R., et al., Virology 287: 211-221 (2009)); (ii) "+E1": indicates that the 3'-end of the VEE "E1" coding region was included; (iii) "−E1": indicates that the 3'-end of the VEE "E1" coding region was not included; (iv) "Alternative": represents a VEE replicon backbone sequence described in, e.g., AddGene catalog number 58977; and Yoshioka, N., et al., Cell Stem Cell. 13(2):246-54 (2013); (v) "Evolved": indicates that a set of mutations that were identified as enhancing VEE replicon expression was included (see, e.g., Li, Y., et al., Scientific Reports 9:6932 (2019)).

Methods of preparing such vectors are known in the art. The vector plasmid was further linearized using I-SceI as follows. Briefly, 1 μg of replicon plasmid vector was treated with I-SceI in CutSmart buffer for 1 hour at 37° C. Then, the enzyme was heat inactivated at 65° C. for 20 minutes. The concentration and volume of the different components are provided in Table 3 (below).

Additional vectors used in the examples were prepared as follows. Alternative Evolved −E1 SGP scar vector was linearized using MIuI by following a similar procedure and conditions as were used for the I-SceI treatment of the VEE vector. A3G+E1 (Clean end repRNA) was digested using SapI by following a similar procedure and conditions as were used for the I-SceI treatment of the VEE vector.

TABLE 3

Vector Plasmid Linearization

| Component | Volume (μL) | Concentration |
|---|---|---|
| DNA template | | 1 μg |
| Cutsmart buffer | 5 | 1x |
| I-SceI | 1 | 5 units |
| Water | 44 | |

For modified RNA (modRNA) template, the DNA vector was generated using a replicon plasmid with forward primer containing T7 promoter (TAA TAC GAC TCA CTA TA ATG GAC TAC GAC ATA GT; SEQ ID NO: 181) and SGP and a reverse primer in the 3'-UTR (GAA ATA TTA AAA ACA AAA TCC GAT TCG GAA AAG AA; SEQ ID NO: 185). The $T_m$ for the forward and reverse primers were 68° C. and 64° C., respectively. Tables 4 and 5 (below) provide additional information relating to the PCR reaction.

TABLE 4

PCR Setup

| COMPONENT | 25 μl REACTION | FINAL CONCENTRATION |
|---|---|---|
| 10 μM Forward Primer | 1.25 μl | 0.5 μM |
| 10 μM Reverse Primer | 1.25 μl | 0.5 μM |
| Template DNA | variable | 10 ng |
| 2X Q5 Hot Start Master mix | 12.5 μl | |
| Nuclease-Free Water | to 25 μl | |

TABLE 5

PCR Cycling Conditions

| STEP | TEMP | TIME |
|---|---|---|
| Initial Denaturation | 98° C. | 30 seconds |
| 30 Cycles | 98° C. | 10 seconds |
| | 65° C. | 15 seconds |
| | 72° C. | 4 minutes |
| Final Extension | 72° C. | 4 minutes |
| Hold | 4-10° C. | |

Plasmid DNA (template) in the PCR reaction was digested by DpnI. More specifically, 1 μL DpnI per μg of initial plasmid was added to the PCR sample and incubated for 1 hour at 37° C.

The PCR (modRNA template) and I-SceI treated replicon DNA (repRNA template) was checked on pre-cast gels to confirm the purity (PCR) and integrity (replicon template) of the replicated construct. Specifically, 20 ng of the DNA was loaded onto a 1.2% DNA gel and ran at 275V for 7-10 minutes. Once confirmed, the DNA was eluted in 20 μL of water.

In Vitro Transcription

To transcribe the above DNA to RNA, a HiScribe High yield T7 kit (New England Biolabs) was used with the modifications described herein. For modified RNA (modRNA) synthesis, the UTP component of the kit was replaced with N1-methylpseudouridine-5'-triphosphate. To begin the in vitro transcription process, the kit components were thawed on ice, mixed, and pulse-spinned in a microfuge. The sample was placed on ice until further use.

Co-transcriptional capping method: For production using cap analog replicon plasmids and modRNA templates, the components shown in Table 6 (below) were mixed, pulse-spun in a microfuge, and then incubated at 37° C. for three hours in the Thermomixer at 400 rpm. A 1 μL aliquot was taken for quality control purposes.

TABLE 6

Co-Transcriptional Capping Components

| Component | Volume | Final Conc. |
|---|---|---|
| Nuclease-free water | X μl | |
| 10X Reaction Buffer (NEB | 2 μl | 1X |
| ATP (100 mM) | 2 μl | 10 mM final |
| GTP (100 mM) | 2 μl | 10 mM final |
| UTP or N1-methylpseudoUTP (100 mM) | 2 μl | 10 mM final |
| CTP (100 mM) | 2 μl | 10 mM final |
| Cap Analog | 1 μl | |
| Template DNA | X μl | 1 μg |
| T7 RNA Polymerase Mix | 2 μl | |
| SUPERase Inh. | 1 μl | |
| Total reaction volume | 20 μl | |

Post-transcriptional enzymatic capping method: In addition to the co-transcriptional capping method that was performed after IVT, a post-transcriptional enzymatic capping method was used for vectors that contained a terminal 'G' in the T7 promoter. This method comprised enzymatic production of a 'Cap 1' mRNA following in vitro transcription. For production using enzymatic replicon plasmids, the reaction was assembled at room temperature in the order shown in Table 7.

TABLE 7

Post-Transcriptional Enzymatic Capping Components

| Component | Volume | Final Conc. |
|---|---|---|
| Nuclease-free water | X μl | |
| 10X Reaction Buffer | 2 μl | 1X |
| ATP (100 mM) | 2 μl | 10 mM final |
| GTP (100 mM) | 2 μl | 10 mM final |
| UTP or N1-methylpseudoUTP (100 mM) | 2 μl | 10 mM final |
| CTP (100 mM) | 2 μl | 10 mM final |
| Template DNA | X μl | 1 μg |
| T7 RNA Polymerase Mix | 2 μl | |
| SUPERase Inh. | 1 μl | |
| Total reaction volume | 20 μl | |

DNAse treatment: After capping with either the co-transcriptional capping method or the post-transcriptional enzymatic capping method, Turbo DNase enzyme was used. There was no need to add the 10× buffer since the enzyme was active in the IVT reactions. The reaction was diluted to 50 μL with nuclease free water. Then, 5 μL of the enzyme (2 U/μL) was added to 20 μL IVT reaction. Then, the mixture was incubated for 30 minutes at 37° C. Afterwards, the RNA was purified using Monarch RNA cleanup kit. A 1 μL aliquot was taken for quality control purposes Capping and 2'-O-methylation: To prepare a methylated guanine-cap with 2'-O-methylation (Cap 1) structure on the 5'-ends of the IVT mRNAs made using the above-described post-transcriptional capping method, the following method was used. First, the uncapped RNA and nuclease-free water were mixed to a final volume of 13 μL. Then, the mixture was heated at 65° C. for 5 minutes. The mixture was then placed on ice for 5 additional minutes. Then, the components provided in Table 8 (below) were added to the mixture and incubated for 60 minutes at 37° C. Next, the RNA was purified using the small Monarch RNA cleanup kit.

TABLE 8

Capping and 2'-O-Methylation Components

| Component | Volume |
|---|---|
| Denatured uncapped RNA (from above) | 13.0 μl |
| 10X Capping Buffer | 2.0 μl |
| GTP (10 mM) | 1.0 μl |
| SAM (4 mM, dilute 32 mM stock to 4 mM) | 1.0 μl |
| Vaccinia Capping Enzyme (10 U/μl) | 1.0 μl |
| mRNA Cap 2'-O-Methyltransferase (50 U/μl) | 1.0 μl |
| SUPERase Inh | 1.0 μl |
| Total | 20 μL |

Poly(A) tail synthesis: To add the poly(A) tails to the modified RNAs, the components provided in Table 9 (below) were added to a reaction tube. Then, the reaction was incubated for 30 minutes at 37° C. Then, the reaction was stopped by directly purifying the RNA with the small Monarch cleanup kit. As a quality control, 200 ng of the RNA was run on a 1.2% RNA gel to confirm the size of the RNA. To do so, RNA was denatured with 50% formaldehyde sample buffer for 5 minutes at 65° C., and then, immediately placed on ice for at least one minute. Then, the denatured RNA was loaded onto a gel and visualized using a Transilluminator.

RNA purification: A poly A containing RNA transcript was purified from IVT reaction impurities.

Table 9 (below) provides a summary of the different IL-12-expressing RNA constructs produced and analyzed in the following examples. Constructs #1-#9 all have a 3'-end scar following the polyA tail (i.e., 3'-end termination with a restriction enzyme after SGP).

TABLE 9

| Name of Construct | Description of Construct |
|---|---|
| repRNA (Cap Analog) (“Construct #1”) | (i) Self-replicating mRNA + (ii) Cap Analog co-transcriptional capping method |
| repRNA (Enzymatic) (“Construct #2”) | (i) Self-replicating mRNA + (ii) enzymatic post-translational capping method |
| repRNA (Cap Analog) A3G + E1 (“Construct #3”) | (i) Self-replicating mRNA + (ii) Cap Analog co-transcriptional capping method + (iii) VEE replicon vector comprising A3G and + E1 modifications |
| repRNA (Enzymatic) A3G + E1 (“Construct #4”) | (i) Self-replicating mRNA + (ii) enzymatic post-translational capping method + (iii) VEE replicon vector comprising A3G and +El modifications |
| repRNA (Cap Analog) Alternative Evolved + E1 (“Construct #5”) | (i) Self-replicating mRNA + (ii) Cap Analog co-transcriptional capping method + (iii) VEE replicon vector comprising Alternative, Evolved, and + E1 modifications |
| repRNA (Enzymatic) Alternative Evolved + E1 (“Construct #6”) | (i) Self-replicating mRNA + (ii) enzymatic post-translational capping method + (iii) VEE replicon vector comprising Alternative, Evolved, and + E1 modifications |
| repRNA (Cap Analog) Alternative + E1 (“Construct #7”) | (i) Self-replicating mRNA + (ii) Cap Analog co-transcriptional capping method + (iii) VEE replicon vector comprising Alternative and + E1 modifications |
| repRNA (Cap Analog) A3G + E1 Evolved (“Construct #8”) | (i) Self-replicating mRNA + (ii) Cap Analog co-transcriptional capping method + (iii) VEE replicon vector comprising A3G, +E1, and Evolved modifications |
| repRNA (Cap Analog) A3G − E1 (“Construct #9) | (i) Self-replicating mRNA + (ii) Cap Analog co-transcriptional capping method + (iii) VEE replicon vector comprising A3G and − El modifications |
| repRNA (Enzymatic) Alternative Evolved − E1 SGP scar (“Construct #10”) | (i) Self-replicating mRNA + (ii) enzymatic post-translational capping method + (iii) VEE replicon vector comprising Alternative, Evolved, and − E1 modifications + (iv) 3'-end termination with a restriction enzyme scar after SGP |
| modRNA (Cap Analog) (“Construct #11”) | Non-self-replicating modified mRNA + Cap Analog co-transcriptional capping method |
| repRNA (Cap Analog) A3G + E1 SGP scar (“Construct #12”) | (i) Self-replicating mRNA + (ii) Cap Analog co-transcriptional capping method + (iii) VEE replicon vector comprising A3G and +E1 modifications + (iv) 3'-end termination with a restriction enzyme scar after SGP |
| repRNA (Cap Analog) A3G + E1 clean 3'-end (“Construct #13”) | (i) Self-replicating mRNA + (ii) Cap Analog co-transcriptional capping method + (iii) VEE replicon vector comprising A3G and + E1 modifications + (iv) 3'-end termination with a clean polyA sequence |

Example 2: mRNA Composition Analysis

Comparison of Capping Methods on Anti-Tumor Efficacy

To begin analyzing the different RNA constructs produced in Example 1 above, a mouse melanoma model was used to compare the anti-tumor efficacy of (i) repRNA co-transcriptionally capped with a 5' cap analog (i.e., Construct #1 in Table 9) to that of (ii) repRNA post-transcriptionally capped by enzymatic addition of 5' cap (i.e., Construct #2 in Table 9). Briefly, melanoma was induced by inoculating the animals with B6-F10 cells (via subcutaneous administration). B16-F10 cell lines were obtained from American Type Culture Collection (ATCC) and grown in DMEM supplemented with 10% fetal bovine serum, 50U/ml Penicillin-Streptomycin, and 2 mM L-Glutamine in a humidified incubator (37° C. and 5% CO2). At ~80% confluence cells were washed in phosphate-buffered saline solution (PBS), harvested from tissue culture flasks by incubating cells in 0.25% Trypsin-EDTA until detached, washed twice in PBS and resuspended PBS at a concentration of 2 million cells per ml. 1 million cells were implanted subcutaneously under the left hind-flank of female 6-8 week old C57BL/6J mice obtained from The Jackson Laboratory. Tumor-bearing mice were monitored until the tumors reached a mean volume of 350 $mm^3$, then mice were randomized and then either of the above-described constructs were delivered by intratumoral injection using a 27 g syringe. Control animals were treated with PBS. Tumor sizes were recorded thrice weekly with a digital caliper and volumes were estimated using the following formula: (l×w^2)×0.5, where l=length (longest measurement) and w=widest diameter of the tumor, axis perpendicular to length.

As shown in FIG. 1A and FIG. 1B, animals treated with Construct #1 (i.e., the repRNA made using Cap Analog co-transcriptional capping) had significantly reduced tumor volume compared to animals from the other treatment groups. Similar to the control group, animals treated with Construct #2 (i.e., the repRNA made using enzymatic post-translational capping method) failed to control the growth of the tumor. This data suggested that the Cap Analog co-transcriptional capping method was much more favorable compared to the enzymatic post-translational capping method in constructing the IL-12 expressing self-replicating constructs described herein.

Comparison of VEE Replicon Backbones on Anti-Tumor Efficacy

Next, to assess whether the different VEE replicon backbones described in Example 1 had any effect on the therapeutic efficacy of the mRNA constructs, the above-described melanoma mouse model was used again. Once optimal tumor size was reached, the animals received a single intratumoral injection of one of the following: (i) PBS; (ii) repRNA made using the A3G +E1 vector and Cap Analog co-transcriptional capping ("Construct #3" in Table 9); (iii) modified mRNA (non-self-replicating) made using Cap Analog co-transcriptional capping ("Construct #5" in Table 9); (iv) repRNA made using the Alternative Evolved vector and Cap Analog co-transcriptional capping ("Construct #6" in Table 9); and (v) repRNA made using the Alternative Evolved vector and enzymatic post-translational capping ("Construct #7" in Table 9). Then, the expression of the IL-12 protein in the tumors was assessed at day 3 post-administration. Survival of the treated animals was also assessed.

Quantification of the IL-12 protein in the tissues (e.g., tumors) was performed as follows. Tissues were dissected out (e.g., at 72 hours post-administration), weighed, snap frozen, and subsequently lysed in radioimmunoprecipitation assay buffer. The concentration of the IL-12 protein in tissue lysates was determined using a commercially available sandwich enzyme-linked immunosorbent assay (ELISA) against the p70 subunit of murine IL-12, according to the manufacturer's (BioLegend) protocol.

As shown in FIG. 2, IL-12 expression in the tumor delivery site was higher in animals that received Construct #3 (i.e., repRNA made using the A3G+E1 vector and Cap Analog co-transcriptional capping) as compared to animals that received either Construct #5 or Construct #6. In agreement with the expression data, animals treated with Construct #3 (i.e., repRNA made using the A3G+E1 vector and Cap Analog co-transcriptional capping) also exhibited the greatest survival (see FIG. 3).

Comparison of Transfection Efficiency and IL-12 Secretion

To further analyze the different RNA constructs described in Example 1, both the transfection efficiency and IL-12 secretion were assessed in vitro. Briefly, B16.F10 cells (100,000 cells per well) were split into 24-well plates one day before transfection. The cells were then transfected using Lipofectamine messengerMAX according to the manufacturer's instructions. Briefly, 100 ng of total RNA was transfected with 1.5 uL Lipofectamine reagent per well and incubated until desired timepoints (i.e., 24 and 48 hours post-transfection). The specific RNA constructs tested included the following: (i) repRNA made using the A3G+E1 vector and Cap Analog co-transcriptional capping ("Construct 3" in Table 9); (ii) repRNA made using the A3G+E1 vector and enzymatic post-translational capping ("Construct #4" in Table 9); (iii) repRNA made using the Alternative Evolved +E1 vector and Cap Analog co-transcriptional capping ("Construct #5" in Table 9); (iv) repRNA made using the Alternative Evolved +E1 vector and enzymatic post-translational capping ("Construct #6" in Table 9); (v) repRNA made using the Alternative +E1 vector and Cap Analog co-transcriptional capping ("Construct #7" in Table 9); (vi) repRNA made using the A3G +E1 Evolved vector and Cap Analog co-transcriptional capping ("Construct #8" in Table 9); (vii) repRNA made using the A3G −E1 vector and Cap Analog co-transcriptional capping ("Construct #9" in Table 9); and (viii) repRNA made using the Alternative Evolved −E1 SGP scar end vector ("Construct #10" in Table 9).

To assess the transfection efficiency of the RNA constructs, FACS analysis was used to measure IL-12 expression in the cells. Briefly, Golgi transport blocking incubation was set up by trypsinizing cells using 100 uL trypsin. Next, complete media with Brefeldin A was added, and the cells then transferred to a 96-well deep well assay plate. The plate was then covered with parafilm and the cells incubated in complete media with Brefeldin A for 4 hours in the cell culture incubator. Staining for dead cell discrimination was performed by spinning down the cells at 5', 400 g. Cells were washed in PBS and subsequently transferred to V-bottom 96-well plates, which were then centrifuged at 400×g. Cells were then resuspended in Zombie Live/Dead Green dye diluted in PBS and incubated for 10 minutes at room temperature in the dark. The cells were then washed in FACS buffer, which comprised 1×PBS ($Ca^{2+}$ and $Mg^{2+}$ free), 2 mM EDTA, 2% BSA, and 0.1% Sodium Azide. Cells were then fixated by resuspending the cells in fixation buffer and incubated for 30 minutes at room temperature in the dark.

Cells were permeabilized and cytoplasmic proteins stained as follows. Cells were washed in permeabilization/wash buffer and centrifuged at 800×g. Cells were resuspended in cytoplasmic antibody cocktail and incubated at room temperature in the dark. Cells were washed in permeabilization/wash buffer and centrifuged at 800×g, which was followed by a wash with FACS buffer and centrifugation at 800×g. Samples were then prepared for flow cytometry by resuspending the cells in FACS buffer. FACS analysis of the cells was performed by using the red and the blue laser on the Attune Flow cytometer. After gating out cell debris and doublets, the single cells were analyzed on the 2 channels of the cytometer and gated to quantify the percent of cells positive for IL-12. The results were subsequently plotted in Prism.

To measure IL-12 secretion, an ELISA assay was used. Briefly, supernatant for cell cultures was collected for subsequent ELISA-based analysis for various different proteins of interest. For each supernatant sample timepoint, the cell culture supernatant from the appropriate well was aspirated into a 96-well deep well plate, which could be stored at −80° C. for future use. After collection of all desired timepoints, the 96-well plate containing the supernatant samples was centrifuged at 500 g for 5 minutes to pellet any remaining cells. Following centrifugation, ~350-400 uL supernatant was aspirated from the plate into a fresh deep well plate without disturbing the cell pellet. The supernatant was then diluted and tested in ELISA assays against mouse IL-12 or human IL-12 using Invitrogen ELISA kits according to the manufacturer's instructions, i.e., Invitrogen Mouse IL-12 p70 uncoated ELISA kit; Invitrogen Human IL-12 p70 Uncoated ELISA kit. Following ELISA assay data acquisition, a standard curve was drawn in Prism using 4PL method, and the concentration data was interpolated for all samples.

As shown in FIGS. 4A and 4B, the A3G and +E1 vector constructs generally performed better as compared to the Alternative, Evolved, −E1 constructs, or combinations. Moreover, in agreement with the earlier data, Cap Analog constructs generally performed better as compared to enzymatic capped constructs. Furthermore, the A3G +E1 repRNA (Construct #3) performed better than the other tested repRNA constructs in IL12 expression and total protein secretion at 24 and 48 hrs (see FIGS. 4A and 4B, respectively).

Comparison of "Clean" and "Scar" 3'-End Termination

Next, the transfection efficiency of self-replicating mRNA with the 3' end terminating with a "clean" polyA sequence was compared to a 3' end terminating with a restriction enzyme "scar." Briefly, the following constructs were used to transfect cells as described above: (i) repRNA made using the Cap Analog co-transcriptional capping method and A3G +E1 vector with a 3'-end terminating with a restriction enzyme scar ("Construct #12" in Table 10; circle and square); (ii) repRNA made using the Cap Analog co-transcriptional capping method and A3G+E1 vector with a 3'-end terminating with a clean polyA sequence ("Construct #13" in Table 10; triangle and inverted triangle). Then, IL-12 expression was assessed in the cells using FACS analysis as described above.

As shown in FIG. 5, 3'-end termination with a clean polyA sequence improved expression in vitro.

Example 3: Lipid Nanoparticle (LNP) Formulation

In the present example, replicating mRNA encapsulated in an LNP formulations comprising cationic, phospho, and PEG lipids and cholesterol and LNP formulations comprising cationic and phospho lipids and cholesterol (with PEG-lipid micelles added to the solution as an independent component rather than part of the LNP per se) were prepared and analyzed. The mRNAs evaluated included mCherry replicating mRNAs as follows: 1. TT3-DMG (A3G +E1 backbone); and 2. TT3-post PEG micelles (A3G +E1 backbone).

To prepare the conventional TT3 LNP formulations, the following procedure was used. The lipid materials were each weighed out and dissolved in ethanol. The ethanol phase was prepared by mixing all the lipid materials according to composition weight ratio in Table 10 below. The aqueous phase was prepared by diluting purified JK001 mCherry repRNA with 20 mM Citrate Buffer (pH 4.0), 300 mM NaCl and water so that the final composition of the salt was 10 mM citrate Buffer (pH 4.0, 150 mM NaCl). The conventional TT3 LNPs were afforded by mixing the ethanol phase and aqueous phase of the LNPs through T-junction mixing at the flow rate ratio of 3:1 (aqueous phase: ethanol phase).

TABLE 10

| TT3 LNP Composition Component | Weight Ratio |
|---|---|
| mRNA | 1.0 |
| TT3 | 10.0 |
| DOPE | 8.0 |
| Cholesterol | 5.6 |
| DMG-PEG-2K | 0.7 |

To prepare the post-PEG micelles TT3 LNPs formulations, the following procedure was used. The lipid materials were each weighed out and dissolved in ethanol. The ethanol phase was prepared by mixing all the lipid materials (i.e., TT3, DOPE, and cholesterol) except from DMG-PEG-2K, according to composition weight ratio described below (see, e.g., Table 11a). The aqueous phase was prepared by diluting purified JK001 mCherry repRNA (i.e., mRNA) with 20 mM Citrate Buffer (pH 4.0), 300 mM NaCl and water so that the final composition of the salt was 10 mM citrate Buffer (pH 4.0, 150 mM NaCl). PEG micelle phase was prepared by adding the corresponding volume of DMG-PEG-2K into TBS buffer and mixing thoroughly via vortex. Finally, the post-PEG micelles TT3 LNPs were afforded by first mixing the ethanol phase and aqueous phase of the LNPs through a T-junction mixing at the flow rate ratio of 3:1 (aqueous phase: ethanol phase), and followed by an immediate in-line dilution with the PEG micelle phase via T-junction mixing at the flow rate ratio of 1:1 (LNP phase:PEG phase). The final lipid composition of Post-PEG micelle TT3 LNP is described in Table 11b.

TABLE 11a

| TT3 LNP Composition Component | Weight Ratio |
|---|---|
| mRNA | 1.0 |
| TT3 | 10.0 |
| DOPE | 8.0 |
| Cholesterol | 5.6 |
| PEG-DMG-2k Micelle | Weight Ratio |
| DMG-PEG-2K | 4.2 (relative to mRNA above, which is not part of the micelle) |

TABLE 11b

| TT3 LNP Composition Component | Weight Ratio |
|---|---|
| mRNA | 1.0 |
| TT3 | 10.0 |
| DOPE | 8.0 |
| Cholesterol | 5.6 |
| DMG-PEG-2K | 4.2 |

The TT3 LNP formulations above were buffer exchanged and freeze/thawed as follows. The afforded TT3 LNPs were transferred to the dialysis cassettes and dialyzed in TBS buffer for 2 hours. 40% sucrose (W/V) in TBS stock solution was added into all the prepared TT3 LNPs to make a final solution of TT3 LNPs in 10% sucrose. The final RNA concentrations of LNPs were measured by dissociating the LNPs with 2% TE+Triton and further detected with Qubit assay. TT3 LNPs were aliquot into 50 μl/tube aliquots and put the at −80° C. for freezing. Before treating cells with LNPs, TT3 LNPs were thawed at room temperature.

Example 4: In Vivo Mouse IL-12 Variant Analysis

In the present example, assays were performed to evaluate various different mouse IL-12 variants in a B16.F10 mouse syngeneic cancer model. Briefly, the animals were treated via intratumoral administration with RNA constructs encoding one of the following mouse IL-12 proteins: (i) mIL-12 alone; (ii) mIL-12 conjugated to albumin; and (iii) mIL-12 conjugated to albumin and lumican. The RNA constructs were administered to the animals at a dose of either 0.25 μg or 2.5 μg. Then, the concentration of IL-12 and/or IFN-γ was measured using ELISA-based assays at days 1, 4, and/or 7 post-administration in one or more of the following tissues: tumor, serum, spleen, draining lymph nodes, and non-draining lymph nodes.

As shown in FIGS. 6A and 6C, at day 1 post-administration, the concentration of the IL-12 protein in the tumors was comparable among the different animals, with modest decrease in animals treated with the RNA construct encoding mIL-12 conjugated to albumin and lumican. Similar results were observed in the serum (FIG. 6B), spleen (FIG. 7A), draining lymph nodes (FIG. 7B), and non-draining lymph nodes (FIG. 7C). At day 4 post-administration, animals treated with 2.5 μg of the RNA construct encoding the mIL-12 alone had the highest IL-12 expression level in the tumor (see FIG. 6C). In the other tissues analyzed, the IL-12 expression levels were more comparable, with slightly higher levels observed in animals treated with the RNA construct encoding mIL-12 conjugated to albumin (see FIGS. 6D, 8A, 8B, 8C, and 9A). IFN-γ expression level was also the highest in animals treated with the RNA construct encoding mIL-12 conjugated to albumin (FIG. 9B).

Example 5: Human IL-12 Codon Optimization

In the present example, human IL-12 codon was optimized as follows. 20301 diverse sequences encoding the fusion protein human light chain leader—hIL12p40—GGS $(GGGS)_3$ linker—hIL12p35—GSGGGS linker—Human serum albumin were generated algorithmically. Codon optimality was calculated as the average frequency with which each codon in a given coding sequence is used to encode a given amino acid in the standard human transcriptome. 1137 representative sequences were identified, and their minimum free energy of folding (MFE) was calculated by ViennaRNA-2.4.14. Representative sequences with low, mid, and high codon optimality and MFE (L1, L2, L3; M1, M2, M3; H1, H2, H3) were modified to contain an identical light chain linker and enable efficient commercial synthesis and assembly and tested experimentally. A sequence (CO) containing the most frequently employed codon for each amino acid was also generated by this algorithm. A separate sequence (CP), containing an optimally frequent set of codon pairs, was generated by a related algorithm.

FIG. 10 presents data related to optimality (avg_codon_score) vs minimum folding free energy in kcal/mol (MFE) for 1137 distinct sequences encoding the fusion protein human light chain leader—hIL12p40—GGS(GGGS)3 linker—hIL12p35—GSGGGS linker—Human serum albumin. The codon optimal ("CO") sequence containing the most frequently used triplet at each position is shown as the triangle. Sequences with >90% and >90% identity to CO are shown as dark gray and light gray dots, respectively. The representative sequences with low, mid, and high codon optimality and MFE (L1, L2, L3; M1, M2, M3; H1, H2, H3), are shown using a circle symbol. Representative sequences with very high codon optimality and MFE are shown as diamonds and were not experimentally tested. Initial screening demonstrated that highly structured and frequently used codons gave high expression from repRNA.

IL-12 expression levels of variant self-replicating mRNAs encoding hIL-12 (A1-A4), hIL12-albumin (B1-B4), and hIL12-albumin-lumican (C1-C3) were measured in an in vitro expression assay in human TNBC cell line. IL-12, IL-12-alb, and IL-12-alb-lum versions of each of these constructs were tested. Human TNBC BT20 cells were transfected via TT3-LNP and incubated for 20 hours prior to expression level measurements by ELISA-based assays.

FIG. 11 presents data related to IL-12 expression level of variant self-replicating mRNAs encoding hIL-12 (A1-A4), hIL12-albumin (B1-B4), and hIL12-albumin-lumican (C1-C3) 20 hours after transfection via TT3-LNP into BT-20 cells. Individual triplicate measurements are shown as triangular, square, octagonal, or circular points, and horizontal bars show the average of triplicate measurements. The best expressing constructs were used in subsequent TNBC PDX mouse experiments. Briefly, patient-derived xenograft (PDX) experiments were performed as follows: PDXs were initially established from fresh surgically resected tumors from TNBC (ER,PR,HER2-negative breast cancer) patients. Tumors specimens were mechanically dissociated into small fragments, mixed with Matrigel solution, and surgically implanted as solid fragments under the skin of NOD.Cg-Prkdc-$^{scid}$ Il2rg-$^{tm1Wjl}$/SzJ (NSG) mice using a trocar. PDX tissue was serially passaged in vivo prior to initiation of the experiment. For the experiments described, PDX tumor fragments were engrafted subcutaneously into NSG mice and randomized upon tumors reaching a mean size of 200-350 mm3. Immediately after randomization mice were treated with indicated agents and serum, spleen, and tumors were collected 24 hours later. Human IL-12 concentrations in the serum, spleen lysates, and tumor lysates were determined by ELISA-based assays.

As shown in FIGS. 12A-12C, in the different tissues analyzed (tumor, serum, and spleen), animals treated with the mRNA construct encoding the human IL-12 alone (i.e., not conjugated to albumin and/or lumican) exhibited the highest IL-12 expression levels. Such results demonstrate the effectiveness of the codon-optimization strategy described above.

Example 6: Analysis of Dosage Effects in Breast Cancer Mouse Model

Further to Example 4 provided above, the anti-tumor effects of the IL-12 constructs provided herein were assessed in a breast cancer animal model. Briefly, triple-negative breast cancer (TNBC) was induced by inoculating the animals with 4T1 cells (via administration in the mammary fat pad). Once the tumors reached an optimal size (~150 $mm^3$), one of the following was injected into the primary tumors of the animals: (i) vehicle control; (ii) 5 ug of self-replicating mRNA encoding IL-12 (repRNA-IL12); (iii) 0.5 ug of self-replicating mRNA encoding IL-12 (repRNA-IL12); (iv) 0.05 ug of self-replicating mRNA encoding IL-12 (repRNA-IL12). Animals received a total of 4 doses on a weekly schedule. Then, tumor volume was assessed at various time points post-treatment.

As shown in FIG. 13, there was a dose dependent inhibition of primary tumor growth over the duration of the study in the repRNA-IL12 treated animals, resulting in an approximate 50% reduction in primary tumor size at the time the study was concluded. These results confirm that the self-replicating mRNA constructs disclosed herein (e.g., encoding IL-12) are effective in treating various cancers, including aggressive and immunotherapy resistant breast cancer.

Example 7: Analysis of the Anti-Tumor Effects of IL-12 Constructs Comprising Modified Nucleoside Triphosphates Next, to assess whether incorporation of different proportions of modified nucleoside triphosphates (modNTPs) into self-replicating mRNAs described herein had any effect on the therapeutic efficacy of the mRNA constructs, the above-described TNBC mouse model (see Example 6) was used. Once optimal tumor size was reached, the animals received weekly intratumoral injections of one of the following: (i) PBS (vehicle control); (ii) 5 ug repRNA made with 0% modNTPs; (iii) 5 ug repRNA made with 25% modNTPs;

(iv) 5 ug repRNA made with 37.5% modNTPs; and (v) 5 ug repRNA made with 50% modNTPs. Then tumor volume was assessed at various time points post-treatment.

As shown in FIG. 14, animals that were treated with the different modified repRNA IL-12 constructs behaved similarly (regardless of the amount) to those treated with the non-modified repRNA construct. This data suggest that the addition of modNTPs had limited impact on the efficacy of the repRNA constructs to control tumor growth.

Example 8: Analysis of the Abscopal Effect in Mouse Model of Melanoma

To assess the ability of repRNA encoding IL-12 (e.g., described herein) to induce systemic anti-tumor immune responses that inhibit the growth of distal untreated tumor lesions, a modified version of the mouse melanoma model described in Example 4 was used. Briefly, to induce formation of two separate primary melanoma tumors, $1\times10^6$ B16-F10 cells were subcutaneously implanted on the left hind flank of the animal, whereas at the same time the $2\times10^5$ B16-F10 cells were implanted on the right hind flank. Once optimal tumor size was reached the animals received a single intratumoral injection in only the left flank tumor of the following: (i) PBS (vehicle control); and (ii) 2.5 ug of repRNA encoding IL-12. Tumor growth was assessed by measuring tumor volumes of both the treated (left flank) and untreated (right flank) tumors at various time points post-treatment.

As shown in FIGS. 15A and 15B, repRNA encoding IL-12 delivered intratumorally was able to control the growth of both the treated tumor and the untreated distal tumors. These data suggest that local delivery of repRNA encoding IL-12 could be an effective therapy in metastatic cancer.

Example 9: Analysis of Payload Expression after Re-Dosing

To evaluate the re-dosability of the mRNA constructs described herein, the TNBC mouse model described in Example 6 was used again. Briefly, mRNA constructs encoding the reporter gene firefly luciferase were delivered by intratumoral injection, 5 ug once weekly for two doses. In some groups, animals were co-administered twice weekly with intraperitoneal injections of 10 mg/kg mouse anti-IFNAR1 antibodies (Clone MAR1-5A3) to inhibit activity of IFN-α. 24 hours after each dose of mRNA constructs, animals received 150 mg/kg D-Luciferin (the substrate that is converted by firefly luciferase into luminescent signal) by intraperitoneal injection and tumors were live imaged using an in vivo imaging system. Relative bioluminescence was quantified 10 minutes after substrate administration.

As shown in FIG. 16, some decrease in payload expression was observed upon second dose compared to the first dose. The payload expression after the second dose was rescued when the IFN-α receptor activity was inhibited by antibody blockade. These data suggest that mRNA constructs described herein can be dosed repeatedly and decreased payload expression observed upon re-dosing is, at least in part, dependent of type interferon induction and can be overcome by IFN receptor antibody blockade.

Example 10: Analysis of Ex Vivo Activity in Human PBMCS

To further demonstrate the activity of the IL-12 constructs provided herein, human TNBC cell line BT20 was transfected with repRNA encoding IL-12. About 24 hours later, supernatant was collected ("conditioned media") and IL-12 level was assessed using a human IL-12 ELISA (Invitrogen). Human peripheral blood mononuclear cells (PBMCs) were isolated from leukapheresis products from healthy human donors according to the IRB approved protocol and manufacturer's recommendations (StemCell technologies). The T cells in PBMCs were activated with IL-2 (10 ng/mL) and anti-CD3/CD28/CD2 antibody cocktail (StemCell technologies) for 2 days. Following the activation, the media was washed and cells were treated with the conditioned media (comprising known concentrations of hIL12 (1 or 10 ng/mL)) for 24 hrs. As a positive control, PBMCs were treated with indicated concentrations of recombinant hIL12 (rhIL12) (StemCell technologies) at various doses (0.01, 0.1, 1. 10, or 100 ng/mL) for the same duration. IL-12 is known to activate T and NK cells within the PBMCs, which leads to the production of Interferon-gamma (IFN-g) which can be tested from the supernatant. The supernatant was collected from the PBMCs and subjected to IFN-g ELISA (Invitrogen) to assay for its levels.

As shown in FIG. 17, the repRNA constructs described herein were able to induce potent IL-12 production, which in turn was able to induce the activation of T and NK cells, and the subsequent production of IFN-γ. The above results further confirm the activity of the IL-12 constructions described herein.

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

What is claimed is:

1. An isolated polynucleotide comprising a first nucleic acid molecule and a second nucleic acid molecule, wherein the first nucleic acid molecule encodes a beta subunit of an IL-12 protein ("IL-12β") and comprises a nucleotide sequence that has at least about 99.5% sequence identity to the sequence set forth SEQ ID NO: 65; and wherein the second nucleic acid molecule encodes an alpha subunit of an IL-12 protein ("IL-12α") and comprises a nucleotide sequence that has at least 99.5% sequence identity to the sequence set forth in SEQ ID NO: 115.

2. The isolated polynucleotide of claim 1, which further comprises: (a) a third nucleic acid molecule encoding a linker that joins the first nucleic acid molecule and the second nucleic acid molecule, (b) an additional nucleic acid molecule encoding a half-life extending moiety, (c) an additional nucleic acid molecule encoding a leader sequence, or (d) any combination of (a) to (c).

3. The isolated polynucleotide of claim 2, wherein the third nucleic acid molecule encoding the linker comprises the sequence set forth in any one of SEQ ID NOs: 90 and 168 to 170, and/or wherein the additional nucleic acid molecule encoding a leader sequence comprises the sequence set forth in any one of SEQ ID NO: 26 to 50.

4. The isolated polynucleotide of claim 1, comprising the sequence set forth in SEQ ID NO: 15.

5. The isolated polynucleotide of claim 1, which further comprises:

(a) a 5'-cap, (b) a regulatory element, (c) a 3' tailing region of linked nucleosides, or (d) any combination of (a) to (c).

6. The isolated polynucleotide of claim 1, which comprises at least one modified nucleoside.

7. The isolated polynucleotide of claim 1, which is capable of self-replicating.

8. The isolated polynucleotide of claim 7, which is a self-amplifying replicon RNA.

9. The isolated polynucleotide of claim 8, wherein the self-amplifying replicon RNA is derived from an alphavirus.

10. The isolated polynucleotide of claim 9, wherein the self-amplifying replicon RNA is derived from a Venezuela Equine Encephalitis virus, Semliki Forest virus, or Sindbis virus.

11. A vector comprising the isolated polynucleotide of claim 1.

12. A pharmaceutical composition, comprising the isolated polynucleotide of claim 1 and a pharmaceutically acceptable carrier.

13. A cell comprising the isolated polynucleotide of claim 1, wherein the cell is an in vitro or ex vivo cell.

14. A lipid nanoparticle comprising (i) the isolated polynucleotide of claim 1, and (ii) one or more types of lipids.

15. The lipid nanoparticle of claim 14, wherein the one or more types of lipid comprises N1,N3,N5-tris(3-(didodecylamino)propyl)benzene-1,3,5-tricarboxamide (TT3), 1,2-Dioleoyl-sn-glycero-3-phosphoethanolamine (DOPE), cholesterol, C14-PEG2000, or any combination thereof.

16. The lipid nanoparticle of claim 15, wherein the C14-PEG2000 comprises 1,2-dimyristoyl-rac-glycero-3-methoxypolyethylene glycol-2000 (DMG-PEG2000), 1,2-dimyristoyl-sn-glycero-3-phosphoethanolamine-N-[methoxy (poly ethylene glycol)-2000] (DMPE-PEG2000), or both.

17. The lipid nanoparticle of claim 15, wherein the C14-PEG2000 is embedded in the lipid nanoparticle.

18. The lipid nanoparticle of claim 15, wherein the C14-PEG2000 has been added after the isolated polynucleotide has been encapsulated in the lipid nanoparticle.

19. A method of making a polynucleotide comprising enzymatically or chemically synthesizing the isolated polynucleotide of claim 1.

20. A method of producing an IL-12 protein, comprising contacting a cell with the isolated polynucleotide of claim 1.

21. An isolated polynucleotide comprising (i) a first nucleic acid molecule encoding a leader sequence, (ii) a second nucleic acid molecule encoding a beta subunit of an IL-12 protein ("IL-12β"), (iii) a third nucleic acid molecule encoding a first linker, and (iv) a fourth nucleic acid molecule encoding an alpha subunit of an IL-12 protein ("IL-12α"), wherein:

a. the first nucleic acid molecule comprises the sequence set forth in SEQ ID NO: 40;

b. the second nucleic acid molecule comprises the sequence set forth in SEQ ID NO: 65;

c. the third nucleic acid molecule comprises the sequence set forth in SEQ ID NO: 90; and d. the fourth nucleic acid molecule comprises the sequence set forth in SEQ ID NO: 115.

* * * * *

SEQUENCE LISTING

<160> NUMBER OF SEQ ID NOS: 185

<210> SEQ ID NO 1
<211> LENGTH: 3393
<212> TYPE: DNA
<213> ORGANISM: Artificial Sequence
<220> FEATURE:
<223> OTHER INFORMATION: L1 Construct

<400> SEQUENCE: 1
atgcgagttc ctgctcagct gcttggtctg ttactgctgt ggttgccggg cgcacgatgt 60
gctatctggg aattaaagaa agatgtgtac gtggtggaat tggattggta cccagatgct 120
ccgggcgaaa tggttgtact cacatgcgat actccggagg aagacggtat cacttggaca 180
ttggatcagt cgagtgaggt tctcggtagt ggtaaaacac taacgatcca agtcaaagaa 240
ttcggtgatg cggggcaata tacctgtcat aaaggcggcg aagtactatc tcatagcctc 300
ctgctgttac acaagaagga agatggcata tggtccaccg acatccttaa ggatcagaaa 360
gaacccaaga acaaaacttt cttgcgttgc gaagctaaga actactccgg ccgcttcaca 420
tgctggtggt tgacaacgat cagtacggat ctaaccttct ctgttaagtc cagtcggggg 480
agttcggacc cccaaggcgt cacgtgtgga gctgccacac tttccgctga gcgcgtacgt 540
ggagataata aagagtatga atactccgtt gagtgccagg aggactccgc gtgccccgct 600
gccgaggaga gtctccccat agaggtgatg gtcgacgctg ttcacaaact gaaatatgag 660
aactatacct catccttctt tatacgtgac ataattaagc cagatccccc gaagaactta 720
caattgaaac cattgaagaa ttcacgtcaa gtcgaggtat cctgggagta tcccgacacc 780
tggtccacgc cacactcata tttctctctg accttctgtg tgcaggtaca aggcaagagc 840
aaacgagaaa aaaaggacag agttttcacg gataagacta gcgccacagt gatatgtagg 900
aaaaacgcat cgatctcagt ccgcgcgcaa gatcggtatt actcaagcag ttggtcagag 960
tgggcatcgg tgccctgctc ggggggttct ggtgggggca gtggaggagg atcaggtggc 1020
ggcagtcgca atctacccgt ggcaacacca gacccgggaa tgttcccatg tctgcaccac 1080
agtcaaaacc tcttaagggc cgtgtcaaat atgctacaga aggcgagaca gactttagaa 1140
ttctaccctt gtacaagcga ggagattgac cacgaggaca tcaccaaaga taagacgagc 1200
accgtcgagg cttgcctgcc tctagaacta acaaaaaatg aatcatgctt gaactcgagg 1260
gagaccagtt tcattactaa cggttcatgt cttgcatcga ggaagacctc attcatgatg 1320
gccctgtgcc tctcgtccat ttatgaagac ctaaagatgt accaggtaga gtttaagacc 1380
atgaacgcca agctcctcat ggatccaaaa cggcaaatat tcttagatca gaatatgctc 1440
gctgttatcg acgaactcat gcaggcgctt aacttcaact cagaaaccgt tccccaaaag 1500
tcgagtctag aagaaccgga cttttataag accaaaatta aactgtgtat actacttcac 1560
gccttcagga taagagcagt gacgattgac agggtgatgt cctacttgaa tgcatcagga 1620
tcagggggag gctcggacgc ccataagagc gaagtcgccc accgcttcaa ggatttgggt 1680
gaggaaaact tcaaagccct ggtcctgata gcgtttgccc aatatttgca gcagtgtcca 1740
ttcgaagatc acgtgaaatt ggtgaacgag gtaacagaat ttgctaagac ttgtgtggct 1800
gacgagtcgg ccgaaaactg tgataagagt cttcatacac tgtttggcga taagctatgt 1860
actgtcgcta cacttaggga gacttacggt gagatggccg actgctgcgc caagcaagag 1920
ccagaacgaa acgagtgttt tctgcaacat aaggacgaca atcccaacct gcccagattg 1980
gttcgccctg aagttgatgt tatgtgcacc gcatttcacg acaacgaaga aacctttctt 2040

```
aaaaagtatc tgtacgagat agctcgacgt caccccttact tctacgcgcc cgaacttctg   2100
tttttcgcca agcgatacaa agccgctttc acagagtgtt gccaagctgc cgacaaagcc   2160
gcttgccttc taccaaagct tgacgagctc agagatgaag ggaaagctag ttcggcaaag   2220
caacgattaa agtgtgcatc actgcaaaaa ttcggcgaac gagcctttaa agcatgggca   2280
gttgccaggt tatcccaaag gttcccgaaa gctgaattcg ctgaggtgag caagttagtc   2340
acggacctta cgaaggtaca taccgaatgc tgccacgggg acctcttgga gtgcgctgac   2400
gacagggcgg acttagctaa atacatttgc gagaatcagg actcaatcag ttctaaactt   2460
aaagaatgct gcgagaaacc gctcctggaa aaatcacatt gcatcgccga ggtggaaaac   2520
gatgagatgc cagcagattt accatctcta gccgccgact tcgtggaaag taaggatgtg   2580
tgtaaaaact atgcggaagc aaaagacgtg ttcctcggaa tgtttctata cgaatacgct   2640
agaaggcatc ctgactattc tgtcgtttta ctgcttagac tagcgaagac atatgaaacg   2700
acgttagaga aatgctgcgc ggccgctgac ccccacgaat gttacgcgaa ggtctttgat   2760
gagttcaagc ccctggttga ggagccgcaa aaccttatta aacagaattg tgagctattt   2820
gagcagttag gcgaatataa attccagaat gcacttctag tacgatacac caaaaaggtc   2880
cctcaagtga gcacccccac tcttgtggag gtatccagaa atctaggaaa ggtaggctct   2940
aaatgctgca agcatcccga agccaagaga atgccatgcg ctgaagacta ccttagcgtt   3000
gttctgaatc agttgtgtgt ccttcacgaa aagacgccgg tgagtgatcg tgtcacgaag   3060
tgctgtacag agagcctcgt caaccgtagg ccatgtttct ccgctctcga ggtggatgaa   3120
acatatgtac ctaaggaatt taatgcggaa actttcacct ttcacgcgga catctgtacc   3180
ctgagcgaga aggagaggca gataaaaaag cagacggctc ttgtagagtt ggtcaaacat   3240
aagcctaagg ccactaaaga gcagctaaag gcagtaatgg acgactttgc ggctttcgtt   3300
gagaagtgct gcaaggccga cgataaagag acctgtttcg cggaagaagg taaaaagtta   3360
gtggccgcct cccaggcggc cctgggcctg tag                                 3393
```

<210> SEQ ID NO 2
<211> LENGTH: 3393
<212> TYPE: DNA
<213> ORGANISM: Artificial Sequence
<220> FEATURE:
<223> OTHER INFORMATION: L2 Construct

<400> SEQUENCE: 2

```
atgcgcgtgc ccgcacaatt gctcggactg ctgctactgt ggctgcccgg ggctcgctgc     60
gcaatttggg aacttaagaa ggacgtatac gttgtggaac ttgactggta ccctgatgct    120
ccaggggaga tggtggtttt gacgtgtgac accccggaag aagatggaat tacatggacc    180
ttagaccaat cctccgaggt tcttggctcg ggcaaaacct tgaccattca ggtcaaggaa    240
tttggcgatg ctggccaata cacctgccat aaaggtggtg aagttttatc tcactcccta    300
ctgttgctcc ataagaaaga agacggcatt tggtcgacag acatattgaa ggatcagaag    360
gaacctaaga ataagacctt cttacgatgt gaggccaaga attattccgg acgttttacg    420
tgttggtggt tgaccacgat ctccactgac ttaaccttct cagtgaaatc ctcacgaggt    480
agttccgatc cccagggtgt gacgtgcggt gcggccacgt taagtgctga gagagtacgg    540
ggcgacaata aggaatacga gtactcagtt gaatgccaag aggactcggc ctgtcccgcg    600
gcagaggaga gtctccctat cgaagtgatg gtggatgcgg tgcacaagct caagtatgaa    660
```

```
aattacacat catctttttt catcagagac attataaagc ccgacccacc aaagaacctc    720
cagttaaagc ccttaaagaa cagtagacag gttgaagtat catgggaata cccagacacc    780
tggtccacac cccattcgta tttttccttg acgttttgcg tacaagttca gggaaagtcc    840
aaacgggaaa agaaagaccg cgtttttaca gacaaaactt ctgccactgt catctgtaga    900
aagaacgcat caattagcgt gcgagcgcaa gacagatact attcaagtag ctggagcgag    960
tgggccagtg ttccatgttc tggcggttcg ggcggagggt ccggcggtgg tagcggaggc   1020
gggagcagga acttgcccgt ggctactcca gaccctggca tgttcccctg tttacaccac   1080
tcccagaact tattacgtgc tgttagcaac atgttgcaaa aggcccgtca aaccctcgag   1140
ttttacccct gtactagtga agaaatcgac cacgaagaca taacaaaaga caagacaagc   1200
acagttgagg catgcttacc cctggagtta acaaagaacg agagctgtct gaactctcga   1260
gagacgagct tcatcaccaa tgggagttgc cttgcttctc gaaaaacgtc gttcatgatg   1320
gccctgtgcc tgtcgtctat ctatgaggat ctgaaaatgt atcaggttga attcaagaca   1380
atgaatgcca aactactcat ggatccaaaa cggcagatat tcctcgatca gaatatgctc   1440
gcagttattg acgaactaat gcaggctctg aattttaaca gcgagaccgt tcctcagaag   1500
tcaagtttgg aagaacctga cttctacaaa actaaaataa aattatgcat cttactgcat   1560
gctttcagaa ttagagctgt cactattgat cgagtgatgt catacttgaa tgcttccgga   1620
tcaggaggtg ggagcgacgc gcacaaaagc gaggtagcgc atcgctttaa agacttagga   1680
gaggaaaact ttaaggcgct ggtgctcatc gcatttgccc aatacttaca gcagtgtcct   1740
tttgaggacc acgtaaagct tgtaaacgaa gtcactgaat tcgccaagac atgtgttgct   1800
gacgaaagcg cagagaactg tgacaaaagc cttcataccc tctttggtga caaactctgc   1860
accgtggcaa ctctaagaga aacctacggg gaaatggcag actgctgcgc aaagcaggaa   1920
cccgaacgca atgagtgttt cctgcagcac aaggatgata atcccaatct gccacgactt   1980
gtacggccgg aggtagatgt tatgtgcact gcttttcatg acaacgagga aactttcctt   2040
aagaaatatc tgtatgagat cgcaaggcgg caccccttact tctacgcacc cgaactgttg   2100
tttttcgcaa agaggtataa ggccgcattt accgagtgtt gtcaggccgc tgataaagcc   2160
gcctgtcttt tgccaaaatt agatgaacta agggacgaag gcaaagcgag tagcgccaaa   2220
caaagattaa aatgtgcaag cctccaaaaa ttcggtgaaa gagcatttaa ggcgtgggct   2280
gtcgcccgac tttcacaacg cttccccaaa gctgaattcg ctgaggtttc gaagctggtt   2340
accgacctaa ctaaagtgca tacagagtgc tgtcatgggg atctcttaga gtgcgcggat   2400
gaccgggcag acctggctaa gtacatatgt gagaaccagg acagtatatc atcaaagctg   2460
aaagagtgtt gtgagaagcc actactcgag aagagtcact gtattgccga ggtggaaaat   2520
gatgagatgc cagccgatct tccttctttg gccgctgact ttgtagagag caaggatgtc   2580
tgtaagaact acgctgaggc caaggatgtc tttttgggga tgttcctcta tgagtacgcc   2640
cgacgacacc ctgactatag tgtagtactt ttgcttagac tggctaaaac atatgagacg   2700
actctcgaaa agtgctgtgc cgctgccgat ccacacgagt gctacgctaa ggtgtttgat   2760
gagtttaagc cgctggtgga ggaaccccag aacctgatca agcagaactg tgaactattc   2820
gagcaactag gggagtacaa attccagaac gcacttttag tgcggtacac caaaaaagtg   2880
ccacaggtca gtacaccaac attagtggaa gtatccagga acctgggcaa agtgggcagc   2940
aaatgctgca aacatccgga ggctaagcgg atgccctgtg cagaggacta cctgtccgtg   3000
gtgcttaacc agctgtgtgt gcttcacgag aaaacgcctg tgtccgaccg ggtgaccaag   3060
```

```
tgctgtacgg agtcactggt aaatcgacga ccgtgttttt cagcactaga agttgatgaa   3120

acttatgtac cgaaagagtt taacgcagag acctttacat tccacgccga catctgcacg   3180

ctgtccgaga aggaaagaca gattaaaaag cagactgccc tagtcgagct tgtcaaacac   3240

aaaccgaagg caaccaagga acagttaaaa gcagtgatgg atgattttgc tgcgttcgtc   3300

gaaaaatgtt gcaaagcgga cgacaaggag acttgcttcg cagaggaagg gaagaaattg   3360

gttgcggcgt cccaagcggc cttagggcta tag                                3393
```

<210> SEQ ID NO 3
<211> LENGTH: 3393
<212> TYPE: DNA
<213> ORGANISM: Artificial Sequence
<220> FEATURE:
<223> OTHER INFORMATION: L3 Construct

<400> SEQUENCE: 3

```
atgagagttc ctgctcaact actagggctg ctgttgttgt ggttgcccgg cgcgcgatgc     60

gcaatatggg agctcaagaa ggacgtttat gtcgttgagc tggattggta ccctgatgcc    120

ccgggcgaaa tggttgtgct tacgtgcgat accccccgagg aggatggcat aacatggacg   180

ttagatcagt cttccgaggt ccttggttcc ggtaagactc ttactatcca ggtgaaggag    240

ttcggcgatg ccggccagta cacttgccat aaaggcggtg aagttctaag ccactctcta    300

ctgcttttgc acaagaagga agatggaata tggtccaccg acatcttgaa ggaccagaaa    360

gaaccaaaaa ataagacatt tttgaggtgt gaggcaaaaa attattcggg acgcttcacc    420

tgctggtggt tgacgacgat ttcaaccgac ctcaccttct cagtaaagag ttcgagaggt    480

agttccgatc cccaaggtgt gacatgtggc gctgcgactc taagcgctga acgcgtaaga    540

ggtgataaca aagagtacga atacagtgtg gaatgccaag aagatagcgc gtgtccagcc    600

gcagaagaat ctttaccaat agaggttatg gttgatgccg ttcacaaatt gaaatatgag    660

aattacacct caagcttttt cattcgagac ataataaagc ccgaccctcc taagaatctt    720

cagttaaaac cgctgaagaa cagtagacaa gttgaggtta gctgggaata tcctgatacc    780

tggtcaacgc cgcactcgta tttctccctg actttctgtg ttcaggttca aggaaaatct    840

aaaagggaga agaaagaccg tgttttcacc gacaagacat ctgccacagt catatgtagg    900

aagaacgctt caatcagcgt gcgagcgcag gaccgatact acagctctag ttggtccgaa    960

tgggccagcg taccatgctc tggcggttcc ggcgggggct cggggggcgg gagcggtgga   1020

ggcagcagga atcttcctgt cgcgacccct gatcccggca tgtttccttg cctgcaccac   1080

agtcagaact tattacgcgc cgtttccaat atgttacaga aggccagaca gacattagag   1140

ttttatcctt gcacatcgga ggagatcgac catgaagata tcacaaaaga taaaacatcc   1200

accgttgagg cctgcctgcc acttgaactt actaaaaacg agagctgcct gaatagccgg   1260

gaaacttctt tcatcactaa tggatcgtgt ctagcaagcc gaaaaaccag cttcatgatg   1320

gctttgtgcc tctcgtccat ctatgaagac ctgaaaatgt atcaagtaga atttaaaacg   1380

atgaatgcca aactgcttat ggatcccaaa cgccagatat ttctagacca gaatatgctg   1440

gccgtcattg atgagctaat gcaggctctc aattttaata gcgaaacagt gccccaaaaa   1500

agctctttgg aagagccgga tttttacaaa accaagatta agctatgtat cctgctgcat   1560

gctttcagaa ttcgagctgt tacaattgat cgggttatga gctacttaaa cgcctcgggt   1620

agtggcgggg ggagcgacgc ccacaagtct gaagtggcac accggttcaa ggacctcggg   1680
```

```
gaggagaatt ttaaagccct cgtgctgatc gctttcgcgc agtacttgca gcagtgccct   1740
tttgaggacc atgtcaaatt agtaaacgaa gtgacggaat tcgcaaagac ttgcgtagcg   1800
gatgagtcag cagagaattg cgacaagtcg ctacacactc tgttcgggga taagttgtgc   1860
acagttgcta ccttacgaga gacctatgga gagatggctg actgctgcgc caaacaagag   1920
cctgaaagaa acgagtgctt cttacaacac aaagacgata acccgaattt gccaaggctt   1980
gtaagacccg aagtagatgt tatgtgcaca gcttttcacg acaacgagga gacgttcctt   2040
aagaaatatc tgtatgaaat agcccgtcgg cacccctatt tttatgctcc cgaactattg   2100
ttcttcgcca aacgatacaa ggctgcgttc actgagtgct gtcaggctgc agacaaagca   2160
gcctgcttgc ttcccaaatt ggacgaacta cgggacgaag gtaaggcgag ctccgcaaaa   2220
cagcggttga aatgcgcgtc actacagaag tttggggaaa gagcgttcaa agcttgggct   2280
gtggcacgat tgagccaacg cttccccaaa gcagagtttg cggaagtttc gaaactcgtg   2340
acagacttaa caaaggttca caccgagtgc tgtcacggcg atctgctcga atgcgctgat   2400
gaccgcgctg acttggctaa atacatttgt gagaaccagg actctatatc gagcaaactc   2460
aaggaatgct gcgaaaagcc cctgcttgag aagtcccact gcatcgctga ggtagagaat   2520
gatgagatgc ctgcggatct tccgagttta gcagctgatt tcgtcgagag caaagatgtg   2580
tgcaaaaatt atgccgaagc aaaagacgta tttcttggga tgttcttata cgagtatgca   2640
cggcgccacc cagattactc cgtagtgcta ctgttaagat tggcgaagac ctatgaaacc   2700
acattggaaa agtgctgcgc cgccgccgac ccccacgagt gttacgcgaa ggtgttcgat   2760
gaatttaaac cgcttgttga ggagccgcaa aacctaataa agcaaaactg tgagctcttt   2820
gagcaactag gtgaatacaa gtttcagaat gcactcctag ttcggtacac caaaaaagta   2880
cctcaggtat ctacgccaac gttagtcgag gtctcgcgga atttgggtaa agtaggttcc   2940
aagtgttgca aacacccgga agctaaacgt atgccgtgtg ctgaggacta tctcagcgtt   3000
gtgttaaacc aactttgcgt actccacgag aaaacacctg tctcagatcg ggtaaccaaa   3060
tgctgcacgg agtcgctagt aaatcgtcgc ccatgctttt ctgcgttaga ggtggacgaa   3120
acttatgtac cgaaagaatt taacgcggaa acctttacat tccatgcaga tatctgtaca   3180
ctgtccgaga aagagagaca gattaagaaa cagacggcgc tggtggagct tgtgaagcac   3240
aagcctaaag ctacgaagga gcaactgaag gcagtcatgg atgactttgc ggcgtttgtg   3300
gagaagtgct gtaaagcgga cgataaggaa acatgcttcg cagaagaagg aaagaagctg   3360
gtcgccgcta gccaagcggc tctgggcctg tag                                3393
```

<210> SEQ ID NO 4
<211> LENGTH: 3393
<212> TYPE: DNA
<213> ORGANISM: Artificial Sequence
<220> FEATURE:
<223> OTHER INFORMATION: M1 Construct

<400> SEQUENCE: 4

```
atgagagtcc ccgcccagct gctggggctt cttttgcttt ggcttcctgg cgcaagatgc     60
gctatctggg agctgaaaaa ggacgtgtac gtggtggaac ttgactggta ccccgacgcc    120
cccggcgaga tggtggtact gacctgcgac actcccgagg aagacggcat tacctggacc    180
ttggaccaga gcagcgaggt tctgggctcc ggaaaaacct tgacaatcca agtgaaagaa    240
ttcggcgacg ctggccagta cacctgccac aagggcggcg aggtgctgtc ccacagcctg    300
ctgctgctgc ataagaaaga agacgggatt tggagcaccg atatactgaa ggatcagaag    360
```

```
gagcccaaga acaagacctt cctgaggtgc gaggccaaaa attacagcgg cagattcacc    420
tgctggtggc tgaccaccat tagcacagac ctgactttca gcgtaaagtc ttcaaggggc    480
agctcagacc cccagggagt aacttgcgga gcggcaacgt tgtctgccga gcgggtcaga    540
ggcgacaata aggagtacga gtattcagta gagtgtcagg aagatagcgc ctgtcccgcc    600
gcggaggaga gcctccccat cgaggtgatg gtggacgccg tgcacaagtt aaagtacgag    660
aattacacca gctcattttt tatcagagac attatcaagc cggaccccccc gaagaactta    720
cagcttaaac ccctaaagaa cagcaggcag gttgaggtca gctgggaata tcctgacacc    780
tggtcaaccc cccacagcta cttctccctt actttctgtg tgcaagtgca gggcaagagc    840
aagagagaaa agaaggaccg ggtgtttacc gacaagacta gcgccaccgt gatttgcaga    900
aagaacgcca gcattagtgt gagagcccag gacaggtatt actccagctc atggtctgag    960
tgggctagtg tgccttgctc tggcggcagc ggcggcggga gcggcggagg ctccgggggga   1020
ggtagccgga atctgcctgt cgccactcca gaccccggca tgttcccatg tctgcatcat   1080
tctcagaacc tgctgagggc cgtatccaat atgctgcaga aagccagaca gaccttagag   1140
ttctatccct gtacaagcga ggagatagat cacgaggata ttacgaagga caaaacttct   1200
actgttgagg cgtgtcttcc attagagctg accaagaacg aaagctgtct gaatagcaga   1260
gagacttcat ttatcaccaa tgggagttgc ttggctagca gaaagaccag cttcatgatg   1320
gccctttgct tgtcttcgat atacgaagat cttaagatgt atcaagtgga atttaagacg   1380
atgaacgcca agctgcttat ggatcccaag cgccaaatct tcctggatca gaacatgttg   1440
gccgtgattg acgagctgat gcaagccctg aatttcaact ccgagaccgt gcctcagaag   1500
agcagcctcg aggagcccga cttctacaaa acaaagatca aactctgcat ccttctgcac   1560
gccttcagaa ttagagccgt gaccatcgac agagttatga gctacctgaa tgccagcggc   1620
agcggcggcg gatccgatgc ccataaatct gaggtggccc atagattcaa ggatctgggc   1680
gaagaaaact tcaaagcctt ggtcttgatc gcctttgccc agtacctgca gcagtgcccc   1740
tttgaggacc acgtgaagct ggtgaatgaa gtgaccgagt ttgccaagac gtgcgtggct   1800
gatgagagcg ccgaaaactg cgacaaaagc ctgcacaccc tgtttggcga caagctgtgc   1860
accgtagcca ccctgagaga aacttacggc gagatggctg actgctgcgc caagcaggag   1920
cccgagagaa acgagtgctt tctgcagcac aaggacgaca atcccaacct gcccagactg   1980
gtgagacccg aagtggatgt tatgtgcacc gctttccacg acaatgaaga gacatttctc   2040
aagaagtact tgtacgagat tgcaagaaga cacccttact tttacgcccc cgaattactg   2100
ttcttcgcta agaggtataa ggcagccttc actgaatgct gccaggctgc cgacaaagca   2160
gcttgcctgc tgccaaagct ggatgaactg cgagacgaag gaaaggcgtc ctccgccaag   2220
cagcgtttga agtgcgccag ccttcagaag tttggcgagc gggccttcaa ggcatgggcc   2280
gtggctcgac ttagccagcg ttttcccaag gctgaatttg cagaggtgag taaactggtt   2340
accgatctga caaaggtgca caccgagtgc tgtcacggtg acctcttaga gtgcgccgac   2400
gacagagccg acctcgccaa gtacatttgt gaaaaccaag actcaatctc ttcaaagtta   2460
aaggagtgct gcgaaaagcc cctgcttgaa aagagccact gcattgccga agtcgagaat   2520
gatgagatgc ctgcagactt gcccagcttg gcagccgact tcgttgagtc taaggacgtg   2580
tgcaagaatt acgccgaggc aaaagacgtg ttcctgggca tgttccttta tgagtacgct   2640
agaagacatc ccgactacag cgtggtcctt ctccttaggc tcgctaagac ttacgagacg   2700
```

```
acgttggaga agtgttgtgc cgctgcggac ccccacgagt gctatgccaa agtgttcgat   2760

gagtttaaac ccctggtgga ggaacctcag aaccttatca agcagaattg tgagttgttc   2820

gaacagctag gcgagtacaa gttccagaat gccctgctgg tgagatacac aaaaaaggtg   2880

ccccaggtgt caaccccgac cttagtggaa gtgtccagaa acctgggcaa ggtgggcagc   2940

aagtgctgca agcaccccga agctaagaga atgccgtgcg cggaggatta cctgagcgtg   3000

gtgctcaacc agctgtgtgt gcttcacgag aaaacacccg tgagcgacag ggtgacaaaa   3060

tgttgcacag aaagccttgt gaaccggaga ccttgtttca gcgccctgga ggttgacgag   3120

acctatgttc ctaaggagtt caacgctgag actttcacat ttcacgctga tatatgtacc   3180

ctgagcgaga aagaaagaca gatcaagaag cagaccgccc tggtcgagct ggtgaaacac   3240

aagcctaagg ccacgaagga gcagctgaag gccgtcatgg acgacttcgc agccttcgtc   3300

gagaaatgct gcaaagccga cgacaaggaa acctgcttcg ccgaagaggg aaagaagctg   3360

gtggccgcct cccaggccgc ccttgggctc tag                                3393
```

<210> SEQ ID NO 5
<211> LENGTH: 3393
<212> TYPE: DNA
<213> ORGANISM: Artificial Sequence
<220> FEATURE:
<223> OTHER INFORMATION: M2 Construct

<400> SEQUENCE: 5

```
atgagagtcc ccgcccagct gctagggctg ctgctgctgt ggttacccgg cgcccggtgt     60

gcaatttggg agttgaagaa ggacgtgtac gtggtggagc tggactggta cccggatgct    120

cccggcgaga tggtggtact cacctgcgac acacctgagg aagacggcat cacctggacc    180

ctcgatcaga gcagcgaggt tctgggaagc ggcaaaaccc tgaccatcca agtgaaagag    240

tttggcgacg ccggtcagta cacctgccac aagggaggcg aggtcctgtc tcactctctg    300

ctgctgctcc ataagaagga ggacggtatt tggagcactg acatcttgaa ggatcaaaaa    360

gagccaaaga ataaaacgtt cctgaggtgc gaagctaaga attactccgg gcgttttacg    420

tgctggtggc tgaccacgat cagcaccgat ctgaccttca gcgtgaagag cagccggggc    480

agcagcgacc cccaaggcgt gacttgcggc gctgcgaccc tgagcgctga gcgtgtgcgc    540

ggcgacaaca aggagtatga gtattcagtg gagtgtcagg aggactccgc ctgtcccgcg    600

gccgaagaga gtctgcctat tgaggtgatg gtggacgccg tgcacaagct gaagtacgag    660

aactacacat cgtcattctt tatccgcgac atcataaagc ccgacccccc caagaacctg    720

cagctgaagc ctctcaagaa ttcccggcaa gtggaggtga gctgggagta ccctgatacc    780

tggtctaccc ctcacagcta ctttagcctg accttctgcg tccaggtgca aggaaagtcg    840

aagcgcgaga agaaagatag agtcttcacc gataaaacca gtgccaccgt gatttgccgc    900

aaaaacgcct ccatcagcgt gcgggctcag gatagatact actctagcag ctggagcgaa    960

tgggcctcag ttccttgcag cggcggcagc ggtggaggaa gcggcggtgg cagtgggggc   1020

gggagcagaa atctgcccgt cgccactcca gatcctggca tgttcccgtg cctgcatcac   1080

agccaaaacc tgctgcgggc ggtgtctaac atgctgcaga aggctaggca gaccttggaa   1140

ttctatccct gcacaagcga ggaaatagac catgaggaca tcaccaagga taagaccagc   1200

acggtcgaag cttgcctgcc actggaactg acaaaaaacg agagttgcct gaactcccgc   1260

gagacatcct tcatcacaaa cggcagctgc ctggctagca ggaagaccag cttcatgatg   1320

gccctgtgcc tgtcttccat ctacgaggac ctgaaaatgt accaagtgga gttcaagact   1380
```

atgaacgcca agctgctaat ggatcccaag cgacagatct ttctagacca gaacatgctg 1440
gccgtcattg acgagctgat gcaggcactc aattttaact cagagaccgt gccacagaag 1500
tccagcctgg aggagcctga cttctataag accaagatta agctgtgcat cctgctgcat 1560
gccttccgaa taagagccgt gaccattgac cgagtgatgt catacttgaa cgcaagcggc 1620
tcaggcggag ggagtgacgc ccacaagtct gaagtggctc accggtttaa ggaccttggc 1680
gaggagaact ttaaagccct ggtgctgatt gcctttgccc agtatttaca acaatgccct 1740
ttcgaagacc acgtgaagct cgtcaatgag gtcaccgagt tcgctaagac ctgcgtagcc 1800
gacgaaagtg ccgagaactg cgacaagagc ctgcacaccc tgttcgggga caaactctgt 1860
accgtggcca ccctacggga gacatatggg gagatggccg actgctgcgc aaaacaggag 1920
cccgagagaa atgagtgctt cctgcagcac aaggatgaca accccaatct gcccagactg 1980
gtgcgccccg aggtagacgt tatgtgcacc gccttccatg acaatgagga gacgttcctg 2040
aagaaatacc tgtacgagat cgcaagacgt cacccctatt tctatgcacc tgagctgctt 2100
ttcttcgcca agagatataa ggccgccttc accgaatgct gccaggcagc cgataaggca 2160
gcttgcctcc tgccaaagct ggacgagctg agagatgagg gcaaggcctc cagcgcgaag 2220
cagagactca aatgcgcaag ccttcagaag ttcggagaac gcgcctttaa agcctgggcc 2280
gtcgccagac tgagccagcg cttccctaaa gccgaattcg cagaagtgag caagctggta 2340
acggacctga caaaggtgca tactgagtgc tgccatggcg atctgctgga gtgcgctgat 2400
gacagagcag atttggcgaa atatatttgc gaaaatcagg atagcatcag ctctaagctc 2460
aaggagtgtt gtgagaagcc cctgctggaa aaaagccact gcattgcaga ggttgagaac 2520
gatgaaatgc cagccgacct tccatcattg gccgccgatt tcgtggagtc gaaggatgtg 2580
tgtaagaact acgccgaggc caaggacgtg ttcctgggca tgttcctgta cgagtatgct 2640
agaagacatc ccgattacag tgtggtgctg ctattgagac tggccaagac ctacgaaacc 2700
accctggaga aatgttgcgc cgcggcagat cctcacgaat gttacgccaa agtgtttgac 2760
gaattcaagc cactggtaga ggagccccag aacttaataa agcagaattg cgagctattc 2820
gagcagttgg gcgagtacaa attccagaac gcccttctgg tgaggtatac caaaaaggtg 2880
ccccaggtgt ctacccctac cctggtggag gtcagccgaa atctgggaaa ggtcggatcc 2940
aagtgctgca agcacccgga ggccaagagg atgccttgcg ctgaggacta tctcagtgtc 3000
gtcctgaatc agctatgcgt gttgcacgag aaaaccccag tgagtgaccg cgtgactaaa 3060
tgctgcaccg aaagcttggt gaatcggagg ccctgtttct ctgcactgga agttgacgag 3120
acttacgtcc cgaaggaatt caacgccgag acattcacct tccatgctga catatgtact 3180
ctgtcagaaa aggagcgtca gatcaagaag cagacagccc tggtggaact ggttaagcat 3240
aagcctaaag cgaccaaaga gcagctgaaa gccgtgatgg acgattttgc cgccttcgtg 3300
gagaaatgtt gtaaggcaga cgacaaagag acatgtttcg ccgaagaggg gaagaaactg 3360
gtggccgcaa gccaggccgc tctgggtctg tag 3393

<210> SEQ ID NO 6
<211> LENGTH: 3393
<212> TYPE: DNA
<213> ORGANISM: Artificial Sequence
<220> FEATURE:
<223> OTHER INFORMATION: M3 Construct

<400> SEQUENCE: 6

```
atgagagtcc cagctcagct gctgggccta ctgctgctat ggctccccgg cgcgcggtgc     60
gccatttggg agctcaagaa ggacgtgtac gtggtggaac ttgactggta cccggacgcg    120
cccggggaaa tggtggtgct aacctgtgac acccccgaag aggacggcat cacctggacc    180
ctggaccaga gcagtgaggt gctaggtagt ggcaaaacgt taaccatcca ggtcaaggag    240
ttcggcgacg ccgggcaata cacctgtcac aaggggggg aggtactatc ccactccctg    300
ctgctcctgc acaagaaaga ggacgggatc tggagcaccg acattctgaa agaccaaaag    360
gagcccaaaa acaaaacctt ccttagatgt gaagccaaga actacagcgg ccgtttcacc    420
tgctggtggc tgaccaccat atctacggac cttacctttt cggtgaagag cagcaggggg    480
agttccgacc cgcaaggcgt aacttgcgga gccgcaaccc tgagcgccga gagagtgcgc    540
ggcgacaaca aggagtacga gtatagcgtg gagtgccaag aggacagcgc atgcccagcc    600
gccgaagaga gcctgccaat agaggtcatg gtagacgccg tgcacaagct aaaatatgaa    660
aactacacca gcagcttttt catcagggat atcatcaaac ccgacccacc aaaaaactta    720
cagcttaagc ctctgaaaaa cagcagacaa gttgaggtca gctgggagta ccccgacact    780
tggagcacac cccactccta tttcagtttg acattctgcg tgcaggtgca gggtaaaagc    840
aagagagaaa agaaggacag agtgttcaca gataagacct cagccacagt gatctgccgt    900
aagaatgcca gcatcagcgt ccgggctcag gacaggtact actcttcctc atggagcgag    960
tgggcctctg tcccctgcag cggcggcagc ggcggtggca gcggcggcgg ttctggcggc   1020
ggttcaagaa acctcccagt cgctaccccc gatcccggaa tgttcccctg cctgcaccac   1080
tcccagaatc tgctccgagc cgttagcaac atgctgcaaa aggcccggca gaccctggag   1140
ttctacccat gcacctcgga agaaatcgat cacgaggaca tcaccaagga caagactagc   1200
accgtcgagg cctgcctgcc gctggaacta accaagaatg aaagctgcct caactcgcgg   1260
gagacctctt tcataaccaa cggctcatgc ctggccagcc ggaaaactag ctttatgatg   1320
gctctgtgct taagcagcat ctacgaggat ctgaagatgt accaggtaga gttcaagacc   1380
atgaatgcca agctgctgat ggaccccaag agacaaatct tcctggacca gaacatgctg   1440
gccgtaattg atgaactgat gcaggccctg aatttcaaca gcgagaccgt accccagaaa   1500
agctcactgg aggagcccga cttttataag acgaaaataa agttgtgcat ccttcttcac   1560
gctttccgga ttagagccgt gaccatcgat agagtgatgt catacctgaa cgcatcgggg   1620
agtggcggtg gcagcgatgc ccacaaaagc gaagtcgcac acagattcaa ggacttgggt   1680
gaggagaact ttaaagccct ggtgctgatc gccttcgcgc agtatctcca gcagtgcccc   1740
ttcgaagatc atgtgaaact ggtgaacgag gtaaccgagt tcgcgaagac atgcgttgct   1800
gatgagagcg ccgaaaattg cgacaaaagc ctgcatactc tgttcgggga caagctgtgc   1860
acggtcgcaa ccctgagaga aacctacggc gagatggcag actgctgcgc caagcaggag   1920
cctgagagga acgagtgttt tctgcagcac aaggacgata atcctaacct tcctcgtcta   1980
gtgagacccg aagtggacgt tatgtgtacc gcctttcacg acaatgagga aacattcctg   2040
aaaaagtacc tgtacgagat cgccagacgg cacccatatt tctacgcccc cgagctgctc   2100
ttcttcgcaa agaggtacaa ggctgccttc accgagtgct gccaggcggc cgacaaggcg   2160
gcgtgtttgc tgcctaagct ggacgaacta cgtgacgaag gaaaagctag cagcgccaag   2220
cagagactta agtgcgcgtc cttacagaag tttggcgaaa gagcgtttaa ggcctgggcc   2280
gtggcaaggc tgtctcaaag attccccaag gcggagttcg ccgaggtgtc aaaactggtg   2340
accgacttaa ccaaggtgca caccgaatgc tgccacggcg atctgctcga gtgcgccgac   2400
```

gacagagccg atctggcaaa atacatctgc gaaaaccagg atagcatcag ctccaaactg 2460
aaggagtgct gtgaaaaacc actgcttgaa aaatcgcatt gtatagcgga ggtggagaat 2520
gacgagatgc ccgccgacct gccaagcctg gccgccgatt tcgttgaatc caaggacgtt 2580
tgcaagaact atgcagaagc gaaggacgtg ttcttaggaa tgttcctata cgagtacgcg 2640
agaagacatc ccgactacag cgtggttctg ctgttgagat tagccaagac gtatgagaca 2700
accctcgaaa agtgctgcgc cgccgccgac ccccacgagt gttacgcaaa ggtgttcgat 2760
gagtttaaac cgctggttga ggaaccgcaa aacctgatca agcagaactg cgagctgttc 2820
gagcagctgg gtgaatacaa gtttcagaat gcactgttgg tgcgatatac caagaaggtg 2880
cctcaggtga gcacccctac ccttgttgag gtgtcccgca atctgggtaa ggttgggagc 2940
aagtgttgca aacaccccga ggccaagaga atgccctgcg cggaagatta tctcagtgtc 3000
gtgcttaatc agttatgtgt cctgcatgag aagacccccg tgagcgacag agtgaccaag 3060
tgctgtaccg aatctctcgt gaacagacgc ccgtgcttca gcgccttgga ggtagacgag 3120
acctacgtgc ccaaggagtt caacgcagag accttcacct ttcacgccga tatctgcacc 3180
ctgtccgaga aggagagaca aatcaagaaa caaacggccc tcgtggagct ggtcaagcac 3240
aaacccaagg ccacaaaaga gcagctgaag gccgtgatgg acgacttcgc agcctttgtg 3300
gagaaatgct gcaaggctga cgacaaggag acatgcttcg ccgaggaagg caagaagttg 3360
gtggccgcca gccaggcggc cctgggcctg tag 3393

<210> SEQ ID NO 7
<211> LENGTH: 3393
<212> TYPE: DNA
<213> ORGANISM: Artificial Sequence
<220> FEATURE:
<223> OTHER INFORMATION: H1 Construct

<400> SEQUENCE: 7
atgagagtgc ccgcccagtt gcttggcctg ctgctcctat ggcttcccgg cgccagatgc 60
gccatctggg agctgaagaa agacgtgtac gtggtggagc tggactggta ccccgacgcc 120
cccggtgaaa tggtggttct gacctgcgac acaccagagg aggacggcat cacctggacc 180
ctggaccagt ccagcgaggt cctgggctct ggcaagaccc tgaccatcca ggttaaggaa 240
tttggcgacg ccggccagta cacctgccac aaaggcggcg aggtcctttc gcacagtctg 300
ctgctgctgc ataaaaagga ggacggcatt tggagcaccg acattctgaa ggatcagaaa 360
gagcccaaga acaagacctt tctgagatgt gaggccaaaa actactctgg acgcttcacc 420
tgttggtggc tgaccaccat cagcacagac ctgaccttct cggtgaagtc tagtaggggc 480
agcagtgacc cccagggcgt aacatgcggc gccgctaccc tgagcgccga gagagtgaga 540
ggcgataaca aggagtacga gtactccgtg gagtgccaag aggactcagc ctgccccgcc 600
gccgaggagt cgctgcccat cgaggtgatg gtggatgcag tgcacaagct gaagtacgag 660
aactacacca gtagcttttt catcagagat atcattaaac ccgaccctcc caagaacctg 720
cagctgaagc ccttaaagaa cagccggcag gtggaagtgt catgggagta cccagacacc 780
tggagcactc cgcacagcta cttcagcctg accttctgcg ttcaggtgca gggaaaaagc 840
aagagagaga agaaagacag agtgttcacc gacaagacca gcgcaaccgt gatctgtaga 900
aagaacgcct cgatcagcgt gagagcccag gacagatact acagcagcag ctggagcgag 960
tgggccagtg taccttgcag cggtggcagc ggcggcggct ccggcggcgg gagtggcggc 1020

```
ggcagcagaa atctgcccgt agccaccccc gaccccggca tgtttccctg tctgcaccat   1080
tctcaaaacc tgttacgggc cgtgagcaac atgctgcaga aggccagaca gacactggag   1140
ttttacccct gtacctcaga ggagatcgat catgaggaca ttactaagga caagaccagc   1200
accgtggaag cctgcctgcc cctagagcta accaagaacg agagctgcct gaactctaga   1260
gagacaagct tcatcacgaa cggctcatgc ctggccagta ggaaaaccag cttcatgatg   1320
gctctgtgcc tgagctccat atatgaggac cttaagatgt accaggtgga gttcaaaacc   1380
atgaacgcca agctgctgat ggacccaaag agacagatct tccttgacca gaacatgctg   1440
gccgttatcg atgagctgat gcaggccctg aacttcaaca gcgagaccgt gccccagaag   1500
agcagcctgg aggaacccga cttctacaaa accaagatca agctgtgcat tctgctgcat   1560
gccttccgca ttagagccgt gaccatcgat agggtgatga gctacctgaa cgccagcggc   1620
tctggcggcg gcagtgacgc ccacaagtcc gaggtcgccc acagattcaa ggatttgggc   1680
gaggagaact tcaaggccct ggtgctgatc gccttcgccc agtacttgca gcagtgtccc   1740
ttcgaggacc atgtgaagct ggtgaacgag gtgaccgagt tcgccaagac ctgtgtggcc   1800
gacgagagcg ccgagaactg cgataagtct ctgcacaccc tttttggcga caaactgtgc   1860
accgtggcca ccctgagaga gacctacggc gagatggccg actgctgtgc gaagcaggag   1920
cccgagcgca atgagtgttt cctgcagcat aaggacgaca accccaacct gcccagactg   1980
gtgagacccg aggtggacgt gatgtgcacc gccttccacg acaacgagga gacctttctg   2040
aaaaaatacc tgtacgagat cgcaagacgc cacccctact tctacgcccc cgagctgctg   2100
ttcttcgcca agcgctacaa ggctgccttc accgagtgct gccaggccgc cgataaggcc   2160
gcgtgcttac tgccaaagct ggacgagctg agagacgagg ggaaagcctc tagcgccaaa   2220
cagagattga agtgtgccag cctgcagaaa ttcggtgaga gagccttcaa ggcctgggcc   2280
gtggccagat tatcacagcg gttccccaag gctgaattcg ccgaggtgag caaacttgtc   2340
accgatctga caaaagtgca caccgagtgc tgccatggcg acctgctgga gtgcgccgac   2400
gaccgggccg acctggccaa gtacatctgc gagaaccagg acagcatctc cagcaagctg   2460
aaggagtgct gcgagaagcc cctgctggag aagagccact gcatcgccga ggtggagaat   2520
gacgaaatgc ccgccgacct gcccagcctg gccgccgact tcgtggaaag caaggacgtg   2580
tgcaaaaatt acgccgaagc caaggatgtg ttcttgggca tgttcttgta cgagtacgcc   2640
agacgccacc ccgactacag cgtggtgctg ctgctgcggc tggccaagac ctacgagacc   2700
accctggaga agtgctgtgc tgccgccgac cccccacgagt gctacgccaa ggtatttgac   2760
gagttcaagc ccctggtgga ggagcctcag aacctgatta agcagaactg tgagctgttc   2820
gagcagctgg gcgagtacaa gttccagaac gccctcctgg tgagatacac caaaaaggtg   2880
cctcaggtaa gcactcccac cctggtggag gtgagcagga acctcggcaa ggtgggcagc   2940
aaatgctgca agcacccaga ggccaaaaga atgccctgcg cagaagacta cctcagcgtg   3000
gtcctgaacc agctgtgcgt gctgcacgaa aagacccctg tgagcgatag agtgacaaag   3060
tgctgcaccg agagcctggt gaacagaaga ccctgtttta gcgccctgga ggtggacgag   3120
acctacgtgc ccaaggagtt caacgccgag acgttcactt tccacgcgga catctgcacc   3180
ctgagcgaga aggagagaca aatcaagaag cagaccgccc tagtcgagct ggtaaaacac   3240
aagcccaagg ccaccaagga gcagctgaag gccgtgatgg acgactttgc agccttcgtg   3300
gagaagtgct gcaaggctga cgacaaggag acctgcttcg ccgaggaggg caagaagctc   3360
gtagccgcca gccaggccgc tctcggcctt tag                                3393
```

<210> SEQ ID NO 8
<211> LENGTH: 3393
<212> TYPE: DNA
<213> ORGANISM: Artificial Sequence
<220> FEATURE:
<223> OTHER INFORMATION: H2 Construct

<400> SEQUENCE: 8
atgagagtgc ccgcccagct gctgggcctg ctgctcttat ggctgcccgg cgcccgctgt 60
gctatttggg agctgaagaa ggacgtgtac gtggtggagc tggattggta tccagacgcc 120
cccggcgaga tggtcgtgtt gacctgcgat actcccgagg aggacggaat cacctggaca 180
cttgaccaga gcagcgaggt gctgggcagc gggaagaccc tgactatcca ggtgaaggag 240
tttggcgatg ccggacagta cacctgccac aagggcggcg aggtgttatc tcatagcctg 300
ctgctgctgc acaaaaagga ggacgggatc tggagcactg acatcctgaa ggaccagaag 360
gagcccaaaa acaagacctt cctgcgttgc gaggccaaga actacagcgg gagattcacc 420
tgttggtggc tgaccactat cagcactgac ctaaccttca gcgtgaagag cagccgggga 480
agctctgacc cccagggggt gacatgcggc gccgccacac tgagcgccga gagggtgaga 540
ggggacaata aggaatacga gtatagcgtg gagtgtcagg aagattccgc ctgccccgcc 600
gccgaggaga gcctgcctat cgaggtcatg gtggacgccg tccataaact gaagtacgaa 660
aactatactt caagcttctt catcagagac atcataaagc ccgacccccc caagaacctg 720
cagctaaagc ccctgaagaa cagcagacag gtcgaagtga gctgggagta ccccgatacc 780
tggagcaccc cgcacagcta cttcagcctg accttttgcg tccaggtgca gggcaagagc 840
aagagagaga agaaggacag ggtgttcact gacaagacaa gcgccactgt tatctgcaga 900
aagaacgcca gtatcagcgt gcgcgcccaa gacaggtatt actccagcag ctggtctgaa 960
tgggccagcg tgccttgcag cgggggggagc ggcggtggca gcgggggcgg cagcggcggg 1020
ggcagcagaa acctgcccgt ggccacaccc gatcccggca tgttcccctg tctgcaccac 1080
agccaaaacc tgctgcgtgc cgtgagcaac atgctgcaga aggcgcggca gaccctggag 1140
ttctatccct gcaccagtga ggagattgac cacgaggata tcaccaaaga caagaccagc 1200
accgtggagg cctgcctccc cctggagctg accaagaacg agtcctgctt gaattcaaga 1260
gagaccagct tcatcaccaa cggctcctgc ttagccagca gaaagactag cttcatgatg 1320
gccttgtgct tgtctagcat ctatgaggat ctgaagatgt accaggtcga gttcaagact 1380
atgaacgcca agctgctgat ggaccccaaa agacagatct tcctggacca gaacatgctg 1440
gccgtcatcg acgagctgat gcaggccctt aatttcaata gcgagacagt gccccagaaa 1500
tcttctctgg aggagcccga tttttacaaa accaagatca aactatgcat cctgttgcac 1560
gccttccgga tccgcgccgt gaccatcgac agagtaatgt cctacctgaa cgccagcggc 1620
agcggcggcg gtagcgacgc ccacaagagc gaagtggccc atagattcaa ggacctgggc 1680
gaggagaact tcaaggccct cgtgctgatc gccttcgccc agtacctgca gcagtgccct 1740
ttcgaggacc acgttaaact ggtgaatgaa gtgaccgagt tcgccaaaac ctgcgtggcc 1800
gacgagtctg ccgaaaattg cgacaaaagc ttacacaccc tgttcggcga caagctgtgc 1860
accgtggcca ccttaagaga aacctacggc gagatggccg actgctgcgc taagcaggag 1920
cccgagagaa acgaatgctt cctgcagcac aaggacgata acccaaatct gcctagactg 1980
gtgagacccg aggtggacgt gatgtgcaca gccttccacg ataacgaaga gacattcctg 2040

```
aaaaagtacc tgtacgagat cgccagaaga catccttact tctatgcccc cgagcttctg   2100
ttcttcgcca agagatataa ggccgccttc accgagtgct gccaagccgc cgacaaggca   2160
gcctgcctgc tgccaaagct tgacgagctg agagacgagg gcaaagccag cagcgccaag   2220
cagagactga agtgcgcctc cctgcagaag ttcggcgaga gagcctttaa ggcctgggcc   2280
gtggccagat tgagtcagag attccccaag gccgagttcg ccgaggtgag caaactggtg   2340
accgacctca ctaaagtgca cacagaatgt tgccatggcg atctcctgga atgcgccgat   2400
gacagggccg acctggccaa gtacatctgt gagaaccagg acagcatttc gagcaagctg   2460
aaggagtgct gcgagaaacc cctgctggag aagtcccact gcatcgccga ggtggagaac   2520
gacgagatgc ccgccgacct gcccagcctg gccgcagatt tcgtggagag caaggacgta   2580
tgcaagaact acgcagaggc caaggatgtg ttcctgggca tgttcctgta cgaatacgcc   2640
agaaggcacc ccgactacag cgtcgtgctg ttactgagac tggccaagac ctacgagaca   2700
accttagaga agtgctgcgc ggccgcagac ccgcacgagt gctacgccaa ggtgttcgac   2760
gagttcaagc ccctggtgga ggaacctcag aatctgatta agcagaattg tgagctgttc   2820
gagcagctgg gagagtacaa gttccagaac gcgctgctgg tgagatatac caagaaggtg   2880
ccccaggtga gcacccccac cctggtggag gtgagtcgca acctgggcaa ggtggggagc   2940
aagtgttgca agcatcccga ggccaaaaga atgccctgcg cagaggacta tctgagcgtt   3000
gtgcttaacc agctgtgcgt gctgcacgag aagacccccg tgagcgacag agtgaccaag   3060
tgttgcaccg agagcctggt aaacagaaga ccctgcttca gcgccctgga ggtggacgag   3120
acctacgtgc ccaaggagtt caacgccgag acctttacct tccacgcaga catttgcacc   3180
ctgagcgaga aagagaggca gatcaagaaa cagaccgctc tggtcgagct tgtgaagcac   3240
aagcccaaag ctaccaagga gcagctgaag gccgtgatgg atgatttcgc cgccttcgta   3300
gagaaatgct gcaaggccga cgataaagag acctgctttg ccgaggaggg caagaaactg   3360
gtggccgcca gccaggcggc cctgggcctg tag                                3393
```

<210> SEQ ID NO 9
<211> LENGTH: 3393
<212> TYPE: DNA
<213> ORGANISM: Artificial Sequence
<220> FEATURE:
<223> OTHER INFORMATION: H3 Construct

<400> SEQUENCE: 9

```
atgagagtgc ccgcccagct gctgggcctg ctgttgctgt ggctgcccgg cgccagatgc     60
gccatctggg aactgaagaa ggacgtctac gtggtggagc tggattggta ccccgacgcc    120
cccggcgaga tggtcgtgct gacctgtgac acccctgagg aggacggaat cacatggacc    180
ctggaccaga gcagcgaagt gttgggcagc ggcaagaccc tgaccatcca agtgaaggaa    240
ttcggcgacg cgggccagta tacttgccac aagggcgggg aggttctgag ccacagcctg    300
ctgctgctcc acaagaaaga ggatggcatc tggtctaccg acatcctgaa ggaccaaaag    360
gagccaaaga acaagacctt cctaagatgc gaggccaaga actactcagg tcgtttcacc    420
tgctggtggc tgaccacaat ctccaccgac ctgaccttca gcgtgaagag cagccgcggc    480
agtagcgacc cacagggcgt gacctgcggg gccgccactc tgagcgccga gagagtgcgc    540
ggcgataata aggaatacga gtacagcgtg gagtgccagg aagactcagc ctgccccgcc    600
gcagaagaaa gtctgccaat agaggtgatg gttgacgccg tgcacaagct aaagtacgag    660
aactacacca gcagcttctt tatccgggac atcatcaagc cagatccccc caagaacctg    720
```

```
cagcttaagc ccctgaagaa cagcagacag gtggaggtgt catgggaata ccccgacacc    780
tggagcaccc cccatagcta cttctcactg accttctgcg tgcaggtgca gggcaagagc    840
aagagagaga agaaggatag ggtattcacg gacaagacct cagccaccgt gatctgccga    900
aagaacgcca gcatcagcgt gagagcccag gacagatact atagctcctc gtggagcgag    960
tgggccagcg taccttgcag cggcgggagc ggcggcggca gcggcggtgg cagtggcggg   1020
ggcagcagaa acctgcccgt ggccaccccc gaccccggga tgtttccttg cctgcaccac   1080
tcccagaacc tcctgagagc cgtgtccaac atgctgcaga aagccagaca gaccctcgag   1140
ttctatccct gcacaagcga ggagatcgac cacgaggaca tcactaagga caagaccagc   1200
acagtggaag cctgcctccc gctggagctg actaagaacg agagctgtct gaacagcagg   1260
gagaccagct tcatcaccaa cggcagctgc ctggcgagca gaaaaacctc ctttatgatg   1320
gcgctctgcc tgagctcaat ctatgaggac ctgaagatgt accaggtgga gtttaaaacc   1380
atgaatgcca agctgcttat ggaccctaag agacagattt tcctggatca gaacatgctg   1440
gccgtgattg atgaattaat gcaggcgctg aactttaaca gcgagaccgt gccccagaag   1500
agcagcctgg aggagcccga cttttacaag accaagatca agttgtgcat cctcctgcac   1560
gccttcagaa tcagagcggt gacgatcgac agagtcatga gctacctcaa cgctagcggc   1620
agcggtggcg gcagcgacgc ccacaagagc gaggtggccc acagattcaa ggatctcggg   1680
gaggagaact tcaaggccct ggtgctgatc gccttcgcac agtacctgca gcagtgcccc   1740
ttcgaggacc acgtaaaact ggtgaacgag gtgacggagt tcgccaagac ctgtgttgcc   1800
gacgagtcgg ccgagaattg cgacaagagc ctgcataccc tgttcggcga caagctgtgc   1860
accgtggcca ccctgagaga gacctacggc gagatggccg actgctgcgc caagcaagag   1920
cccgagagaa acgagtgctt cctgcagcac aaggacgaca accccaacct gccccggctg   1980
gtgagacccg aggtggacgt gatgtgcacc gccttccacg acaacgagga gaccttcctg   2040
aagaagtatc tgtacgagat cgccagaaga caccccttatt tttacgcccc cgagctgctc   2100
ttcttcgcta agagatataa ggcagccttc accgagtgtt gtcaggccgc cgataaggcc   2160
gcttgcctgc tgcccaagtt ggacgagctc agagacgagg gcaaggcgag cagcgccaag   2220
cagagactga agtgcgccag cctgcagaag ttcggcgaga gggccttcaa ggcctgggcg   2280
gtggccagac tgtcccagag atttcccaag gccgagttcg ccgaggtaag caagctggtc   2340
accgacctga ccaaggtgca caccgagtgt tgccacggcg acctgctgga atgcgccgat   2400
gaccgtgccg acctggccaa gtacatctgc gagaatcagg actccatcag cagcaaactg   2460
aaggagtgtt gcgagaagcc cctgctggag aagagccatt gcatcgctga ggtggaaaac   2520
gacgagatgc ccgcagacct gcccagcctg gccgcagact ttgtggaaag taaggacgtg   2580
tgcaagaact acgcggaggc caaagacgtg tttctgggca tgttcctata cgagtatgcc   2640
agaagacacc ccgactacag cgttgtgtta ttgctgagac tggccaagac ctacgagact   2700
accttggaga agtgctgcgc cgccgccgac ccccacgagt gctatgccaa ggtgttcgac   2760
gagttcaagc ccctggtgga ggagccccag aatctgatta agcagaattg cgagcttttt   2820
gagcagctgg gcgagtataa gttccagaac gccctgctgg tgagatacac caaaaaggta   2880
cctcaggtga gcacccccac cctggtggag gtgagcagaa atctgggcaa ggtgggcagc   2940
aagtgctgca agcacccgga ggccaagaga atgccctgtg ccgaggatta cctgtcagtg   3000
gtgctgaacc agctgtgcgt tctgcacgaa aagacgcccg tgtcggacag agtgaccaag   3060
```

-continued

```
tgctgcacgg agagcctggt gaacagaaga ccgtgcttca gcgccctaga ggtggacgag   3120

acctacgtgc ccaaggagtt caacgccgag accttcacct tccacgccga catctgtacc   3180

ctgtcagaga aggagagaca gatcaagaag cagaccgcct tagtggagct ggtgaagcac   3240

aagcccaagg ccaccaagga gcagctgaaa gccgtgatgg acgatttcgc agccttcgtc   3300

gagaagtgct gcaaggccga cgacaaggaa acttgcttcg ccgaggaggg caagaagctg   3360

gtggctgcct cgcaggccgc cctcggcctg tag                                3393
```

<210> SEQ ID NO 10
<211> LENGTH: 3393
<212> TYPE: DNA
<213> ORGANISM: Artificial Sequence
<220> FEATURE:
<223> OTHER INFORMATION: CO Construct

<400> SEQUENCE: 10

```
atgagagtgc ccgcccagct gctgggcctg ctgctgctgt ggctgcccgg cgccagatgc     60

gccatctggg agctgaagaa ggacgtgtac gtggtggagc tggactggta ccccgacgcc    120

cccggcgaga tggtggtgct gacctgcgac acccccgagg aggacggcat cacctggacc    180

ctggaccaga gcagcgaggt gctgggcagc ggcaagaccc tgaccatcca ggtgaaggag    240

ttcggcgacg ccggccagta cacctgccac aagggcggcg aggtgctgag ccacagcctg    300

ctgctgctgc acaagaagga ggacggcatc tggagcaccg acatcctgaa ggaccagaag    360

gagcccaaga acaagacctt cctgagatgc gaggccaaga actacagcgg cagattcacc    420

tgctggtggc tgaccaccat cagcaccgac ctgaccttca gcgtgaagag cagcagaggc    480

agcagcgacc cccagggcgt gacctgcggc gccgccaccc tgagcgccga gagagtgaga    540

ggcgacaaca aggagtacga gtacagcgtg gagtgccagg aggacagcgc ctgccccgcc    600

gccgaggaga gcctgcccat cgaggtgatg gtggacgccg tgcacaagct gaagtacgag    660

aactacacca gcagcttctt catcagagac atcatcaagc ccgacccccc caagaacctg    720

cagctgaagc ccctgaagaa cagcagacag gtggaggtga gctgggagta ccccgacacc    780

tggagcaccc cccacagcta cttcagcctg accttctgcg tgcaggtgca gggcaagagc    840

aagagagaga agaaggacag agtgttcacc gacaagacca gcgccaccgt gatctgcaga    900

aagaacgcca gcatcagcgt gagagcccag gacagatact acagcagcag ctggagcgag    960

tgggccagcg tgccctgcag cggcggcagc ggcggcggca gcggcggcgg cagcggcggc   1020

ggcagcagaa acctgcccgt ggccaccccc gaccccggca tgttcccctg cctgcaccac   1080

agccagaacc tgctgagagc cgtgagcaac atgctgcaga aggccagaca gaccctggag   1140

ttctacccct gcaccagcga ggagatcgac cacgaggaca tcaccaagga caagaccagc   1200

accgtggagg cctgcctgcc cctggagctg accaagaacg agagctgcct gaacagcaga   1260

gagaccagct tcatcaccaa cggcagctgc ctggccagca gaaagaccag cttcatgatg   1320

gccctgtgcc tgagcagcat ctacgaggac ctgaagatgt accaggtgga gttcaagacc   1380

atgaacgcca agctgctgat ggaccccaag agacagatct tcctggacca gaacatgctg   1440

gccgtgatcg acgagctgat gcaggccctg aacttcaaca gcgagaccgt gccccagaag   1500

agcagcctgg aggagcccga cttctacaag accaagatca agctgtgcat cctgctgcac   1560

gccttcagaa tcagagccgt gaccatcgac agagtgatga gctacctgaa cgccagcggc   1620

agcggcggcg gcagcgacgc ccacaagagc gaggtggccc acagattcaa ggacctgggc   1680

gaggagaact tcaaggccct ggtgctgatc gccttcgccc agtacctgca gcagtgcccc   1740
```

ttcgaggacc acgtgaagct ggtgaacgag gtgaccgagt tcgccaagac ctgcgtggcc 1800
gacgagagcg ccgagaactg cgacaagagc ctgcacaccc tgttcggcga caagctgtgc 1860
accgtggcca ccctgagaga gacctacggc gagatggccg actgctgcgc caagcaggag 1920
cccgagagaa acgagtgctt cctgcagcac aaggacgaca accccaacct gcccagactg 1980
gtgagacccg aggtggacgt gatgtgcacc gccttccacg acaacgagga gaccttcctg 2040
aagaagtacc tgtacgagat cgccagaaga cacccctact tctacgcccc cgagctgctg 2100
ttcttcgcca agagatacaa ggccgccttc accgagtgct gccaggccgc cgacaaggcc 2160
gcctgcctgc tgcccaagct ggacgagctg agagacgagg gcaaggccag cagcgccaag 2220
cagagactga agtgcgccag cctgcagaag ttcggcgaga gagccttcaa ggcctgggcc 2280
gtggccagac tgagccagag attccccaag gccgagttcg ccgaggtgag caagctggtg 2340
accgacctga ccaaggtgca caccgagtgc tgccacggcg acctgctgga gtgcgccgac 2400
gacagagccg acctggccaa gtacatctgc gagaaccagg acagcatcag cagcaagctg 2460
aaggagtgct gcgagaagcc cctgctggag aagagccact gcatcgccga ggtggagaac 2520
gacgagatgc ccgccgacct gcccagcctg gccgccgact tcgtggagag caaggacgtg 2580
tgcaagaact acgccgaggc caaggacgtg ttcctgggca tgttcctgta cgagtacgcc 2640
agaagacacc ccgactacag cgtggtgctg ctgctgagac tggccaagac ctacgagacc 2700
accctggaga agtgctgcgc cgccgccgac ccccacgagt gctacgccaa ggtgttcgac 2760
gagttcaagc ccctggtgga ggagccccag aacctgatca agcagaactg cgagctgttc 2820
gagcagctgg gcgagtacaa gttccagaac gccctgctgg tgagatacac caagaaggtg 2880
ccccaggtga gcacccccac cctggtggag gtgagcagaa acctgggcaa ggtgggcagc 2940
aagtgctgca agcaccccga ggccaagaga atgccctgcg ccgaggacta cctgagcgtg 3000
gtgctgaacc agctgtgcgt gctgcacgag aagacccccg tgagcgacag agtgaccaag 3060
tgctgcaccg agagcctggt gaacagaaga ccctgcttca gcgccctgga ggtggacgag 3120
acctacgtgc ccaaggagtt caacgccgag accttcacct tccacgccga catctgcacc 3180
ctgagcgaga aggagagaca gatcaagaag cagaccgccc tggtggagct ggtgaagcac 3240
aagcccaagg ccaccaagga gcagctgaag gccgtgatgg acgacttcgc cgccttcgtg 3300
gagaagtgct gcaaggccga cgacaaggag acctgcttcg ccgaggaggg caagaagctg 3360
gtggccgcca gccaggccgc cctgggcctg tag 3393

<210> SEQ ID NO 11
<211> LENGTH: 3390
<212> TYPE: DNA
<213> ORGANISM: Artificial Sequence
<220> FEATURE:
<223> OTHER INFORMATION: CP Construct

<400> SEQUENCE: 11
atgagggtcc ccgctcagct cctggggctc ctgctgctct ggctcccagg tgcacgatgt 60
gccatctggg agctgaagaa ggatgtgtat gtggtggagc tggactggta cccagatgcc 120
cctggagaga tggtggtgct gacctgtgac accccagagg aggatggcat cacctggacc 180
ctggaccaga gcagcgaggt gctgggcagc ggcaagaccc tgaccatcca ggtgaaggag 240
tttggagatg ctggccagta cacctgccac aagggcgggg aggtgctgag ccacagcctg 300
ctgctgctgc acaagaagga ggatggcatc tggagcacag acatcctgaa ggaccagaag 360

-continued gagcccaaga acaagacctt cctgcgctgt gaggccaaga actacagcgg ccgcttcacc 420
tgctggtggc tgaccaccat cagcacagac ctgaccttct ctgtgaaaag cagccggggc 480
agcagtgacc cccagggcgt gacctgtggg gccgccaccc tgtctgctga gcgggtgcgg 540
ggggacaaca aggagtatga gtacagcgtg gagtgccagg aggacagcgc ctgcccagct 600
gctgaggaga gcctgcccat cgaggtgatg gtggatgctg tgcacaagct gaagtatgag 660
aactacacca gcagcttctt catccgggac atcatcaagc cagacccccc caagaacctg 720
cagctgaagc ccctgaagaa cagccggcag gtggaggtgt cctgggagta cccagacacc 780
tggagcaccc cccacagcta cttcagcctg accttctgtg tgcaggtgca gggcaagagc 840
aagcgggaga agaaggacag agtcttcaca gacaagacca gcgccaccgt catctgcagg 900
aagaatgcca gcatctctgt gcgggcccag gaccgctact acagcagctc ctggagcgag 960
tgggcctctg tgccctgcag cggcggcagc ggcggcggca gcggcggcgg cagcggcggc 1020
ggcagcagga acctgcctgt ggccacccca gaccccggca tgttcccctg cctgcaccac 1080
agccagaacc tgctgcgggc tgtgagcaac atgctgcaga aggcccggca gaccctggag 1140
ttctacccct gcaccagcga ggagattgac cacgaggaca tcaccaagga caagaccagc 1200
acagtggagg cctgcctgcc cctggagctg accaagaatg aaagctgcct gaacagccgg 1260
gagaccagct tcatcaccaa cggcagctgc ctggccagca ggaagaccag cttcatgatg 1320
gccctgtgcc tgagcagcat ctatgaggac ctgaagatgt accaggtgga gttcaagacc 1380
atgaatgcca agctgctgat ggaccccaag aggcagatct tcctggacca gaacatgctg 1440
gccgtgattg atgagctgat gcaggccctg aacttcaaca gcgagaccgt gccccagaaa 1500
agcagcctgg aggagccaga cttctacaag accaagatca agctgtgcat cctgctgcac 1560
gccttccgca tccgggctgt gaccatcgac agagtgatga gctacctgaa tgccagcggc 1620
agcggcggcg gcagtgatgc ccacaagtct gaggtggccc accgcttcaa ggacctgggg 1680
gaggagaact tcaaggccct ggtgctgatt gcctttgccc agtacctgca gcagtgcccc 1740
tttgaggacc acgtgaagct ggtgaatgag gtgacagaat ttgccaagac ctgtgtggct 1800
gatgaatctg ctgagaactg tgacaagagc ctgcacaccc tgtttggaga caagctgtgc 1860
accgtggcca ccctgcggga gacctatgga gagatggctg actgctgtgc caagcaggag 1920
cctgagagaa atgaatgctt cctgcagcac aaggatgaca accccaacct gccccggctg 1980
gtgcggcctg aggtggatgt gatgtgcaca gccttccatg acaatgagga gaccttcctg 2040
aagaagtacc tgtatgaaat tgcccggcgg cacccctact tctacgcccc tgagctgctg 2100
ttctttgcca agcgctacaa ggccgccttc acagagtgct gccaggccgc tgacaaggcc 2160
gcctgcctgc tgcccaagct ggatgagctg agagatgagg gcaaggccag cagcgccaag 2220
cagaggctga agtgtgccag cctgcagaag tttggagagc gggccttcaa ggcctgggcc 2280
gtggcccggc tgagccagcg cttccccaag gccgagtttg ctgaggtgtc caagctggtg 2340
acagacctga ccaaggtgca cacagagtgc tgccacgggg acctgctgga gtgtgctgat 2400
gacagagctg acctggccaa gtacatctgt gagaaccagg acagcatcag cagcaagctg 2460
aaggagtgct gtgagaagcc cctgctggaa aagagccact gcatcgccga ggtggagaat 2520
gatgagatgc ctgctgacct gcccagcctg gccgctgact ttgtggagag caaggatgtg 2580
tgcaagaact atgcagaggc caaggatgtg ttcctgggca tgttcctgta tgaatatgcc 2640
cggcggcacc cagactacag cgtggtgctg ctgctgcggc tggccaagac ctatgagacc 2700
accctggaga agtgctgtgc cgctgctgac ccccatgaat gttatgccaa ggtgtttgat 2760

```
gagttcaagc ccctggtgga ggagccccag aacctgatca agcagaactg tgagctgttt   2820

gagcagctgg gggagtacaa gttccagaat gccctgctgg tgcgctacac caagaaggtg   2880

ccccaggtgt ccaccccac cctggtggag gtgtccagga acctgggcaa ggtgggcagc   2940

aagtgctgca agcaccctga ggccaagagg atgccctgtg ccgaggacta cctgtctgtg   3000

gtgctgaacc agctgtgtgt gctgcacgag aagacccctg tgtctgacag agtgaccaag   3060

tgctgcacag agagcctggt gaacagaaga ccctgcttca gcgccctgga ggtggatgag   3120

acctacgtgc ccaaggagtt caatgctgag accttcacct tccacgccga catctgcacc   3180

ctgtctgaga aggagcggca gatcaagaag cagacagccc tggtggagct ggtgaagcac   3240

aagcccaagg ccaccaagga gcagctgaag gctgtgatgg atgactttgc tgcctttgtg   3300

gagaagtgct gcaaggcaga tgacaaggag acctgctttg ctgaggaggg caagaagctg   3360

gtggccgcca gccaggccgc cctgggcctg                                    3390
```

```
<210> SEQ ID NO 12
<211> LENGTH: 3393
<212> TYPE: DNA
<213> ORGANISM: Artificial Sequence
<220> FEATURE:
<223> OTHER INFORMATION: vH1 Construct

<400> SEQUENCE: 12
```

```
atgagagtgc ccgcccagct gctgggcctg ctgctgctgt ggctgcccgg cgccagatgc     60

gccatctggg agctgaagaa ggacgtgtac gtggtggagc tggactggta ccccgacgcc    120

cccggcgaga tggtggtgct gacctgcgac acccccgagg aggacgggat cacctggacc    180

ctggatcaga gcagcgaggt gctgggcagc ggcaagaccc tgaccatcca ggtgaaggag    240

tttggtgacg ccggccagta cacctgccac aagggcggcg aggtgctgag ccactcactg    300

ctgctgctgc acaagaagga ggacggcatc tggagcaccg acattctgaa ggatcagaag    360

gagcccaaga acaagacctt cctgagatgc gaggccaaga actacagcgg cagattcacc    420

tgttggtggc tgactactat cagcactgat ctgaccttca gcgtgaagag ctcaagaggc    480

agcagcgatc cccagggcgt gacctgcggc gccgccaccc tgagcgccga gagagtgaga    540

ggcgacaaca aggagtacga gtacagcgtg gagtgccagg aagacagcgc ctgccccgct    600

gcagaggagt ctctgcccat cgaggtgatg gtggacgccg tgcacaagct taagtacgag    660

aactacacca gctccttctt cattagagac atcatcaagc ccgacccgcc caaaaacctg    720

cagctgaagc ccctgaagaa cagcagacag gtggaggtca gctgggagta ccccgacacc    780

tggagcaccc cccacagcta cttcagcctg accttctgcg tgcaggtgca gggcaagagc    840

aagagagaga agaaggacag agtgttcacc gacaaaacca gcgccaccgt gatctgcaga    900

aaaaacgcca gcattagcgt gagagctcag gatagatact acagcagcag ctggagtgag    960

tgggccagcg tgccctgcag cggcggctca ggcggcggct caggcggcgg cagcggcggc   1020

ggcagcagaa acctgcccgt ggccacgccc gaccccggca tgtttccctg cctgcaccat   1080

agccagaatc tgctgagagc cgtgagcaac atgctgcaga aggccagaca gacgctcgag   1140

ttctacccct gcaccagcga ggagattgac cacgaggaca tcaccaagga caagaccagc   1200

accgtggagg cctgcctgcc cctcgagctg accaagaacg agagctgcct gaacagcaga   1260

gagaccagct tcatcaccaa cggcagctgc ctggccagca gaaagaccag cttcatgatg   1320

gccctgtgcc tgagcagcat ctacgaggac ctgaagatgt accaggtgga gttcaagaca   1380
```

```
atgaacgcca agctgctgat ggaccccaag aggcagattt ttctggacca gaacatgctg   1440

gccgttatcg acgagctgat gcaggccctg aatttcaata gcgaaaccgt gccccagaag   1500

agcagcctgg aggagcctga cttctacaaa accaagatca agctttgcat cctgctgcac   1560

gccttcagaa tcagagccgt gaccatcgac agagtgatga gctacctgaa cgccagcggc   1620

agcggcggcg gcagcgacgc ccacaagagc gaggtggccc ataggttcaa ggacctgggc   1680

gaggagaact tcaaggccct ggtactcatc gccttcgccc aatacctgca acagtgcccc   1740

ttcgaggacc atgttaagct ggtgaacgag gtgaccgagt tcgccaagac ctgcgtggcc   1800

gacgagagcg ccgagaactg cgacaagagc ctgcacaccc tgttcggcga caagctgtgc   1860

accgtggcca ccctgagaga gacctacggc gagatggccg actgctgcgc caagcaggag   1920

cccgaacgta acgagtgctt cctgcagcac aaggacgaca accccaacct gccccgactg   1980

gtcagacccg aggtggacgt gatgtgcaca gccttccacg acaacgagga gaccttcctg   2040

aagaagtacc tctacgagat cgccagaaga catccatact tctacgcccc cgagctgctg   2100

ttcttcgcca agaggtacaa ggccgccttc acagagtgct gccaggccgc cgacaaggcc   2160

gcttgcctgc tgcctaagtt ggacgagctg agagacgagg gcaaggccag cagcgccaag   2220

cagagactga agtgcgcaag cctgcagaaa ttcggcgaga gagcctttaa ggcctgggcc   2280

gtggccagac tgagccagcg cttccccaag gccgagttcg ccgaggtgag caagctggtg   2340

accgacctga ccaaagtgca caccgagtgc tgccacggcg acctgctgga gtgcgccgac   2400

gacagagccg acctggccaa gtacatctgc gagaaccagg acagcatcag cagcaagttg   2460

aaggagtgct gcgagaagcc cctgctggag aagagccact gcatcgccga ggtggagaac   2520

gacgagatgc ccgccgacct gcccagcctg gccgccgact tcgtggagag caaggacgtg   2580

tgcaagaact acgccgaggc caaggacgtg ttcctgggca tgttcctgta cgagtacgcc   2640

cggagacacc ccgactacag cgtggtgctg ctgctgagac tggccaagac ctacgagacc   2700

accctggaga agtgctgtgc cgccgccgac ccccacgagt gctacgccaa ggtgttcgac   2760

gagttcaagc ccctggtgga ggagccccag aacctgatca agcagaactg cgagctgttc   2820

gagcagctgg gcgagtataa gttccagaac gccctgctgg tgagatacac caagaaggtg   2880

ccccaggtca gcacccccac cctggtggag gtgagcagaa atctgggcaa ggtgggcagc   2940

aaatgctgca agcaccccga ggccaagaga atgccctgcg ccgaggacta cctgtcagtg   3000

gtgctgaacc agctgtgtgt gctgcacgag aagacccccg tgagcgacag agtgaccaag   3060

tgctgcaccg agagtctcgt gaacagacgg ccctgcttca gcgccctgga ggtggacgaa   3120

acatacgtgc ccaaggagtt caacgcagag accttcacct tccacgcaga catctgcacc   3180

ctgagcgaga aggagagaca gatcaagaag cagaccgccc tggttgagct tgtgaagcac   3240

aagcccaagg ccaccaagga gcagctgaag gccgtgatgg acgacttcgc cgccttcgtg   3300

gagaagtgct gcaaggccga cgacaaggag acctgcttcg ccgaggaggg caagaagctg   3360

gtggccgcca gccaggccgc cctgggcctg tag                               3393
```

<210> SEQ ID NO 13
<211> LENGTH: 3393
<212> TYPE: DNA
<213> ORGANISM: Artificial Sequence
<220> FEATURE:
<223> OTHER INFORMATION: vH2 Construct

<400> SEQUENCE: 13

```
atgagagtgc ccgcccagct gctgggcctg ctgctgctgt ggctgcccgg cgccagatgt     60
```

```
gccatctggg agctgaagaa ggacgtgtac gtggtggagc tggactggta ccccgacgcc    120
cccggagaga tggtggtgct gacctgcgac acccccgaag aggacggcat cacctggacc    180
ctggaccaga gcagcgaggt gctgggcagc gggaagaccc tgaccatcca ggtgaaggag    240
ttcggcgacg ccggccagta cacctgtcac aagggcggcg aggtgctgag ccacagcctg    300
ctgctgctgc acaagaagga ggacggcata tggagcaccg acatcctgaa ggaccagaag    360
gagcccaaga acaagacctt tctgagatgc gaggctaaga attacagcgg cagattcacc    420
tgctggtggc tgaccaccat cagcaccgac ctgaccttca gcgtgaagag cagcagaggc    480
agcagcgacc cccagggcgt gacatgcggc gccgccaccc tgagcgccga gagagtgaga    540
ggcgacaaca aggagtacga gtacagcgtg gagtgccagg aggactccgc ttgccccgcc    600
gccgaggaga gcttgcccat cgaggtgatg gtggacgccg tgcacaagct caagtacgaa    660
aactacacca gcagcttctt catcagagac atcatcaagc ccgacccccc caagaacctg    720
cagctgaagc ccctgaaaaa cagcagacag gtggaggtga gctgggagta ccccgacacc    780
tggagcaccc cccacagcta cttcagcctg accttctgcg tgcaggtgca gggaaaaagc    840
aagagagaga agaaggacag agtgttcacc gacaagacca gcgccaccgt gatctgcaga    900
aagaacgcca gcatctccgt gagagcccag gacagatact acagcagcag ctggagcgag    960
tgggccagcg tgccctgtag cggcggcagc ggcggcggca gcggcggcgg cagcggcggc   1020
ggcagcagaa acctgcccgt ggccaccccc gaccccggca tgttcccctg cctgcaccac   1080
agccagaacc tgctgagagc cgtgagcaac atgctgcaga aggccagaca gaccctggag   1140
ttctacccct gcaccagcga ggagatcgac catgaggaca tcaccaagga caagaccagc   1200
accgtggagg cctgcctgcc cctggagctg accaagaacg aaagctgcct gaacagcaga   1260
gagaccagct tcatcaccaa cggcagctgt ctggcctcaa gaaagaccag ctttatgatg   1320
gccctgtgcc tgtctagcat ctacgaggat ctgaagatgt accaggtgga gttcaagacc   1380
atgaacgcca agctgctgat ggaccccaag agacagatct tcctggacca gaacatgtta   1440
gccgtgattg acgagctgat gcaggccctg aacttcaata gcgagaccgt gccccagaaa   1500
agcagcctgg aggagcccga cttctacaag accaagatca agctgtgcat cctgctgcac   1560
gccttcagaa tcagagccgt aaccatcgac agagtgatga gctacctgaa cgccagtggc   1620
agcggcggtg gcagcgacgc tcacaagagc gaggtggccc acagattcaa ggacctgggc   1680
gaggagaact tcaaggccct ggtcctgatc gccttcgccc agtacctgca gcagtgcccc   1740
ttcgaggacc acgtgaagct ggtgaacgag gtgaccgagt tcgccaagac ctgcgtggcc   1800
gacgagtcgg ccgagaactg cgacaagagc ctgcacaccc tgttcggcga caagctgtgc   1860
accgtggcca ccctgagaga aacctacggg gagatggccg actgctgcgc aaagcaggag   1920
cccgagcgaa acgagtgctt cctgcagcac aaggacgaca accccaactt gcccagactg   1980
gtaagacccg aggtggacgt catgtgcacc gctttccacg acaacgagga gaccttcctg   2040
aagaagtacc tgtacgagat cgccagaaga cacccctatt tctatgcccc tgagctgctg   2100
ttcttcgcca agcgctacaa ggccgccttc accgagtgct gccaggccgc cgacaaggcc   2160
gcctgcctgc tccccaagct ggacgagctg agagacgaag gcaaggccag cagcgccaag   2220
cagagactga agtgcgccag cctgcagaag ttcggcgaga gagccttcaa ggcctgggcc   2280
gtggccagac tgtcgcagag attccccaag gccgagttcg ccgaggtgag caagctggtt   2340
accgacctga ctaaggtgca caccgagtgc tgccacggcg acctgctgga gtgcgccgac   2400
```

gacagagccg acctggccaa gtacatctgc gagaaccagg atagcatcag cagcaagctg 2460
aaggagtgct gcgagaagcc ccttctggag aagtcccact gcatcgccga ggtggagaac 2520
gacgagatgc ccgccgacct gcctagcctg gccgccgact tcgtggagag caaggacgtg 2580
tgcaagaact acgccgaggc caaggacgtg ttcctgggca tgttcctgta cgagtacgcc 2640
agaagacacc ccgactacag cgtggtgctg ctgctgagac tggccaagac ctacgagact 2700
acccttgaga agtgctgcgc cgccgccgac ccacatgagt gctacgccaa ggtgttcgac 2760
gagttcaagc ccctggtgga agagccccag aacctgatca agcagaactg cgagctgttc 2820
gagcagctgg gcgagtacaa gttccagaac gcccttctgg tgagatacac caagaaggtg 2880
cctcaggtga gcacccccac ccttgtggag gtgagcagaa acctcggcaa ggtgggcagc 2940
aagtgctgca agcatccaga ggccaagaga atgccctgcg ccgaggacta cctgagcgtg 3000
gtgctgaacc agctgtgcgt gctgcacgag aaaactcccg tgagcgacag agtgaccaag 3060
tgctgcaccg agagtctggt gaacagaaga ccctgcttca gcgccctgga ggtggacgag 3120
acctacgtgc ccaaggagtt caacgccgag accttcacct tccacgccga catctgcacc 3180
ctgagcgaga aggagcggca gatcaagaag cagaccgccc tggtggagct ggtgaagcac 3240
aagcccaagg ccaccaagga gcagctcaag gccgtgatgg acgacttcgc cgcgttcgtg 3300
gagaagtgct gcaaggccga cgacaaagag acctgcttcg ccgaggaggg caagaagctt 3360
gtggccgcca gccaggccgc cctgggcctg tag 3393

<210> SEQ ID NO 14
<211> LENGTH: 3393
<212> TYPE: DNA
<213> ORGANISM: Artificial Sequence
<220> FEATURE:
<223> OTHER INFORMATION: vH3 Construct

<400> SEQUENCE: 14
atgagagtgc ccgcccagct tctgggcctg ctgctgctgt ggctgcccgg cgccagatgc 60
gccatctggg agctgaagaa ggacgtgtac gtggtggagc tggactggta cccggacgcc 120
ccgggcgaga tggtcgtgct gacctgcgac acccccgagg aggacggcat cacctggacc 180
ctggaccagt ctagcgaggt gctgggcagc ggcaagaccc tgaccatcca ggtgaaggag 240
ttcggcgacg ccggccagta cacctgccac aagggcggcg aggtgctgag ccacagcctg 300
ctgctgctgc acaagaagga ggacggcatc tggagcaccg acatcctgaa ggaccagaag 360
gagcctaaga acaagacctt cctgagatgt gaggccaaga actacagcgg cagattcacc 420
tgctggtggc tgaccaccat cagcaccgat ctgaccttca gcgtgaagag cagcagaggc 480
agctcagacc cccagggcgt gacctgcggc gccgcgaccc tgagcgccga gagagtgaga 540
ggcgacaaca aggagtacga gtacagcgtg gagtgccagg aggacagcgc ctgccccgcg 600
gccgaggaga gcctgcccat cgaggtgatg gtggacgccg tgcataagct gaagtacgag 660
aactacacca gcagcttctt catcagagac atcatcaagc ccgatccccc caagaacctg 720
cagctgaagc cactgaagaa cagcagacag gtggaggtga gctgggagta ccccgacacc 780
tggagcaccc cccacagcta cttcagcctg accttctgcg tgcaggtgca gggcaagagc 840
aagagagaga agaaggaccg ggtgttcacc gacaagacca gcgccactgt gatctgcaga 900
aagaacgcca gcatcagcgt gagagcccag gacagatact acagctccag ctggtcagag 960
tgggccagcg tgccctgcag cggcggcagc ggtggcggga gcggcggcgg gagcggcggc 1020
ggaagcagaa acctgcccgt ggccacccct gaccccggca tgttcccctg cctgcaccac 1080

```
agccagaacc tgctgagagc cgtaagcaac atgctgcaga aggccagaca gactctggag   1140
ttctacccct gcaccagcga ggagatcgat cacgaggaca tcaccaagga caagaccagt   1200
accgtggagg cctgcctgcc cctggagctg accaagaacg agagctgcct gaacagcaga   1260
gagaccagct ttataaccaa cggcagctgt ctggctagca gaaagaccag cttcatgatg   1320
gccctgtgcc tgagcagcat ctacgaggac ttgaagatgt accaggtgga gttcaagacc   1380
atgaacgcca agcttctgat ggaccccaag agacagatct ttctggacca gaacatgctg   1440
gccgtgatcg atgaactgat gcaggccctg aacttcaaca gcgagaccgt gccccagaag   1500
agcagtctgg aggagcccga cttctacaag actaagatca agctgtgcat cctgctgcac   1560
gccttcagaa tcagagccgt gaccatcgac agagtgatga gctacctgaa cgcctcaggc   1620
agcggcggcg ggagcgacgc ccacaagagc gaggtggccc acagattcaa ggacctcggc   1680
gaggagaact tcaaggccct ggtgctgatc gctttcgccc agtacctgca gcagtgcccc   1740
ttcgaggacc acgtgaaact ggtgaacgag gtgaccgagt tcgccaagac ctgcgtggcc   1800
gacgagagcg ccgagaactg cgacaagagc ctgcacacgt tgttcggcga caagctgtgc   1860
accgtggcca ccctgagaga gacctacggc gagatggccg actgctgcgc caagcaggag   1920
cccgagagaa acgaatgctt cctgcagcac aaggacgaca accccaacct gccccgcctg   1980
gtgagacccg aggtggacgt gatgtgcacc gccttccacg acaacgagga gaccttcctg   2040
aagaagtact tgtacgagat cgcaagaaga cacccgtact tctacgcccc cgagctgctg   2100
ttcttcgcca agagatacaa ggccgccttc accgagtgct gccaggccgc cgacaaggcc   2160
gcctgcctgc tgcccaagct ggacgagctc agagacgagg gcaaggccag cagcgccaag   2220
cagagactga agtgcgccag cctgcagaag ttcggcgaga gagcctttaa ggcctgggcc   2280
gtggccagac tgagccagag attccccaag gccgagttcg ccgaagtgag caagctggtg   2340
accgacctga cgaaggtgca caccgagtgc tgccacggcg acctgctgga gtgcgccgac   2400
gacagagcag acctggccaa gtacatctgc gagaaccagg acagcatcag cagcaagctg   2460
aaggagtgct gcgagaagcc cctgctggag aagagccact gcatcgccga ggtggagaac   2520
gacgagatgc ccgccgacct gcccagtctg gccgcagact tcgtggagag caaggatgtg   2580
tgcaagaact acgccgaggc caaggacgtg ttcctgggca tgttcctgta cgagtacgca   2640
agaagacacc ccgactacag cgtggtgctg ctgctgagac tggccaagac ctacgagacc   2700
accctggaga agtgctgcgc cgccgccgac ccccacgagt gctacgccaa ggtgttcgac   2760
gagttcaagc ccctggtgga ggagccccag aacctgatca agcagaactg cgaactgttc   2820
gagcagcttg gcgagtacaa gtttcagaac gccctgctgg tcagatacac caagaaggtg   2880
ccccaggtga gcacccccac cctggtggag gtgtccagaa acctgggcaa ggtgggcagc   2940
aagtgctgca agcaccccga ggcaaagaga atgccctgcg ccgaggacta tctgagcgtg   3000
gtgctgaacc agctgtgcgt gctgcacgag aagacccccg tgagcgacag agtgaccaag   3060
tgctgcaccg agagcctggt gaatagaaga ccctgcttca gcgcactgga ggtggacgag   3120
acctacgtgc ccaaggagtt caacgccgag acattcacct tccacgccga tatctgcacc   3180
ctgagcgaga aggagagaca gatcaagaag cagaccgccc tggtggagct ggtgaagcac   3240
aagcccaagg ccaccaagga gcagttgaag gccgtgatgg acgacttcgc cgccttcgtg   3300
gagaaatgct gcaaggccga cgacaaggag acctgcttcg ccgaggaggg caagaagctg   3360
gtggccgcca gccaggccgc cctgggcctg tag                                3393
```

<210> SEQ ID NO 15
<211> LENGTH: 1617
<212> TYPE: DNA
<213> ORGANISM: Artificial Sequence
<220> FEATURE:
<223> OTHER INFORMATION: A1 Construct

<400> SEQUENCE: 15
atgagggtcc ccgctcagct cctggggctc ctgctgctct ggctcccagg tgcacgatgt 60
gccatctggg agctgaagaa agacgtgtac gtggtggagc ttgactggta ccccgacgcc 120
cccggtgaaa tggtggttct gacctgcgac acaccagagg aggacggcat cacctggacc 180
ctggaccagt ccagcgaggt cctgggatct ggcaagaccc tgaccatcca ggttaaggaa 240
tttggcgacg ccggccagta cacctgccac aaaggcggcg aggtcctttc gcacagtctg 300
ctgctgctgc ataaaaagga ggacggcatt tggagcaccg acattctgaa ggatcagaaa 360
gagcccaaga acaagacctt tctgagatgt gaggccaaaa actactctgg acgcttcacc 420
tgttggtggc tgaccaccat cagcacagac ctgaccttct cggtgaagtc tagtaggggc 480
agcagtgacc cccagggcgt aacatgcggc gccgctaccc tgagcgccga gagagtgaga 540
ggcgataaca aggagtacga gtactccgtg gagtgccaag aggactcagc ctgccccgcc 600
gccgaggagt cgctgcccat cgaggtgatg gtggatgcag tgcacaagct gaagtacgag 660
aactacacca gtagcttttt catcagagat atcattaaac ccgaccctcc caagaacctg 720
cagctgaagc ccttaaagaa cagccggcag gtggaagtgt catgggagta cccagacacc 780
tggagcactc cgcacagcta cttcagcctg accttctgcg ttcaggtgca gggaaaaagc 840
aagagagaga agaaagacag agtgttcacc gacaagacca gcgcaaccgt gatctgtaga 900
aagaacgcct cgatcagcgt gagagcccag gacagatact acagcagcag ctggagcgag 960
tgggccagtg taccttgcag cggtggaagc ggcggaggct ctggcggagg gagtggcgga 1020
ggcagcagaa atcttccagt agctaccccc gaccccggca tgtttccctg tctgcaccat 1080
tctcaaaacc tgttacgggc cgtgagcaac atgctgcaga aggccagaca gacactggag 1140
ttttacccct gtacctcaga ggagatcgat catgaggaca ttactaagga caagaccagc 1200
accgtggaag cctgcctgcc cctagagcta accaagaacg agagctgcct gaactctaga 1260
gagacaagct tcatcacgaa cggctcatgc ctggccagta ggaaaaccag cttcatgatg 1320
gctctgtgcc tgagctccat atatgaggac cttaagatgt accaggtgga gttcaaaacc 1380
atgaacgcca agctgctgat ggacccaaag agacagatct tccttgacca gaacatgctg 1440
gccgttatcg atgagctgat gcaggccctg aacttcaaca gcgagaccgt gccccagaaa 1500
agcagcctgg aggaacccga cttctacaaa accaagatca agctgtgcat tctgctgcat 1560
gccttccgca ttagagccgt gaccatcgat agggtgatga gctacctgaa cgccagc 1617

<210> SEQ ID NO 16
<211> LENGTH: 1614
<212> TYPE: DNA
<213> ORGANISM: Artificial Sequence
<220> FEATURE:
<223> OTHER INFORMATION: A2 Construct

<400> SEQUENCE: 16
atgagggtcc ccgctcagct cctggggctc ctgctgctct ggctcccagg tgcacgatgt 60
gccatctggg aactgaagaa ggacgtctac gtggtggagc tggattggta ccccgacgcc 120
cccggcgaga tggtcgtgct gacctgtgac acccctgagg aggacggaat cacatggacc 180

```
ctggaccaga gcagcgaagt gttgggcagc ggcaagaccc tgaccatcca agtgaaggaa    240

ttcggcgacg cgggccagta tacttgccac aagggcgggg aggttctgag ccacagcctg    300

ctgctgctcc acaagaaaga ggatggcatc tggtctaccg acatcctgaa ggaccaaaag    360

gagccaaaga acaagacctt cctaagatgc gaggccaaga actactcagg tcgtttcacc    420

tgctggtggc tgaccacaat ctccaccgac ctgaccttca gcgtgaaaag cagccgcggc    480

agtagcgacc cacagggcgt gacctgcggg gccgccactc tgagcgccga gagagtgcgc    540

ggcgataata aggaatacga gtacagcgtg gagtgccagg aagactcagc ctgccccgcc    600

gcagaagaaa gtctgccaat agaggtgatg gttgacgccg tgcacaagct aaagtacgag    660

aactacacca gcagcttctt tatccgggac atcatcaagc cagatccccc caagaacctg    720

cagcttaagc ccctgaagaa cagcagacag gtggaggtgt catgggaata ccccgacacc    780

tggagcaccc cccatagcta cttctcactg accttctgcg tgcaggtgca gggcaagagc    840

aagagagaga agaaggatag ggtattcacg gacaagacct cagccaccgt gatctgccga    900

aagaacgcca gcatcagcgt gagagcccag gacagatact atagctcctc gtggagcgag    960

tgggccagcg taccttgcag cggcgggagc ggcggcggca gcggaggtgg cagtggcgga   1020

ggcagcagaa acctccccgt ggcaacccct gaccccggga tgtttccttg cctgcaccac   1080

tcccagaacc tcctgagagc cgtgtccaac atgctgcaga aagccagaca gaccctcgag   1140

ttctatccct gcacaagcga ggagatcgac cacgaggaca tcactaagga caagaccagc   1200

acagtggaag cctgcctccc gctggagctg actaagaacg agagctgtct gaacagcagg   1260

gagaccagct tcatcaccaa cggcagctgc ctggcgagca gaaaaacctc ctttatgatg   1320

gcgctctgcc tgagctcaat ctatgaggac ctgaagatgt accaggtgga gtttaaaacc   1380

atgaatgcca agctgcttat ggaccctaag agacagattt tcctggatca gaacatgctg   1440

gccgtgattg atgaattaat gcaggcgctg aactttaaca gcgagaccgt gccccagaaa   1500

agcagcctgg aggagcccga cttttacaag accaagatca agttgtgcat cctcctgcac   1560

gccttcagaa tcagagcggt gacgatcgac agagtcatga gctacctcaa cgct         1614
```

<210> SEQ ID NO 17
<211> LENGTH: 1617
<212> TYPE: DNA
<213> ORGANISM: Artificial Sequence
<220> FEATURE:
<223> OTHER INFORMATION: A3 Construct

<400> SEQUENCE: 17

```
atgagggtcc ccgctcagct cctggggctc ctgctgctct ggctcccagg tgcacgatgt     60

gccatctggg agctgaagaa ggacgtgtac gtggtggagc tggactggta ccccgacgcc    120

cccggcgaga tggtggtgct gacctgcgac acccccgagg aggacggcat cacctggacc    180

ctggaccaga gcagcgaggt gctgggcagc ggcaagaccc tgaccatcca ggtgaaggag    240

ttcggcgacg ccggccagta cacctgccac aagggcggcg aggtgctgag ccacagcctg    300

ctgctgctgc acaagaagga ggacggcatc tggagcaccg acatcctgaa ggaccagaag    360

gagcccaaga acaagacctt cctgagatgc gaggccaaga actacagcgg cagattcacc    420

tgctggtggc tgaccaccat cagcaccgac ctgaccttca gcgtgaaaag cagcagaggc    480

agcagcgacc cccagggcgt gacctgcggc gccgccaccc tgagcgccga gagagtgaga    540

ggcgacaaca aggagtacga gtacagcgtg gagtgccagg aggacagcgc ctgccccgcc    600
```

gccgaggaga gcctgcccat cgaggtgatg gtggacgccg tgcacaagct gaagtacgag 660
aactacacca gcagcttctt catcagagac atcatcaagc ccgacccccc caagaacctg 720
cagctgaagc ccctgaagaa cagcagacag gtggaggtga gctgggagta ccccgacacc 780
tggagcaccc cccacagcta cttcagcctg accttctgcg tgcaggtgca gggcaagagc 840
aagagagaga agaaggacag agtgttcacc gacaagacca gcgccaccgt gatctgcaga 900
aagaacgcca gcatcagcgt gagagcccag gacagatact acagcagcag ctggagcgag 960
tgggccagcg tgccctgcag cggcggcagc ggcggcggca gcggcggcgg cagcggcggc 1020
ggcagcagaa acctgcccgt ggccaccccc gaccccggca tgttcccctg cctgcaccac 1080
agccagaacc tgctgagagc cgtgagcaac atgctgcaga aggccagaca gaccctggag 1140
ttctacccct gcaccagcga ggagatcgac cacgaggaca tcaccaagga caagaccagc 1200
accgtggagg cctgcctgcc cctggagctg accaagaacg agagctgcct gaacagcaga 1260
gagaccagct tcatcaccaa cggcagctgc ctggccagca gaaagaccag cttcatgatg 1320
gccctgtgcc tgagcagcat ctacgaggac ctgaagatgt accaggtgga gttcaagacc 1380
atgaacgcca agctgctgat ggaccccaag agacagatct tcctggacca gaacatgctg 1440
gccgtgatcg acgagctgat gcaggccctg aacttcaaca gcgagaccgt gccccagaaa 1500
agcagcctgg aggagcccga cttctacaag accaagatca agctgtgcat cctgctgcac 1560
gccttcagaa tcagagccgt gaccatcgac agagtgatga gctacctgaa cgccagc 1617

<210> SEQ ID NO 18
<211> LENGTH: 1617
<212> TYPE: DNA
<213> ORGANISM: Artificial Sequence
<220> FEATURE:
<223> OTHER INFORMATION: A4 Construct

<400> SEQUENCE: 18
atgagggtcc ccgctcagct cctggggctc ctgctgctct ggctcccagg tgcacgatgt 60
gccatctggg agctgaagaa ggatgtgtat gtggtggagc tggactggta cccagatgcc 120
cctggagaga tggtggtgct gacctgtgac accccagagg aggatggcat cacctggacc 180
ctggaccaga gcagcgaggt gctgggcagc ggcaagaccc tgaccatcca ggtgaaggag 240
tttggagatg ctggccagta cacctgccac aagggcgggg aggtgctgag ccacagcctg 300
ctgctgctgc acaagaagga ggatggcatc tggagcacag acatcctgaa ggaccagaag 360
gagcccaaga acaagacctt cctgcgctgt gaggccaaga actacagcgg ccgcttcacc 420
tgctggtggc tgaccaccat cagcacagac ctgaccttct ctgtgaaaag cagccggggc 480
agcagtgacc cccagggcgt gacctgtggg gccgccaccc tgtctgctga gcgggtgcgg 540
ggggacaaca aggagtatga gtacagcgtg gagtgccagg aggacagcgc ctgcccagct 600
gctgaggaga gcctgcccat cgaggtgatg gtggatgctg tgcacaagct gaagtatgag 660
aactacacca gcagcttctt catccgggac atcatcaagc cagacccccc caagaacctg 720
cagctgaagc ccctgaagaa cagccggcag gtggaggtgt cctgggagta cccagacacc 780
tggagcaccc cccacagcta cttcagcctg accttctgtg tgcaggtgca gggcaagagc 840
aagcgggaga agaaggacag agtcttcaca gacaagacca gcgccaccgt catctgcagg 900
aagaatgcca gcatctctgt gcgggcccag gaccgctact acagcagctc ctggagcgag 960
tgggcctctg tgccctgcag cggcggcagc ggcggcggca gcggcggcgg cagcggcggc 1020
ggcagcagga acctgcctgt ggccacccca gaccccggca tgttcccctg cctgcaccac 1080

```
agccagaacc tgctgcgggc tgtgagcaac atgctgcaga aggcccggca gaccctggag   1140

ttctacccct gcaccagcga ggagattgac cacgaggaca tcaccaagga caagaccagc   1200

acagtggagg cctgcctgcc cctggagctg accaagaatg aaagctgcct gaacagccgg   1260

gagaccagct tcatcaccaa cggcagctgc ctggccagca ggaagaccag cttcatgatg   1320

gccctgtgcc tgagcagcat ctatgaggac ctgaagatgt accaggtgga gttcaagacc   1380

atgaatgcca agctgctgat ggaccccaag aggcagatct tcctggacca gaacatgctg   1440

gccgtgattg atgagctgat gcaggccctg aacttcaaca gcgagaccgt gccccagaaa   1500

agcagcctgg aggagccaga cttctacaag accaagatca agctgtgcat cctgctgcac   1560

gccttccgca tccgggctgt gaccatcgac agagtgatga gctacctgaa tgccagc      1617
```

<210> SEQ ID NO 19
<211> LENGTH: 3390
<212> TYPE: DNA
<213> ORGANISM: Artificial Sequence
<220> FEATURE:
<223> OTHER INFORMATION: B1 Construct

<400> SEQUENCE: 19

```
atgagggtcc ccgctcagct cctggggctc ctgctgctct ggctcccagg tgcacgatgt     60

gccatctggg agctgaagaa agacgtgtac gtggtggagc ttgactggta ccccgacgcc    120

cccggtgaaa tggtggttct gacctgcgac acaccagagg aggacggcat cacctggacc    180

ctggaccagt ccagcgaggt cctgggatct ggcaagaccc tgaccatcca ggttaaggaa    240

tttggcgacg ccggccagta cacctgccac aaaggcggcg aggtcctttc gcacagtctg    300

ctgctgctgc ataaaaagga ggacggcatt tggagcaccg acattctgaa ggatcagaaa    360

gagcccaaga acaagacctt tctgagatgt gaggccaaaa actactctgg acgcttcacc    420

tgttggtggc tgaccaccat cagcacagac ctgaccttct cggtgaagtc tagtaggggc    480

agcagtgacc cccagggcgt aacatgcggc gccgctaccc tgagcgccga gagagtgaga    540

ggcgataaca aggagtacga gtactccgtg gagtgccaag aggactcagc ctgccccgcc    600

gccgaggagt cgctgcccat cgaggtgatg gtggatgcag tgcacaagct gaagtacgag    660

aactacacca gtagcttttt catcagagat atcattaaac ccgaccctcc caagaacctg    720

cagctgaagc ccttaaagaa cagccggcag gtggaagtgt catgggagta cccagacacc    780

tggagcactc cgcacagcta cttcagcctg accttctgcg ttcaggtgca gggaaaaagc    840

aagagagaga agaaagacag agtgttcacc gacaagacca gcgcaaccgt gatctgtaga    900

aagaacgcct cgatcagcgt gagagcccag gacagatact acagcagcag ctggagcgag    960

tgggccagtg taccttgcag cggtggaagc ggcggaggct ctggcggagg gagtggcgga   1020

ggcagcagaa atcttccagt agctaccccc gaccccggca tgtttccctg tctgcaccat   1080

tctcaaaacc tgttacgggc cgtgagcaac atgctgcaga aggccagaca gacactggag   1140

ttttacccct gtacctcaga ggagatcgat catgaggaca ttactaagga caagaccagc   1200

accgtggaag cctgcctgcc cctagagcta accaagaacg agagctgcct gaactctaga   1260

gagacaagct tcatcacgaa cggctcatgc ctggccagta ggaaaaccag cttcatgatg   1320

gctctgtgcc tgagctccat atatgaggac cttaagatgt accaggtgga gttcaaaacc   1380

atgaacgcca agctgctgat ggacccaaag agacagatct tccttgacca gaacatgctg   1440

gccgttatcg atgagctgat gcaggccctg aacttcaaca gcgagaccgt gccccagaaa   1500
```

agcagcctgg aggaacccga cttctacaaa accaagatca agctgtgcat tctgctgcat 1560
gccttccgca ttagagccgt gaccatcgat agggtgatga gctacctgaa cgccagcggc 1620
tctggcggcg gcagtgacgc ccacaagtcc gaggtcgccc acagattcaa ggatttgggc 1680
gaggagaact tcaaggccct ggtgctgatc gccttcgccc agtacttgca gcagtgtccc 1740
ttcgaggacc atgtgaagct ggtgaacgag gtgaccgagt tcgccaagac ctgtgtggcc 1800
gacgagagcg ccgagaactg cgataagtct ctgcacaccc tttttggcga caaactgtgc 1860
accgtggcca ccctgagaga gacctacggc gagatggccg actgctgtgc gaagcaggag 1920
cccgagcgca atgagtgttt cctgcagcat aaggacgaca accccaacct gcccagactg 1980
gtgagacccg aggtggacgt gatgtgcacc gccttccacg acaacgagga gacctttctg 2040
aaaaaatacc tgtacgagat cgcaagacgc cacccctact tctacgcccc cgagctgctg 2100
ttcttcgcca agcgctacaa ggctgccttc accgaatgct gccaggccgc cgataaggcc 2160
gcgtgcttac tgccaaagct ggacgagctg agagacgagg ggaaagcctc tagcgccaaa 2220
cagagattga agtgtgccag cctgcagaaa ttcggtgaga gagccttcaa ggcctgggcc 2280
gtggccagat tatcacagcg gttccccaag gctgaattcg ccgaggtgag caaacttgtc 2340
accgatctga caaaagtgca caccgagtgc tgccatggcg acctgctgga gtgcgccgac 2400
gaccgggccg acctggccaa gtacatctgc gagaaccagg acagcatctc cagcaagctg 2460
aaggagtgct gcgagaagcc cctgctggag aaaagccact gcatcgccga ggtggagaat 2520
gacgaaatgc ccgccgacct gcccagcctg gccgccgact tcgtggaaag caaggacgtg 2580
tgcaaaaatt acgccgaagc caaggatgtg ttcttgggca tgttcttgta cgagtacgcc 2640
agacgccacc ccgactacag cgtggtgctg ctgctgcggc tggccaagac ctacgagacc 2700
accctggaga agtgctgtgc tgccgccgac ccccacgagt gctacgccaa ggtatttgac 2760
gagttcaagc ccctggtgga ggagcctcag aacctgatta agcagaactg tgagctgttc 2820
gagcagctgg gcgagtacaa gttccagaac gccctcctgg tgagatacac caaaaaggtg 2880
cctcaggtaa gcactcccac cctggtggag gtgagcagga acctcggcaa ggtgggcagc 2940
aaatgctgca agcacccaga ggccaaaaga atgccctgcg cagaagacta cctcagcgtg 3000
gtcctgaacc agctgtgcgt gctgcacgaa aagacccctg tgagcgatag agtgacaaag 3060
tgctgcaccg agagcctggt gaacagaaga ccctgtttta gcgccctgga ggtggacgag 3120
acctacgtgc ccaaggagtt caacgccgag acgttcactt tccacgcgga catctgcacc 3180
ctgagcgaga aggagagaca aatcaagaag cagaccgccc tagtcgagct ggtaaaacac 3240
aagcccaagg ccaccaagga gcagctgaag gccgtgatgg acgactttgc agccttcgtg 3300
gagaagtgct gcaaggctga cgacaaggag acctgcttcg ccgaggaggg caagaagctc 3360
gtagccgcca gccaggccgc tctcggcctt 3390

<210> SEQ ID NO 20
<211> LENGTH: 3390
<212> TYPE: DNA
<213> ORGANISM: Artificial Sequence
<220> FEATURE:
<223> OTHER INFORMATION: B2 Construct

<400> SEQUENCE: 20
atgagggtcc ccgctcagct cctggggctc ctgctgctct ggctcccagg tgcacgatgt 60
gccatctggg aactgaagaa ggacgtctac gtggtggagc tggattggta ccccgacgcc 120
cccggcgaga tggtcgtgct gacctgtgac acccctgagg aggacggaat cacatggacc 180

```
ctggaccaga gcagcgaagt gttgggcagc ggcaagaccc tgaccatcca agtgaaggaa    240
ttcggcgacg cgggccagta tacttgccac aagggcgggg aggttctgag ccacagcctg    300
ctgctgctcc acaagaaaga ggatggcatc tggtctaccg acatcctgaa ggaccaaaag    360
gagccaaaga acaagacctt cctaagatgc gaggccaaga actactcagg tcgtttcacc    420
tgctggtggc tgaccacaat ctccaccgac ctgaccttca gcgtgaaaag cagccgcggc    480
agtagcgacc cacagggcgt gacctgcggg gccgccactc tgagcgccga gagagtgcgc    540
ggcgataata aggaatacga gtacagcgtg gagtgccagg aagactcagc ctgccccgcc    600
gcagaagaaa gtctgccaat agaggtgatg gttgacgccg tgcacaagct aaagtacgag    660
aactacacca gcagcttctt tatccgggac atcatcaagc cagatccccc caagaacctg    720
cagcttaagc ccctgaagaa cagcagacag gtggaggtgt catgggaata ccccgacacc    780
tggagcaccc cccatagcta cttctcactg accttctgcg tgcaggtgca gggcaagagc    840
aagagagaga agaaggatag ggtattcacg gacaagacct cagccaccgt gatctgccga    900
aagaacgcca gcatcagcgt gagagcccag gacagatact atagctcctc gtggagcgag    960
tgggccagcg taccttgcag cggcgggagc ggcggcggca gcggaggtgg cagtggcgga   1020
ggcagcagaa acctccccgt ggcaacccct gaccccggga tgtttccttg cctgcaccac   1080
tcccagaacc tcctgagagc cgtgtccaac atgctgcaga aagccagaca gaccctcgag   1140
ttctatccct gcacaagcga ggagatcgac cacgaggaca tcactaagga caagaccagc   1200
acagtggaag cctgcctccc gctggagctg actaagaacg agagctgtct gaacagcagg   1260
gagaccagct tcatcaccaa cggcagctgc ctggcgagca gaaaaacctc ctttatgatg   1320
gcgctctgcc tgagctcaat ctatgaggac ctgaagatgt accaggtgga gtttaaaacc   1380
atgaatgcca agctgcttat ggaccctaag agacagattt tcctggatca gaacatgctg   1440
gccgtgattg atgaattaat gcaggcgctg aactttaaca gcgagaccgt gccccagaaa   1500
agcagcctgg aggagcccga cttttacaag accaagatca agttgtgcat cctcctgcac   1560
gccttcagaa tcagagcggt gacgatcgac agagtcatga gctacctcaa cgctagcggc   1620
agcggtggcg gcagcgacgc ccacaagagc gaggtggccc acagattcaa ggatctcggg   1680
gaggagaact tcaaggccct ggtgctgatc gccttcgcac agtacctgca gcagtgcccc   1740
ttcgaggacc acgtaaaact ggtgaacgag gtgacggagt tcgccaagac ctgtgttgcc   1800
gacgagtcgg ccgagaattg cgacaagagc ctgcataccc tgttcggcga caagctgtgc   1860
accgtggcca ccctgagaga gacctacggc gagatggccg actgctgcgc caagcaagag   1920
cccgagagaa acgagtgctt cctgcagcac aaggacgaca accccaacct gccccggctg   1980
gtgagacccg aggtggacgt gatgtgcacc gccttccacg acaacgagga gaccttcctg   2040
aagaagtatc tgtacgagat cgccagaaga cacccttatt tttacgcccc cgagctgctg   2100
ttcttcgcta agagatataa ggcagccttc accgagtgtt gtcaggccgc cgataaggcc   2160
gcttgcctgc tgcccaagtt ggacgagctc agagacgagg gcaaggcgag cagcgccaag   2220
cagagactga agtgcgccag cctgcagaag ttcggcgaga gggccttcaa ggcctgggcg   2280
gtggccagac tgtcccagag atttcccaag gccgagttcg ccgaggtaag caagctggtc   2340
accgacctga ccaaggtgca caccgagtgt tgccacggcg acctgctgga atgcgccgat   2400
gaccgtgccg acctggccaa gtacatctgc gagaatcagg actccatcag cagcaaactg   2460
aaggagtgtt gcgagaagcc cctgctggaa aagagccatt gcatcgctga ggtggaaaac   2520
```

gacgagatgc ccgcagacct gcccagcctg gccgcagact ttgtggaaag taaggacgtg 2580
tgcaagaact acgcggaggc caaagacgtg tttctgggca tgttcctata cgagtatgcc 2640
agaagacacc ccgactacag cgttgtgtta ttgctgagac tggccaagac ctacgagact 2700
accttggaga agtgctgcgc cgccgccgac ccccacgagt gctatgccaa ggtgttcgac 2760
gagttcaagc ccctggtgga ggagccccag aatctgatta agcagaattg cgagcttttt 2820
gagcagctgg gcgagtataa gttccagaac gccctgctgg tgagatacac caaaaaggta 2880
cctcaggtga gcacccccac cctggtggag gtgagcagaa atctgggcaa ggtgggcagc 2940
aagtgctgca agcacccgga ggccaagaga atgccctgtg ccgaggatta cctgtcagtg 3000
gtgctgaacc agctgtgcgt tctgcacgaa aagacgcccg tgtcggacag agtgaccaag 3060
tgctgcacgg agagcctggt gaacagaaga ccgtgcttca gcgccctaga ggtggacgag 3120
acctacgtgc ccaaggagtt caacgccgag accttcacct tccacgccga catctgtacc 3180
ctgtcagaga aggagagaca gatcaagaag cagaccgcct tagtggagct ggtgaagcac 3240
aagcccaagg ccaccaagga gcagctgaaa gccgtgatgg acgatttcgc agccttcgtc 3300
gagaagtgct gcaaggccga cgacaaggaa acttgcttcg ccgaggaggg caagaagctg 3360
gtggctgcct cgcaggccgc cctcggcctg 3390

<210> SEQ ID NO 21
<211> LENGTH: 3390
<212> TYPE: DNA
<213> ORGANISM: Artificial Sequence
<220> FEATURE:
<223> OTHER INFORMATION: B3 Construct

<400> SEQUENCE: 21
atgagggtcc ccgctcagct cctggggctc ctgctgctct ggctcccagg tgcacgatgt 60
gccatctggg agctgaagaa ggacgtgtac gtggtggagc tggactggta ccccgacgcc 120
cccggcgaga tggtggtgct gacctgcgac acccccgagg aggacggcat cacctggacc 180
ctggaccaga gcagcgaggt gctgggcagc ggcaagaccc tgaccatcca ggtgaaggag 240
ttcggcgacg ccggccagta cacctgccac aagggcggcg aggtgctgag ccacagcctg 300
ctgctgctgc acaagaagga ggacggcatc tggagcaccg acatcctgaa ggaccagaag 360
gagcccaaga acaagacctt cctgagatgc gaggccaaga actacagcgg cagattcacc 420
tgctggtggc tgaccaccat cagcaccgac ctgaccttca gcgtgaaaag cagcagaggc 480
agcagcgacc cccagggcgt gacctgcggc gccgccaccc tgagcgccga gagagtgaga 540
ggcgacaaca aggagtacga gtacagcgtg gagtgccagg aggacagcgc ctgccccgcc 600
gccgaggaga gcctgcccat cgaggtgatg gtggacgccg tgcacaagct gaagtacgag 660
aactacacca gcagcttctt catcagagac atcatcaagc ccgacccccc caagaacctg 720
cagctgaagc ccctgaagaa cagcagacag gtggaggtga gctgggagta ccccgacacc 780
tggagcaccc cccacagcta cttcagcctg accttctgcg tgcaggtgca gggcaagagc 840
aagagagaga agaaggacag agtgttcacc gacaagacca gcgccaccgt gatctgcaga 900
aagaacgcca gcatcagcgt gagagcccag gacagatact acagcagcag ctggagcgag 960
tgggccagcg tgccctgcag cggcggcagc ggcggcggca gcggcggcgg cagcggcggc 1020
ggcagcagaa acctgcccgt ggccaccccc gaccccggca tgttcccctg cctgcaccac 1080
agccagaacc tgctgagagc cgtgagcaac atgctgcaga aggccagaca gaccctggag 1140
ttctacccct gcaccagcga ggagatcgac cacgaggaca tcaccaagga caagaccagc 1200
accgtggagg cctgcctgcc cctggagctg accaagaacg agagctgcct gaacagcaga 1260
gagaccagct tcatcaccaa cggcagctgc ctggccagca gaaagaccag cttcatgatg 1320
gccctgtgcc tgagcagcat ctacgaggac ctgaagatgt accaggtgga gttcaagacc 1380
atgaacgcca agctgctgat ggaccccaag agacagatct tcctggacca gaacatgctg 1440
gccgtgatcg acgagctgat gcaggccctg aacttcaaca gcgagaccgt gccccagaaa 1500
agcagcctgg aggagcccga cttctacaag accaagatca agctgtgcat cctgctgcac 1560
gccttcagaa tcagagccgt gaccatcgac agagtgatga gctacctgaa cgccagcggc 1620
agcggcggcg gcagcgacgc ccacaagagc gaggtggccc acagattcaa ggacctgggc 1680
gaggagaact tcaaggccct ggtgctgatc gccttcgccc agtacctgca gcagtgcccc 1740
ttcgaggacc acgtgaagct ggtgaacgag gtgaccgagt tcgccaagac ctgcgtggcc 1800
gacgagagcg ccgagaactg cgacaagagc ctgcacaccc tgttcggcga caagctgtgc 1860
accgtggcca ccctgagaga gacctacggc gagatggccg actgctgcgc caagcaggag 1920
cccgagagaa acgagtgctt cctgcagcac aaggacgaca accccaacct gcccagactg 1980
gtgagacccg aggtggacgt gatgtgcacc gccttccacg acaacgagga gaccttcctg 2040
aagaagtacc tgtacgagat cgccagaaga cacccctact tctacgcccc cgagctgctg 2100
ttcttcgcca agagatacaa ggccgccttc accgagtgct gccaggccgc cgacaaggcc 2160
gcctgcctgc tgcccaagct ggacgagctg agagacgagg gcaaggccag cagcgccaag 2220
cagagactga agtgcgccag cctgcagaag ttcggcgaga gagccttcaa ggcctgggcc 2280
gtggccagac tgagccagag attccccaag gccgagttcg ccgaggtgag caagctggtg 2340
accgacctga ccaaggtgca caccgagtgc tgccacggcg acctgctgga gtgcgccgac 2400
gacagagccg acctggccaa gtacatctgc gagaaccagg acagcatcag cagcaagctg 2460
aaggagtgct gcgagaagcc cctgctggag aaaagccact gcatcgccga ggtggagaac 2520
gacgagatgc ccgccgacct gcccagcctg gccgccgact tcgtggagag caaggacgtg 2580
tgcaagaact acgccgaggc caaggacgtg ttcctgggca tgttcctgta cgagtacgcc 2640
agaagacacc ccgactacag cgtggtgctg ctgctgagac tggccaagac ctacgagacc 2700
accctggaga agtgctgcgc cgccgccgac ccccacgagt gctacgccaa ggtgttcgac 2760
gagttcaagc ccctggtgga ggagccccag aacctgatca agcagaactg cgagctgttc 2820
gagcagctgg gcgagtacaa gttccagaac gccctgctgg tgagatacac caagaaggtg 2880
ccccaggtga gcacccccac cctggtggag gtgagcagaa acctgggcaa ggtgggcagc 2940
aagtgctgca agcaccccga ggccaagaga atgccctgcg ccgaggacta cctgagcgtg 3000
gtgctgaacc agctgtgcgt gctgcacgag aagacccccg tgagcgacag agtgaccaag 3060
tgctgcaccg agagcctggt gaacagaaga ccctgcttca gcgccctgga ggtggacgag 3120
acctacgtgc ccaaggagtt caacgccgag accttcacct tccacgccga catctgcacc 3180
ctgagcgaga aggagagaca gatcaagaag cagaccgccc tggtggagct ggtgaagcac 3240
aagcccaagg ccaccaagga gcagctgaag gccgtgatgg acgacttcgc cgccttcgtg 3300
gagaagtgct gcaaggccga cgacaaggag acctgcttcg ccgaggaggg caagaagctg 3360
gtggccgcca gccaggccgc cctgggcctg 3390

<210> SEQ ID NO 22
<211> LENGTH: 3390
<212> TYPE: DNA

<213> ORGANISM: Artificial Sequence
<220> FEATURE:
<223> OTHER INFORMATION: B4 Construct

<400> SEQUENCE: 22
atgagggtcc ccgctcagct cctggggctc ctgctgctct ggctcccagg tgcacgatgt 60
gccatctggg agctgaagaa ggatgtgtat gtggtggagc tggactggta cccagatgcc 120
cctggagaga tggtggtgct gacctgtgac accccagagg aggatggcat cacctggacc 180
ctggaccaga gcagcgaggt gctgggcagc ggcaagaccc tgaccatcca ggtgaaggag 240
tttggagatg ctggccagta cacctgccac aagggcgggg aggtgctgag ccacagcctg 300
ctgctgctgc acaagaagga ggatggcatc tggagcacag acatcctgaa ggaccagaag 360
gagcccaaga acaagacctt cctgcgctgt gaggccaaga actacagcgg ccgcttcacc 420
tgctggtggc tgaccaccat cagcacagac ctgaccttct ctgtgaaaag cagccggggc 480
agcagtgacc cccagggcgt gacctgtggg gccgccaccc tgtctgctga gcgggtgcgg 540
ggggacaaca aggagtatga gtacagcgtg gagtgccagg aggacagcgc ctgcccagct 600
gctgaggaga gcctgcccat cgaggtgatg gtggatgctg tgcacaagct gaagtatgag 660
aactacacca gcagcttctt catccgggac atcatcaagc cagacccccc caagaacctg 720
cagctgaagc ccctgaagaa cagccggcag gtggaggtgt cctgggagta cccagacacc 780
tggagcaccc cccacagcta cttcagcctg accttctgtg tgcaggtgca gggcaagagc 840
aagcgggaga agaaggacag agtcttcaca gacaagacca gcgccaccgt catctgcagg 900
aagaatgcca gcatctctgt gcgggcccag gaccgctact acagcagctc ctggagcgag 960
tgggcctctg tgccctgcag cggcggcagc ggcggcggca gcggcggcgg cagcggcggc 1020
ggcagcagga acctgcctgt ggccacccca gaccccggca tgttcccctg cctgcaccac 1080
agccagaacc tgctgcgggc tgtgagcaac atgctgcaga aggcccggca gaccctggag 1140
ttctacccct gcaccagcga ggagattgac cacgaggaca tcaccaagga caagaccagc 1200
acagtggagg cctgcctgcc cctggagctg accaagaatg aaagctgcct gaacagccgg 1260
gagaccagct tcatcaccaa cggcagctgc ctggccagca ggaagaccag cttcatgatg 1320
gccctgtgcc tgagcagcat ctatgaggac ctgaagatgt accaggtgga gttcaagacc 1380
atgaatgcca agctgctgat ggaccccaag aggcagatct tcctggacca gaacatgctg 1440
gccgtgattg atgagctgat gcaggccctg aacttcaaca gcgagaccgt gccccagaaa 1500
agcagcctgg aggagccaga cttctacaag accaagatca agctgtgcat cctgctgcac 1560
gccttccgca tccgggctgt gaccatcgac agagtgatga gctacctgaa tgccagcggc 1620
agcggcggcg gcagtgatgc ccacaagtct gaggtggccc accgcttcaa ggacctgggg 1680
gaggagaact tcaaggccct ggtgctgatt gcctttgccc agtacctgca gcagtgcccc 1740
tttgaggacc acgtgaagct ggtgaatgag gtgacagaat ttgccaagac ctgtgtggct 1800
gatgaatctg ctgagaactg tgacaagagc ctgcacaccc tgtttggaga caagctgtgc 1860
accgtggcca ccctgcggga gacctatgga gagatggctg actgctgtgc caagcaggag 1920
cctgagagaa atgaatgctt cctgcagcac aaggatgaca accccaacct gccccggctg 1980
gtgcggcctg aggtggatgt gatgtgcaca gccttccatg acaatgagga gaccttcctg 2040
aagaagtacc tgtatgaaat tgcccggcgg cacccctact tctacgcccc tgagctgctg 2100
ttctttgcca agcgctacaa ggccgccttc acagagtgct gccaggccgc tgacaaggcc 2160
gcctgcctgc tgcccaagct ggatgagctg agagatgagg gcaaggccag cagcgccaag 2220

```
cagaggctga agtgtgccag cctgcagaag tttggagagc gggccttcaa ggcctgggcc   2280
gtggcccggc tgagccagcg cttccccaag gccgagtttg ctgaggtgtc caagctggtg   2340
acagacctga ccaaggtgca cacagagtgc tgccacgggg acctgctgga gtgtgctgat   2400
gacagagctg acctggccaa gtacatctgt gagaaccagg acagcatcag cagcaagctg   2460
aaggagtgct gtgagaagcc cctgctggaa aagagccact gcatcgccga ggtggagaat   2520
gatgagatgc ctgctgacct gcccagcctg gccgctgact ttgtggagag caaggatgtg   2580
tgcaagaact atgcagaggc caaggatgtg ttcctgggca tgttcctgta tgaatatgcc   2640
cggcggcacc cagactacag cgtggtgctg ctgctgcggc tggccaagac ctatgagacc   2700
accctggaga agtgctgtgc cgctgctgac ccccatgaat gttatgccaa ggtgtttgat   2760
gagttcaagc ccctggtgga ggagccccag aacctgatca agcagaactg tgagctgttt   2820
gagcagctgg gggagtacaa gttccagaat gccctgctgg tgcgctacac caagaaggtg   2880
ccccaggtgt ccacccccac cctggtggag gtgtccagga acctgggcaa ggtgggcagc   2940
aagtgctgca agcaccctga ggccaagagg atgccctgtg ccgaggacta cctgtctgtg   3000
gtgctgaacc agctgtgtgt gctgcacgag aagacccctg tgtctgacag agtgaccaag   3060
tgctgcacag agagcctggt gaacagaaga ccctgcttca gcgccctgga ggtggatgag   3120
acctacgtgc ccaaggagtt caatgctgag accttcacct tccacgccga catctgcacc   3180
ctgtctgaga aggagcggca gatcaagaag cagacagccc tggtggagct ggtgaagcac   3240
aagcccaagg ccaccaagga gcagctgaag gctgtgatgg atgactttgc tgcctttgtg   3300
gagaagtgct gcaaggcaga tgacaaggag acctgctttg ctgaggaggg caagaagctg   3360
gtggccgcca gccaggccgc cctgggcctg                                     3390
```

<210> SEQ ID NO 23
<211> LENGTH: 4374
<212> TYPE: DNA
<213> ORGANISM: Artificial Sequence
<220> FEATURE:
<223> OTHER INFORMATION: C1 Construct

<400> SEQUENCE: 23

```
atgagggtcc ccgctcagct cctggggctc ctgctgctct ggctcccagg tgcacgatgt     60
gccatctggg agctgaaaaa ggacgtgtac gtggtggaac ttgactggta ccccgacgcc    120
cccggcgaga tggtggtact gacctgcgac actcccgagg aagacggcat tacctggacc    180
ttggaccaga gcagcgaggt tctgggctcc ggaaaaacct tgacaatcca agtgaaagaa    240
ttcggcgacg ctggccagta cacctgccac aagggcggcg aggtgctgtc ccacagcctg    300
ctgctgctgc ataagaaaga agacgggatt tggagcaccg atatactgaa ggatcagaag    360
gagcccaaga acaagacctt cctgaggtgc gaggccaaaa attacagcgg cagattcacc    420
tgctggtggc tgaccaccat tagcacagac ctgactttca gcgtaaagtc ttcaaggggc    480
agctcagacc cccagggagt aacttgcgga gcggcaacgt tgtctgccga gcgggtcaga    540
ggcgacaata aggagtacga gtattcagta gagtgtcagg aagatagcgc ctgtcccgcc    600
gcggaggaga gcctccccat cgaggtgatg gtggacgccg tgcacaagtt aaagtacgag    660
aattacacca gctcattttt tatcagagac attatcaagc cggaccccccc gaagaactta    720
cagcttaaac ccctaaagaa cagcaggcag gttgaggtca gctgggaata tcctgacacc    780
tggtcaaccc cccacagcta cttctccctt actttctgtg tgcaagtgca gggcaagagc    840
```

aagagagaaa agaaggaccg ggtgtttacc gacaagacta gcgccaccgt gatttgcaga 900
aagaacgcca gcattagtgt gagagcccag gacaggtatt actccagctc atggtctgag 960
tgggctagtg tgccttgctc tggaggcagc ggtggcggga gcggcggagg ctccggggga 1020
ggtagccgga atctgcctgt cgccactcca gaccccggca tgttcccatg tctgcatcat 1080
tctcagaacc tgctgagggc cgtatccaat atgctgcaga aagccagaca gaccttagag 1140
ttctatccct gtacaagcga ggagatagat cacgaggata ttacgaagga caaaacttct 1200
actgttgagg cgtgtcttcc attagagctg accaagaacg aaagctgtct gaatagcaga 1260
gagacttcat ttatcaccaa tgggagttgc ttggctagca gaaagaccag cttcatgatg 1320
gccctttgct tgtcttcgat atacgaagat cttaagatgt atcaagtgga atttaagacg 1380
atgaacgcca agctgcttat ggatcccaag cgccaaatct tcctggatca gaacatgttg 1440
gccgtgattg acgagctgat gcaagccctg aatttcaact ccgagaccgt gcctcagaaa 1500
agcagcctcg aggagcccga cttctacaaa acaaagatca aactctgcat ccttctgcac 1560
gccttcagaa ttagagccgt gaccatcgac agagttatga gctacctgaa tgccagcggc 1620
agcggcggcg gatccgatgc ccataaatct gaggtggccc atagattcaa ggatctgggc 1680
gaagaaaact tcaaagcctt ggtcttgatc gcctttgccc agtacctgca gcagtgcccc 1740
tttgaggacc acgtgaagct ggtgaatgaa gtgaccgagt ttgccaagac gtgcgtggct 1800
gatgagagcg ccgaaaactg cgacaaaagc ctgcacaccc tgtttggcga caagctgtgc 1860
accgtagcca ccctgagaga aacttacggc gagatggctg actgctgcgc caagcaggag 1920
cccgagagaa acgagtgctt tctgcagcac aaggacgaca atcccaacct gcccagactg 1980
gtgagacccg aagtggatgt tatgtgcacc gctttccacg acaatgaaga gacatttctc 2040
aagaagtact tgtacgagat tgcaagaaga caccccttact tttacgcccc cgaattactg 2100
ttcttcgcta agaggtataa ggcagccttc actgaatgct gccaggctgc cgacaaagca 2160
gcttgcctgc tgccaaagct ggatgaactg cgagacgaag gaaaggcgtc ctccgccaag 2220
cagcgtttga agtgcgccag ccttcagaag tttggcgagc gggccttcaa ggcatgggcc 2280
gtggctcgac ttagccagcg ttttcccaag gctgaatttg cagaggtgag taaactggtt 2340
accgatctga caaaggtgca caccgagtgc tgtcacggtg acctcttaga gtgcgccgac 2400
gacagagccg acctcgccaa gtacatttgt gaaaaccaag actcaatctc ttcaaagtta 2460
aaggagtgct gcgaaaagcc cctgcttgaa aagagccact gcattgccga agtcgagaat 2520
gatgagatgc ctgcagactt gcccagcttg gcagccgact tcgttgagtc taaggacgtg 2580
tgcaagaatt acgccgaggc aaaagacgtg ttcctgggca tgttccttta tgagtacgct 2640
agaagacatc ccgactacag cgtggtcctt ctccttaggc tcgctaagac ttacgagacg 2700
acgttggaga agtgttgtgc cgctgcggac cccacgagt gctatgccaa agtgttcgat 2760
gagtttaaac ccctggtgga ggaacctcag aaccttatca agcagaattg tgagttgttc 2820
gaacagctag gcgagtacaa gttccagaat gccctgctgg tgagatacac aaaaaaggtg 2880
ccccaggtgt caaccccgac cttagtggaa gtgtccagaa acctgggcaa ggtgggcagc 2940
aagtgctgca agcaccccga agctaagaga atgccgtgcg cggaggatta cctgagcgtg 3000
gtgctcaacc agctgtgtgt gcttcacgag aaaacacccg tgagcgacag ggtgacaaaa 3060
tgttgcacag aaagccttgt gaaccggaga ccttgtttca gcgccctgga ggttgacgag 3120
acctatgttc ctaaggagtt caacgctgag actttcacat ttcacgctga tatatgtacc 3180
ctgagcgaga aagaaagaca gatcaagaag cagaccgccc tggtcgagct ggtgaaacac 3240
aagcctaagg ccacgaagga gcagctgaag gccgtcatgg acgacttcgc agccttcgtc 3300
gagaaatgct gcaaagccga cgacaaggaa acctgcttcg ccgaagaggg aaagaagctg 3360
gtggccgcct cccaggccgc ccttgggctc ggtggcgggt ctggtggcgg ttctcagtac 3420
tacgattacg acttcccccct gagtatctac ggtcagtcct cacctaactg cgccccagag 3480
tgtaactgcc ccgaaagcta cccgagcgcc atgtactgcg acgagctgaa gttgaagtcc 3540
gtgcccatgg tgcccccagg catcaagtac ttatacttga ggaacaacca aatcgatcat 3600
atcgacgaga aggccttcga aaacgtaacc gacctgcagt ggctgatact ggatcacaat 3660
ctgctagaga attccaagat caagggcaga gtgttctcga agctgaaaca actgaagaag 3720
ctgcacatca accataacaa tctcaccgag agcgtgggtc ccctgcccaa gtcgctggag 3780
gacctgcagc tgacccacaa caaaataacc aaactaggca gcttcgaggg gttggtgaat 3840
ctgaccttca tccatttgca gcataacaga ctaaaggagg atgccgtgag cgccgccttc 3900
aaaggcctca agagccttga gtacctggac ctgagcttca accagatcgc ccggctgccc 3960
agtgggctgc ccgtgagcct gctgacgctg tatctggaca ataacaaaat cagcaacatc 4020
cccgacgaat acttcaaaag attcaacgcc ttacagtacc tgcgactcag ccacaatgag 4080
ctcgctgaca gcggcatccc tggcaacagc ttcaacgtgt catccctggt ggagctggac 4140
ctgagttaca ataagctgaa gaacatccca actgtcaatg agaatttgga aaactactac 4200
ctggaggtga accagctgga gaagttcgac attaagagct tttgcaaaat cctgggccca 4260
ctgtcatata gcaagatcaa gcacctgcga ctggacggca accgaatcag tgaaacttcc 4320
ctaccccctg acatgtacga gtgcctgaga gtagcaaatg aggtgaccct gaac 4374

<210> SEQ ID NO 24
<211> LENGTH: 4374
<212> TYPE: DNA
<213> ORGANISM: Artificial Sequence
<220> FEATURE:
<223> OTHER INFORMATION: C2 Construct

<400> SEQUENCE: 24
atgagggtcc ccgctcagct cctggggctc ctgctgctct ggctcccagg tgcacgatgt 60
gccatctggg agctgaagaa agacgtgtac gtggtggagc ttgactggta ccccgacgcc 120
cccggtgaaa tggtggttct gacctgcgac acaccagagg aggacggcat cacctggacc 180
ctggaccagt ccagcgaggt cctgggatct ggcaagaccc tgaccatcca ggttaaggaa 240
tttggcgacg ccggccagta cacctgccac aaaggcggcg aggtcctttc gcacagtctg 300
ctgctgctgc ataaaaagga ggacggcatt tggagcaccg acattctgaa ggatcagaaa 360
gagcccaaga acaagacctt tctgagatgt gaggccaaaa actactctgg acgcttcacc 420
tgttggtggc tgaccaccat cagcacagac ctgaccttct cggtgaagtc tagtaggggc 480
agcagtgacc cccagggcgt aacatgcggc gccgctaccc tgagcgccga gagagtgaga 540
ggcgataaca aggagtacga gtactccgtg gagtgccaag aggactcagc ctgccccgcc 600
gccgaggagt cgctgcccat cgaggtgatg gtggatgcag tgcacaagct gaagtacgag 660
aactacacca gtagcttttt catcagagat atcattaaac ccgaccctcc caagaacctg 720
cagctgaagc ccttaaagaa cagccggcag gtggaagtgt catgggagta cccagacacc 780
tggagcactc cgcacagcta cttcagcctg accttctgcg ttcaggtgca gggaaaaagc 840
aagagagaga agaaagacag agtgttcacc gacaagacca gcgcaaccgt gatctgtaga 900
aagaacgcct cgatcagcgt gagagcccag gacagatact acagcagcag ctggagcgag 960
tgggccagtg taccttgcag cggtggaagc ggcggaggct ctggcggagg gagtggcgga 1020
ggcagcagaa atcttccagt agctaccccc gaccccggca tgtttccctg tctgcaccat 1080
tctcaaaacc tgttacgggc cgtgagcaac atgctgcaga aggccagaca gacactggag 1140
ttttacccct gtacctcaga ggagatcgat catgaggaca ttactaagga caagaccagc 1200
accgtggaag cctgcctgcc cctagagcta accaagaacg agagctgcct gaactctaga 1260
gagacaagct tcatcacgaa cggctcatgc ctggccagta ggaaaaccag cttcatgatg 1320
gctctgtgcc tgagctccat atatgaggac cttaagatgt accaggtgga gttcaaaacc 1380
atgaacgcca agctgctgat ggacccaaag agacagatct tccttgacca gaacatgctg 1440
gccgttatcg atgagctgat gcaggccctg aacttcaaca gcgagaccgt gccccagaaa 1500
agcagcctgg aggaacccga cttctacaaa accaagatca agctgtgcat tctgctgcat 1560
gccttccgca ttagagccgt gaccatcgat agggtgatga gctacctgaa cgccagcggc 1620
tctggcggcg gcagtgacgc ccacaagtcc gaggtcgccc acagattcaa ggatttgggc 1680
gaggagaact tcaaggccct ggtgctgatc gccttcgccc agtacttgca gcagtgtccc 1740
ttcgaggacc atgtgaagct ggtgaacgag gtgaccgagt tcgccaagac ctgtgtggcc 1800
gacgagagcg ccgagaactg cgataagtct ctgcacaccc tttttggcga caaactgtgc 1860
accgtggcca ccctgagaga gacctacggc gagatggccg actgctgtgc gaagcaggag 1920
cccgagcgca atgagtgttt cctgcagcat aaggacgaca accccaacct gcccagactg 1980
gtgagacccg aggtggacgt gatgtgcacc gccttccacg acaacgagga gacctttctg 2040
aaaaaatacc tgtacgagat cgcaagacgc cacccctact tctacgcccc cgagctgctg 2100
ttcttcgcca agcgctacaa ggctgccttc accgaatgct gccaggccgc cgataaggcc 2160
gcgtgcttac tgccaaagct ggacgagctg agagacgagg ggaaagcctc tagcgccaaa 2220
cagagattga agtgtgccag cctgcagaaa ttcggtgaga gagccttcaa ggcctgggcc 2280
gtggccagat tatcacagcg gttccccaag gctgaattcg ccgaggtgag caaacttgtc 2340
accgatctga caaaagtgca caccgagtgc tgccatggcg acctgctgga gtgcgccgac 2400
gaccgggccg acctggccaa gtacatctgc gagaaccagg acagcatctc cagcaagctg 2460
aaggagtgct gcgagaagcc cctgctggag aaaagccact gcatcgccga ggtggagaat 2520
gacgaaatgc ccgccgacct gcccagcctg gccgccgact tcgtggaaag caaggacgtg 2580
tgcaaaaatt acgccgaagc caaggatgtg ttcttgggca tgttcttgta cgagtacgcc 2640
agacgccacc ccgactacag cgtggtgctg ctgctgcggc tggccaagac ctacgagacc 2700
accctggaga agtgctgtgc tgccgccgac ccccacgagt gctacgccaa ggtatttgac 2760
gagttcaagc ccctggtgga ggagcctcag aacctgatta agcagaactg tgagctgttc 2820
gagcagctgg gcgagtacaa gttccagaac gccctcctgg tgagatacac caaaaaggtg 2880
cctcaggtaa gcactcccac cctggtggag gtgagcagga acctcggcaa ggtgggcagc 2940
aaatgctgca agcacccaga ggccaaaaga atgccctgcg cagaagacta cctcagcgtg 3000
gtcctgaacc agctgtgcgt gctgcacgaa aagacccctg tgagcgatag agtgacaaag 3060
tgctgcaccg agagcctggt gaacagaaga ccctgtttta gcgccctgga ggtggacgag 3120
acctacgtgc ccaaggagtt caacgccgag acgttcactt tccacgcgga catctgcacc 3180
ctgagcgaga aggagagaca aatcaagaag cagaccgccc tagtcgagct ggtaaaacac 3240
aagcccaagg ccaccaagga gcagctgaag gccgtgatgg acgactttgc agccttcgtg 3300
gagaagtgct gcaaggctga cgacaaggag acctgcttcg ccgaggaggg caagaagctc 3360
gtagccgcca gccaggccgc tctcggcctt ggtggcgggt ctggtggcgg ttctcagtat 3420
tacgactacg atttccccct gagcatctat ggccagagca gccctaactg cgccccggag 3480
tgcaactgcc ccgaaagcta cccaagcgcc atgtactgcg atgagctgaa gctgaagtct 3540
gtgcctatgg tgcctcccgg catcaagtac ctgtacctga gaaacaacca gatagaccac 3600
atcgatgaga aagccttcga gaacgtcacc gacctgcagt ggctgattct ggaccacaat 3660
ttactggaga actccaagat caagggcaga gtgttctcca agttaaagca gctgaagaaa 3720
ctgcacatca atcacaacaa cctgaccgag agcgtgggcc cactgcccaa gagcctagag 3780
gatctgcagc tcacccacaa caagatcact aagttgggca gcttcgaggg cctcgtaaac 3840
ttgacattca tacatctgca gcacaacaga cttaaggaag acgccgtgag tgcggccttt 3900
aagggtctga aaagcctgga gtacttagac ctgagcttca accagatcgc aaggctgccc 3960
agcggccttc cggtcagtct gctgaccctg tatctggaca acaacaagat cagcaacatc 4020
cccgacgagt acttcaagcg gtttaacgcc ctccagtacc tgagactgag ccacaacgag 4080
ttagctgact cgggcatacc cggtaacagc ttcaatgtta gcagcctagt tgagcttgac 4140
ttgagctaca acaagcttaa gaacatccca accgtgaacg agaacctcga gaattactac 4200
ctggaagtca accagctgga gaagttcgac attaagagct tctgcaaaat cctgggccca 4260
ctgtcctata gcaagatcaa gcacctgcgc cttgacggaa acagaattag cgagaccagc 4320
cttccaccag acatgtacga gtgcctgagg gtggccaacg aggtgaccct gaac 4374

<210> SEQ ID NO 25
<211> LENGTH: 4374
<212> TYPE: DNA
<213> ORGANISM: Artificial Sequence
<220> FEATURE:
<223> OTHER INFORMATION: C3 Construct

<400> SEQUENCE: 25
atgagggtcc ccgctcagct cctggggctc ctgctgctct ggctcccagg tgcacgatgt 60
gccatctggg aactgaagaa ggacgtctac gtggtggagc tggattggta ccccgacgcc 120
cccggcgaga tggtcgtgct gacctgtgac acccctgagg aggacggaat cacatggacc 180
ctggaccaga gcagcgaagt gttgggcagc ggcaagaccc tgaccatcca agtgaaggaa 240
ttcggcgacg cgggccagta tacttgccac aagggcgggg aggttctgag ccacagcctg 300
ctgctgctcc acaagaaaga ggatggcatc tggtctaccg acatcctgaa ggaccaaaag 360
gagccaaaga acaagacctt cctaagatgc gaggccaaga actactcagg tcgtttcacc 420
tgctggtggc tgaccacaat ctccaccgac ctgaccttca gcgtgaaaag cagccgcggc 480
agtagcgacc cacagggcgt gacctgcggg gccgccactc tgagcgccga gagagtgcgc 540
ggcgataata aggaatacga gtacagcgtg gagtgccagg aagactcagc ctgccccgcc 600
gcagaagaaa gtctgccaat agaggtgatg gttgacgccg tgcacaagct aaagtacgag 660
aactacacca gcagcttctt tatccgggac atcatcaagc cagatccccc caagaacctg 720
cagcttaagc ccctgaagaa cagcagacag gtggaggtgt catgggaata ccccgacacc 780
tggagcaccc cccatagcta cttctcactg accttctgcg tgcaggtgca gggcaagagc 840
aagagagaga agaaggatag ggtattcacg gacaagacct cagccaccgt gatctgccga 900
aagaacgcca gcatcagcgt gagagcccag gacagatact atagctcctc gtggagcgag 960

```
tgggccagcg taccttgcag cggcgggagc ggcggcggca gcggaggtgg cagtggcgga   1020
ggcagcagaa acctccccgt ggcaacccct gaccccggga tgtttccttg cctgcaccac   1080
tcccagaacc tcctgagagc cgtgtccaac atgctgcaga aagccagaca gaccctcgag   1140
ttctatccct gcacaagcga ggagatcgac cacgaggaca tcactaagga caagaccagc   1200
acagtggaag cctgcctccc gctggagctg actaagaacg agagctgtct gaacagcagg   1260
gagaccagct tcatcaccaa cggcagctgc ctggcgagca gaaaaacctc ctttatgatg   1320
gcgctctgcc tgagctcaat ctatgaggac ctgaagatgt accaggtgga gtttaaaacc   1380
atgaatgcca agctgcttat ggaccctaag agacagattt tcctggatca gaacatgctg   1440
gccgtgattg atgaattaat gcaggcgctg aactttaaca gcgagaccgt gccccagaaa   1500
agcagcctgg aggagcccga cttttacaag accaagatca agttgtgcat cctcctgcac   1560
gccttcagaa tcagagcggt gacgatcgac agagtcatga gctacctcaa cgctagcggc   1620
agcggtggcg gcagcgacgc ccacaagagc gaggtggccc acagattcaa ggatctcggg   1680
gaggagaact tcaaggccct ggtgctgatc gccttcgcac agtacctgca gcagtgcccc   1740
ttcgaggacc acgtaaaact ggtgaacgag gtgacggagt tcgccaagac ctgtgttgcc   1800
gacgagtcgg ccgagaattg cgacaagagc ctgcataccc tgttcggcga caagctgtgc   1860
accgtggcca ccctgagaga gacctacggc gagatggccg actgctgcgc caagcaagag   1920
cccgagagaa acgagtgctt cctgcagcac aaggacgaca accccaacct gccccggctg   1980
gtgagacccg aggtggacgt gatgtgcacc gccttccacg acaacgagga gaccttcctg   2040
aagaagtatc tgtacgagat cgccagaaga cacccttatt tttacgcccc cgagctgctg   2100
ttcttcgcta agagatataa ggcagccttc accgagtgtt gtcaggccgc cgataaggcc   2160
gcttgcctgc tgcccaagtt ggacgagctc agagacgagg gcaaggcgag cagcgccaag   2220
cagagactga agtgcgccag cctgcagaag ttcggcgaga gggccttcaa ggcctgggcg   2280
gtggccagac tgtcccagag atttcccaag gccgagttcg ccgaggtaag caagctggtc   2340
accgacctga ccaaggtgca caccgagtgt tgccacggcg acctgctgga atgcgccgat   2400
gaccgtgccg acctggccaa gtacatctgc gagaatcagg actccatcag cagcaaactg   2460
aaggagtgtt gcgagaagcc cctgctggaa aagagccatt gcatcgctga ggtggaaaac   2520
gacgagatgc ccgcagacct gcccagcctg gccgcagact ttgtggaaag taaggacgtg   2580
tgcaagaact acgcggaggc caaagacgtg tttctgggca tgttcctata cgagtatgcc   2640
agaagacacc ccgactacag cgttgtgtta ttgctgagac tggccaagac ctacgagact   2700
accttggaga agtgctgcgc cgccgccgac ccccacgagt gctatgccaa ggtgttcgac   2760
gagttcaagc ccctggtgga ggagccccag aatctgatta agcagaattg cgagcttttt   2820
gagcagctgg gcgagtataa gttccagaac gccctgctgg tgagatacac caaaaaggta   2880
cctcaggtga gcacccccac cctggtggag gtgagcagaa atctgggcaa ggtgggcagc   2940
aagtgctgca agcacccgga ggccaagaga atgccctgtg ccgaggatta cctgtcagtg   3000
gtgctgaacc agctgtgcgt tctgcacgaa aagacgcccg tgtcggacag agtgaccaag   3060
tgctgcacgg agagcctggt gaacagaaga ccgtgcttca gcgccctaga ggtggacgag   3120
acctacgtgc ccaaggagtt caacgccgag accttcacct tccacgccga catctgtacc   3180
ctgtcagaga aggagagaca gatcaagaag cagaccgcct tagtggagct ggtgaagcac   3240
aagcccaagg ccaccaagga gcagctgaaa gccgtgatgg acgatttcgc agccttcgtc   3300
gagaagtgct gcaaggccga cgacaaggaa acttgcttcg ccgaggaggg caagaagctg   3360
```

gtggctgcct cgcaggccgc cctcggcctg ggtggcgggt ctggtggcgg ttctcagtac 3420
tacgactacg atttccccct atccatctac gggcagagct cgcctaactg cgcccccgag 3480
tgtaactgcc ccgagtcgta ccccagcgcc atgtactgtg acgagctgaa gctgaaaagc 3540
gtgcccatgg tgcccccggg catcaagtac ctgtacttga gaaacaacca gatcgaccac 3600
attgacgaaa aggccttcga gaacgtaacc gacctgcagt ggctgatcct ggaccacaac 3660
ctgcttgaga acagcaagat caagggccgc gtgttcagca agctgaagca gctgaagaag 3720
ctgcacatca accacaacaa cttgactgag tctgttggcc ccctaccaaa gagcctggag 3780
gacctgcagc tgacccacaa taagataacc aagctgggct cattcgaggg cctggtgaac 3840
ttgaccttta ttcacctgca gcataacaga ctgaaggagg acgccgtgag cgccgccttt 3900
aaggggctga aaagcctgga gtacctggac ctgagtttta accagatcgc cagactgccc 3960
tcaggcctgc ccgtgagttt gctgactctg tacctggaca acaataagat cagcaacatt 4020
cctgacgagt atttcaaaag attcaatgct ctgcagtacc tgagactaag ccacaacgag 4080
ctggccgaca gcggaatccc cggcaacagc ttcaacgtga gcagcttggt ggagttggac 4140
ctgagctaca acaaactgaa gaacatcccc accgtcaatg agaacttgga gaattactac 4200
ctcgaggtta accagcttga gaagttcgac atcaagagct tctgcaagat cctgggcccc 4260
ctcagctaca gcaagatcaa gcacttgaga ctggacggga acagaatcag cgaaaccagc 4320
cttcctcccg acatgtacga gtgccttaga gtggcaaatg aggtgaccct gaac 4374

<210> SEQ ID NO 26
<211> LENGTH: 63
<212> TYPE: DNA
<213> ORGANISM: Artificial Sequence
<220> FEATURE:
<223> OTHER INFORMATION: Leader Sequence of L1

<400> SEQUENCE: 26
atgcgagttc ctgctcagct gcttggtctg ttactgctgt ggttgccggg cgcacgatgt 60
gct 63

<210> SEQ ID NO 27
<211> LENGTH: 63
<212> TYPE: DNA
<213> ORGANISM: Artificial Sequence
<220> FEATURE:
<223> OTHER INFORMATION: Leader Sequence of L2

<400> SEQUENCE: 27
atgcgcgtgc ccgcacaatt gctcggactg ctgctactgt ggctgcccgg ggctcgctgc 60
gca 63

<210> SEQ ID NO 28
<211> LENGTH: 63
<212> TYPE: DNA
<213> ORGANISM: Artificial Sequence
<220> FEATURE:
<223> OTHER INFORMATION: Leader Sequence of L3

<400> SEQUENCE: 28
atgagagttc ctgctcaact actagggctg ctgttgttgt ggttgcccgg cgcgcgatgc 60
gca 63

<210> SEQ ID NO 29

<211> LENGTH: 63
<212> TYPE: DNA
<213> ORGANISM: Artificial Sequence
<220> FEATURE:
<223> OTHER INFORMATION: Leader Sequence of M1

<400> SEQUENCE: 29
atgagagtcc ccgcccagct gctggggctt cttttgcttt ggcttcctgg cgcaagatgc 60
gct 63

<210> SEQ ID NO 30
<211> LENGTH: 63
<212> TYPE: DNA
<213> ORGANISM: Artificial Sequence
<220> FEATURE:
<223> OTHER INFORMATION: Leader Sequence of M2

<400> SEQUENCE: 30
atgagagtcc ccgcccagct gctagggctg ctgctgctgt ggttacccgg cgcccggtgt 60
gca 63

<210> SEQ ID NO 31
<211> LENGTH: 63
<212> TYPE: DNA
<213> ORGANISM: Artificial Sequence
<220> FEATURE:
<223> OTHER INFORMATION: Leader Sequence of M3

<400> SEQUENCE: 31
atgagagtcc cagctcagct gctgggccta ctgctgctat ggctccccgg cgcgcggtgc 60
gcc 63

<210> SEQ ID NO 32
<211> LENGTH: 65
<212> TYPE: DNA
<213> ORGANISM: Artificial Sequence
<220> FEATURE:
<223> OTHER INFORMATION: Leader Sequence of H1

<400> SEQUENCE: 32
cvatgagagt gcccgcccag ttgcttggcc tgctgctcct atggcttccc ggcgccagat 60
gcgcc 65

<210> SEQ ID NO 33
<211> LENGTH: 63
<212> TYPE: DNA
<213> ORGANISM: Artificial Sequence
<220> FEATURE:
<223> OTHER INFORMATION: Leader Sequence of H2

<400> SEQUENCE: 33
atgagagtgc ccgcccagct gctgggcctg ctgctcttat ggctgcccgg cgcccgctgt 60
gct 63

<210> SEQ ID NO 34
<211> LENGTH: 63
<212> TYPE: DNA
<213> ORGANISM: Artificial Sequence
<220> FEATURE:
<223> OTHER INFORMATION: Leader Sequence of H3

<400> SEQUENCE: 34
atgagagtgc ccgcccagct gctgggcctg ctgttgctgt ggctgcccgg cgccagatgc 60
gcc 63

<210> SEQ ID NO 35
<211> LENGTH: 63
<212> TYPE: DNA
<213> ORGANISM: Artificial Sequence
<220> FEATURE:
<223> OTHER INFORMATION: Leader Sequence of CO

<400> SEQUENCE: 35
atgagagtgc ccgcccagct gctgggcctg ctgctgctgt ggctgcccgg cgccagatgc 60
gcc 63

<210> SEQ ID NO 36
<211> LENGTH: 63
<212> TYPE: DNA
<213> ORGANISM: Artificial Sequence
<220> FEATURE:
<223> OTHER INFORMATION: Leader Sequence of CP

<400> SEQUENCE: 36
atgagggtcc ccgctcagct cctggggctc ctgctgctct ggctcccagg tgcacgatgt 60
gcc 63

<210> SEQ ID NO 37
<211> LENGTH: 63
<212> TYPE: DNA
<213> ORGANISM: Artificial Sequence
<220> FEATURE:
<223> OTHER INFORMATION: Leader Sequence of vH1

<400> SEQUENCE: 37
atgagagtgc ccgcccagct gctgggcctg ctgctgctgt ggctgcccgg cgccagatgc 60
gcc 63

<210> SEQ ID NO 38
<211> LENGTH: 63
<212> TYPE: DNA
<213> ORGANISM: Artificial Sequence
<220> FEATURE:
<223> OTHER INFORMATION: Leader Sequence of vH2

<400> SEQUENCE: 38
atgagagtgc ccgcccagct gctgggcctg ctgctgctgt ggctgcccgg cgccagatgt 60
gcc 63

<210> SEQ ID NO 39
<211> LENGTH: 63
<212> TYPE: DNA
<213> ORGANISM: Artificial Sequence
<220> FEATURE:
<223> OTHER INFORMATION: Leader Sequence of vH3

<400> SEQUENCE: 39
atgagagtgc ccgcccagct tctgggcctg ctgctgctgt ggctgcccgg cgccagatgc 60
gcc 63

<210> SEQ ID NO 40
<211> LENGTH: 63
<212> TYPE: DNA
<213> ORGANISM: Artificial Sequence
<220> FEATURE:

<223> OTHER INFORMATION: Leader Sequence of A1

<400> SEQUENCE: 40
atgagggtcc ccgctcagct cctggggctc ctgctgctct ggctcccagg tgcacgatgt 60
gcc 63

<210> SEQ ID NO 41
<211> LENGTH: 63
<212> TYPE: DNA
<213> ORGANISM: Artificial Sequence
<220> FEATURE:
<223> OTHER INFORMATION: Leader Sequence of A2

<400> SEQUENCE: 41
atgagggtcc ccgctcagct cctggggctc ctgctgctct ggctcccagg tgcacgatgt 60
gcc 63

<210> SEQ ID NO 42
<211> LENGTH: 63
<212> TYPE: DNA
<213> ORGANISM: Artificial Sequence
<220> FEATURE:
<223> OTHER INFORMATION: Leader Sequence of A3

<400> SEQUENCE: 42
atgagggtcc ccgctcagct cctggggctc ctgctgctct ggctcccagg tgcacgatgt 60
gcc 63

<210> SEQ ID NO 43
<211> LENGTH: 63
<212> TYPE: DNA
<213> ORGANISM: Artificial Sequence
<220> FEATURE:
<223> OTHER INFORMATION: Leader Sequence of A4

<400> SEQUENCE: 43
atgagggtcc ccgctcagct cctggggctc ctgctgctct ggctcccagg tgcacgatgt 60
gcc 63

<210> SEQ ID NO 44
<211> LENGTH: 63
<212> TYPE: DNA
<213> ORGANISM: Artificial Sequence
<220> FEATURE:
<223> OTHER INFORMATION: Leader Sequence of B1

<400> SEQUENCE: 44
atgagggtcc ccgctcagct cctggggctc ctgctgctct ggctcccagg tgcacgatgt 60
gcc 63

<210> SEQ ID NO 45
<211> LENGTH: 63
<212> TYPE: DNA
<213> ORGANISM: Artificial Sequence
<220> FEATURE:
<223> OTHER INFORMATION: Leader Sequence of B2

<400> SEQUENCE: 45
atgagggtcc ccgctcagct cctggggctc ctgctgctct ggctcccagg tgcacgatgt 60
gcc 63

<210> SEQ ID NO 46
<211> LENGTH: 63
<212> TYPE: DNA
<213> ORGANISM: Artificial Sequence
<220> FEATURE:
<223> OTHER INFORMATION: Leader Sequence of B3

<400> SEQUENCE: 46
atgagggtcc ccgctcagct cctggggctc ctgctgctct ggctcccagg tgcacgatgt 60
gcc 63

<210> SEQ ID NO 47
<211> LENGTH: 63
<212> TYPE: DNA
<213> ORGANISM: Artificial Sequence
<220> FEATURE:
<223> OTHER INFORMATION: Leader Sequence of B4

<400> SEQUENCE: 47
atgagggtcc ccgctcagct cctggggctc ctgctgctct ggctcccagg tgcacgatgt 60
gcc 63

<210> SEQ ID NO 48
<211> LENGTH: 63
<212> TYPE: DNA
<213> ORGANISM: Artificial Sequence
<220> FEATURE:
<223> OTHER INFORMATION: Leader Sequence of C1

<400> SEQUENCE: 48
atgagggtcc ccgctcagct cctggggctc ctgctgctct ggctcccagg tgcacgatgt 60
gcc 63

<210> SEQ ID NO 49
<211> LENGTH: 63
<212> TYPE: DNA
<213> ORGANISM: Artificial Sequence
<220> FEATURE:
<223> OTHER INFORMATION: Leader Sequence of C2

<400> SEQUENCE: 49
atgagggtcc ccgctcagct cctggggctc ctgctgctct ggctcccagg tgcacgatgt 60
gcc 63

<210> SEQ ID NO 50
<211> LENGTH: 63
<212> TYPE: DNA
<213> ORGANISM: Artificial Sequence
<220> FEATURE:
<223> OTHER INFORMATION: Leader Sequene of C3

<400> SEQUENCE: 50
atgagggtcc ccgctcagct cctggggctc ctgctgctct ggctcccagg tgcacgatgt 60
gcc 63

<210> SEQ ID NO 51
<211> LENGTH: 918
<212> TYPE: DNA
<213> ORGANISM: Artificial Sequence
<220> FEATURE:
<223> OTHER INFORMATION: IL-12b of L1

<400> SEQUENCE: 51
atctgggaat taaagaaaga tgtgtacgtg gtggaattgg attggtaccc agatgctccg 60
ggcgaaatgg ttgtactcac atgcgatact ccggaggaag acggtatcac ttggacattg 120
gatcagtcga gtgaggttct cggtagtggt aaaacactaa cgatccaagt caaagaattc 180
ggtgatgcgg ggcaatatac ctgtcataaa ggcggcgaag tactatctca tagcctcctg 240
ctgttacaca agaaggaaga tggcatatgg tccaccgaca tccttaagga tcagaaagaa 300
cccaagaaca aaactttctt gcgttgcgaa gctaagaact actccggccg cttcacatgc 360
tggtggttga caacgatcag tacggatcta accttctctg ttaagtccag tcgggggagt 420
tcggaccccc aaggcgtcac gtgtggagct gccacacttt ccgctgagcg cgtacgtgga 480
gataataaag agtatgaata ctccgttgag tgccaggagg actccgcgtg ccccgctgcc 540
gaggagagtc tccccataga ggtgatggtc gacgctgttc acaaactgaa atatgagaac 600
tatacctcat ccttctttat acgtgacata attaagccag atcccccgaa gaacttacaa 660
ttgaaaccat tgaagaattc acgtcaagtc gaggtatcct gggagtatcc cgacacctgg 720
tccacgccac actcatattt ctctctgacc ttctgtgtgc aggtacaagg caagagcaaa 780
cgagaaaaaa aggacagagt tttcacggat aagactagcg ccacagtgat atgtaggaaa 840
aacgcatcga tctcagtccg cgcgcaagat cggtattact caagcagttg gtcagagtgg 900
gcatcggtgc cctgctcg 918

<210> SEQ ID NO 52
<211> LENGTH: 918
<212> TYPE: DNA
<213> ORGANISM: Artificial Sequence
<220> FEATURE:
<223> OTHER INFORMATION: IL-12b of L2

<400> SEQUENCE: 52
atttgggaac ttaagaagga cgtatacgtt gtggaacttg actggtaccc tgatgctcca 60
ggggagatgg tggttttgac gtgtgacacc ccggaagaag atggaattac atggacctta 120
gaccaatcct ccgaggttct tggctcgggc aaaaccttga ccattcaggt caaggaattt 180
ggcgatgctg gccaatacac ctgccataaa ggtggtgaag ttttatctca ctccctactg 240
ttgctccata agaaagaaga cggcatttgg tcgacagaca tattgaagga tcagaaggaa 300
cctaagaata agaccttctt acgatgtgag gccaagaatt attccggacg ttttacgtgt 360
tggtggttga ccacgatctc cactgactta accttctcag tgaaatcctc acgaggtagt 420
tccgatcccc agggtgtgac gtgcggtgcg gccacgttaa gtgctgagag agtacggggc 480
gacaataagg aatacgagta ctcagttgaa tgccaagagg actcggcctg tcccgcggca 540
gaggagagtc tccctatcga agtgatggtg gatgcggtgc acaagctcaa gtatgaaaat 600
tacacatcat cttttttcat cagagacatt ataaagcccg acccaccaaa gaacctccag 660
ttaaagccct taaagaacag tagacaggtt gaagtatcat gggaataccc agacacctgg 720
tccacacccc attcgtattt ttccttgacg ttttgcgtac aagttcaggg aaagtccaaa 780
cgggaaaaga aagaccgcgt ttttacagac aaaacttctg ccactgtcat ctgtagaaag 840
aacgcatcaa ttagcgtgcg agcgcaagac agatactatt caagtagctg gagcgagtgg 900
gccagtgttc catgttct 918

<210> SEQ ID NO 53
<211> LENGTH: 918
<212> TYPE: DNA
<213> ORGANISM: Artificial Sequence
<220> FEATURE:
<223> OTHER INFORMATION: IL-12b of L3

<400> SEQUENCE: 53

```
atatgggagc tcaagaagga cgtttatgtc gttgagctgg attggtaccc tgatgccccg     60
ggcgaaatgg ttgtgcttac gtgcgatacc cccgaggagg atggcataac atggacgtta    120
gatcagtctt ccgaggtcct tggttccggt aagactctta ctatccaggt gaaggagttc    180
ggcgatgccg gccagtacac ttgccataaa ggcggtgaag ttctaagcca ctctctactg    240
cttttgcaca agaaggaaga tggaatatgg tccaccgaca tcttgaagga ccagaaagaa    300
ccaaaaaata agacattttt gaggtgtgag gcaaaaaatt attcgggacg cttcacctgc    360
tggtggttga cgacgatttc aaccgacctc accttctcag taaagagttc gagaggtagt    420
tccgatcccc aaggtgtgac atgtggcgct gcgactctaa gcgctgaacg cgtaagaggt    480
gataacaaag agtacgaata cagtgtggaa tgccaagaag atagcgcgtg tccagccgca    540
gaagaatctt taccaataga ggttatggtt gatgccgttc acaaattgaa atatgagaat    600
tacacctcaa gctttttcat tcgagacata ataaagcccg accctcctaa gaatcttcag    660
ttaaaaccgc tgaagaacag tagacaagtt gaggttagct gggaatatcc tgatacctgg    720
tcaacgccgc actcgtattt ctccctgact ttctgtgttc aggttcaagg aaaatctaaa    780
agggagaaga aagaccgtgt tttcaccgac aagacatctg ccacagtcat atgtaggaag    840
aacgcttcaa tcagcgtgcg agcgcaggac cgatactaca gctctagttg gtccgaatgg    900
gccagcgtac catgctct                                                  918
```

<210> SEQ ID NO 54
<211> LENGTH: 918
<212> TYPE: DNA
<213> ORGANISM: Artificial Sequence
<220> FEATURE:
<223> OTHER INFORMATION: IL12b of M1

<400> SEQUENCE: 54

```
atctgggagc tgaaaaagga cgtgtacgtg gtggaacttg actggtaccc cgacgccccc     60
ggcgagatgg tggtactgac ctgcgacact cccgaggaag acggcattac ctggaccttg    120
gaccagagca gcgaggttct gggctccgga aaaaccttga caatccaagt gaaagaattc    180
ggcgacgctg gccagtacac ctgccacaag ggcggcgagg tgctgtccca cagcctgctg    240
ctgctgcata agaaagaaga cgggatttgg agcaccgata tactgaagga tcagaaggag    300
cccaagaaca agaccttcct gaggtgcgag gccaaaaatt acagcggcag attcacctgc    360
tggtggctga ccaccattag cacagacctg actttcagcg taaagtcttc aaggggcagc    420
tcagaccccc agggagtaac ttgcggagcg gcaacgttgt ctgccgagcg ggtcagaggc    480
gacaataagg agtacgagta ttcagtagag tgtcaggaag atagcgcctg tcccgccgcg    540
gaggagagcc tccccatcga ggtgatggtg gacgccgtgc acaagttaaa gtacgagaat    600
tacaccagct catttttat cagagacatt atcaagccgg accccccgaa gaacttacag     660
cttaaacccc taaagaacag caggcaggtt gaggtcagct gggaatatcc tgacacctgg    720
tcaacccccc acagctactt ctcccttact ttctgtgtgc aagtgcaggg caagagcaag    780
agagaaaaga aggaccgggt gtttaccgac aagactagcg ccaccgtgat ttgcagaaag    840
aacgccagca ttagtgtgag agcccaggac aggtattact ccagctcatg gtctgagtgg    900
gctagtgtgc cttgctct                                                  918
```

<210> SEQ ID NO 55
<211> LENGTH: 918
<212> TYPE: DNA
<213> ORGANISM: Artificial Sequence
<220> FEATURE:
<223> OTHER INFORMATION: IL12b of M2

<400> SEQUENCE: 55
atttgggagt tgaagaagga cgtgtacgtg gtggagctgg actggtaccc ggatgctccc 60
ggcgagatgg tggtactcac ctgcgacaca cctgaggaag acggcatcac ctggaccctc 120
gatcagagca gcgaggttct gggaagcggc aaaaccctga ccatccaagt gaaagagttt 180
ggcgacgccg gtcagtacac ctgccacaag ggaggcgagg tcctgtctca ctctctgctg 240
ctgctccata agaaggagga cggtatttgg agcactgaca tcttgaagga tcaaaaagag 300
ccaaagaata aaacgttcct gaggtgcgaa gctaagaatt actccgggcg ttttacgtgc 360
tggtggctga ccacgatcag caccgatctg accttcagcg tgaagagcag ccggggcagc 420
agcgaccccc aaggcgtgac ttgcggcgct gcgaccctga gcgctgagcg tgtgcgcggc 480
gacaacaagg agtatgagta ttcagtggag tgtcaggagg actccgcctg tcccgcggcc 540
gaagagagtc tgcctattga ggtgatggtg gacgccgtgc acaagctgaa gtacgagaac 600
tacacatcgt cattctttat ccgcgacatc ataaagcccg acccccccaa gaacctgcag 660
ctgaagcctc tcaagaattc ccggcaagtg gaggtgagct gggagtaccc tgatacctgg 720
tctacccctc acagctactt tagcctgacc ttctgcgtcc aggtgcaagg aaagtcgaag 780
cgcgagaaga aagatagagt cttcaccgat aaaaccagtg ccaccgtgat ttgccgcaaa 840
aacgcctcca tcagcgtgcg ggctcaggat agatactact ctagcagctg gagcgaatgg 900
gcctcagttc cttgcagc 918

<210> SEQ ID NO 56
<211> LENGTH: 918
<212> TYPE: DNA
<213> ORGANISM: Artificial Sequence
<220> FEATURE:
<223> OTHER INFORMATION: IL12b of M3

<400> SEQUENCE: 56
atttgggagc tcaagaagga cgtgtacgtg gtggaacttg actggtaccc ggacgcgccc 60
ggggaaatgg tggtgctaac ctgtgacacc cccgaagagg acggcatcac ctggaccctg 120
gaccagagca gtgaggtgct aggtagtggc aaaacgttaa ccatccaggt caaggagttc 180
ggcgacgccg ggcaatacac ctgtcacaag gggggggagg tactatccca ctccctgctg 240
ctcctgcaca agaaagagga cgggatctgg agcaccgaca ttctgaaaga ccaaaaggag 300
cccaaaaaca aaaccttcct tagatgtgaa gccaagaact acagcggccg tttcacctgc 360
tggtggctga ccaccatatc tacggacctt accttttcgg tgaagagcag caggggggagt 420 tccgacccgc aaggcgtaac ttgcggagcc gcaaccctga gcgccgagag agtgcgcggc 480
gacaacaagg agtacgagta tagcgtggag tgccaagagg acagcgcatg cccagccgcc 540
gaagagagcc tgccaataga ggtcatggta gacgccgtgc acaagctaaa atatgaaaac 600
tacaccagca gctttttcat cagggatatc atcaaacccg acccaccaaa aaacttacag 660
cttaagcctc tgaaaaacag cagacaagtt gaggtcagct gggagtaccc cgacacttgg 720
agcacacccc actcctattt cagtttgaca ttctgcgtgc aggtgcaggg taaaagcaag 780
agagaaaaga aggacagagt gttcacagat aagacctcag ccacagtgat ctgccgtaag 840
aatgccagca tcagcgtccg ggctcaggac aggtactact cttcctcatg gagcgagtgg 900
gcctctgtcc cctgcagc 918

<210> SEQ ID NO 57
<211> LENGTH: 918
<212> TYPE: DNA
<213> ORGANISM: Artificial Sequence
<220> FEATURE:
<223> OTHER INFORMATION: IL12b of H1

<400> SEQUENCE: 57
atctgggagc tgaagaaaga cgtgtacgtg gtggagctgg actggtaccc cgacgccccc 60
ggtgaaatgg tggttctgac ctgcgacaca ccagaggagg acggcatcac ctggaccctg 120
gaccagtcca gcgaggtcct gggctctggc aagaccctga ccatccaggt taaggaattt 180
ggcgacgccg gccagtacac ctgccacaaa ggcggcgagg tcctttcgca cagtctgctg 240
ctgctgcata aaaaggagga cggcatttgg agcaccgaca ttctgaagga tcagaaagag 300
cccaagaaca agacctttct gagatgtgag gccaaaaact actctggacg cttcacctgt 360
tggtggctga ccaccatcag cacagacctg accttctcgg tgaagtctag taggggcagc 420
agtgaccccc agggcgtaac atgcggcgcc gctaccctga gcgccgagag agtgagaggc 480
gataacaagg agtacgagta ctccgtggag tgccaagagg actcagcctg ccccgccgcc 540
gaggagtcgc tgcccatcga ggtgatggtg gatgcagtgc acaagctgaa gtacgagaac 600
tacaccagta gctttttcat cagagatatc attaaacccg accctcccaa gaacctgcag 660
ctgaagccct taaagaacag ccggcaggtg gaagtgtcat gggagtaccc agacacctgg 720
agcactccgc acagctactt cagcctgacc ttctgcgttc aggtgcaggg aaaaagcaag 780
agagagaaga aagacagagt gttcaccgac aagaccagcg caaccgtgat ctgtagaaag 840
aacgcctcga tcagcgtgag agcccaggac agatactaca gcagcagctg gagcgagtgg 900
gccagtgtac cttgcagc 918

<210> SEQ ID NO 58
<211> LENGTH: 918
<212> TYPE: DNA
<213> ORGANISM: Artificial Sequence
<220> FEATURE:
<223> OTHER INFORMATION: IL12b of H2

<400> SEQUENCE: 58
atttgggagc tgaagaagga cgtgtacgtg gtggagctgg attggtatcc agacgccccc 60
ggcgagatgg tcgtgttgac ctgcgatact cccgaggagg acggaatcac ctggacactt 120
gaccagagca gcgaggtgct gggcagcggg aagaccctga ctatccaggt gaaggagttt 180
ggcgatgccg gacagtacac ctgccacaag ggcggcgagg tgttatctca tagcctgctg 240
ctgctgcaca aaaaggagga cggatctgg agcactgaca tcctgaagga ccagaaggag 300
cccaaaaaca agaccttcct gcgttgcgag gccaagaact acagcgggag attcacctgt 360
tggtggctga ccactatcag cactgaccta accttcagcg tgaagagcag ccggggaagc 420
tctgaccccc agggggtgac atgcggcgcc gccacactga gcgccgagag ggtgagaggg 480
gacaataagg aatacgagta tagcgtggag tgtcaggaag attccgcctg ccccgccgcc 540
gaggagagcc tgcctatcga ggtcatggtg gacgccgtcc ataaactgaa gtacgaaaac 600
tatacttcaa gcttcttcat cagagacatc ataaagcccg acccccccaa gaacctgcag 660
ctaaagcccc tgaagaacag cagacaggtc gaagtgagct gggagtaccc cgatacctgg 720
agcaccccgc acagctactt cagcctgacc ttttgcgtcc aggtgcaggg caagagcaag 780
agagagaaga aggacagggt gttcactgac aagacaagcg ccactgttat ctgcagaaag 840
aacgccagta tcagcgtgcg cgcccaagac aggtattact ccagcagctg gtctgaatgg 900
gccagcgtgc cttgcagc 918

<210> SEQ ID NO 59
<211> LENGTH: 918
<212> TYPE: DNA
<213> ORGANISM: Artificial Sequence
<220> FEATURE:
<223> OTHER INFORMATION: IL12b of H3

<400> SEQUENCE: 59
atctgggaac tgaagaagga cgtctacgtg gtggagctgg attggtaccc cgacgccccc 60
ggcgagatgg tcgtgctgac ctgtgacacc cctgaggagg acggaatcac atggaccctg 120
gaccagagca gcgaagtgtt gggcagcggc aagaccctga ccatccaagt gaaggaattc 180
ggcgacgcgg gccagtatac ttgccacaag ggcggggagg ttctgagcca cagcctgctg 240
ctgctccaca agaaagagga tggcatctgg tctaccgaca tcctgaagga ccaaaaggag 300
ccaaagaaca agaccttcct aagatgcgag gccaagaact actcaggtcg tttcacctgc 360
tggtggctga ccacaatctc caccgacctg accttcagcg tgaagagcag ccgcggcagt 420
agcgacccac agggcgtgac ctgcggggcc gccactctga gcgccgagag agtgcgcggc 480
gataataagg aatacgagta cagcgtggag tgccaggaag actcagcctg ccccgccgca 540
gaagaaagtc tgccaataga ggtgatggtt gacgccgtgc acaagctaaa gtacgagaac 600
tacaccagca gcttctttat ccgggacatc atcaagccag atcccccaa gaacctgcag 660 cttaagcccc tgaagaacag cagacaggtg gaggtgtcat gggaataccc cgacacctgg 720
agcacccccc atagctactt ctcactgacc ttctgcgtgc aggtgcaggg caagagcaag 780
agagagaaga aggatagggt attcacggac aagacctcag ccaccgtgat ctgccgaaag 840
aacgccagca tcagcgtgag agcccaggac agatactata gctcctcgtg gagcgagtgg 900
gccagcgtac cttgcagc 918

<210> SEQ ID NO 60
<211> LENGTH: 918
<212> TYPE: DNA
<213> ORGANISM: Artificial Sequence
<220> FEATURE:
<223> OTHER INFORMATION: IL12b of CO

<400> SEQUENCE: 60
atctgggagc tgaagaagga cgtgtacgtg gtggagctgg actggtaccc cgacgccccc 60
ggcgagatgg tggtgctgac ctgcgacacc cccgaggagg acggcatcac ctggaccctg 120
gaccagagca gcgaggtgct gggcagcggc aagaccctga ccatccaggt gaaggagttc 180
ggcgacgccg gccagtacac ctgccacaag ggcggcgagg tgctgagcca cagcctgctg 240
ctgctgcaca agaaggagga cggcatctgg agcaccgaca tcctgaagga ccagaaggag 300
cccaagaaca agaccttcct gagatgcgag gccaagaact acagcggcag attcacctgc 360
tggtggctga ccaccatcag caccgacctg accttcagcg tgaagagcag cagaggcagc 420
agcgaccccc agggcgtgac ctgcggcgcc gccaccctga gcgccgagag agtgagaggc 480
gacaacaagg agtacgagta cagcgtggag tgccaggagg acagcgcctg ccccgccgcc 540
gaggagagcc tgcccatcga ggtgatggtg gacgccgtgc acaagctgaa gtacgagaac 600
tacaccagca gcttcttcat cagagacatc atcaagcccg acccccccaa gaacctgcag 660
ctgaagcccc tgaagaacag cagacaggtg gaggtgagct gggagtaccc cgacacctgg 720
agcacccccc acagctactt cagcctgacc ttctgcgtgc aggtgcaggg caagagcaag 780
agagagaaga aggacagagt gttcaccgac aagaccagcg ccaccgtgat ctgcagaaag 840
aacgccagca tcagcgtgag agcccaggac agatactaca gcagcagctg gagcgagtgg 900
gccagcgtgc cctgcagc 918

<210> SEQ ID NO 61
<211> LENGTH: 918
<212> TYPE: DNA
<213> ORGANISM: Artificial Sequence
<220> FEATURE:
<223> OTHER INFORMATION: IL12b of CP

<400> SEQUENCE: 61
atctgggagc tgaagaagga tgtgtatgtg gtggagctgg actggtaccc agatgcccct 60
ggagagatgg tggtgctgac ctgtgacacc ccagaggagg atggcatcac ctggaccctg 120
gaccagagca gcgaggtgct gggcagcggc aagaccctga ccatccaggt gaaggagttt 180
ggagatgctg gccagtacac ctgccacaag ggcggggagg tgctgagcca cagcctgctg 240
ctgctgcaca agaaggagga tggcatctgg agcacagaca tcctgaagga ccagaaggag 300
cccaagaaca agaccttcct gcgctgtgag gccaagaact acagcggccg cttcacctgc 360
tggtggctga ccaccatcag cacagacctg accttctctg tgaaaagcag ccggggcagc 420
agtgaccccc agggcgtgac ctgtggggcc gccaccctgt ctgctgagcg ggtgcggggg 480
gacaacaagg agtatgagta cagcgtggag tgccaggagg acagcgcctg cccagctgct 540
gaggagagcc tgcccatcga ggtgatggtg gatgctgtgc acaagctgaa gtatgagaac 600
tacaccagca gcttcttcat ccgggacatc atcaagccag acccccccaa gaacctgcag 660
ctgaagcccc tgaagaacag ccggcaggtg gaggtgtcct gggagtaccc agacacctgg 720
agcacccccc acagctactt cagcctgacc ttctgtgtgc aggtgcaggg caagagcaag 780
cgggagaaga aggacagagt cttcacagac aagaccagcg ccaccgtcat ctgcaggaag 840
aatgccagca tctctgtgcg ggcccaggac cgctactaca gcagctcctg gagcgagtgg 900
gcctctgtgc cctgcagc 918

<210> SEQ ID NO 62
<211> LENGTH: 918
<212> TYPE: DNA
<213> ORGANISM: Artificial Sequence
<220> FEATURE:
<223> OTHER INFORMATION: IL12b of vH1

<400> SEQUENCE: 62
atctgggagc tgaagaagga cgtgtacgtg gtggagctgg actggtaccc cgacgccccc 60
ggcgagatgg tggtgctgac ctgcgacacc cccgaggagg acgggatcac ctggaccctg 120
gatcagagca gcgaggtgct gggcagcggc aagaccctga ccatccaggt gaaggagttt 180
ggtgacgccg gccagtacac ctgccacaag ggcggcgagg tgctgagcca ctcactgctg 240
ctgctgcaca agaaggagga cggcatctgg agcaccgaca ttctgaagga tcagaaggag 300
cccaagaaca agaccttcct gagatgcgag gccaagaact acagcggcag attcacctgt 360

```
tggtggctga ctactatcag cactgatctg accttcagcg tgaagagctc aagaggcagc    420

agcgatcccc agggcgtgac ctgcggcgcc gccaccctga gcgccgagag agtgagaggc    480

gacaacaagg agtacgagta cagcgtggag tgccaggaag acagcgcctg ccccgctgca    540

gaggagtctc tgcccatcga ggtgatggtg gacgccgtgc acaagcttaa gtacgagaac    600

tacaccagct ccttcttcat tagagacatc atcaagcccg acccgcccaa aaacctgcag    660

ctgaagcccc tgaagaacag cagacaggtg gaggtcagct gggagtaccc cgacacctgg    720

agcacccccc acagctactt cagcctgacc ttctgcgtgc aggtgcaggg caagagcaag    780

agagagaaga aggacagagt gttcaccgac aaaaccagcg ccaccgtgat ctgcagaaaa    840

aacgccagca ttagcgtgag agctcaggat agatactaca gcagcagctg gagtgagtgg    900

gccagcgtgc cctgcagc                                                  918
```

<210> SEQ ID NO 63
<211> LENGTH: 918
<212> TYPE: DNA
<213> ORGANISM: Artificial Sequence
<220> FEATURE:
<223> OTHER INFORMATION: IL12b of vH2

<400> SEQUENCE: 63

```
atctgggagc tgaagaagga cgtgtacgtg gtggagctgg actggtaccc cgacgccccc     60

ggagagatgg tggtgctgac ctgcgacacc cccgaagagg acggcatcac ctggaccctg    120

gaccagagca gcgaggtgct gggcagcggg aagaccctga ccatccaggt gaaggagttc    180

ggcgacgccg gccagtacac ctgtcacaag ggcggcgagg tgctgagcca cagcctgctg    240

ctgctgcaca agaaggagga cggcatatgg agcaccgaca tcctgaagga ccagaaggag    300

cccaagaaca agacctttct gagatgcgag gctaagaatt acagcggcag attcacctgc    360

tggtggctga ccaccatcag caccgacctg accttcagcg tgaagagcag cagaggcagc    420

agcgaccccc agggcgtgac atgcggcgcc gccaccctga gcgccgagag agtgagaggc    480

gacaacaagg agtacgagta cagcgtggag tgccaggagg actccgcttg ccccgccgcc    540

gaggagagct tgcccatcga ggtgatggtg gacgccgtgc acaagctcaa gtacgaaaac    600

tacaccagca gcttcttcat cagagacatc atcaagcccg accccccaa gaacctgcag    660

ctgaagcccc tgaaaaacag cagacaggtg gaggtgagct gggagtaccc cgacacctgg    720

agcacccccc acagctactt cagcctgacc ttctgcgtgc aggtgcaggg aaaaagcaag    780

agagagaaga aggacagagt gttcaccgac aagaccagcg ccaccgtgat ctgcagaaag    840

aacgccagca tctccgtgag agcccaggac agatactaca gcagcagctg gagcgagtgg    900

gccagcgtgc cctgtagc                                                  918
```

<210> SEQ ID NO 64
<211> LENGTH: 918
<212> TYPE: DNA
<213> ORGANISM: Artificial Sequence
<220> FEATURE:
<223> OTHER INFORMATION: IL12b of vH3

<400> SEQUENCE: 64

```
atctgggagc tgaagaagga cgtgtacgtg gtggagctgg actggtaccc ggacgccccg     60

ggcgagatgg tcgtgctgac ctgcgacacc cccgaggagg acggcatcac ctggaccctg    120

gaccagtcta gcgaggtgct gggcagcggc aagaccctga ccatccaggt gaaggagttc    180

ggcgacgccg gccagtacac ctgccacaag ggcggcgagg tgctgagcca cagcctgctg    240
```

ctgctgcaca agaaggagga cggcatctgg agcaccgaca tcctgaagga ccagaaggag 300
cctaagaaca agaccttcct gagatgtgag gccaagaact acagcggcag attcacctgc 360
tggtggctga ccaccatcag caccgatctg accttcagcg tgaagagcag cagaggcagc 420
tcagaccccc agggcgtgac ctgcggcgcc gcgaccctga gcgccgagag agtgagaggc 480
gacaacaagg agtacgagta cagcgtggag tgccaggagg acagcgcctg ccccgcggcc 540
gaggagagcc tgcccatcga ggtgatggtg gacgccgtgc ataagctgaa gtacgagaac 600
tacaccagca gcttcttcat cagagacatc atcaagcccg atccccccaa gaacctgcag 660
ctgaagccac tgaagaacag cagacaggtg gaggtgagct gggagtaccc cgacacctgg 720
agcacccccc acagctactt cagcctgacc ttctgcgtgc aggtgcaggg caagagcaag 780
agagagaaga aggaccgggt gttcaccgac aagaccagcg ccactgtgat ctgcagaaag 840
aacgccagca tcagcgtgag agcccaggac agatactaca gctccagctg gtcagagtgg 900
gccagcgtgc cctgcagc 918

<210> SEQ ID NO 65
<211> LENGTH: 918
<212> TYPE: DNA
<213> ORGANISM: Artificial Sequence
<220> FEATURE:
<223> OTHER INFORMATION: IL12b of A1

<400> SEQUENCE: 65
atctgggagc tgaagaaaga cgtgtacgtg gtggagcttg actggtaccc cgacgccccc 60
ggtgaaatgg tggttctgac ctgcgacaca ccagaggagg acggcatcac ctggaccctg 120
gaccagtcca gcgaggtcct gggatctggc aagaccctga ccatccaggt taaggaattt 180
ggcgacgccg gccagtacac ctgccacaaa ggcggcgagg tcctttcgca cagtctgctg 240
ctgctgcata aaaaggagga cggcatttgg agcaccgaca ttctgaagga tcagaaagag 300
cccaagaaca agacctttct gagatgtgag gccaaaaact actctggacg cttcacctgt 360
tggtggctga ccaccatcag cacagacctg accttctcgg tgaagtctag taggggcagc 420
agtgaccccc agggcgtaac atgcggcgcc gctaccctga gcgccgagag agtgagaggc 480
gataacaagg agtacgagta ctccgtggag tgccaagagg actcagcctg ccccgccgcc 540
gaggagtcgc tgcccatcga ggtgatggtg gatgcagtgc acaagctgaa gtacgagaac 600
tacaccagta gctttttcat cagagatatc attaaacccg accctcccaa gaacctgcag 660
ctgaagccct taaagaacag ccggcaggtg gaagtgtcat gggagtaccc agacacctgg 720
agcactccgc acagctactt cagcctgacc ttctgcgttc aggtgcaggg aaaaagcaag 780
agagagaaga aagacagagt gttcaccgac aagaccagcg caaccgtgat ctgtagaaag 840
aacgcctcga tcagcgtgag agcccaggac agatactaca gcagcagctg gagcgagtgg 900
gccagtgtac cttgcagc 918

<210> SEQ ID NO 66
<211> LENGTH: 918
<212> TYPE: DNA
<213> ORGANISM: Artificial Sequence
<220> FEATURE:
<223> OTHER INFORMATION: IL12b of A2

<400> SEQUENCE: 66
atctgggaac tgaagaagga cgtctacgtg gtggagctgg attggtaccc cgacgccccc 60
ggcgagatgg tcgtgctgac ctgtgacacc cctgaggagg acggaatcac atggaccctg 120
gaccagagca gcgaagtgtt gggcagcggc aagaccctga ccatccaagt gaaggaattc 180
ggcgacgcgg gccagtatac ttgccacaag ggcggggagg ttctgagcca cagcctgctg 240
ctgctccaca agaaagagga tggcatctgg tctaccgaca tcctgaagga ccaaaaggag 300
ccaaagaaca agaccttcct aagatgcgag gccaagaact actcaggtcg tttcacctgc 360
tggtggctga ccacaatctc caccgacctg accttcagcg tgaaaagcag ccgcggcagt 420
agcgacccac agggcgtgac ctgcggggcc gccactctga gcgccgagag agtgcgcggc 480
gataataagg aatacgagta cagcgtggag tgccaggaag actcagcctg ccccgccgca 540
gaagaaagtc tgccaataga ggtgatggtt gacgccgtgc acaagctaaa gtacgagaac 600
tacaccagca gcttctttat ccgggacatc atcaagccag atccccccaa gaacctgcag 660
cttaagcccc tgaagaacag cagacaggtg gaggtgtcat gggaataccc cgacacctgg 720
agcacccccc atagctactt ctcactgacc ttctgcgtgc aggtgcaggg caagagcaag 780
agagagaaga aggatagggt attcacggac aagacctcag ccaccgtgat ctgccgaaag 840
aacgccagca tcagcgtgag agcccaggac agatactata gctcctcgtg gagcgagtgg 900
gccagcgtac cttgcagc 918

<210> SEQ ID NO 67
<211> LENGTH: 918
<212> TYPE: DNA
<213> ORGANISM: Artificial Sequence
<220> FEATURE:
<223> OTHER INFORMATION: IL12b of A3

<400> SEQUENCE: 67
atctgggagc tgaagaagga cgtgtacgtg gtggagctgg actggtaccc cgacgccccc 60
ggcgagatgg tggtgctgac ctgcgacacc cccgaggagg acggcatcac ctggaccctg 120
gaccagagca gcgaggtgct gggcagcggc aagaccctga ccatccaggt gaaggagttc 180
ggcgacgccg gccagtacac ctgccacaag ggcggcgagg tgctgagcca cagcctgctg 240
ctgctgcaca agaaggagga cggcatctgg agcaccgaca tcctgaagga ccagaaggag 300
cccaagaaca agaccttcct gagatgcgag gccaagaact acagcggcag attcacctgc 360
tggtggctga ccaccatcag caccgacctg accttcagcg tgaaaagcag cagaggcagc 420
agcgaccccc agggcgtgac ctgcggcgcc gccaccctga gcgccgagag agtgagaggc 480
gacaacaagg agtacgagta cagcgtggag tgccaggagg acagcgcctg ccccgccgcc 540
gaggagagcc tgcccatcga ggtgatggtg gacgccgtgc acaagctgaa gtacgagaac 600
tacaccagca gcttcttcat cagagacatc atcaagcccg acccccccaa gaacctgcag 660
ctgaagcccc tgaagaacag cagacaggtg gaggtgagct gggagtaccc cgacacctgg 720
agcacccccc acagctactt cagcctgacc ttctgcgtgc aggtgcaggg caagagcaag 780
agagagaaga aggacagagt gttcaccgac aagaccagcg ccaccgtgat ctgcagaaag 840
aacgccagca tcagcgtgag agcccaggac agatactaca gcagcagctg gagcgagtgg 900
gccagcgtgc cctgcagc 918

<210> SEQ ID NO 68
<211> LENGTH: 918
<212> TYPE: DNA
<213> ORGANISM: Artificial Sequence
<220> FEATURE:
<223> OTHER INFORMATION: IL12b of A4

<400> SEQUENCE: 68
atctgggagc tgaagaagga tgtgtatgtg gtggagctgg actggtaccc agatgcccct 60
ggagagatgg tggtgctgac ctgtgacacc ccagaggagg atggcatcac ctggaccctg 120
gaccagagca gcgaggtgct gggcagcggc aagaccctga ccatccaggt gaaggagttt 180
ggagatgctg gccagtacac ctgccacaag ggcggggagg tgctgagcca cagcctgctg 240
ctgctgcaca agaaggagga tggcatctgg agcacagaca tcctgaagga ccagaaggag 300
cccaagaaca agaccttcct gcgctgtgag gccaagaact acagcggccg cttcacctgc 360
tggtggctga ccaccatcag cacagacctg accttctctg tgaaaagcag ccggggcagc 420
agtgaccccc agggcgtgac ctgtggggcc gccaccctgt ctgctgagcg ggtgcggggg 480
gacaacaagg agtatgagta cagcgtggag tgccaggagg acagcgcctg cccagctgct 540
gaggagagcc tgcccatcga ggtgatggtg gatgctgtgc acaagctgaa gtatgagaac 600
tacaccagca gcttcttcat ccgggacatc atcaagccag acccccccaa gaacctgcag 660
ctgaagcccc tgaagaacag ccggcaggtg gaggtgtcct gggagtaccc agacacctgg 720
agcacccccc acagctactt cagcctgacc ttctgtgtgc aggtgcaggg caagagcaag 780
cgggagaaga aggacagagt cttcacagac aagaccagcg ccaccgtcat ctgcaggaag 840
aatgccagca tctctgtgcg ggcccaggac cgctactaca gcagctcctg gagcgagtgg 900
gcctctgtgc cctgcagc 918

<210> SEQ ID NO 69
<211> LENGTH: 918
<212> TYPE: DNA
<213> ORGANISM: Artificial Sequence
<220> FEATURE:
<223> OTHER INFORMATION: IL12b of B1

<400> SEQUENCE: 69
atctgggagc tgaagaaaga cgtgtacgtg gtggagcttg actggtaccc cgacgccccc 60
ggtgaaatgg tggttctgac ctgcgacaca ccagaggagg acggcatcac ctggaccctg 120
gaccagtcca gcgaggtcct gggatctggc aagaccctga ccatccaggt taaggaattt 180
ggcgacgccg gccagtacac ctgccacaaa ggcggcgagg tcctttcgca cagtctgctg 240
ctgctgcata aaaaggagga cggcatttgg agcaccgaca ttctgaagga tcagaaagag 300
cccaagaaca agacctttct gagatgtgag gccaaaaact actctggacg cttcacctgt 360
tggtggctga ccaccatcag cacagacctg accttctcgg tgaagtctag taggggcagc 420
agtgaccccc agggcgtaac atgcggcgcc gctaccctga gcgccgagag agtgagaggc 480
gataacaagg agtacgagta ctccgtggag tgccaagagg actcagcctg ccccgccgcc 540
gaggagtcgc tgcccatcga ggtgatggtg gatgcagtgc acaagctgaa gtacgagaac 600
tacaccagta gctttttcat cagagatatc attaaacccg accctcccaa gaacctgcag 660
ctgaagccct taaagaacag ccggcaggtg gaagtgtcat gggagtaccc agacacctgg 720
agcactccgc acagctactt cagcctgacc ttctgcgttc aggtgcaggg aaaaagcaag 780
agagagaaga aagacagagt gttcaccgac aagaccagcg caaccgtgat ctgtagaaag 840
aacgcctcga tcagcgtgag agcccaggac agatactaca gcagcagctg gagcgagtgg 900
gccagtgtac cttgcagc 918

<210> SEQ ID NO 70

<211> LENGTH: 918
<212> TYPE: DNA
<213> ORGANISM: Artificial Sequence
<220> FEATURE:
<223> OTHER INFORMATION: IL12b of B2

<400> SEQUENCE: 70

```
atctgggaac tgaagaagga cgtctacgtg gtggagctgg attggtaccc cgacgccccc     60
ggcgagatgg tcgtgctgac ctgtgacacc cctgaggagg acggaatcac atggaccctg    120
gaccagagca gcgaagtgtt gggcagcggc aagaccctga ccatccaagt gaaggaattc    180
ggcgacgcgg gccagtatac ttgccacaag ggcggggagg ttctgagcca cagcctgctg    240
ctgctccaca agaaagagga tggcatctgg tctaccgaca tcctgaagga ccaaaaggag    300
ccaaagaaca agaccttcct aagatgcgag gccaagaact actcaggtcg tttcacctgc    360
tggtggctga ccacaatctc caccgacctg accttcagcg tgaaaagcag ccgcggcagt    420
agcgacccac agggcgtgac ctgcggggcc gccactctga gcgccgagag agtgcgcggc    480
gataataagg aatacgagta cagcgtggag tgccaggaag actcagcctg ccccgccgca    540
gaagaaagtc tgccaataga ggtgatggtt gacgccgtgc acaagctaaa gtacgagaac    600
tacaccagca gcttctttat ccgggacatc atcaagccag atccccccaa gaacctgcag    660
cttaagcccc tgaagaacag cagacaggtg gaggtgtcat gggaataccc cgacacctgg    720
agcacccccc atagctactt ctcactgacc ttctgcgtgc aggtgcaggg caagagcaag    780
agagagaaga aggatagggt attcacggac aagacctcag ccaccgtgat ctgccgaaag    840
aacgccagca tcagcgtgag agcccaggac agatactata gctcctcgtg gagcgagtgg    900
gccagcgtac cttgcagc                                                  918
```

<210> SEQ ID NO 71
<211> LENGTH: 918
<212> TYPE: DNA
<213> ORGANISM: Artificial Sequence
<220> FEATURE:
<223> OTHER INFORMATION: IL12b of B3

<400> SEQUENCE: 71

```
atctgggagc tgaagaagga cgtgtacgtg gtggagctgg actggtaccc cgacgccccc     60
ggcgagatgg tggtgctgac ctgcgacacc cccgaggagg acggcatcac ctggaccctg    120
gaccagagca gcgaggtgct gggcagcggc aagaccctga ccatccaggt gaaggagttc    180
ggcgacgccg gccagtacac ctgccacaag ggcggcgagg tgctgagcca cagcctgctg    240
ctgctgcaca agaaggagga cggcatctgg agcaccgaca tcctgaagga ccagaaggag    300
cccaagaaca agaccttcct gagatgcgag gccaagaact acagcggcag attcacctgc    360
tggtggctga ccaccatcag caccgacctg accttcagcg tgaaaagcag cagaggcagc    420
agcgaccccc agggcgtgac ctgcggcgcc gccaccctga gcgccgagag agtgagaggc    480
gacaacaagg agtacgagta cagcgtggag tgccaggagg acagcgcctg ccccgccgcc    540
gaggagagcc tgcccatcga ggtgatggtg gacgccgtgc acaagctgaa gtacgagaac    600
tacaccagca gcttcttcat cagagacatc atcaagcccg acccccccaa gaacctgcag    660
ctgaagcccc tgaagaacag cagacaggtg gaggtgagct gggagtaccc cgacacctgg    720
agcacccccc acagctactt cagcctgacc ttctgcgtgc aggtgcaggg caagagcaag    780
agagagaaga aggacagagt gttcaccgac aagaccagcg ccaccgtgat ctgcagaaag    840
aacgccagca tcagcgtgag agcccaggac agatactaca gcagcagctg gagcgagtgg    900
```

gccagcgtgc cctgcagc 918

<210> SEQ ID NO 72
<211> LENGTH: 918
<212> TYPE: DNA
<213> ORGANISM: Artificial Sequence
<220> FEATURE:
<223> OTHER INFORMATION: IL12b of B4

<400> SEQUENCE: 72
atctgggagc tgaagaagga tgtgtatgtg gtggagctgg actggtaccc agatgcccct 60
ggagagatgg tggtgctgac ctgtgacacc ccagaggagg atggcatcac ctggaccctg 120
gaccagagca gcgaggtgct gggcagcggc aagaccctga ccatccaggt gaaggagttt 180
ggagatgctg gccagtacac ctgccacaag ggcggggagg tgctgagcca cagcctgctg 240
ctgctgcaca agaaggagga tggcatctgg agcacagaca tcctgaagga ccagaaggag 300
cccaagaaca agaccttcct gcgctgtgag gccaagaact acagcggccg cttcacctgc 360
tggtggctga ccaccatcag cacagacctg accttctctg tgaaaagcag ccggggcagc 420
agtgaccccc agggcgtgac ctgtggggcc gccaccctgt ctgctgagcg ggtgcggggg 480
gacaacaagg agtatgagta cagcgtggag tgccaggagg acagcgcctg cccagctgct 540
gaggagagcc tgcccatcga ggtgatggtg gatgctgtgc acaagctgaa gtatgagaac 600
tacaccagca gcttcttcat ccgggacatc atcaagccag acccccccaa gaacctgcag 660
ctgaagcccc tgaagaacag ccggcaggtg gaggtgtcct gggagtaccc agacacctgg 720
agcacccccc acagctactt cagcctgacc ttctgtgtgc aggtgcaggg caagagcaag 780
cgggagaaga aggacagagt cttcacagac aagaccagcg ccaccgtcat ctgcaggaag 840
aatgccagca tctctgtgcg ggcccaggac cgctactaca gcagctcctg gagcgagtgg 900
gcctctgtgc cctgcagc 918

<210> SEQ ID NO 73
<211> LENGTH: 918
<212> TYPE: DNA
<213> ORGANISM: Artificial Sequence
<220> FEATURE:
<223> OTHER INFORMATION: IL12b of C1

<400> SEQUENCE: 73
atctgggagc tgaaaaagga cgtgtacgtg gtggaacttg actggtaccc cgacgccccc 60
ggcgagatgg tggtactgac ctgcgacact cccgaggaag acggcattac ctggaccttg 120
gaccagagca gcgaggttct gggctccgga aaaaccttga caatccaagt gaaagaattc 180
ggcgacgctg gccagtacac ctgccacaag ggcggcgagg tgctgtccca cagcctgctg 240
ctgctgcata agaaagaaga cgggatttgg agcaccgata tactgaagga tcagaaggag 300
cccaagaaca agaccttcct gaggtgcgag gccaaaaatt acagcggcag attcacctgc 360
tggtggctga ccaccattag cacagacctg actttcagcg taaagtcttc aaggggcagc 420
tcagaccccc agggagtaac ttgcggagcg gcaacgttgt ctgccgagcg ggtcagaggc 480
gacaataagg agtacgagta ttcagtagag tgtcaggaag atagcgcctg tcccgccgcg 540
gaggagagcc tccccatcga ggtgatggtg gacgccgtgc acaagttaaa gtacgagaat 600
tacaccagct catttttat cagagacatt atcaagccgg accccccgaa gaacttacag 660
cttaaacccc taaagaacag caggcaggtt gaggtcagct gggaatatcc tgacacctgg 720

```
tcaacccccc acagctactt ctcccttact ttctgtgtgc aagtgcaggg caagagcaag    780

agagaaaaga aggaccgggt gtttaccgac aagactagcg ccaccgtgat ttgcagaaag    840

aacgccagca ttagtgtgag agcccaggac aggtattact ccagctcatg gtctgagtgg    900

gctagtgtgc cttgctct                                                   918


<210> SEQ ID NO 74
<211> LENGTH: 918
<212> TYPE: DNA
<213> ORGANISM: Artificial Sequence
<220> FEATURE:
<223> OTHER INFORMATION: IL12b of C2

<400> SEQUENCE: 74

atctgggagc tgaagaaaga cgtgtacgtg gtggagcttg actggtaccc cgacgccccc     60

ggtgaaatgg tggttctgac ctgcgacaca ccagaggagg acggcatcac ctggaccctg    120

gaccagtcca gcgaggtcct gggatctggc aagaccctga ccatccaggt taaggaattt    180

ggcgacgccg gccagtacac ctgccacaaa ggcggcgagg tcctttcgca cagtctgctg    240

ctgctgcata aaaaggagga cggcatttgg agcaccgaca ttctgaagga tcagaaagag    300

cccaagaaca agacctttct gagatgtgag gccaaaaact actctggacg cttcacctgt    360

tggtggctga ccaccatcag cacagacctg accttctcgg tgaagtctag taggggcagc    420

agtgaccccc agggcgtaac atgcggcgcc gctaccctga gcgccgagag agtgagaggc    480

gataacaagg agtacgagta ctccgtggag tgccaagagg actcagcctg ccccgccgcc    540

gaggagtcgc tgcccatcga ggtgatggtg gatgcagtgc acaagctgaa gtacgagaac    600

tacaccagta gctttttcat cagagatatc attaaacccg accctcccaa gaacctgcag    660

ctgaagccct taaagaacag ccggcaggtg gaagtgtcat gggagtaccc agacacctgg    720

agcactccgc acagctactt cagcctgacc ttctgcgttc aggtgcaggg aaaaagcaag    780

agagagaaga aagacagagt gttcaccgac aagaccagcg caaccgtgat ctgtagaaag    840

aacgcctcga tcagcgtgag agcccaggac agatactaca gcagcagctg gagcgagtgg    900

gccagtgtac cttgcagc                                                   918


<210> SEQ ID NO 75
<211> LENGTH: 918
<212> TYPE: DNA
<213> ORGANISM: Artificial Sequence
<220> FEATURE:
<223> OTHER INFORMATION: IL12b of C3

<400> SEQUENCE: 75

atctgggaac tgaagaagga cgtctacgtg gtggagctgg attggtaccc cgacgccccc     60

ggcgagatgg tcgtgctgac ctgtgacacc cctgaggagg acggaatcac atggaccctg    120

gaccagagca gcgaagtgtt gggcagcggc aagaccctga ccatccaagt gaaggaattc    180

ggcgacgcgg gccagtatac ttgccacaag ggcggggagg ttctgagcca cagcctgctg    240

ctgctccaca agaaagagga tggcatctgg tctaccgaca tcctgaagga ccaaaaggag    300

ccaaagaaca agaccttcct aagatgcgag gccaagaact actcaggtcg tttcacctgc    360

tggtggctga ccacaatctc caccgacctg accttcagcg tgaaaagcag ccgcggcagt    420

agcgacccac agggcgtgac ctgcggggcc gccactctga gcgccgagag agtgcgcggc    480

gataataagg aatacgagta cagcgtggag tgccaggaag actcagcctg ccccgccgca    540

gaagaaagtc tgccaataga ggtgatggtt gacgccgtgc acaagctaaa gtacgagaac    600
```

```
tacaccagca gcttctttat ccgggacatc atcaagccag atcccccaa gaacctgcag    660

cttaagcccc tgaagaacag cagacaggtg gaggtgtcat gggaataccc cgacacctgg    720

agcacccccc atagctactt ctcactgacc ttctgcgtgc aggtgcaggg caagagcaag    780

agagagaaga aggatagggt attcacggac aagacctcag ccaccgtgat ctgccgaaag    840

aacgccagca tcagcgtgag agcccaggac agatactata gctcctcgtg gagcgagtgg    900

gccagcgtac cttgcagc                                                  918


<210> SEQ ID NO 76
<211> LENGTH: 45
<212> TYPE: DNA
<213> ORGANISM: Artificial Sequence
<220> FEATURE:
<223> OTHER INFORMATION: GS Linker of L1

<400> SEQUENCE: 76

gggggttctg gtgggggcag tggaggagga tcaggtggcg gcagt                     45


<210> SEQ ID NO 77
<211> LENGTH: 45
<212> TYPE: DNA
<213> ORGANISM: Artificial Sequence
<220> FEATURE:
<223> OTHER INFORMATION: GS Linker of L2

<400> SEQUENCE: 77

ggcggttcgg gcggagggtc cggcggtggt agcggaggcg ggagc                     45


<210> SEQ ID NO 78
<211> LENGTH: 45
<212> TYPE: DNA
<213> ORGANISM: Artificial Sequence
<220> FEATURE:
<223> OTHER INFORMATION: GS Linker of L3

<400> SEQUENCE: 78

ggcggttccg gcgggggctc ggggggcggg agcggtggag gcagc                     45


<210> SEQ ID NO 79
<211> LENGTH: 45
<212> TYPE: DNA
<213> ORGANISM: Artificial Sequence
<220> FEATURE:
<223> OTHER INFORMATION: GS Linker of M1

<400> SEQUENCE: 79

ggcggcagcg gcggcgggag cggcggaggc tccgggggag gtagc                     45


<210> SEQ ID NO 80
<211> LENGTH: 45
<212> TYPE: DNA
<213> ORGANISM: Artificial Sequence
<220> FEATURE:
<223> OTHER INFORMATION: GS Linker of M2

<400> SEQUENCE: 80

ggcggcagcg gtggaggaag cggcggtggc agtgggggcg ggagc                     45


<210> SEQ ID NO 81
<211> LENGTH: 45
<212> TYPE: DNA
<213> ORGANISM: Artificial Sequence
<220> FEATURE:
```

<223> OTHER INFORMATION: GS Linker of M3

<400> SEQUENCE: 81
ggcggcagcg gcggtggcag cggcggcggt tctggcggcg gttca 45

<210> SEQ ID NO 82
<211> LENGTH: 45
<212> TYPE: DNA
<213> ORGANISM: Artificial Sequence
<220> FEATURE:
<223> OTHER INFORMATION: GS Linker of H1

<400> SEQUENCE: 82
ggtggcagcg gcggcggctc cggcggcggg agtggcggcg gcagc 45

<210> SEQ ID NO 83
<211> LENGTH: 45
<212> TYPE: DNA
<213> ORGANISM: Artificial Sequence
<220> FEATURE:
<223> OTHER INFORMATION: GS Linker of H2

<400> SEQUENCE: 83 gggggggagcg gcggtggcag cgggggcggc agcggcgggg gcagc 45

<210> SEQ ID NO 84
<211> LENGTH: 45
<212> TYPE: DNA
<213> ORGANISM: Artificial Sequence
<220> FEATURE:
<223> OTHER INFORMATION: GS Linker of H3

<400> SEQUENCE: 84
ggcgggagcg gcggcggcag cggcggtggc agtggcgggg gcagc 45

<210> SEQ ID NO 85
<211> LENGTH: 45
<212> TYPE: DNA
<213> ORGANISM: Artificial Sequence
<220> FEATURE:
<223> OTHER INFORMATION: GS Linker of CO

<400> SEQUENCE: 85
ggcggcagcg gcggcggcag cggcggcggc agcggcggcg gcagc 45

<210> SEQ ID NO 86
<211> LENGTH: 45
<212> TYPE: DNA
<213> ORGANISM: Artificial Sequence
<220> FEATURE:
<223> OTHER INFORMATION: GS Linker of CP

<400> SEQUENCE: 86
ggcggcagcg gcggcggcag cggcggcggc agcggcggcg gcagc 45

<210> SEQ ID NO 87
<211> LENGTH: 45
<212> TYPE: DNA
<213> ORGANISM: Artificial Sequence
<220> FEATURE:
<223> OTHER INFORMATION: GS Linker of vH1

<400> SEQUENCE: 87
ggcggctcag gcggcggctc aggcggcggc agcggcggcg gcagc 45

<210> SEQ ID NO 88
<211> LENGTH: 45
<212> TYPE: DNA
<213> ORGANISM: Artificial Sequence
<220> FEATURE:
<223> OTHER INFORMATION: GS Linker of vH2

<400> SEQUENCE: 88
ggcggcagcg gcggcggcag cggcggcggc agcggcggcg gcagc 45

<210> SEQ ID NO 89
<211> LENGTH: 45
<212> TYPE: DNA
<213> ORGANISM: Artificial Sequence
<220> FEATURE:
<223> OTHER INFORMATION: GS Linker of vH3

<400> SEQUENCE: 89
ggcggcagcg gtggcgggag cggcggcggg agcggcggcg gaagc 45

<210> SEQ ID NO 90
<211> LENGTH: 45
<212> TYPE: DNA
<213> ORGANISM: Artificial Sequence
<220> FEATURE:
<223> OTHER INFORMATION: GS Linker of A1

<400> SEQUENCE: 90
ggtggaagcg gcggaggctc tggcggaggg agtggcggag gcagc 45

<210> SEQ ID NO 91
<211> LENGTH: 45
<212> TYPE: DNA
<213> ORGANISM: Artificial Sequence
<220> FEATURE:
<223> OTHER INFORMATION: GS Linker of A2

<400> SEQUENCE: 91
ggcgggagcg gcggcggcag cggaggtggc agtggcggag gcagc 45

<210> SEQ ID NO 92
<211> LENGTH: 45
<212> TYPE: DNA
<213> ORGANISM: Artificial Sequence
<220> FEATURE:
<223> OTHER INFORMATION: GS Linker of A3

<400> SEQUENCE: 92
ggcggcagcg gcggcggcag cggcggcggc agcggcggcg gcagc 45

<210> SEQ ID NO 93
<211> LENGTH: 45
<212> TYPE: DNA
<213> ORGANISM: Artificial Sequence
<220> FEATURE:
<223> OTHER INFORMATION: GS Linker of A4

<400> SEQUENCE: 93
ggcggcagcg gcggcggcag cggcggcggc agcggcggcg gcagc 45

<210> SEQ ID NO 94
<211> LENGTH: 45
<212> TYPE: DNA
<213> ORGANISM: Artificial Sequence
<220> FEATURE:
<223> OTHER INFORMATION: GS Linker of B1

<400> SEQUENCE: 94
ggtggaagcg gcggaggctc tggcggaggg agtggcggag gcagc 45

<210> SEQ ID NO 95
<211> LENGTH: 45
<212> TYPE: DNA
<213> ORGANISM: Artificial Sequence
<220> FEATURE:
<223> OTHER INFORMATION: GS Linker of B2

<400> SEQUENCE: 95
ggcgggagcg gcggcggcag cggaggtggc agtggcggag gcagc 45

<210> SEQ ID NO 96
<211> LENGTH: 45
<212> TYPE: DNA
<213> ORGANISM: Artificial Sequence
<220> FEATURE:
<223> OTHER INFORMATION: GS Linker of B3

<400> SEQUENCE: 96
ggcggcagcg gcggcggcag cggcggcggc agcggcggcg gcagc 45

<210> SEQ ID NO 97
<211> LENGTH: 45
<212> TYPE: DNA
<213> ORGANISM: Artificial Sequence
<220> FEATURE:
<223> OTHER INFORMATION: GS Linker of B4

<400> SEQUENCE: 97
ggcggcagcg gcggcggcag cggcggcggc agcggcggcg gcagc 45

<210> SEQ ID NO 98
<211> LENGTH: 45
<212> TYPE: DNA
<213> ORGANISM: Artificial Sequence
<220> FEATURE:
<223> OTHER INFORMATION: GS Linker of C1

<400> SEQUENCE: 98
ggaggcagcg gtggcgggag cggcggaggc tccgggggag gtagc 45

<210> SEQ ID NO 99
<211> LENGTH: 45
<212> TYPE: DNA
<213> ORGANISM: Artificial Sequence
<220> FEATURE:
<223> OTHER INFORMATION: GS Linker of C2

<400> SEQUENCE: 99
ggtggaagcg gcggaggctc tggcggaggg agtggcggag gcagc 45

<210> SEQ ID NO 100
<211> LENGTH: 45
<212> TYPE: DNA
<213> ORGANISM: Artificial Sequence
<220> FEATURE:
<223> OTHER INFORMATION: GS Linker of C3

<400> SEQUENCE: 100
ggcgggagcg gcggcggcag cggaggtggc agtggcggag gcagc 45

<210> SEQ ID NO 101
<211> LENGTH: 591

<212> TYPE: DNA
<213> ORGANISM: Artificial Sequence
<220> FEATURE:
<223> OTHER INFORMATION: IL12a of L1

<400> SEQUENCE: 101
cgcaatctac ccgtggcaac accagacccg ggaatgttcc catgtctgca ccacagtcaa 60
aacctcttaa gggccgtgtc aaatatgcta cagaaggcga gacagacttt agaattctac 120
ccttgtacaa gcgaggagat tgaccacgag gacatcacca aagataagac gagcaccgtc 180
gaggcttgcc tgcctctaga actaacaaaa aatgaatcat gcttgaactc gagggagacc 240
agtttcatta ctaacggttc atgtcttgca tcgaggaaga cctcattcat gatggccctg 300
tgcctctcgt ccatttatga agacctaaag atgtaccagg tagagtttaa gaccatgaac 360
gccaagctcc tcatggatcc aaaacggcaa atattcttag atcagaatat gctcgctgtt 420
atcgacgaac tcatgcaggc gcttaacttc aactcagaaa ccgttcccca aaagtcgagt 480
ctagaagaac cggactttta taagaccaaa attaaactgt gtatactact tcacgccttc 540
aggataagag cagtgacgat tgacagggtg atgtcctact tgaatgcatc a 591

<210> SEQ ID NO 102
<211> LENGTH: 591
<212> TYPE: DNA
<213> ORGANISM: Artificial Sequence
<220> FEATURE:
<223> OTHER INFORMATION: IL12a of L2

<400> SEQUENCE: 102
aggaacttgc ccgtggctac tccagaccct ggcatgttcc cctgtttaca ccactcccag 60
aacttattac gtgctgttag caacatgttg caaaaggccc gtcaaaccct cgagttttac 120
ccctgtacta gtgaagaaat cgaccacgaa gacataacaa aagacaagac aagcacagtt 180
gaggcatgct taccccctgga gttaacaaag aacgagagct gtctgaactc tcgagagacg 240
agcttcatca ccaatgggag ttgccttgct tctcgaaaaa cgtcgttcat gatggccctg 300
tgcctgtcgt ctatctatga ggatctgaaa atgtatcagg ttgaattcaa gacaatgaat 360
gccaaactac tcatggatcc aaaacggcag atattcctcg atcagaatat gctcgcagtt 420
attgacgaac taatgcaggc tctgaatttt aacagcgaga ccgttcctca gaagtcaagt 480
ttggaagaac ctgacttcta caaaactaaa ataaaattat gcatcttact gcatgctttc 540
agaattagag ctgtcactat tgatcgagtg atgtcatact tgaatgcttc c 591

<210> SEQ ID NO 103
<211> LENGTH: 591
<212> TYPE: DNA
<213> ORGANISM: Artificial Sequence
<220> FEATURE:
<223> OTHER INFORMATION: IL12a of L3

<400> SEQUENCE: 103
aggaatcttc ctgtcgcgac ccctgatccc ggcatgtttc cttgcctgca ccacagtcag 60
aacttattac gcgccgtttc caatatgtta cagaaggcca gacagacatt agagttttat 120
ccttgcacat cggaggagat cgaccatgaa gatatcacaa aagataaaac atccaccgtt 180
gaggcctgcc tgccacttga acttactaaa aacgagagct gcctgaatag ccgggaaact 240
tctttcatca ctaatggatc gtgtctagca agccgaaaaa ccagcttcat gatggctttg 300
tgcctctcgt ccatctatga agacctgaaa atgtatcaag tagaatttaa aacgatgaat 360
gccaaactgc ttatggatcc caaacgccag atatttctag accagaatat gctggccgtc 420
attgatgagc taatgcaggc tctcaatttt aatagcgaaa cagtgcccca aaaaagctct 480
ttggaagagc cggattttta caaaaccaag attaagctat gtatcctgct gcatgctttc 540
agaattcgag ctgttacaat tgatcgggtt atgagctact taaacgcctc g 591

<210> SEQ ID NO 104
<211> LENGTH: 591
<212> TYPE: DNA
<213> ORGANISM: Artificial Sequence
<220> FEATURE:
<223> OTHER INFORMATION: IL12a of M1

<400> SEQUENCE: 104
cggaatctgc ctgtcgccac tccagacccc ggcatgttcc catgtctgca tcattctcag 60
aacctgctga gggccgtatc caatatgctg cagaaagcca gacagacctt agagttctat 120
ccctgtacaa gcgaggagat agatcacgag gatattacga aggacaaaac ttctactgtt 180
gaggcgtgtc ttccattaga gctgaccaag aacgaaagct gtctgaatag cagagagact 240
tcatttatca ccaatgggag ttgcttggct agcagaaaga ccagcttcat gatggccctt 300
tgcttgtctt cgatatacga agatcttaag atgtatcaag tggaatttaa gacgatgaac 360
gccaagctgc ttatggatcc caagcgccaa atcttcctgg atcagaacat gttggccgtg 420
attgacgagc tgatgcaagc cctgaatttc aactccgaga ccgtgcctca gaagagcagc 480
ctcgaggagc ccgacttcta caaaacaaag atcaaactct gcatccttct gcacgccttc 540
agaattagag ccgtgaccat cgacagagtt atgagctacc tgaatgccag c 591

<210> SEQ ID NO 105
<211> LENGTH: 591
<212> TYPE: DNA
<213> ORGANISM: Artificial Sequence
<220> FEATURE:
<223> OTHER INFORMATION: IL12a of M2

<400> SEQUENCE: 105
agaaatctgc ccgtcgccac tccagatcct ggcatgttcc cgtgcctgca tcacagccaa 60
aacctgctgc gggcggtgtc taacatgctg cagaaggcta ggcagacctt ggaattctat 120
ccctgcacaa gcgaggaaat agaccatgag gacatcacca aggataagac cagcacggtc 180
gaagcttgcc tgccactgga actgacaaaa aacgagagtt gcctgaactc ccgcgagaca 240
tccttcatca caaacggcag ctgcctggct agcaggaaga ccagcttcat gatggccctg 300
tgcctgtctt ccatctacga ggacctgaaa atgtaccaag tggagttcaa gactatgaac 360
gccaagctgc taatggatcc caagcgacag atctttctag accagaacat gctggccgtc 420
attgacgagc tgatgcaggc actcaatttt aactcagaga ccgtgccaca gaagtccagc 480
ctggaggagc ctgacttcta taagaccaag attaagctgt gcatcctgct gcatgccttc 540
cgaataagag ccgtgaccat tgaccgagtg atgtcatact tgaacgcaag c 591

<210> SEQ ID NO 106
<211> LENGTH: 591
<212> TYPE: DNA
<213> ORGANISM: Artificial Sequence
<220> FEATURE:
<223> OTHER INFORMATION: IL12a of M3

<400> SEQUENCE: 106
agaaacctcc cagtcgctac ccccgatccc ggaatgttcc cctgcctgca ccactcccag 60

```
aatctgctcc gagccgttag caacatgctg caaaaggccc ggcagaccct ggagttctac    120

ccatgcacct cggaagaaat cgatcacgag gacatcacca aggacaagac tagcaccgtc    180

gaggcctgcc tgccgctgga actaaccaag aatgaaagct gcctcaactc gcgggagacc    240

tctttcataa ccaacggctc atgcctggcc agccggaaaa ctagctttat gatggctctg    300

tgcttaagca gcatctacga ggatctgaag atgtaccagg tagagttcaa gaccatgaat    360

gccaagctgc tgatggaccc caagagacaa atcttcctgg accagaacat gctggccgta    420

attgatgaac tgatgcaggc cctgaatttc aacagcgaga ccgtacccca gaaaagctca    480

ctggaggagc ccgactttta taagacgaaa ataaagttgt gcatccttct tcacgctttc    540

cggattagag ccgtgaccat cgatagagtg atgtcatacc tgaacgcatc g             591


<210> SEQ ID NO 107
<211> LENGTH: 591
<212> TYPE: DNA
<213> ORGANISM: Artificial Sequence
<220> FEATURE:
<223> OTHER INFORMATION: IL12a of H1

<400> SEQUENCE: 107

agaaatctgc ccgtagccac ccccgacccc ggcatgtttc cctgtctgca ccattctcaa     60

aacctgttac gggccgtgag caacatgctg cagaaggcca gacagacact ggagttttac    120

ccctgtacct cagaggagat cgatcatgag gacattacta aggacaagac cagcaccgtg    180

gaagcctgcc tgcccctaga gctaaccaag aacgagagct gcctgaactc tagagagaca    240

agcttcatca cgaacggctc atgcctggcc agtaggaaaa ccagcttcat gatggctctg    300

tgcctgagct ccatatatga ggaccttaag atgtaccagg tggagttcaa aaccatgaac    360

gccaagctgc tgatggaccc aaagagacag atcttccttg accagaacat gctggccgtt    420

atcgatgagc tgatgcaggc cctgaacttc aacagcgaga ccgtgcccca gaagagcagc    480

ctggaggaac ccgacttcta caaaaccaag atcaagctgt gcattctgct gcatgccttc    540

cgcattagag ccgtgaccat cgatagggtg atgagctacc tgaacgccag c             591


<210> SEQ ID NO 108
<211> LENGTH: 591
<212> TYPE: DNA
<213> ORGANISM: Artificial Sequence
<220> FEATURE:
<223> OTHER INFORMATION: IL12a of H2

<400> SEQUENCE: 108

agaaacctgc ccgtggccac acccgatccc ggcatgttcc cctgtctgca ccacagccaa     60

aacctgctgc gtgccgtgag caacatgctg cagaaggcgc ggcagaccct ggagttctat    120

ccctgcacca gtgaggagat tgaccacgag gatatcacca aagacaagac cagcaccgtg    180

gaggcctgcc tcccccctgga gctgaccaag aacgagtcct gcttgaattc aagagagacc    240

agcttcatca ccaacggctc ctgcttagcc agcagaaaga ctagcttcat gatggccttg    300

tgcttgtcta gcatctatga ggatctgaag atgtaccagg tcgagttcaa gactatgaac    360

gccaagctgc tgatggaccc caaaagacag atcttcctgg accagaacat gctggccgtc    420

atcgacgagc tgatgcaggc ccttaatttc aatagcgaga cagtgcccca gaaatcttct    480

ctggaggagc ccgattttta caaaaccaag atcaaactat gcatcctgtt gcacgccttc    540

cggatccgcg ccgtgaccat cgacagagta atgtcctacc tgaacgccag c             591
```

<210> SEQ ID NO 109
<211> LENGTH: 591
<212> TYPE: DNA
<213> ORGANISM: Artificial Sequence
<220> FEATURE:
<223> OTHER INFORMATION: IL12a of H3

<400> SEQUENCE: 109
agaaacctgc ccgtggccac ccccgacccc gggatgtttc cttgcctgca ccactcccag 60
aacctcctga gagccgtgtc caacatgctg cagaaagcca gacagaccct cgagttctat 120
ccctgcacaa gcgaggagat cgaccacgag gacatcacta aggacaagac cagcacagtg 180
gaagcctgcc tcccgctgga gctgactaag aacgagagct gtctgaacag cagggagacc 240
agcttcatca ccaacggcag ctgcctggcg agcagaaaaa cctcctttat gatggcgctc 300
tgcctgagct caatctatga ggacctgaag atgtaccagg tggagtttaa aaccatgaat 360
gccaagctgc ttatggaccc taagagacag attttcctgg atcagaacat gctggccgtg 420
attgatgaat taatgcaggc gctgaacttt aacagcgaga ccgtgcccca gaagagcagc 480
ctggaggagc ccgactttta caagaccaag atcaagttgt gcatcctcct gcacgccttc 540
agaatcagag cggtgacgat cgacagagtc atgagctacc tcaacgctag c 591

<210> SEQ ID NO 110
<211> LENGTH: 591
<212> TYPE: DNA
<213> ORGANISM: Artificial Sequence
<220> FEATURE:
<223> OTHER INFORMATION: IL12a of CO

<400> SEQUENCE: 110
agaaacctgc ccgtggccac ccccgacccc ggcatgttcc cctgcctgca ccacagccag 60
aacctgctga gagccgtgag caacatgctg cagaaggcca gacagaccct ggagttctac 120
ccctgcacca gcgaggagat cgaccacgag gacatcacca aggacaagac cagcaccgtg 180
gaggcctgcc tgcccctgga gctgaccaag aacgagagct gcctgaacag cagagagacc 240
agcttcatca ccaacggcag ctgcctggcc agcagaaaga ccagcttcat gatggccctg 300
tgcctgagca gcatctacga ggacctgaag atgtaccagg tggagttcaa gaccatgaac 360
gccaagctgc tgatggaccc caagagacag atcttcctgg accagaacat gctggccgtg 420
atcgacgagc tgatgcaggc cctgaacttc aacagcgaga ccgtgcccca gaagagcagc 480
ctggaggagc ccgacttcta caagaccaag atcaagctgt gcatcctgct gcacgccttc 540
agaatcagag ccgtgaccat cgacagagtg atgagctacc tgaacgccag c 591

<210> SEQ ID NO 111
<211> LENGTH: 591
<212> TYPE: DNA
<213> ORGANISM: Artificial Sequence
<220> FEATURE:
<223> OTHER INFORMATION: IL12a of CP

<400> SEQUENCE: 111
aggaacctgc ctgtggccac cccagacccc ggcatgttcc cctgcctgca ccacagccag 60
aacctgctgc gggctgtgag caacatgctg cagaaggccc ggcagaccct ggagttctac 120
ccctgcacca gcgaggagat tgaccacgag gacatcacca aggacaagac cagcacagtg 180
gaggcctgcc tgcccctgga gctgaccaag aatgaaagct gcctgaacag ccgggagacc 240
agcttcatca ccaacggcag ctgcctggcc agcaggaaga ccagcttcat gatggccctg 300

```
tgcctgagca gcatctatga ggacctgaag atgtaccagg tggagttcaa gaccatgaat    360

gccaagctgc tgatggaccc caagaggcag atcttcctgg accagaacat gctggccgtg    420

attgatgagc tgatgcaggc cctgaacttc aacagcgaga ccgtgcccca gaaaagcagc    480

ctggaggagc cagacttcta caagaccaag atcaagctgt gcatcctgct gcacgccttc    540

cgcatccggg ctgtgaccat cgacagagtg atgagctacc tgaatgccag c             591


<210> SEQ ID NO 112
<211> LENGTH: 591
<212> TYPE: DNA
<213> ORGANISM: Artificial Sequence
<220> FEATURE:
<223> OTHER INFORMATION: IL12a of vH1

<400> SEQUENCE: 112

agaaacctgc ccgtggccac gcccgacccc ggcatgtttc cctgcctgca ccatagccag     60

aatctgctga gagccgtgag caacatgctg cagaaggcca gacagacgct cgagttctac    120

ccctgcacca gcgaggagat tgaccacgag gacatcacca aggacaagac cagcaccgtg    180

gaggcctgcc tgcccctcga gctgaccaag aacgagagct gcctgaacag cagagagacc    240

agcttcatca ccaacggcag ctgcctggcc agcagaaaga ccagcttcat gatggccctg    300

tgcctgagca gcatctacga ggacctgaag atgtaccagg tggagttcaa gacaatgaac    360

gccaagctgc tgatggaccc caagaggcag atttttctgg accagaacat gctggccgtt    420

atcgacgagc tgatgcaggc cctgaatttc aatagcgaaa ccgtgcccca gaagagcagc    480

ctggaggagc ctgacttcta caaaaccaag atcaagcttt gcatcctgct gcacgccttc    540

agaatcagag ccgtgaccat cgacagagtg atgagctacc tgaacgccag c             591


<210> SEQ ID NO 113
<211> LENGTH: 591
<212> TYPE: DNA
<213> ORGANISM: Artificial Sequence
<220> FEATURE:
<223> OTHER INFORMATION: IL12a of vH2

<400> SEQUENCE: 113

agaaacctgc ccgtggccac ccccgacccc ggcatgttcc cctgcctgca ccacagccag     60

aacctgctga gagccgtgag caacatgctg cagaaggcca gacagaccct ggagttctac    120

ccctgcacca gcgaggagat cgaccatgag gacatcacca aggacaagac cagcaccgtg    180

gaggcctgcc tgcccctgga gctgaccaag aacgaaagct gcctgaacag cagagagacc    240

agcttcatca ccaacggcag ctgtctggcc tcaagaaaga ccagctttat gatggccctg    300

tgcctgtcta gcatctacga ggatctgaag atgtaccagg tggagttcaa gaccatgaac    360

gccaagctgc tgatggaccc caagagacag atcttcctgg accagaacat gttagccgtg    420

attgacgagc tgatgcaggc cctgaacttc aatagcgaga ccgtgcccca gaaaagcagc    480

ctggaggagc ccgacttcta caagaccaag atcaagctgt gcatcctgct gcacgccttc    540

agaatcagag ccgtaaccat cgacagagtg atgagctacc tgaacgccag t             591


<210> SEQ ID NO 114
<211> LENGTH: 591
<212> TYPE: DNA
<213> ORGANISM: Artificial Sequence
<220> FEATURE:
<223> OTHER INFORMATION: IL12a of vH3
```

<400> SEQUENCE: 114
agaaacctgc ccgtggccac ccctgacccc ggcatgttcc cctgcctgca ccacagccag 60
aacctgctga gagccgtaag caacatgctg cagaaggcca gacagactct ggagttctac 120
ccctgcacca gcgaggagat cgatcacgag gacatcacca aggacaagac cagtaccgtg 180
gaggcctgcc tgcccctgga gctgaccaag aacgagagct gcctgaacag cagagagacc 240
agctttataa ccaacggcag ctgtctggct agcagaaaga ccagcttcat gatggccctg 300
tgcctgagca gcatctacga ggacttgaag atgtaccagg tggagttcaa gaccatgaac 360
gccaagcttc tgatggaccc caagagacag atctttctgg accagaacat gctggccgtg 420
atcgatgaac tgatgcaggc cctgaacttc aacagcgaga ccgtgcccca gaagagcagt 480
ctggaggagc ccgacttcta caagactaag atcaagctgt gcatcctgct gcacgccttc 540
agaatcagag ccgtgaccat cgacagagtg atgagctacc tgaacgcctc a 591

<210> SEQ ID NO 115
<211> LENGTH: 591
<212> TYPE: DNA
<213> ORGANISM: Artificial Sequence
<220> FEATURE:
<223> OTHER INFORMATION: IL12a of A1

<400> SEQUENCE: 115
agaaatcttc cagtagctac ccccgacccc ggcatgtttc cctgtctgca ccattctcaa 60
aacctgttac gggccgtgag caacatgctg cagaaggcca gacagacact ggagttttac 120
ccctgtacct cagaggagat cgatcatgag gacattacta aggacaagac cagcaccgtg 180
gaagcctgcc tgcccctaga gctaaccaag aacgagagct gcctgaactc tagagagaca 240
agcttcatca cgaacggctc atgcctggcc agtaggaaaa ccagcttcat gatggctctg 300
tgcctgagct ccatatatga ggaccttaag atgtaccagg tggagttcaa aaccatgaac 360
gccaagctgc tgatggaccc aaagagacag atcttccttg accagaacat gctggccgtt 420
atcgatgagc tgatgcaggc cctgaacttc aacagcgaga ccgtgcccca gaaaagcagc 480
ctggaggaac ccgacttcta caaaaccaag atcaagctgt gcattctgct gcatgccttc 540
cgcattagag ccgtgaccat cgatagggtg atgagctacc tgaacgccag c 591

<210> SEQ ID NO 116
<211> LENGTH: 588
<212> TYPE: DNA
<213> ORGANISM: Artificial Sequence
<220> FEATURE:
<223> OTHER INFORMATION: IL12a of A2

<400> SEQUENCE: 116
agaaacctcc ccgtggcaac ccctgacccc gggatgtttc cttgcctgca ccactcccag 60
aacctcctga gagccgtgtc caacatgctg cagaaagcca gacagaccct cgagttctat 120
ccctgcacaa gcgaggagat cgaccacgag gacatcacta aggacaagac cagcacagtg 180
gaagcctgcc tcccgctgga gctgactaag aacgagagct gtctgaacag cagggagacc 240
agcttcatca ccaacggcag ctgcctggcg agcagaaaaa cctcctttat gatggcgctc 300
tgcctgagct caatctatga ggacctgaag atgtaccagg tggagtttaa aaccatgaat 360
gccaagctgc ttatggaccc taagagacag attttcctgg atcagaacat gctggccgtg 420
attgatgaat taatgcaggc gctgaacttt aacagcgaga ccgtgcccca gaaaagcagc 480
ctggaggagc ccgactttta caagaccaag atcaagttgt gcatcctcct gcacgccttc 540
agaatcagag cggtgacgat cgacagagtc atgagctacc tcaacgct 588

<210> SEQ ID NO 117
<211> LENGTH: 591
<212> TYPE: DNA
<213> ORGANISM: Artificial Sequence
<220> FEATURE:
<223> OTHER INFORMATION: IL12a of A3

<400> SEQUENCE: 117
agaaacctgc ccgtggccac ccccgacccc ggcatgttcc cctgcctgca ccacagccag 60
aacctgctga gagccgtgag caacatgctg cagaaggcca gacagaccct ggagttctac 120
ccctgcacca gcgaggagat cgaccacgag gacatcacca aggacaagac cagcaccgtg 180
gaggcctgcc tgcccctgga gctgaccaag aacgagagct gcctgaacag cagagagacc 240
agcttcatca ccaacggcag ctgcctggcc agcagaaaga ccagcttcat gatggccctg 300
tgcctgagca gcatctacga ggacctgaag atgtaccagg tggagttcaa gaccatgaac 360
gccaagctgc tgatggaccc caagagacag atcttcctgg accagaacat gctggccgtg 420
atcgacgagc tgatgcaggc cctgaacttc aacagcgaga ccgtgcccca gaaaagcagc 480
ctggaggagc ccgacttcta caagaccaag atcaagctgt gcatcctgct gcacgccttc 540
agaatcagag ccgtgaccat cgacagagtg atgagctacc tgaacgccag c 591

<210> SEQ ID NO 118
<211> LENGTH: 591
<212> TYPE: DNA
<213> ORGANISM: Artificial Sequence
<220> FEATURE:
<223> OTHER INFORMATION: IL12a of A4

<400> SEQUENCE: 118
aggaacctgc ctgtggccac cccagacccc ggcatgttcc cctgcctgca ccacagccag 60
aacctgctgc gggctgtgag caacatgctg cagaaggccc ggcagaccct ggagttctac 120
ccctgcacca gcgaggagat tgaccacgag gacatcacca aggacaagac cagcacagtg 180
gaggcctgcc tgcccctgga gctgaccaag aatgaaagct gcctgaacag ccgggagacc 240
agcttcatca ccaacggcag ctgcctggcc agcaggaaga ccagcttcat gatggccctg 300
tgcctgagca gcatctatga ggacctgaag atgtaccagg tggagttcaa gaccatgaat 360
gccaagctgc tgatggaccc caagaggcag atcttcctgg accagaacat gctggccgtg 420
attgatgagc tgatgcaggc cctgaacttc aacagcgaga ccgtgcccca gaaaagcagc 480
ctggaggagc cagacttcta caagaccaag atcaagctgt gcatcctgct gcacgccttc 540
cgcatccggg ctgtgaccat cgacagagtg atgagctacc tgaatgccag c 591

<210> SEQ ID NO 119
<211> LENGTH: 591
<212> TYPE: DNA
<213> ORGANISM: Artificial Sequence
<220> FEATURE:
<223> OTHER INFORMATION: IL12a of B1

<400> SEQUENCE: 119
agaaatcttc cagtagctac ccccgacccc ggcatgtttc cctgtctgca ccattctcaa 60
aacctgttac gggccgtgag caacatgctg cagaaggcca gacagacact ggagttttac 120
ccctgtacct cagaggagat cgatcatgag gacattacta aggacaagac cagcaccgtg 180
gaagcctgcc tgcccctaga gctaaccaag aacgagagct gcctgaactc tagagagaca 240
agcttcatca cgaacggctc atgcctggcc agtaggaaaa ccagcttcat gatggctctg 300
tgcctgagct ccatatatga ggaccttaag atgtaccagg tggagttcaa aaccatgaac 360
gccaagctgc tgatggaccc aaagagacag atcttccttg accagaacat gctggccgtt 420
atcgatgagc tgatgcaggc cctgaacttc aacagcgaga ccgtgcccca gaaaagcagc 480
ctggaggaac ccgacttcta caaaaccaag atcaagctgt gcattctgct gcatgccttc 540
cgcattagag ccgtgaccat cgatagggtg atgagctacc tgaacgccag c 591

<210> SEQ ID NO 120
<211> LENGTH: 591
<212> TYPE: DNA
<213> ORGANISM: Artificial Sequence
<220> FEATURE:
<223> OTHER INFORMATION: IL12a of B2

<400> SEQUENCE: 120
agaaacctcc ccgtggcaac ccctgacccc gggatgtttc cttgcctgca ccactcccag 60
aacctcctga gagccgtgtc caacatgctg cagaaagcca gacagaccct cgagttctat 120
ccctgcacaa gcgaggagat cgaccacgag gacatcacta aggacaagac cagcacagtg 180
gaagcctgcc tcccgctgga gctgactaag aacgagagct gtctgaacag cagggagacc 240
agcttcatca ccaacggcag ctgcctggcg agcagaaaaa cctcctttat gatggcgctc 300
tgcctgagct caatctatga ggacctgaag atgtaccagg tggagtttaa aaccatgaat 360
gccaagctgc ttatggaccc taagagacag attttcctgg atcagaacat gctggccgtg 420
attgatgaat taatgcaggc gctgaacttt aacagcgaga ccgtgcccca gaaaagcagc 480
ctggaggagc ccgactttta caagaccaag atcaagttgt gcatcctcct gcacgccttc 540
agaatcagag cggtgacgat cgacagagtc atgagctacc tcaacgctag c 591

<210> SEQ ID NO 121
<211> LENGTH: 591
<212> TYPE: DNA
<213> ORGANISM: Artificial Sequence
<220> FEATURE:
<223> OTHER INFORMATION: IL12a of B3

<400> SEQUENCE: 121
agaaacctgc ccgtggccac ccccgacccc ggcatgttcc cctgcctgca ccacagccag 60
aacctgctga gagccgtgag caacatgctg cagaaggcca gacagaccct ggagttctac 120
ccctgcacca gcgaggagat cgaccacgag gacatcacca aggacaagac cagcaccgtg 180
gaggcctgcc tgcccctgga gctgaccaag aacgagagct gcctgaacag cagagagacc 240
agcttcatca ccaacggcag ctgcctggcc agcagaaaga ccagcttcat gatggccctg 300
tgcctgagca gcatctacga ggacctgaag atgtaccagg tggagttcaa gaccatgaac 360
gccaagctgc tgatggaccc caagagacag atcttcctgg accagaacat gctggccgtg 420
atcgacgagc tgatgcaggc cctgaacttc aacagcgaga ccgtgcccca gaaaagcagc 480
ctggaggagc ccgacttcta caagaccaag atcaagctgt gcatcctgct gcacgccttc 540
agaatcagag ccgtgaccat cgacagagtg atgagctacc tgaacgccag c 591

<210> SEQ ID NO 122
<211> LENGTH: 591
<212> TYPE: DNA
<213> ORGANISM: Artificial Sequence
<220> FEATURE:
<223> OTHER INFORMATION: IL12a of B4

<400> SEQUENCE: 122
aggaacctgc ctgtggccac cccagacccc ggcatgttcc cctgcctgca ccacagccag 60
aacctgctgc gggctgtgag caacatgctg cagaaggccc ggcagaccct ggagttctac 120
ccctgcacca gcgaggagat tgaccacgag gacatcacca aggacaagac cagcacagtg 180
gaggcctgcc tgcccctgga gctgaccaag aatgaaagct gcctgaacag ccgggagacc 240
agcttcatca ccaacggcag ctgcctggcc agcaggaaga ccagcttcat gatggccctg 300
tgcctgagca gcatctatga ggacctgaag atgtaccagg tggagttcaa gaccatgaat 360
gccaagctgc tgatggaccc caagaggcag atcttcctgg accagaacat gctggccgtg 420
attgatgagc tgatgcaggc cctgaacttc aacagcgaga ccgtgcccca gaaaagcagc 480
ctggaggagc cagacttcta caagaccaag atcaagctgt gcatcctgct gcacgccttc 540
cgcatccggg ctgtgaccat cgacagagtg atgagctacc tgaatgccag c 591

<210> SEQ ID NO 123
<211> LENGTH: 591
<212> TYPE: DNA
<213> ORGANISM: Artificial Sequence
<220> FEATURE:
<223> OTHER INFORMATION: IL12a of C1

<400> SEQUENCE: 123
cggaatctgc ctgtcgccac tccagacccc ggcatgttcc catgtctgca tcattctcag 60
aacctgctga gggccgtatc caatatgctg cagaaagcca gacagacctt agagttctat 120
ccctgtacaa gcgaggagat agatcacgag gatattacga aggacaaaac ttctactgtt 180
gaggcgtgtc ttccattaga gctgaccaag aacgaaagct gtctgaatag cagagagact 240
tcatttatca ccaatgggag ttgcttggct agcagaaaga ccagcttcat gatggccctt 300
tgcttgtctt cgatatacga agatcttaag atgtatcaag tggaatttaa gacgatgaac 360
gccaagctgc ttatggatcc caagcgccaa atcttcctgg atcagaacat gttggccgtg 420
attgacgagc tgatgcaagc cctgaatttc aactccgaga ccgtgcctca gaaaagcagc 480
ctcgaggagc ccgacttcta caaaacaaag atcaaactct gcatccttct gcacgccttc 540
agaattagag ccgtgaccat cgacagagtt atgagctacc tgaatgccag c 591

<210> SEQ ID NO 124
<211> LENGTH: 591
<212> TYPE: DNA
<213> ORGANISM: Artificial Sequence
<220> FEATURE:
<223> OTHER INFORMATION: IL12a of C2

<400> SEQUENCE: 124
agaaatcttc cagtagctac ccccgacccc ggcatgtttc cctgtctgca ccattctcaa 60
aacctgttac gggccgtgag caacatgctg cagaaggcca gacagacact ggagttttac 120
ccctgtacct cagaggagat cgatcatgag gacattacta aggacaagac cagcaccgtg 180
gaagcctgcc tgcccctaga gctaaccaag aacgagagct gcctgaactc tagagagaca 240
agcttcatca cgaacggctc atgcctggcc agtaggaaaa ccagcttcat gatggctctg 300
tgcctgagct ccatatatga ggaccttaag atgtaccagg tggagttcaa aaccatgaac 360
gccaagctgc tgatggaccc aaagagacag atcttccttg accagaacat gctggccgtt 420
atcgatgagc tgatgcaggc cctgaacttc aacagcgaga ccgtgcccca gaaaagcagc 480
ctggaggaac ccgacttcta caaaaccaag atcaagctgt gcattctgct gcatgccttc 540
cgcattagag ccgtgaccat cgatagggtg atgagctacc tgaacgccag c 591

<210> SEQ ID NO 125
<211> LENGTH: 591
<212> TYPE: DNA
<213> ORGANISM: Artificial Sequence
<220> FEATURE:
<223> OTHER INFORMATION: IL12a of C3

<400> SEQUENCE: 125
agaaacctcc ccgtggcaac ccctgacccc gggatgtttc cttgcctgca ccactcccag 60
aacctcctga gagccgtgtc caacatgctg cagaaagcca gacagaccct cgagttctat 120
ccctgcacaa gcgaggagat cgaccacgag gacatcacta aggacaagac cagcacagtg 180
gaagcctgcc tcccgctgga gctgactaag aacgagagct gtctgaacag cagggagacc 240
agcttcatca ccaacggcag ctgcctggcg agcagaaaaa cctcctttat gatggcgctc 300
tgcctgagct caatctatga ggacctgaag atgtaccagg tggagtttaa aaccatgaat 360
gccaagctgc ttatggaccc taagagacag attttcctgg atcagaacat gctggccgtg 420
attgatgaat taatgcaggc gctgaacttt aacagcgaga ccgtgcccca gaaaagcagc 480
ctggaggagc ccgactttta caagaccaag atcaagttgt gcatcctcct gcacgccttc 540
agaatcagag cggtgacgat cgacagagtc atgagctacc tcaacgctag c 591

<210> SEQ ID NO 126
<211> LENGTH: 18
<212> TYPE: DNA
<213> ORGANISM: Artificial Sequence
<220> FEATURE:
<223> OTHER INFORMATION: GS Linker of L1

<400> SEQUENCE: 126
ggatcagggg gaggctcg 18

<210> SEQ ID NO 127
<211> LENGTH: 18
<212> TYPE: DNA
<213> ORGANISM: Artificial Sequence
<220> FEATURE:
<223> OTHER INFORMATION: GS Linker of L2

<400> SEQUENCE: 127
ggatcaggag gtgggagc 18

<210> SEQ ID NO 128
<211> LENGTH: 18
<212> TYPE: DNA
<213> ORGANISM: Artificial Sequence
<220> FEATURE:
<223> OTHER INFORMATION: GS Linker of L3

<400> SEQUENCE: 128
ggtagtggcg gggggagc 18

<210> SEQ ID NO 129
<211> LENGTH: 18
<212> TYPE: DNA
<213> ORGANISM: Artificial Sequence
<220> FEATURE:
<223> OTHER INFORMATION: GS Linker of M1

<400> SEQUENCE: 129
ggcagcggcg gcggatcc 18

<210> SEQ ID NO 130
<211> LENGTH: 18
<212> TYPE: DNA
<213> ORGANISM: Artificial Sequence
<220> FEATURE:
<223> OTHER INFORMATION: GS Linker of M2

<400> SEQUENCE: 130
ggctcaggcg gagggagt 18

<210> SEQ ID NO 131
<211> LENGTH: 18
<212> TYPE: DNA
<213> ORGANISM: Artificial Sequence
<220> FEATURE:
<223> OTHER INFORMATION: GS Linker of M3

<400> SEQUENCE: 131
gggagtggcg gtggcagc 18

<210> SEQ ID NO 132
<211> LENGTH: 18
<212> TYPE: DNA
<213> ORGANISM: Artificial Sequence
<220> FEATURE:
<223> OTHER INFORMATION: GS Linker of H1

<400> SEQUENCE: 132
ggctctggcg gcggcagt 18

<210> SEQ ID NO 133
<211> LENGTH: 18
<212> TYPE: DNA
<213> ORGANISM: Artificial Sequence
<220> FEATURE:
<223> OTHER INFORMATION: GS Linker of H2

<400> SEQUENCE: 133
ggcagcggcg gcggtagc 18

<210> SEQ ID NO 134
<211> LENGTH: 18
<212> TYPE: DNA
<213> ORGANISM: Artificial Sequence
<220> FEATURE:
<223> OTHER INFORMATION: GS Linker of H3

<400> SEQUENCE: 134
ggcagcggtg gcggcagc 18

<210> SEQ ID NO 135
<211> LENGTH: 18
<212> TYPE: DNA
<213> ORGANISM: Artificial Sequence
<220> FEATURE:
<223> OTHER INFORMATION: GS Linker of CO

<400> SEQUENCE: 135
ggcagcggcg gcggcagc 18

<210> SEQ ID NO 136

<211> LENGTH: 18
<212> TYPE: DNA
<213> ORGANISM: Artificial Sequence
<220> FEATURE:
<223> OTHER INFORMATION: GS Linker of CP

<400> SEQUENCE: 136
ggcagcggcg gcggcagt 18

<210> SEQ ID NO 137
<211> LENGTH: 18
<212> TYPE: DNA
<213> ORGANISM: Artificial Sequence
<220> FEATURE:
<223> OTHER INFORMATION: GS Linker of vH1

<400> SEQUENCE: 137
ggcagcggcg gcggcagc 18

<210> SEQ ID NO 138
<211> LENGTH: 18
<212> TYPE: DNA
<213> ORGANISM: Artificial Sequence
<220> FEATURE:
<223> OTHER INFORMATION: GS Linker of vH2

<400> SEQUENCE: 138
ggcagcggcg gtggcagc 18

<210> SEQ ID NO 139
<211> LENGTH: 18
<212> TYPE: DNA
<213> ORGANISM: Artificial Sequence
<220> FEATURE:
<223> OTHER INFORMATION: GS Linker of vH3

<400> SEQUENCE: 139
ggcagcggcg gcgggagc 18

<210> SEQ ID NO 140
<211> LENGTH: 18
<212> TYPE: DNA
<213> ORGANISM: Artificial Sequence
<220> FEATURE:
<223> OTHER INFORMATION: GS Linker of B1

<400> SEQUENCE: 140
ggctctggcg gcggcagt 18

<210> SEQ ID NO 141
<211> LENGTH: 18
<212> TYPE: DNA
<213> ORGANISM: Artificial Sequence
<220> FEATURE:
<223> OTHER INFORMATION: GS Linker of B2

<400> SEQUENCE: 141
ggcagcggtg gcggcagc 18

<210> SEQ ID NO 142
<211> LENGTH: 18
<212> TYPE: DNA
<213> ORGANISM: Artificial Sequence
<220> FEATURE:
<223> OTHER INFORMATION: GS Linker of B3

<400> SEQUENCE: 142
ggcagcggcg gcggcagc 18

<210> SEQ ID NO 143
<211> LENGTH: 18
<212> TYPE: DNA
<213> ORGANISM: Artificial Sequence
<220> FEATURE:
<223> OTHER INFORMATION: GS Linker of B4

<400> SEQUENCE: 143
ggcagcggcg gcggcagt 18

<210> SEQ ID NO 144
<211> LENGTH: 18
<212> TYPE: DNA
<213> ORGANISM: Artificial Sequence
<220> FEATURE:
<223> OTHER INFORMATION: GS Linker of C1

<400> SEQUENCE: 144
ggcagcggcg gcggatcc 18

<210> SEQ ID NO 145
<211> LENGTH: 18
<212> TYPE: DNA
<213> ORGANISM: Artificial Sequence
<220> FEATURE:
<223> OTHER INFORMATION: GS Linker of C2

<400> SEQUENCE: 145
ggctctggcg gcggcagt 18

<210> SEQ ID NO 146
<211> LENGTH: 18
<212> TYPE: DNA
<213> ORGANISM: Artificial Sequence
<220> FEATURE:
<223> OTHER INFORMATION: GS Linker of C3

<400> SEQUENCE: 146
ggcagcggtg gcggcagc 18

<210> SEQ ID NO 147
<211> LENGTH: 1758
<212> TYPE: DNA
<213> ORGANISM: Artificial Sequence
<220> FEATURE:
<223> OTHER INFORMATION: Albumin of L1

<400> SEQUENCE: 147
gacgcccata agagcgaagt cgcccaccgc ttcaaggatt tgggtgagga aaacttcaaa 60
gccctggtcc tgatagcgtt tgcccaatat ttgcagcagt gtccattcga agatcacgtg 120
aaattggtga acgaggtaac agaatttgct aagacttgtg tggctgacga gtcggccgaa 180
aactgtgata agagtcttca tacactgttt ggcgataagc tatgtactgt cgctacactt 240
agggagactt acggtgagat ggccgactgc tgcgccaagc aagagccaga acgaaacgag 300
tgttttctgc aacataagga cgacaatccc aacctgccca gattggttcg ccctgaagtt 360
gatgttatgt gcaccgcatt tcacgacaac gaagaaacct ttcttaaaaa gtatctgtac 420
gagatagctc gacgtcaccc ttacttctac gcgcccgaac ttctgttttt cgccaagcga 480
tacaaagccg ctttcacaga gtgttgccaa gctgccgaca aagccgcttg ccttctacca 540

```
aagcttgacg agctcagaga tgaagggaaa gctagttcgg caaagcaacg attaaagtgt    600

gcatcactgc aaaaattcgg cgaacgagcc tttaaagcat gggcagttgc caggttatcc    660

caaaggttcc cgaaagctga attcgctgag gtgagcaagt tagtcacgga ccttacgaag    720

gtacataccg aatgctgcca cggggacctc ttggagtgcg ctgacgacag ggcggactta    780

gctaaataca tttgcgagaa tcaggactca atcagttcta aacttaaaga atgctgcgag    840

aaaccgctcc tggaaaaatc acattgcatc gccgaggtgg aaaacgatga gatgccagca    900

gatttaccat ctctagccgc cgacttcgtg gaaagtaagg atgtgtgtaa aaactatgcg    960

gaagcaaaag acgtgttcct cggaatgttt ctatacgaat acgctagaag gcatcctgac   1020

tattctgtcg ttttactgct tagactagcg aagacatatg aaacgacgtt agagaaatgc   1080

tgcgcggccg ctgacccccca cgaatgttac gcgaaggtct ttgatgagtt caagcccctg   1140

gttgaggagc cgcaaaacct tattaaacag aattgtgagc tatttgagca gttaggcgaa   1200

tataaattcc agaatgcact tctagtacga tacaccaaaa aggtccctca agtgagcacc   1260

cccactcttg tggaggtatc cagaaatcta ggaaaggtag gctctaaatg ctgcaagcat   1320

cccgaagcca agagaatgcc atgcgctgaa gactacctta gcgttgttct gaatcagttg   1380

tgtgtccttc acgaaaagac gccggtgagt gatcgtgtca cgaagtgctg tacagagagc   1440

ctcgtcaacc gtaggccatg tttctccgct ctcgaggtgg atgaaacata tgtacctaag   1500

gaatttaatg cggaaacttt cacctttcac gcggacatct gtaccctgag cgagaaggag   1560

aggcagataa aaaagcagac ggctcttgta gagttggtca aacataagcc taaggccact   1620

aaagagcagc taaaggcagt aatggacgac tttgcggctt tcgttgagaa gtgctgcaag   1680

gccgacgata aagagacctg tttcgcggaa gaaggtaaaa agttagtggc cgcctcccag   1740

gcggccctgg gcctgtag                                                 1758
```

<210> SEQ ID NO 148
<211> LENGTH: 1758
<212> TYPE: DNA
<213> ORGANISM: Artificial Sequence
<220> FEATURE:
<223> OTHER INFORMATION: Albumin of L2

<400> SEQUENCE: 148

```
gacgcgcaca aaagcgaggt agcgcatcgc tttaaagact taggagagga aaactttaag     60

gcgctggtgc tcatcgcatt tgcccaatac ttacagcagt gtccttttga ggaccacgta    120

aagcttgtaa acgaagtcac tgaattcgcc aagacatgtg ttgctgacga aagcgcagag    180

aactgtgaca aaagccttca taccctcttt ggtgacaaac tctgcaccgt ggcaactcta    240

agagaaacct acggggaaat ggcagactgc tgcgcaaagc aggaacccga acgcaatgag    300

tgtttcctgc agcacaagga tgataatccc aatctgccac gacttgtacg gccggaggta    360

gatgttatgt gcactgcttt tcatgacaac gaggaaactt tccttaagaa atatctgtat    420

gagatcgcaa ggcggcaccc ttacttctac gcacccgaac tgttgttttt cgcaaagagg    480

tataaggccg catttaccga gtgttgtcag gccgctgata aagccgcctg tcttttgcca    540

aaattagatg aactaaggga cgaaggcaaa gcgagtagcg ccaaacaaag attaaaatgt    600

gcaagcctcc aaaaattcgg tgaaagagca tttaaggcgt gggctgtcgc ccgactttca    660

caacgcttcc ccaaagctga attcgctgag gtttcgaagc tggttaccga cctaactaaa    720

gtgcatacag agtgctgtca tggggatctc ttagagtgcg cggatgaccg ggcagacctg    780

gctaagtaca tatgtgagaa ccaggacagt atatcatcaa agctgaaaga gtgttgtgag    840
```

```
aagccactac tcgagaagag tcactgtatt gccgaggtgg aaaatgatga gatgccagcc    900
gatcttcctt ctttggccgc tgactttgta gagagcaagg atgtctgtaa gaactacgct    960
gaggccaagg atgtcttttt ggggatgttc ctctatgagt acgcccgacg acaccctgac   1020
tatagtgtag tacttttgct tagactggct aaaacatatg agacgactct cgaaaagtgc   1080
tgtgccgctg ccgatccaca cgagtgctac gctaaggtgt ttgatgagtt taagccgctg   1140
gtggaggaac cccagaacct gatcaagcag aactgtgaac tattcgagca actaggggag   1200
tacaaattcc agaacgcact tttagtgcgg tacaccaaaa aagtgccaca ggtcagtaca   1260
ccaacattag tggaagtatc caggaacctg ggcaaagtgg gcagcaaatg ctgcaaacat   1320
ccggaggcta agcggatgcc ctgtgcagag gactacctgt ccgtggtgct taaccagctg   1380
tgtgtgcttc acgagaaaac gcctgtgtcc gaccgggtga ccaagtgctg tacggagtca   1440
ctggtaaatc gacgaccgtg tttttcagca ctagaagttg atgaaactta tgtaccgaaa   1500
gagtttaacg cagagacctt tacattccac gccgacatct gcacgctgtc cgagaaggaa   1560
agacagatta aaaagcagac tgccctagtc gagcttgtca aacacaaacc gaaggcaacc   1620
aaggaacagt taaaagcagt gatggatgat tttgctgcgt tcgtcgaaaa atgttgcaaa   1680
gcggacgaca aggagacttg cttcgcagag gaagggaaga aattggttgc ggcgtcccaa   1740
gcggccttag ggctatag                                                 1758
```

<210> SEQ ID NO 149
<211> LENGTH: 1758
<212> TYPE: DNA
<213> ORGANISM: Artificial Sequence
<220> FEATURE:
<223> OTHER INFORMATION: Albumin of L3

<400> SEQUENCE: 149

```
gacgcccaca agtctgaagt ggcacaccgg ttcaaggacc tcggggagga gaattttaaa     60
gccctcgtgc tgatcgcttt cgcgcagtac ttgcagcagt gcccttttga ggaccatgtc    120
aaattagtaa acgaagtgac ggaattcgca aagacttgcg tagcggatga gtcagcagag    180
aattgcgaca agtcgctaca cactctgttc ggggataagt tgtgcacagt tgctacctta    240
cgagagacct atggagagat ggctgactgc tgcgccaaac aagagcctga aagaaacgag    300
tgcttcttac aacacaaaga cgataacccg aatttgccaa ggcttgtaag acccgaagta    360
gatgttatgt gcacagcttt tcacgacaac gaggagacgt tccttaagaa atatctgtat    420
gaaatagccc gtcggcaccc ctatttttat gctcccgaac tattgttctt cgccaaacga    480
tacaaggctg cgttcactga gtgctgtcag gctgcagaca aagcagcctg cttgcttccc    540
aaattggacg aactacggga cgaaggtaag gcgagctccg caaaacagcg gttgaaatgc    600
gcgtcactac agaagtttgg ggaaagagcg ttcaaagctt gggctgtggc acgattgagc    660
caacgcttcc ccaaagcaga gtttgcggaa gtttcgaaac tcgtgacaga cttaacaaag    720
gttcacaccg agtgctgtca cggcgatctg ctcgaatgcg ctgatgaccg cgctgacttg    780
gctaaataca tttgtgagaa ccaggactct atatcgagca aactcaagga atgctgcgaa    840
aagcccctgc ttgagaagtc ccactgcatc gctgaggtag agaatgatga gatgcctgcg    900
gatcttccga gtttagcagc tgatttcgtc gagagcaaag atgtgtgcaa aaattatgcc    960
gaagcaaaag acgtatttct tgggatgttc ttatacgagt atgcacggcg ccacccagat   1020
tactccgtag tgctactgtt aagattggcg aagacctatg aaaccacatt ggaaaagtgc   1080
```

```
tgcgccgccg ccgaccccca cgagtgttac gcgaaggtgt tcgatgaatt taaaccgctt   1140

gttgaggagc cgcaaaacct aataaagcaa aactgtgagc tctttgagca actaggtgaa   1200

tacaagtttc agaatgcact cctagttcgg tacaccaaaa aagtacctca ggtatctacg   1260

ccaacgttag tcgaggtctc gcggaatttg ggtaaagtag gttccaagtg ttgcaaacac   1320

ccggaagcta aacgtatgcc gtgtgctgag gactatctca gcgttgtgtt aaaccaactt   1380

tgcgtactcc acgagaaaac acctgtctca gatcgggtaa ccaaatgctg cacggagtcg   1440

ctagtaaatc gtcgcccatg cttttctgcg ttagaggtgg acgaaactta tgtaccgaaa   1500

gaatttaacg cggaaacctt tacattccat gcagatatct gtacactgtc cgagaaagag   1560

agacagatta agaaacagac ggcgctggtg gagcttgtga agcacaagcc taaagctacg   1620

aaggagcaac tgaaggcagt catggatgac tttgcggcgt ttgtggagaa gtgctgtaaa   1680

gcggacgata aggaaacatg cttcgcagaa gaaggaaaga agctggtcgc cgctagccaa   1740

gcggctctgg gcctgtag                                                 1758
```

```
<210> SEQ ID NO 150
<211> LENGTH: 1758
<212> TYPE: DNA
<213> ORGANISM: Artificial Sequence
<220> FEATURE:
<223> OTHER INFORMATION: Albumin of M1

<400> SEQUENCE: 150

gatgcccata aatctgaggt ggcccataga ttcaaggatc tgggcgaaga aaacttcaaa     60

gccttggtct tgatcgcctt tgcccagtac ctgcagcagt gcccctttga ggaccacgtg    120

aagctggtga atgaagtgac cgagtttgcc aagacgtgcg tggctgatga gagcgccgaa    180

aactgcgaca aaagcctgca caccctgttt ggcgacaagc tgtgcaccgt agccaccctg    240

agagaaactt acggcgagat ggctgactgc tgcgccaagc aggagcccga gagaaacgag    300

tgctttctgc agcacaagga cgacaatccc aacctgccca gactggtgag acccgaagtg    360

gatgttatgt gcaccgcttt ccacgacaat gaagagacat ttctcaagaa gtacttgtac    420

gagattgcaa gaagacaccc ttacttttac gcccccgaat tactgttctt cgctaagagg    480

tataaggcag ccttcactga atgctgccag gctgccgaca aagcagcttg cctgctgcca    540

aagctggatg aactgcgaga cgaaggaaag gcgtcctccg ccaagcagcg tttgaagtgc    600

gccagccttc agaagtttgg cgagcgggcc ttcaaggcat gggccgtggc tcgacttagc    660

cagcgttttc ccaaggctga atttgcagag gtgagtaaac tggttaccga tctgacaaag    720

gtgcacaccg agtgctgtca cggtgacctc ttagagtgcg ccgacgacag agccgacctc    780

gccaagtaca tttgtgaaaa ccaagactca atctcttcaa agttaaagga gtgctgcgaa    840

aagcccctgc ttgaaaagag ccactgcatt gccgaagtcg agaatgatga gatgcctgca    900

gacttgccca gcttggcagc cgacttcgtt gagtctaagg acgtgtgcaa gaattacgcc    960

gaggcaaaag acgtgttcct gggcatgttc ctttatgagt acgctagaag acatcccgac   1020

tacagcgtgg tccttctcct taggctcgct aagacttacg agacgacgtt ggagaagtgt   1080

tgtgccgctg cggaccccca cgagtgctat gccaaagtgt tcgatgagtt taaacccctg   1140

gtggaggaac ctcagaacct tatcaagcag aattgtgagt tgttcgaaca gctaggcgag   1200

tacaagttcc agaatgccct gctggtgaga tacacaaaaa aggtgcccca ggtgtcaacc   1260

ccgaccttag tggaagtgtc cagaaacctg ggcaaggtgg gcagcaagtg ctgcaagcac   1320

cccgaagcta agagaatgcc gtgcgcggag gattacctga gcgtggtgct caaccagctg   1380
```

tgtgtgcttc acgagaaaac acccgtgagc gacagggtga caaaatgttg cacagaaagc 1440
cttgtgaacc ggagaccttg tttcagcgcc ctggaggttg acgagaccta tgttcctaag 1500
gagttcaacg ctgagacttt cacatttcac gctgatatat gtaccctgag cgagaaagaa 1560
agacagatca agaagcagac cgccctggtc gagctggtga aacacaagcc taaggccacg 1620
aaggagcagc tgaaggccgt catggacgac ttcgcagcct tcgtcgagaa atgctgcaaa 1680
gccgacgaca aggaaacctg cttcgccgaa gagggaaaga agctggtggc cgcctcccag 1740
gccgcccttg ggctctag 1758

<210> SEQ ID NO 151
<211> LENGTH: 1758
<212> TYPE: DNA
<213> ORGANISM: Artificial Sequence
<220> FEATURE:
<223> OTHER INFORMATION: Albumin of M2

<400> SEQUENCE: 151
gacgcccaca agtctgaagt ggctcaccgg tttaaggacc ttggcgagga gaactttaaa 60
gccctggtgc tgattgcctt tgcccagtat ttacaacaat gccctttcga agaccacgtg 120
aagctcgtca atgaggtcac cgagttcgct aagacctgcg tagccgacga aagtgccgag 180
aactgcgaca agagcctgca caccctgttc ggggacaaac tctgtaccgt ggccacccta 240
cgggagacat atggggagat ggccgactgc tgcgcaaaac aggagcccga gagaaatgag 300
tgcttcctgc agcacaagga tgacaacccc aatctgccca gactggtgcg ccccgaggta 360
gacgttatgt gcaccgcctt ccatgacaat gaggagacgt tcctgaagaa atacctgtac 420
gagatcgcaa gacgtcaccc ctatttctat gcacctgagc tgcttttctt cgccaagaga 480
tataaggccg ccttcaccga atgctgccag gcagccgata aggcagcttg cctcctgcca 540
aagctggacg agctgagaga tgagggcaag gcctccagcg cgaagcagag actcaaatgc 600
gcaagccttc agaagttcgg agaacgcgcc tttaaagcct gggccgtcgc cagactgagc 660
cagcgcttcc ctaaagccga attcgcagaa gtgagcaagc tggtaacgga cctgacaaag 720
gtgcatactg agtgctgcca tggcgatctg ctggagtgcg ctgatgacag agcagatttg 780
gcgaaatata tttgcgaaaa tcaggatagc atcagctcta agctcaagga gtgttgtgag 840
aagcccctgc tggaaaaaag ccactgcatt gcagaggttg agaacgatga aatgccagcc 900
gaccttccat cattggccgc cgatttcgtg gagtcgaagg atgtgtgtaa gaactacgcc 960
gaggccaagg acgtgttcct gggcatgttc ctgtacgagt atgctagaag acatcccgat 1020
tacagtgtgg tgctgctatt gagactggcc aagacctacg aaaccaccct ggagaaatgt 1080
tgcgccgcgg cagatcctca cgaatgttac gccaaagtgt ttgacgaatt caagccactg 1140
gtagaggagc cccagaactt aataaagcag aattgcgagc tattcgagca gttgggcgag 1200
tacaaattcc agaacgccct tctggtgagg tataccaaaa aggtgcccca ggtgtctacc 1260
cctaccctgg tggaggtcag ccgaaatctg ggaaaggtcg gatccaagtg ctgcaagcac 1320
ccggaggcca agaggatgcc ttgcgctgag gactatctca gtgtcgtcct gaatcagcta 1380
tgcgtgttgc acgagaaaac cccagtgagt gaccgcgtga ctaaatgctg caccgaaagc 1440
ttggtgaatc ggaggccctg tttctctgca ctggaagttg acgagactta cgtcccgaag 1500
gaattcaacg ccgagacatt caccttccat gctgacatat gtactctgtc agaaaaggag 1560
cgtcagatca agaagcagac agccctggtg gaactggtta agcataagcc taaagcgacc 1620
aaagagcagc tgaaagccgt gatggacgat tttgccgcct tcgtggagaa atgttgtaag 1680
gcagacgaca aagagacatg tttcgccgaa gaggggaaga aactggtggc cgcaagccag 1740
gccgctctgg gtctgtag 1758

<210> SEQ ID NO 152
<211> LENGTH: 1758
<212> TYPE: DNA
<213> ORGANISM: Artificial Sequence
<220> FEATURE:
<223> OTHER INFORMATION: Albumin of M3

<400> SEQUENCE: 152
gatgcccaca aaagcgaagt cgcacacaga ttcaaggact tgggtgagga gaactttaaa 60
gccctggtgc tgatcgcctt cgcgcagtat ctccagcagt gccccttcga agatcatgtg 120
aaactggtga acgaggtaac cgagttcgcg aagacatgcg ttgctgatga gagcgccgaa 180
aattgcgaca aaagcctgca tactctgttc ggggacaagc tgtgcacggt cgcaaccctg 240
agagaaacct acggcgagat ggcagactgc tgcgccaagc aggagcctga gaggaacgag 300
tgttttctgc agcacaagga cgataatcct aaccttcctc gtctagtgag acccgaagtg 360
gacgttatgt gtaccgcctt tcacgacaat gaggaaacat tcctgaaaaa gtacctgtac 420
gagatcgcca gacggcaccc atatttctac gcccccgagc tgctcttctt cgcaaagagg 480
tacaaggctg ccttcaccga gtgctgccag gcggccgaca aggcggcgtg tttgctgcct 540
aagctggacg aactacgtga cgaaggaaaa gctagcagcg ccaagcagag acttaagtgc 600
gcgtccttac agaagtttgg cgaaagagcg tttaaggcct gggccgtggc aaggctgtct 660
caaagattcc ccaaggcgga gttcgccgag gtgtcaaaac tggtgaccga cttaaccaag 720
gtgcacaccg aatgctgcca cggcgatctg ctcgagtgcg ccgacgacag agccgatctg 780
gcaaaataca tctgcgaaaa ccaggatagc atcagctcca aactgaagga gtgctgtgaa 840
aaaccactgc ttgaaaaatc gcattgtata gcggaggtgg agaatgacga gatgcccgcc 900
gacctgccaa gcctggccgc cgatttcgtt gaatccaagg acgtttgcaa gaactatgca 960
gaagcgaagg acgtgttctt aggaatgttc ctatacgagt acgcgagaag acatcccgac 1020
tacagcgtgg ttctgctgtt gagattagcc aagacgtatg agacaaccct cgaaaagtgc 1080
tgcgccgccg ccgaccccca cgagtgttac gcaaaggtgt tcgatgagtt taaaccgctg 1140
gttgaggaac cgcaaaacct gatcaagcag aactgcgagc tgttcgagca gctgggtgaa 1200
tacaagtttc agaatgcact gttggtgcga tataccaaga aggtgcctca ggtgagcacc 1260
cctacccttg ttgaggtgtc ccgcaatctg ggtaaggttg ggagcaagtg ttgcaaacac 1320
cccgaggcca agagaatgcc ctgcgcggaa gattatctca gtgtcgtgct taatcagtta 1380
tgtgtcctgc atgagaagac ccccgtgagc gacagagtga ccaagtgctg taccgaatct 1440
ctcgtgaaca gacgcccgtg cttcagcgcc ttggaggtag acgagaccta cgtgcccaag 1500
gagttcaacg cagagacctt caccttcac gccgatatct gcaccctgtc cgagaaggag 1560
agacaaatca agaaacaaac ggccctcgtg gagctggtca agcacaaacc caaggccaca 1620
aaagagcagc tgaaggccgt gatggacgac ttcgcagcct ttgtggagaa atgctgcaag 1680
gctgacgaca aggagacatg cttcgccgag gaaggcaaga agttggtggc cgccagccag 1740
gcggccctgg gcctgtag 1758

<210> SEQ ID NO 153
<211> LENGTH: 1758

```
<212> TYPE: DNA
<213> ORGANISM: Artificial Sequence
<220> FEATURE:
<223> OTHER INFORMATION: Albumin of H1

<400> SEQUENCE: 153

gacgcccaca agtccgaggt cgcccacaga ttcaaggatt tgggcgagga gaacttcaag     60

gccctggtgc tgatcgcctt cgcccagtac ttgcagcagt gtcccttcga ggaccatgtg    120

aagctggtga acgaggtgac cgagttcgcc aagacctgtg tggccgacga gagcgccgag    180

aactgcgata agtctctgca caccctttt ggcgacaaac tgtgcaccgt ggccaccctg    240

agagagacct acggcgagat ggccgactgc tgtgcgaagc aggagcccga gcgcaatgag    300

tgtttcctgc agcataagga cgacaacccc aacctgccca gactggtgag acccgaggtg    360

gacgtgatgt gcaccgcctt ccacgacaac gaggagacct ttctgaaaaa atacctgtac    420

gagatcgcaa gacgccaccc ctacttctac gcccccgagc tgctgttctt cgccaagcgc    480

tacaaggctg ccttcaccga gtgctgccag gccgccgata aggccgcgtg cttactgcca    540

aagctggacg agctgagaga cgaggggaaa gcctctagcg ccaaacagag attgaagtgt    600

gccagcctgc agaaattcgg tgagagagcc ttcaaggcct gggccgtggc cagattatca    660

cagcggttcc ccaaggctga attcgccgag gtgagcaaac ttgtcaccga tctgacaaaa    720

gtgcacaccg agtgctgcca tggcgacctg ctggagtgcg ccgacgaccg ggccgacctg    780

gccaagtaca tctgcgagaa ccaggacagc atctccagca agctgaagga gtgctgcgag    840

aagcccctgc tggagaagag ccactgcatc gccgaggtgg agaatgacga aatgcccgcc    900

gacctgccca gcctggccgc cgacttcgtg gaaagcaagg acgtgtgcaa aaattacgcc    960

gaagccaagg atgtgttctt gggcatgttc ttgtacgagt acgccagacg ccacccccgac   1020

tacagcgtgg tgctgctgct gcggctggcc aagacctacg agaccaccct ggagaagtgc   1080

tgtgctgccg ccgaccccca cgagtgctac gccaaggtat ttgacgagtt caagcccctg   1140

gtggaggagc ctcagaacct gattaagcag aactgtgagc tgttcgagca gctgggcgag   1200

tacaagttcc agaacgccct cctggtgaga tacaccaaaa aggtgcctca ggtaagcact   1260

cccaccctgg tggaggtgag caggaacctc ggcaaggtgg gcagcaaatg ctgcaagcac   1320

ccagaggcca aaagaatgcc ctgcgcagaa gactacctca gcgtggtcct gaaccagctg   1380

tgcgtgctgc acgaaaagac ccctgtgagc gatagagtga caaagtgctg caccgagagc   1440

ctggtgaaca gaagaccctg ttttagcgcc ctggaggtgg acgagaccta cgtgcccaag   1500

gagttcaacg ccgagacgtt cactttccac gcggacatct gcaccctgag cgagaaggag   1560

agacaaatca agaagcagac cgccctagtc gagctggtaa aacacaagcc caaggccacc   1620

aaggagcagc tgaaggccgt gatggacgac tttgcagcct tcgtggagaa gtgctgcaag   1680

gctgacgaca aggagacctg cttcgccgag gagggcaaga agctcgtagc cgccagccag   1740

gccgctctcg gcctttag                                                 1758


<210> SEQ ID NO 154
<211> LENGTH: 1758
<212> TYPE: DNA
<213> ORGANISM: Artificial Sequence
<220> FEATURE:
<223> OTHER INFORMATION: Albumin of H2

<400> SEQUENCE: 154

gacgcccaca agagcgaagt ggcccataga ttcaaggacc tgggcgagga gaacttcaag     60
```

```
gccctcgtgc tgatcgcctt cgcccagtac ctgcagcagt gccctttcga ggaccacgtt    120

aaactggtga atgaagtgac cgagttcgcc aaaacctgcg tggccgacga gtctgccgaa    180

aattgcgaca aaagcttaca caccctgttc ggcgacaagc tgtgcaccgt ggccacctta    240

agagaaacct acggcgagat ggccgactgc tgcgctaagc aggagcccga gagaaacgaa    300

tgcttcctgc agcacaagga cgataaccca aatctgccta gactggtgag acccgaggtg    360

gacgtgatgt gcacagcctt ccacgataac gaagagacat tcctgaaaaa gtacctgtac    420

gagatcgcca gaagacatcc ttacttctat gcccccgagc ttctgttctt cgccaagaga    480

tataaggccg ccttcaccga gtgctgccaa gccgccgaca aggcagcctg cctgctgcca    540

aagcttgacg agctgagaga cgagggcaaa gccagcagcg ccaagcagag actgaagtgc    600

gcctccctgc agaagttcgg cgagagagcc tttaaggcct gggccgtggc cagattgagt    660

cagagattcc ccaaggccga gttcgccgag gtgagcaaac tggtgaccga cctcactaaa    720

gtgcacacag aatgttgcca tggcgatctc ctggaatgcg ccgatgacag ggccgacctg    780

gccaagtaca tctgtgagaa ccaggacagc atttcgagca agctgaagga gtgctgcgag    840

aaacccctgc tggagaagtc ccactgcatc gccgaggtgg agaacgacga gatgcccgcc    900

gacctgccca gcctggccgc agatttcgtg gagagcaagg acgtatgcaa gaactacgca    960

gaggccaagg atgtgttcct gggcatgttc ctgtacgaat acgccagaag gcacccccgac   1020

tacagcgtcg tgctgttact gagactggcc aagacctacg agacaacctt agagaagtgc   1080

tgcgcggccg cagacccgca cgagtgctac gccaaggtgt tcgacgagtt caagcccctg   1140

gtggaggaac ctcagaatct gattaagcag aattgtgagc tgttcgagca gctgggagag   1200

tacaagttcc agaacgcgct gctggtgaga tataccaaga aggtgcccca ggtgagcacc   1260

cccaccctgg tggaggtgag tcgcaacctg ggcaaggtgg ggagcaagtg ttgcaagcat   1320

cccgaggcca aaagaatgcc ctgcgcagag gactatctga gcgttgtgct taaccagctg   1380

tgcgtgctgc acgagaagac ccccgtgagc gacagagtga ccaagtgttg caccgagagc   1440

ctggtaaaca gaagaccctg cttcagcgcc ctggaggtgg acgagaccta cgtgcccaag   1500

gagttcaacg ccgagacctt taccttccac gcagacattt gcaccctgag cgagaaagag   1560

aggcagatca agaaacagac cgctctggtc gagcttgtga agcacaagcc caaagctacc   1620

aaggagcagc tgaaggccgt gatggatgat ttcgccgcct tcgtagagaa atgctgcaag   1680

gccgacgata aagagacctg ctttgccgag gagggcaaga aactggtggc cgccagccag   1740

gcggccctgg gcctgtag                                                  1758
```

<210> SEQ ID NO 155
<211> LENGTH: 1758
<212> TYPE: DNA
<213> ORGANISM: Artificial Sequence
<220> FEATURE:
<223> OTHER INFORMATION: Albumin of H3

<400> SEQUENCE: 155

```
gacgcccaca agagcgaggt ggcccacaga ttcaaggatc tcggggagga gaacttcaag     60

gccctggtgc tgatcgcctt cgcacagtac ctgcagcagt gccccttcga ggaccacgta    120

aaactggtga acgaggtgac ggagttcgcc aagacctgtg ttgccgacga gtcggccgag    180

aattgcgaca agagcctgca taccctgttc ggcgacaagc tgtgcaccgt ggccaccctg    240

agagagacct acggcgagat ggccgactgc tgcgccaagc aagagcccga gagaaacgag    300

tgcttcctgc agcacaagga cgacaacccc aacctgcccc ggctggtgag acccgaggtg    360
```

gacgtgatgt gcaccgcctt ccacgacaac gaggagacct tcctgaagaa gtatctgtac 420
gagatcgcca gaagacaccc ttatttttac gcccccgagc tgctcttctt cgctaagaga 480
tataaggcag ccttcaccga gtgttgtcag gccgccgata aggccgcttg cctgctgccc 540
aagttggacg agctcagaga cgagggcaag gcgagcagcg ccaagcagag actgaagtgc 600
gccagcctgc agaagttcgg cgagagggcc ttcaaggcct gggcggtggc cagactgtcc 660
cagagatttc ccaaggccga gttcgccgag gtaagcaagc tggtcaccga cctgaccaag 720
gtgcacaccg agtgttgcca cggcgacctg ctggaatgcg ccgatgaccg tgccgacctg 780
gccaagtaca tctgcgagaa tcaggactcc atcagcagca aactgaagga gtgttgcgag 840
aagcccctgc tggagaagag ccattgcatc gctgaggtgg aaaacgacga gatgcccgca 900
gacctgccca gcctggccgc agactttgtg gaaagtaagg acgtgtgcaa gaactacgcg 960
gaggccaaag acgtgtttct gggcatgttc ctatacgagt atgccagaag acaccccgac 1020
tacagcgttg tgttattgct gagactggcc aagacctacg agactacctt ggagaagtgc 1080
tgcgccgccg ccgaccccca cgagtgctat gccaaggtgt tcgacgagtt caagcccctg 1140
gtggaggagc cccagaatct gattaagcag aattgcgagc tttttgagca gctgggcgag 1200
tataagttcc agaacgccct gctggtgaga tacaccaaaa aggtacctca ggtgagcacc 1260
cccaccctgg tggaggtgag cagaaatctg ggcaaggtgg gcagcaagtg ctgcaagcac 1320
ccggaggcca agagaatgcc ctgtgccgag gattacctgt cagtggtgct gaaccagctg 1380
tgcgttctgc acgaaaagac gcccgtgtcg gacagagtga ccaagtgctg cacggagagc 1440
ctggtgaaca gaagaccgtg cttcagcgcc ctagaggtgg acgagaccta cgtgcccaag 1500
gagttcaacg ccgagacctt caccttccac gccgacatct gtaccctgtc agagaaggag 1560
agacagatca agaagcagac cgccttagtg gagctggtga agcacaagcc caaggccacc 1620
aaggagcagc tgaaagccgt gatggacgat ttcgcagcct tcgtcgagaa gtgctgcaag 1680
gccgacgaca aggaaacttg cttcgccgag gagggcaaga agctggtggc tgcctcgcag 1740
gccgccctcg gcctgtag 1758

<210> SEQ ID NO 156
<211> LENGTH: 1758
<212> TYPE: DNA
<213> ORGANISM: Artificial Sequence
<220> FEATURE:
<223> OTHER INFORMATION: Albumin of CO

<400> SEQUENCE: 156
gacgcccaca agagcgaggt ggcccacaga ttcaaggacc tgggcgagga gaacttcaag 60
gccctggtgc tgatcgcctt cgcccagtac ctgcagcagt gccccttcga ggaccacgtg 120
aagctggtga acgaggtgac cgagttcgcc aagacctgcg tggccgacga gagcgccgag 180
aactgcgaca agagcctgca caccctgttc ggcgacaagc tgtgcaccgt ggccaccctg 240
agagagacct acggcgagat ggccgactgc tgcgccaagc aggagcccga gagaaacgag 300
tgcttcctgc agcacaagga cgacaacccc aacctgccca gactggtgag acccgaggtg 360
gacgtgatgt gcaccgcctt ccacgacaac gaggagacct tcctgaagaa gtacctgtac 420
gagatcgcca gaagacaccc ctacttctac gcccccgagc tgctgttctt cgccaagaga 480
tacaaggccg ccttcaccga gtgctgccag gccgccgaca aggccgcctg cctgctgccc 540
aagctggacg agctgagaga cgagggcaag gccagcagcg ccaagcagag actgaagtgc 600
gccagcctgc agaagttcgg cgagagagcc ttcaaggcct gggccgtggc cagactgagc 660
cagagattcc ccaaggccga gttcgccgag gtgagcaagc tggtgaccga cctgaccaag 720
gtgcacaccg agtgctgcca cggcgacctg ctggagtgcg ccgacgacag agccgacctg 780
gccaagtaca tctgcgagaa ccaggacagc atcagcagca agctgaagga gtgctgcgag 840
aagcccctgc tggagaagag ccactgcatc gccgaggtgg agaacgacga gatgcccgcc 900
gacctgccca gcctggccgc cgacttcgtg gagagcaagg acgtgtgcaa gaactacgcc 960
gaggccaagg acgtgttcct gggcatgttc ctgtacgagt acgccagaag acaccccgac 1020
tacagcgtgg tgctgctgct gagactggcc aagacctacg agaccaccct ggagaagtgc 1080
tgcgccgccg ccgaccccca cgagtgctac gccaaggtgt tcgacgagtt caagcccctg 1140
gtggaggagc cccagaacct gatcaagcag aactgcgagc tgttcgagca gctgggcgag 1200
tacaagttcc agaacgccct gctggtgaga tacaccaaga aggtgcccca ggtgagcacc 1260
cccaccctgg tggaggtgag cagaaacctg ggcaaggtgg gcagcaagtg ctgcaagcac 1320
cccgaggcca agagaatgcc ctgcgccgag gactacctga gcgtggtgct gaaccagctg 1380
tgcgtgctgc acgagaagac ccccgtgagc gacagagtga ccaagtgctg caccgagagc 1440
ctggtgaaca gaagaccctg cttcagcgcc ctggaggtgg acgagaccta cgtgcccaag 1500
gagttcaacg ccgagacctt caccttccac gccgacatct gcaccctgag cgagaaggag 1560
agacagatca agaagcagac cgccctggtg gagctggtga agcacaagcc caaggccacc 1620
aaggagcagc tgaaggccgt gatggacgac ttcgccgcct tcgtggagaa gtgctgcaag 1680
gccgacgaca aggagacctg cttcgccgag gagggcaaga agctggtggc cgccagccag 1740
gccgccctgg gcctgtag 1758

<210> SEQ ID NO 157
<211> LENGTH: 1755
<212> TYPE: DNA
<213> ORGANISM: Artificial Sequence
<220> FEATURE:
<223> OTHER INFORMATION: Albumin of CP

<400> SEQUENCE: 157
gatgcccaca agtctgaggt ggcccaccgc ttcaaggacc tgggggagga gaacttcaag 60
gccctggtgc tgattgcctt tgcccagtac ctgcagcagt gcccctttga ggaccacgtg 120
aagctggtga atgaggtgac agaatttgcc aagacctgtg tggctgatga atctgctgag 180
aactgtgaca agagcctgca caccctgttt ggagacaagc tgtgcaccgt ggccaccctg 240
cgggagacct atggagagat ggctgactgc tgtgccaagc aggagcctga gagaaatgaa 300
tgcttcctgc agcacaagga tgacaacccc aacctgcccc ggctggtgcg gcctgaggtg 360
gatgtgatgt gcacagcctt ccatgacaat gaggagacct tcctgaagaa gtacctgtat 420
gaaattgccc ggcggcaccc ctacttctac gcccctgagc tgctgttctt tgccaagcgc 480
tacaaggccg ccttcacaga gtgctgccag gccgctgaca aggccgcctg cctgctgccc 540
aagctggatg agctgagaga tgagggcaag gccagcagcg ccaagcagag gctgaagtgt 600
gccagcctgc agaagtttgg agagcgggcc ttcaaggcct gggccgtggc ccggctgagc 660
cagcgcttcc ccaaggccga gtttgctgag gtgtccaagc tggtgacaga cctgaccaag 720
gtgcacacag agtgctgcca cggggacctg ctggagtgtg ctgatgacag agctgacctg 780
gccaagtaca tctgtgagaa ccaggacagc atcagcagca agctgaagga gtgctgtgag 840
aagcccctgc tggaaaagag ccactgcatc gccgaggtgg agaatgatga gatgcctgct 900
gacctgccca gcctggccgc tgactttgtg gagagcaagg atgtgtgcaa gaactatgca 960
gaggccaagg atgtgttcct gggcatgttc ctgtatgaat atgcccggcg gcacccagac 1020
tacagcgtgg tgctgctgct gcggctggcc aagacctatg agaccaccct ggagaagtgc 1080
tgtgccgctg ctgaccccca tgaatgttat gccaaggtgt ttgatgagtt caagcccctg 1140
gtggaggagc cccagaacct gatcaagcag aactgtgagc tgtttgagca gctgggggag 1200
tacaagttcc agaatgccct gctggtgcgc tacaccaaga aggtgcccca ggtgtccacc 1260
cccaccctgg tggaggtgtc caggaacctg ggcaaggtgg gcagcaagtg ctgcaagcac 1320
cctgaggcca agaggatgcc ctgtgccgag gactacctgt ctgtggtgct gaaccagctg 1380
tgtgtgctgc acgagaagac ccctgtgtct gacagagtga ccaagtgctg cacagagagc 1440
ctggtgaaca gaagaccctg cttcagcgcc ctggaggtgg atgagaccta cgtgcccaag 1500
gagttcaatg ctgagacctt caccttccac gccgacatct gcaccctgtc tgagaaggag 1560
cggcagatca agaagcagac agccctggtg gagctggtga agcacaagcc caaggccacc 1620
aaggagcagc tgaaggctgt gatggatgac tttgctgcct ttgtggagaa gtgctgcaag 1680
gcagatgaca aggagacctg ctttgctgag gagggcaaga agctggtggc cgccagccag 1740
gccgccctgg gcctg 1755

<210> SEQ ID NO 158
<211> LENGTH: 1758
<212> TYPE: DNA
<213> ORGANISM: Artificial Sequence
<220> FEATURE:
<223> OTHER INFORMATION: Albumin of vH1

<400> SEQUENCE: 158
gacgcccaca agagcgaggt ggcccatagg ttcaaggacc tgggcgagga gaacttcaag 60
gccctggtac tcatcgcctt cgcccaatac ctgcaacagt gccccttcga ggaccatgtt 120
aagctggtga acgaggtgac cgagttcgcc aagacctgcg tggccgacga gagcgccgag 180
aactgcgaca agagcctgca caccctgttc ggcgacaagc tgtgcaccgt ggccaccctg 240
agagagacct acggcgagat ggccgactgc tgcgccaagc aggagcccga acgtaacgag 300
tgcttcctgc agcacaagga cgacaacccc aacctgcccc gactggtcag acccgaggtg 360
gacgtgatgt gcacagcctt ccacgacaac gaggagacct tcctgaagaa gtacctctac 420
gagatcgcca gaagacatcc atacttctac gcccccgagc tgctgttctt cgccaagagg 480
tacaaggccg ccttcacaga gtgctgccag gccgccgaca aggccgcttg cctgctgcct 540
aagttggacg agctgagaga cgagggcaag gccagcagcg ccaagcagag actgaagtgc 600
gcaagcctgc agaaattcgg cgagagagcc tttaaggcct gggccgtggc cagactgagc 660
cagcgcttcc ccaaggccga gttcgccgag gtgagcaagc tggtgaccga cctgaccaaa 720
gtgcacaccg agtgctgcca cggcgacctg ctggagtgcg ccgacgacag agccgacctg 780
gccaagtaca tctgcgagaa ccaggacagc atcagcagca agttgaagga gtgctgcgag 840
aagcccctgc tggagaagag ccactgcatc gccgaggtgg agaacgacga gatgcccgcc 900
gacctgccca gcctggccgc cgacttcgtg gagagcaagg acgtgtgcaa gaactacgcc 960
gaggccaagg acgtgttcct gggcatgttc ctgtacgagt acgcccggag acaccccgac 1020
tacagcgtgg tgctgctgct gagactggcc aagacctacg agaccaccct ggagaagtgc 1080
tgtgccgccg ccgaccccca cgagtgctac gccaaggtgt tcgacgagtt caagcccctg 1140
gtggaggagc cccagaacct gatcaagcag aactgcgagc tgttcgagca gctgggcgag 1200
tataagttcc agaacgccct gctggtgaga tacaccaaga aggtgcccca ggtcagcacc 1260
cccaccctgg tggaggtgag cagaaatctg ggcaaggtgg gcagcaaatg ctgcaagcac 1320
cccgaggcca agagaatgcc ctgcgccgag gactacctgt cagtggtgct gaaccagctg 1380
tgtgtgctgc acgagaagac ccccgtgagc gacagagtga ccaagtgctg caccgagagt 1440
ctcgtgaaca gacggccctg cttcagcgcc ctggaggtgg acgaaacata cgtgcccaag 1500
gagttcaacg cagagacctt caccttccac gcagacatct gcaccctgag cgagaaggag 1560
agacagatca agaagcagac cgccctggtt gagcttgtga agcacaagcc caaggccacc 1620
aaggagcagc tgaaggccgt gatggacgac ttcgccgcct tcgtggagaa gtgctgcaag 1680
gccgacgaca aggagacctg cttcgccgag gagggcaaga agctggtggc cgccagccag 1740
gccgccctgg gcctgtag 1758

<210> SEQ ID NO 159
<211> LENGTH: 1758
<212> TYPE: DNA
<213> ORGANISM: Artificial Sequence
<220> FEATURE:
<223> OTHER INFORMATION: Albumin of vH2

<400> SEQUENCE: 159
gacgctcaca agagcgaggt ggcccacaga ttcaaggacc tgggcgagga gaacttcaag 60
gccctggtcc tgatcgcctt cgcccagtac ctgcagcagt gccccttcga ggaccacgtg 120
aagctggtga acgaggtgac cgagttcgcc aagacctgcg tggccgacga gtcggccgag 180
aactgcgaca agagcctgca caccctgttc ggcgacaagc tgtgcaccgt ggccaccctg 240
agagaaacct acggggagat ggccgactgc tgcgcaaagc aggagcccga gcgaaacgag 300
tgcttcctgc agcacaagga cgacaacccc aacttgccca gactggtaag acccgaggtg 360
gacgtcatgt gcaccgcttt ccacgacaac gaggagacct tcctgaagaa gtacctgtac 420
gagatcgcca gaagacaccc ctatttctat gcccctgagc tgctgttctt cgccaagcgc 480
tacaaggccg ccttcaccga gtgctgccag gccgccgaca aggccgcctg cctgctcccc 540
aagctggacg agctgagaga cgaaggcaag gccagcagcg ccaagcagag actgaagtgc 600
gccagcctgc agaagttcgg cgagagagcc ttcaaggcct gggccgtggc cagactgtcg 660
cagagattcc ccaaggccga gttcgccgag gtgagcaagc tggttaccga cctgactaag 720
gtgcacaccg agtgctgcca cggcgacctg ctggagtgcg ccgacgacag agccgacctg 780
gccaagtaca tctgcgagaa ccaggatagc atcagcagca agctgaagga gtgctgcgag 840 aagcccttc tggagaagtc ccactgcatc gccgaggtgg agaacgacga gatgcccgcc 900
gacctgccta gcctggccgc cgacttcgtg gagagcaagg acgtgtgcaa gaactacgcc 960
gaggccaagg acgtgttcct gggcatgttc ctgtacgagt acgccagaag acaccccgac 1020
tacagcgtgg tgctgctgct gagactggcc aagacctacg agactaccct tgagaagtgc 1080
tgcgccgccg ccgacccaca tgagtgctac gccaaggtgt tcgacgagtt caagcccctg 1140
gtggaagagc cccagaacct gatcaagcag aactgcgagc tgttcgagca gctgggcgag 1200
tacaagttcc agaacgccct tctggtgaga tacaccaaga aggtgcctca ggtgagcacc 1260
cccacccttg tggaggtgag cagaaacctc ggcaaggtgg gcagcaagtg ctgcaagcat 1320
ccagaggcca agagaatgcc ctgcgccgag gactacctga gcgtggtgct gaaccagctg 1380
tgcgtgctgc acgagaaaac tcccgtgagc gacagagtga ccaagtgctg caccgagagt 1440
ctggtgaaca gaagaccctg cttcagcgcc ctggaggtgg acgagaccta cgtgcccaag 1500
gagttcaacg ccgagacctt caccttccac gccgacatct gcaccctgag cgagaaggag 1560
cggcagatca agaagcagac cgccctggtg gagctggtga agcacaagcc caaggccacc 1620
aaggagcagc tcaaggccgt gatggacgac ttcgccgcgt tcgtggagaa gtgctgcaag 1680
gccgacgaca aagagacctg cttcgccgag gagggcaaga agcttgtggc cgccagccag 1740
gccgccctgg gcctgtag 1758

<210> SEQ ID NO 160
<211> LENGTH: 1758
<212> TYPE: DNA
<213> ORGANISM: Artificial Sequence
<220> FEATURE:
<223> OTHER INFORMATION: Albumin of vH3

<400> SEQUENCE: 160
gacgcccaca agagcgaggt ggcccacaga ttcaaggacc tcggcgagga gaacttcaag 60
gccctggtgc tgatcgcttt cgcccagtac ctgcagcagt gccccttcga ggaccacgtg 120
aaactggtga acgaggtgac cgagttcgcc aagacctgcg tggccgacga gagcgccgag 180
aactgcgaca agagcctgca cacgttgttc ggcgacaagc tgtgcaccgt ggccaccctg 240
agagagacct acggcgagat ggccgactgc tgcgccaagc aggagcccga gagaaacgaa 300
tgcttcctgc agcacaagga cgacaacccc aacctgcccc gcctggtgag acccgaggtg 360
gacgtgatgt gcaccgcctt ccacgacaac gaggagacct tcctgaagaa gtacttgtac 420
gagatcgcaa gaagacaccc gtacttctac gcccccgagc tgctgttctt cgccaagaga 480
tacaaggccg ccttcaccga gtgctgccag gccgccgaca aggccgcctg cctgctgccc 540
aagctggacg agctcagaga cgagggcaag gccagcagcg ccaagcagag actgaagtgc 600
gccagcctgc agaagttcgg cgagagagcc tttaaggcct gggccgtggc cagactgagc 660
cagagattcc ccaaggccga gttcgccgaa gtgagcaagc tggtgaccga cctgacgaag 720
gtgcacaccg agtgctgcca cggcgacctg ctggagtgcg ccgacgacag agcagacctg 780
gccaagtaca tctgcgagaa ccaggacagc atcagcagca agctgaagga gtgctgcgag 840
aagcccctgc tggagaagag ccactgcatc gccgaggtgg agaacgacga gatgcccgcc 900
gacctgccca gtctggccgc agacttcgtg gagagcaagg atgtgtgcaa gaactacgcc 960
gaggccaagg acgtgttcct gggcatgttc ctgtacgagt acgcaagaag acaccccgac 1020
tacagcgtgg tgctgctgct gagactggcc aagacctacg agaccaccct ggagaagtgc 1080
tgcgccgccg ccgaccccca cgagtgctac gccaaggtgt tcgacgagtt caagcccctg 1140
gtggaggagc cccagaacct gatcaagcag aactgcgaac tgttcgagca gcttggcgag 1200
tacaagtttc agaacgccct gctggtcaga tacaccaaga aggtgcccca ggtgagcacc 1260
cccaccctgg tggaggtgtc cagaaacctg ggcaaggtgg gcagcaagtg ctgcaagcac 1320
cccgaggcaa agagaatgcc ctgcgccgag gactatctga gcgtggtgct gaaccagctg 1380
tgcgtgctgc acgagaagac ccccgtgagc gacagagtga ccaagtgctg caccgagagc 1440
ctggtgaata gaagaccctg cttcagcgca ctggaggtgg acgagaccta cgtgcccaag 1500
gagttcaacg ccgagacatt caccttccac gccgatatct gcaccctgag cgagaaggag 1560
agacagatca agaagcagac cgccctggtg gagctggtga agcacaagcc caaggccacc 1620
aaggagcagt tgaaggccgt gatggacgac ttcgccgcct tcgtggagaa atgctgcaag 1680
gccgacgaca aggagacctg cttcgccgag gagggcaaga agctggtggc cgccagccag 1740
gccgccctgg gcctgtag 1758

<210> SEQ ID NO 161
<211> LENGTH: 1755
<212> TYPE: DNA
<213> ORGANISM: Artificial Sequence
<220> FEATURE:
<223> OTHER INFORMATION: Albumin of B1

<400> SEQUENCE: 161
gacgcccaca agtccgaggt cgcccacaga ttcaaggatt tgggcgagga gaacttcaag 60
gccctggtgc tgatcgcctt cgcccagtac ttgcagcagt gtcccttcga ggaccatgtg 120
aagctggtga acgaggtgac cgagttcgcc aagacctgtg tggccgacga gagcgccgag 180
aactgcgata agtctctgca cacccttttt ggcgacaaac tgtgcaccgt ggccaccctg 240
agagagacct acggcgagat ggccgactgc tgtgcgaagc aggagcccga gcgcaatgag 300
tgtttcctgc agcataagga cgacaacccc aacctgccca gactggtgag acccgaggtg 360
gacgtgatgt gcaccgcctt ccacgacaac gaggagacct ttctgaaaaa atacctgtac 420
gagatcgcaa gacgccaccc ctacttctac gcccccgagc tgctgttctt cgccaagcgc 480
tacaaggctg ccttcaccga atgctgccag gccgccgata aggccgcgtg cttactgcca 540
aagctggacg agctgagaga cgaggggaaa gcctctagcg ccaaacagag attgaagtgt 600
gccagcctgc agaaattcgg tgagagagcc ttcaaggcct gggccgtggc cagattatca 660
cagcggttcc ccaaggctga attcgccgag gtgagcaaac ttgtcaccga tctgacaaaa 720
gtgcacaccg agtgctgcca tggcgacctg ctggagtgcg ccgacgaccg ggccgacctg 780
gccaagtaca tctgcgagaa ccaggacagc atctccagca agctgaagga gtgctgcgag 840
aagcccctgc tggagaaaag ccactgcatc gccgaggtgg agaatgacga aatgcccgcc 900
gacctgccca gcctggccgc cgacttcgtg gaaagcaagg acgtgtgcaa aaattacgcc 960
gaagccaagg atgtgttctt gggcatgttc ttgtacgagt acgccagacg ccaccccgac 1020
tacagcgtgg tgctgctgct gcggctggcc aagacctacg agaccaccct ggagaagtgc 1080
tgtgctgccg ccgaccccca cgagtgctac gccaaggtat ttgacgagtt caagcccctg 1140
gtggaggagc ctcagaacct gattaagcag aactgtgagc tgttcgagca gctgggcgag 1200
tacaagttcc agaacgccct cctggtgaga tacaccaaaa aggtgcctca ggtaagcact 1260
cccaccctgg tggaggtgag caggaacctc ggcaaggtgg gcagcaaatg ctgcaagcac 1320
ccagaggcca aaagaatgcc ctgcgcagaa gactacctca gcgtggtcct gaaccagctg 1380
tgcgtgctgc acgaaaagac ccctgtgagc gatagagtga caaagtgctg caccgagagc 1440
ctggtgaaca gaagaccctg ttttagcgcc ctggaggtgg acgagaccta cgtgcccaag 1500
gagttcaacg ccgagacgtt cactttccac gcggacatct gcaccctgag cgagaaggag 1560
agacaaatca agaagcagac cgccctagtc gagctggtaa aacacaagcc caaggccacc 1620
aaggagcagc tgaaggccgt gatggacgac tttgcagcct tcgtggagaa gtgctgcaag 1680
gctgacgaca aggagacctg cttcgccgag gagggcaaga agctcgtagc cgccagccag 1740
gccgctctcg gcctt 1755

<210> SEQ ID NO 162
<211> LENGTH: 1755
<212> TYPE: DNA
<213> ORGANISM: Artificial Sequence
<220> FEATURE:
<223> OTHER INFORMATION: Albumin of B2

<400> SEQUENCE: 162
gacgcccaca agagcgaggt ggcccacaga ttcaaggatc tcggggagga gaacttcaag 60
gccctggtgc tgatcgcctt cgcacagtac ctgcagcagt gccccttcga ggaccacgta 120
aaactggtga acgaggtgac ggagttcgcc aagacctgtg ttgccgacga gtcggccgag 180
aattgcgaca agagcctgca taccctgttc ggcgacaagc tgtgcaccgt ggccaccctg 240
agagagacct acggcgagat ggccgactgc tgcgccaagc aagagcccga gagaaacgag 300
tgcttcctgc agcacaagga cgacaacccc aacctgcccc ggctggtgag acccgaggtg 360
gacgtgatgt gcaccgcctt ccacgacaac gaggagacct tcctgaagaa gtatctgtac 420
gagatcgcca gaagacaccc ttatttttac gcccccgagc tgctgttctt cgctaagaga 480
tataaggcag ccttcaccga gtgttgtcag gccgccgata aggccgcttg cctgctgccc 540
aagttggacg agctcagaga cgagggcaag gcgagcagcg ccaagcagag actgaagtgc 600
gccagcctgc agaagttcgg cgagagggcc ttcaaggcct gggcggtggc cagactgtcc 660
cagagatttc ccaaggccga gttcgccgag gtaagcaagc tggtcaccga cctgaccaag 720
gtgcacaccg agtgttgcca cggcgacctg ctggaatgcg ccgatgaccg tgccgacctg 780
gccaagtaca tctgcgagaa tcaggactcc atcagcagca aactgaagga gtgttgcgag 840
aagcccctgc tggaaaagag ccattgcatc gctgaggtgg aaaacgacga gatgcccgca 900
gacctgccca gcctggccgc agactttgtg gaaagtaagg acgtgtgcaa gaactacgcg 960
gaggccaaag acgtgtttct gggcatgttc ctatacgagt atgccagaag acaccccgac 1020
tacagcgttg tgttattgct gagactggcc aagacctacg agactacctt ggagaagtgc 1080
tgcgccgccg ccgaccccca cgagtgctat gccaaggtgt tcgacgagtt caagcccctg 1140
gtggaggagc cccagaatct gattaagcag aattgcgagc tttttgagca gctgggcgag 1200
tataagttcc agaacgccct gctggtgaga tacaccaaaa aggtacctca ggtgagcacc 1260
cccaccctgg tggaggtgag cagaaatctg ggcaaggtgg gcagcaagtg ctgcaagcac 1320
ccggaggcca agagaatgcc ctgtgccgag gattacctgt cagtggtgct gaaccagctg 1380
tgcgttctgc acgaaaagac gcccgtgtcg gacagagtga ccaagtgctg cacggagagc 1440
ctggtgaaca gaagaccgtg cttcagcgcc ctagaggtgg acgagaccta cgtgcccaag 1500
gagttcaacg ccgagacctt caccttccac gccgacatct gtaccctgtc agagaaggag 1560
agacagatca agaagcagac cgccttagtg gagctggtga agcacaagcc caaggccacc 1620
aaggagcagc tgaaagccgt gatggacgat ttcgcagcct tcgtcgagaa gtgctgcaag 1680
gccgacgaca aggaaacttg cttcgccgag gagggcaaga agctggtggc tgcctcgcag 1740
gccgccctcg gcctg 1755

<210> SEQ ID NO 163
<211> LENGTH: 1755
<212> TYPE: DNA
<213> ORGANISM: Artificial Sequence
<220> FEATURE:
<223> OTHER INFORMATION: Albumin of B3

<400> SEQUENCE: 163
gacgcccaca agagcgaggt ggcccacaga ttcaaggacc tgggcgagga gaacttcaag 60
gccctggtgc tgatcgcctt cgcccagtac ctgcagcagt gccccttcga ggaccacgtg 120

```
aagctggtga acgaggtgac cgagttcgcc aagacctgcg tggccgacga gagcgccgag    180
aactgcgaca agagcctgca caccctgttc ggcgacaagc tgtgcaccgt ggccaccctg    240
agagagacct acggcgagat ggccgactgc tgcgccaagc aggagcccga gagaaacgag    300
tgcttcctgc agcacaagga cgacaacccc aacctgccca gactggtgag acccgaggtg    360
gacgtgatgt gcaccgcctt ccacgacaac gaggagacct tcctgaagaa gtacctgtac    420
gagatcgcca gaagacaccc ctacttctac gcccccgagc tgctgttctt cgccaagaga    480
tacaaggccg ccttcaccga gtgctgccag gccgccgaca aggccgcctg cctgctgccc    540
aagctggacg agctgagaga cgagggcaag gccagcagcg ccaagcagag actgaagtgc    600
gccagcctgc agaagttcgg cgagagagcc ttcaaggcct gggccgtggc cagactgagc    660
cagagattcc ccaaggccga gttcgccgag gtgagcaagc tggtgaccga cctgaccaag    720
gtgcacaccg agtgctgcca cggcgacctg ctggagtgcg ccgacgacag agccgacctg    780
gccaagtaca tctgcgagaa ccaggacagc atcagcagca agctgaagga gtgctgcgag    840
aagcccctgc tggagaaaag ccactgcatc gccgaggtgg agaacgacga gatgcccgcc    900
gacctgccca gcctggccgc cgacttcgtg gagagcaagg acgtgtgcaa gaactacgcc    960
gaggccaagg acgtgttcct gggcatgttc ctgtacgagt acgccagaag acaccccgac   1020
tacagcgtgg tgctgctgct gagactggcc aagacctacg agaccaccct ggagaagtgc   1080
tgcgccgccg ccgaccccca cgagtgctac gccaaggtgt tcgacgagtt caagcccctg   1140
gtggaggagc cccagaacct gatcaagcag aactgcgagc tgttcgagca gctgggcgag   1200
tacaagttcc agaacgccct gctggtgaga tacaccaaga aggtgcccca ggtgagcacc   1260
cccaccctgg tggaggtgag cagaaacctg ggcaaggtgg gcagcaagtg ctgcaagcac   1320
cccgaggcca agagaatgcc ctgcgccgag gactacctga gcgtggtgct gaaccagctg   1380
tgcgtgctgc acgagaagac ccccgtgagc gacagagtga ccaagtgctg caccgagagc   1440
ctggtgaaca gaagaccctg cttcagcgcc ctggaggtgg acgagaccta cgtgcccaag   1500
gagttcaacg ccgagacctt caccttccac gccgacatct gcaccctgag cgagaaggag   1560
agacagatca agaagcagac cgccctggtg gagctggtga agcacaagcc caaggccacc   1620
aaggagcagc tgaaggccgt gatggacgac ttcgccgcct tcgtggagaa gtgctgcaag   1680
gccgacgaca aggagacctg cttcgccgag gagggcaaga agctggtggc cgccagccag   1740
gccgccctgg gcctg                                                    1755
```

<210> SEQ ID NO 164
<211> LENGTH: 1755
<212> TYPE: DNA
<213> ORGANISM: Artificial Sequence
<220> FEATURE:
<223> OTHER INFORMATION: Albumin of B4

<400> SEQUENCE: 164

```
gatgcccaca agtctgaggt ggcccaccgc ttcaaggacc tgggggagga gaacttcaag     60
gccctggtgc tgattgcctt tgcccagtac ctgcagcagt gcccctttga ggaccacgtg    120
aagctggtga atgaggtgac agaatttgcc aagacctgtg tggctgatga atctgctgag    180
aactgtgaca agagcctgca caccctgttt ggagacaagc tgtgcaccgt ggccaccctg    240
cgggagacct atggagagat ggctgactgc tgtgccaagc aggagcctga gagaaatgaa    300
tgcttcctgc agcacaagga tgacaacccc aacctgcccc ggctggtgcg gcctgaggtg    360
gatgtgatgt gcacagcctt ccatgacaat gaggagacct tcctgaagaa gtacctgtat    420
```

```
gaaattgccc ggcggcaccc ctacttctac gcccctgagc tgctgttctt tgccaagcgc    480

tacaaggccg ccttcacaga gtgctgccag gccgctgaca aggccgcctg cctgctgccc    540

aagctggatg agctgagaga tgagggcaag gccagcagcg ccaagcagag gctgaagtgt    600

gccagcctgc agaagtttgg agagcgggcc ttcaaggcct gggccgtggc ccggctgagc    660

cagcgcttcc ccaaggccga gtttgctgag gtgtccaagc tggtgacaga cctgaccaag    720

gtgcacacag agtgctgcca cggggacctg ctggagtgtg ctgatgacag agctgacctg    780

gccaagtaca tctgtgagaa ccaggacagc atcagcagca agctgaagga gtgctgtgag    840

aagcccctgc tggaaaagag ccactgcatc gccgaggtgg agaatgatga gatgcctgct    900

gacctgccca gcctggccgc tgactttgtg gagagcaagg atgtgtgcaa gaactatgca    960

gaggccaagg atgtgttcct gggcatgttc ctgtatgaat atgcccggcg gcacccagac   1020

tacagcgtgg tgctgctgct gcggctggcc aagacctatg agaccaccct ggagaagtgc   1080

tgtgccgctg ctgaccccca tgaatgttat gccaaggtgt ttgatgagtt caagcccctg   1140

gtggaggagc cccagaacct gatcaagcag aactgtgagc tgtttgagca gctgggggag   1200

tacaagttcc agaatgccct gctggtgcgc tacaccaaga aggtgcccca ggtgtccacc   1260

cccaccctgg tggaggtgtc caggaacctg ggcaaggtgg gcagcaagtg ctgcaagcac   1320

cctgaggcca agaggatgcc ctgtgccgag gactacctgt ctgtggtgct gaaccagctg   1380

tgtgtgctgc acgagaagac ccctgtgtct gacagagtga ccaagtgctg cacagagagc   1440

ctggtgaaca gaagaccctg cttcagcgcc ctggaggtgg atgagaccta cgtgcccaag   1500

gagttcaatg ctgagacctt caccttccac gccgacatct gcaccctgtc tgagaaggag   1560

cggcagatca agaagcagac agccctggtg gagctggtga agcacaagcc caaggccacc   1620

aaggagcagc tgaaggctgt gatggatgac tttgctgcct ttgtggagaa gtgctgcaag   1680

gcagatgaca aggagacctg ctttgctgag gagggcaaga agctggtggc cgccagccag   1740

gccgccctgg gcctg                                                    1755
```

<210> SEQ ID NO 165
<211> LENGTH: 1755
<212> TYPE: DNA
<213> ORGANISM: Artificial Sequence
<220> FEATURE:
<223> OTHER INFORMATION: Albumin of C1

<400> SEQUENCE: 165

```
gatgcccata aatctgaggt ggcccataga ttcaaggatc tgggcgaaga aaacttcaaa     60

gccttggtct tgatcgcctt tgcccagtac ctgcagcagt gcccctttga ggaccacgtg    120

aagctggtga atgaagtgac cgagtttgcc aagacgtgcg tggctgatga gagcgccgaa    180

aactgcgaca aaagcctgca caccctgttt ggcgacaagc tgtgcaccgt agccaccctg    240

agagaaactt acggcgagat ggctgactgc tgcgccaagc aggagcccga gagaaacgag    300

tgctttctgc agcacaagga cgacaatccc aacctgccca gactggtgag acccgaagtg    360

gatgttatgt gcaccgcttt ccacgacaat gaagagacat ttctcaagaa gtacttgtac    420

gagattgcaa gaagacaccc ttacttttac gcccccgaat tactgttctt cgctaagagg    480

tataaggcag ccttcactga atgctgccag gctgccgaca aagcagcttg cctgctgcca    540

aagctggatg aactgcgaga cgaaggaaag gcgtcctccg ccaagcagcg tttgaagtgc    600

gccagccttc agaagtttgg cgagcgggcc ttcaaggcat gggccgtggc tcgacttagc    660
```

cagcgttttc ccaaggctga atttgcagag gtgagtaaac tggttaccga tctgacaaag 720
gtgcacaccg agtgctgtca cggtgacctc ttagagtgcg ccgacgacag agccgacctc 780
gccaagtaca tttgtgaaaa ccaagactca atctcttcaa agttaaagga gtgctgcgaa 840
aagcccctgc ttgaaaagag ccactgcatt gccgaagtcg agaatgatga gatgcctgca 900
gacttgccca gcttggcagc cgacttcgtt gagtctaagg acgtgtgcaa gaattacgcc 960
gaggcaaaag acgtgttcct gggcatgttc ctttatgagt acgctagaag acatcccgac 1020
tacagcgtgg tccttctcct taggctcgct aagacttacg agacgacgtt ggagaagtgt 1080
tgtgccgctg cggaccccca cgagtgctat gccaaagtgt tcgatgagtt taaacccctg 1140
gtggaggaac ctcagaacct tatcaagcag aattgtgagt tgttcgaaca gctaggcgag 1200
tacaagttcc agaatgccct gctggtgaga tacacaaaaa aggtgcccca ggtgtcaacc 1260
ccgaccttag tggaagtgtc cagaaacctg ggcaaggtgg gcagcaagtg ctgcaagcac 1320
cccgaagcta agagaatgcc gtgcgcggag gattacctga gcgtggtgct caaccagctg 1380
tgtgtgcttc acgagaaaac acccgtgagc gacagggtga caaaatgttg cacagaaagc 1440
cttgtgaacc ggagaccttg tttcagcgcc ctggaggttg acgagaccta tgttcctaag 1500
gagttcaacg ctgagacttt cacatttcac gctgatatat gtaccctgag cgagaaagaa 1560
agacagatca agaagcagac cgccctggtc gagctggtga aacacaagcc taaggccacg 1620
aaggagcagc tgaaggccgt catggacgac ttcgcagcct tcgtcgagaa atgctgcaaa 1680
gccgacgaca aggaaacctg cttcgccgaa gagggaaaga agctggtggc cgcctcccag 1740
gccgcccttg ggctc 1755

<210> SEQ ID NO 166
<211> LENGTH: 1755
<212> TYPE: DNA
<213> ORGANISM: Artificial Sequence
<220> FEATURE:
<223> OTHER INFORMATION: Albumin of C2

<400> SEQUENCE: 166
gacgcccaca agtccgaggt cgcccacaga ttcaaggatt tgggcgagga gaacttcaag 60
gccctggtgc tgatcgcctt cgcccagtac ttgcagcagt gtcccttcga ggaccatgtg 120
aagctggtga acgaggtgac cgagttcgcc aagacctgtg tggccgacga gagcgccgag 180
aactgcgata agtctctgca caccctttt ggcgacaaac tgtgcaccgt ggccaccctg 240
agagagacct acggcgagat ggccgactgc tgtgcgaagc aggagcccga gcgcaatgag 300
tgtttcctgc agcataagga cgacaacccc aacctgccca gactggtgag acccgaggtg 360
gacgtgatgt gcaccgcctt ccacgacaac gaggagacct ttctgaaaaa atacctgtac 420
gagatcgcaa gacgccaccc ctacttctac gcccccgagc tgctgttctt cgccaagcgc 480
tacaaggctg ccttcaccga atgctgccag gccgccgata aggccgcgtg cttactgcca 540
aagctggacg agctgagaga cgaggggaaa gcctctagcg ccaaacagag attgaagtgt 600
gccagcctgc agaaattcgg tgagagagcc ttcaaggcct gggccgtggc cagattatca 660
cagcggttcc ccaaggctga attcgccgag gtgagcaaac ttgtcaccga tctgacaaaa 720
gtgcacaccg agtgctgcca tggcgacctg ctggagtgcg ccgacgaccg ggccgacctg 780
gccaagtaca tctgcgagaa ccaggacagc atctccagca agctgaagga gtgctgcgag 840
aagcccctgc tggagaaaag ccactgcatc gccgaggtgg agaatgacga aatgcccgcc 900
gacctgccca gcctggccgc cgacttcgtg gaaagcaagg acgtgtgcaa aaattacgcc 960
gaagccaagg atgtgttctt gggcatgttc ttgtacgagt acgccagacg ccaccccgac 1020
tacagcgtgg tgctgctgct gcggctggcc aagacctacg agaccaccct ggagaagtgc 1080
tgtgctgccg ccgaccccca cgagtgctac gccaaggtat ttgacgagtt caagcccctg 1140
gtggaggagc ctcagaacct gattaagcag aactgtgagc tgttcgagca gctgggcgag 1200
tacaagttcc agaacgccct cctggtgaga tacaccaaaa aggtgcctca ggtaagcact 1260
cccaccctgg tggaggtgag caggaacctc ggcaaggtgg gcagcaaatg ctgcaagcac 1320
ccagaggcca aaagaatgcc ctgcgcagaa gactacctca gcgtggtcct gaaccagctg 1380
tgcgtgctgc acgaaaagac ccctgtgagc gatagagtga caaagtgctg caccgagagc 1440
ctggtgaaca gaagaccctg ttttagcgcc ctggaggtgg acgagaccta cgtgcccaag 1500
gagttcaacg ccgagacgtt cactttccac gcggacatct gcaccctgag cgagaaggag 1560
agacaaatca agaagcagac cgccctagtc gagctggtaa aacacaagcc caaggccacc 1620
aaggagcagc tgaaggccgt gatggacgac tttgcagcct tcgtggagaa gtgctgcaag 1680
gctgacgaca aggagacctg cttcgccgag gagggcaaga agctcgtagc cgccagccag 1740
gccgctctcg gcctt 1755

<210> SEQ ID NO 167
<211> LENGTH: 1755
<212> TYPE: DNA
<213> ORGANISM: Artificial Sequence
<220> FEATURE:
<223> OTHER INFORMATION: Albumin of C3

<400> SEQUENCE: 167
gacgcccaca agagcgaggt ggcccacaga ttcaaggatc tcggggagga gaacttcaag 60
gccctggtgc tgatcgcctt cgcacagtac ctgcagcagt gcccccttcga ggaccacgta 120 aaactggtga acgaggtgac ggagttcgcc aagacctgtg ttgccgacga gtcggccgag 180
aattgcgaca agagcctgca taccctgttc ggcgacaagc tgtgcaccgt ggccaccctg 240
agagagacct acggcgagat ggccgactgc tgcgccaagc aagagcccga gagaaacgag 300
tgcttcctgc agcacaagga cgacaacccc aacctgcccc ggctggtgag acccgaggtg 360
gacgtgatgt gcaccgcctt ccacgacaac gaggagacct tcctgaagaa gtatctgtac 420
gagatcgcca gaagacaccc ttatttttac gcccccgagc tgctgttctt cgctaagaga 480
tataaggcag ccttcaccga gtgttgtcag gccgccgata aggccgcttg cctgctgccc 540
aagttggacg agctcagaga cgagggcaag gcgagcagcg ccaagcagag actgaagtgc 600
gccagcctgc agaagttcgg cgagagggcc ttcaaggcct gggcggtggc cagactgtcc 660
cagagatttc ccaaggccga gttcgccgag gtaagcaagc tggtcaccga cctgaccaag 720
gtgcacaccg agtgttgcca cggcgacctg ctggaatgcg ccgatgaccg tgccgacctg 780
gccaagtaca tctgcgagaa tcaggactcc atcagcagca aactgaagga gtgttgcgag 840
aagcccctgc tggaaaagag ccattgcatc gctgaggtgg aaaacgacga gatgcccgca 900
gacctgccca gcctggccgc agactttgtg gaaagtaagg acgtgtgcaa gaactacgcg 960
gaggccaaag acgtgtttct gggcatgttc ctatacgagt atgccagaag acaccccgac 1020
tacagcgttg tgttattgct gagactggcc aagacctacg agactacctt ggagaagtgc 1080
tgcgccgccg ccgaccccca cgagtgctat gccaaggtgt tcgacgagtt caagcccctg 1140
gtggaggagc cccagaatct gattaagcag aattgcgagc tttttgagca gctgggcgag 1200

```
tataagttcc agaacgccct gctggtgaga tacaccaaaa aggtacctca ggtgagcacc   1260

cccaccctgg tggaggtgag cagaaatctg ggcaaggtgg gcagcaagtg ctgcaagcac   1320

ccggaggcca agagaatgcc ctgtgccgag gattacctgt cagtggtgct gaaccagctg   1380

tgcgttctgc acgaaaagac gcccgtgtcg gacagagtga ccaagtgctg cacggagagc   1440

ctggtgaaca gaagaccgtg cttcagcgcc ctagaggtgg acgagaccta cgtgcccaag   1500

gagttcaacg ccgagacctt caccttccac gccgacatct gtaccctgtc agagaaggag   1560

agacagatca agaagcagac cgccttagtg gagctggtga agcacaagcc caaggccacc   1620

aaggagcagc tgaaagccgt gatggacgat ttcgcagcct tcgtcgagaa gtgctgcaag   1680

gccgacgaca aggaaacttg cttcgccgag gagggcaaga agctggtggc tgcctcgcag   1740

gccgccctcg gcctg                                                    1755
```

<210> SEQ ID NO 168
<211> LENGTH: 24
<212> TYPE: DNA
<213> ORGANISM: Artificial Sequence
<220> FEATURE:
<223> OTHER INFORMATION: GS Linker of C1

<400> SEQUENCE: 168

```
ggtggcgggt ctggtggcgg ttct                                            24
```

<210> SEQ ID NO 169
<211> LENGTH: 24
<212> TYPE: DNA
<213> ORGANISM: Artificial Sequence
<220> FEATURE:
<223> OTHER INFORMATION: GS Linker of C2

<400> SEQUENCE: 169

```
ggtggcgggt ctggtggcgg ttct                                            24
```

<210> SEQ ID NO 170
<211> LENGTH: 24
<212> TYPE: DNA
<213> ORGANISM: Artificial Sequence
<220> FEATURE:
<223> OTHER INFORMATION: GS Linker of C3

<400> SEQUENCE: 170

```
ggtggcgggt ctggtggcgg ttct                                            24
```

<210> SEQ ID NO 171
<211> LENGTH: 960
<212> TYPE: DNA
<213> ORGANISM: Artificial Sequence
<220> FEATURE:
<223> OTHER INFORMATION: Lumican of C1

<400> SEQUENCE: 171

```
cagtactacg attacgactt ccccctgagt atctacggtc agtcctcacc taactgcgcc     60

ccagagtgta actgccccga aagctacccg agcgccatgt actgcgacga gctgaagttg    120

aagtccgtgc ccatggtgcc cccaggcatc aagtacttat acttgaggaa caaccaaatc    180

gatcatatcg acgagaaggc cttcgaaaac gtaaccgacc tgcagtggct gatactggat    240

cacaatctgc tagagaattc caagatcaag ggcagagtgt tctcgaagct gaaacaactg    300

aagaagctgc acatcaacca taacaatctc accgagagcg tgggtcccct gcccaagtcg    360

ctggaggacc tgcagctgac ccacaacaaa ataaccaaac taggcagctt cgaggggttg    420
```

gtgaatctga ccttcatcca tttgcagcat aacagactaa aggaggatgc cgtgagcgcc 480
gccttcaaag gcctcaagag ccttgagtac ctggacctga gcttcaacca gatcgcccgg 540
ctgcccagtg ggctgcccgt gagcctgctg acgctgtatc tggacaataa caaaatcagc 600
aacatccccg acgaatactt caaaagattc aacgccttac agtacctgcg actcagccac 660
aatgagctcg ctgacagcgg catccctggc aacagcttca acgtgtcatc cctggtggag 720
ctggacctga gttacaataa gctgaagaac atcccaactg tcaatgagaa tttggaaaac 780
tactacctgg aggtgaacca gctggagaag ttcgacatta agagcttttg caaaatcctg 840
ggcccactgt catatagcaa gatcaagcac ctgcgactgg acggcaaccg aatcagtgaa 900
acttccctac cccctgacat gtacgagtgc ctgagagtag caaatgaggt gaccctgaac 960

<210> SEQ ID NO 172
<211> LENGTH: 960
<212> TYPE: DNA
<213> ORGANISM: Artificial Sequence
<220> FEATURE:
<223> OTHER INFORMATION: Lumican of C2

<400> SEQUENCE: 172
cagtattacg actacgattt ccccctgagc atctatggcc agagcagccc taactgcgcc 60
ccggagtgca actgccccga aagctaccca agcgccatgt actgcgatga gctgaagctg 120
aagtctgtgc ctatggtgcc tcccggcatc aagtacctgt acctgagaaa caaccagata 180
gaccacatcg atgagaaagc cttcgagaac gtcaccgacc tgcagtggct gattctggac 240
cacaatttac tggagaactc caagatcaag ggcagagtgt tctccaagtt aaagcagctg 300
aagaaactgc acatcaatca caacaacctg accgagagcg tgggcccact gcccaagagc 360
ctagaggatc tgcagctcac ccacaacaag atcactaagt tgggcagctt cgagggcctc 420
gtaaacttga cattcataca tctgcagcac aacagactta aggaagacgc cgtgagtgcg 480
gcctttaagg gtctgaaaag cctggagtac ttagacctga gcttcaacca gatcgcaagg 540
ctgcccagcg gccttccggt cagtctgctg accctgtatc tggacaacaa caagatcagc 600
aacatccccg acgagtactt caagcggttt aacgccctcc agtacctgag actgagccac 660
aacgagttag ctgactcggg catacccggt aacagcttca atgttagcag cctagttgag 720
cttgacttga gctacaacaa gcttaagaac atcccaaccg tgaacgagaa cctcgagaat 780
tactacctgg aagtcaacca gctggagaag ttcgacatta agagcttctg caaaatcctg 840
ggcccactgt cctatagcaa gatcaagcac ctgcgccttg acggaaacag aattagcgag 900
accagccttc caccagacat gtacgagtgc ctgagggtgg ccaacgaggt gaccctgaac 960

<210> SEQ ID NO 173
<211> LENGTH: 960
<212> TYPE: DNA
<213> ORGANISM: Artificial Sequence
<220> FEATURE:
<223> OTHER INFORMATION: Lumican of C3

<400> SEQUENCE: 173
cagtactacg actacgattt ccccctatcc atctacgggc agagctcgcc taactgcgcc 60
cccgagtgta actgccccga gtcgtacccc agcgccatgt actgtgacga gctgaagctg 120
aaaagcgtgc ccatggtgcc ccccggcatc aagtacctgt acttgagaaa caaccagatc 180
gaccacattg acgaaaaggc cttcgagaac gtaaccgacc tgcagtggct gatcctggac 240

```
cacaacctgc ttgagaacag caagatcaag ggccgcgtgt tcagcaagct gaagcagctg    300

aagaagctgc acatcaacca caacaacttg actgagtctg ttggcccccct accaaagagc    360

ctggaggacc tgcagctgac ccacaataag ataaccaagc tgggctcatt cgagggcctg    420

gtgaacttga cctttattca cctgcagcat aacagactga aggaggacgc cgtgagcgcc    480

gcctttaagg ggctgaaaag cctggagtac ctggacctga gttttaacca gatcgccaga    540

ctgccctcag gcctgcccgt gagtttgctg actctgtacc tggacaacaa taagatcagc    600

aacattcctg acgagtattt caaaagattc aatgctctgc agtacctgag actaagccac    660

aacgagctgg ccgacagcgg aatccccggc aacagcttca acgtgagcag cttggtggag    720

ttggacctga gctacaacaa actgaagaac atccccaccg tcaatgagaa cttggagaat    780

tactacctcg aggttaacca gcttgagaag ttcgacatca agagcttctg caagatcctg    840

ggcccccctca gctacagcaa gatcaagcac ttgagactgg acgggaacag aatcagcgaa    900

accagccttc ctcccgacat gtacgagtgc cttagagtgg caaatgaggt gaccctgaac    960
```

<210> SEQ ID NO 174
<211> LENGTH: 13
<212> TYPE: DNA
<213> ORGANISM: Artificial Sequence
<220> FEATURE:
<223> OTHER INFORMATION: Kozak Sequence

<400> SEQUENCE: 174

```
gccgccrcca ugg                                                        13
```

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 21
<212> TYPE: PRT
<213> ORGANISM: Artificial Sequence
<220> FEATURE:
<223> OTHER INFORMATION: Leader Sequence

<400> SEQUENCE: 180

```
Met Arg Val Pro Ala Gln Leu Leu Gly Leu Leu Leu Leu Trp Leu Pro
1               5                   10                  15

Gly Ala Arg Cys Ala
            20
```

<210> SEQ ID NO 181
<211> LENGTH: 34
<212> TYPE: DNA
<213> ORGANISM: Artificial Sequence
<220> FEATURE:
<223> OTHER INFORMATION: Forward Primer

<400> SEQUENCE: 181

```
taatacgact cactataatg gactacgaca tagt                                 34
```

<210> SEQ ID NO 182
<211> LENGTH: 547
<212> TYPE: PRT
<213> ORGANISM: Artificial Sequence
<220> FEATURE:
<223> OTHER INFORMATION: Wild-type IL-12

<400> SEQUENCE: 182

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser Met Cys His Gln Gln
    210                 215                 220

Leu Val Ile Ser Trp Phe Ser Leu Val Phe Leu Ala Ser Pro Leu Val
225                 230                 235                 240

Ala Ile Trp Glu Leu Lys Lys Asp Val Tyr Val Val Glu Leu Asp Trp
                245                 250                 255

Tyr Pro Asp Ala Pro Gly Glu Met Val Val Leu Thr Cys Asp Thr Pro
```

```
            260                 265                 270

Glu Glu Asp Gly Ile Thr Trp Thr Leu Asp Gln Ser Ser Glu Val Leu
        275                 280                 285

Gly Ser Gly Lys Thr Leu Thr Ile Gln Val Lys Glu Phe Gly Asp Ala
    290                 295                 300

Gly Gln Tyr Thr Cys His Lys Gly Gly Glu Val Leu Ser His Ser Leu
305                 310                 315                 320

Leu Leu Leu His Lys Lys Glu Asp Gly Ile Trp Ser Thr Asp Ile Leu
                325                 330                 335

Lys Asp Gln Lys Glu Pro Lys Asn Lys Thr Phe Leu Arg Cys Glu Ala
            340                 345                 350

Lys Asn Tyr Ser Gly Arg Phe Thr Cys Trp Trp Leu Thr Thr Ile Ser
        355                 360                 365

Thr Asp Leu Thr Phe Ser Val Lys Ser Ser Arg Gly Ser Ser Asp Pro
    370                 375                 380

Gln Gly Val Thr Cys Gly Ala Ala Thr Leu Ser Ala Glu Arg Val Arg
385                 390                 395                 400

Gly Asp Asn Lys Glu Tyr Glu Tyr Ser Val Glu Cys Gln Glu Asp Ser
                405                 410                 415

Ala Cys Pro Ala Ala Glu Glu Ser Leu Pro Ile Glu Val Met Val Asp
            420                 425                 430

Ala Val His Lys Leu Lys Tyr Glu Asn Tyr Thr Ser Ser Phe Phe Ile
        435                 440                 445

Arg Asp Ile Ile Lys Pro Asp Pro Pro Lys Asn Leu Gln Leu Lys Pro
    450                 455                 460

Leu Lys Asn Ser Arg Gln Val Glu Val Ser Trp Glu Tyr Pro Asp Thr
465                 470                 475                 480

Trp Ser Thr Pro His Ser Tyr Phe Ser Leu Thr Phe Cys Val Gln Val
                485                 490                 495

Gln Gly Lys Ser Lys Arg Glu Lys Lys Asp Arg Val Phe Thr Asp Lys
            500                 505                 510

Thr Ser Ala Thr Val Ile Cys Arg Lys Asn Ala Ser Ile Ser Val Arg
        515                 520                 525

Ala Gln Asp Arg Tyr Tyr Ser Ser Ser Trp Ser Glu Trp Ala Ser Val
    530                 535                 540

Pro Cys Ser
545


<210> SEQ ID NO 183
<211> LENGTH: 219
<212> TYPE: PRT
<213> ORGANISM: Artificial Sequence
<220> FEATURE:
<223> OTHER INFORMATION: Wild-type IL12a

<400> SEQUENCE: 183

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
```

```
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215


<210> SEQ ID NO 184
<211> LENGTH: 328
<212> TYPE: PRT
<213> ORGANISM: Artificial Sequence
<220> FEATURE:
<223> OTHER INFORMATION: Wild-type IL12b

<400> SEQUENCE: 184

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
```

```
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 185
<211> LENGTH: 35
<212> TYPE: DNA
<213> ORGANISM: Artificial Sequence
<220> FEATURE:
<223> OTHER INFORMATION: Reverse Primer

<400> SEQUENCE: 185

gaaatattaa aaacaaaatc cgattcggaa aagaa                              35
```